(12) United States Patent
Bamdad et al.

(10) Patent No.: US 12,006,371 B2
(45) Date of Patent: *Jun. 11, 2024

(54) HUMANIZED ANTI-MUC1* ANTIBODIES

(71) Applicant: Minerva Biotechnologies Corporation, Waltham, MA (US)

(72) Inventors: Cynthia Bamdad, Waltham, MA (US); Benoit Smagghe, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/817,525

(22) Filed: Aug. 4, 2022

(65) Prior Publication Data

US 2023/0183373 A1 Jun. 15, 2023

Related U.S. Application Data

(63) Continuation of application No. 15/549,942, filed as application No. PCT/US2016/017422 on Feb. 10, 2016, now Pat. No. 11,746,159.

(60) Provisional application No. 62/114,526, filed on Feb. 10, 2015.

(51) Int. Cl.
*C07K 16/30* (2006.01)
*A61K 39/00* (2006.01)

(52) U.S. Cl.
CPC .... *C07K 16/3092* (2013.01); *A61K 39/00117* (2018.08); *A61K 2039/5156* (2013.01); *A61K 2039/5158* (2013.01); *C07K 2317/24* (2013.01); *C07K 2317/34* (2013.01); *C07K 2317/52* (2013.01); *C07K 2317/622* (2013.01); *C07K 2319/02* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 4,675,189 A | 6/1987 | Kent et al. | |
| 5,075,109 A | 12/1991 | Tice et al. | |
| 5,108,933 A | 4/1992 | Liberti et al. | |
| 5,133,974 A | 7/1992 | Paradissis et al. | |
| 5,342,947 A | 8/1994 | Lackey et al. | |
| 5,407,686 A | 4/1995 | Patel et al. | |
| 5,736,152 A | 4/1998 | Dunn | |
| 5,767,135 A | 6/1998 | Fernandez-Pol | |
| 6,127,393 A | 10/2000 | Fernandez-Pol | |
| 6,548,643 B1 | 4/2003 | McKenzie et al. | |
| 7,538,088 B2 | 5/2009 | Anderson et al. | |
| 7,825,092 B2 | 11/2010 | Vesely | |
| 9,932,407 B2 | 4/2018 | Bamdad | |
| 10,421,819 B2 | 9/2019 | Bamdad et al. | |
| 11,560,435 B2* | 1/2023 | Bamdad | C12N 5/0693 |
| 11,746,159 B2* | 9/2023 | Bamdad | A61K 39/00117 |
| | | | 424/133.1 |
| 2002/0018750 A1 | 2/2002 | Hansen et al. | |
| 2002/0042089 A1 | 4/2002 | Bodmer et al. | |
| 2002/0052311 A1 | 5/2002 | Solomon et al. | |
| 2002/0064528 A1 | 5/2002 | Zhu et al. | |
| 2002/0136725 A1 | 9/2002 | Blackburn et al. | |
| 2002/0156112 A1 | 10/2002 | Bamdad et al. | |
| 2003/0036199 A1 | 2/2003 | Bamdad et al. | |
| 2003/0119018 A1 | 6/2003 | Omura et al. | |
| 2003/0119834 A1 | 6/2003 | Bamdad | |
| 2003/0130293 A1 | 7/2003 | Bamdad | |
| 2003/0170237 A1 | 9/2003 | Ni et al. | |
| 2003/0235868 A1 | 12/2003 | Hoogenboom et al. | |
| 2004/0057952 A1 | 3/2004 | Payne et al. | |
| 2004/0120955 A1 | 6/2004 | Anderson et al. | |
| 2004/0131612 A1 | 7/2004 | Watkins et al. | |
| 2005/0019324 A1 | 1/2005 | Wreschner et al. | |
| 2005/0287145 A1 | 12/2005 | Stewart et al. | |
| 2006/0122377 A1 | 6/2006 | Dennis | |
| 2006/0147451 A1 | 7/2006 | Kirchhofer et al. | |
| 2006/0173171 A1 | 8/2006 | Bamdad | |
| 2006/0222637 A1 | 10/2006 | Bamdad | |
| 2007/0212350 A1 | 9/2007 | Govindan et al. | |
| 2009/0299039 A1 | 12/2009 | Kataoka et al. | |
| 2010/0150918 A1 | 6/2010 | Kufer et al. | |
| 2010/0316688 A1 | 12/2010 | Bamdad | |
| 2011/0165167 A1 | 7/2011 | Pullen | |
| 2011/0318757 A1 | 12/2011 | Behrens et al. | |
| 2012/0040375 A1 | 2/2012 | Nishimura et al. | |
| 2013/0177555 A1 | 7/2013 | Wilkinson et al. | |
| 2013/0266551 A1 | 10/2013 | Campana et al. | |

(Continued)

FOREIGN PATENT DOCUMENTS

| | | |
|---|---|---|
| CA | 2947646 A1 | 11/2015 |
| CN | 102264754 A | 11/2011 |

(Continued)

OTHER PUBLICATIONS

DeSimone (Current Opin. Oncol. Mar. 2015;27(2):128-33) (Year: 2015).*

(Continued)

*Primary Examiner* — Peter J Reddig

(74) *Attorney, Agent, or Firm* — WILSON SONSINI GOODRICH & ROSATI

(57) ABSTRACT

The present application discloses humanized antibodies and antibody like proteins and fragments thereof.

29 Claims, 62 Drawing Sheets
(57 of 62 Drawing Sheet(s) Filed in Color)
Specification includes a Sequence Listing.

(56) References Cited

U.S. PATENT DOCUMENTS

| | | | |
|---|---|---|---|
| 2016/0340442 | A1 | 11/2016 | Kufe et al. |
| 2017/0051037 | A1 | 2/2017 | Galetto |
| 2017/0204191 | A1 | 7/2017 | Bamdad et al. |
| 2018/0044424 | A1 | 2/2018 | June et al. |
| 2018/0112007 | A1 | 4/2018 | Bamdad et al. |
| 2019/0290692 | A1 | 9/2019 | Bamdad et al. |
| 2020/0239594 | A1 | 7/2020 | Bamdad et al. |
| 2020/0390870 | A1 | 12/2020 | Bamdad |
| 2022/0184120 | A1* | 6/2022 | Bamdad ............... A61P 35/00 |
| 2023/0279142 | A1* | 9/2023 | Bamdad ........... A61K 39/00117 424/133.1 |

FOREIGN PATENT DOCUMENTS

| | | | |
|---|---|---|---|
| CN | 102574926 A | 7/2012 | |
| CN | 103483453 A | 1/2014 | |
| CN | 103880956 A | 6/2014 | |
| EP | 0369816 A2 | 5/1990 | |
| EP | 2329822 A1 | 6/2011 | |
| WO | WO-9109134 A1 | 6/1991 | |
| WO | WO-9207000 A1 | 4/1992 | |
| WO | WO-9524929 A2 | 9/1995 | |
| WO | WO-9603502 A2 | 2/1996 | |
| WO | WO-9735024 A1 | 9/1997 | |
| WO | WO-9835554 A2 | 8/1998 | |
| WO | WO-0029029 A1 | 5/2000 | |
| WO | WO-0034783 A1 | 6/2000 | |
| WO | WO-0043783 A2 | 7/2000 | |
| WO | WO-0043791 A2 | 7/2000 | |
| WO | WO-0134145 A1 | 5/2001 | |
| WO | WO-0222685 A2 | 3/2002 | |
| WO | WO-02056022 A2 | 7/2002 | |
| WO | WO-02078598 A2 | 10/2002 | |
| WO | WO-03020279 A2 | 3/2003 | |
| WO | WO-03020280 A2 | 3/2003 | |
| WO | WO-03054154 A2 | 7/2003 | |
| WO | WO-03089451 A2 | 10/2003 | |
| WO | WO-2004005470 A1 | 1/2004 | |
| WO | WO-2005019269 A2 | 3/2005 | |
| WO | WO-2008070171 A2 | 6/2008 | |
| WO | WO-2008073817 A2 | 6/2008 | |
| WO | WO-2008101231 A2 | 8/2008 | |
| WO | WO-2010042562 A2 | 4/2010 | |
| WO | WO-2010042891 A2 | 4/2010 | |
| WO | WO-2013059373 A2 | 4/2013 | |
| WO | WO-2013157102 A1 | 10/2013 | |
| WO | WO-2014018679 A2 | 1/2014 | |
| WO | WO-2014028668 A2 | 2/2014 | |
| WO | WO-2014055657 A1 | 4/2014 | |
| WO | WO-2014079000 A1 * | 5/2014 | ............ A61P 31/04 |
| WO | WO-2014130741 A2 | 8/2014 | |
| WO | WO-2015009740 A2 | 1/2015 | |
| WO | WO-2015157322 A2 | 10/2015 | |
| WO | WO-2016008973 A1 * | 1/2016 | ......... C07K 14/7051 |
| WO | WO-2016130726 A1 | 8/2016 | |

OTHER PUBLICATIONS

Jain et al. (Blood Jun. 5, 2015, 126(3): 354-362) (Year: 2015).*
Kufe DW (Cancer Biology & Therapy Jul. 1, 2009, 8 (13): 1197-1203) (Year: 2009).*
Aboud-Pirak et al. Inhibition of human tumor growth in nude mice by a conjugate of doxorubicin with monoclonal antibodies to epidermal growth factor receptor. PNAS USA 86(10):3778-81 (1989).
Bachmann et al., Recall proliferation potential of memory CD8+ T cells and antiviral protection. J Immunol. 175(7):4677-4685 (2005).
Baeckstrom et al., Purification and characterization of a membrane-bound and a secreted mucin-type glycoprotein carrying the carcinoma-associated sialyl-Lea epitope on distinct core proteins. J Biol Chem. 266(32):21537-21547 (1991).
Baeuerle et al. Bispecific T-cell engaging antibodies for cancer therapy. Cancer Res 69:4941-4944 (2009).
Baker et al., Humanization of an anti-mucin antibody for breast and ovarian cancer therapy. Adv Exp Med Biol. 353:61-82 (1994).
Bakhtiari et al. Anti-MUC1 nanobody can redirect T-body cytotoxic effector function. Hybridoma (Larchmt). 28(2):85-92 (2009).
Baldus et al., Correlation of the immunohistochemical reactivity of mucin peptide cores MUC1 and MUC2 with the histopathological subtype and prognosis of gastric carcinomas. Int J Cancer 79(2):133-138 (1998).
Blockzjil et al., Epitope characterization of MUC1 antibodies. Tumour Biol. 19 Suppl 1:46-56 (1998).
Bortoletto et al. Optimizing anti-CD3 affinity for effective T cell targeting against tumor cells. Eur J Immunol 32:3102-3107 (2002).
Brand et al. Prospect for Anti-HER2 Receptor Therapy in Breast Cancer. Anticancer Research 26(1B):463-470 (2006).
Bruenke et al. Effective lysis of lymphoma cells with a stabilized bispecific single-chain Fv antibody against CD19 and FcgammaRIII (CD16). Br J Haematol. 130(2):218-28 (2005).
Brugger et al., Expression of MUC-1 epitopes on normal bone marrow: implications for the detection of micrometastatic tumor cells. J Clin Oncol. 17(5):1535-1544 (1999).
Burgess et al. Possible dissociation of the heparin-binding and mitogenic activities of heparin-binding (acidic fibroblast) growth factor-1 from its receptor-binding activities by site-directed mutagenesis of a single lysine residue. J Cell Biol. 111:2129-2138 (1990).
Byrd et al., Deglycosylation of mucin from LS174T colon cancer cells by hydrogen fluoride treatment. Biochem J. 261(2):617-625 (1989).
Cao et al. Construction and characterization of an enhanced GFP-tagged anti-BAFF scFv antibody. Appl Microbiol Biotechnol. 79(3):423-31 (2008).
Chames et al. Bispecific Antibodies for Cancer Therapy. Curr Opin Drug Discov Devel. 12(2):276-83 (2009).
Chen et al., Labeling of proteins with [35S]methionine and/or [35S]cysteine in the absence of cells. Anal Biochem. 269(1):179-188 (1999).
Czajkowsky, et al. Fc-fusion proteins: new developments and future perspectives. EMBO Mol Med. Oct. 2012; 4(10): 1015-1028. Published online Jul. 26, 2012 . . . .
Dai et al. Chimeric Antigen Receptors Modified T-Cells for Cancer Therapy. J Natl Cancer Inst. 108(7):djv439 (2016).
Devine et al., Expression of MUC1 and MUC2 mucins by human tumor cell lines. Tumour Biol. 13(5-6):268-277 (1992).
Efferson et al., Stimulation of human T cells by an influenza A vector expressing a CTL epitope from the HER-2/neu protooncogene results in higher numbers of antigen-specific TCRhi cells than stimulation with peptide. Divergent roles of IL-2 and IL-15. Anticancer Res. 25(2A):715-724 (2005).
Ellison et al. Linkage and sequence homology of two human immunoglobulin γ heavy chain constant region genes. Proc. Nat. Acad. Sci. 79:1984-1988 (1982).
Fessler et al. MUC1 is a determinant of trastuzumab (Herceptin) resistance in breast cancer cells. Breast Cancer Res Treat 118:113-134 (2009).
Finlay et al. Affinity maturation of a humanized rat antibody for anti-RAGE therapy: comprehensive mutagenesis reveals a high level of mutational plasticity both inside and outside the complementarity-determining regions. J Mol Biol. 388(3):541-58 (2009).
Fraley et al. New generation liposomes: the engineering of an efficient vehicle for intracellular delivery of nucleic acids. Trends Biochem. Sci. 6:77 (1981).
Gendler, et al. Molecular cloning and expression of human tumor-associated polymorphic epithelial mucin. J Biol Chem. 265:15286-15293 (1990).
Girling et al., A core protein epitope of the polymorphic epithelial mucin detected by the monoclonal antibody SM-3 is selectively exposed in a range of primary carcinomas. Int J Cancer 43(6):1072-1076 (1989).
Gottlieb et al., The covalent structure of a human gamma G-immunoglobulin. VI. Amino acid sequence of the light chain. Biochemistry 9(16):3155-3161 (1970).
Gregoriadis. Liposomes for drugs and vaccines. Trends in Biotechnology 3:235-241 (1985).

(56) References Cited

OTHER PUBLICATIONS

Hartman et al., MUC1 isoform specific monoclonal antibody 6E6/2 detects preferential expression of the novel MUC1/Y protein in breast and ovarian cancer. Int J Cancer 82(2):256-267 (1999).
Hartsough M., Nm23/nucleoside diphosphate kinase in human cancers. J Bioenerg Biomembr. 32(3):301-308 (2000).
Hieken et al., Beta3 integrin expression in melanoma predicts subsequent metastasis. J Surg Res. 63(1):169-173 (1996).
Hikita et al. MUC1 Mediates the Growth of Human Pluripotent Stem Cells. PLoS One 3(10):1-13 (2008).
Holliger et al. "Diabodies": small bivalent and bispecific antibody fragments. PNAS USA 90(14):6444-6448 (1993).
Hombach et al. 0X40 costimulation by a chimericantigen receptor abrogates CD28 and IL-2 induced IL-10 secretion by redirectedCD4(+) T cells. Oncoimmunology 1(4):458-466 (2012).
Horton. The aV133 integrin vitronectin receptor. Int Biochem Cell Biol 29:721 (1997).
Hurwitz et al. The Covalent Binding of Daunomycin and Adriamycin to Antibodies, with Retention of Both Drug and Antibody Activities. Cancer Res 35:1175-1181 (1975).
Ikezoe et al., A novel treatment strategy targeting Aurora kinases in acute myelogenous leukemia. Mol Cancer Ther. 6(6):1851-1857 (2007).
ImmunoGlobe GmbH, The art of selecting an epitope. pp. 1-3 https://www.immunoglobe.com/epitope-selection.html (2011).
Iri-Sofla et al. Nanobody-based chimeric receptor gene integration in Jurkat cells mediated by φC31 integrase. Exp Cell Res 317(18):2630-2641 (2011).
Jakobovits et al. From XenoMouse technoloby to panitumumab, the first fully human antibody product from transgenic mice. Nat Biotechnol. 25(10):1134-43 (2007).
Johansson et al. Efficient expression of recombinant human monoclonal antibodies in *Drosophila* S2 cells. J Immunol Methods 318(1-2):37-46 (2007).
Juarez-Gonzalez et al Directed Evolution, Phage Display and Combination of Evolved Mutants: A Strategy to Recover the Neutralization Properties of the scFv Version of BCF2 a Neutralizing Monoclonal Antibody Specific to Scorpion Toxin Cn2). J Mol Biol. 346(5):1287-97 (2005).
Katayose et al., MUC1-specific targeting immunotherapy with bispecific antibodies: inhibition of xenografted human bile duct carcinoma growth. Cancer Res. 56(18):4205-4212 (1996).
Kettleborough et al. Optimization of primers for cloning libraries of mouse immunoglobulin genes using the polymerase chain reaction. Eur. J. Immunol. 23:206-211 (1993).
Kowolik et al. CD28 costimulation provided through a CD19-specific chimeric antigen receptor enhances in vivo persistence and antitumor efficacy of adoptively transferred T cells. Cancer Res 66(22):10995-11004 (2006).
Kufe, et al. Differential reactivity of a novel monoclonal antibody (DF3) with human malignant versus benign breast tumors. Hybridoma 3:223-232 (1984).
Lan et al., Cloning and sequencing of a human pancreatic tumor mucin cDNA. J Biol Chem. 265(25):15294-15299 (1990).
Lazar et al. Transforming growth factor alpha: mutation of aspartic acid 47 and leucine 48 results in different biological activities. Mol Cell Biol. 8:1247-1252 (1988).
Ligtenberg et al., Cell-associated episialin is a complex containing two proteins derived from a common precursor. J Biol Chem. 267(9):6171-6177 (1992).
Lonberg et al., Human antibodies from transgenic animals. Nature Biotechnology 23(9):1117-1125 (2005).
Loskog et al. Addition of the CD28 signaling domain to chimeric T-cell receptors enhances chimeric T-cell resistance to T regulatory cells. Leukemia 20(10):1819-1828 (2006).
Lu et al. Simultaneous Blockade of Both the Epidermal Growth Factor Receptor and the Insulin-like Growth Factor Receptor Signaling Pathways in Cancer Cells with a Fully Human Recombinant Bispecific Antibody. J Biol Chem. 279(4):2856-65 (2004).
Lyman G., A comparison of international guidelines for the prevention of chemotherapy-induced neutropenia. Curr Opin Hematol. 18(1):1-10 (2011).
Ma et al., Specific cytotoxicity of MUC1 chimeric antigen receptor-engineered Jurkat T cells against hepatocellular carcinoma. Academic Journal of Second Military Medical University 35(11):1177-1182 (2014).
Mahanta et al. A Minimal Fragment of MUCI Mediates Growth of Cancer Cells. PLoS One 3(4):e2054 (2008).
Maher et al., CAR mechanics: driving T cells into the MUC of cancer. Cancer Res. 69(11):4559-4562 (2009).
Majors et al. MC1-1 overexpression leads to higher viabilities and increased production of humanized monoclonal antibody in Chinese hamster ovary cells. Biotechnol Prog. Jul.-Aug. 2009;25(4):1161-8.
Mao et al., Loss of nm23 expression predicts distal metastases and poorer survival for breast cancer. Int J Oncol. 18(3):587-591 (2001).
Mazor et al., Humanization and epitope mapping of the H23 anti-MUC1 monoclonal antibody reveals a dual epitope specificity. Mol Immunol. 42(1):55-69 (2005).
McCall et al. Isolation and characterization of an anti-CD16 single-chain Fv fragment and construction of an anti-HER2/neu/anti-CD16 bispecific scFv that triggers CD16-dependent tumor cytolysis Mol Immunol. 36(7):433-46 (1999).
McCarron et al. Antibody Conjugates and Therapeutic Strategies. Mol Interv 5:368-380 (2005).
Meerzaman et al., Involvement of the MAP kinase ERK2 in MUC1 mucin signaling. Am J Physiol Lung Cell Mol Physiol. 281(1):L86-L91 (2001).
Milone et al. Chimeric receptors containing CD137 signal transduction domains mediate enhanced survival of T cells and increased antileukemic efficacy in vivo. Mol Ther 17(8):1453-1464 (2009).
Morrison. Cloning, expression, and modification of antibody V regions. Curr Protoc Immunol Chapter 2:Unit 2.12 (2002).
Muller et al., Localization of O-glycosylation sites on glycopeptide fragments from lactation-associated MUC1. All putative sites within the tandem repeat are glycosylation targets in vivo. J Biol Chem. 272(40):24780-24793 (1997).
Muzard J et al. Design and humanization of a murine scFv that blocks human platelet glycoprotein VI in vitro. FEBS J. 276(15):4207-22 (2009).
Nahary et al. Design of a human synthetic combinatorial library of single-chain antibodies. Methods Mol Biol 525:61-80 (2009).
Paterson et al., Variation in IgG1 heavy chain allotype does not contribute to differences in biological activity of two human anti-Rhesus (D) monoclonal antibodies. Immunotechnology 4(1):37-47 (1998).
PCT/US2016/017422 International Search Report and Written Opinion dated Jul. 26, 2016.
Pegram et al., Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. J Clin Oncol. 16(8):2659-2671 (1998).
Pemberton et al., Antibodies to the cytoplasmic domain of the MUC1 mucin show conservation throughout mammals. J.Biochem Biophys Res Commun. 185(1):167-175 (1992).
Pemberton et al., The epithelial mucin MUC1 contains at least two discrete signals specifying membrane localization in cells. J Biol Chem. 271(4):2332-2340 (1996).
Pilkington et al., Recombinant human Fab antibody fragments to HIV-1 Rev and Tat regulatory proteins: direct selection from a combinatorial phage display library. Mol Immunol. 33(4-5):439-450 (1996).
Pule et al. A chimeric T cell antigen receptor that augments cytokine release and supports clonal expansion of primary human T cells. Mol Ther 12(5):933-941 (2005).
Razai et al. Molecular evolution of antibody affinity for sensitive detection of botulinum neurotoxin type A. J Mol Biol. 351(1):158-69 (2005).
Robinson et al. Targeting ErbB2 and ErbB3 with a bispecific single-chain Fv enhances targeting specificity and induces a therapeutic effect in vitro. Br J Cancer 99(9):1415-25 (2008).

(56) References Cited

OTHER PUBLICATIONS

Ross et al., The HER-2/neu oncogene in breast cancer: prognostic factor, predictive factor, and target for therapy. Stem Cells 16(6):413-428 (1998).
Salek et al., Quantitative phosphoproteome analysis unveils LAT as a modulator of CD3ζ and ZAP-70 tyrosine phosphorylation. PLoS One 8(10):e77423 [1-9] (2013).
Sawhney, et al. Bioerodible hydrogels based on photopolymerized poly(ethylene glycol)-co-poly(.alpha.-hydroxy acid) diacrylate macromers. Macromolecules 26(4):581-587 (1993).
Schneider et al., nm23 expression in advanced and borderline ovarian carcinoma. Anticancer Res. 16(3A):1197-1202 (1996).
Skolnick, et al. From genes to protein structure and function: novel applications of computational approaches in the genomic era. Trends Biotechnol. Jan. 2000;18(1):34-9.
Song et al. In Vivo Persistence, Tumor Localization, and Antitumor Activity of CAR-Engineered T Cells Is Enhanced by Costimulatory Signaling through CD137 (4-1BB). Cancer Res 71(13):4617-4627 (2011).
Spicer et al. Molecular cloning and analysis of the mouse homologue of the tumor-associated mucin, MUC1, reveals conservation of potential O-glycosylation sites, transmembrane, and cytoplasmic domains and a loss of minisatellite-like polymorphism. J. Biol. Chem 266(23):15099—15109 (1991).
Strausberg, et al. Generation and initial analysis of more than 15,000 full-length human and mouse cDNA sequences. Proc Natl Acad Sci U S A. Dec. 24, 2002;99(26):16899-903. Epub Dec. 11, 2002.
Strome et al. A mechanistic perspective of monoclonal antibodies in cancer therapy beyond target-related effects. The Oncologist 12:1084-95 (2007).
Treon et al., Muc-1 core protein is expressed on multiple myeloma cells and is induced by dexamethasone. Blood 93(4):1287-1298 (1999).
U.S. Appl. No. 15/549,942 Office Action dated Apr. 10, 2019.
U.S. Appl. No. 15/549,942 Office Action dated Aug. 26, 2020.
U.S. Appl. No. 15/549,942 Office Action dated Dec. 18, 2019.
U.S. Appl. No. 15/549,942 Office Action dated Jan. 10, 2022.
U.S. Appl. No. 15/549,942 Office Action dated Jun. 27, 2022.
U.S. Appl. No. 15/549,942 Office Action dated Mar. 19, 2021.
U.S. Appl. No. 15/549,942 Restriction Requirement dated Dec. 12, 2018.
U.S. Appl. No. 16/539,247 Office Action dated Jun. 1, 2022.
U.S. Appl. No. 16/539,247 Terminal Disclaimer filed Aug. 30, 2022.
Vailhe et al. In vitro angiogenesis is modulated by the mechanical properties of fibrin gels and is related to alpha(v)beta3 integrin localization. In Vitro Cell Dev Biol Anim. 33:763-73 (1997).
Varner et al., Integrins and cancer. Curr Opin Cell Biol. 8:724 (1996).
Wang et al. Universal PCR amplification of mouse immunoglobulin gene variable regions: The design of degenerate primers and an assessment of the effect of DNA polymerase 3' to 5' exonuclease activity. J. Immunol. Methods 233:167-177 (2000).
Wheeler C., Preventive vaccines for cervical cancer. Salud Publica Mex. 39(4):283-287 (1997).
Wilkie et al., Retargeting of human T cells to tumor-associated MUC1: the evolution of a chimeric antigen receptor. J Immunol. 180(7):4901-4909 (2008).
Wilkinson et al., Monovalent IgG4 molecules: immunoglobulin Fc mutations that result in a monomeric structure. MAbs 5(3):406-417 (2013).
Xiong et al. Development of tumor targeting anti-MUC-1 multimer: effects of di-scFv unpaired cysteine location on PEGylation and tumor binding. Protein Eng Des Sel 19(8):359-367 (2006).
Yang et al., Identification of glycosylated 38-kDa connective tissue growth factor (IGFBP-related protein 2) and proteolytic fragments in human biological fluids, and up-regulation of IGFBP-rP2 expression by TGF-beta in Hs578T human breast cancer cells. J Clin Endocrinol Metab. 83(7):2593-2596 (1998).
Yonezawa et al., Differential mucin gene expression in human pancreatic and colon cancer cells. Biochem J. 276(Pt 3):599-605 (1991).
MacIan. NFAT Proteins: Key Regulators of T-Cell Development and Function. Nat. Rev. Immunol. 5(6):472-84 (2005).
Panka et al. Variable region framework differences result in decreased or increased affinity of variant anti-digoxin antibodies. PNAS USA 85:3080-3084 (1988).
Rudikoff et al. Single amino acid substitution altering antigen-binding specificity. Proc Natl Acad Sci U S A. 79(6):1979-83 (1982).
U.S. Appl. No. 15/549,942 Office Action dated Jan. 11, 2023.
U.S. Appl. No. 17/817,515 Office Action dated Apr. 26, 2023.
U.S. Appl. No. 17/817,515 Office Action dated Jan. 10, 2023.

\* cited by examiner

Figure 25. Humanized MN-E6 scFv inhibits growth of MUC1* positive cancer cells in a concentration dependent manner; shown are 1500 MUC1* + breast cancer cells

HUMANIZED ANTI-MUC1* ANTIBODIES

CROSS-REFERENCE TO RELATED APPLICATIONS

This application is a continuation of U.S. patent application Ser. No. 15/549,942, filed Aug. 9, 2017, which is a national stage entry of International Application No. PCT/US2016/017422, filed Feb. 10, 2016, which claims the benefit of U.S. Provisional Application No. 62/114,526, filed Feb. 10, 2015, which applications are incorporated herein by reference in their entirety.

SEQUENCE LISTING

The instant application contains a Sequence Listing which has been submitted electronically in XML format and is hereby incorporated by reference in its entirety. Said XML copy, created on Aug. 3, 2022, is named 56699-731_302SL.xml and is 993,008 bytes in size.

BACKGROUND OF THE INVENTION

1. Field of the Invention

The present application relates to humanized anti-MUC1* antibodies and methods of making and using them.

2. General Background and State of the Art

We previously discovered that a cleaved form of the MUC1 (SEQ ID NO:1) transmembrane protein is a growth factor receptor that drives the growth of over 75% of all human cancers. The cleaved form of MUC1, which we called MUC1* (pronounced muk 1 star), is a powerful growth factor receptor. Cleavage and release of the bulk of the extracellular domain of MUC1 unmasks a binding site for activating ligands dimeric NME1, NME6 or NME7. It is an ideal target for cancer drugs as it is aberrantly expressed on over 75% of all cancers and is likely overexpressed on an even higher percentage of metastatic cancers (Fessler S P, Wotkowicz M T, Mahanta S K and Bamdad C. (2009). MUC1* is a determinant of trastuzumab (Herceptin) resistance in breast cancer cells. Breast Cancer Res Treat. 118(1):113-124). After MUC1 cleavage most of its extracellular domain is shed from the cell surface. The remaining portion has a truncated extracellular domain that at least comprises the primary growth factor receptor sequence, PSMGFR (SEQ ID NO:2).

Antibodies are increasingly used to treat human diseases. Antibodies generated in non-human species have historically been used as therapeutics in humans, such as horse antibodies. More recently, antibodies are engineered or selected so that they contain mostly human sequences in order to avoid a generalized rejection of the foreign antibody. The process of engineering recognition fragments of a non-human antibody into a human antibody is generally called 'humanizing'. The amount of non-human sequences that are used to replace the human antibody sequences determines whether they are called chimeric, humanized or fully human.

Alternative technologies exist that enable generation of humanized or fully human antibodies. These strategies involve screening libraries of human antibodies or antibody fragments and identifying those that bind to the target antigen, rather than immunizing an animal with the antigen. Another approach is to engineer the variable region(s) of an antibody into an antibody-like molecule. The present invention is intended to also encompass these approaches for use with recognition fragments of antibodies that the inventors have determined bind to the extracellular domain of MUC1*.

In addition to treating patients with an antibody, cancer immunotherapies have recently been shown to be effective in the treatment of cancers. T-cell based cancer immunotherapy is an attractive approach to overcome the cancer cells evasion from the immune system. A first immunotherapy, called CAR T (chimeric antigen receptor T cell) therapy relies on the expression of a CAR on the surface of the patient T cells for adoptive T-cell therapy (Dai H, Wang Y, Lu X, Han W. (2016) Chimeric Antigen Receptors Modified T-Cells for Cancer Therapy. J Natl Cancer Inst. 108(7): djv439). Such receptor is composed of an anti cancer scFv linked to a T cell transmembrane and signaling domains. Upon binding of the receptor to a cancer associated antigen, a signal is transmitted resulting in T-cell activation, propagation and the targeted killing of the cancer cells. In practice, a patient's T cells are isolated and transduced with a CAR, expanded and then injected back into the patient. When the patient's CAR T cells bind to the antigen on a cancer cell, the CAR T cells expand and attack the cancer cells. A drawback of this method is the risk of activating the patient's immune system to destroy cells bearing the target antigen, when most cancer antigens are expressed on some healthy tissues, but overexpressed on cancerous tissues. To minimize the risk of off-tumor/on-target effects, the cancer antigen should be minimally expressed on healthy tissues.

A second cancer immunotherapy involves BiTEs (Bispecific T cell Engagers). The BiTE approach attempts to eliminate the CAR T associated risk of off-tumor/on-target effects. Unlike CAR T, BiTEs are bispecific antibodies that should not pose any greater risk than regular antibody-based therapies. However, unlike typical anti-cancer antibodies that bind to and block a cancer antigen, BiTEs are designed to bind to an antigen on the tumor cell and simultaneously bind to an antigen on an immune cell, such as a T cell. In this way, a BiTE recruits the T cell to the tumor. BiTEs are engineered proteins that simultaneously bind to a cancer associated antigen and a T-cell surface protein such as CD3-epsilon. BiTEs are antibodies made by genetically linking the scFv's of an antibody that binds to a T cell antigen, like anti-CD3-epsilon to a scFv of a therapeutic monoclonal antibody that binds to a cancer antigen (Patrick A. Baeuerle, and Carsten Reinhardt (2009) Bispecific T-cell engaging antibodies for cancer therapy. Cancer Res. 69(12): 4941-4944).

SUMMARY OF THE INVENTION

In one aspect, the present invention is directed to a human or humanized anti-MUC1* antibody or antibody fragment or antibody-like protein that binds to a region on extracellular domain of MUC1 isoform or cleavage product that is devoid of the tandem repeat domains. The human or humanized anti-MUC1* antibody or antibody fragment or antibody-like protein may specifically bind to
  (i) PSMGFR region of MUC1;
  (ii) PSMGFR peptide;
  (iii) a peptide having amino acid sequence of SNIKFRPGSVVVQLTLAFREGTINVHD-VETQFNQYKTEAASRY (SEQ ID NO:620);

(iv) a peptide having amino acid sequence of SVVVQLT-LAFREGTINVHDVETQFNQYKTEAASRY (SEQ ID NO:621);
(v) a peptide having amino acid sequence of VQLT-LAFREGTINVHDVETQFNQY (SEQ ID NO:622); or
(vi) a peptide having amino acid sequence of SNIKFRPGSVVVQLTLAFREGTIN (SEQ ID NO:623).

The human or humanized antibody may be IgG1, IgG2, IgG3, IgG4 or IgM. The human or humanized antibody fragment or antibody-like protein may be scFv or scFv-Fc.

The human or humanized antibody, antibody fragment or antibody-like protein as in above may comprise a heavy chain variable region and light chain variable region which is derived from mouse monoclonal MN-E6 antibody, and has at least 80%, 90% or 95% or 98% sequence identity to the mouse monoclonal MN-E6 antibody. The heavy chain variable region may have at least 90% or 95% or 98% sequence identity to SEQ ID NO:13 and the light chain variable region may have at least 90% or 95% or 98% sequence identity to SEQ ID NO:66.

The human or humanized antibody, antibody fragment or antibody-like protein according to above may include complementarity determining regions (CDRs) in the heavy chain variable region and light chain variable region having at least 90% or 95% or 98% sequence identity to CDR1, CDR2 or CDR3 regions having sequence as follows:
CDR1 heavy chain SEQ ID NO:17
CDR1 light chain SEQ ID NO:70,
CDR2 heavy chain SEQ ID NO:21
CDR2 light chain SEQ ID NO:74,
CDR3 heavy chain SEQ ID NO:25
CDR3 light chain SEQ ID NO:78.

The human or humanized antibody, antibody fragment or antibody-like protein described above may include a heavy chain variable region and light chain variable region which is derived from mouse monoclonal MN-C2 antibody, and has at least 80%, 90% or 95% or 98% sequence identity to the mouse monoclonal MN-C2 antibody. The heavy chain variable region may have at least 90% or 95% or 98% sequence identity to SEQ ID NO:119 and the light chain variable region has at least 90% or 95% or 98% sequence identity to SEQ ID NO:169. The complementarity determining regions (CDRs) in the heavy chain variable region and light chain variable region may have at least 90% or 95% or 98% sequence identity to CDR1, CDR2 or CDR3 regions having sequence as follows:
CDR1 heavy chain SEQ ID NO:123
CDR1 light chain SEQ ID NO:173,
CDR2 heavy chain SEQ ID NO:127
CDR2 light chain SEQ ID NO:177,
CDR3 heavy chain SEQ ID NO:131
CDR3 light chain SEQ ID NO:181.

The human or humanized antibody, antibody fragment or antibody-like protein as in above may include a heavy chain variable region and light chain variable region which is derived from mouse monoclonal MN-C3 antibody, and may have at least 80%, 90% or 95% or 98% sequence identity to the mouse monoclonal MN-C3 antibody. The heavy chain variable region may have at least 90% or 95% or 98% sequence identity to SEQ ID NO:414 and the light chain variable region may have at least 90% or 95% or 98% sequence identity to SEQ ID NO:459. The complementarity determining regions (CDRs) in the heavy chain variable region and light chain variable region may have at least 90% or 95% or 98% sequence identity to CDR1, CDR2 or CDR3 regions having sequence as follows:
CDR1 heavy chain SEQ ID NO:418
CDR1 light chain SEQ ID NO:463,
CDR2 heavy chain SEQ ID NO:422
CDR2 light chain SEQ ID NO:467,
CDR3 heavy chain SEQ ID NO:426,
CDR3 light chain SEQ ID NO:471.

The human or humanized antibody, antibody fragment or antibody-like protein described above may include a heavy chain variable region and light chain variable region which is derived from mouse monoclonal MN-C8 antibody, and has at least 80%, 90% or 95% or 98% sequence identity to the mouse monoclonal MN-C8 antibody. The heavy chain variable region may have at least 90% or 95% or 98% sequence identity to SEQ ID NO:506 and the light chain variable region may have at least 90% or 95% or 98% sequence identity to SEQ ID NO:544. The complementarity determining regions (CDRs) in the heavy chain variable region and light chain variable region may have at least 90% or 95% or 98% sequence identity to CDR1, CDR2 or CDR3 regions having sequence as follows:
CDR1 heavy chain SEQ ID NO:508
CDR1 light chain SEQ ID NO:546,
CDR2 heavy chain SEQ ID NO:510
CDR2 light chain SEQ ID NO:548,
CDR3 heavy chain SEQ ID NO:512,
CDR3 light chain SEQ ID NO:550.

In another aspect, the present invention is directed to an anti-MUC1* extracellular domain antibody comprised of sequences of a humanized MN-E6 represented by humanized IgG2 heavy chain, or humanized IgG1 heavy chain, paired with humanized Kappa light chain, or humanized Lambda light chain. The humanized IgG2 heavy chain may be SEQ ID NOS:53, humanized IgG1 heavy chain may be SEQ ID NO:57, humanized Kappa light chain may be SEQ ID NO:108, and humanized Lambda light chain may be SEQ ID NO:112, or a sequence having 90%, 95% or 98% sequence identity thereof.

In another aspect, the invention is directed to an anti-MUC1* extracellular domain antibody comprised of sequences of a humanized MN-C2 represented by humanized IgG1 heavy chain, humanized IgG2 heavy chain, paired with humanized Lambda light chain, and humanized Kappa light chain. The humanized IgG1 heavy chain MN-C2 may be SEQ ID NOS:159 or IgG2 heavy chain may be SEQ ID NOS:164 paired with Lambda light chain (SEQ ID NO:219) or Kappa light chain (SEQ ID NO:213), or a sequence having 90%, 95% or 98% sequence identity thereof.

In another aspect, the invention is directed to an anti-MUC1* extracellular domain antibody comprised of sequences of a humanized MN-C3 represented by humanized IgG1 heavy chain or humanized IgG2 heavy chain paired with humanized Lambda light chain or humanized Kappa light chain. The humanized MN-C3 IgG1 heavy chain may be SEQ ID NOS:454, IgG2 heavy chain may be SEQ ID NOS:456, Lambda light chain may be SEQ ID NO:501, and Kappa light chain may be SEQ ID NO:503, or a sequence having 90%, 95% or 98% sequence identity thereof.

In another aspect, the invention is directed to an anti-MUC1* extracellular domain antibody comprised of sequences of a humanized MN-C8 represented by humanized IgG1 heavy chain or humanized IgG2 heavy chain paired with humanized Lambda light chain or humanized Kappa light chain. The humanized MN-C8 IgG1 heavy chain may be SEQ ID NOS:540, IgG2 heavy chain may be SEQ ID NOS:542, Lambda light chain may be SEQ ID NO:580 and Kappa light chain may be SEQ ID NO:582, or a sequence having 90%, 95% or 98% sequence identity thereof.

In another aspect, the invention is directed to a human or humanized anti-MUC1* antibody or antibody fragment or antibody-like protein according to above, which inhibits the binding of NME protein to MUC1*. The NME may be NME1, NME6, NME7AB, NME7 or NME8.

In yet another aspect, the invention is directed to a single chain variable fragment (scFv) comprising a heavy and light chain variable regions connected via a linker, further comprising CDRs of antibodies that bind to MUC1* extracellular domain. The CDRs may be derived from MN-E6, MN-C2, MN-C3 or MN-C8 antibodies or humanized antibodies thereof. The scFv may be one that possesses the SEQ ID NOS:233, 235 and 237 (E6); SEQ ID NOS:239, 241, and 243 (C2); SEQ ID NOS:245, 247, and 249 (C3); or SEQ ID NOS:251, 253, and 255 (C8).

In still another aspect, the invention is directed to a chimeric antigen receptor (CAR) comprising a scFv or a humanized variable region that binds to the extracellular domain of a MUC1 that is devoid of tandem repeats, a linker molecule, a transmembrane domain and a cytoplasmic domain. The single chain antibody fragment may bind to
(i) PSMGFR region of MUC1,
(ii) PSMGFR peptide,
(iii) a peptide having amino acid sequence SNIKFRPGSVVVQLTLAFREGTINVHDVETQFNQYKTEAASRY (SEQ ID NO:620);
(iv) a peptide having amino acid sequence of SVVVQLTLAFREGTINVHDVETQFNQYKTEAASRY (SEQ ID NO:621);
(v) a peptide having amino acid sequence of VQLTLAFREGTINVHDVETQFNQY (SEQ ID NO:622); or
(vi) a peptide having amino acid sequence of SNIKFRPGSVVVQLTLAFREGTIN (SEQ ID NO:623).

In the CAR as describe above, portions of any of the variable regions set forth and described above, or combination thereof may be used in the extracellular domain, a transmembrane region and a cytoplasmic tail that comprises sequence motifs that signal immune system activation. The extracellular domain may be comprised of humanized single chain antibody fragments of an MN-E6 scFv, MN-C2 scFv, MN-C3 scFv or MN-C8 scFv.

In the CAR as described above, the extracellular domain include humanized single chain antibody fragments of an MN-E6 scFv set forth as SEQ ID NOS: 233, 235, or 237), MN-C2 scFv (SEQ ID NOS:239, 241, or 243), MN-C3 scFv (SEQ ID NOS: 245, 247, or 249) or MN-C8 scFv (SEQ ID NOS:251, 253, or 255).

In any of the CAR described above, the cytoplasmic tail may be comprised of one or more of signaling sequence motifs CD3-zeta, CD27, CD28, 4-1BB, OX40, CD30, CD40, PD-1, ICAm-1, LFA-1, ICOS, CD2, CD5, or CD7.

In any of the CAR described above, the sequence may be CARMN-E6 CD3z (SEQ ID NOS:295), CARMN-E6 CD28/CD3z (SEQ ID NOS:298); CARMN-E6 4-1BB/CD3z (SEQ ID NOS:301); CARMN-E6 OX40/CD3z (SEQ ID NOS:617); CARMN-E6 CD28/4-1BB/CD3z (SEQ ID NOS:304); CARMN-E6 CD28/OX40/CD3z (SEQ ID NOS: 619); CAR MN-C2 CD3z (SEQ ID NOS:607); CAR MN-C2 CD28/CD3z (SEQ ID NOS:609); CAR MN-C2 4-1BB/CD3z (SEQ ID NOS:611); CAR MN-C2 OX40/CD3z (SEQ ID NOS:613); CAR MN-C2 CD28/4-1BB/CD3z (SEQ ID NOS:307); or CAR MN-C2 CD28/OX40/CD3z (SEQ ID NOS:615).

In another aspect, the CAR may have an extracellular domain unit that recognizes a peptide. The peptide may be PSMGFR (SEQ ID NO:2). The peptide may be a peptide derived from NME7. The peptide may be

```
NME7A peptide 1 (A domain):
                                    (SEQ ID NO: 7)
MLSRKEALDFHVDHQS;

NME7A peptide 2 (A domain):
                                    (SEQ ID NO: 8)
SGVARTDASES;

NME7B peptide 1 (B domain):
                                    (SEQ ID NO: 9)
DAGFEISAMQMFNMDRVNVE;

NME7B peptide 2 (B domain):
                                    (SEQ ID NO: 10)
EVYKGVVTEYHDMVTE;
or NME7B peptide 3 (B domain):
                                    (SEQ ID NO: 11)
AIFGKTKIQNAVHCTDLPEDGLLEVQYFF.
```

In another aspect, the invention is directed a composition that includes at least two CARs with different extracellular domain units transfected into the same cell.

The at least two CARs may have one CAR that does not have a targeting recognition unit and the other CAR does have a targeting recognition unit. Or, one of the extracellular domain recognition units may bind to MUC1* extracellular domain. Or, one of the extracellular domain recognition units may bind PD-1. Or, one of the extracellular domain recognition units is an antibody fragment and the other is a peptide. Or, one is an anti-MUC1* scFv chosen from the group consisting of scFv of MN-E6 antibody, scFv of MN-C2 antibody, scFv of MN-C3 antibody or scFv of MN-C8 antibody and the other is a peptide derived from NME7 or chosen from the group consisting of

```
NME7A peptide 1 (A domain):
                                    (SEQ ID NO: 7)
MLSRKEALDFHVDHQS;

NME7A peptide 2 (A domain):
                                    (SEQ ID NO: 8)
SGVARTDASES;

NME7B peptide 1 (B domain):
                                    (SEQ ID NO: 9)
DAGFEISAMQMFNMDRVNVE;

NME7B peptide 2 (B domain):
                                    (SEQ ID NO: 10)
EVYKGVVTEYHDMVTE;
and NME7B peptide 3 (B domain):
                                    (SEQ ID NO: 11)
AIFGKTKIQNAVHCTDLPEDGLLEVQYFF.
```

In another aspect, the invention is directed to a cell comprising a CAR with an extracellular domain that binds to MUC1* transfected or transduced cell. The cell that includes the CAR may be an immune system cell, preferably a T cell or dendritic cell or mast cell.

In another aspect, the invention is directed to an engineered antibody-like protein.

In another aspect, the invention is directed to a method of screening a library of antibodies or antibody fragments that are human, for those that bind to (i) PSMGFR peptide;
(ii) a peptide having amino acid sequence SNIKFRPGSVVVQLTLAFREGTINVHD-VETQFNQYKTEAASRY (SEQ ID NO:620);
(iii) a peptide having amino acid sequence of SVVVQLT-LAFREGTINVHDVETQFNQYKTEAASRY (SEQ ID NO:621);
(iv) a peptide having amino acid sequence of VQLT-LAFREGTINVHDVETQFNQY (SEQ ID NO:622);
(v) a peptide having amino acid sequence of SNIKFRPGSVVVQLTLAFREGTIN (SEQ ID NO:623);
(vi) NME7 protein; or
(vii) a peptide fragment of NME7 protein.

In another aspect, the invention is directed to a method for treating a disease in a subject comprising administering an antibody according to any claim above, to a person suffering from the disease, wherein the subject expresses MUC1 aberrantly. The disease may be cancer, such as breast cancer, lung cancer, colon cancer, gastric cancer.

In another aspect, the invention is directed to a method for treating a disease in a subject comprising administering an NME peptide, to a person suffering from the disease, wherein the subject expresses MUC1 aberrantly.

In another aspect, the invention is directed to a method of proliferating or expanding stem cell population comprising contacting the cells with the antibody according to any method or composition described above.

In another aspect, the invention is directed to a method of facilitating stem cell attachment to a surface comprising coating the surface with a humanized MN-C3 or MN-C8 antibody, antibody fragment or single chain antibody thereof and contacting stem cell to the surface.

In another aspect, the invention is directed to a method of delivering stem cell in vitro or in vivo comprising the steps of coating a surface with a humanized MN-C3 or MN-C8 antibody, antibody fragment or single chain antibody thereof, contacting the stem cell to the surface and delivering the stem cell to a specific location.

In another aspect, the invention is directed to a method of isolating stem cell comprising the steps of coating a surface with a humanized MN-C3 or MN-C8 antibody, antibody fragment or single chain antibody thereof, and contacting a mixed population of cells to the surface and isolating stem cell.

In another aspect, the invention is directed to a scFv comprising variable domain fragments derived from an antibody that binds to a extracellular domain of MUC1 isoform or cleavage product that is devoid of the tandem repeat domains. The variable domain fragments may be derived from mouse monoclonal antibody MN-E6 (SEQ ID NO:13 and 66) or from the humanized MN-E6 (SEQ ID NO: 39 and 94), or from MN-E6 scFv (SEQ ID NO: 233, 235 and 237). Or, the variable domain fragments may be derived from mouse monoclonal antibody MN-C2 (SEQ ID NO: 119 and 169) or from the humanized MN-C2 (SEQ ID NO: 145 and 195), or from MN-C2 scFv (SEQ ID NO: 239, 241 and 243). Or, the variable domain fragments may be derived from mouse monoclonal antibody MN-C3 (SEQ ID NO: 414 and 459) or from the humanized MN-C3 (SEQ ID NO: 440 and 487), or from MN-C3 scFv (SEQ ID NO: 245, 247 and 249). Or, the variable domain fragments may be derived from mouse monoclonal antibody MN-C8 (SEQ ID NO: 505 and 544) or from the humanized MN-C8 (SEQ ID NO: 526 and 566), or from MN-C8 scFv (SEQ ID NO: 251, 253, 255).

In another aspect, the invention is directed to a method for the treatment of a person diagnosed with, suspected of having or at risk of developing a MUC1 Or MUC1* positive cancer involving administering to the person an effective amount of the scFv described above.

In another aspect, the invention is directed to a scFv-Fc construct comprising the scFv as described above. The scFv-Fc may be dimerized. Or, the Fc component may be mutated so that scFv-Fc is monomeric. The mutation may include mutating or deleting hinge region on Fc, making F405Q, Y407R, T366W/L368W, and T364R/L368R mutation or combinations thereof on the Fc represented by SEQ ID NO: 281, 279, 285 and 287.

In another aspect, the invention is directed to a polypeptide comprising at least two different scFv sequences, wherein one of the scFv sequences is a sequence that binds to extracellular domain of MUC1 isoform or cleavage product that is devoid of the tandem repeat domains. The polypeptide may bind to
(i) PSMGFR region of MUC1;
(ii) PSMGFR peptide;
(iii) peptide having amino acid sequence of SNIKFRPGSVVVQLTLAFREGTINVHD-VETQFNQYKTEAASRY (SEQ ID NO:620);
(iv) a peptide having amino acid sequence of VQLT-LAFREGTINVHDVETQFNQYKTEAASRY (SEQ ID NO:621);
(v) a peptide having amino acid sequence of VQLT-LAFREGTINVHDVETQFNQY (SEQ ID NO:622); or
(vi) a peptide having amino acid sequence of SNIKFRPGSVVVQLTLAFREGTIN (SEQ ID NO:623).

The polypeptide may bind to a receptor on an immune cell, such as T cell, and in particular, CD3 on T-cell.

In another aspect, the invention is directed to a method of detecting presence of a cell that expresses MUC1* aberrantly, comprising contacting a sample of cells with the scFv-Fc described above and detecting for the presence of the binding of scFv-Fc to the cell. The cell may be cancer cell.

In another aspect, the invention is directed to a method for testing a subject's cancer for suitability of treatment with a composition comprising portions of the variable regions of MN-E6, MN-C2, MN-C3 or MN-C8, comprising the steps of contacting a bodily specimen from the patient with the corresponding MN-E6 scFv-Fc, MN-C3 scFv-Fc, MN-C3 scFv-Fc or MN-C8 scFv-Fc.

In another aspect, the invention is directed to a method of treating a subject suffering from a disease comprising, exposing T cells from the subject to MUC1* peptides wherein through various rounds of maturation, T cells develop MUC1* specific receptors, creating adapted T cells, and expanding and administering the adapted T cells to the donor patient who is diagnosed with, suspected of having, or is at risk of developing a MUC1* positive cancer.

These and other objects of the invention will be more fully understood from the following description of the invention, the referenced drawings attached hereto and the claims appended hereto.

BRIEF DESCRIPTION OF THE DRAWINGS

The patent or application file contains at least one drawing executed in color. Copies of this patent or parent application publication with color drawings will be provided by the Office upon request and payment of the necessary fee.

The present invention will become more fully understood from the detailed description given herein below, and the accompanying drawings which are given by way of illustration only, and thus are not limitative of the present invention, and wherein.

From 1 to 9 are:
1. E6scFv-Fc-8-41BB-CD3z (Human Fc as hinge region with CD8 TM);
2: E6scFv-FcH-8-41BB-CD3z (Human Fc hingeless as hinge region with CD8 TM)
3: E6scFv-Fc-4-41BB-CD3z (Human Fc as hinge region with CD4 TM)
4: E6scFv-FcH-4-41BB-CD3z (Human Fc as hingeless hinge region with CD4 TM)

5: E6scFv-IgD-8-41BB-CD3z (hinge region from human IgD with CD8 TM)

6: E6scFv-IgD-4-41BB-CD3z (hinge region from human IgD with CD4 TM)

7: E6scFv-X4-8-41BB-CD3z (Long flexible linker as hinge region with CD8 TM)

8: E6scFv-X4-4-41BB-CD3z (Long flexible linker as hinge region with CD4 TM)

9: E6scFv-8-4-41BB-CD3z (Hinge region from CD8 and CD4 a with CD4 TM).

Figure 41:
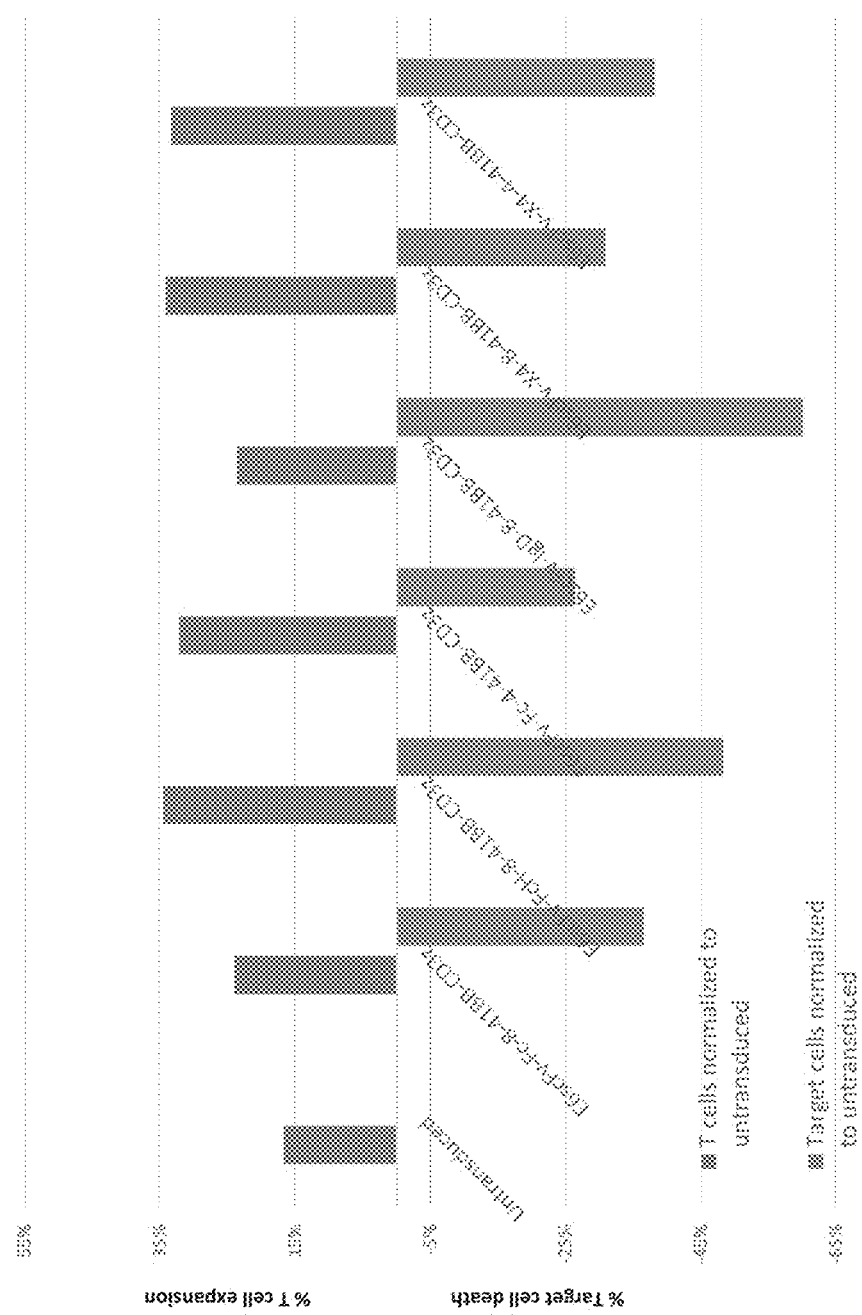

FIG. 41 shows graphs of FACS scans of T47D breast cancer cells co-cultured with human T cells that were transduced with MN-E6scFv-Fc-8-41BB-CD3z, MN-E6scFv-FcH-8-41BB-CD3z, MN-E6scFv-Fc-4-41BB-CD3z, MN-E6scFv-IgD-8-41BB-CD3z, MN-E6scFv-X4-8-41BB-CD3z and MN-E6scFv-X4-4-41BB-CD3z. T cells and cancer cells were co-cultured at a 1:1 ratio for 48 hours. T cell counts were normalized to an average of all untransduced T cells and target cells were normalized to each specific cell type when co-cultured with untransduced T cells. The graph shows that when the CAR T cells are co-cultured with MUC1* positive cancer cells, the T cell population expands and the targeted cancer cell population decreases.

Figure 42:
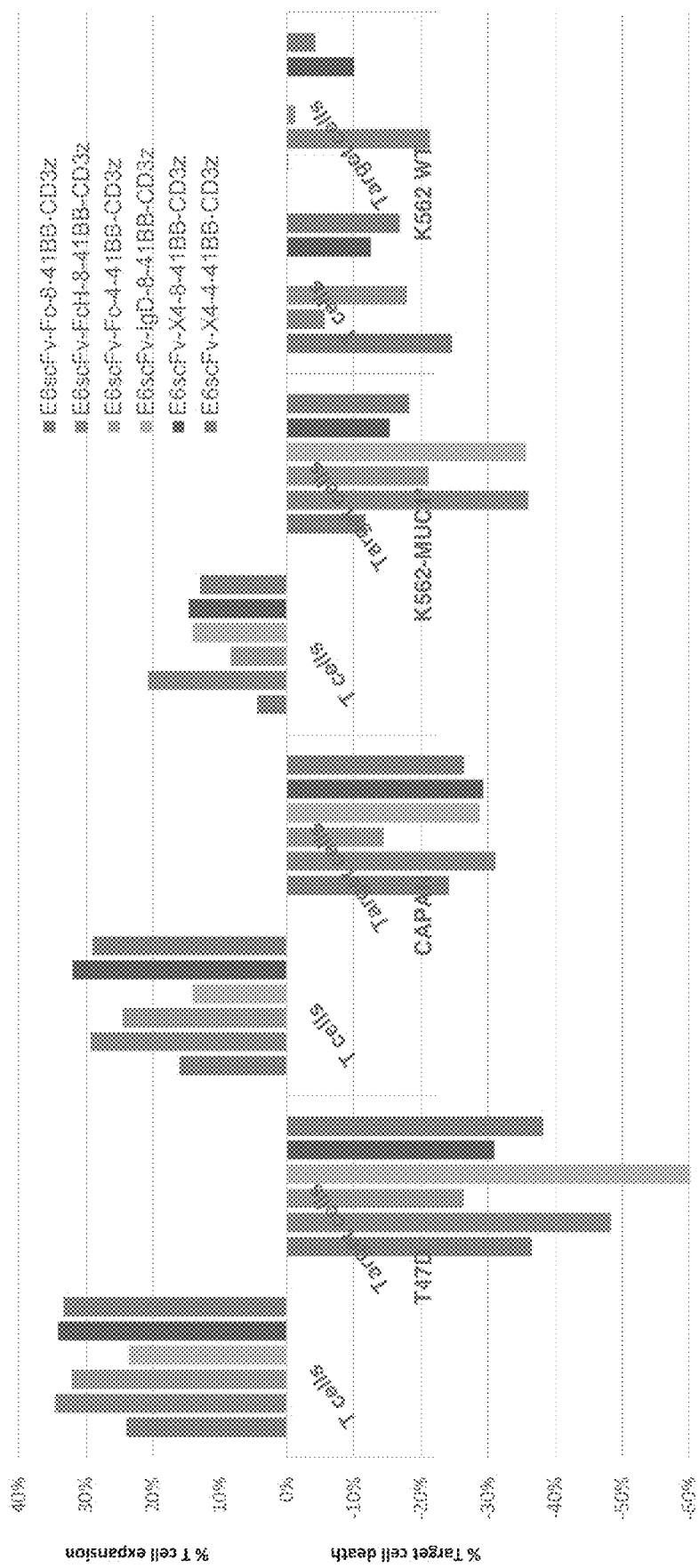

FIG. 42 shows graphs of FACS scans of T47D breast cancer cells, Capan-2 pancreatic cancer cells, K562-MUC1* transfected cells, and K562-wt cells that were co-cultured with human T cells that were transduced with MN-E6scFv-Fc-8-41BB-CD3z, MN-E6scFv-FcH-8-41BB-CD3z, MN-E6scFv-Fc-4-41BB-CD3z, MN-E6scFv-IgD-8-41BB-CD3z, MN-E6scFv-X4-8-41BB-CD3z and MN-E6scFv-X4-4-41BB-CD3z. T cells and cancer cells were co-cultured at a 1:1 ratio for 48 hours. T cell counts were normalized to an average of all untransduced T cells and target cells were normalized to each specific cell type when co-cultured with untransduced T cells. The graph shows that when the CAR T cells are co-cultured with MUC1* positive cancer cells, the T cell population expands and the targeted cancer cell population decreases.

Figure 43:
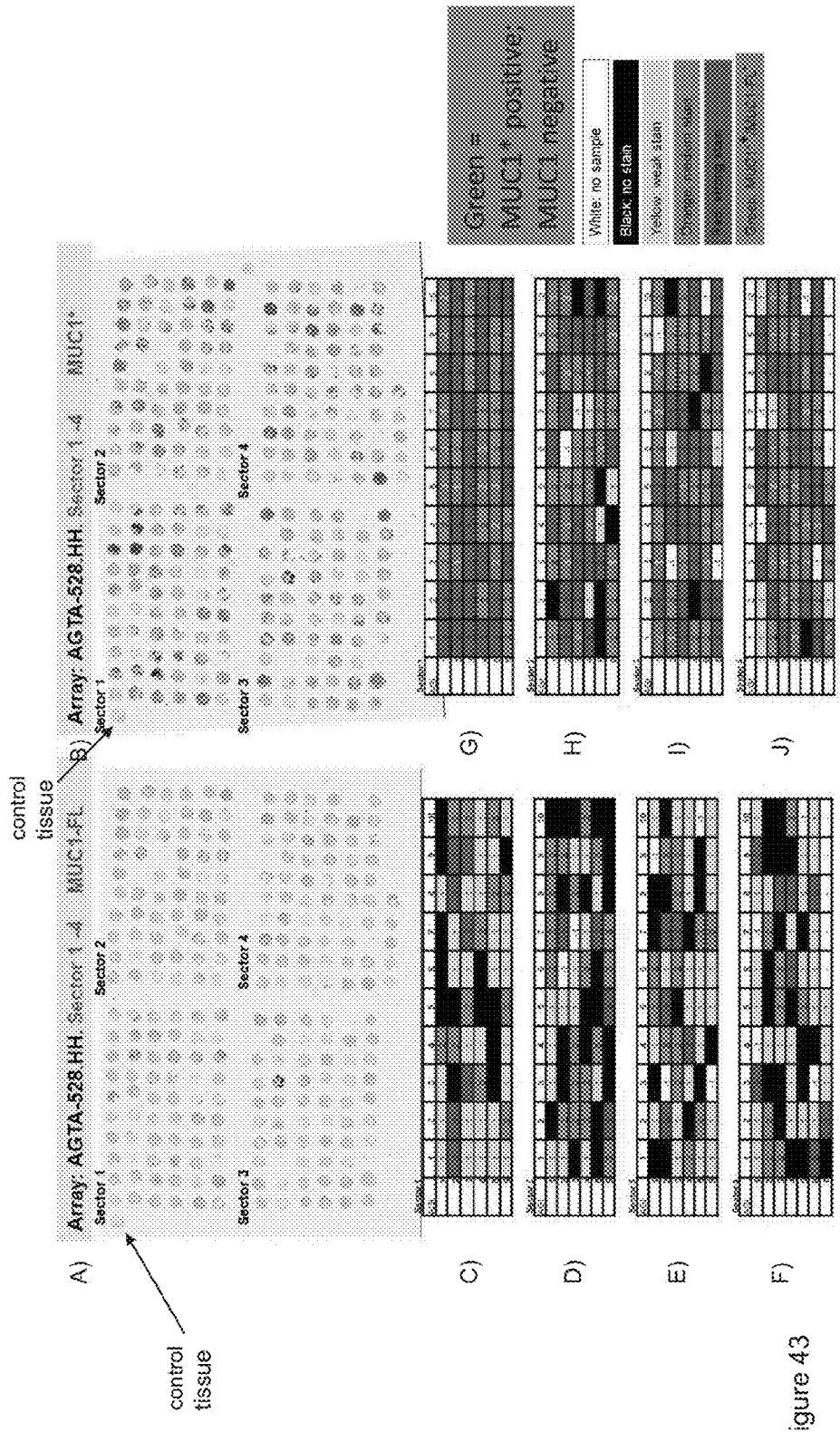

FIG. 43 shows photographs of breast cancer tissue arrays. A) was stained with VU4H5 which recognizes MUC1-FL (full length); B) was stained with mouse monoclonal antibody MN-C2 which recognizes cancerous MUC1*. Following automated staining (Clarient Diagnostics), the tissue staining was scored using Allred scoring method which combines an intensity score and a distribution score. C,D,E,F are color coded graphs showing the score calculated for MUC1 full-length staining for each patient's tissue. G,H,I,J are color coded graphs showing the score calculated for MUC1* staining for each patient's tissue.

Figure 44:
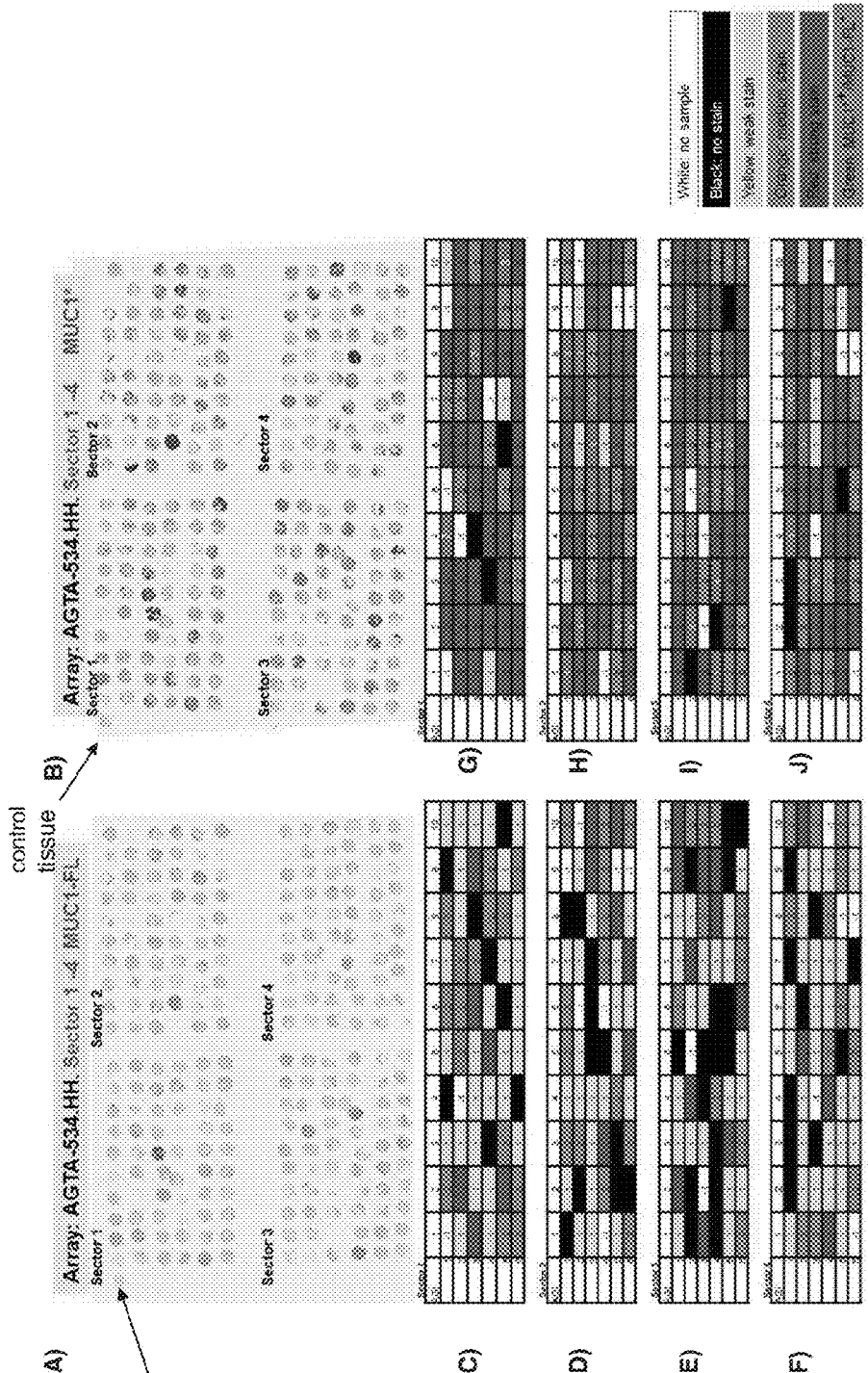

FIG. 44 shows photographs of breast cancer tissue arrays. A) was stained with VU4H5 which recognizes MUC1-FL (full length); B) was stained with mouse monoclonal antibody MN-C2 which recognizes cancerous MUC1*. Following automated staining (Clarient Diagnostics), the tissue staining was scored using Allred scoring method which combines an intensity score and a distribution score. C,D,E,F are color coded graphs showing the score calculated for MUC1 full-length staining for each patient's tissue. G,H,I,J are color coded graphs showing the score calculated for MUC1* staining for each patient's tissue.

Figure 45:
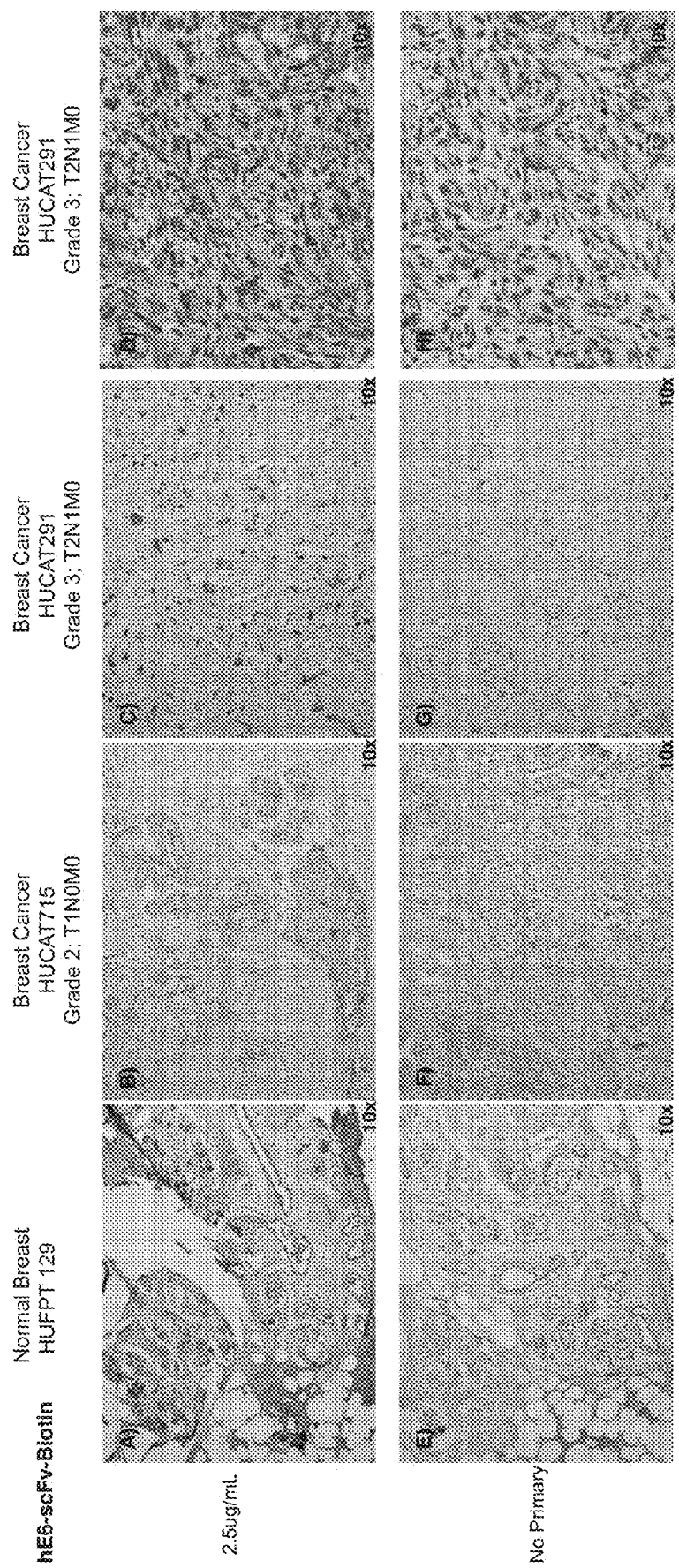

FIG. 45 shows photographs of normal breast and breast cancer tissues stained with humanized MN-E6-scFv-Fc biotinylated anti-MUC1* antibody at 2.5 ug/mL, then stained with a secondary streptavidin HRP antibody. A) is a normal breast tissue. B-D are breast cancer tissues from patients as denoted in the figure. E-H are photographs of the corresponding serial sections that were stained with the secondary antibody alone.

Figure 46:
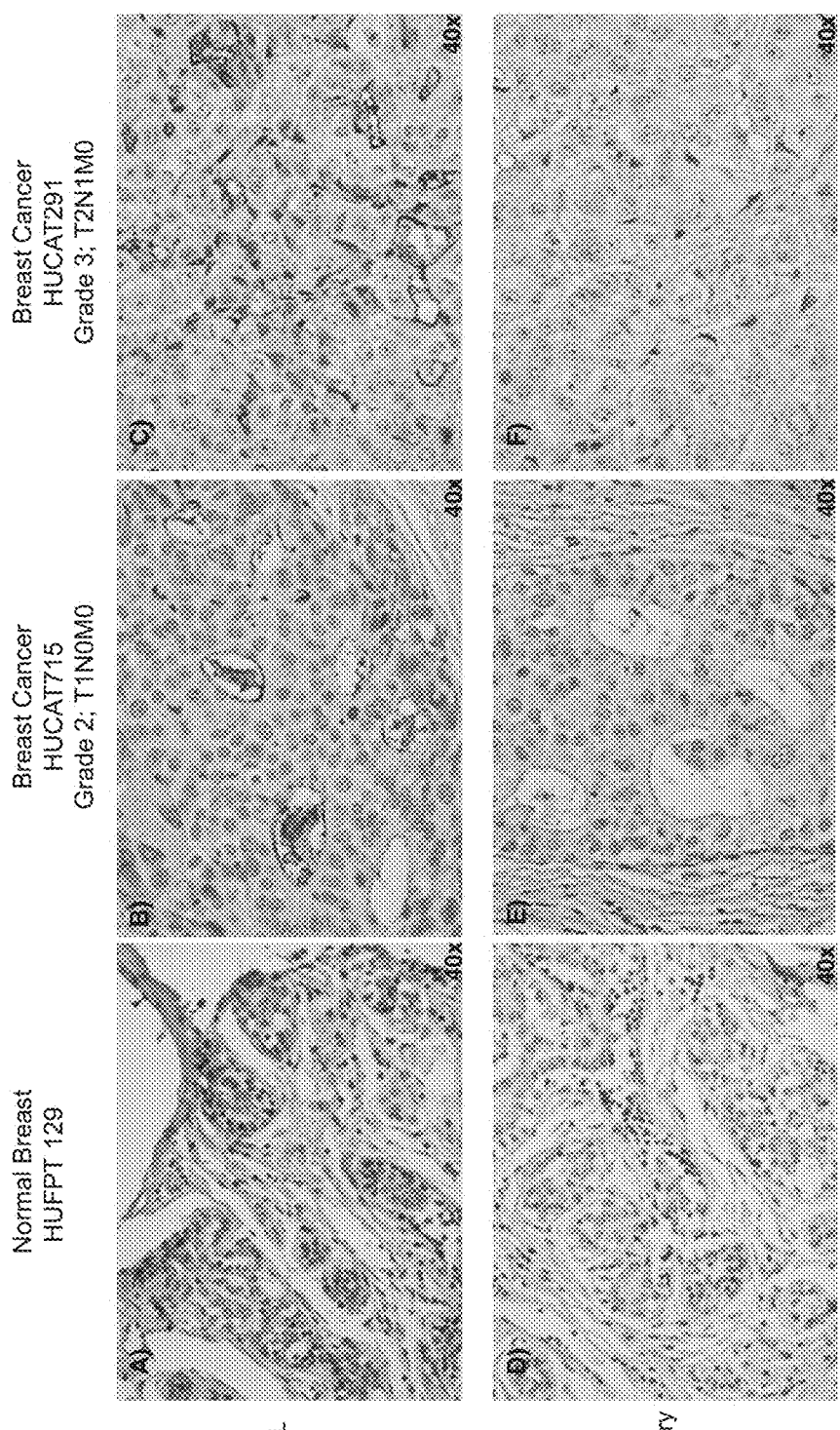

FIG. 46 shows photographs of normal breast and breast cancer tissues stained with humanized MN-E6-scFv-Fc biotinylated anti-MUC1* antibody at 2.5 ug/mL, then stained with a secondary streptavidin HRP antibody. A) is a normal breast tissue. B-C are breast cancer tissues from patients as denoted in the figure. D-F are photographs of the corresponding serial sections that were stained with the secondary antibody alone.

Figure 47:
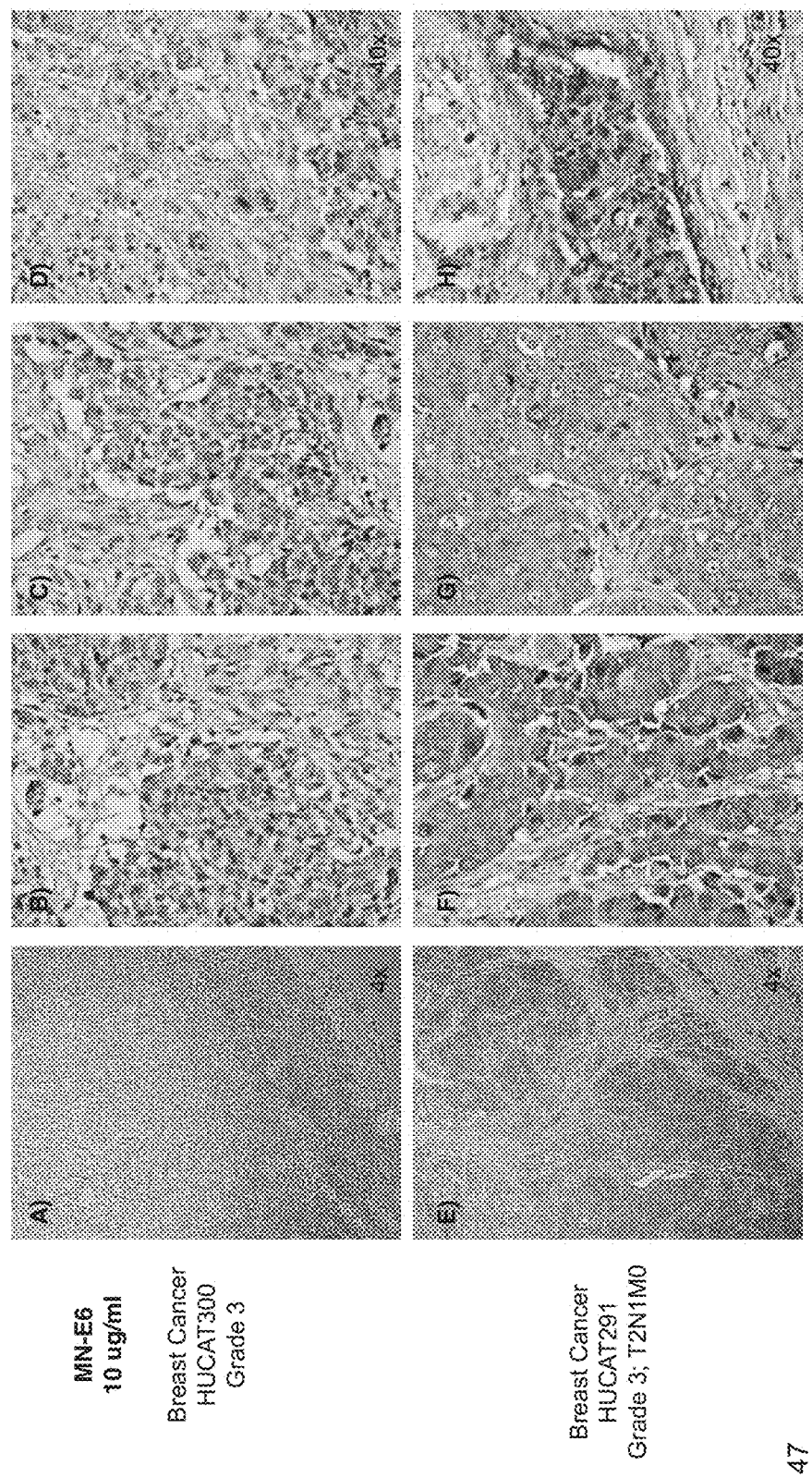

FIG. 47 shows photographs of breast cancer tissues stained with MN-E6 anti-MUC1* antibody at 10 ug/mL, then stained with a rabbit anti mouse secondary HRP antibody. A-D are breast cancer tissues from patient #300. E-H are breast cancer tissues from metastatic patient #291.

Figure 48:
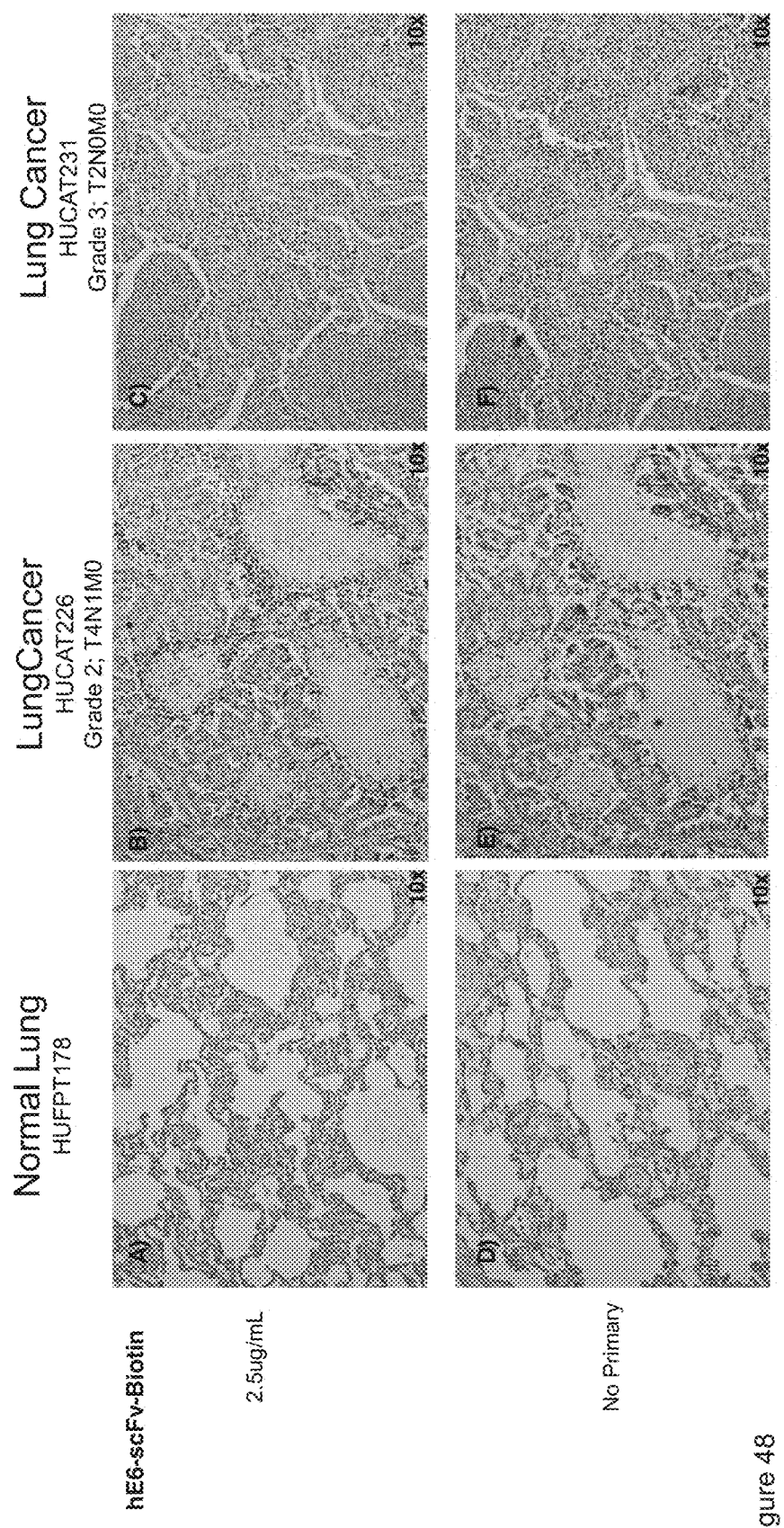

FIG. 48 shows photographs of normal lung and lung cancer tissues stained with humanized MN-E6-scFv-Fc biotinylated anti-MUC1* antibody at 2.5 ug/mL, then stained with a secondary streptavidin HRP antibody. A) is a normal lung tissue. B,C are lung cancer tissues from patients as denoted in the figure. D-F are photographs of the corresponding serial sections that were stained with the secondary antibody alone.

Figure 49:
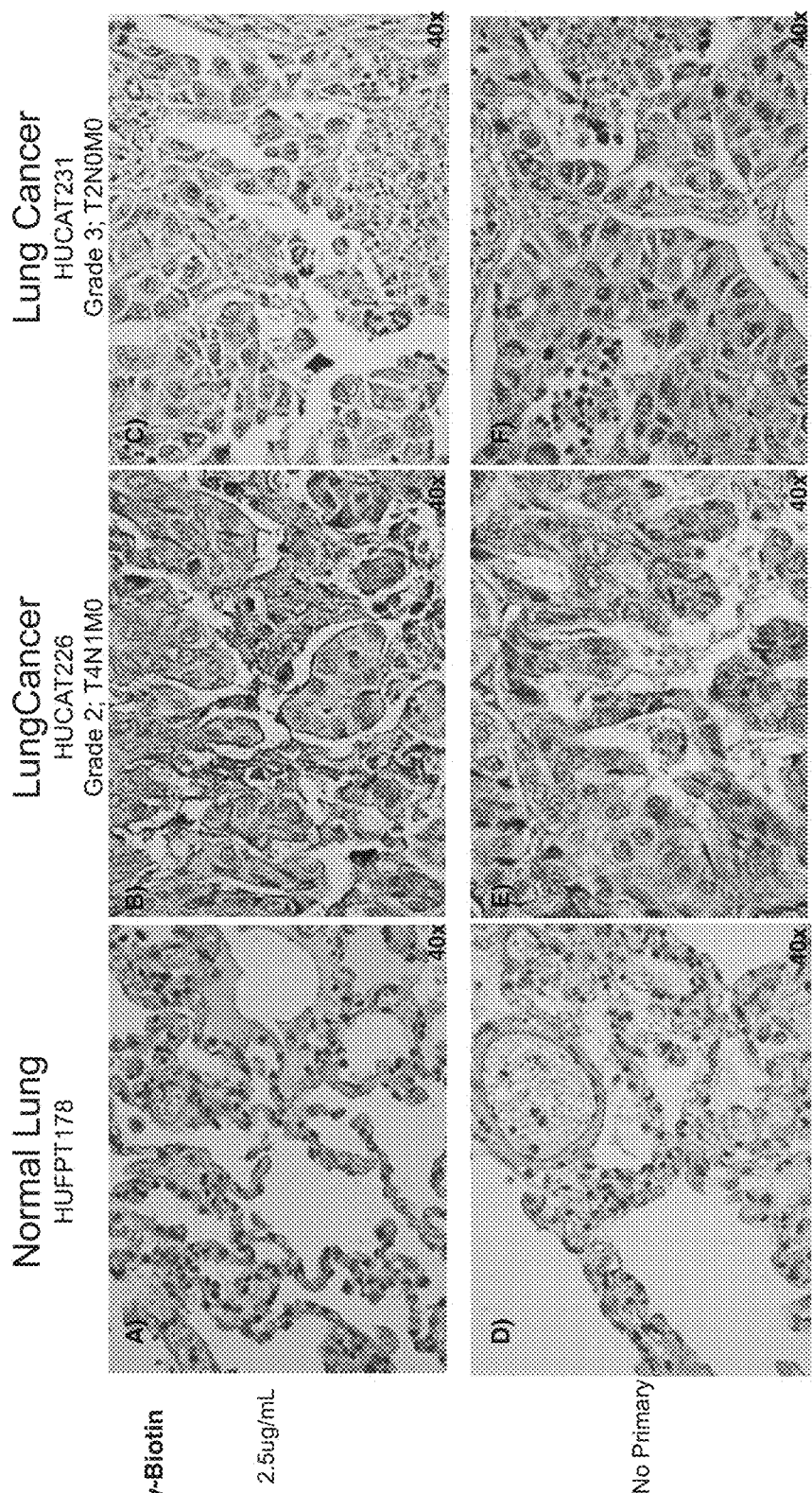

FIG. 49 shows photographs of normal lung and lung cancer tissues stained with humanized MN-E6-scFv-Fc biotinylated anti-MUC1* antibody at 2.5 ug/mL, then stained with a secondary streptavidin HRP antibody. A) is a normal lung tissue. B,C are lung cancer tissues from patients as denoted in the figure. D-F are photographs of the corresponding serial sections that were stained with the secondary antibody alone.

Figure 50:
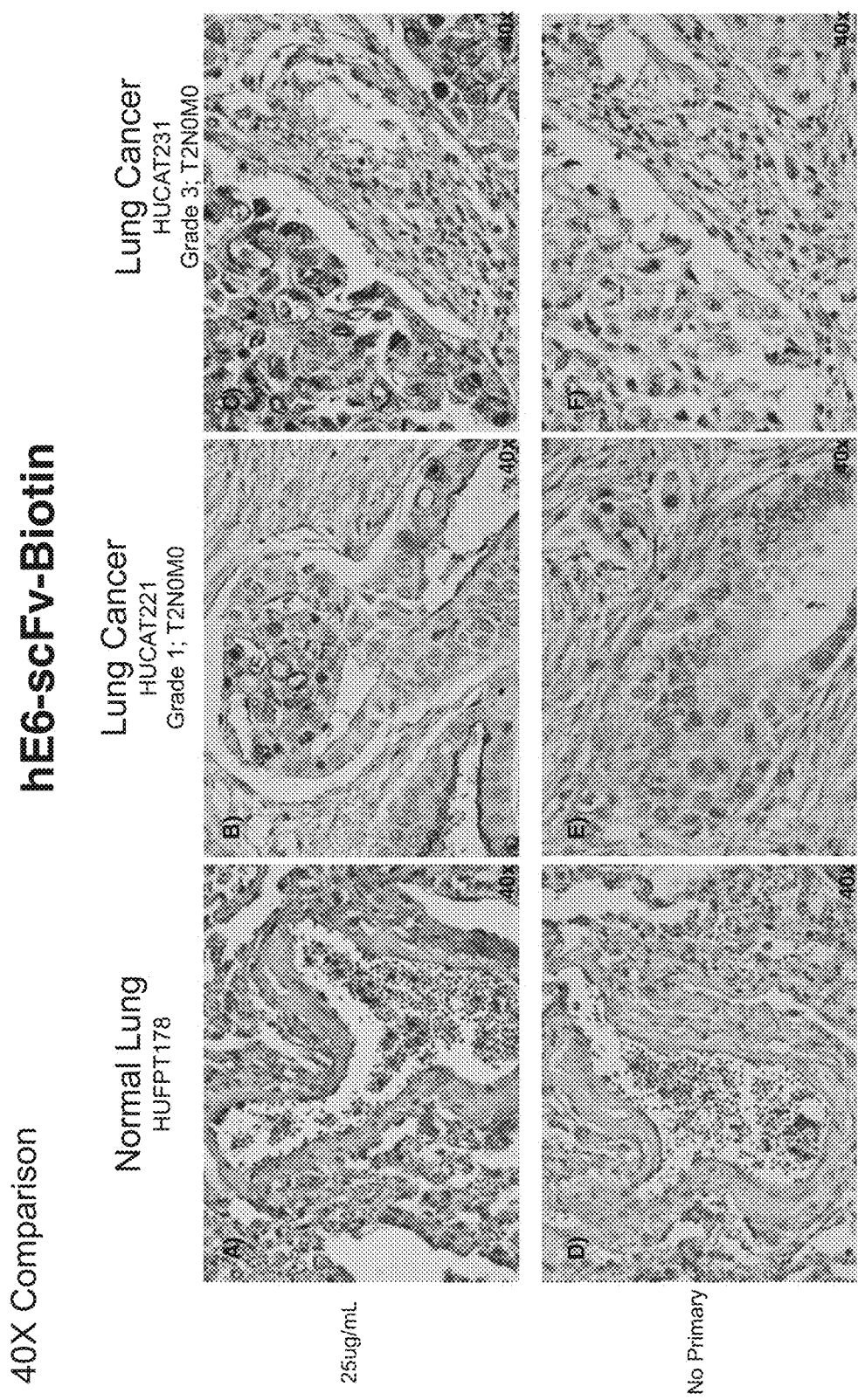

FIG. 50 shows photographs of normal lung and lung cancer tissues stained with humanized MN-E6-scFv-Fc biotinylated anti-MUC1* antibody at 25 ug/mL, then stained with a secondary streptavidin HRP antibody. A) is a normal lung tissue. B,C are lung cancer tissues from patients as denoted in the figure. D-F are photographs of the corresponding serial sections that were stained with the secondary antibody alone.

Figure 51:
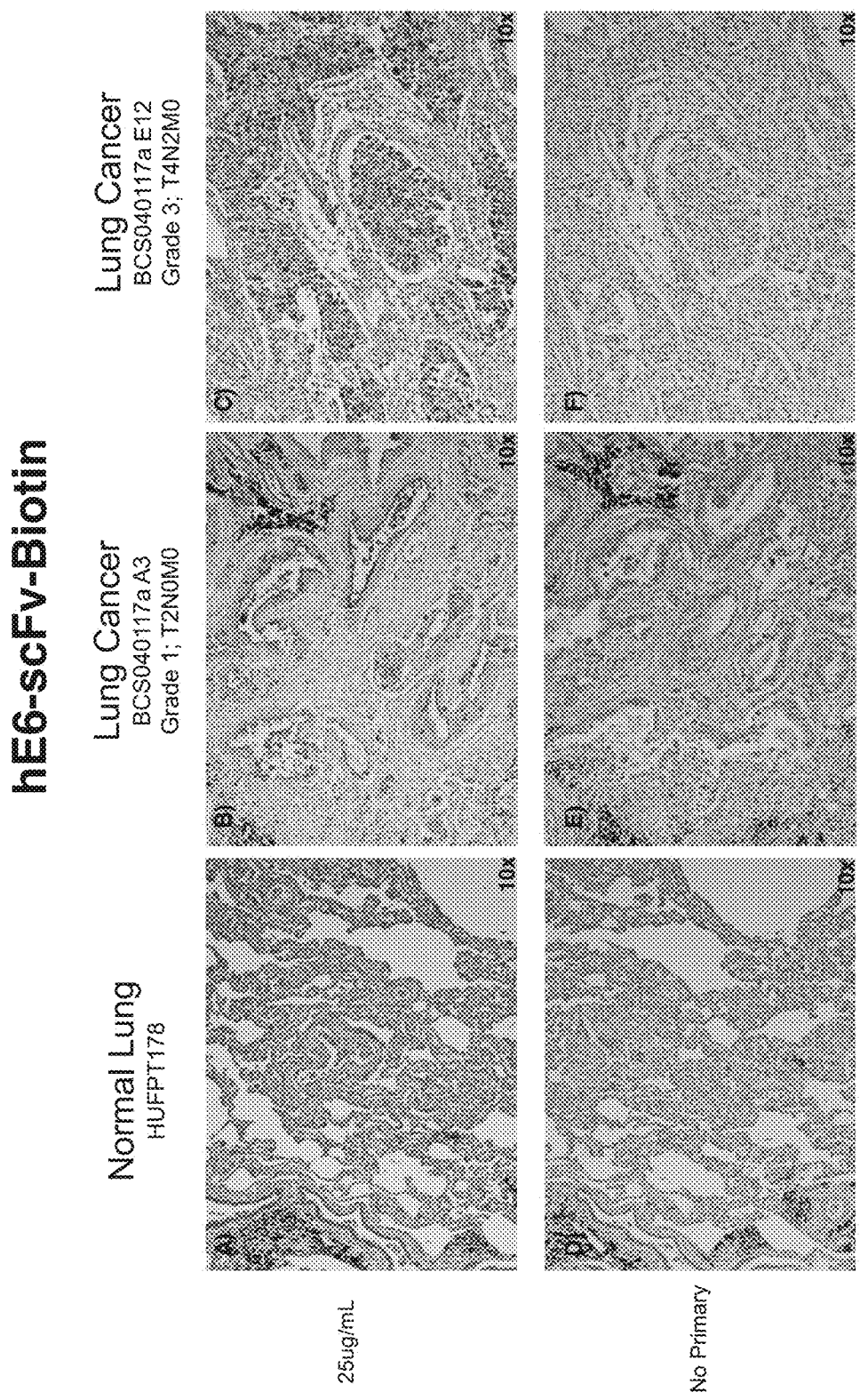

FIG. 51 shows photographs of normal lung and lung cancer tissues stained with humanized MN-E6-scFv-Fc biotinylated anti-MUC1* antibody at 25 ug/mL, then stained with a secondary streptavidin HRP antibody. A) is a normal lung tissue. B,C are lung cancer tissues from patients as denoted in the figure. D-F are photographs of the corresponding serial sections that were stained with the secondary antibody alone.

Figure 52:
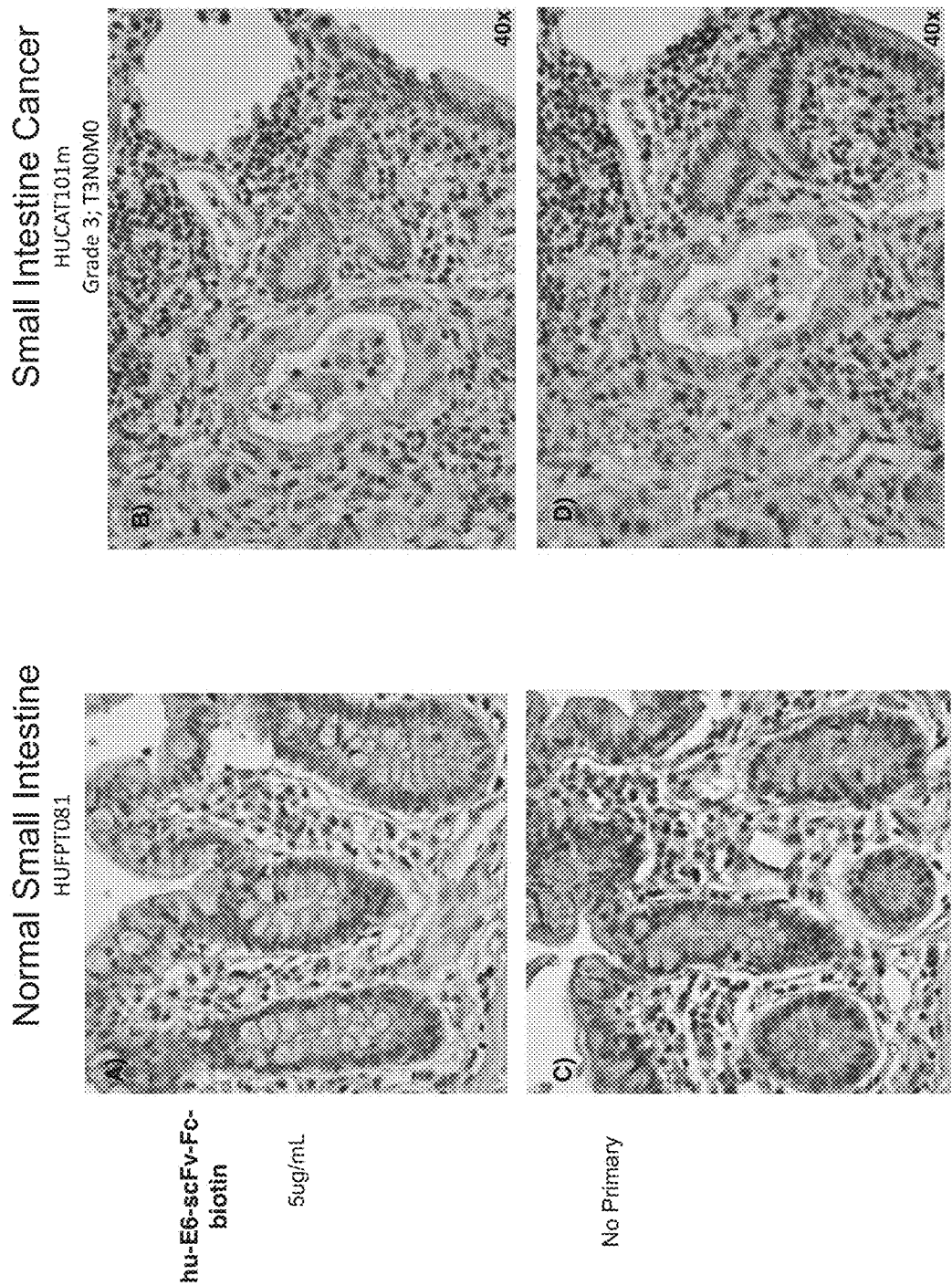

FIG. 52 shows photographs of normal small intestine and cancerous small intestine tissues stained with humanized MN-E6-scFv-Fc biotinylated anti-MUC1* antibody at 5 ug/mL, then stained with a secondary streptavidin HRP antibody. A) is a normal small intestine tissue. B) is small intestine cancer from patient as denoted in the figure. C,D are photographs of the corresponding serial sections that were stained with the secondary antibody alone.

Figure 53:
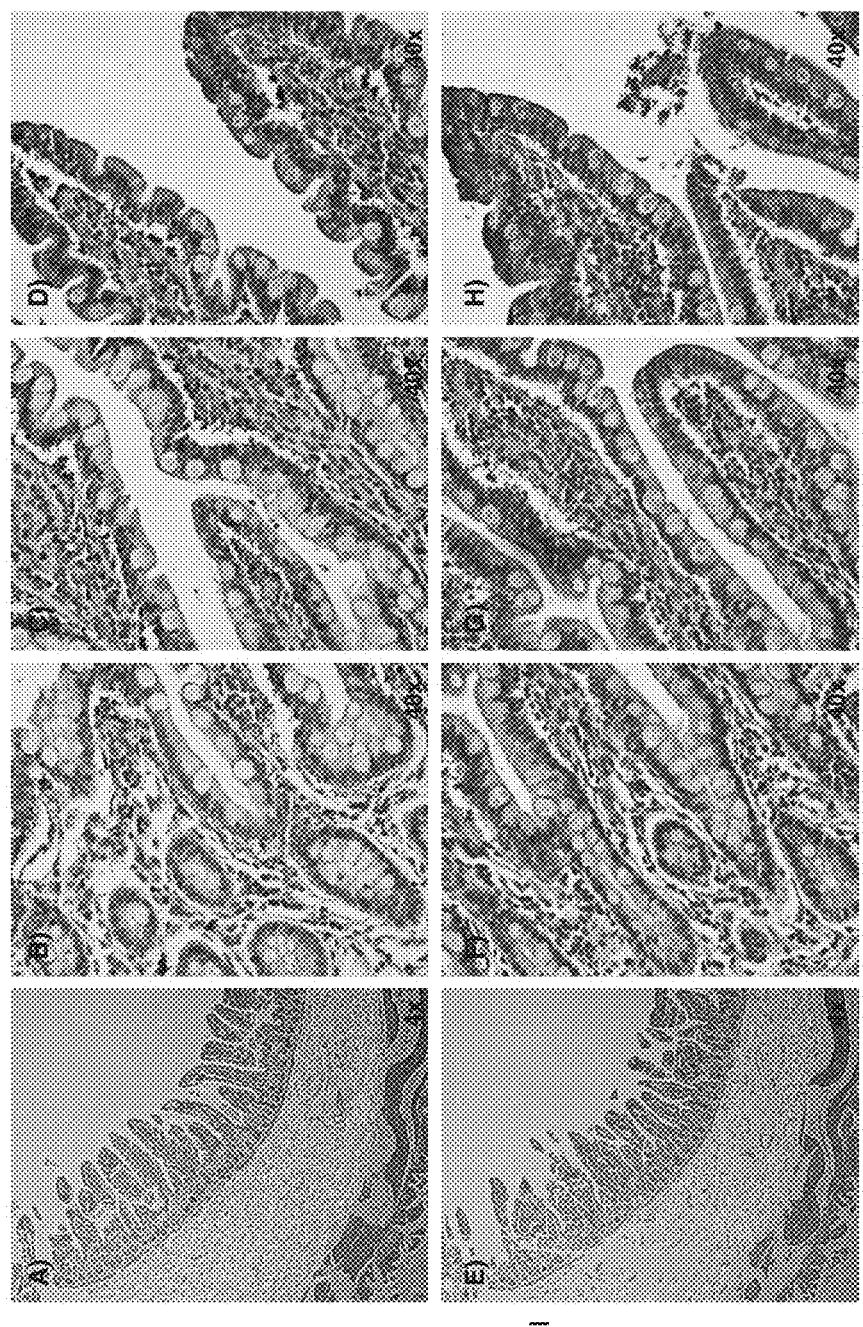

FIG. 53 shows photographs of normal small intestine tissues stained with humanized MN-E6-scFv-Fc anti-MUC1* antibody at 50 ug/mL, then stained with a secondary goat-anti-human HRP antibody. A-D are normal small intestine tissue. E-H are photographs of the corresponding serial sections that were stained with the secondary antibody alone.

Figure 54:
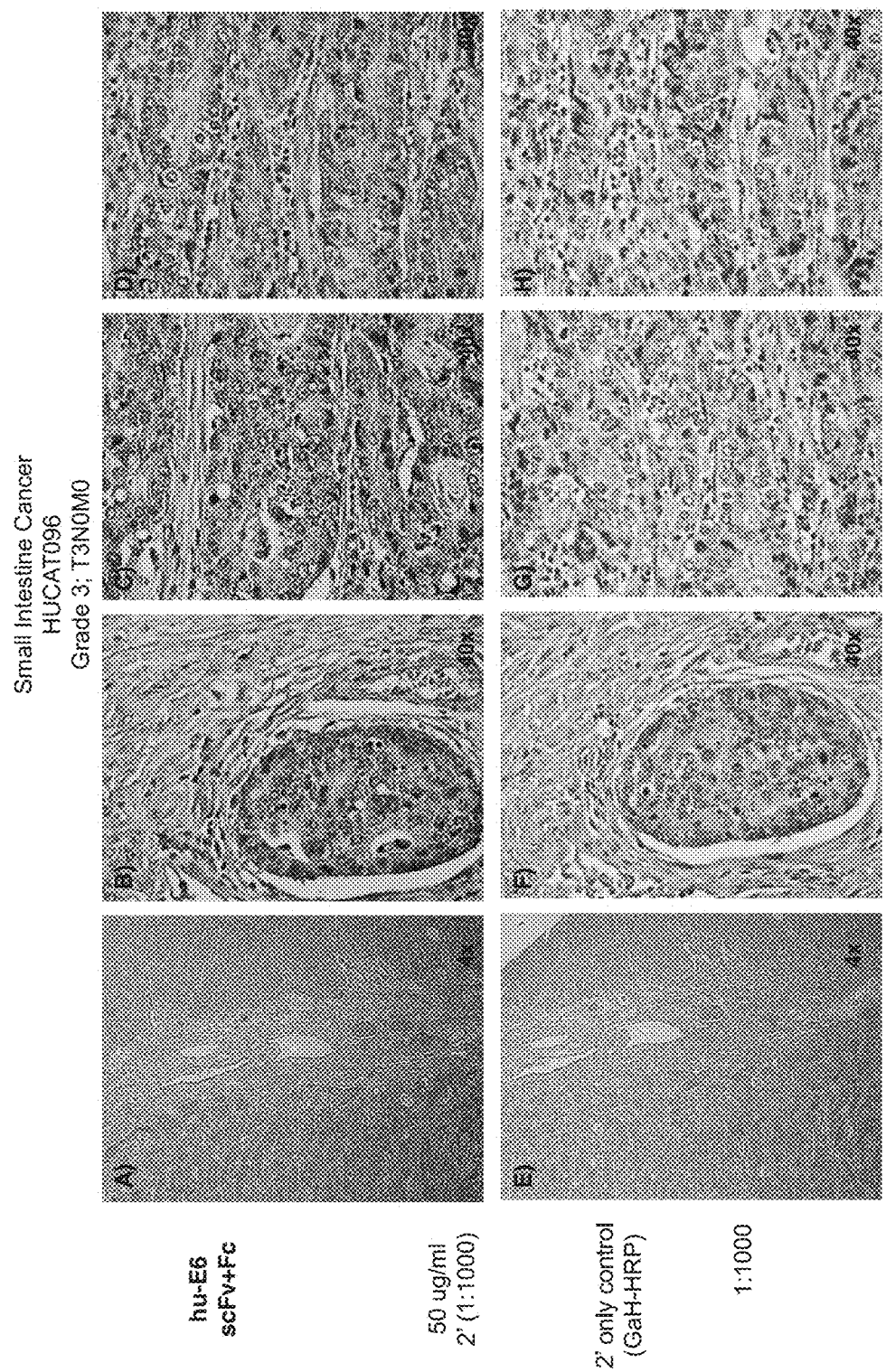

FIG. 54 shows photographs of cancerous small intestine tissues stained with humanized MN-E6-scFv-Fc anti-MUC1* antibody at 50 ug/mL, then stained with a secondary goat-anti-human HRP antibody. A-D are cancerous small intestine tissue from a patient as denoted in figure. E-H are photographs of the corresponding serial sections that were stained with the secondary antibody alone.

Figure 55:
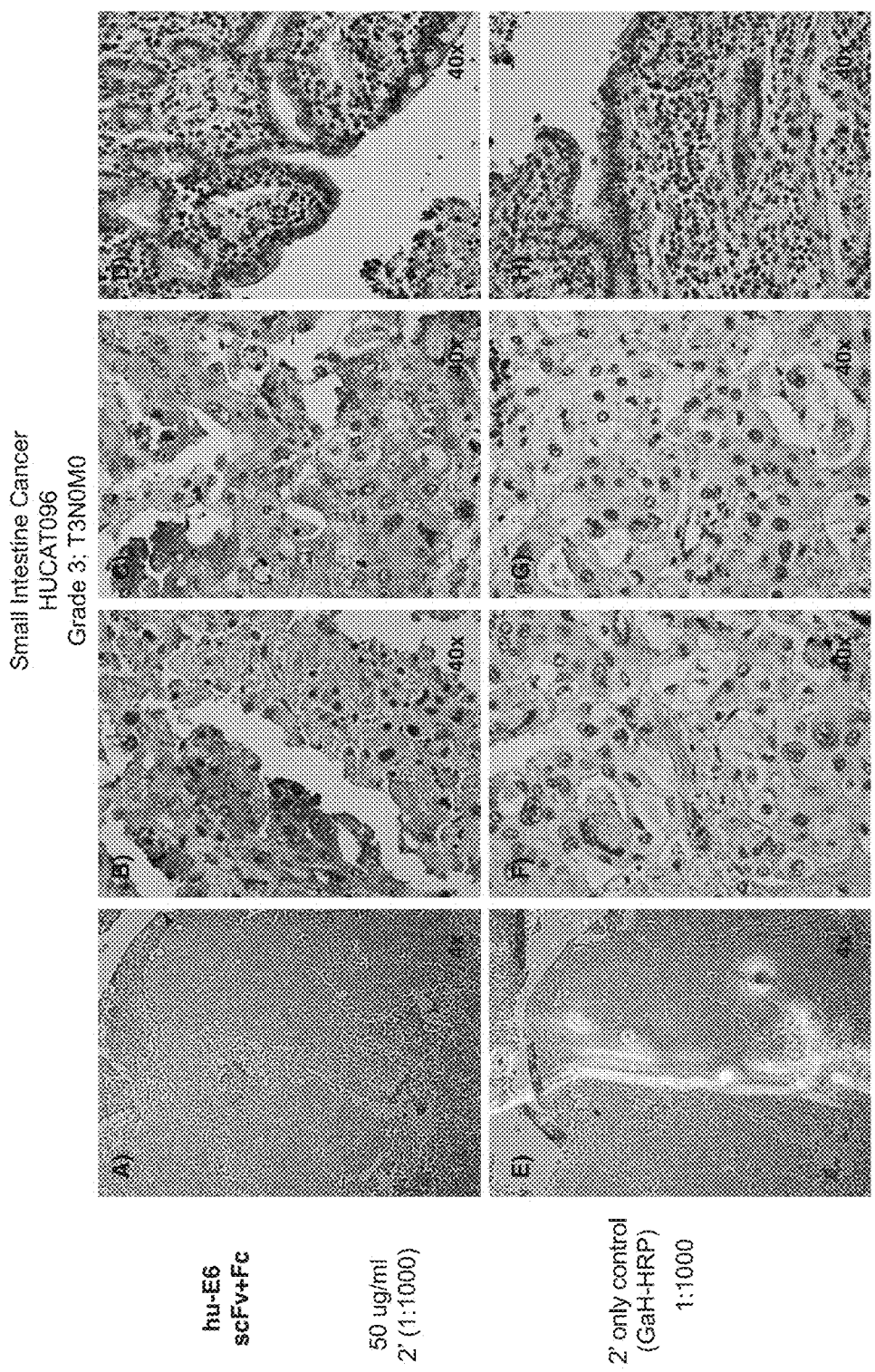

FIG. 55 shows photographs of cancerous small intestine tissues stained with humanized MN-E6-scFv-Fc anti-MUC1* antibody at 50 ug/mL, then stained with a secondary goat-anti-human HRP antibody. A-D are cancerous small intestine tissue from a patient as denoted in figure. E-H are photographs of the corresponding serial sections that were stained with the secondary antibody alone.

Figure 56:
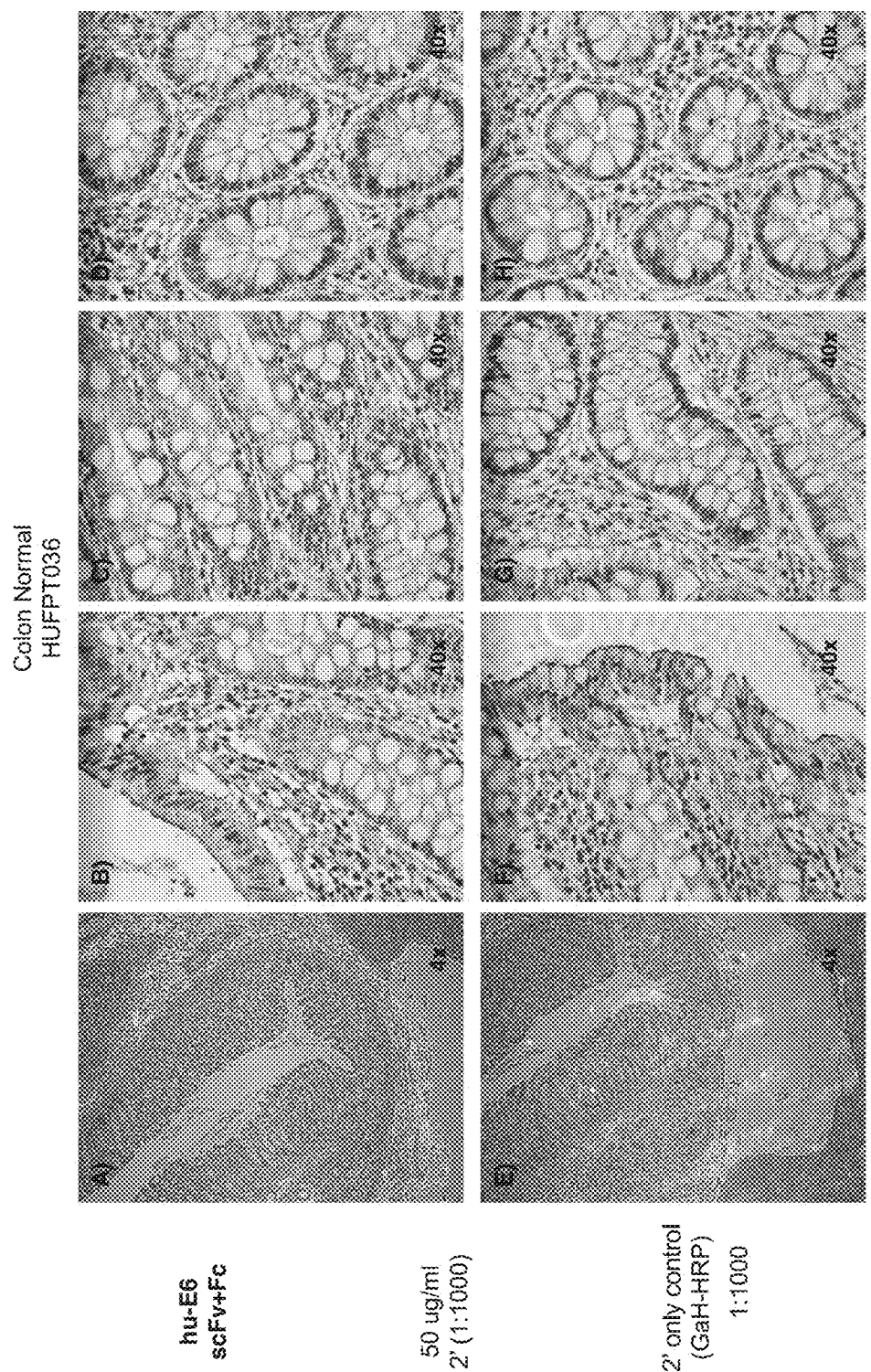

FIG. 56 shows photographs of normal colon tissues stained with humanized MN-E6-scFv-Fc anti-MUC1* antibody at 50 ug/mL, then stained with a secondary goat-anti-human HRP antibody. A-D are normal colon. E-H are photographs of the corresponding serial sections that were stained with the secondary antibody alone.

Figure 57:
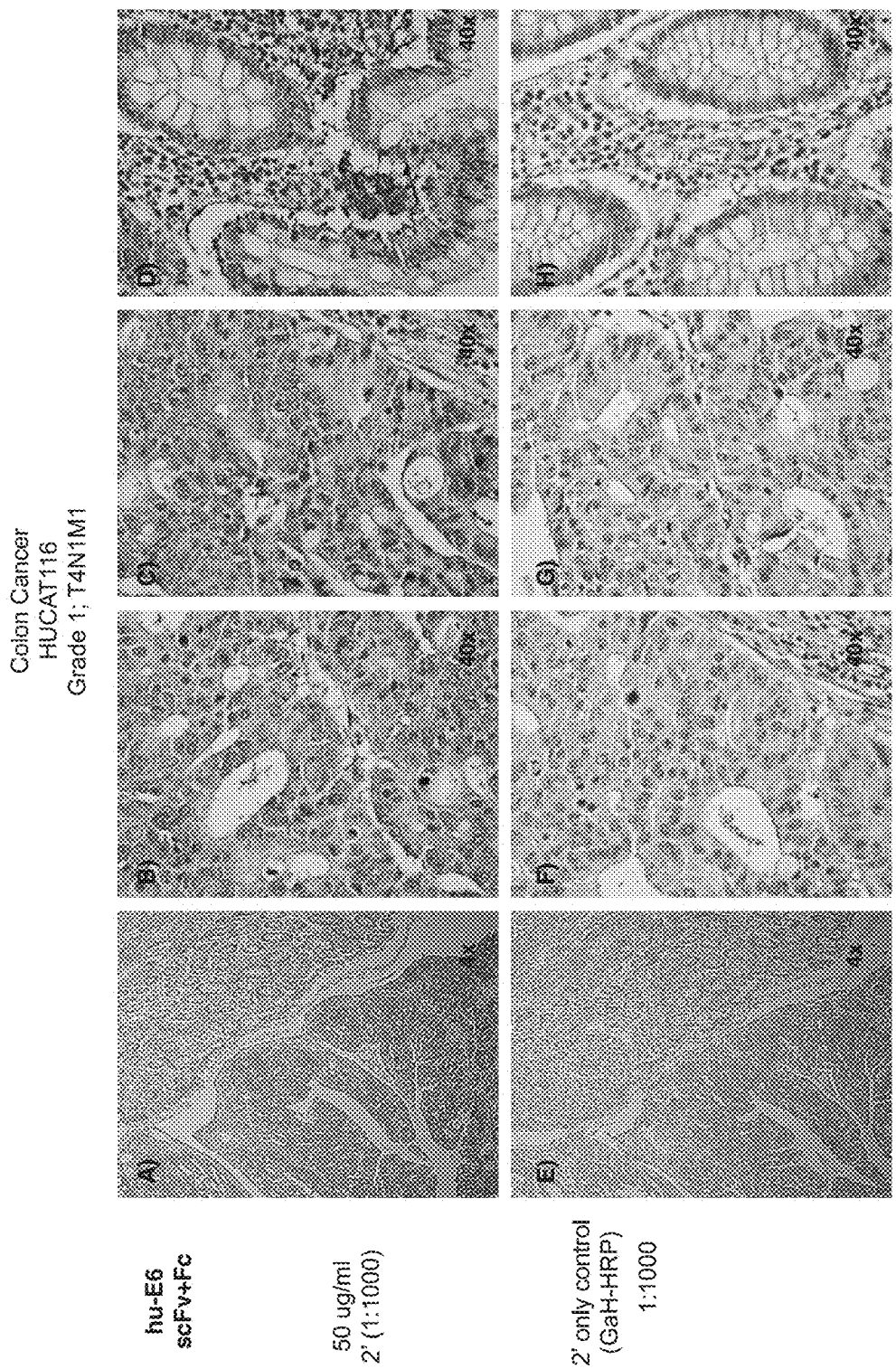

FIG. 57 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a metastatic patient as denoted in figure. E-H are photographs of the corresponding serial sections that were stained with the secondary antibody alone.

Figure 58:
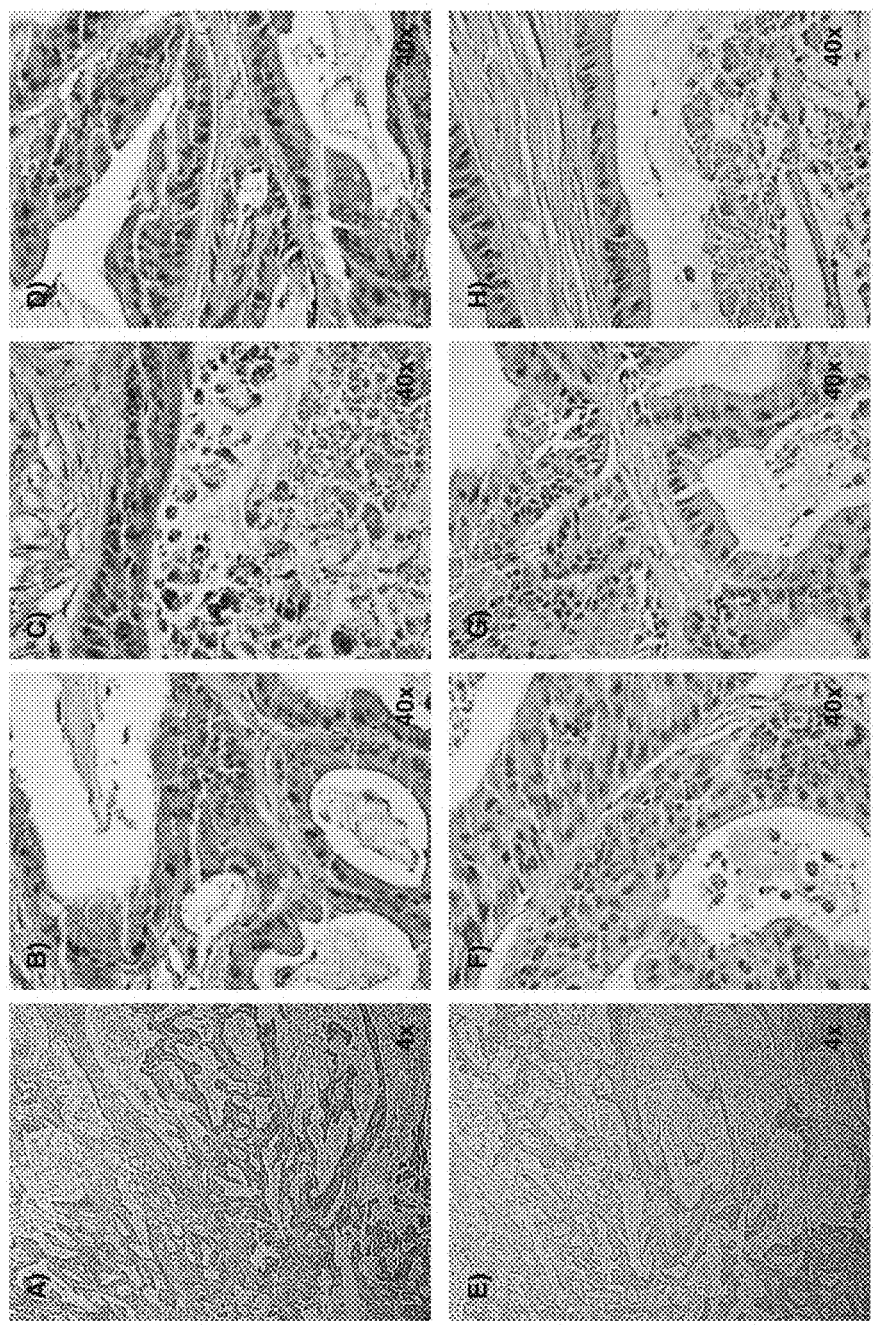

FIG. 58 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a Grade 2 patient as denoted in figure. E-H are photographs of the corresponding serial sections that were stained with the secondary antibody alone.

Figure 59:
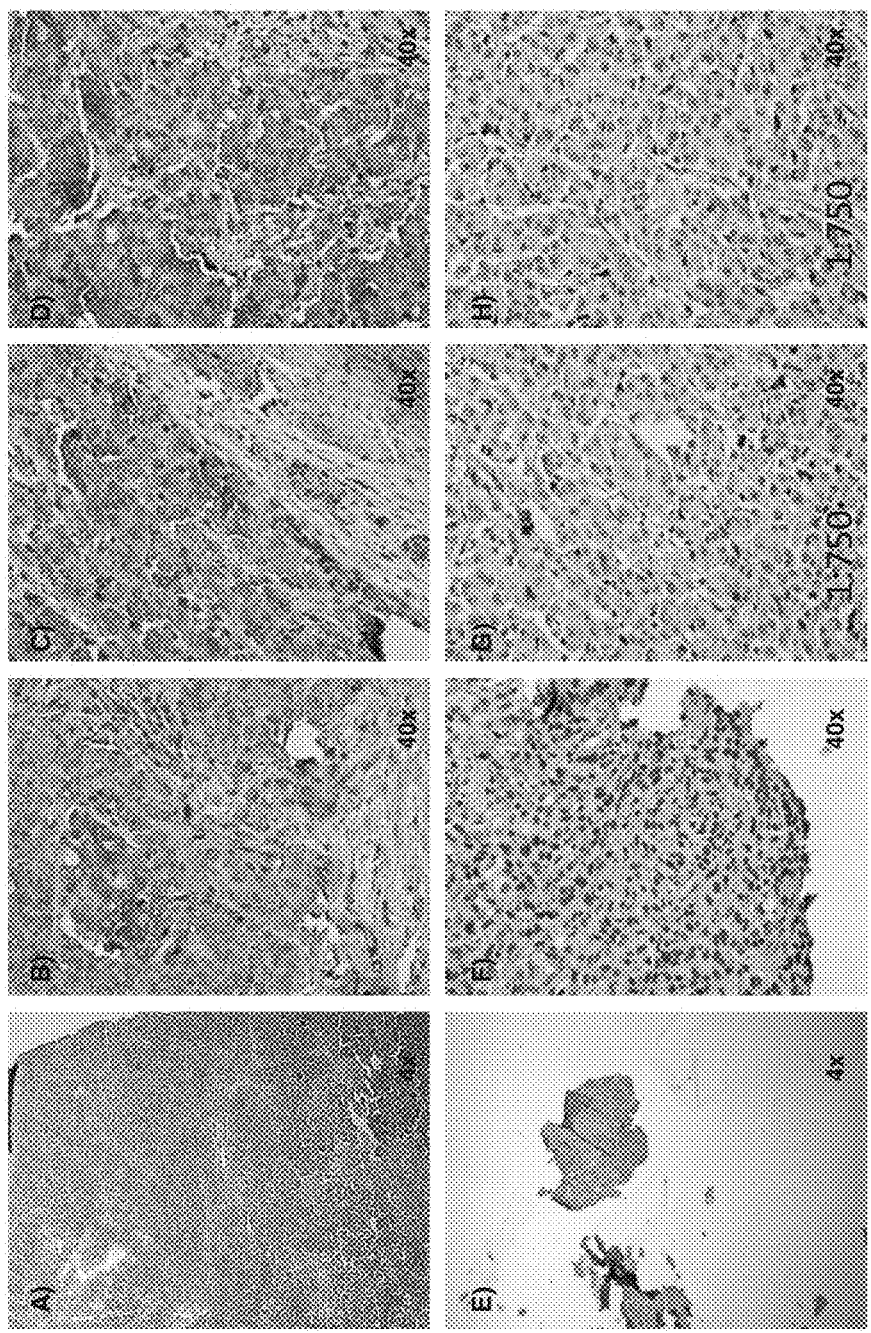

FIG. 59 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a metastatic patient as denoted in figure. E-H are photographs of the corresponding serial sections that were stained with the secondary antibody alone.

Figure 60:
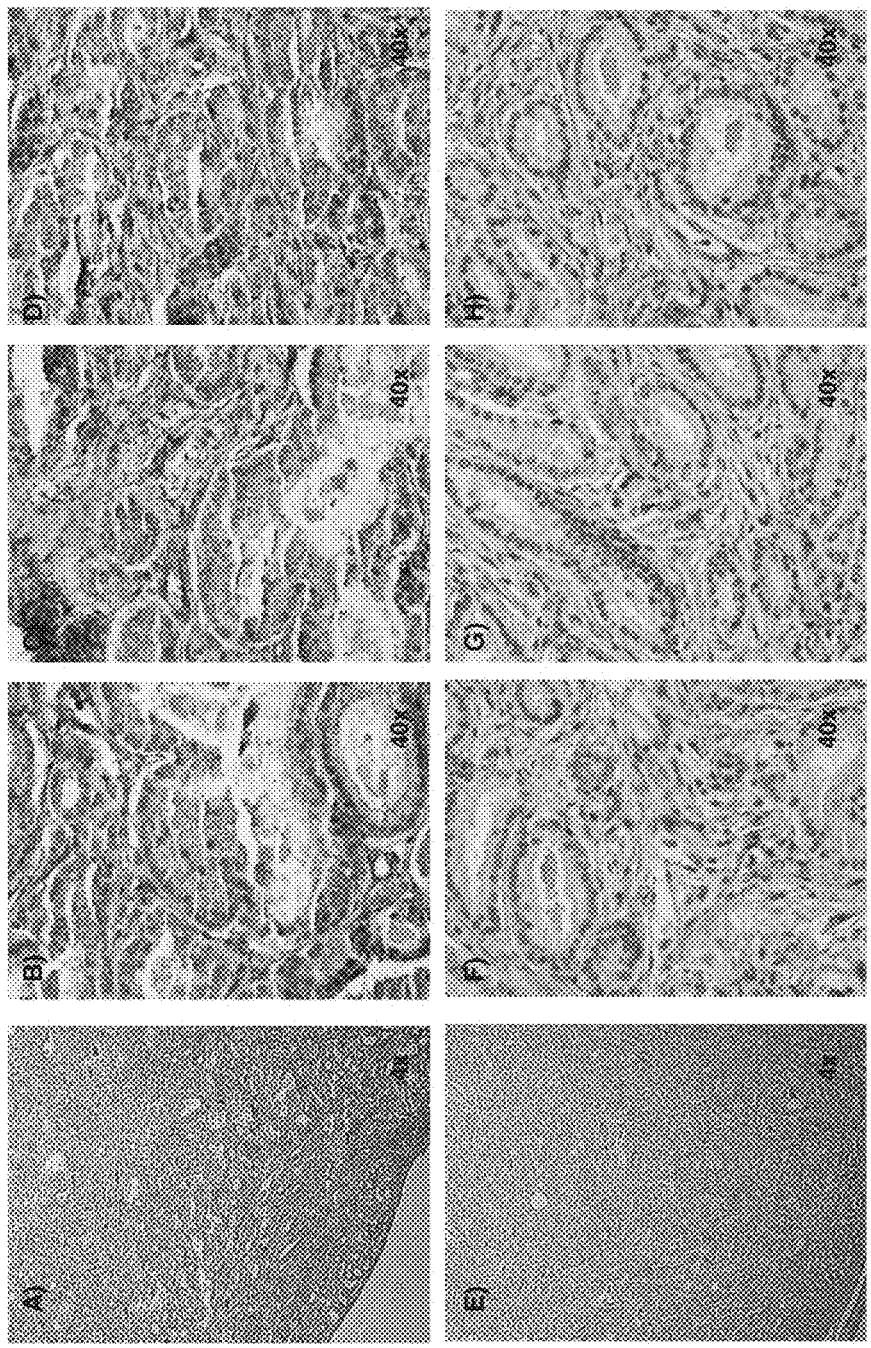

FIG. 60 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone.

Figure 61:
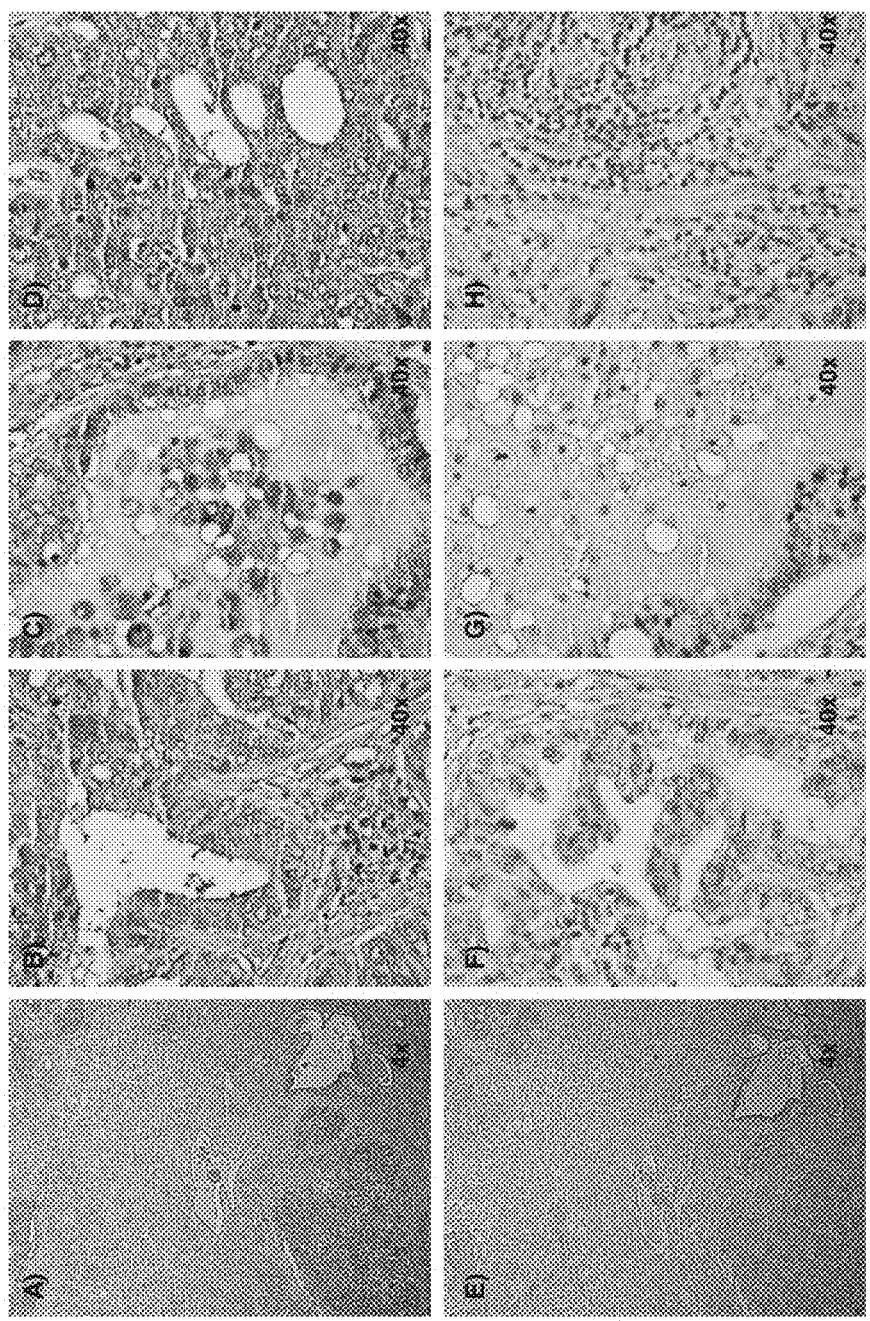

FIG. 61 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone.

Figure 62:
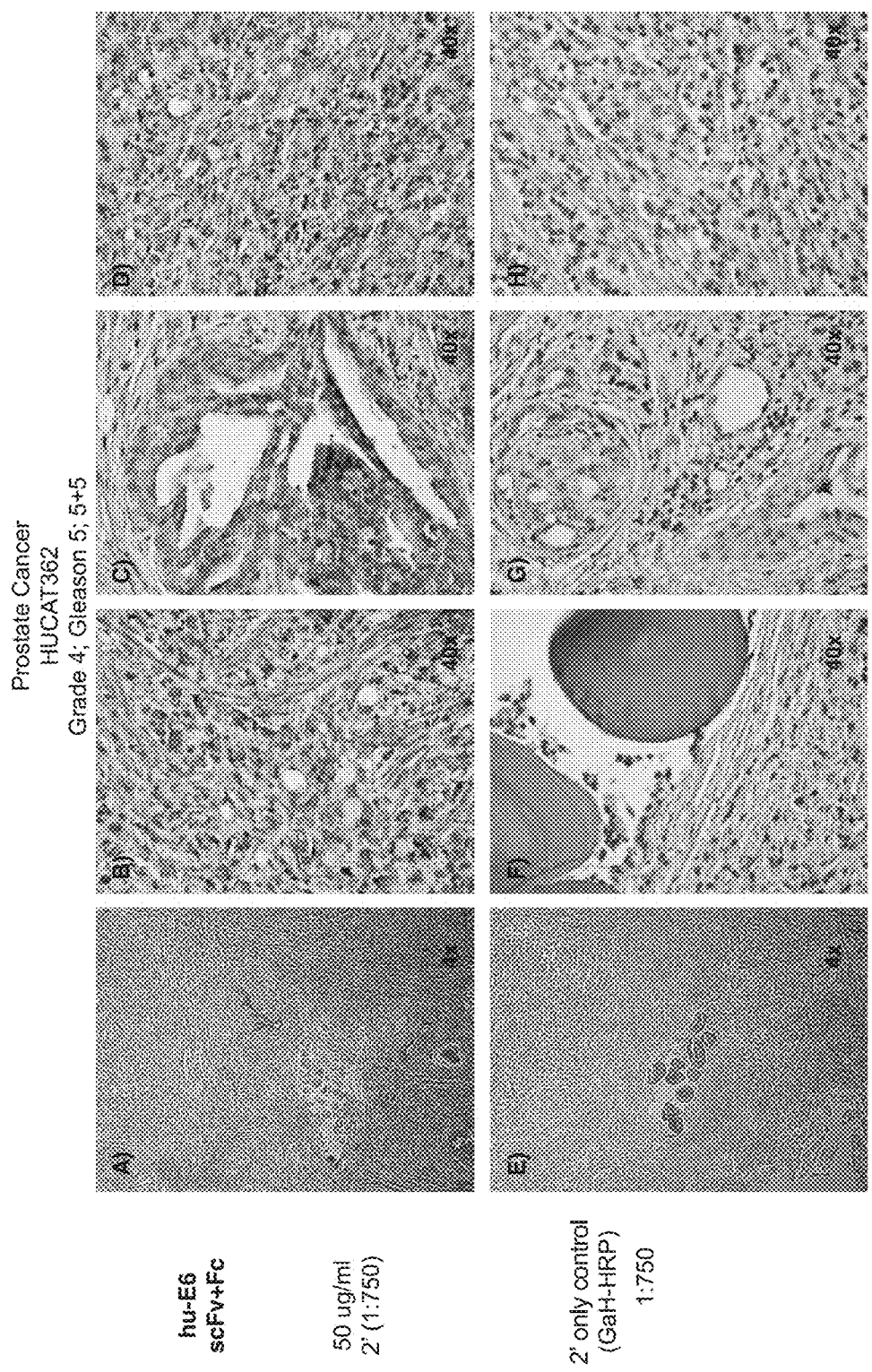

FIG. 62 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone.

DETAILED DESCRIPTION OF THE PREFERRED EMBODIMENTS

In the present application, "a" and "an" are used to refer to both single and a plurality of objects.

As used herein, "h" or "hu" placed before an antibody construct is short-hand for humanized.

As used herein, the term "antibody-like" means a molecule that may be engineered such that it contains portions of antibodies but is not an antibody that would naturally occur in nature. Examples include but are not limited to CAR (chimeric antigen receptor) T cell technology and the Ylanthia® technology. The CAR technology uses an antibody epitope fused to a portion of a T cell so that the body's immune system is directed to attack a specific target protein or cell. The Ylanthia® technology consists of an "antibody-like" library that is a collection of synthetic human Fabs that are then screened for binding to peptide epitopes from target proteins. The selected Fab regions can then be engineered into a scaffold or framework so that they resemble antibodies.

As used herein, the antibodies MN-C2, MN-E6, MN-C3 and MN-C8, may also be referred to as C2, E6, C3 and C8, respectively.

As used herein, "PSMGFR" is abbreviation for Primary Sequence of the MUC1 Growth Factor Receptor which is identified by SEQ ID NO:2, and thus is not to be confused with a six amino acid sequence. "PSMGFR peptide" or "PSMGFR region" refers to a peptide or region that incorporates the Primary Sequence of the MUC1 Growth Factor Receptor (SEQ ID NO:2).

As used herein, the "MUC1*" extra cellular domain is defined primarily by the PSMGFR sequence (GTINVHDVETQFNQYKTEAAS-RYNLTISDVSVSDVPFPFSAQSGA (SEQ ID NO:2)). Because the exact site of MUC1 cleavage depends on the enzyme that clips it, and that the cleavage enzyme varies depending on cell type, tissue type or the time in the evolution of the cell, the exact sequence of the MUC1* extra cellular domain may vary at the N-terminus.

Other clipped amino acid sequences may include SNIKFRPGSVVVQLTLAFREGTINVHDVETQFNQYK-TEAASRY (SEQ ID NO:620); or SVVVQLTLAFREGT-INVHDVETQFNQYKTEAASRY (SEQ ID NO:621).

As used herein, the term "PSMGFR" is an acronym for Primary Sequence of MUC1 Growth Factor Receptor as set forth as GTINVHDVETQFNQYKTEAAS-RYNLTISDVSVSDVPFPFSAQSGA (SEQ ID NO:2). In this regard, the "N-number" as in "N-10 PSMGFR", "N-15 PSMGFR", or "N-20 PSMGFR" refers to the number of amino acid residues that have been deleted at the N-terminal end of PSMGFR. Likewise "C-number" as in "C-10 PSMGFR", "C-15 PSMGFR", or "C-20 PSMGFR" refers to the number of amino acid residues that have been deleted at the C-terminal end of PSMGFR.

As used herein, the "extracellular domain of MUC1*" refers to the extracellular portion of a MUC1 protein that is devoid of the tandem repeat domain. In most cases, MUC1* is a cleavage product wherein the MUC1* portion consists of a short extracellular domain devoid of tandem repeats, a transmembrane domain and a cytoplasmic tail. The precise location of cleavage of MUC1 is not known perhaps because it appears that it can be cleaved by more than one enzyme. The extracellular domain of MUC1* will include most of the PSMGFR sequence but may have an additional 10-20 N-terminal amino acids.

As used herein "sequence identity" means homology in sequence of a particular polypeptide or nucleic acid to a reference sequence of nucleic acid or amino acid such that the function of the homologous peptide is the same as the reference peptide or nucleic acid. Such homology can be so close with the reference peptide such that at times the two sequences may be 90%, 95% or 98% identical yet possess the same function in binding or other biological activities.

MUC1* Antibodies (Anti-PSMGFR) for Treatment or Prevention of Cancers

We discovered that a cleaved form of the MUC1 (SEQ ID NO:1) transmembrane protein is a growth factor receptor that drives the growth of over 75% of all human cancers. The cleaved form of MUC1, which we called MUC1* (pronounced muk 1 star), is a powerful growth factor receptor. Enzymatic cleavage releases the bulk of the MUC1 extracellular domain. It is the remaining portion comprising a truncated extracellular domain, transmembrane and cytoplasmic tail that is called MUC1*. Cleavage and release of the bulk of the extracellular domain of MUC1 unmasks a binding site for activating ligands dimeric NME1, NME6, NME8, NME7-AB or NME7. Cell growth assays show that it is ligand-induced dimerization of the MUC1* extracellular domain that promotes growth (FIG. 1A-D). MUC1* positive cells treated with either bivalent 'by' anti-MUC1* antibody, monovalent 'my' or Fab, NM23-H1 dimers or NME7-AB. Bivalent anti-MUC1* antibodies stimulate growth of cancer cells whereas the monovalent Fab inhibits growth. Classic bell-shaped curve indicates ligand induced dimerization stimulates growth. Dimeric NM23-H1, aka NME1, stimulates growth of MUC1* positive cancer cells but siRNA to suppress MUC1 expression eliminate its effect (C). NME7-AB also stimulates the growth of MUC1* positive cells (D).

Figure 1:
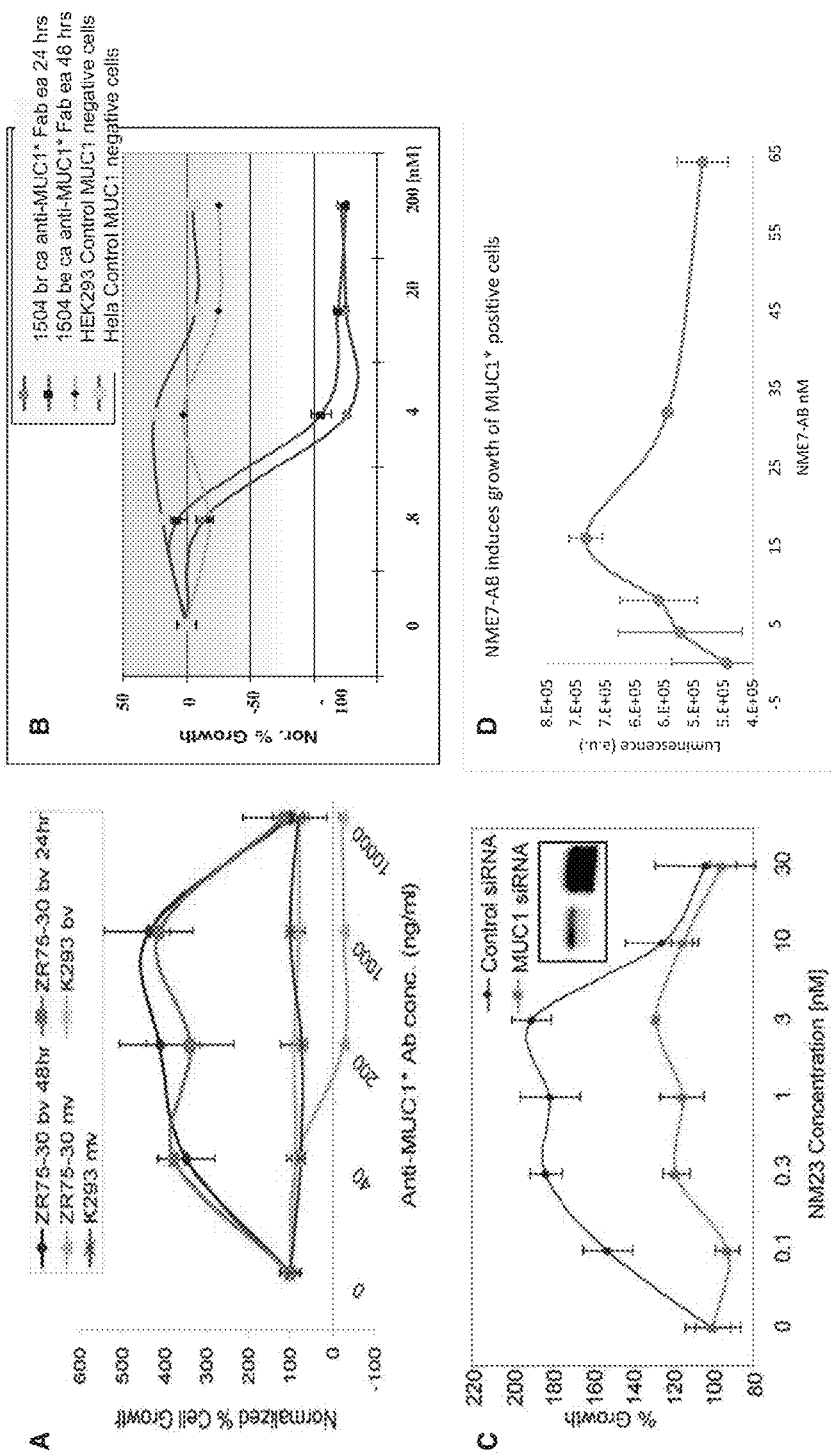
FIG. 1 shows cell growth assay graphs of MUC1* positive cells treated with either bivalent 'by' anti-MUC1* antibody, monovalent 'my' or Fab, NM23-H1 dimers or NME7-AB. Bivalent anti-MUC1* antibodies stimulate growth of cancer cells whereas the monovalent Fab inhibits growth (A, B). Classic bell-shaped curve indicates ligand induced dimerization stimulates growth. Dimeric NM23-H1, aka NME1, stimulates growth of MUC1* positive cancer cells but siRNA to suppress MUC1 expression eliminate its effect (C). NME7-AB also stimulates the growth of MUC1* positive cells (D).
Figure 2:
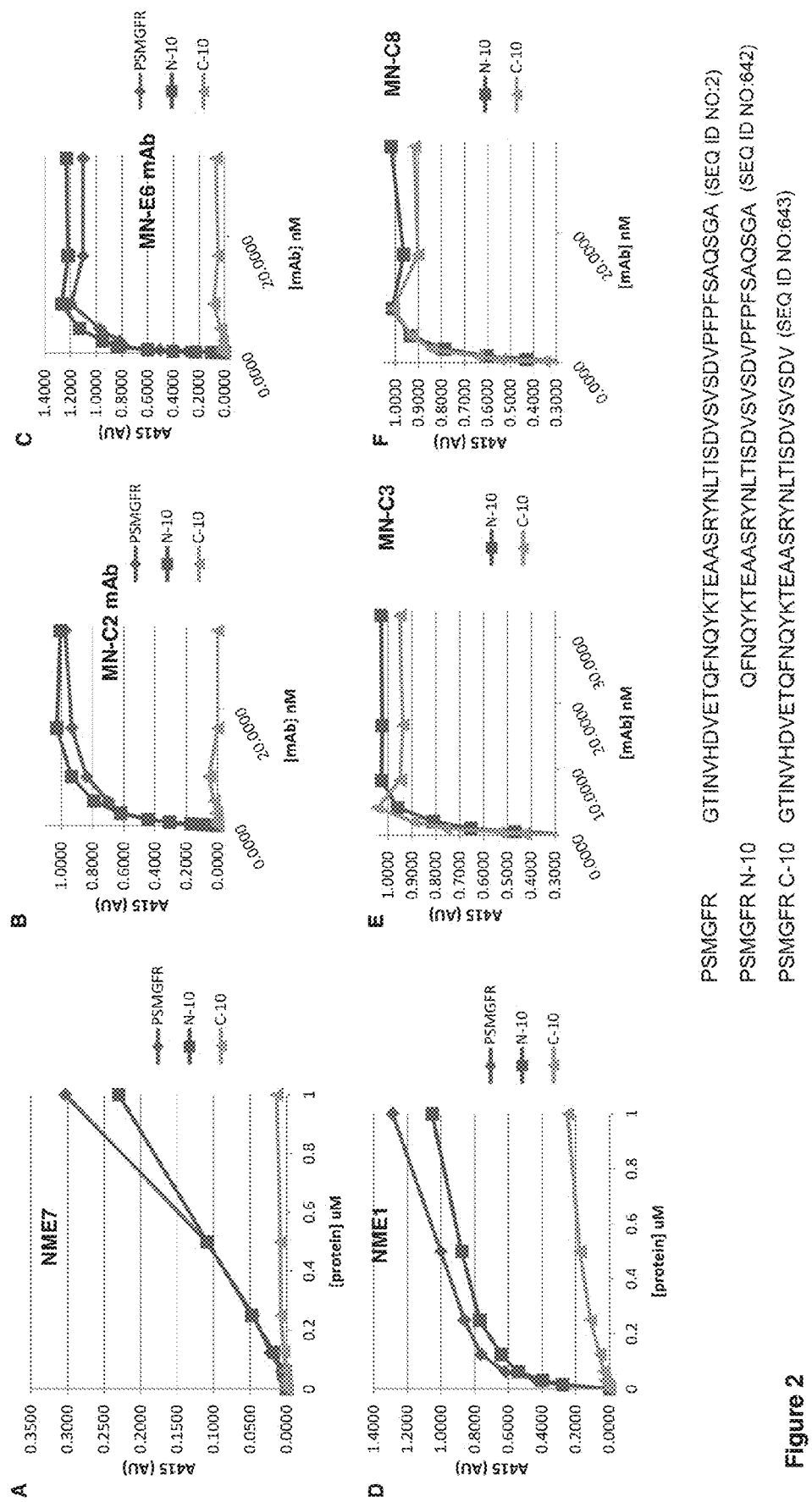
FIG. 2 shows results of ELISA assays. MUC1* peptides PSMGFR, PSMGFR minus 10 amino acids from the N-terminus aka N-10, or PSMGFR minus 10 amino acids from the C-terminus, aka C-10 are immobilized on the plate and the following are assayed for binding: NME7-AB (A), MN-C2 monoclonal antibody (B), MN-E6 monoclonal antibody (C), or dimeric NME1 (D). These assays show that NME1, NME7-AB and monoclonal antibodies MN-C2 and MN-E6 all require the first membrane proximal 10 amino acids of the MUC1* extracellular domain to bind. MUC1* peptides PSMGFR minus 10 amino acids from the N-terminus aka N-10, or PSMGFR minus 10 amino acids from the C-terminus, aka C-10, are immobilized on the plate and the following are assayed for binding: MN-C3 (E) and MN-C8 (F).

MUC1* is an ideal target for cancer drugs as it is aberrantly expressed on over 75% of all cancers and is likely overexpressed on an even higher percentage of metastatic cancers (Fessler S P, Wotkowicz M T, Mahanta S K and Bamdad C. (2009). MUC1* is a determinant of trastuzumab (Herceptin) resistance in breast cancer cells. Breast Cancer Res Treat. 118(1):113-124). After MUC1 cleavage most of its extracellular domain is shed from the cell surface. The remaining portion has a truncated extracellular domain that at least comprises the primary growth factor receptor sequence, PSMGFR (SEQ ID NO:2). Antibodies that bind to the PSMGFR sequence and especially those that competitively inhibit the binding of activating ligands such as NME proteins, including NME1, NME6, NME8 and NME7, are ideal therapeutics and can be used to treat or prevent MUC1 positive or MUC1* positive cancers, as stand-alone antibodies, antibody fragments or variable region fragments thereof incorporated into bispecific antibodies, or chimeric antigen receptors also called CARs. Therapeutics anti-MUC1* antibodies can be monoclonal, polyclonal, antibody mimics, engineered antibody-like molecules, full antibodies or antibody fragments. Examples of antibody fragments include but are not limited to Fabs, scFv, and scFv-Fc. Human or humanized antibodies are preferred for use in the treatment or prevention of cancers. In any of these antibody-like molecules, mutations can be introduced to prevent or minimize dimer formation. Anti-MUC1* antibodies that are monovalent or bispecific are preferred because MUC1* function is activated by ligand induced dimerization. Typical binding assays show that NME1 and NME7 bind to the PSMGFR peptide portion of MUC1* (FIGS. 2A, D). Further, they show that these activating growth factors bind to the membrane proximal portion of MUC1*, as they do not bind to the PSMGFR peptide if the 10 C-terminal amino acids are missing. Similarly, anti-MUC1* antibodies MN-C2 and MN-E6 bind to the PSMGFR peptide if an only if the 10 C-terminal amino acids are present (FIGS. 2 B, C). Antibodies MN-C3 and MN-C8 bind to epitopes that are different from MN-C2 and MN-E6, as they do not depend on the presence of the 10 C-terminal amino acids of the PSMGFR peptide (FIGS. 2 E, F). Antibodies MN-C2, MN-E6, MN-C3 or MN-C8, or fragments derived from them, as stand-alone antibodies or incorporated into bispecific antibodies, BiTEs or chimeric antigen receptors also called CARs expressed by immune cells are all potent anti-cancer therapeutics.

Therapeutic anti-MUC1* antibodies for use as a stand alone antibody therapeutic or for integration into a BiTE or a CAR can be selected based on specific criteria. The parent antibody can be generated using typical methods for generating monoclonal antibodies in animals. Alternatively, they can be selected by screening antibody and antibody fragment libraries for their ability to bind to a MUC1* peptide, which can be the PSMGFR peptide (SEQ ID NO:2), SNIKFRPGSVVVQLTLAFREGTINVHDVETQFNQYK-TEAASRY (SEQ ID NO:620); or SVVVQLTLAFREGT-INVHDVETQFNQYKTEAASRY (SEQ ID NO:621).

Figure 3:
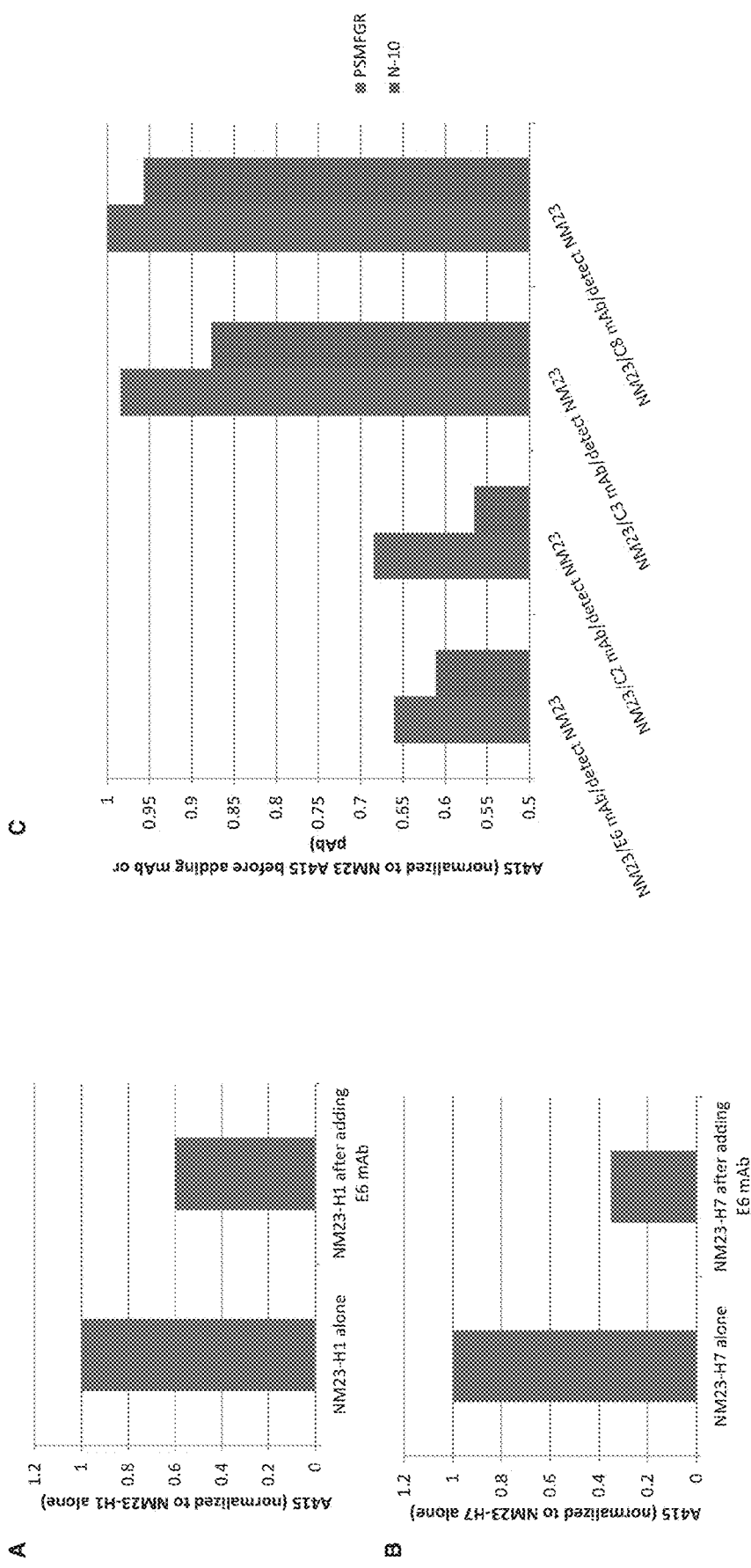
FIG. 3 shows results of competitive ELISA assays. The PSMGFR MUC1* peptide is immobilized on the plate and dimeric NM23-H1, aka NME1, is added either alone or after the MN-E6 antibody has been added (A). The same experiment was performed wherein NM23-H7, NME7-AB, is added alone or after MN-E6 has been added (B). Results show that MN-E6 competitively inhibits the binding of MUC1* activating ligands NME1 and NME7. In a similar experiment (C), PSMGFR or PSMGFR minus 10 amino acids from the N-terminus, aka N-10, is immobilized on the plate. Dimeric NM23-H1 is then added. Anti-MUC1* antibodies MN-E6, MN-C2, MN-C3 or MN-C8 are then tested for their ability to compete off the NM23-H1. Results show that although all three antibodies bind to the PSMGFR peptides, MN-E6 and MN-C2 competitively inhibit binding of the MUC1* activating ligands.

Resultant antibodies or antibody fragments generated or selected in this way can then be further selected by passing additional screens. For example, antibodies or antibody fragments become more preferred based on their ability to bind to MUC1* positive cancer cells or tissues but not to MUC1 negative cancer cells or tissues. Further, anti-MUC1* antibodies or antibody fragments may be de-selected as anti-cancer therapeutics if they bind to stem or progenitor cells. Anti-MUC1* antibodies or antibody fragments become more preferred if they have the ability to competitively inhibit the binding of activating ligands to MUC1*. FIG. 3A-C shows that MN-E6 and MN-C2 competitively inhibit the binding of activating ligands NME1 and NME7 to MUC1*. A process for selecting anti-MUC1* antibodies for use in treating a patient diagnosed with a MUC1 positive cancer, at risk of developing a MUC1 positive cancer or suspected of having a MUC1 positive cancer comprises one or more of the following steps of selecting antibodies or antibody fragments that 1) bind to the PSMGFR peptide; 2) bind to the N-10 PSMGFR peptide; 3) bind to cancer cells; 4) do not bind to stem or progenitor cells; and 5) competitively inhibited the binding of dimeric NME1 or NME7-AB to the PSMGFR peptide. For example, FIG. 3A-C show that monoclonals MN-E6 and MN-C2 satisfy all five criteria, while monoclonals MN-C3 and MN-C8 do not competitively inhibit the binding of activating ligands NME1 and NME7 (Figure M3 C). However, antibodies or antibody fragments derived from MN-C3 and MN-C8 are equally potent as anti-cancer agents when integrated into a BiTE or a CAR as in these methods, the killing effect of the immune cells is more important than the ability to inhibit the binding of activating ligands. In addition, toxic agents conjugated to MN-E6, MN-C2, MN-C3 or MN-C8 are potent anti-cancer therapeutics. Recall that the MUC1* growth factor receptor is activated by ligand-induced dimerization of its extracellular domain. Therefore the ideal antibody therapeutic should not dimerize the MUC1* extracellular domain. Preferably, suitable antibodies in this regard include monovalent antibodies such as those generated in lamas and camels, Fabs, scFv's, single domain antibodies (sdAb), scFv-Fc as long as the Fc portion is constructed such that it does not homo-dimerize.

Figure 4:
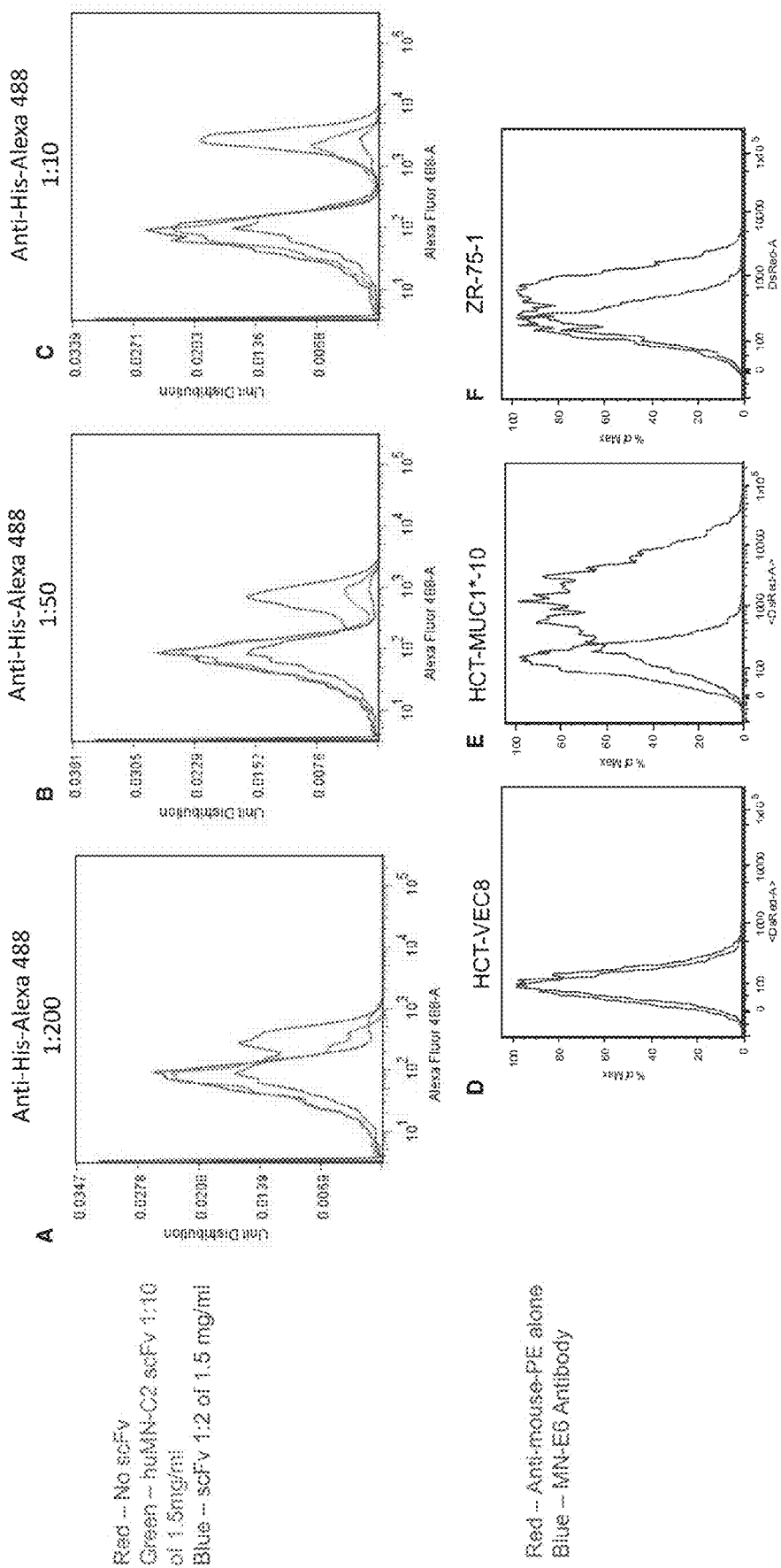
FIG. 4 shows FACS scans of anti-MUC1* antibodies binding specifically to MUC1* positive cancer cells and MUC1* transfected cells but not MUC1* or MUC1 negative cells. ZR-75-1, aka 1500, MUC1* positive breast cancer cells were stained with 1:2 or 1:10 dilutions of the 1.5 ug/ml humanized MN-C2. After two washes, cells were stained with secondary antibody, Anti-Penta-His antibody at conjugated to Alexa 488 (Qiagen) dilutions of 1:200 (A), 1:50 (B), or 1:10 (C) to detect the 6xHis tag on the huMN-C2 scFv. Flow cytometric analysis revealed a concentration-dependent shift of a subset of cells, indicating specific binding, which is unseen in the absence of the MN-C2 scFv (A-C). In another case, MN-E6 was used to stain MUC1 negative HCT-116 colon cancer cells transfected with the empty vector, single cell clone #8 (D), HCT-116 colon cancer cells transfected with MUC1* single cell clone #10 (E), or ZR-75-1, aka 1500, MUC1* positive breast cancer cells (F). As the FACS scans show, both MN-C2 and MN-E6 only stain MUC1* positive cells and not MUC1 or MUC1* negative cells.
Figure 5:
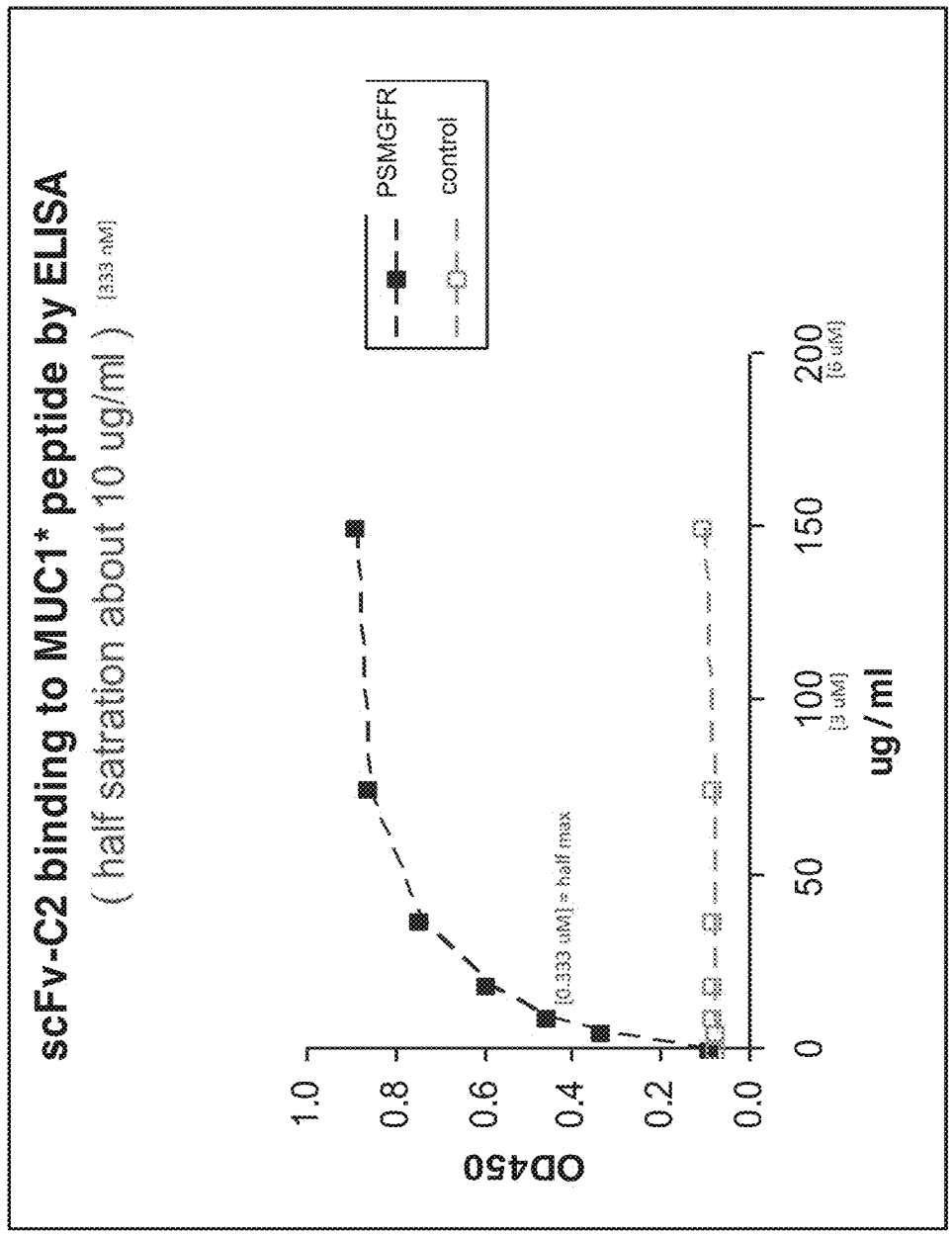
FIG. 5 shows a graph of an ELISA in which surface is coated with either the MUC1* PSMGFR peptide or a control peptide. Humanized MN-C2 scFv is then incubated with the surface, washed and detected according to standard methods. The ELISA shows that the huMN-C2 scFv binds to the MUC1* peptide with an EC-50 of about 333 nM.
Figure 6:
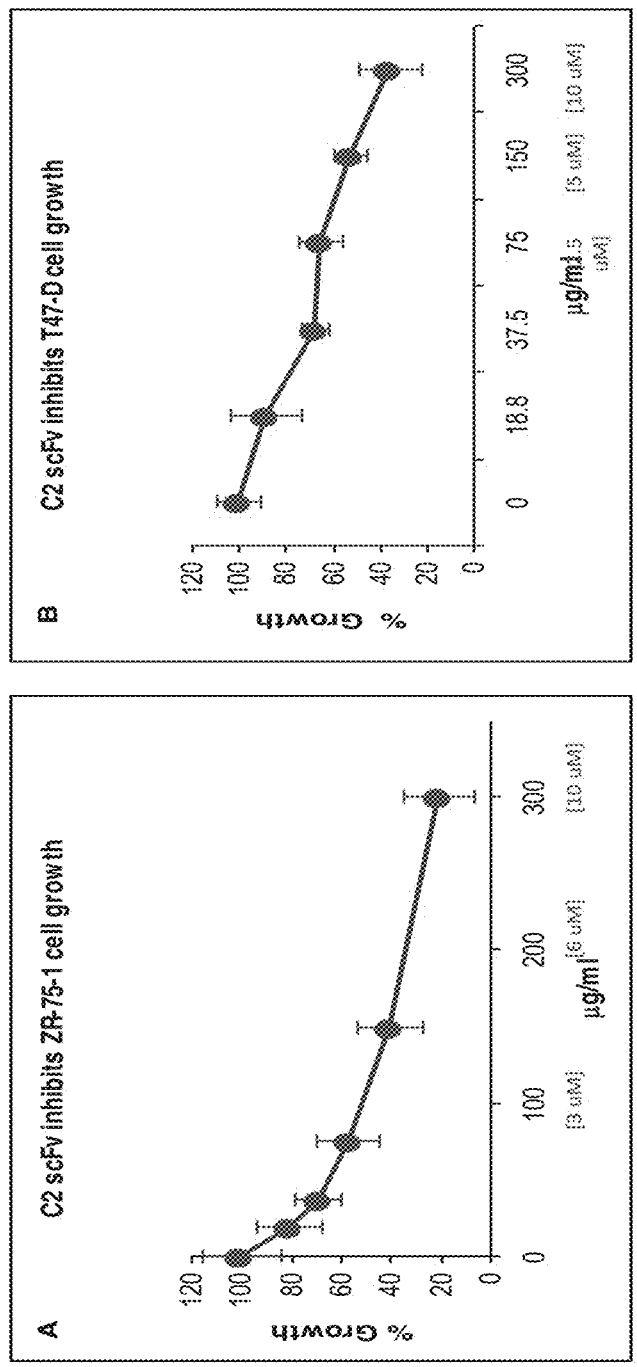
FIG. 6 shows graphs of cancer cell growth inhibition by MUC1* antibody variable region fragment humanized MN-C2 scFv. hMN-C2 scFv potently inhibited the growth of ZR-75-1, aka 1500, MUC1* positive breast cancer cells (A) and T47D MUC1* positive breast cancer cells (B) with approximately the same EC-50 as the in vitro ELISAs.

FACS scans show that anti-MUC1* antibodies MN-C2, MN-E6, MN-C3 and MN-C8 specifically bind to MUC1* positive cancer cells and MUC1* transfected cells but not MUC1* or MUC1 negative cells. In one example, a humanized MN-C2 scFv is shown to bind to ZR-75-1, aka 1500, MUC1* positive breast cancer cells (FIG. 4A-C). MN-E6 was shown to bind to MUC1 negative HCT-116 colon cancer cells if an only if they were transfected with MUC1*. MN-E6 also bound to MUC1* positive cancer cells such as ZR-75-1, aka 1500, MUC1* positive breast cancer cells (FIGS. 4 D-F). Binding assays such as ELISAs, immunofluorescence, and the like all confirm that MN-C2 and MN-E6 bind to the PSMGFR peptide and to live MUC1 positive cancer cells. Humanized anti-MUC1* antibodies are selected based on their ability to also bind to the PSMGFR peptide or to MUC1 positive cancer cells. FIG. 5 shows that humanized MN-C2 scFv binds with high affinity to the MUC1* peptide PSMGFR with an EC-50 of about 333 nM. Humanized MN-C2 scFv, like Fabs, potently inhibits the growth of MUC1* positive cancer cells as is shown in one example in FIG. 6A, B.

Figure 7:
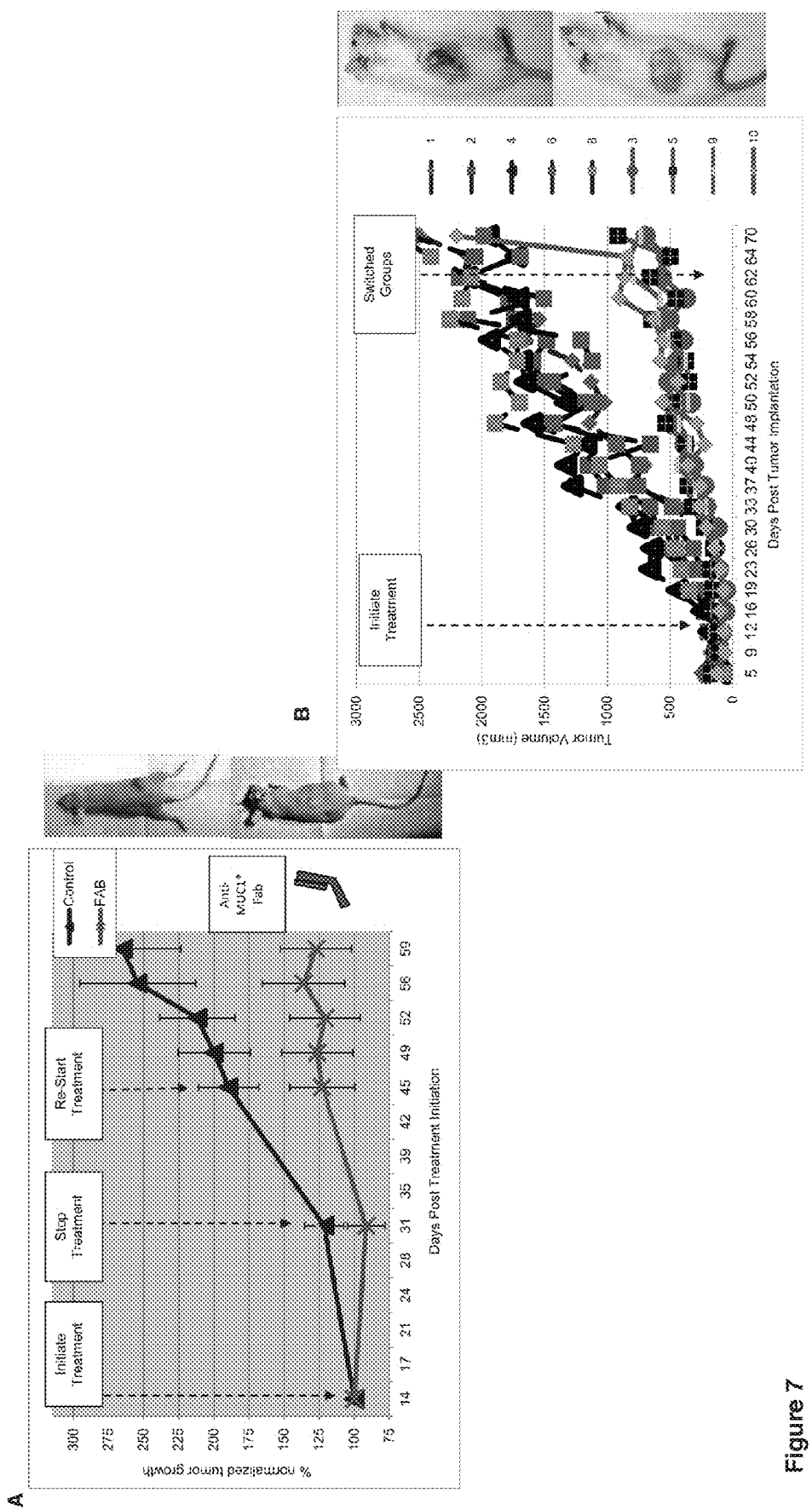
FIG. 7 shows graphs of tumor growth in immune compromised mice that have been implanted with human tumors then treated with anti-MUC1* antibody MN-E6 Fab or mock treatment. Female nu/nu mice implanted with 90-day estrogen pellets were implanted with 6 million T47D human breast cancer cells that had been mixed 50/50 with Matrigel. Mice bearing tumors that were at least 150 mm 3 and had three successive increases in tumor volume were selected for treatment. Animals were injected subcutaneously twice per week with 80 mg/kg MN-E6 Fab and an equal number of mice fitting the same selection criteria were injected with vehicle alone (A). Male NOD/SCID mice were implanted with 6 million DU-145 human prostate cancer cells that had been mixed 50/50 with Matrigel. Mice bearing tumors that were at least 150 mm 3 and had three successive increases in tumor volume were selected for treatment. Animals were injected subcutaneously every 48 hours with 160 mg/kg MN-E6 Fab and an equal number of mice fitting the same selection criteria were injected with vehicle alone (B). Tumors were measured independently by two researchers twice per week and recorded. Statistics were blindly calculated by independent statistician, giving a P value of 0.0001 for each. Anti-MUC1* Fab inhibited breast cancer growth and prostate cancer growth. Treatment had no effect on weight, bone marrow cell type or number.

The Fabs of MN-E6 and MN-C2 or the comparable single chain variable regions derived from them potently inhibit the growth of MUC1* positive cancers in vitro and in vivo. In several examples, the Fabs of Anti-MUC1* antibodies inhibited the growth of human MUC1* positive cancers in vivo. In one case, immune-compromised mice were implanted with human breast tumors then treated with MN-E6 Fab after tumor engraftment. FIG. 7A shows that MN-E6 Fab potently inhibited the growth of MUC1* positive breast cancers. Female nu/nu mice implanted with 90-day estrogen pellets were implanted with 6 million T47D human breast cancer cells that had been mixed 50/50 with Matrigel. Mice bearing tumors that were at least 150 mm^3 and had three successive increases in tumor volume were selected for treatment. Animals were injected sub cutaneously twice per week with 80 mg/kg MN-E6 Fab and an equal number of mice fitting the same selection criteria were injected with vehicle alone (A). In another aspect, MN E6 was shown to halt the growth of prostate cancer. FIG. 7B shows that MN-E6 Fab potently inhibited the growth of MUC1* positive prostate cancers. Male NOD/SCID mice were implanted with 6 million DU-145 human prostate cancer cells that had been mixed 50/50 with Matrigel. Mice bearing tumors that were at least 150 mm^3 and had three successive increases in tumor volume were selected for treatment. Animals were injected sub-cutaneously every 48 hours with 160 mg/kg MN-E6 Fab and an equal number of mice fitting the same selection criteria were injected with vehicle alone (B). Tumors were measured independently by two researchers twice per week and recorded. Statistics were blindly calculated by independent statistician, giving a P value of 0.0001 for each. Anti-MUC1* Fab inhibited breast cancer growth and prostate cancer growth. Treatment had no effect on weight, bone marrow cell type or number. The MN-E6 Fab effectively inhibited the growth of the tumors, while the control group's tumors continued to grow until sacrifice. No adverse effects of treatment were observed or detected.

Figure 13:
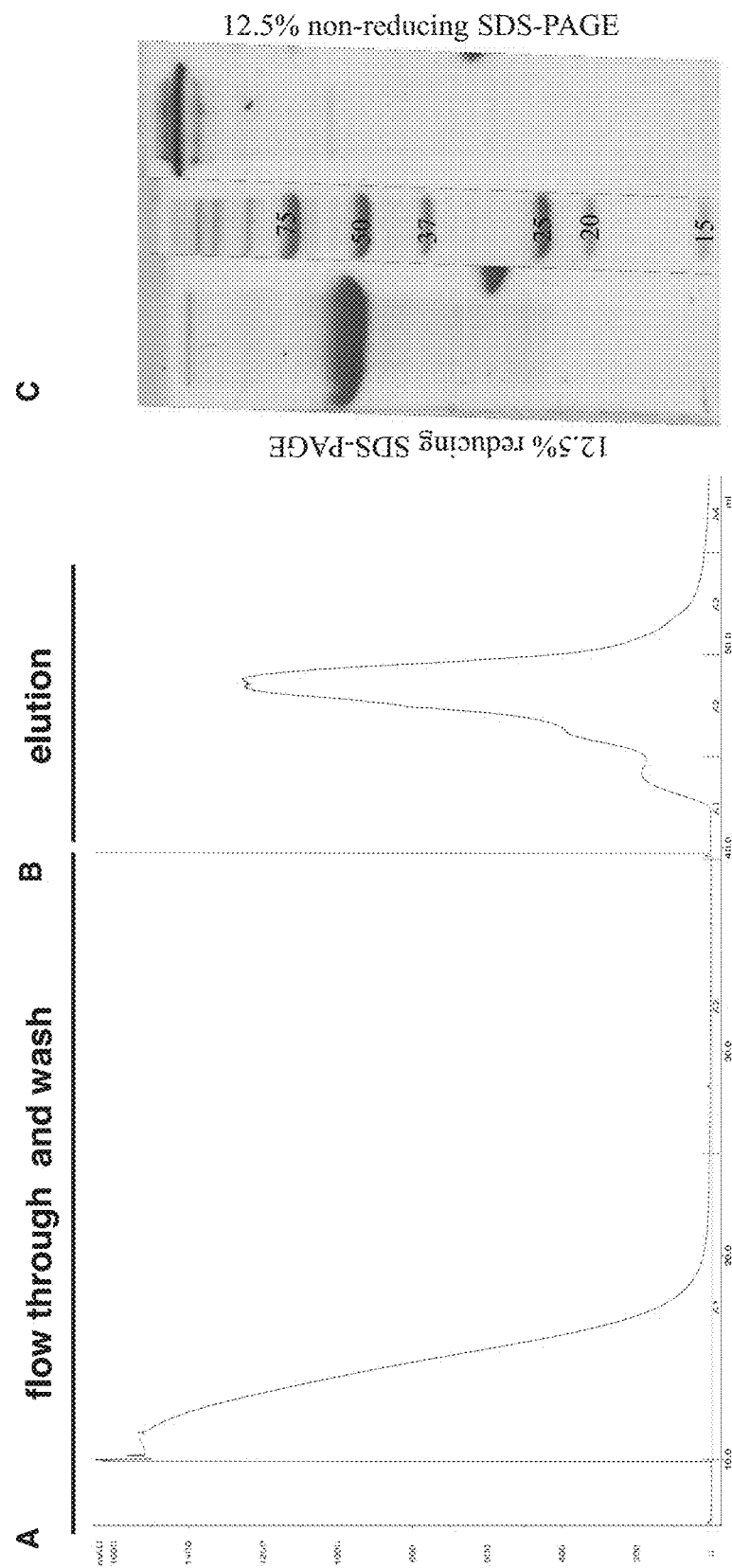
FIG. 13 shows FPLC traces of the purification of MN-E6 scFv-Fc fusion protein that was grown in low IgG FBS over a Protein A affinity column. A) is the trace of the flow through. B) is the trace of the elution. C) shows the purified protein on a reducing or non-reducing gel.
Figure 14:
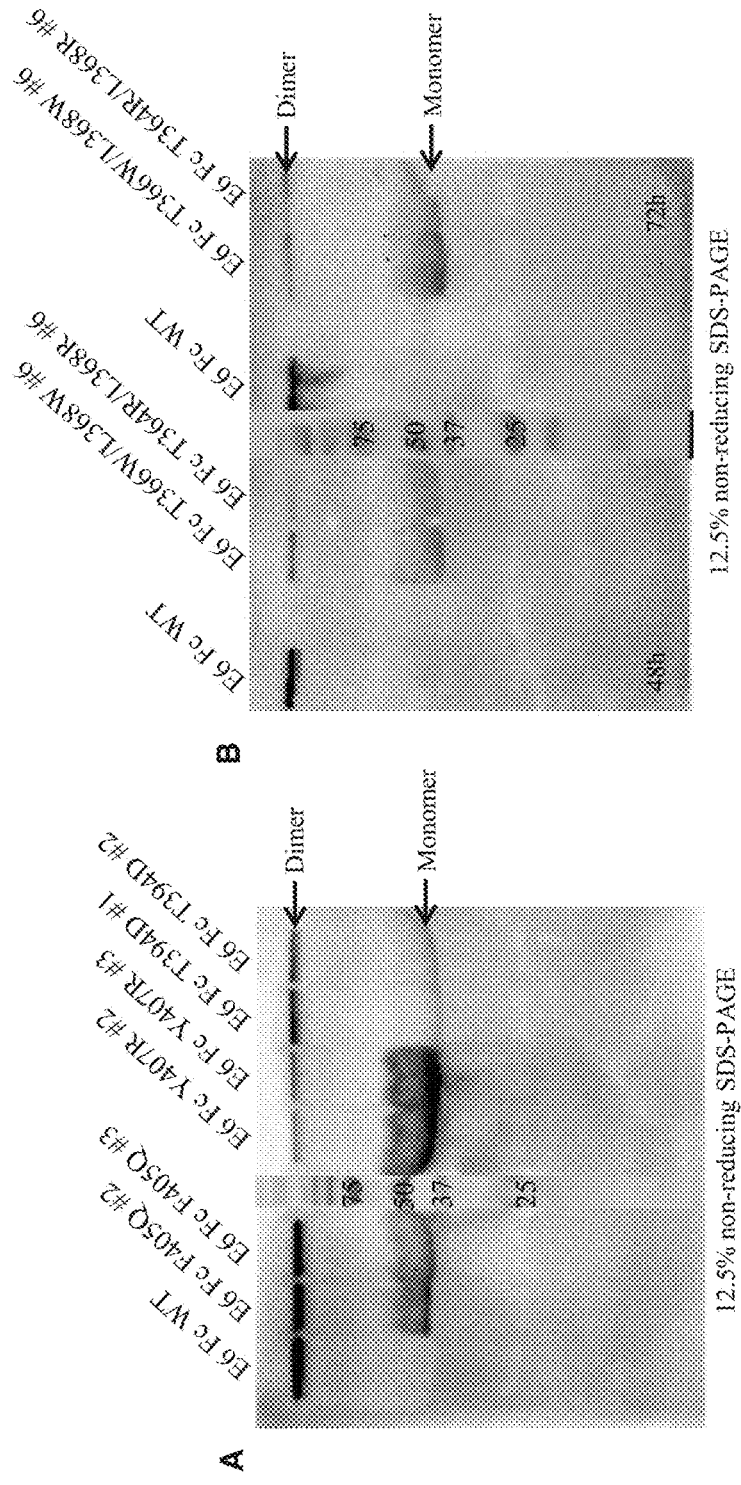
FIG. 14 shows photographs of SDS-PAGE characterization of purified MN-E6 scFv-Fc fusion proteins on a non-reducing gels, wherein the Fc portion that was fused to the MN-E6 was either wild type (wt) or mutated as follows: A) F405Q, Y407R, T394D; B) T366W/L368W, T364R/L368R, T366W/L368W or T364R/L368R. Fc mutants F405Q, Y407R, T366W/L368W, T364R/L368R, T366W/L368W and T364R/L368R all favored monomer over dimer formation. The reference construct amino acid sequence for the indicated mutations is SEQ ID NO:273.
Figure 15:
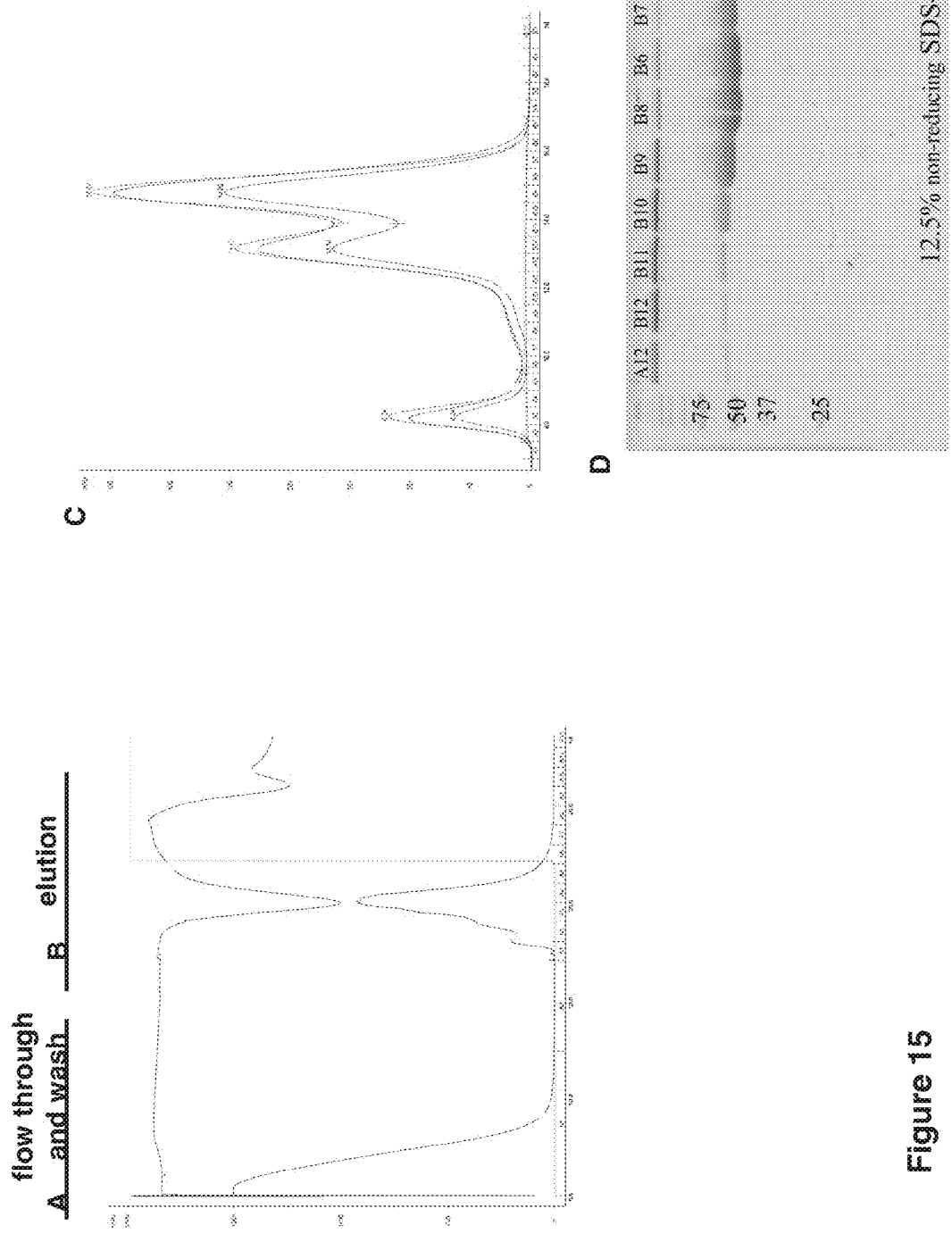
FIG. 15 shows FPLC traces of the purification of MN-E6 scFv-Fc Y407Q fusion protein that was grown in low IgG FBS over a Protein A affinity column. A) is the trace of the flow through. B) is the trace of the elution. The protein was further purified by size exclusion over an 5200 column (C). (D) is a photograph of an SDS-PAGE gel showing which fractions had a predominance of monomer. The reference construct amino acid sequence for the indicated mutations is SEQ ID NO:273.
Figure 16:
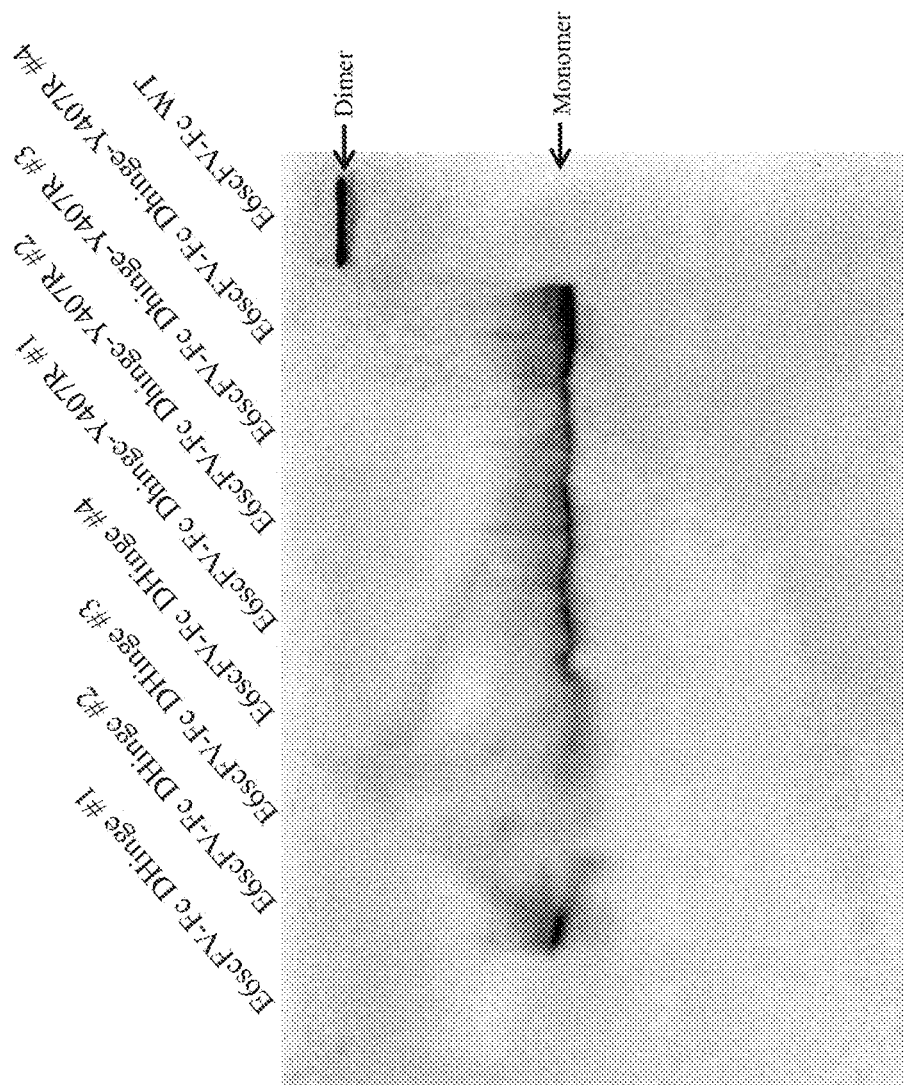
FIG. 16 shows a photograph of SDS-PAGE characterization of purified MN-E6 scFv-Fc-mutant fusion proteins on a non-reducing gel, wherein the Fc portion that was fused to the MN-E6 scFv was either wild type (wt) or mutated by elimination of the hinge region, 'DHinge', of the Fc or elimination of the hinge region of the Fc and also bearing the Y407R mutation. All the Fc mutants favored monomer over dimer formation. The reference construct amino acid sequence for the indicated mutations is SEQ ID NO:273.
Figure 17:
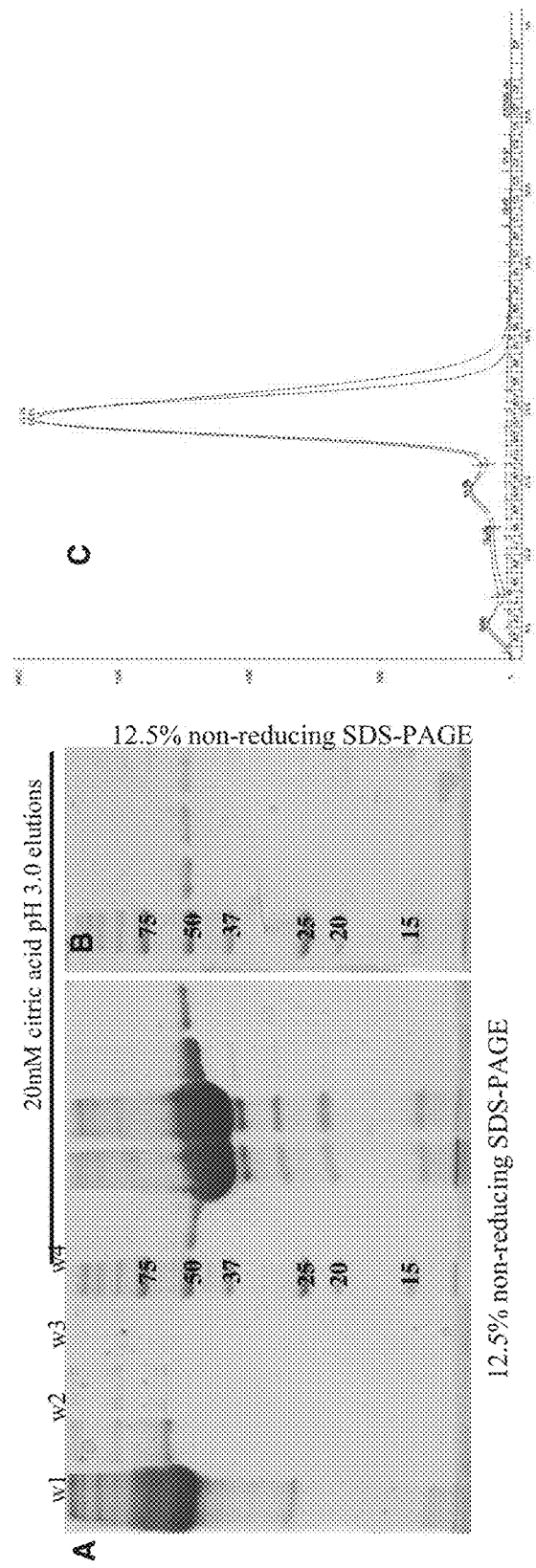
FIGS. 17. A and B show photograph of non-reducing SDS-PAGE characterization of large scale expression and purification of MN-E6 scFv-Fc hingeless mutant, showing that it is a monomer. FPLC characterization and purification of MN-E6 scFv-Fc hingeless mutant is shown (C).
Figure 18:
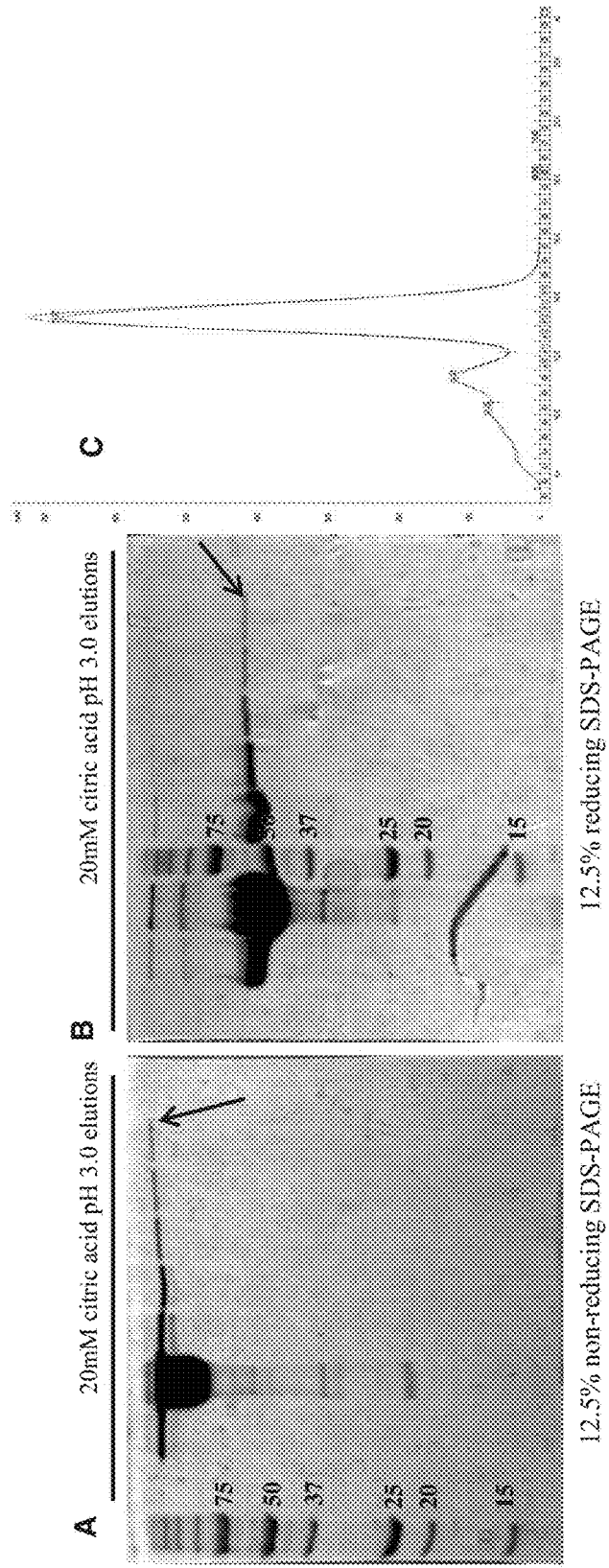
FIG. 18 shows photographs of the SDS-PAGE characterization of the purified MN-C3 scFv-Fc fusion protein on a non-reducing gel (A) or a reducing gel (B). The protein was purified by size exclusion. The FPLC trace is shown (C).
Figure 19:
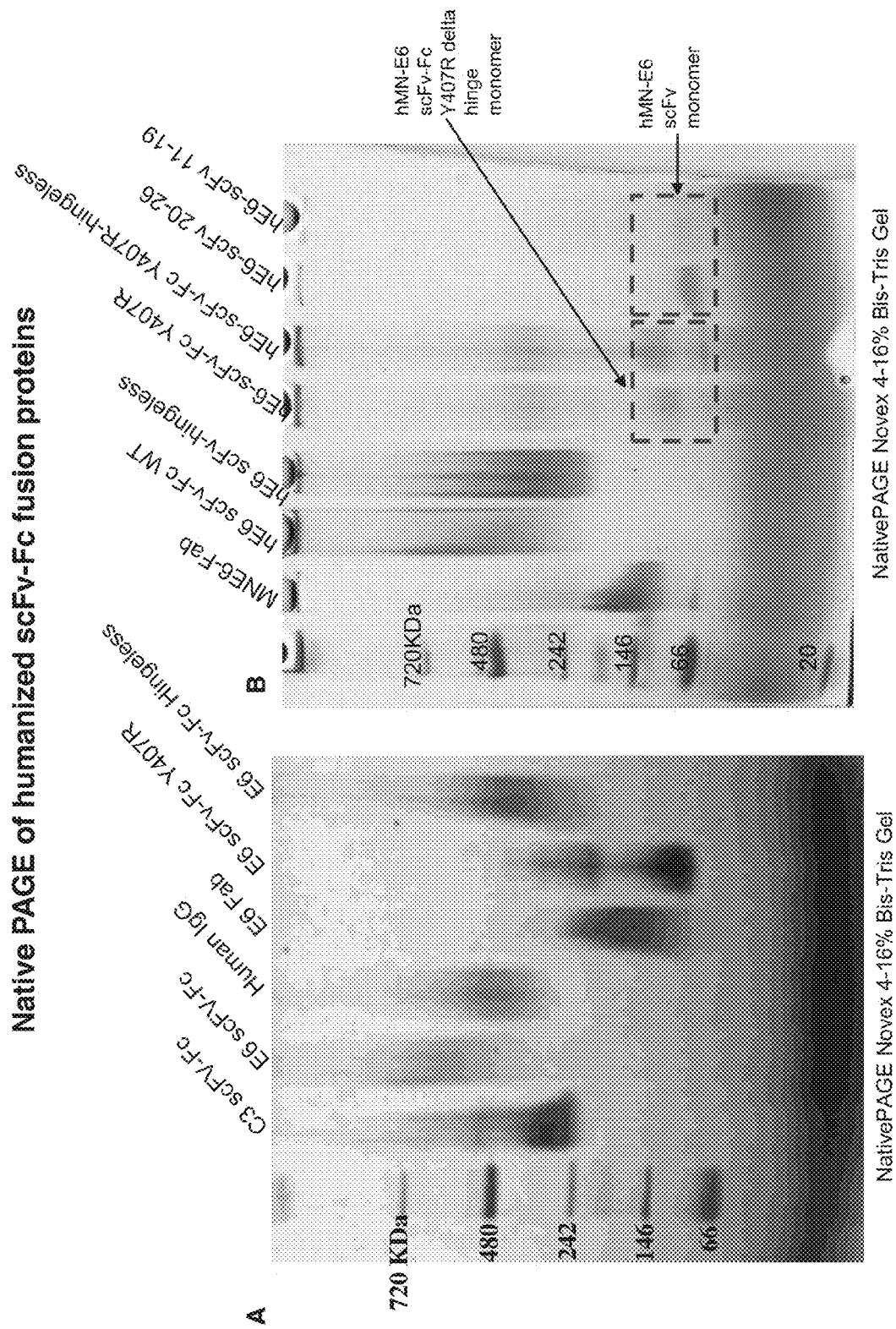
FIG. 19 shows photographs of Native gels of MN-C3 or MN-E6 Fabs, scFv, scFv-Fc, wherein the Fc portion is wild type or mutants that prefer or are exclusively monomers. Native gels show that the Y407R Fc mutation (A) and the double mutant Y407R and a deleted hinge (B) favor monomer over dimer the best. Note that proteins are loaded onto a gel at much higher concentrations than typical use concentrations. The dimer formation of other Fc mutants may only reflect the fact that loading concentration is very high.

A recombinant MN-E6 was constructed that like the Fab is monomeric. In this case, MN-E6 was humanized. There are a number of methods known to those skilled in the art for humanizing antibodies. In addition to humanizing, libraries of human antibodies can be screened to identify other fully human antibodies that bind to the PSMGFR. A single chain of the humanized MN-E6 variable region, called an scFv, was genetically engineered such that it was connected to the Fc portion of the antibody (SEQ ID NO:256 and 257). Fc regions impart certain benefits to antibody fragments for use as therapeutics. The Fc portion of an antibody recruits complement, which in general means it can recruit other aspects of the immune system and thus amplify the anti-tumor response beyond just inhibiting the target. The addition of the Fc portion also increases the half-life of the antibody fragment (Czajkowsky D M, Hu J, Shao Z and Pleass R J. (2012) Fc-fusion proteins: new developments and future perspectives. EMBO Mol Med. 4(10):1015-1028). However, the Fc portion of an antibody homodimerizes, which in the case of anti-MUC1* antibody based therapeutics is not optimal since ligand-induced dimerization of the MUC1* receptor stimulates growth. As can be seen in FIG. 13 B, humanized MN-E6 scFv-Fc is a dimer, in part due to disulfide bonding. Therefore, mutations in the Fc region that resist dimer formation are preferred for anti-MUC1* anti-cancer therapeutics. Deletion of the hinge region (hingeless also called delta hinge or Dhinge in some figures and examples SEQ ID NO: 288 and 289) and other mutations in the Fc region that make the Fc-mutant resistant to dimerization were made. The following mutations were made in the CH3 domain to create a monomeric scFv-Fc fusion protein: Y407R (SEQ ID NO: 278 and 279), F405Q (SEQ ID NO: 280 and 281), T394D (SEQ ID NO: 282 and 283), T366W/L368W (SEQ ID NO: 284 and 285), T364R/L368R (SE ID NO: 286 and 287). FIG. 14 shows photographs of SDS-PAGE characterization of purified MN-E6 scFv-Fc fusion proteins on a non-reducing gels, wherein the Fc portion that was fused to the MN-E6 was either wild type (wt) or mutated as follows: A) F405Q, Y407R, T394D; B) T366W/L368W, T364R/L368R, T366W/L368W or T364R/L368R. Fc mutants F405Q, Y407R, T366W/L368W, T364R/L368R, T366W/L368W and T364R/L368R all favored monomer over dimer formation. FIG. 15 shows FPLC traces of the purification of MN-E6 scFv-Fc Y407Q fusion protein that was grown in low IgG FBS over a Protein A affinity column. A) is the trace of the flow through. B) is the trace of the elution. The protein was further purified by size exclusion over an 5200 column (C). (D) is a photograph of an SDS-PAGE gel showing which fractions had a predominance of monomer. FIG. 16 shows a photograph of SDS-PAGE characterization of purified MN-E6 scFv-Fc-mutant fusion proteins on a non-reducing gel, wherein the Fc portion that was fused to the MN-E6 scFv was either wild type (wt) or mutated by elimination of the hinge region, 'DHinge', of the Fc or elimination of the hinge region of the Fc and also bearing the Y407R mutation. All the Fc mutants favored monomer over dimer formation. The reference construct amino acid sequence for the indicated mutation is SEQ ID NO:273. Other relevant sequences are SEQ ID NOS:289 and 279. FIG. 17A-C. A and B show photograph of non-reducing SDS-PAGE characterization of large scale expression and purification of MN-E6 scFv-Fc hingeless mutant, showing that it is a monomer. FPLC characterization and purification of MN-E6 scFv-Fc hingeless mutant is shown (C). FIG. 18A-C shows photographs of the SDS-PAGE characterization of the purified MN-C3 scFv-Fc fusion protein on a non-reducing gel (A) or a reducing gel (B). The protein was purified by size exclusion. The FPLC trace is shown (C). FIG. 19A-B shows photographs of Native gels of MN-C3 or MN-E6 Fabs, scFv, scFv-Fc, wherein the Fc portion is wild type or mutants that prefer or are exclusively monomers. Native gels show that the Y407R Fc mutation (A) and the double mutant Y407R and a deleted hinge (B) favor monomer over dimer the best. Note that proteins are loaded onto a gel at much higher concentrations than typical use concentrations. The dimer formation of other Fc mutants may only reflect the fact that loading concentration is very high.

Figure 10:
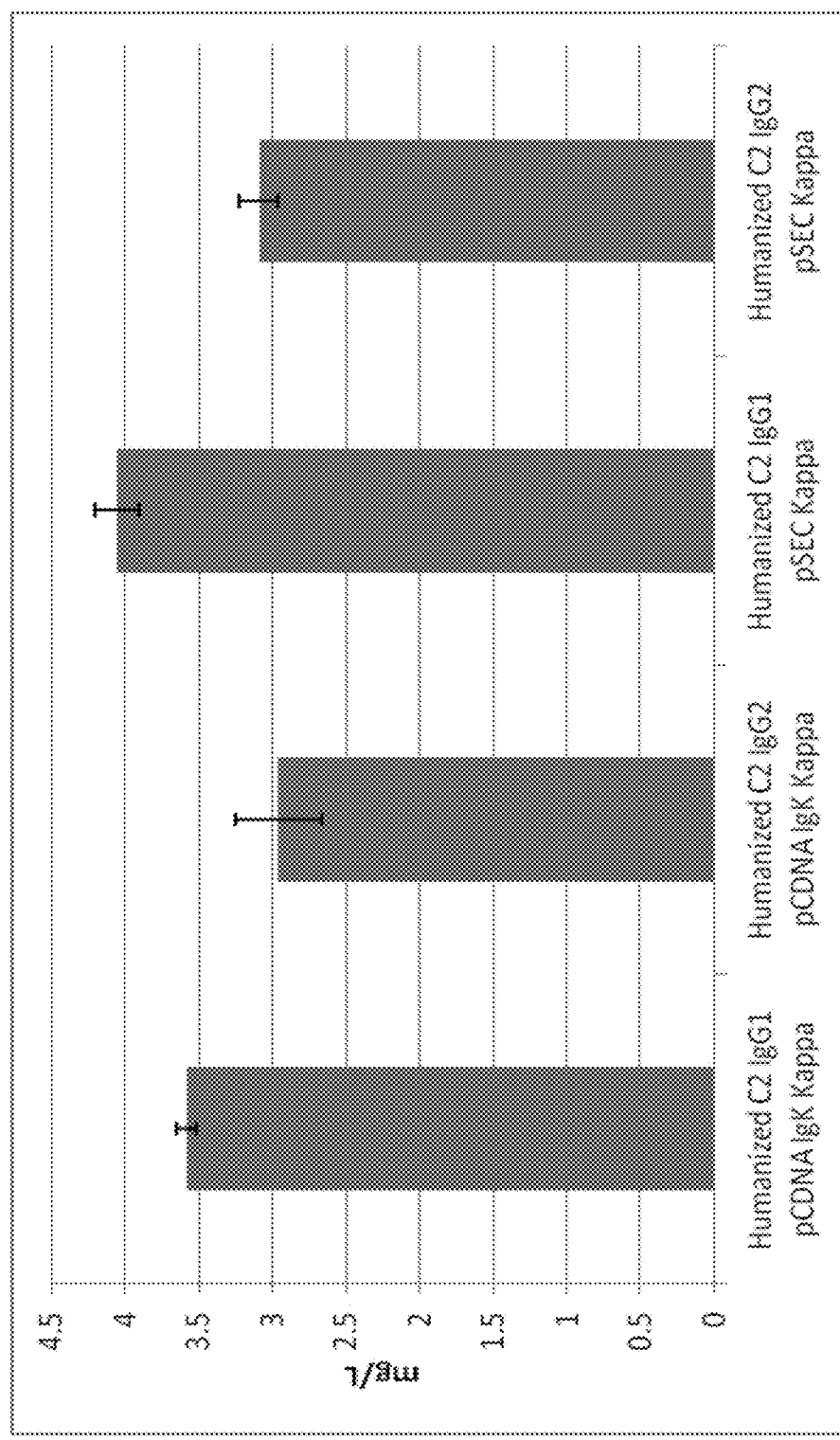
FIG. 10 is a graph of an ELISA assay showing differing levels of expression of humanized MN-C2 anti-MUC1* antibody depending on whether the light chain was kappa or lambda and whether the variable portion was fused to a human IgG1 or IgG2.

Some mutations or deletions were so effective that, even when loaded onto a gel at high concentrations, they resist dimer formation (FIG. 14A, B). The Y407R mutation results in a nearly pure population of dimeric scFv-Fc (FIG. 10). Similarly deletions of the hinge region of the Fc result in fusion proteins that are monomers rather than dimers. Combinations of mutations can result in even more effective resistance of dimer formation (FIGS. 16 and 17). These and other mutations and combinations thereof were introduced into CH2-CH3 (SEQ ID NO:274 and 275) and CH3 (SEQ ID NO:276 and 277) fusion proteins such as scFv or in the hingeless Fc-fusion proteins such as scFv and were shown to eliminate or minimize dimerization.

Figure 20:
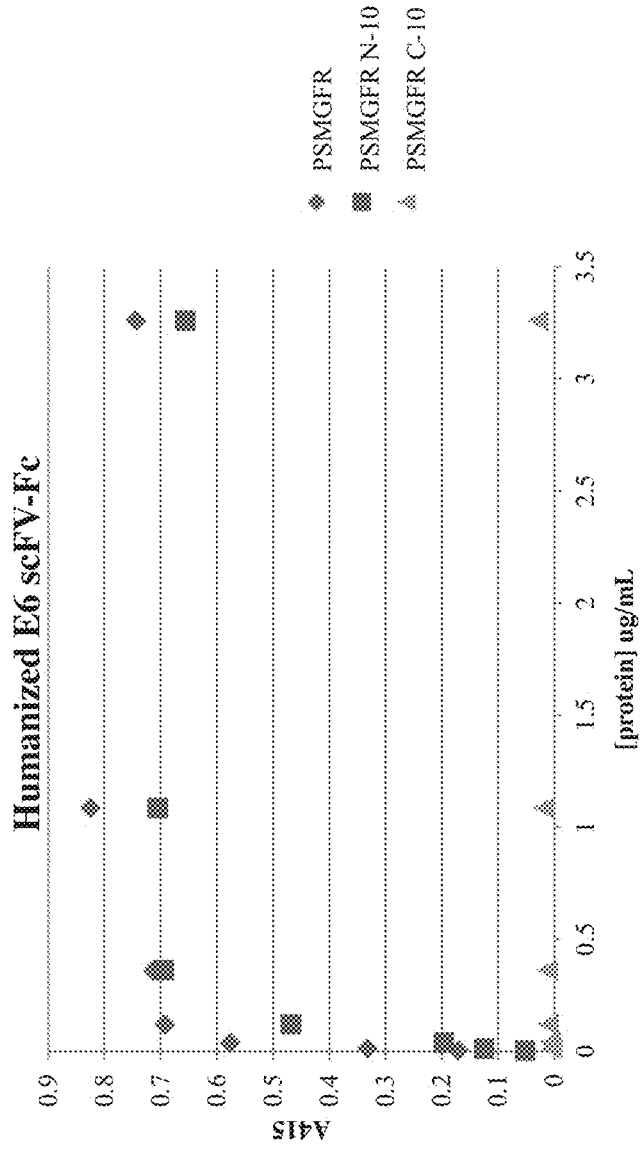
FIG. 20 shows a graph of an ELISA wherein the surface was immobilized with either PSMGFR peptide, PSMGFR minus 10 amino acids from the N-terminus or minus 10 amino acids from the C-terminus. The hu MN-E6 scFv-Fc bound to the PSMGFR peptide and to the PSMGFR N-10 peptide but not to the PSMGFR C-10 peptide. The parent MN-E6 antibody and the humanized MN-E6 require the C-terminal 10 amino acids of PSMGFR for binding.
Figure 21:
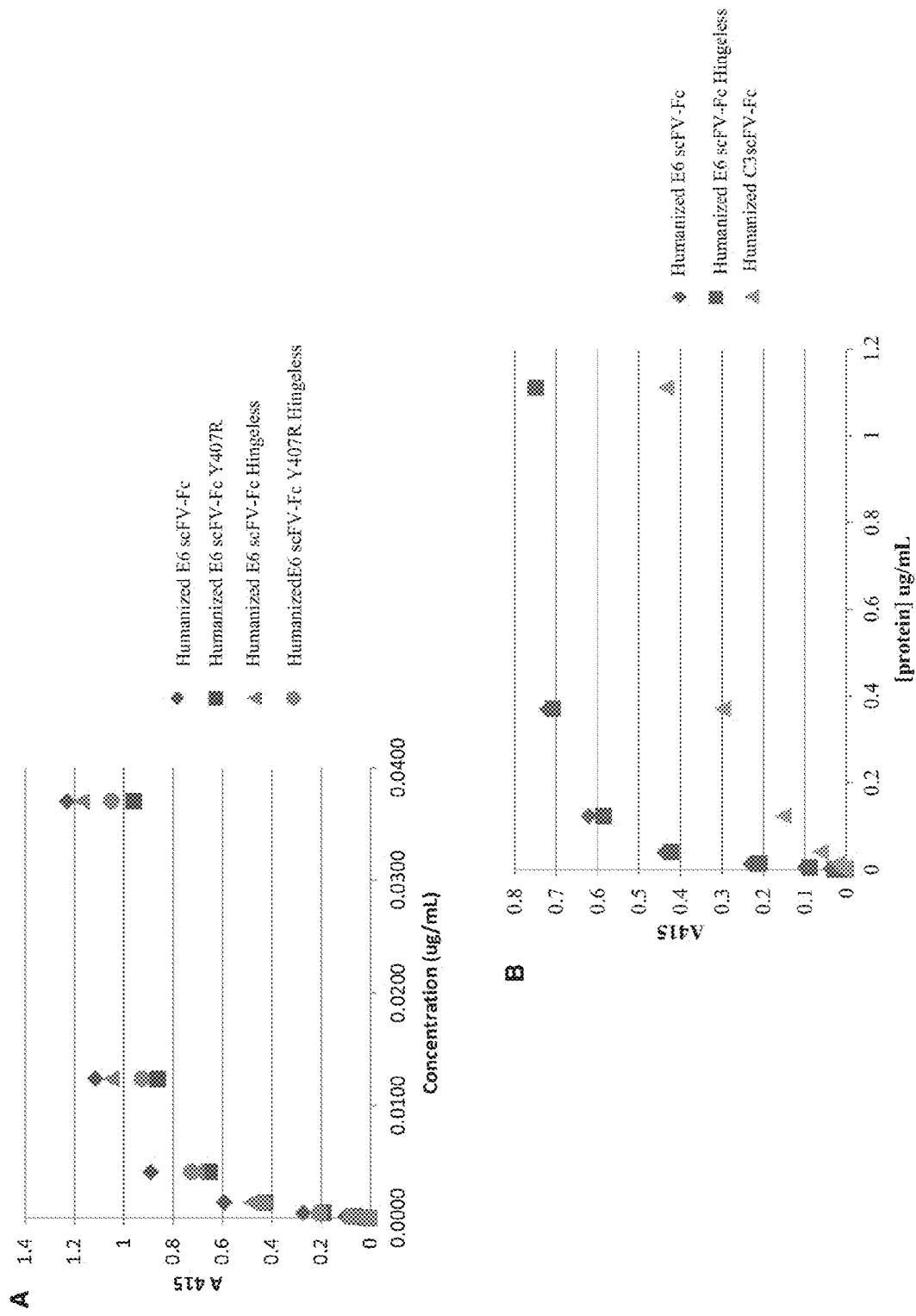
FIG. 21 shows an ELISA graph of several anti-MUC1* scFv-Fc fusion proteins wherein the Fc region has been eliminated or mutated. Shown are hu MN-E6 scFv-Fc-wt, hu MN-E6 scFv-Fc-Y407R, hu MN-E6 scFv-Fc-hingeless, and hu MN-E6 scFv-Fc-Y407R-hingeless. All mutants bind to the PSMGFR peptide of the MUC1* extracellular domain (A). An ELISA graph of several anti-MUC1* scFv-Fc fusion proteins wherein the Fc region is either wild type or mutated. Shown are hu MN-E6 scFv-Fc-wt, hu MN-E6 scFv-Fc-hingeless, and hu MN-E6 scFv-Fc is shown (B). All bind to the PSMGFR peptide of the MUC1* extracellular domain.
Figure 22:
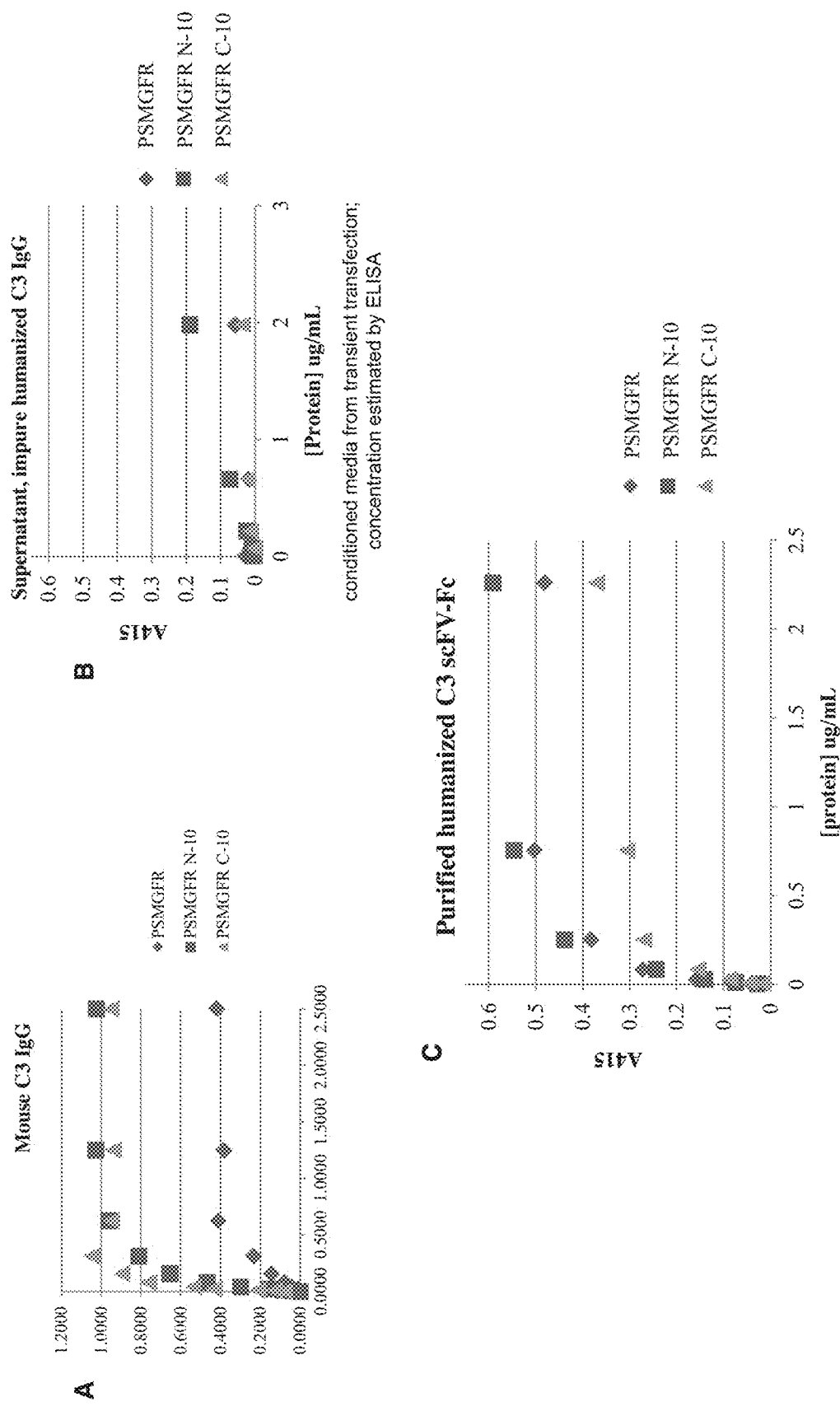
FIG. 22 shows graphs of ELISAs wherein the assay plate surface was immobilized with either PSMGFR peptide, PSMGFR minus 10 amino acids from the N-terminus or minus 10 amino acids from the C-terminus. The MN-C3 antibody variants were then assayed for binding to the various MUC1* peptides. A) Purified mouse monoclonal MN-C3 antibody; B) Impure humanized MN-C3 antibody; and C) the humanized MN-C3 scFv-Fc. ELISAs show binding to the PSMGFR peptide as well as to certain deletion peptides.
Figure 23:
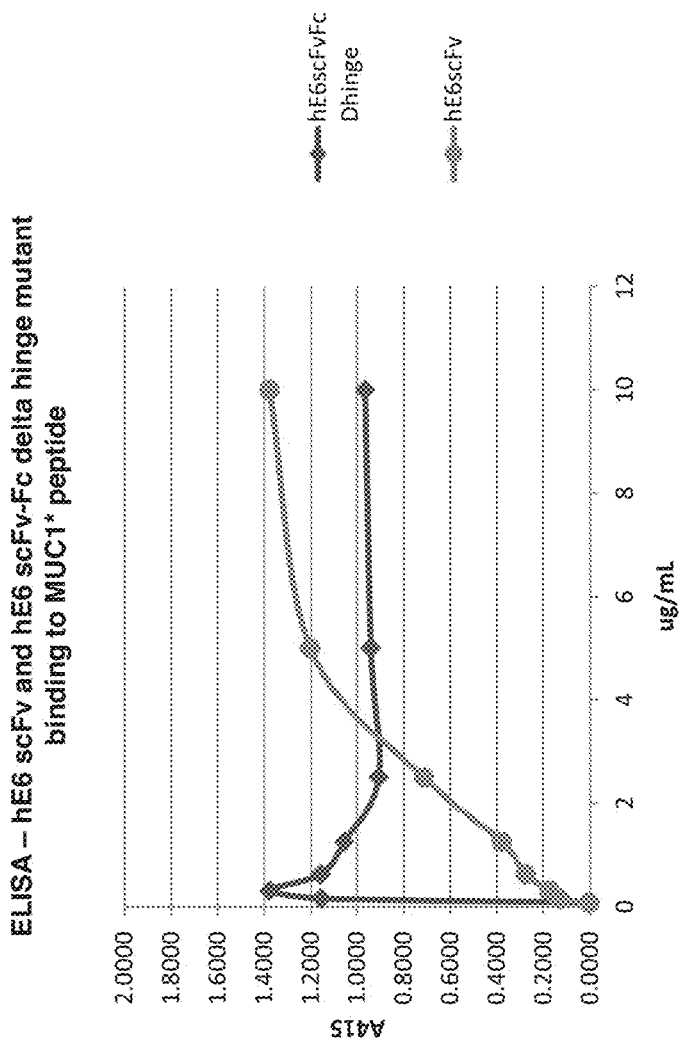
FIG. 23 shows a graph of an ELISA assay that quantifies the binding of humanized MN-E6 scFv-Fc-delta hinge, aka Dhinge or hingeless, and humanized MN-E6 scFv to the MUC1* peptide PSMGFR.

Like the parent mouse monoclonal antibodies, human or humanized antibodies as well as single chain constructs, scFv's, scFv-Fc fusions or scFv-Fc-mutants specifically bind to the synthetic MUC1* peptides (FIGS. 20-22). Figure E23 shows a graph of an ELISA assay that quantifies the binding of humanized MN-E6 scFv-Fc-delta hinge, aka Dhinge or hingeless, and humanized MN-E6 scFv to the MUC1* peptide PSMGFR.

Figure 24:
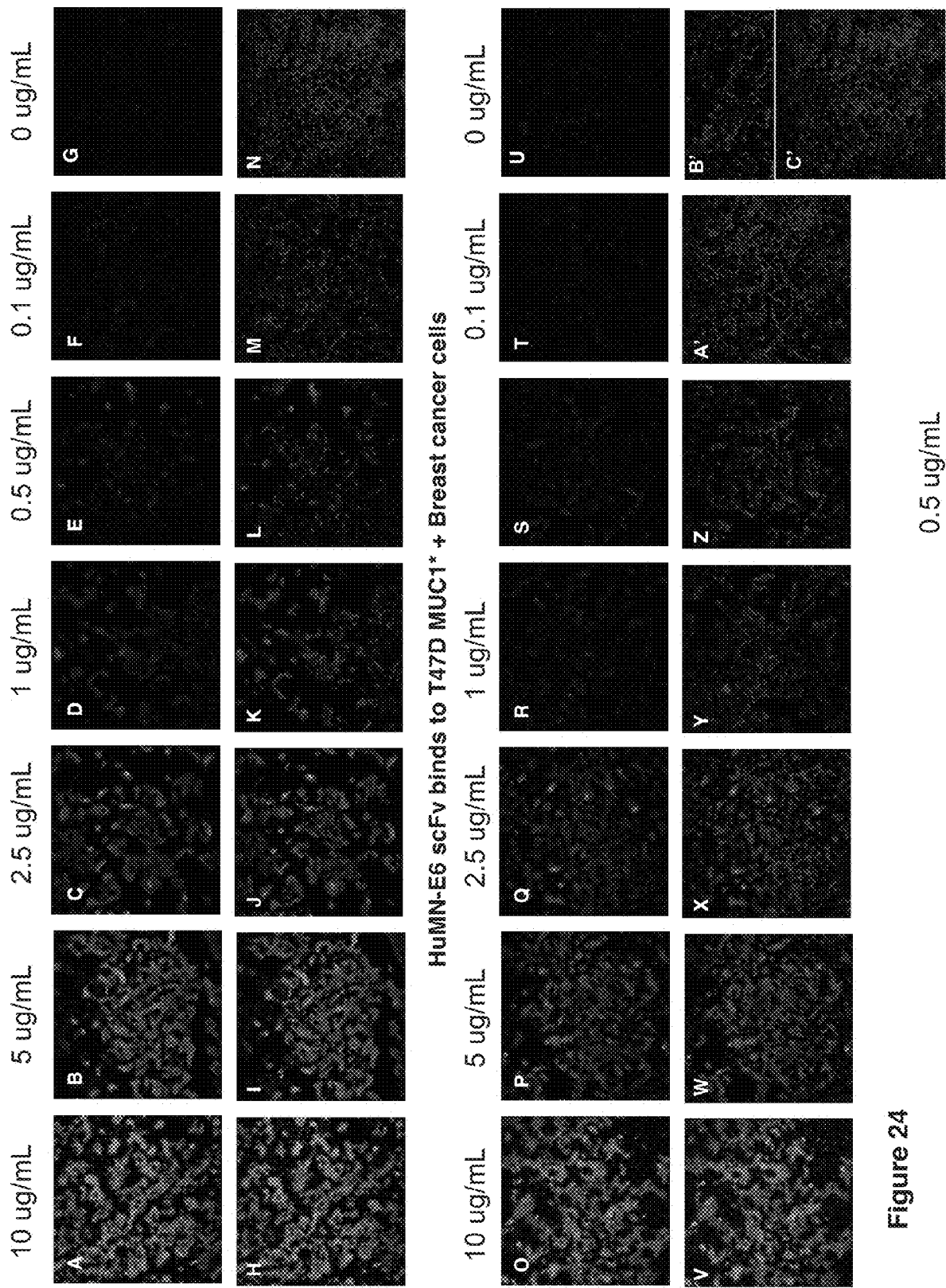
FIG. 24 shows photographs of immunofluorescence experiments in which humanized MN-C2 scFv or MN-E6 scFv specifically binds to MUC1* positive breast cancer cells in an identical concentration dependent manner. A-G: hu MN-C2 scFv binding to T47D breast cancer cells at concentrations indicated. H-N shows the fluorescently labeled scFv and DAPI. O-U: hu MN-E6 scFv binding to T47D breast cancer cells at concentrations indicated. V-B' shows the fluorescently labeled scFv and DAPI. C' is the secondary antibody control.
Figure 25:
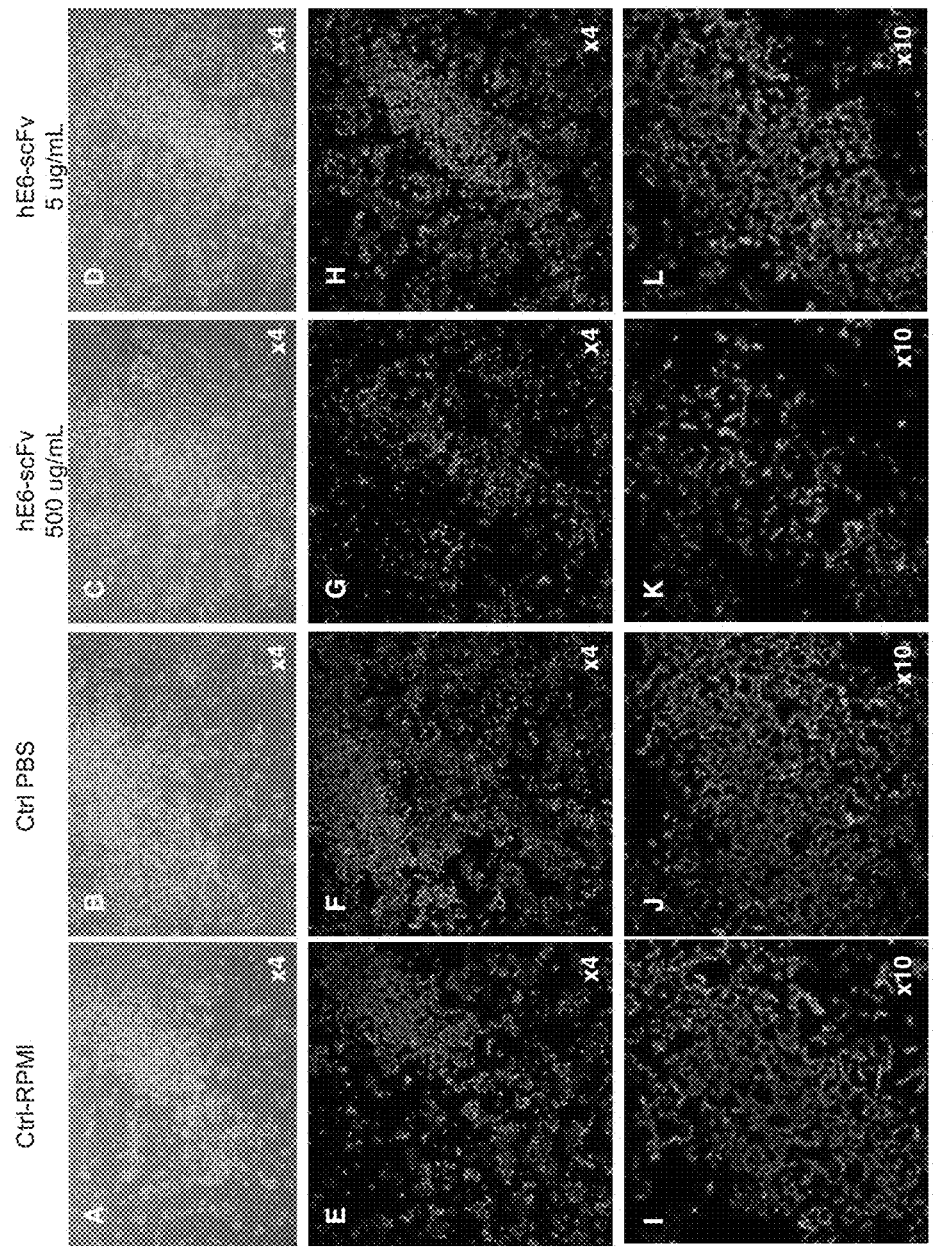
FIG. 25 shows photographs of 1500 MUC1* positive breast cancer cells that have been cultured in normal medium or in the presence of humanized MN-E6 scFv. A-D are bright field images taken at 4× magnification. E-H are calcein fluorescent images taken at 4× magnification. I-L are calcein fluorescent images taken at 10× magnification. A, E, I show control cells cultured in normal RPMI medium. B, F, J show control cells cultured in normal RPMI medium plus a volume of PBS equal to the volume of MN-E6 scFv in PBS that is added to experimental wells. C, G, K show cells cultured in normal RPMI medium plus 500 ug/mL MN-E6 scFv. D, H, L show cells cultured in normal RPMI medium plus 5 ug/mL MN-E6 scFv. The photographs show killing and/or growth inhibition of MUC1* positive cells by MN-E6 scFv at 5 ug/mL and an even greater effect at 500 ug/mL. Images were taken at 96 hours post addition of test molecule.
Figure 26:
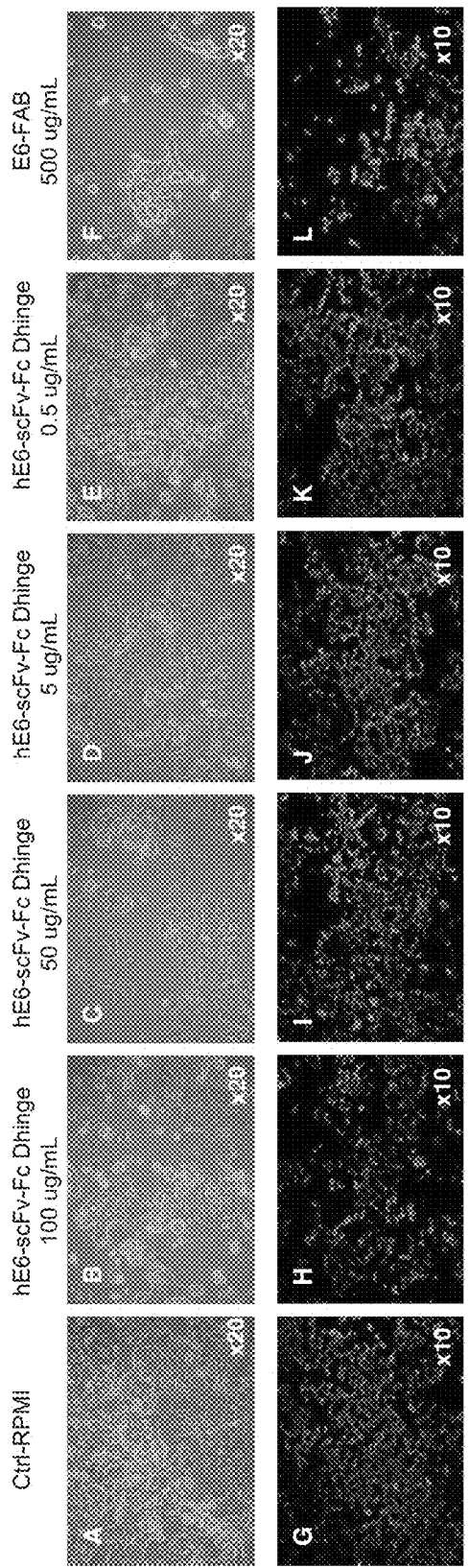
FIG. 26 shows photographs of 1500 MUC1* positive breast cancer cells that have been cultured in normal medium or in the presence of humanized MN-E6 scFv-Fc Dhinge, which is a hingeless or delta hinge mutant. A-F are bright field images taken at 20× magnification. G-L are calcein fluorescent images taken at 4× magnification. A, G show control cells cultured in normal RPMI medium. B, H show cells cultured in normal RPMI medium plus 100 ug/mL hMN-E6 scFv-Fc Dhinge. C, I show cells cultured in normal RPMI medium plus 50 ug/mL hMN-E6 scFv-Fc Dhinge. D, J show cells cultured in normal RPMI medium plus 5 ug/mL hMN-E6 scFv-Fc Dhinge. E, K show cells cultured in normal RPMI medium plus 0.5 ug/mL hMN-E6 scFv-Fc Dhinge. F, L show cells cultured in normal RPMI medium plus 500 ug/mL of MN-E6 Fab. The photographs show killing and/or growth inhibition of MUC1* positive cells by hMN-E6 scFv-Fc Dhinge 5 ug/mL, an even greater effect at 50 ug/mL and yet an even greater effect at 100 ug/mL. Comparing cell morphology to the control cells, cancer cells grown in MN-E6 Fab or in an effective amount of hMN-E6 scFv-Fc Dhinge, show rounding up of the cells which morphology change occurs before cell death. Images were taken at 96 hours post addition of test molecule.

The human or humanized anti-MUC1* antibody fragments described here specifically bind to MUC1 and MUC1* positive cancer cells. FIG. 24 shows photographs of immunofluorescence experiments in which humanized MN-C2 scFv or MN-E6 scFv specifically binds to MUC1* positive breast cancer cells in an identical concentration dependent manner. A-G: hu MN-C2 scFv binding to T47D breast cancer cells at concentrations indicated. H-N shows the fluorescently labeled scFv and DAPI. O-U: hu MN-E6 scFv binding to T47D breast cancer cells at concentrations indicated. V-B' shows the fluorescently labeled scFv and DAPI. C' is the secondary antibody control.

Figure 27:
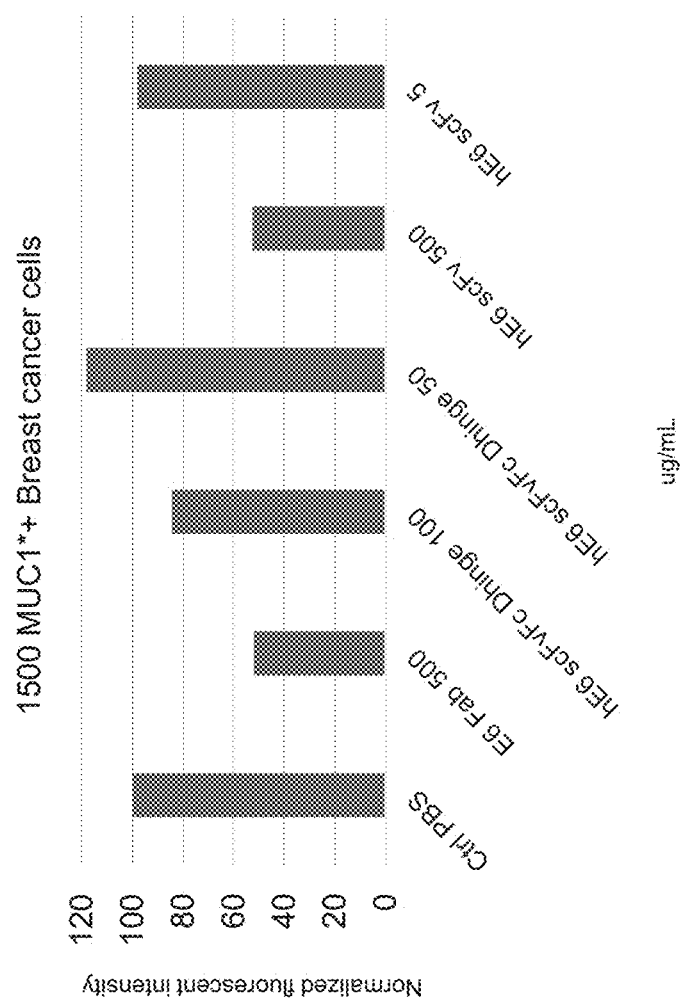
FIG. 27 shows a graph of the image analysis of the fluorescent images of FIGS. 25 and 26. Image J was used to quantify the number of cells remaining after 96 hours treatment in humanized MN-E6scFv or MN-E6 scFv-Fc-delta hinge, aka Dhinge. The analysis software uses pixel counting and pixel fluorescence intensity to quantify the number of cells in each photograph. Analysis was performed over the entire image 512×512 pixels, 8-bit image. For comparison, the inhibition of mouse monoclonal MN-E6 Fab is also analyzed.

In addition to binding to MUC1* positive cancer cells, the anti-MUC1* antibody variable region fragments, scFv's, scFv-Fc's and scFv-Fc-mutants inhibited growth of MUC1-positive cancer cells. FIG. 25A-L shows photographs of MUC1* positive breast cancer cells that have been cultured in normal medium or in the presence of humanized MN-E6 scFv. The photographs show killing and/or growth inhibition of MUC1* positive cells by MN-E6 scFv at 5 ug/mL and an even greater effect at 500 ug/mL. FIG. 26A-L shows photographs of MUC1* positive breast cancer cells that have been cultured in normal medium or in the presence of humanized MN-E6 scFv-Fc Dhinge, which is a hingeless or delta hinge mutant. The photographs show killing and/or growth inhibition of MUC1* positive cells by hMN-E6 scFv-Fc Dhinge 5 ug/mL, an even greater effect at 50 ug/mL and yet an even greater effect at 100 ug/mL. FIG. 27 shows a graph of the image analysis of the fluorescent images of FIGS. 25 and 26. Image J was used to quantify the number of cells remaining after 96 hours treatment in humanized MN-E6scFv or MN-E6 scFv-Fc-delta hinge, aka Dhinge. The analysis software uses pixel counting and pixel fluorescence intensity to quantify the number of cells in each photograph. Analysis was performed over the entire image 512×512 pixels, 8-bit image. For comparison, the inhibition of mouse monoclonal MN-E6 Fab is also analyzed.

These data show that a human or humanized MN-E6 antibody or antibody fragment, Fab, MN-E6 scFv or hu MN-E6 scFv-Fc$_{mut}$ are effective anti-cancer agents that can be administered to a person diagnosed with a MUC1 or MUC1* positive cancer, suspected of having a MUC1 or MUC1* positive cancer or is at risk of developing a MUC1 or MUC1* positive cancer.

In these specific examples, the dimer resistant Fc that was fused onto an antibody fragment or scFv is hu MN-E7 scFv. However, any of these Fc region mutations or combinations thereof that eliminate or minimize dimerization can be fused onto variable region fragments or single chain constructs of MN-E6, MN-C2, MN-C3 or MN-C8 or other antibodies identified that selectively bind to MUC1* as it exists on cancer cells or tissues. In addition, the Fabs of these antibodies can be used as an anti-cancer therapeutic. In one aspect of the invention, a person diagnosed with, suspected of having or is at risk of developing a MUC1* or MUC1 positive cancer is treated with an effective amount of human or humanized MN-E6 scFv, MN-C2 scFv, MN-C3 scFv, or MN-C8 scFv. In another aspect of the invention, a person diagnosed with, suspected of having or is at risk of developing a MUC1* or MUC1 positive cancer is treated with an effective amount of human or humanized MN-E6 scFv-Fc$_{Y407R}$, MN-C2 scFv-Fc$_{Y407R}$, MN-C3 scFv-Fc$_{Y407R}$, or MN-C8 scFv-Fc$_{Y407R}$. In another aspect of the invention, a person diagnosed with, suspected of having or is at risk of developing a MUC1* or MUC1 positive cancer is treated with an effective amount of human or humanized MN-E6 scFv-Fc mutant$_{Dhinge}$, MN-C2 scFv-Fc mutant$_{Dhinge}$, MN-C3 scFv-Fc mutant$_{Dhinge}$, or MN-C8 scFv-Fc mutant$_{Dhinge}$. In yet another aspect of the invention, a person diagnosed with, suspected of having or is at risk of developing a MUC1* or MUC1 positive cancer is treated with an effective amount of human or humanized MN-E6 scFv-Fc MUtant$_{Y407R-Dhinge}$, MN-C2 SCFV-FC mutant$_{Y407R-Dhinge}$, MN-C3 SCFV-Fc mutallt$_{Y407R-Dhinge}$, or MN-C8 scFv-Fc mutant$_{Y407R-Dhinge}$. One aspect of the invention is a method for treating a patient diagnosed with, suspected of having, or at risk of developing a MUC1 positive or MUC1* positive cancer, wherein the patient is administered an effective amount of a monomeric MN-E6 scFv, MN-C2 scFv, MN-C3 scFv, MN-C8 scFv, or MN-E6 scFv-Fc, MN-C2 scFv-Fc, MN-C3 scFv-Fc, MN-C8 scFv-Fc, wherein the Fc portion of the antibody-like protein has been mutated such that it resists dimer formation.

Humanizing

Humanized antibodies or antibody fragments or fully human antibodies that bind to the extracellular domain of -MUC1* are preferred for therapeutic use. The techniques described herein for humanizing antibodies are but a few of a variety of methods known to those skilled in the art. The invention is not meant to be limited by the technique used to humanize the antibody.

Humanization is the process of replacing the non-human regions of a therapeutic antibody (usually mouse monoclonal antibody) by human one without changing its binding specificity and affinity. The main goal of humanization is to reduce immunogenicity of the therapeutic monoclonal antibody when administered to human. Three distinct types of humanization are possible. First, a chimeric antibody is made by replacing the non-human constant region of the antibody by the human constant region. Such antibody will contain the mouse Fab region and will contain about 80-90% of human sequence. Second, a humanized antibody is made by grafting of the mouse CDR regions (responsible of the binding specificity) onto the variable region of a human antibody, replacing the human CDR (CDR-grafting method). Such antibody will contain about 90-95% of human sequence. Third and last, a full human antibody (100% human sequence) can be created by phage display, where a library of human antibodies is screened to select antigen specific human antibody or by immunizing transgenic mice expressing human antibody.

A general technique for humanizing an antibody is practiced approximately as follows. Monoclonal antibodies are generated in a host animal, typically in mice. Monoclonal antibodies are then screened for affinity and specificity of binding to the target. Once a monoclonal antibody that has the desired effect and desired characteristics is identified, it is sequenced. The sequence of the animal-generated antibody is then aligned with the sequences of many human antibodies in order to find human antibodies with sequences that are the most homologous to the animal antibody. Biochemistry techniques are employed to paste together the human antibody sequences and the animal antibody sequences. Typically, the non-human CDRs are grafted into the human antibodies that have the highest homology to the non-human antibody. This process can generate many candidate humanized antibodies that need to be tested to identify which antibody or antibodies has the desired affinity and specificity.

Once a human antibody or a humanized antibody has been generated it can be further modified for use as an Fab fragment, as a full antibody, or as an antibody-like entity such as a single chain molecule containing the variable regions, such as scFv or an scFv-Fc. In some cases it is desirable to have Fc region of the antibody or antibody-like molecule mutated such that it does not dimerize.

In addition to methods that introduce human sequences into antibodies generated in non-human species, fully human antibodies can be obtained by screening human antibody libraries with a peptide fragment of an antigen. A fully human antibody that functions like MN-E6 or MN-C2 is generated by screening a human antibody library with a peptide having the sequence of the PSMGFR N-10 peptide. A fully human antibody that functions like MN-C3 or MN-C8 is generated by screening a human antibody library with a peptide having the sequence of the PSMGFR C-10 peptide.

Humanized anti-MUC1* antibodies were generated based on the sequences of the mouse monoclonal antibodies MN-E6, MN-C2, MN-C3 and MN-C8. In one aspect of the invention, a patient diagnosed with a MUC1* positive cancer is treated with an effective amount of humanized MN-E6, MN-C2, MN-C3 or MN-C8. In a preferred embodiment, a patient diagnosed with a MUC1* positive cancer is treated with an effective amount of humanized MN-E6 or MN-C2. In another aspect of the invention, a patient diagnosed with a MUC1* positive cancer is treated with an effective amount of humanized monovalent MN-E6, MN-C2, MN-C3 or MN-C8, wherein monovalent means the corresponding Fab fragment, the corresponding scFv or the corresponding scFv-Fc fusion. In a preferred embodiment, a patient diagnosed with a MUC1* positive cancer is treated with an effective amount of a humanized scFv or monomeric humanized scFv-Fc of MN-E6 or MN-C2. Since the MUC1* growth factor receptor is activated by ligand induced dimerization of its extracellular domain, and because the Fc portion of an antibody homo-dimerizes, it is preferable that a construct that includes an Fc portion uses a mutated Fc region that prevents or minimizes dimerization.

Antibodies that bind to PSMGFR (SEQ ID NO:2) peptide of the extracellular domain of the MUC1* receptor are potent anti-cancer therapeutics that are effective for the treatment or prevention of MUC1* positive cancers. They have been shown to inhibit the binding of activating ligands dimeric NME1 (SEQ ID NOS: 3 and 4) and NME7 (SEQ ID NOS: 5 and 6) to the extracellular domain of MUC1*. Anti-MUC1* antibodies that bind to the PSMGFR sequence inhibit the growth of MUC1*-positive cancer cells, specifically if they inhibit ligand-induced receptor dimerization. Fabs of anti-MUC1* antibodies have been demonstrated to block tumor growth in animals. Thus, antibodies or antibody fragments that bind to the extracellular domain of MUC1* would be beneficial for the treatment of cancers wherein the cancerous tissues express MUC1*.

Antibodies that bind to PSMGFR region of MUC1* or bind to a synthetic PSMGFR peptide are preferred. We have identified several monoclonal antibodies that bind to the extracellular domain of MUC1*. Among this group are mouse monoclonal antibodies MN-E6, MN-C2, MN-C3 and MN-C8, the variable regions of which were sequenced and are given as for MN-E6 SEQ ID NOS: 12-13 and 65-66, for MN-C2 SEQ ID NOS: 118-119 and 168-169, for MN-C3 SEQ ID NOS: 413-414 and 458-459 and for MN-C8 SEQ ID NOS: 505-506 and 543-554. The CDRs of these antibodies make up the recognition units of the antibodies and are the most important parts of the mouse antibody that should be retained when grafting into a human antibody. The sequences of the CDRs for each mouse monoclonal are as follows, heavy chain sequence followed by light chain: MN-E6 CDR1 (SEQ ID NO:16-17 and 69-70) CDR2 (SEQ ID NO:20-21 and 73-74) CDR3 (SEQ ID NO: 24-25 and 77-78), MN-C2 CDR1 (SEQ ID NO:122-123 and 172-173) CDR2 (SEQ ID NO:126-127 and 176-177) CDR3 (SEQ ID NO:130-131 and 180-181), MN-C3 CDR1 (SEQ ID NO:417-418 and 462-463) CDR2 (SEQ ID NO:421-422 and 466-467) CDR3 (SEQ ID NO:425-426 and 470-471), MN-C8 CDR1 (SEQ ID NO:507-508 and 545-546) CDR2 (SEQ ID NO:509-510 and 547-548) CDR3 (SEQ ID NO:511-512 and 549-550). In some cases, portions of the framework regions that by modeling are thought to be important for the 3-dimensional structure of the CDRs, are also imported from the mouse sequence.

Monoclonal antibodies MN-E6 and MN-C2 have greater affinity for MUC1* as it appears on cancer cells. Monoclonal antibodies MN-C3 and MN-C8 have greater affinity for MUC1* as it appears on stem cells. By sequence alignment the following human antibodies were chosen as being sufficiently homologous to the mouse antibody that substitution of the mouse CDRs would result in an antibody that retained ability to recognize the target. Mouse MN-E6 heavy chain variable region was homologous to human IGHV3-21*03 heavy chain variable region (SEQ ID NO: 26-27) and the light chain variable region was homologous to human IGKV3-11*02 light chain variable region (SEQ ID NO: 79-80). Mouse MN-C2 heavy chain variable region was homologous to human IGHV3-21*04 heavy chain variable region (SEQ ID NO: 132-133) and the light chain variable region was homologous to human IGKV7-3*01 light chain variable region (SEQ ID NO: 182-183). Mouse MN-C3 heavy chain variable region was homologous to human IGHV1-18*04 heavy chain variable region (SEQ ID NO: 427-428) and the light chain variable region was homologous to human IGKV2-29*03 light chain variable region (SEQ ID NO:472-473). Mouse MN-C8 heavy chain variable region was homologous to human IGHV3-21*04 heavy chain variable region (SEQ ID NO: 513-514) and the light chain variable region was homologous to human Z00023 light chain variable region (SEQ ID NO:551-552).

All four antibodies have been humanized, which process has resulted in several humanized forms of each antibody. CDRs derived from the variable regions of the mouse antibodies were biochemically grafted into a homologous human antibody variable region sequence. Humanized variable regions of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 543-544) were generated by grafting the mouse CDRs into the variable region of a homologous human antibody. The humanized heavy chain variable constructs were then fused into constant regions of either human IgG1 heavy chain constant region (SEQ ID NOS:58-59) or human IgG2 heavy chain constant region (SEQ ID NO:54-55), which are then paired with either humanized light chain variable constructs fused to a human kappa chain (SEQ ID NO: 109-110) or human lambda chain (SEQ ID NO: 113-114) constant region. Other IgG isotypes could be used as constant region including IgG3 or IgG4.

Examples of humanized MN-E6 variable region into an IgG2 heavy chain (SEQ ID NOS:52-53) and into an IgG1 heavy chain (SEQ ID NOS:56-57), humanized MN-C2 variable into an IgG1 heavy chain (SEQ ID NOS: 158-159) or into an IgG2 heavy chain (SEQ ID NOS: 163-164) paired with either Lambda light chain (SEQ ID NO: 111-112 and 216-219) or Kappa chain (SEQ ID NO:107-108 and 210-213) and, humanized MN-C3 (SEQ ID NOS: 455-456, 453-454 and 500-501, 502-503) and MN-C8 (SEQ ID NOS: 541-542, 539-540 and 579-580, 581-582) antibodies were generated. Which IgG constant region is fused to the humanized variable region depends on the desired effect since each isotype has its own characteristic activity. The isotype of the human constant region is selected on the basis of things such as whether antibody dependent cell cytotoxicity (ADCC) or complement dependent cytotoxicity (CDC) is desired but can also depend on the yield of antibody that is generated in cell-based protein expression systems. In a preferred embodiment, humanized anti-MUC1* antibodies or antibody fragments are administered to a person diagnosed with or at risk of developing a MUC1-positive cancer.

One method for testing and selecting the humanized anti-MUC1* antibodies that would be most useful for the treatment of persons with cancer or at risk of developing cancers is to test them for their ability to inhibit the binding of activating ligands to the MUC1* extracellular domain. Dimeric NME1 can bind to and dimerize the MUC1* extracellular domain and in so doing stimulates cancer cell growth. Antibodies and antibody fragments that compete with NME1 for binding to the MUC1* extracellular domain are therefore anti-cancer agents. NME7 is another activating ligand of MUC1*. In some cases, it is preferable to identify antibodies that block the binding of NME7, or an NME7 truncation or cleavage product, to the MUC1* extracellular domain. Antibodies and antibody fragments that compete with NME7 and NME7 variants for binding to the MUC1* extracellular domain are effective as anti-cancer therapeutics. These antibodies include but are not limited to MN-E6, MN-C2, MN-C3, MN-C8 as well as single chain versions, such as scFv, of these antibodies and humanized version thereof. Other NME proteins also bind to MUC1 or MUC1* including NME6 and NME8. Antibodies that compete with these proteins for binding to MUC1* may also be useful as therapeutics. In a preferred embodiment, humanized anti-MUC1* antibodies or antibody fragments are administered to a person diagnosed with or at risk of developing a MUC1-positive cancer. In a more preferred embodiment, single chain antibody fragments, or monomeric scFv-Fc fusions, derived from humanized sequences of MN-E6 and MN-C2 are administered to a person diagnosed with or at risk of developing a MUC1-positive cancer.

Single chain variable fragments, scFv, or other forms that result in a monovalent antibody or antibody-like protein are also useful. In some cases it is desired to prevent dimerization of the MUC1* extracellular domain. Single chain variable fragments, Fabs and other monovalent antibody-like proteins have been shown to be effective in binding to the extracellular domain of MUC1* and blocking MUC1* dimerization. These single chain variable fragments, Fabs and other monovalent antibody-like molecules effectively blocked cancer growth in vitro and in animals xenografted with human MUC1-positive cancer cells. Thus, humanized single chain variable fragments or monovalent anti-MUC1* antibodies or antibody-like molecules would be very effective as an anti-cancer therapeutic. Such humanized single chain antibodies, Fabs and other monovalent antibody-like molecules that bind to the MUC1* extracellular domain or to a PSMGFR peptide are therefore useful as anti-cancer therapeutics. Anti-MUC1* single chain variable fragments are generated by grafting non-human CDRs of antibodies, which bind to extracellular domain of MUC1* or bind to PSMGFR peptide, into a framework of a homologous variable region human antibody. The resultant humanized heavy and light chain variable regions are then connected to each other via a suitable linker, wherein the linker should be flexible and of length that it allows heavy chain binding to light chain but discourages heavy chain of one molecule binding to the light chain of another. For example a linker of about 10-15 residues. Preferably, the linker includes [(Glycine)$_4$ (Serine)$_1$]$_3$ (SEQ ID NOS: 401-402), but is not limited to this sequence as other sequences are possible.

In one aspect, the humanized variable regions of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 565-566) are biochemically grafted into a construct that connects heavy and light chains via a linker. Examples of humanized single chain anti-MUC1* antibodies comprising humanized sequences from the variable regions of MN-E6, MN-C2, MN-C3 and MN-C8 were generated. Several humanized MN-E6 single chain proteins were generated (SEQ ID NOS: 232-237). Several humanized MN-C2 single chain proteins were generated (SEQ ID NOS: 238-243). Several humanized MN-C3 single chain proteins were generated (SEQ ID NOS: 244-249). Several humanized MN-C8 single chain proteins were generated (SEQ ID NOS: 250-255). In a preferred embodiment, humanized anti-MUC1* antibody fragments, including variable fragments, scFv antibody fragments MN-E6 scFv, MN-C2 scFv, MN-C3 scFv, or MN-C8 scFv are administered to a person diagnosed with or at risk of developing a MUC1-positive cancer. In a more preferred embodiment, single chain antibody fragments, such as variable fragments derived from humanized sequences of MN-E6 and MN-C2, are administered to a person diagnosed with or at risk of developing a MUC1-positive cancer.

In another aspect, the humanized variable regions of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 565-566) are biochemically grafted into a single chain variable fragment, scFv, that also contains an Fc portion of an antibody. Examples of humanized single chain variable fragment of MN-E6, MN-C2, MN-C3 and MN-C8 fused to a Fc region of an antibody were generated (SEQ ID NOS: 256-257, 260-261, 264-265 and 268-269). Inclusion of an Fc region serves several purposes. It increases the molecular weight of the antibody fragment, which slows degradation and increases half-life. An Fc region also recruits immune system complement to the tumor site. Additionally, the addition of an antibody Fc region makes the scFv a convenient diagnostic tool, as the secondary antibodies detect and label the Fc portion. However, the Fc portion homo-dimerizes. Thus an scFv-Fc would be bivalent and could dimerize and activate the MUC1* growth factor receptor. In order to get the benefits of having an Fc attached to an anti-MUC1* scFv, without the drawback of inducing MUC1* dimerization, the Fc region was mutated to minimize or eliminate Fc homo-dimerization. The following mutations were made in the CH3 domain to create a monomeric scFv-Fc fusion protein: Y407R (SEQ ID NOS: 278 and 279), F405Q (SEQ ID NOS: 280 and 281), T394D (SEQ ID NOS: 282 and 283), T366W/L368W (SEQ ID NOD: 284 and 285), T364R/L368R (SEQ ID NOS: 286 and 285). Any combinations of those mutations can be tested and could be introduced into Fc (SEQ ID NOS: 272-273), CH2-CH3 (SEQ ID NOS: 274-275) or CH3 (SEQ ID NOS: 276-277) fusion proteins or in the hingeless Fc-fusion proteins (SEQ ID NOS: 288-289).

One aspect of the invention is a method for treating a patient diagnosed with, suspected of having, or at risk of developing a MUC1 positive or MUC1* positive cancer, wherein the patient is administered an effective amount of a monomeric MN-E6 scFv, MN-C2 scFv, MN-C3 scFv, MN-C8 scFv, or MN-E6 scFv-Fc, MN-C2 scFv-Fc, MN-C3 scFv-Fc, MN-C8 scFv-Fc, wherein the antibody variable fragment portions are human or have been humanized and wherein the Fc portion of the antibody-like protein has been mutated such that it resists dimer formation.

CAR T and Cancer Immuno Therapy Techniques

In another aspect of the invention, some or all of the single chain portions of anti-MUC1* antibody fragments are biochemically fused onto immune system molecules, using several different chimeric antigen receptor, 'CAR' strategies. The idea is to fuse the recognition portion of an antibody, typically as a single chain variable fragment, to an immune system molecule that has a transmembrane domain and a cytoplasmic tail that is able to transmit signals that activate the immune system. The recognition unit can be an antibody fragment, a single chain variable fragment, scFv, or a peptide. In one aspect, the recognition portion of the extracellular domain of the CAR is comprised of sequences from the humanized variable region of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 565-566). In another aspect, it is comprised of sequences from a single chain variable fragment. Examples of single chain constructs are given. Several humanized MN-E6 single chain proteins, scFv, were generated (SEQ ID NOS: 232-237). Several humanized MN-C2 single chain proteins, scFv, were generated (SEQ ID NOS: 238-243). Several humanized MN-C3 single chain proteins, scFv, were generated (SEQ ID NOS: 244-249). Several humanized MN-C8 single chain proteins, scFv, were generated (SEQ ID NOS: 250-255). The transmembrane region of the CAR can be derived from CD8, CD4, antibody domains or other transmembrane region, including the transmembrane region of the proximal cytoplasmic co-stimulatory domain. The cytoplasmic tail of the CAR can be comprised of one or more motifs that signal immune system activation. This group of cytoplasmic signaling motifs, sometimes referred to as, co-stimulatory cytoplasmic domains, includes but is not limited to CD3-zeta, CD27, CD28, 4-1BB, OX40, CD30, CD40, PD-1, ICAm-1, LFA-1, ICOS, CD2, CD5, CD7 and Fc receptor gamma domain. A minimal CAR may have the CD3-zeta or an Fc receptor gamma domain then one or two of the above domains in tandem on the cytoplasmic tail. In one aspect, the cytoplasmic tail comprises CD3-zeta, CD28, 4-1BB and/or OX40. Several examples of humanized MN-E6 CARs were generated: CAR MN-E6 CD3z (SEQ ID NOS: 294-295); CAR MN-E6 CD28/CD3z (SEQ ID NOS: 297-298); CAR MN-E6 4-1BB/CD3z (SEQ ID NOS: 300-301); CAR MN-E6 OX40/CD3z (SEQ ID NOS: 616-617); CAR MN-E6 CD28/OX40/CD3z (SEQ ID NOS: 618-619); CAR MN-E6 CD28/4-1BB/CD3z (SEQ ID NOS: 303-304). Several examples of humanized MN-C2 CARs were generated: CAR MN-C2 CD3z (SEQ ID NOS: 606-607); CAR MN-C2 CD28/CD3z (SEQ ID NOS: 608-609); CAR MN-C2 4-1BB/CD3z (SEQ ID NOS: 610-611); CAR MN-C2 OX40/CD3z (SEQ ID NOS: 612-613); CAR MN-C2 CD28/4-1BB/CD3z (SEQ ID NOS: 306-307); CAR MN-C2 CD28/OX40/CD3z (SEQ ID NOS: 614-615). Humanized MN-C3 CAR was generated: CAR MN-C3 4-1BB/CD3z (SEQ ID NOS: 600-601).

Several examples of humanized MN-E6 CARs with different hinge regions (SEQ ID NOS:345-360) were generated: CAR MN-E6-Fc/8/41BB/CD3z (SEQ ID NOS:310-311); CAR MN-E6 FcH/8/41BB/CD3z (SEQ ID NOS:315-316); CAR MN-E6 Fc/4/41BB/CD3z (SEQ ID NOS:318-319); CAR MN-E6 FcH/4/41BB/CD3z (SEQ ID NOS:321-322); CAR MN-E6 IgD/8/41BB/CD3z (SEQ ID NOS:323-324); CAR MN-E6 IgD/4/41BB/CD3z (SEQ ID NOS:327-328); CAR MN-E6 X4/8/41BB/CD3z (SEQ ID NOS:330-331); CAR MN-E6 X4/4/41BB/CD3z (SEQ ID NOS:333-334); CAR MN-E6 8+4/4/41BB/CD3z (SEQ ID NOS:336-337). In addition, several humanized MN-C3 single chain variable fragment and humanized MN-C8 single chain variable fragments were also generated.

The extracellular domain recognition unit of a MUC1* targeting CAR can comprise the variable regions of humanized MN-E6, MN-C2, MN-C3 or MN-C8 or other antibody that binds to the PSMGFR portion of MUC1* or a PSMGFR peptide. In one aspect, the extracellular domain recognition unit of a CAR is comprised essentially of a humanized MN-E6, MN-C2, MN-C3 or MN-C8 single chain variable fragment scFv. The transmembrane region of the CAR can be derived from CD8 (SEQ ID NOS:363-364), or can be the transmembrane domain of CD3-zeta, CD28, 41bb, OX40 or other transmembrane region (SEQ ID NOS:361-372) and the cytoplasmic domain of a CAR with antibody fragment targeting MUC1* extracellular domain can be comprised of one or more selected from the group comprising an immune system co-stimulatory cytoplasmic domain. The group of immune system co-stimulatory domains includes but is not limited to CD3-zeta, CD27, CD28, 4-1BB, OX40, CD30, CD40, PD-1, ICAm-1, LFA-1, ICOS, CD2, CD5, CD7 and Fc receptor gamma domain (SEQ ID NOS:373-382). Alternatively, the recognition unit portion of a CAR can comprise a peptide wherein the peptide binds to the target. NME7 binds to and activates MUC1*. In one aspect of the invention, the recognition unit of a CAR is a peptide derived from NME7 (SEQ ID NOS: 5-6) or a peptide derived from NME7, including but not limited to NME7 peptide A1 (SEQ ID NO: 7), NME7 peptide A2 (SEQ ID NO: 8), NME7 peptide B1 (SEQ ID NO: 9), NME7 peptide B2 (SEQ ID NO: 10) and NME7 peptide B3 (SEQ ID NO: 11).

Some strategies for generating CARs include a portion of the molecule that dimerizes with itself. In some cases, dimerization of the target is not desirable. Therefore CARs can be constructed such that they heterodimerize. In one case the recognition unit of the first CAR binds to a first target while the recognition unit of the second CAR binds to a second target. Both recognition units can be antibody fragments, both can be peptides or one can be an antibody fragment and the other a peptide. A first target of the CAR can be the extracellular domain of MUC1*. The recognition unit of the CAR would be comprised of an antibody fragment that binds to MUC1* extracellular domain or to a PSMGFR peptide. Alternatively, the recognition unit of the CAR would be comprised of a peptide that binds to MUC1* extracellular domain, such peptides include peptides derived from an NME protein such as NME1 or NME7, more particularly NME7 derived peptides listed as SEQ ID NOS:

7-11. A second target of a heterodimeric CAR may be a peptide or antibody fragment that binds to NME7. Alternatively, a second target of a heterodimeric CAR may be a peptide or antibody fragment that binds to PD1 or other target on a MUC1*-presenting cell. A second target may be a peptide or antibody fragment that binds to NME1. Because it is desirable to prevent dimerization of MUC1 induced by a CAR, heterodimeric CARs can be constructed so that only the extracellular domain of one molecule has an extracellular recognition unit that binds to a target (SEQ ID NOS: 584-587). The other molecule can have a truncated extracellular domain that is devoid of a target recognition unit or antibody fragment (SEQ ID NOS:588-599). The CARs described can be transfected or transduced into a cell of the immune system. In a preferred embodiment, a MUC1* targeting CAR is transfected or transduced into a T cell. In one aspect the T cell is a CD3+/CD28+ T cell. In another case it is a dendritic cell. In another case it is a B cell. In another case it is a mast cell. The recipient cell can be from a patient or from a donor. If from a donor, it can be engineered to remove molecules that would trigger rejection. Cells transfected or transduced with a CAR of the invention can be expanded ex vivo or in vitro then administered to a patient. Administrative routes are chosen from a group containing but not limited to bone marrow transplant, intravenous injection, in situ injection or transplant. In a preferred embodiment, the MUC1* targeting CAR is administered to a person diagnosed with or at risk of developing a MUC1-positive cancer.

There are many possible anti-MUC1* CAR constructs that can be transduced into T cells or other immune cells for the treatment or prevention of MUC1* positive cancers. CARs are made up of modules and the identity of some of the modules is relatively unimportant, while the identity of other modules is critically important.

Figure 28:
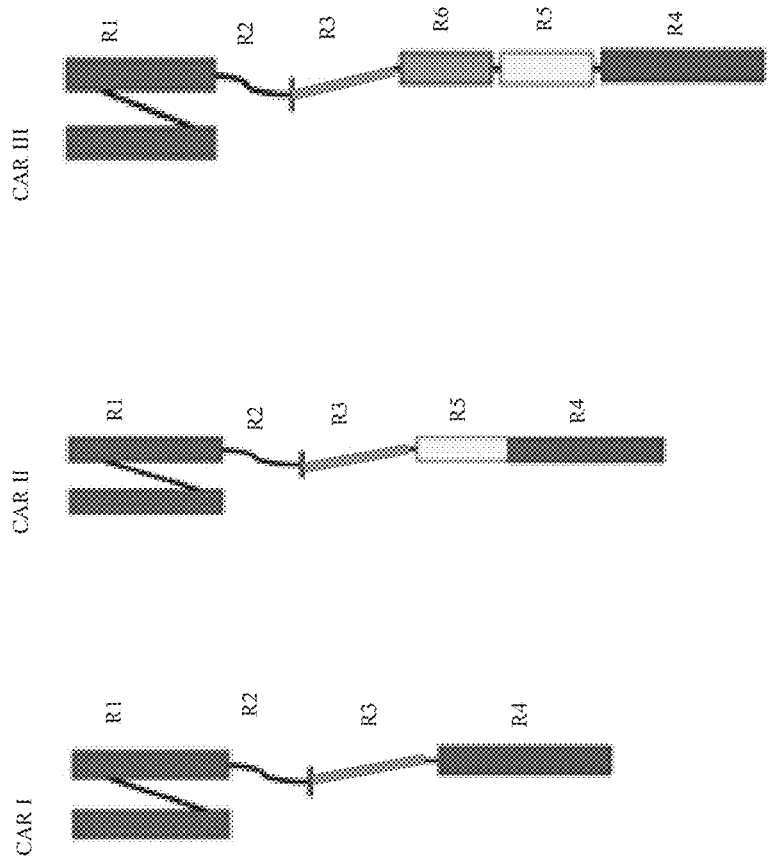
FIG. 28 shows schematics of CAR sequence components.

Our experiments demonstrate that the antibody recognition fragment at the outermost portion of the CAR is critically important because it targets the immune cell bearing the CAR to the tumor site. The intracellular signaling motifs are also very important but can be interchanged. FIG. 28 shows a schematic of the components of CAR and the various sequences that may be included in a CAR. Referring to FIG. 28, R1 is: nothing; or a ligand or a fragment of a ligand of a cancer associated antigen; or a ligand or a fragment of a ligand of MUC1 or MUC1*; or an antibody or antibody fragment wherein the antibody or antibody fragment binds to MUC1 or MUC1*; or an antibody or antibody fragment wherein the antibody or antibody fragment binds to PSMGFR*, wherein the antibody may be human or humanized; or an antibody or antibody fragment of MN-E6, MN-C2, MN-C3 or MN-C8 or humanized MN-E6, MN-C2, MN-C3 or MN-C8; or a single chain variable fragment of an antibody, scFv, that binds to a cleaved MUC1 or MUC1*; or a scFv of MN-E6, MN-C2, MN-C3 or MN-C8, which may be humanized; or a peptide that binds to MUC1* or PSMGFR peptide; or is an antibody fragment, a scFv, or a peptide that binds the PSMGFR portion of MUC1*; or is comprised of sequence from the humanized variable region of MN-E6 (SEQ ID NOS: 38-39 and 93-94), MN-C2 (SEQ ID NOS: 144-145 and 194-195), MN-C3 (SEQ ID NOS: 439-440 and 486-487) and MN-C8 (SEQ ID NOS: 525-526 and 565-566). In one aspect R1 is a scFv that binds the PSMGFR portion of MUC1* comprised of sequence from humanized MN-E6 scFv (SEQ ID NOS: 232-237), humanized MN-C2 scFv (SEQ ID NOS: 238-243), humanized MN-C3 scFv (SEQ ID NOS: 244-249) or humanized MN-C8 scFv (SEQ ID NOS: 250-255). In another aspect R1 is a scFv that binds the PSMGFR portion of MUC1* comprised of sequence from humanized MN-E6 scFv (SEQ ID NOS: 232-237) or humanized MN-C2 scFv (SEQ ID NOS: 238-243).

In one example R1 is a scFv that binds the PSMGFR portion of MUC1* comprised of sequence from humanized MN-E6 scFv (SEQ ID NOS: 232-237)

R2 is a polypeptide flexible linker that connects the recognition portion to the transmembrane domain of the CAR. In one aspect, R2 can be a polypeptide linker of different length from 5 to 250 amino acids. In another aspect, R2 is a polypeptide linker of human origin. In one aspect R2 can be made of or a modification of the Fc region of a human immunoglobulin (IgG, IgA, IgE, IgM or IgD). I another aspect, R2 can be the hinge region or a modification of the hinge region of a human immunoglobulin (IgG, IgA, IgE, IgM or IgD). In one aspect, R2 can be the hinge region or a modification of the hinge region of a T-cell receptor (CD8a, CD28 or CD4). In one example, R2 is the hinge region of CD8a, the hinge region of human IgD or the Fc domain of human IgG1.

R3 is a transmembrane domain. In one aspect, R3 can be a transmembrane domain or a modification of a transmembrane domain of any transmembrane human proteins. In another aspect, R3 can be a transmembrane domain or a modification of a transmembrane domain from human cell receptor. In one aspect, R3 can be a transmembrane domain or a modification of a transmembrane domain of a T-cell receptor (CD8a, CD4, CD28, CD3z, OX40 or 41-BB). In another aspect, R3 is a transmembrane domain from the first cytoplasmic co-stimulatory domain of the CAR. In one aspect, R3 can be a transmembrane domain or a modification of a transmembrane domain of a T-cell receptor extended with 1, 2, 3, 4 or 5 amino acids of the cytoplasmic domain associated to the transmembrane domain. In another aspect, R3 can be a transmembrane domain or a modification of a transmembrane domain of a T-cell receptor extended with 1, 2, 3, 4 or five amino acids of the cytoplasmic domain associated to the transmembrane domain followed by a cystein for disulfide bond formation. In one example, R3 is the transmembrane domain of CD8a or CD4.

R4 is a signaling domain from a T-cell receptor. In one aspect, R4 can be the cytoplasmic signaling domain of CD3-zeta, CD27, CD28, 4-1BB, OX40, CD30, CD40, PD-1, ICAm-1, LFA-1, ICOS, CD2, CD5, CD7 and Fc receptor gamma domain. In one example, R4 is the cytoplasmic domain of CD3-zeta. Several examples of humanized CAR with single signaling domain (CAR I) were regenerated: CAR MN-E6 CD3z (SEQ ID NOS: 294-295); CAR MN-C2 CD3z (SEQ ID NOS: 606-607)

R5 is a co-stimulatory domain from a T-cell receptor. In one aspect, R5 can be the cytoplasmic signaling domain of CD27, CD28, 4-1BB, OX40, CD30, CD40, PD-1, ICAm-1, LFA-1, ICOS, CD2, CD5, CD7 and Fc receptor gamma domain. R5 will be different from R4 and R6. In one example, R5 is the cytoplasmic domain of CD28, 4-1BB or OX40. Several examples of humanized CAR with two signaling domain (CAR II) were regenerated: CAR MN-E6 CD28/CD3z (SEQ ID NOS: 297-298); CAR MN-E6 4-1BB/CD3z (SEQ ID NOS: 300-301); CAR MN-E6 OX40/CD3z (SEQ ID NOS: 616-617); CAR MN-C2 CD28/CD3z (SEQ ID NOS: 608-609); CAR MN-C2 4-1BB/CD3z (SEQ ID NOS: 610-611); CAR MN-C2 OX40/CD3z (SEQ ID NOS: 612-613); MN-C3 4-1BB/CD3z (SEQ ID NOS: 600-601); CAR MN-E6-Fc/8/41BB/CD3z (SEQ ID NOS:310-311); CAR MN-E6 FcH/8/41BB/CD3z (SEQ ID NOS:315-316); CAR MN-E6 Fc/4/41BB/CD3z (SEQ ID NOS:318-319); CAR MN-E6 FcH/4/41BB/CD3z (SEQ ID NOS:321-322); CAR MN-E6 IgD/8/41BB/CD3z (SEQ ID NOS:323-324); CAR MN-E6 IgD/4/41BB/CD3z (SEQ ID NOS:327-328); CAR MN-E6 X4/8/41BB/CD3z (SEQ ID NOS:330-331); CAR MN-E6 X4/4/41BB/CD3z (SEQ ID NOS:333-334); CAR MN-E6 8+4/4/41BB/CD3z (SEQ ID NOS:336-337).

R6 is a co-stimulatory domain from a T-cell receptor. In one aspect, R6 can be the cytoplasmic signaling domain of CD27, CD28, 4-1BB, OX40, CD30, CD40, PD-1, ICAm-1, LFA-1, ICOS, CD2, CD5, CD7 and Fc receptor gamma domain. R6 will be different from R4 and R5. In one example, R5 is the cytoplasmic domain of CD28. Several examples of humanized CAR with two signaling domain (CAR III) were regenerated: CAR MN-E6 CD28/OX40/CD3z (SEQ ID NOS: 618-619); CAR MN-E6 CD28/4-1BB/CD3z (SEQ ID NOS: 303-304); CAR MN-C2 CD28/4-1BB/CD3z (SEQ ID NOS: 306-307); CAR MN-C2 CD28/OX40/CD3z (SEQ ID NOS: 614-615)

We and others (Pulè M A, Straathof K C, Dotti G, Heslop H E, Rooney C M and Brenner M K. (2005) A chimeric T cell antigen receptor that augments cytokine release and supports clonal expansion of primary human T cells. Mol Ther. 12(5):933-941; Hombach A A, Heiders J, Foppe M, Chmielewski M and Abken H. (2012) OX40 costimulation by a chimeric antigen receptor abrogates CD28 and IL-2 induced IL-10 secretion by redirected CD4(+) T cells. Oncoimmunology. 1(4):458-466; Kowolik C M, Topp M S, Gonzalez S, Pfeiffer T, Olivares S, Gonzalez N, Smith D D, Forman S J, Jensen M C and Cooper L J. (2006) CD28 costimulation provided through a CD19-specific chimeric antigen receptor enhances in vivo persistence and antitumor efficacy of adoptively transferred T cells. Cancer Res. 66(22):10995-11004; Loskog A, Giandomenico V, Rossig C, Pule M, Dotti G and Brenner M K. (2006) Addition of the CD28 signaling domain to chimeric T-cell receptors enhances chimeric T-cell resistance to T regulatory cells. Leukemia. 20(10):1819-1828; Milone M C, Fish J D, Carpenito C, Carroll R G, Binder G K, Teachey D, Samanta M, Lakhal M, Gloss B, Danet-Desnoyers G, Campana D, Riley J L, Grupp S A and June C H. (2009) Chimeric receptors containing CD137 signal transduction domains mediate enhanced survival of T cells and increased antileukemic efficacy in vivo. Mol Ther. 17(8):1453-1464; Song D G, Ye Q, Carpenito C, Poussin M, Wang L P, Ji C, Figini M, June C H, Coukos G, Powell D J Jr. (2011) In vivo persistence, tumor localization, and antitumor activity of CAR-engineered T cells is enhanced by costimulatory signaling through CD137 (4-1BB). Cancer Res. 71(13):4617-4627) have shown that intracellular signaling modules, such as CD3-zeta (SEQ ID NOS: 373-376), CD28 (SEQ ID NOS: 377-378) and 41BB (SEQ ID NOS: 379-380), alone or in combinations stimulate immune cell expansion, cytokine secretion and immune cell mediated killing of the targeted tumor cells. Less important is the identity of the short extracellular piece that presents the antibody fragment, the transmembrane domain, and the short cytoplasmic tail that comes before the intracellular signaling motifs.

The identity of the recognition antibody fragment that targets the CAR to a tumor is critically important. For the treatment of MUC1 positive or MUC1* positive cancers, that antibody recognition fragment must bind to the extracellular domain of portion of MUC1 that remains after cleavage and shedding of the bulk of the extracellular domain, which contains the tandem repeat domains. In one aspect of the invention, the portion that remains comprises the PSMGFR sequence. In another aspect of the invention, the portion of MUC1 that remains after cleavage and shedding contains the PSMGFR sequence plus nine (9) more amino acids extended at the N-terminus. In another aspect of the invention, the portion of MUC1 that remains after cleavage and shedding contains the PSMGFR sequence plus twenty one (21) more amino acids extended at the N-terminus. In one aspect the antibody recognition fragment binds to a PSMGFR peptide. In another aspect of the invention, the antibody recognition fragment binds to a peptide comprising the sequence SNIKFRPGSVVVQLTLAFREGTINVHDVETQFNQYKTEAASRY (SEQ ID NO:620); or SVVVQLTLAFREGTINVHDVETQFNQYKTEAASRY (SEQ ID NO:621) As a demonstration, a single chain antibody fragment that included the variable domain of the monoclonal anti-MUC1* antibodies called MN-E6 or MN-C2 were engineered into a panel of CARs. The MUC1* targeting CARs were then transduced, separately or in combinations, into immune cells. When challenged with surfaces presenting a MUC1* peptide, an antigen presenting cell transfected with MUC1*, or MUC1* positive cancer cells, the immune cells that were transduced with MUC1* targeting CARs elicited immune responses, including cytokine release, killing of the targeted cells and expansion of the immune cells. In one case, human jurkat cells were transduced with MUC1*-targeting CARs and upon exposure to a surface presenting the PSMGFR peptide, K562 antigen presenting cells that had been transfected with MUC1* or MUC1* positive cancer cells, the jurkhat cells secreted IL-2. In another case, purified human T cells were transduced with MUC1*-targeting CARs and upon exposure to a surface presenting the PSMGFR peptide, K562 antigen presenting cells that had been transfected with MUC1* or MUC1* positive cancer cells, the T cells secreted IL-2, interferon gamma, and killed the targeted antigen presenting cells and cancer cells, while the T cells expanded. As demonstrated, CARs that comprise an antibody fragment, wherein the antibody fragment is able to bind to the PSMGFR peptide, a transmembrane domain and a cytoplasmic tail bearing co-stimulatory domains, elicit an immune system anti-tumor cell response when said CARs are transduced into immune cells, which include T cells. Therefore, other antibodies, antibody fragments or antibody mimics that are able to bind to the PSMGFR peptide will perform similarly and can be used to treat or prevent cancers. Those skilled in the art will recognize that there are a number of technologies available for transfecting or transducing cells with CARs and the invention is not limited by the method used for making the immune cell express a MUC1*-targeting CAR. For example, retroviruses, adeno viruses, lenti viruses and the like can be used. Similarly, the identity of molecules that make up the non-targeting, portions of the CAR such as the extracellular domain, transmembrane domain and membrane proximal portion of the cytoplasmic domain, are not essential to the function of a MUC1*-targeting CAR. For example, the extracellular domain, transmembrane domain and membrane proximal portion of the cytoplasmic domain can be comprised of portions of CD8, CD4, CD28, or generic antibody domains such as Fc, CH2CH3, or CH3. Further, the non-targeting portions of a CAR can be a composite of portions of one or more of these molecules or other family members.

One aspect of the invention is a method for treating a patient diagnosed with, suspected of having, or at risk of developing a MUC1 positive or MUC1* positive cancer, wherein the patient is administered an effective amount of immune cells that have been transduced with a MUC1* targeting CAR. In another aspect of the invention, the immune cells are T cells isolated from a patient, which are then transduced with CARs wherein the targeting head of the CAR binds to MUC1*, and after expansion of transduced T cells, the CAR T cells are administered in an effective amount to the patient. In yet another aspect of the invention, the immune cells are T cells isolated from a patient, which are then transduced with CARs wherein the targeting head of the CAR comprises portions of huMN-E6, huMN-C2, huMN-C3 or huMN-C8, and after optional expansion of transduced T cells, the CAR T cells are administered in an effective amount to the patient.

Specifics of CARs Made and Tested

Figure 29:
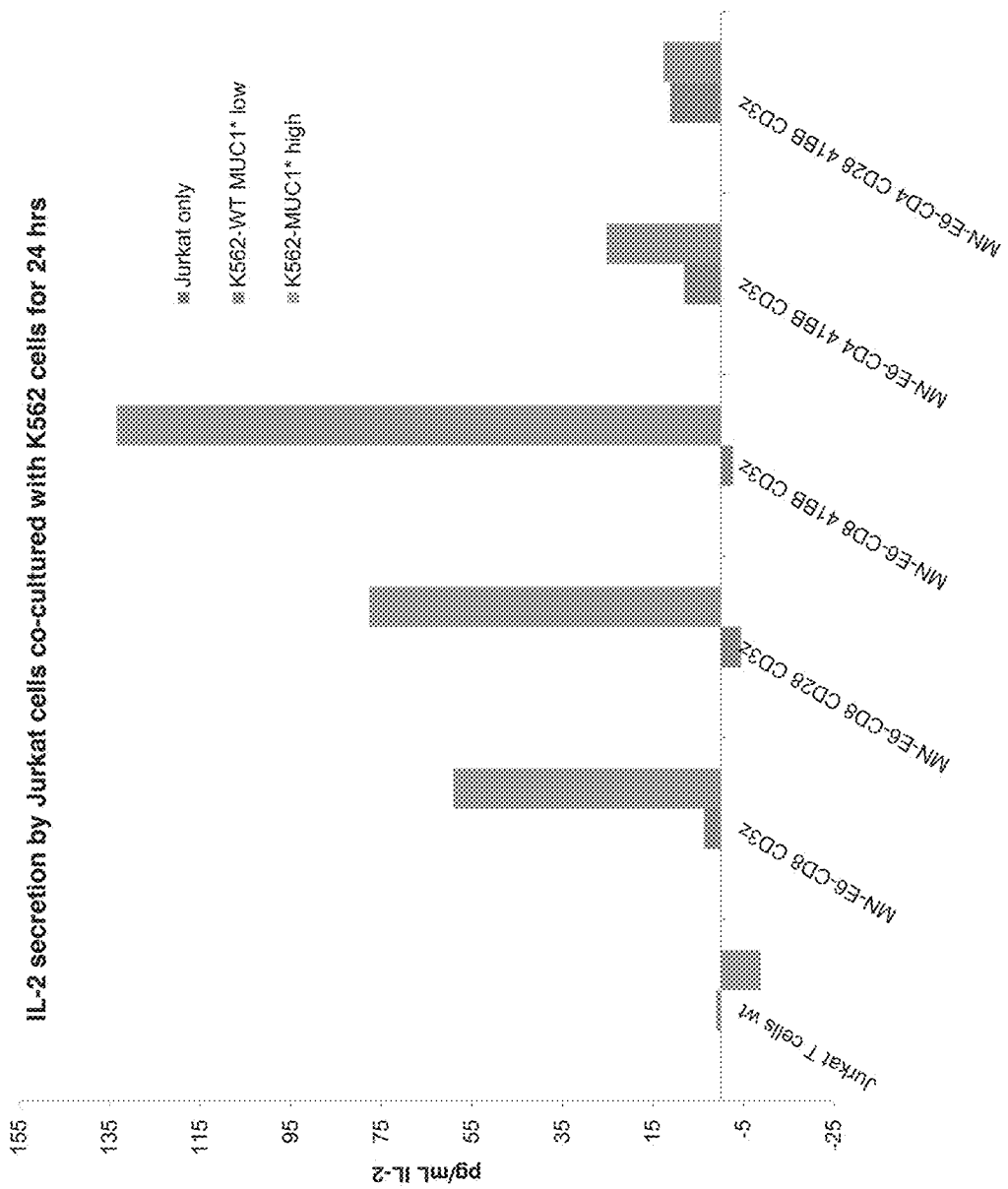
FIG. 29 is a graph of an experiment measuring IL-2 cytokine secretion by Jurkat T cells that were transduced with a panel of CARs, including MN-E6-CD8-3z, MN-E6-CD8-CD28-3z, MN-E6-CD8-41BB-3z, MN-E6-CD4-CD28-3z and MN-E6-CD4-CD28-41BB-3z, when the CAR T cells were exposed to K562-wt cells or K562 cells that had been transfected with MUC1*.
Figure 30:
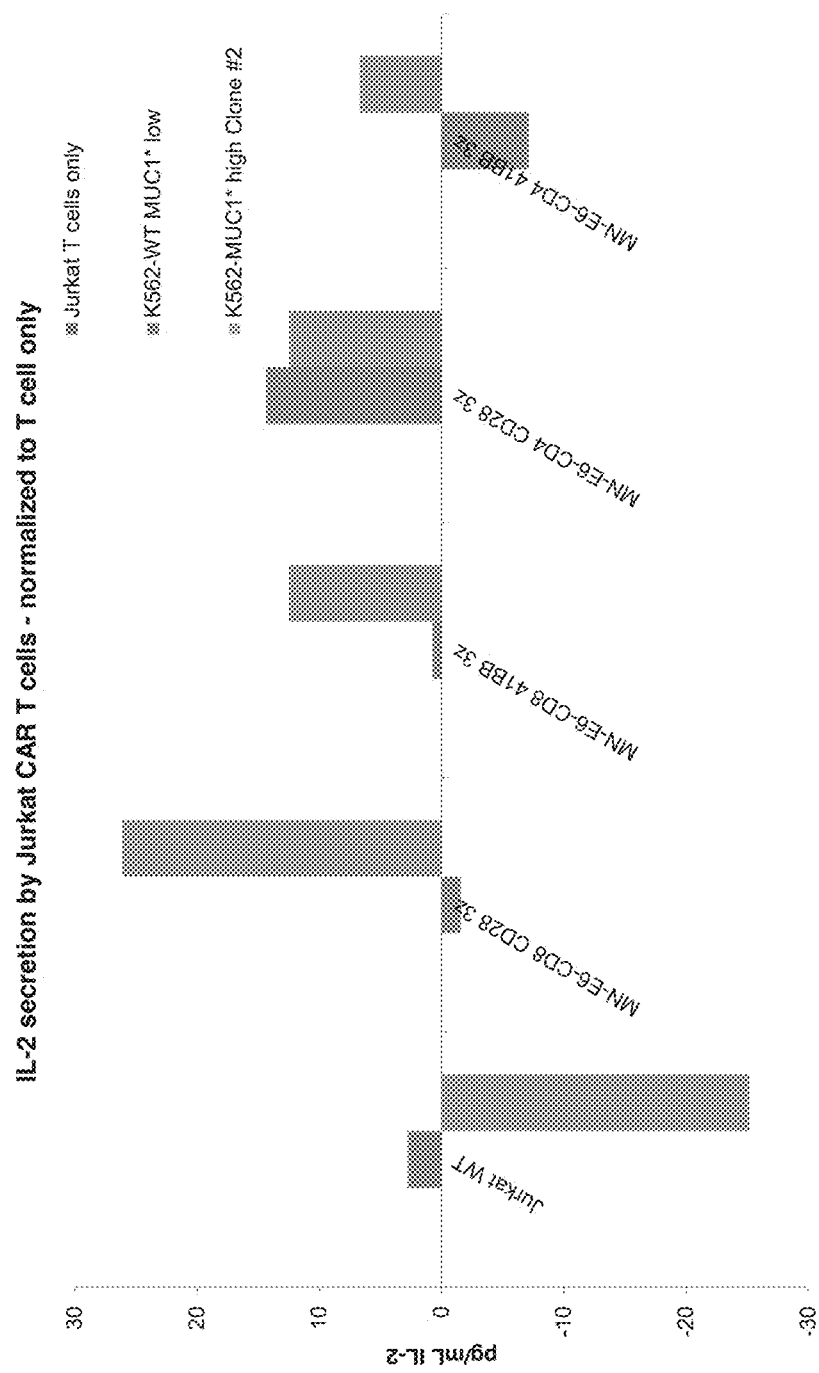
FIG. 30 is a graph of an experiment measuring IL-2 cytokine secretion by Jurkat T cells that were transduced with a panel of CARs, including MN-E6-CD8-CD28-3z, MN-E6-CD8-41BB-3z, MN-E6-CD4-CD28-3z and MN-E6-CD4-41BB-3z, when the CAR T cells were exposed to K562-wt cells or K562 cells that had been transfected with MUC1*.
Figure 31:
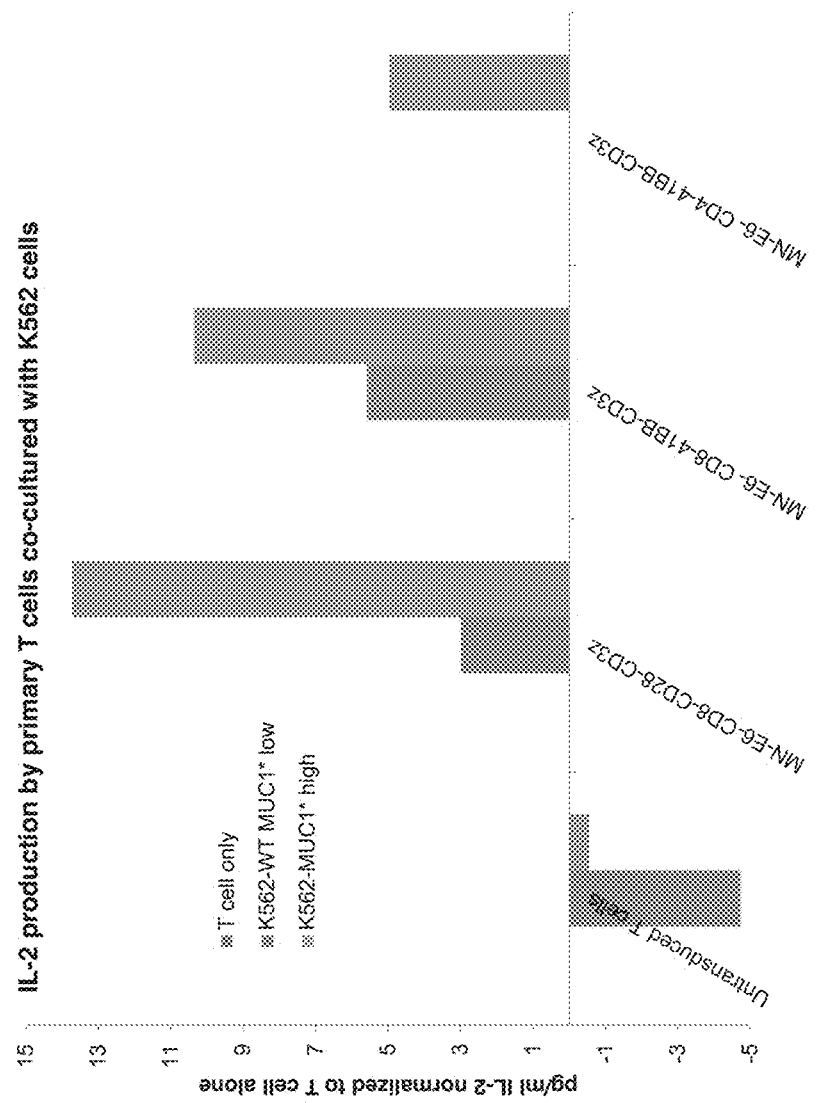
FIG. 31 is a graph of an experiment measuring IL-2 cytokine secretion by primary human T cells, isolated from a blood sample, that were transduced with a panel of CARs, including MN-E6-CD8-CD28-3z, MN-E6-CD8-41BB-3z and MN-E6-CD4-41BB-3z, when the CAR T cells were exposed to K562-wt cells or K562 cells that had been transfected with MUC1*.
Figure 32:
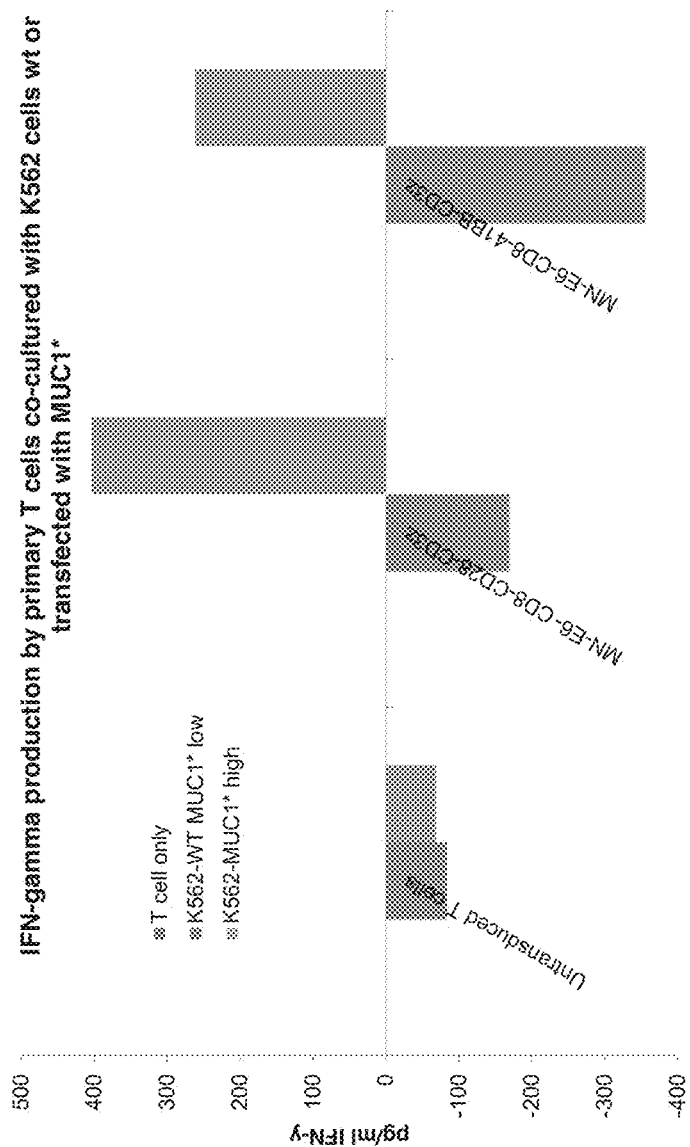
FIG. 32 is a graph of an experiment measuring interferon-gamma (IFN-g) cytokine secretion by primary human T cells, isolated from a blood sample, that were transduced with a panel of CARs, including MN-E6-CD8-CD28-3z and MN-E6-CD4-41BB-3z, when the CAR T cells were exposed to K562-wt cells or K562 cells that had been transfected with MUC1*.
Figure 33:
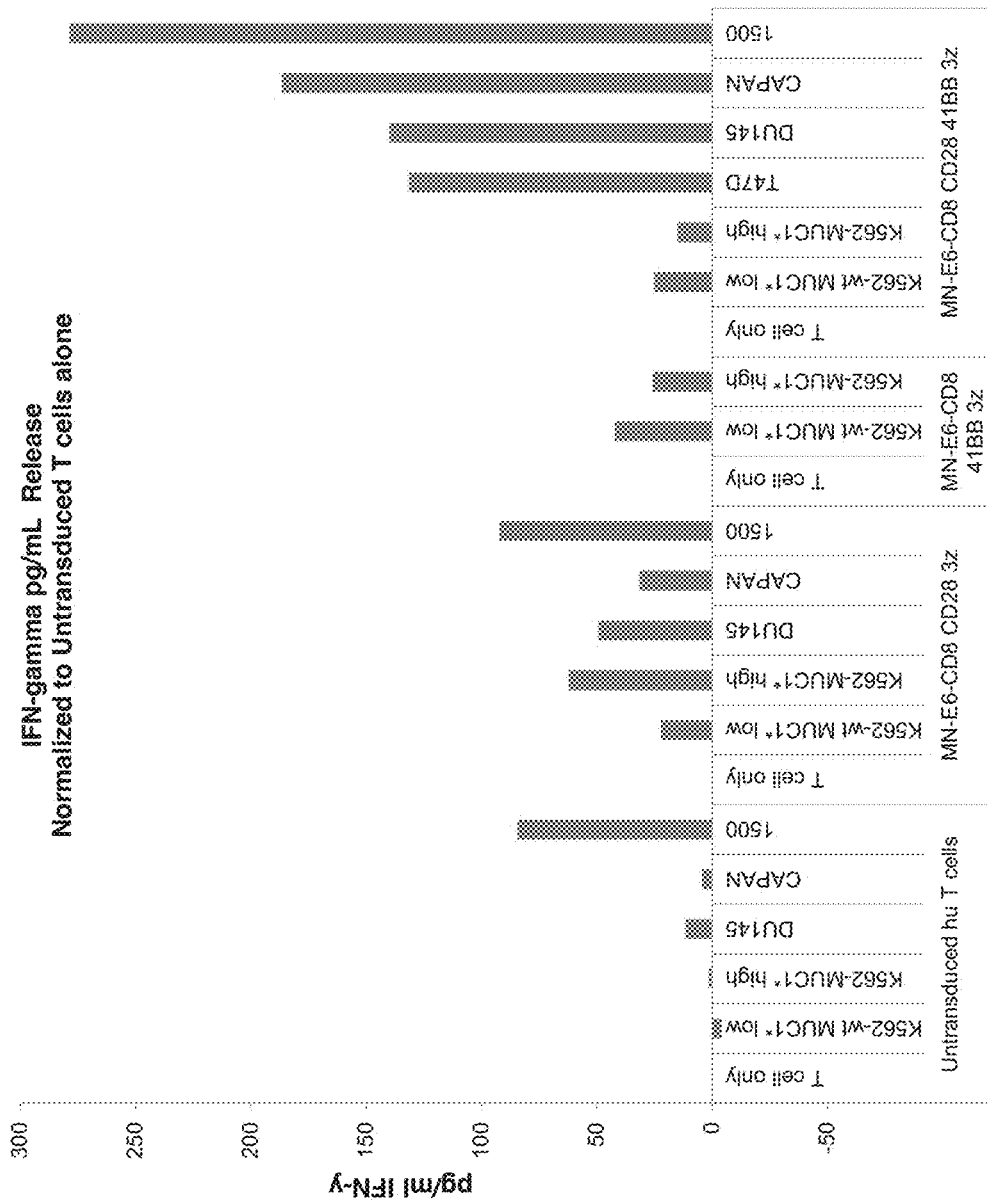
FIG. 33 is a graph of an experiment measuring interferon-gamma (IFN-g) cytokine secretion by primary human T cells, isolated from a blood sample, that were transduced with a panel of CARs, including MN-E6-CD8-CD28-3z, MN-E6-CD8-41BB-3z and MN-E6-CD8-CD28-41BB-3z, when the CAR T cells were exposed to K562-wt cells, K562 cells that had been transfected with MUC1*, or MUC1* positive cancer cells of prostate cancer, breast cancer or pancreatic cancer.

Many MUC1* targeting CARs were generated wherein the targeting antibody fragment at the distal end of the CAR was either MN-E6, MN-C2, MN-C3 or MN-C8. The DNA of each CAR was sequenced to verify that cloning was correctly done. Each construct was then shuffled into an expression plasmid, transfected into cells and then verified that the construct had successfully inserted by Western blot. Surface expression was verified by FACS. The MUC1* targeting CARs were then virally transduced into immune cells. In one aspect they were transduced into Jurkat cells. In another aspect they were transduced into primary human T cells that were purified from blood. A series of functional assays were performed and verified that the CARs were functional. Functional assays showed that both Jurkat cells and primary T cells transduced with MUC1* targeting CAR secreted the cytokine IL-2 when challenged with cells presenting MUC1*. FIG. 29 is a graph of an experiment measuring IL-2 cytokine secretion by Jurkat cells that were transduced with a panel of CARs, including MN-E6 CD8/CD3z, MN-E6 CD8/CD28/CD3z, MN-E6 CD8/41BB/CD3z, MN-E6 CD4/CD28/CD3z and MN-E6 CD4/CD28/41BB/CD3z. IL-2 was secreted only when the CAR Jurkat cells were exposed to K562-wt cells or K562 cells that had been transfected with MUC1*. It should be noted that the parent K562-wt cells express very low levels of MUC1*. Another group of CARs transfected into Jurkat cells was similarly tested for cytokine secretion. FIG. 30 shows IL-2 secretion by Jurkat T cells that were transduced with MN-E6 CD8/CD28/CD3z, MN-E6 CD8/41BB/CD3z, MN-E6 CD4/CD28/CD3z or MN-E6 CD4/41BB/CD3z, when the CAR T cells were exposed to K562-wt cells or K562 cells that had been transfected with MUC1*. Similarly, FIG. 31 shows IL-2 cytokine secretion by primary human T cells that were transduced with MN-E6 CD8/CD28/CD3z, MN-E6 CD8/41BB/CD3z or MN-E6 CD4/41BB/CD3z. Cytokine secretion only occurred when the MUC1* targeting CAR T cells were exposed to K562-wt cells or K562 cells that had been transfected with MUC1*. Another cytokine that is secreted by activated T cells when they see a target cell is interferon-gamma (IFN-g). FIG. 32 shows that interferon-gamma was secreted by primary human T cells that were transduced with a panel of CARs, including MN-E6 CD8/CD28/CD3z and MN-E6 CD4/41BB/CD3z, when the CAR T cells were exposed to K562-wt cells or K562 cells that had been transfected with MUC1*. Interferon-gamma was similarly secreted by primary human T cells that were transduced with a panel of CARs, including MN-E6 CD8/CD28/CD3z, MN-E6 CD8/41BB/CD3z and MN-E6 CD8/CD28/41BB/CD3z, when the MUC1* targeting CAR T cells were exposed to K562-wt cells, K562 cells that had been transfected with MUC1*, or MUC1* positive cancer cells of prostate cancer (DU145), breast cancer (1500) or pancreatic cancer (Capan) (FIG. 33).

Figure 34:
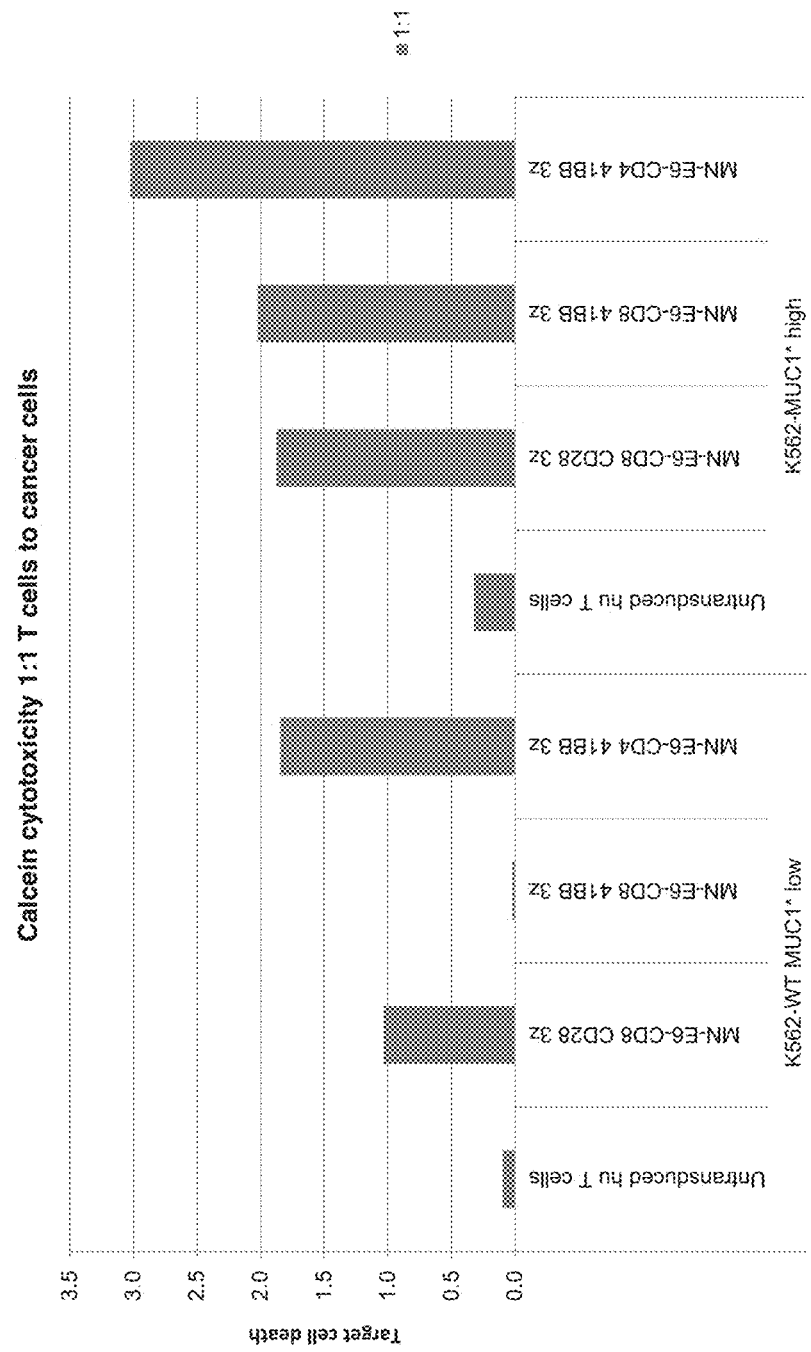
FIG. 34 is a graph of an experiment measuring target cell death when primary human T cells, isolated from a blood sample, that were transduced with a panel of CARs, including MN-E6-CD8-CD28-3z, MN-E6-CD8-41BB-3z and MN-E6-CD4-41BB-3z, when the CAR T cells were exposed to K562-wt cells or K562 cells that had been transfected with MUC1*. The ratio of T cells to target cells was 1:1 and the cells were co-cultured for 24 hours.
Figure 35:
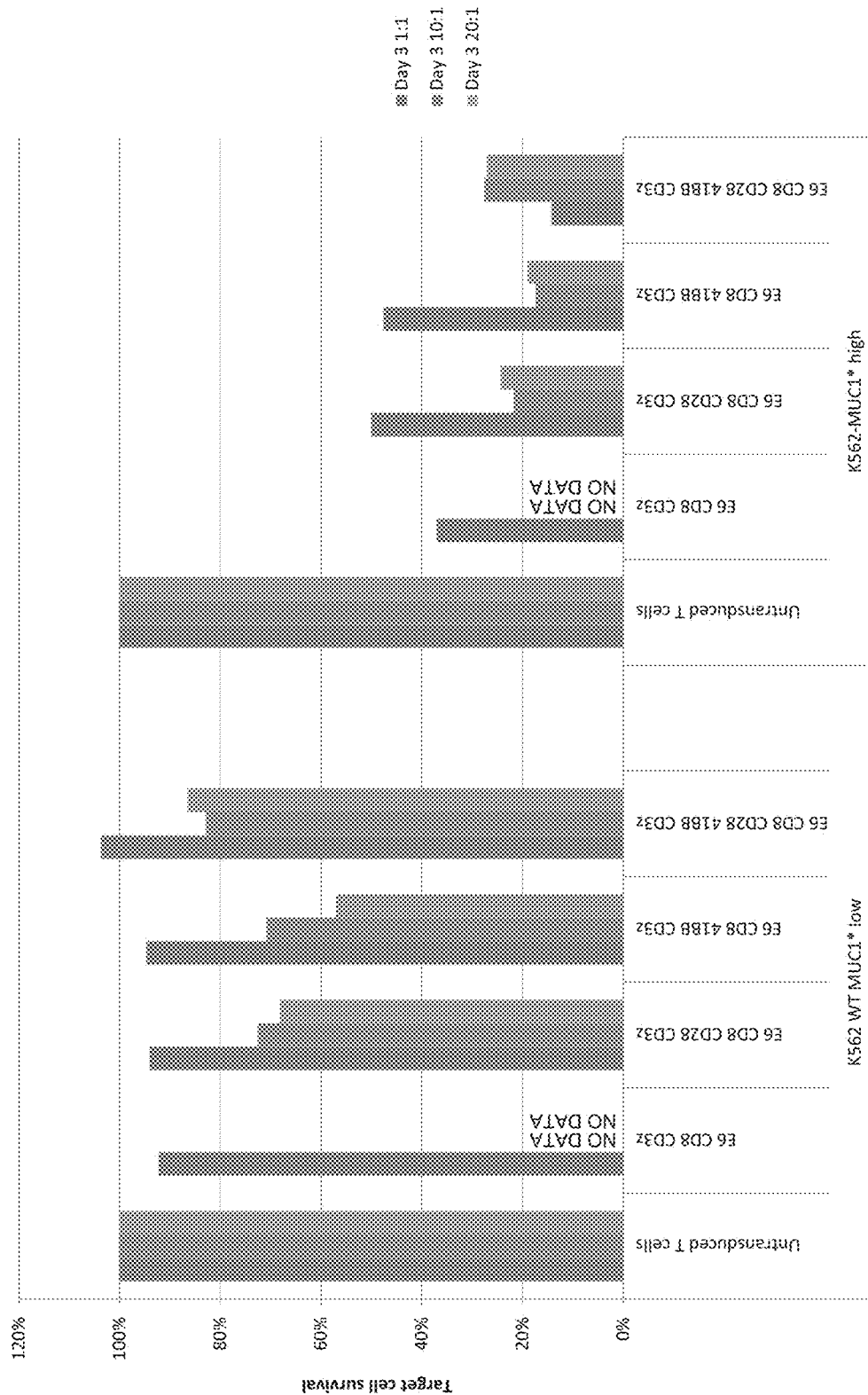
FIG. 35 is a graph of FACS measuring target cell survival on Day 3. Primary human T cells, isolated from a blood sample, were transduced with a panel of CARs, including humanized MN-E6-CD8-3z, MN-E6-CD8-CD28-3z, MN-E6-CD8-41BB-3z and MN-E6-CD8-CD28-41BB-3z. The CAR T cells were then exposed to K562-wt cells that naturally express low levels of MUC1*, or K562 cells that had been transfected with MUC1* high. The ratio of MUC1* targeting CART cells to target cells was either 1:1, 10:1, or 20:1. Surviving cells were detected and measured on Day 3.

Another measure of function of CAR T cells is whether or not they induce killing of the targeted cells. T cells transfected with a variety of CARs comprising antibody fragments that bind to the PSMGFR sequence of MUC1* killed MUC1* expressing cells in co-culture assays. In one assay, target MUC1* expressing cells are incubated with calcein. When they are mixed with CAR T cells wherein the CAR comprises an antibody fragment such as MN-E6, MN-C2, MN-C3 or MN-C8 the CAR T cells kill the MUC1* presenting cells which causes the target cells to lyse and releases calcein into the supernatant. FIG. 34 is a graph of an experiment measuring target cell death when primary human T cells, isolated from a blood sample, that were transduced with a panel of CARs, including MN-E6 CD8/CD28/CD3z, MN-E6 CD8/41BB/CD3z and MN-E6 CD4/41BB/CD3z, when the CAR T cells were exposed to K562-wt cells or K562 cells that had been transfected with MUC1*. The ratio of T cells to target cells was 1:1 and the cells were co-cultured for 24 hours. FIG. 35 is a graph of FACS measuring target cell survival on Day 3. Primary human T cells, isolated from a blood sample, were transduced with a panel of CARs, including humanized MN-E6-CD8-3z, MN-E6-CD8-CD28-3z, MN-E6-CD8-41BB-3z and MN-E6-CD8-CD28-41BB-3z. The CAR T cells were then exposed to K562-wt cells that naturally express low levels of MUC1*, or K562 cells that had been transfected with MUC1* high. The ratio of MUC1* targeting CAR T cells to target cells was either 1:1, 10:1, or 20:1. Surviving cells were detected and measured at Day 3.

Figure 36:
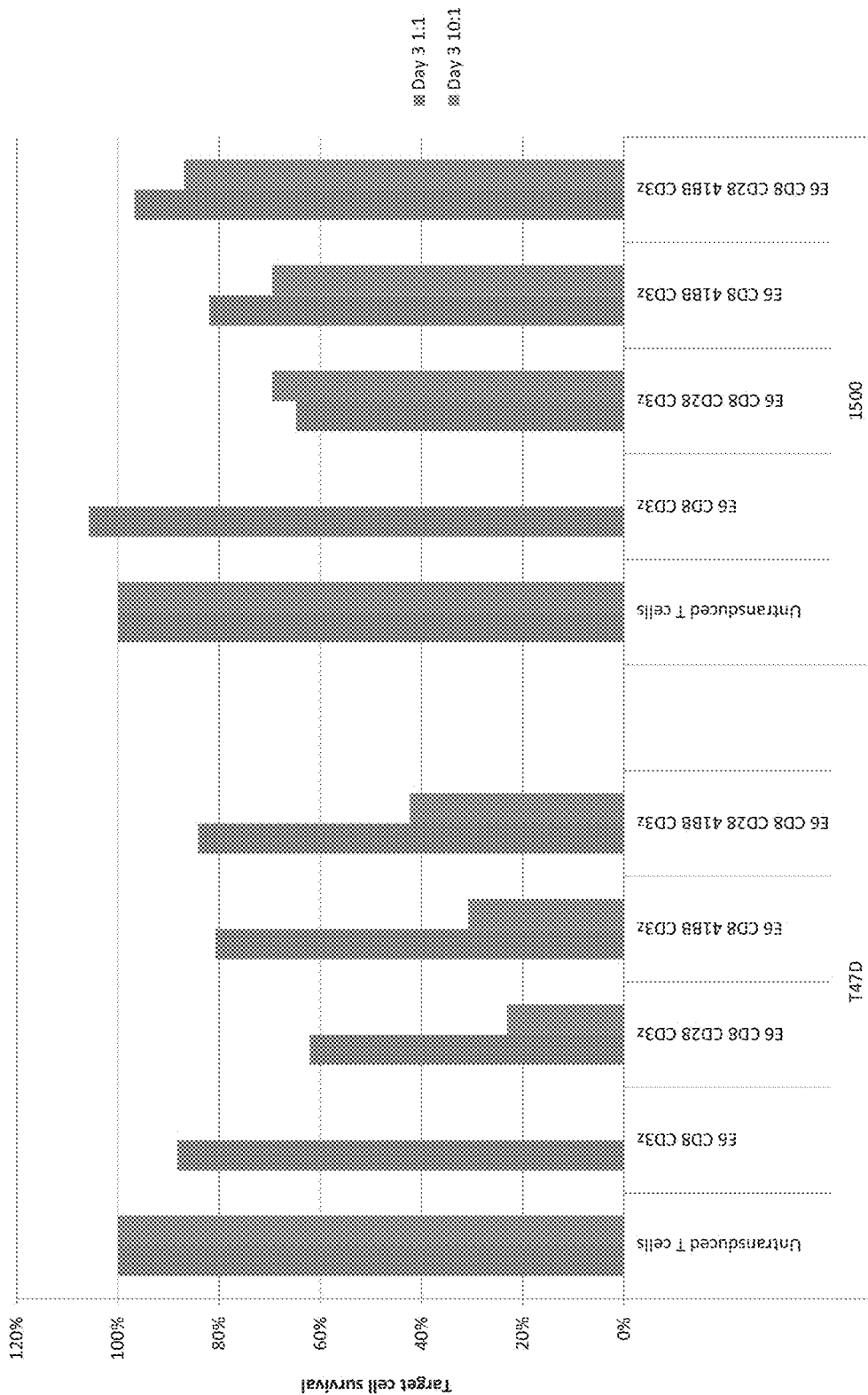
FIG. 36 is a graph of FACS measurements of target cell survival at Day 3 of co-culture experiment. Primary human T cells were transduced with a panel of CARs, including humanized MN-E6-CD8-3z, MN-E6-CD8-CD28-3z, MN-E6-CD8-41BB-3z and MN-E6-CD8-CD28-41BB-3z. The CAR T cells were then exposed to MUC1* positive T47D breast cancer cells or MUC1* positive 1500 aka ZR-75-1 breast cancer cells. The ratio of MUC1* targeting CAR T cells to target cells was either 1:1 or 10:1. As can be seen from the graph, T cells transduced with a MUC1* targeting CAR have a much greater killing effect on MUC1* cancer cells than the untransduced control T cells. In addition, the killing effect is much greater when the ratio of T cells: target cells is increased.
Figure 37:
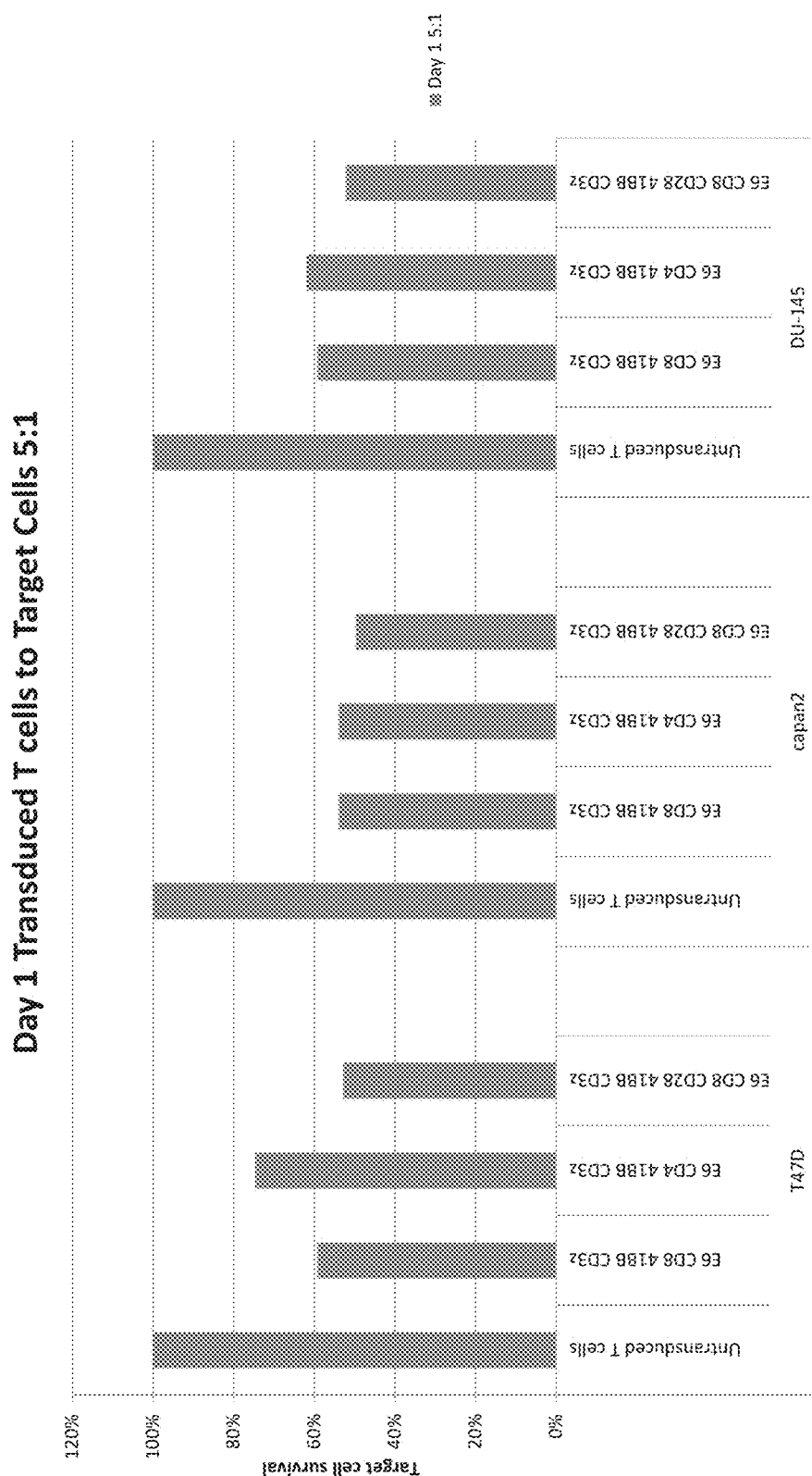
FIG. 37 is a graph of FACS measurements of target cell survival at Day 1 of co-culture experiment. Primary human T cells were transduced with a panel of CARs, including humanized MN-E6-CD8-41BB-3z, MN-E6-CD4-41BB-3z, and MN-E6-CD8-CD28-41BB-3z. The CART cells were then exposed to the following MUC1* positive cancer cells: T47D breast cancer; capan2 pancreatic cancer; or DU-145 prostate cancer. The ratio of MUC1* targeting CAR T cells to target cells was 5:1. As can be seen from the graph, T cells transduced with a MUC1* targeting CAR have a much greater killing effect on MUC1* cancer cells than the untransduced control T cells. Note that the measurements were taken after 24 hours with only a 5:1 T cell to target cell ratio. Also note that MUC1* targeting CARs that have a CD4 extracellular domain-transmembrane-cytoplasmic tail work equally well as CD8 constructs.
Figure 38:
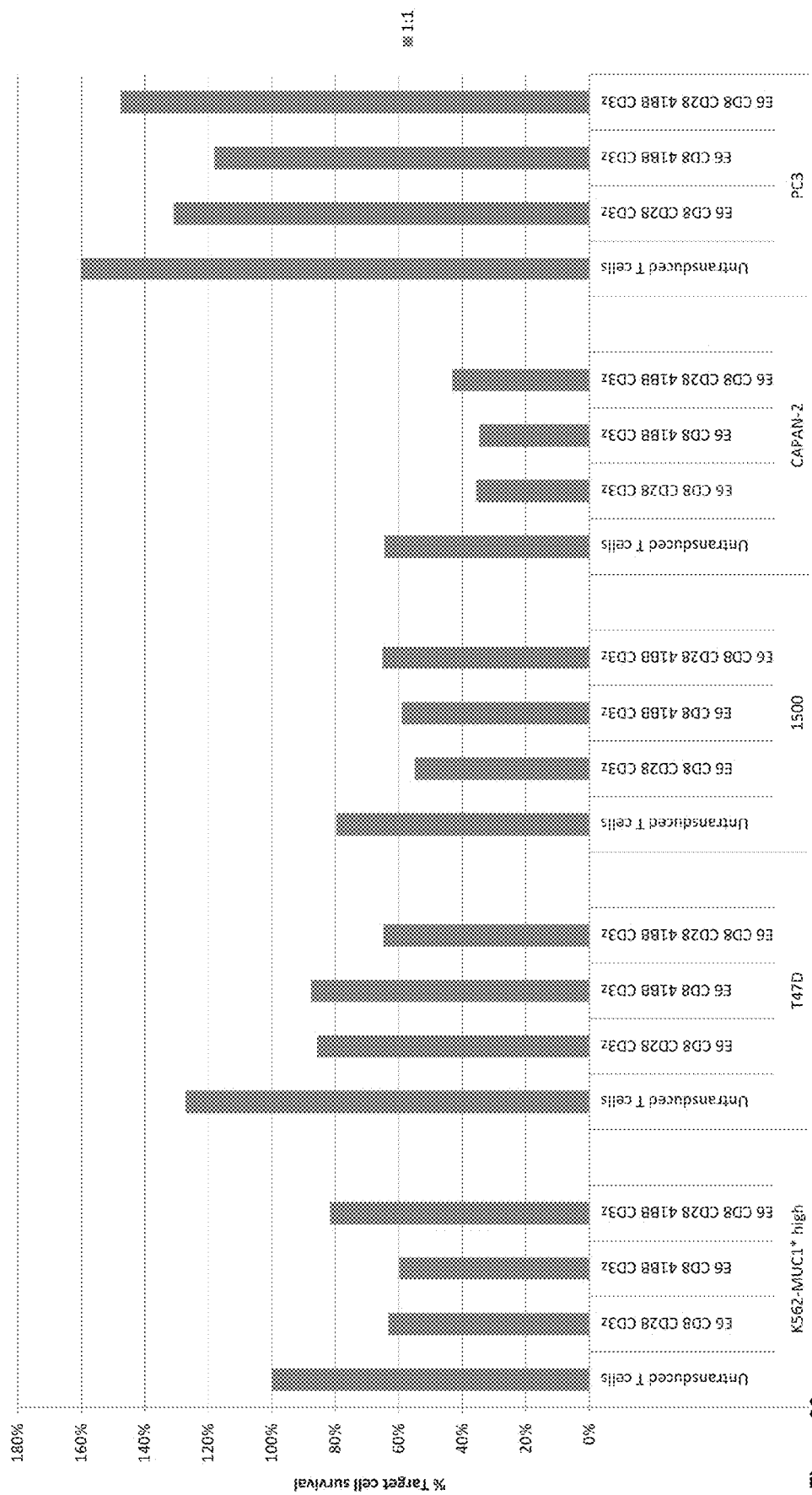
FIG. 38 is a graph of FACS measurements of target cell survival at Day 3 of co-culture experiment. Primary human T cells were transduced with a panel of CARs, including humanized MN-E6-CD8-41BB-3z, MN-E6-CD4-41BB-3z, and MN-E6-CD8-CD28-41BB-3z. The CART cells were then exposed to the following MUC1* positive cancer cells: K562 leukemia cells transfected with MUC1*; T47D breast cancer; 1500 aka ZR-75-1 breast cancer cells; or CAPAN-2 pancreatic cancer cells. In addition to the untransduced T cell controls, the assay was performed on PC3 MUC1* negative prostate cancer cells. The ratio of MUC1* targeting CAR T cells to target cells was 1:1. As can be seen from the graph, T cells transduced with a MUC1* targeting CAR have a much greater killing effect on MUC1* cancer cells than the untransduced control T cells. In addition, the killing effect is specific for MUC1* positive cells. Note that MUC1* targeting CARs that have a CD4 extracellular domain-transmembrane-cytoplasmic tail work equally well as CD8 constructs.
Figure 39:
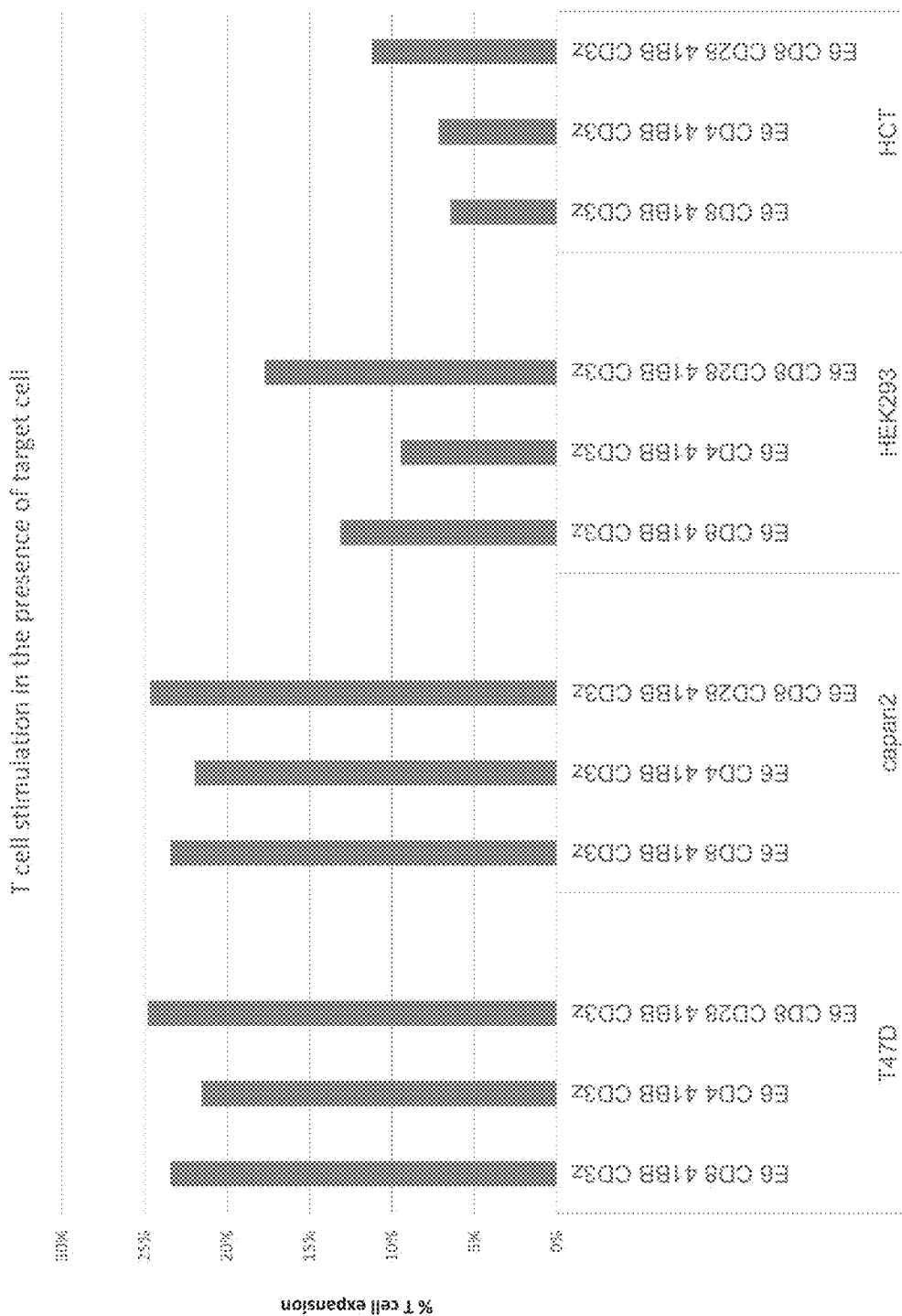
FIG. 39 is a graph of FACS measurements of CAR T cell expansion over 24 hours in co-culture with target cells at a ratio of 5:1 CAR T cells to target cells. The primary human T cells were transduced with a panel of CARs, including humanized MN-E6-CD8-41BB-3z, MN-E6-CD4-41BB-3z, and MN-E6-CD8-CD28-41BB-3z. The CAR T cells were co-cultured with MUC1* positive T47D breast cancer cells, MUC1* positive Capan pancreatic cancer cells, and MUC1-negative cells HCT-116 colon cancer cells and HEK-293 human embryonic kidney cells. As can be seen from the graph, the CAR T population is increased in the presence of MUC1* positive cells.
Figure 40:
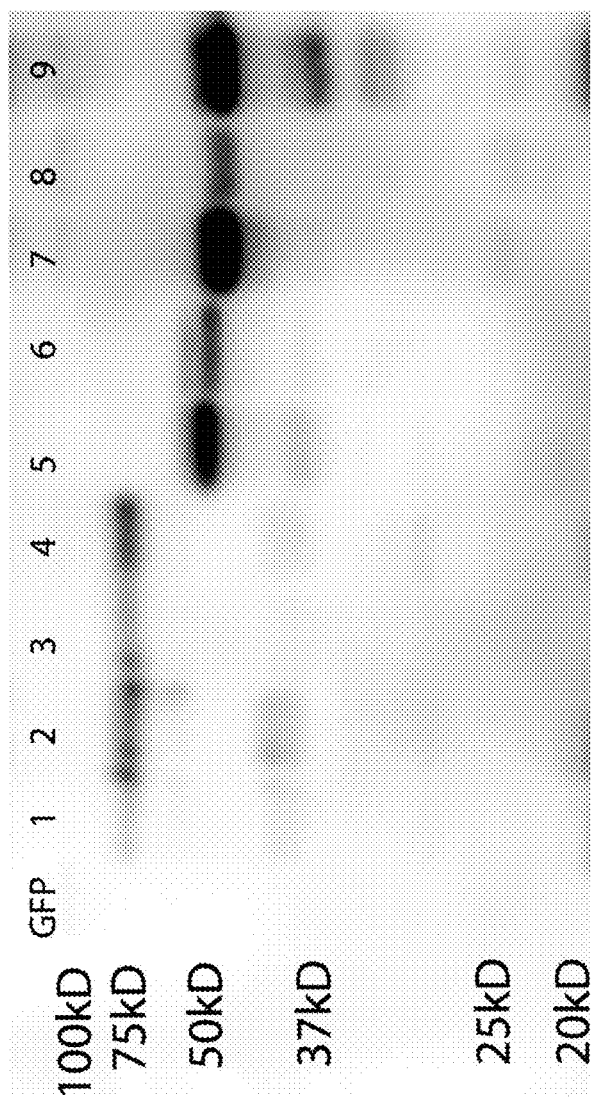
FIG. 40 shows a photograph of a Western blot of MUC1* targeting CARs.

FIG. 36 is a graph of FACS measurements of target cell survival at Day 3 of co-culture experiment. Primary human T cells were transduced with a panel of CARs, including humanized MN-E6-CD8-3z, MN-E6-CD8-CD28-3z, MN-E6-CD8-41BB-3z and MN-E6-CD8-CD28-41BB-3z. The CAR T cells were then exposed to MUC1* positive T47D breast cancer cells or MUC1* positive 1500 aka ZR-75-1 breast cancer cells. The ratio of MUC1* targeting CAR T cells to target cells was either 1:1 or 10:1. As can be seen from the graph, T cells transduced with a MUC1* targeting CAR have a much greater killing effect on MUC1* cancer cells than the untransduced control T cells. In addition, the killing effect is much greater when the ratio of T cells: target cells is increased. FIG. 37 is a graph of FACS measurements of target cell survival at Day 1 of co-culture experiment. Primary human T cells were transduced with a panel of CARs, including humanized MN-E6-CD8-41BB-3z, MN-E6-CD4-41BB-3z, and MN-E6-CD8-CD28-41BB-3z. The CAR T cells were then exposed to the following MUC1* positive cancer cells: T47D breast cancer; capan2 pancreatic cancer; or DU-145 prostate cancer. The ratio of MUC1* targeting CAR T cells to target cells was 5:1. As can be seen from the graph, T cells transduced with a MUC1* targeting CAR have a much greater killing effect on MUC1* cancer cells than the untransduced control T cells. Note that the measurements were taken after 24 hours with only a 5:1 T cell to target cell ratio. Also note that MUC1* targeting CARs that have a CD4 extracellular domain-transmembrane-cytoplasmic tail work equally well as CD8 constructs. FIG. 38 is a graph of FACS measurements of target cell survival at Day 3 of co-culture experiment. Primary human T cells were transduced with a panel of CARs, including humanized MN-E6-CD8-41BB-3z, MN-E6-CD4-41BB-3z, and MN-E6-CD8-CD28-41BB-3z. The CART cells were then exposed to the following MUC1* positive cancer cells:

K562 leukemia cells transfected with MUC1*; T47D breast cancer; 1500 aka ZR-75-1 breast cancer cells; or CAPAN-2 pancreatic cancer cells. In addition to the untransduced T cell controls, the assay was performed on PC3 MUC1* negative prostate cancer cells. The ratio of MUC1* targeting CAR T cells to target cells was 1:1. As can be seen from the graph, T cells transduced with a MUC1* targeting CAR have a much greater killing effect on MUC1* cancer cells than the untransduced control T cells. In addition, the killing effect is specific for MUC1* positive cells. Note that MUC1* targeting CARs that have a CD4 extracellular domain-transmembrane-cytoplasmic tail work equally well as CD8 constructs. FIG. 39 is a graph of FACS measurements of CAR T cell expansion over 24 hours in co-culture with target cells at a ratio of 5:1 CAR T cells to target cells. The primary human T cells were transduced with a panel of CARs, including humanized MN-E6-CD8-41BB-3z, MN-E6-CD4-41BB-3z, and MN-E6-CD8-CD28-41BB-3z. The CAR T cells were co-cultured with MUC1* positive T47D breast cancer cells, MUC1* positive Capan pancreatic cancer cells, and MUC1-negative cells HCT-116 colon cancer cells and HEK-293 human embryonic kidney cells. As can be seen from the graph, the CAR T population is increased in the presence of MUC1* positive cells. FIG. 40 shows a photograph of a Western blot of MUC1* targeting CARs. From 1 to 9 are: 1. MN-E6scFv-Fc-8-41BB-CD3z (Human Fc as hinge region with CD8 TM); 2: MN-E6scFv-FcH-8-41BB-CD3z (Human Fc hingeless as hinge region with CD8 TM); 3: MN-E6scFv-Fc-4-41BB-CD3z (Human Fc as hinge region with CD4 TM); 4: MN-E6scFv-FcH-4-41BB-CD3z (Human Fc as hingeless hinge region with CD4 TM); 5: MN-E6scFv-IgD-8-41BB-CD3z (hinge region from human IgD with CD8 TM); 6: MN-E6scFv-IgD-4-41BB-CD3z (hinge region from human IgD with CD4 TM); 7: MN-E6scFv-X4-8-41BB-CD3z (Long flexible linker as hinge region with CD8 TM); 8: MN-E6scFv-X4-4-41BB-CD3z (Long flexible linker as hinge region with CD4 TM); 9: MN-E6scFv-8-4-41BB-CD3z (Hinge region from CD8 and CD4 a with CD4 TM).

FIG. 41 shows graphs of FACS scans of T47D breast cancer cells co-cultured with human T cells that were transduced with MN-E6scFv-Fc-8-41BB-CD3z, MN-E6scFv-FcH-8-41BB-CD3z (hingeless), MN-E6scFv-Fc-4-41BB-CD3z, MN-E6scFv-IgD-8-41BB-CD3z, MN-E6scFv-X4-8-41BB-CD3z and MN-E6scFv-X4-4-41BB-CD3z. T cells and cancer cells were co-cultured at a 1:1 ratio for 48 hours. T cell counts were normalized to an average of all untransduced T cells and target cells were normalized to each specific cell type when co-cultured with untransduced T cells. The graph shows that when the CAR T cells are co-cultured with MUC1* positive cancer cells, the T cell population expands and the targeted cancer cell population decreases.

FIG. 42 shows graphs of FACS scans of T47D breast cancer cells, Capan-2 pancreatic cancer cells, K562-MUC1* transfected cells, and K562-wt cells that were co-cultured with human T cells that were transduced with MN-E6scFv-Fc-8-41BB-CD3z, MN-E6scFv-FcH-8-41BB-CD3z, MN-E6scFv-Fc-4-41BB-CD3z, MN-E6scFv-IgD-8-41BB-CD3z, MN-E6scFv-X4-8-41BB-CD3z and MN-E6scFv-X4-4-41BB-CD3z. T cells and cancer cells were co-cultured at a 1:1 ratio for 48 hours. T cell counts were normalized to an average of all untransduced T cells and target cells were normalized to each specific cell type when co-cultured with untransduced T cells. The graph shows that when the CAR T cells are co-cultured with MUC1* positive cancer cells, the T cell population expands and the targeted cancer cell population decreases.

As these experiments demonstrate, the critical portion of a CAR is the antibody fragment that directs the immune cell to the tumor cell. As we will show in the following section, MN-E6 and MN-C2 are specific for the form of MUC1* that is expressed on tumor cells. The next most important part of a CAR is the cytoplasmic tail bearing immune system co-stimulatory domains. The identity of these domains modulates the degree of immune response but in no way effect the specificity. As shown, the identity of the transmembrane portion of a CAR is the least important. It appears that as long as the transmembrane portion has some flexibility and is long enough to allow the antibody fragment to reach its cognate receptor on the tumor cell, it will suffice. This is demonstrated in FIGS. 40-42. CARs comprising the MN-E6 targeting antibody fragment, and intracellular co-stimulatory domains 41BB and CD3-zeta but having a variety of different extracellular, transmembrane and short cytoplasmic tail all worked in that they specifically killed the targeted cells while stimulating the expansion of the host T cells. These CARs with variable mid-sections are: MN-E6scFv-Fc-8-41BB-CD3z (Human Fc as hinge region with CD8 TM); 2: MN-E6scFv-FcH-8-41BB-CD3z (Human Fc hingeless as hinge region with CD8 TM); 3: MN-E6scFv-Fc-4-41BB-CD3z (Human Fc as hinge region with CD4 TM); 4: MN-E6scFv-FcH-4-41BB-CD3z (Human Fc as hingeless hinge region with CD4 TM); 5: MN-E6scFv-IgD-8-41BB-CD3z (hinge region from human IgD with CD8 TM); 6: MN-E6scFv-IgD-4-41BB-CD3z (hinge region from human IgD with CD4 TM); 7: MN-E6scFv-X4-8-41BB-CD3z (Long flexible linker as hinge region with CD8 TM); 8: MN-E6scFv-X4-4-41BB-CD3z (Long flexible linker as hinge region with CD4 TM); 9: MN-E6scFv-8-4-41BB-CD3z (Hinge region from CD8 and CD4 a with CD4 TM).

One aspect of the invention is a method for treating a patient diagnosed with, suspected of having, or at risk of developing a MUC1 positive or MUC1* positive cancer, wherein the patient is administered an effective amount of immune cells that have been transduced with a MUC1* targeting CAR, wherein the CAR is chosen from among the group consisting of MN-E6-CD8-3z; MN-E6-CD4-3z; MN-E6-CD8-CD28-3z; MN-E6-CD4-CD28-3z; MN-E6-CD8-41BB-3z; MN-E6-CD4-41BB-3z; MN-E6-CD8-CD28-41BB-3z; MN-E6-CD4-CD28-41BB-3z; MN-E6scFv-Fc-8-41BB-CD3z; MN-E6scFv-FcH-8-41BB-CD3z; MN-E6scFv-Fc-4-41BB-CD3z; MN-E6scFv-FcH-4-41BB-CD3z; MN-E6scFv-IgD-8-41BB-CD3z; MN-E6scFv-IgD-4-41BB-CD3z; MN-E6scFv-X4-8-41BB-CD3z; MN-E6scFv-X4-4-41BB-CD3z; MN-E6scFv-8-4-41BB-CD3z, or any of the aforementioned CARs wherein the MN-E6 is replaced by MN-C2, MN-C3 or MN-C8. Another aspect of the invention is a method for treating a patient diagnosed with, suspected of having, or at risk of developing a cancer, wherein the patient is administered an effective amount of immune cells that have been transduced with one of the aforementioned CARs wherein the MN-E6 is replaced by a peptide comprising antibody variable domain fragments that are specific for a cancer antigen. In any of the above methods, the immune cell may be a T cell and may further be isolated from the patient to be treated.

Specificity of Anti-MUC1* Targeting Antibodies

The most accurate way of demonstrating antibody specificity is testing the antibody on normal human tissue specimens compared to cancerous tissue specimens. MN-C2 and MN-E6 were shown to specifically bind to MUC1 or MUC1* positive cancer cells. Several breast tumor arrays were assayed using several anti-MUC1 or MUC1* antibodies. Essentially the studies involving serial sections of breast cancer tissue specimens from over 1,200 different breast cancer patients showed that very little full-length MUC1 remains on breast cancer tissues. The vast majority of the MUC1 expressed is MUC1* and is stained by MN-C2. The analysis was performed by Clarient Diagnostics and tissue staining was scored using the Allred method. For example, FIG. 43 shows serial sections of breast cancer tissue arrays that were stained with either VU4H5, a commercially available anti-MUC1 antibody that binds to the tandem repeats, or MN-C2 that binds to MUC1*. FIGS. 43 and 44 are photographs of breast cancer tissue arrays stained with either VU4H5 which recognizes MUC1-FL (full length) or MN-C2 which recognizes cancerous MUC1*. Tissue staining was scored using Allred scoring method which combines an intensity score and a distribution score. Below the photographs of the tissue arrays are color-coded graphs displaying the results. As can be seen, the arrays stained with VU4H5 are very light and many tissues do not stain at all despite the published reports that MUC1 is aberrantly expressed on over 96% of all breast cancers as evidenced by nucleic acid based diagnostics. In contrast, the arrays stained with MN-C2 are very dark (red versus yellow or white in graph). Additionally, many tissues did not stain at all with anti-full-length MUC1 but stained very dark with MN-C2, (see green boxes in graph). Similarly, we stained normal or cancerous breast tissues with humanized MN-E6 scFv-Fc. The antibody fragment was biotinylated so it could be visualized by a secondary streptavidin based secondary. As can be seen in FIG. 45, hMN-E6 scFv-Fc does not stain normal breast tissue but stains cancerous breast tissue. Further, the intensity and homogeneity of staining increases with tumor grade and/or metastatic grade of the patient (FIGS. 45 and 46). Similarly, hMN-E6 scFv-Fc did not stain normal lung tissue but did stain lung cancer tissue (FIGS. 47-51) and the intensity and distribution of staining increased as tumor grade or metastatic grade increased. FIG. 52 shows photographs of normal small intestine and cancerous small intestine tissues stained with humanized MN-E6-scFv-Fc biotinylated anti-MUC1* antibody at 5 ug/mL, then stained with a secondary streptavidin HRP antibody. A) is a normal small intestine tissue. B) is small intestine cancer from patient as denoted in the figure. C,D are photographs of the corresponding serial sections that were stained with the secondary antibody alone. FIG. 53 shows photographs of normal small intestine tissues stained with humanized MN-E6-scFv-Fc anti-MUC1* antibody at 50 ug/mL, then stained with a secondary goat-anti-human HRP antibody. A-D are normal small intestine tissue. E-H are photographs of the corresponding serial sections that were stained with the secondary antibody alone. FIG. 54 shows photographs of cancerous small intestine tissues stained with humanized MN-E6-scFv-Fc anti-MUC1* antibody at 50 ug/mL, then stained with a secondary goat-anti-human HRP antibody. A-D are cancerous small intestine tissue from a patient as denoted in figure. E-H are photographs of the corresponding serial sections that were stained with the secondary antibody alone. FIG. 55 shows photographs of cancerous small intestine tissues stained with humanized MN-E6-scFv-Fc anti-MUC1* antibody at 50 ug/mL, then stained with a secondary goat-anti-human HRP antibody. A-D are cancerous small intestine tissue from a patient as denoted in figure. E-H are photographs of the corresponding serial sections that were stained with the secondary antibody alone. FIG. 56 shows photographs of normal colon tissues stained with humanized MN-E6-scFv-Fc anti-MUC1* antibody at 50 ug/mL, then stained with a secondary goat-anti-human HRP antibody. A-D are normal colon. E-H are photographs of the corresponding serial sections that were stained with the secondary antibody alone. FIG. 57 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a metastatic patient as denoted in figure. E-H are photographs of the corresponding serial sections that were stained with the secondary antibody alone. FIG. 58 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a Grade 2 patient as denoted in figure. E-H are photographs of the corresponding serial sections that were stained with the secondary antibody alone. FIG. 59 shows photographs of colon cancer tissues stained with humanized MN-E6-scFv-Fc anti-MUC1* antibody at 50 ug/mL, then stained with a secondary goat-anti-human HRP antibody. A-D are colon cancer tissue from a metastatic patient as denoted in figure. E-H are photographs of the corresponding serial sections that were stained with the secondary antibody alone. FIG. 60 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone. FIG. 61 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone. FIG. 62 shows photographs of prostate cancer tissues stained with humanized MN-E6-scFv-Fc anti-MUC1* antibody at 50 ug/mL, then stained with a secondary goat-anti-human HRP antibody. A-D are prostate cancer tissue from a patient as denoted in figure. E-H are photographs of the corresponding serial sections that were stained with the secondary antibody alone.

One aspect of the invention is a method for treating a patient diagnosed with, suspected of having, or at risk of developing a MUC1 positive or MUC1* positive cancer, wherein a specimen is obtained from the patient's cancer and is tested for reactivity with an antibody that binds to PSMGFR SEQ ID NO:2, SNIKFRPGSVVVQLTLAFREGTINVHDVETQFNQYKTEAASRY (SEQ ID NO:620) or SVVVQLTLAFREGTINVHDVETQFNQYKTEAASRY (SEQ ID NO:621). The patient is then treated with an scFv, scFv-Fc or CAR T that comprises antibody variable fragments from the antibody that reacted with their cancer specimen. Another aspect of the invention is a method for treating a patient diagnosed with, suspected of having, or at risk of developing a MUC1 positive or MUC1* positive cancer, wherein a specimen is obtained from the patient's cancer and is tested for reactivity with MN-E6-scFv, MN-C2-scFv, MN-C3-scFv or MN-C8-scFv; the patient is then treated with the scFv, scFv-Fc-mut or CAR T that comprises portions of the antibody that reacted with their cancer specimen.

BiTEs

Divalent (or bivalent) single-chain variable fragments (di-scFvs, bi-scFvs) can be engineered by linking two scFvs.

This can be done by producing a single peptide chain with two $V_H$ and two $V_L$ regions, yielding tandem scFvs. Another possibility is the creation of scFvs with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Consequently, diabody drugs could be dosed much lower than other therapeutic antibodies and are capable of highly specific targeting of tumors in vivo. Still shorter linkers (one or two amino acids) lead to the formation of trimers, so-called triabodies or tribodies. Tetrabodies have also been produced. They exhibit an even higher affinity to their targets than diabodies.

All of these formats can be composed from variable fragments with specificity for two different antigens, in which case they are types of bispecific antibodies. The furthest developed of these are bispecific tandem di-scFvs, known as bi-specific T-cell engagers (BiTE antibody constructs). BiTEs are fusion proteins consisting of two scFvs of different antibodies, on a single peptide chain of about 55 kilodaltons. One of the scFvs may bind to T cells such as via the CD3 receptor, and the other to a tumor cell via a tumor specific molecule, such aberrantly expressed MUC1*.

Another aspect of the invention is a method for treating a patient diagnosed with, suspected of having, or at risk of developing a MUC1 positive or MUC1* positive cancer, wherein the patient is administered an effective amount of a BiTE wherein one antibody variable fragment of the BiTE binds to a T cell surface antigen and the other antibody variable fragment of the BiTE binds to PSMGFR SEQ ID NO:2, SNIKFRPGSVVVQLTLAFREGTINVHDVETQFNQYKTEAASRY (SEQ ID NO:620) or SVVVQLTLAFREGTINVHDVETQFNQYKTEAASRY (SEQ ID NO:621). In one case, the antibody variable fragment of the BiTE that binds to MUC1* comprises portions of huMN-E6, huMN-C2, huMN-C3, or huMN-C8.

In another aspect of the invention, MUC1* peptides including PSMGFR SEQ ID NO:2, most or all of SNIKFRPGSVVVQLTLAFREGTINVHDVETQFNQYKTEAASRY (SEQ ID NO:620) or SVVVQLTLAFREGTINVHDVETQFNQYKTEAASRY (SEQ ID NO:621) are used in adoptive T cell approaches. In this case, a patient's T cells are exposed to the MUC1* peptides and through various rounds of maturation, the T cells develop MUC1* specific receptors. The adapted T cells are then expanded and administered to the donor patient who is diagnosed with, suspected of having, or is at risk of developing a MUC1* positive cancer.

Other MUC1 Cleavage Sites

However, MUC1 is cleaved to the growth factor receptor form, MUC1*, on some healthy cells in addition to cancer cells. For example, MUC1 is cleaved to MUC1* on healthy stem and progenitor cells. A large percentage of bone marrow cells are MUC1* positive. Portions of the intestine are MUC1* positive.

The inventors have discovered that MUC1 can be cleaved at different positions that are relatively close to each other but the location of cleavage changes the fold of the remaining portion of the extracellular domain. As a result, monoclonal antibodies can be identified that bind to MUC1* cleaved at a first position but do not bind to MUC1* that has been cleaved at a second position. This discovery is disclosed in WO2014/028668, filed Aug. 14, 2013, the contents of which are incorporated by reference herein its entirety. We identified a set of anti-MUC1* monoclonal antibodies that bind to a MUC1* as it appears on cancer cells but do not bind to MUC1* as it appears on stem and progenitor cells. Conversely, we identified a second set of monoclonal antibodies that bind to stem and progenitor cells but do not bind to cancer cells. One method used to identify stem specific antibodies is as follows: supernatants from monoclonal hybridomas were separately adsorbed onto 2 multi-well plates. Stem cells, which are non-adherent cells, were put into one plate and cancer cells which are adherent were put into an identical plate. After an incubation period, the plates were rinsed and inverted. If the non-adherent stem cells stuck to the plate, then the monoclonal in that particular well recognizes stem cells and will not recognize cancer cells. Antibodies that did not capture stem cells or antibodies that captured cancer cells were identified as cancer specific stem cells. FACS analysis has confirmed this method works. Antibodies MN-E6 and MN-C2 are examples of cancer-specific antibodies. Antibodies MN-C3 and MN-C8 are examples of stem-specific antibodies. Although both sets of antibodies are able to bind to a peptide having the PSMGFR sequence, FACS analysis shows that the anti-MUC1* polyclonal antibody and MN-C3 bind to MUC1* positive bone marrow cells but MN-E6 does not. The MUC1* polyclonal antibody was generated by immunizing a rabbit with the PSMGFR peptide. Similarly, MN-C3 binds to stem cells of the intestinal crypts but MN-E6 does not. Conversely, MN-E6 antibody binds to cancerous tissue while the stem-specific MN-C3 does not. Competition ELISA experiments indicate that the C-terminal 10 amino acids of the PSMGFR peptide are required for MN-E6 and MN-C2 binding, but not for MN-C3 and MN-C8. Therefore, another method for identifying antibodies that are cancer specific is to immunize with a peptide having the sequence of the PSMGFR peptide minus the 10 N-terminal amino acids or use that peptide to screen for antibodies or antibody fragments that will be cancer specific. Antibodies that bind to a peptide with a sequence of PSMGFR peptide minus the N-terminal 10 amino acids but do not bind to a peptide with a sequence of PSMGFR peptide minus the C-terminal 10 amino acids are cancer specific antibodies for use in the treatment or prevention of cancers.

The extracellular domain of MUC1 is also cleaved on stem cells and some progenitor cells, where activation of cleaved MUC1 by ligands NME1 in dimer form or NME7 promotes growth and pluripotency and inhibits differentiation. The transmembrane portion of MUC1 that remains after cleavage is called MUC1* and the extracellular domain is comprised essentially of the Primary Sequence of MUC1 Growth Factor Receptor (PSMGFR) sequence. However, the exact site of cleavage can vary depending on cell type, tissue type, or which cleavage enzyme a particular person expresses or overexpresses. In addition to the cleavage site that we previously identified which leaves the transmembrane portion of MUC1* comprising most or all of the PSMGFR SEQ ID NO:2, other cleavage sites result in an extended MUC1* comprised of most or all of SNIKFRPGSVVVQLTLAFREGTINVHDVETQFNQYKTEAASRY (SEQ ID NO:620); or SVVVQLTLAFREGTINVHDVETQFNQYKTEAASRY (SEQ ID NO:621). The site of MUC1 cleavage affects how the remaining extracellular domain folds. We have identified monoclonal antibodies that bind to cleaved MUC1* on cancer cells but do not bind to cleaved MUC1* as it exists on healthy stem and progenitor cells.

Whereas an anti-MUC1* antibody or antibody-like molecule may be most effective if it competitively inhibits the binding of NME1, NME6, NME8 or NME7 or NME7-AB to MUC1*, for example an antibody that binds to the PSMGFR sequence especially if said antibody is unable to bind to a PSMGFR peptide if the 10 C-terminal amino acids are missing, antibodies or antibody-like molecules that carry a payload need not competitively inhibit the binding of MUC1* ligands to be effective as anti-cancer agents. For example antibodies or antibody-like molecules that are conjugated to a toxin could be effective at killing target cancer cells without necessarily inhibiting binding of the activating ligands. For example, antibodies or antibody-like molecules such as CARs or BiTEs which recruit the patient's immune system to the tumor can be effective as anti-cancer agents even if the antibody fragment targets a portion of MUC1* such that antibody fragment binding does not competitively inhibit the binding of NME1, NME6, NME8, NME7-AB or NME7. In a preferred embodiment the antibody fragment incorporated into a CAR, an adaptive T cell receptor or a BiTE does competitively inhibit the binding of NME1, NME6, NME8, NME7-AB or NME7 to MUC1*.

Antibodies that are able to bind to the extracellular domain of the remaining transmembrane portion block the interaction between the MUC1* extracellular domain and activating ligands and in this way can be used as therapeutic agents, for example for the treatment of cancers. Anti-MUC1* antibodies are also useful for the growth, delivery, identification or isolation of stem cells both in vitro and in vivo.

General Strategy for Using Antibodies, Antibody Fragments and CARs that Target the Extracellular Domain of MUC1*

Monoclonal antibodies MN-C3 and MN-C8 have a greater binding affinity for stem cells than cancer cells. Humanized antibodies and antibody fragments containing sequences derived from the variable regions of MN-C3 and MN-C8 can be used as an adhesion surface coating for human stem cells.

Alternatively, humanized antibodies and antibody fragments containing sequences derived from the variable regions of MN-C3 and MN-C8 can be used to deliver stem cells to a specific location such as for in situ human therapeutics. In one case, a substrate coated with humanized MN-C3 or MN-C8 derived antibodies or antibody fragments is loaded with stem cells then inserted into a patient. In another case, a substrate coated with humanized MN-C3 or MN-C8 derived antibodies or antibody fragments is inserted into a patient in order to recruit the patient's own stem cells to a specific area for therapy. Human therapies in which antibodies that bind to human stem cells will be of therapeutic use include spinal cord repair. Substrates coated with humanized MN-C3 or MN-C8 derived antibodies or antibody fragments are also used to identify or isolate human antibodies. Humanized MN-C3 or MN-C8 derived antibodies can also be used to stimulate the growth of stem cells.

Sequence Listing Free Text: xml text file named "56699-731_3025L" having byte size of 993,008, created Aug. 3, 2022 is incorporated by reference herein.

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

```
MUC1 Receptor
(Mucin 1 precursor, Genbank Accession number: P15941)
                                                            (SEQ ID NO: 1)
MTPGTQSPFFLLLLLTVLTVVTGSGHASSTPGGEKETSATQRSSVPSSTEKNAVSMTSSVLSSHSPGS

GSSTTQGQDVTLAPATEPASGSAATWGQDVTSVPVTRPALGSTTPPAHDVTSAPDNKPAPGSTAPPAH

GVTSAPDTRPAPGSTAPPAHGVTSAPDTRPAPGSTAPPAHGVTSAPDTRPAPGSTAPPAHGVTSAPDT

RPAPGSTAPPAHGVTSAPDTRPAPGSTAPPAHGVTSAPDTRPAPGSTAPPAHGVTSAPDTRPAPGSTA

PPAHGVTSAPDTRPAPGSTAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGSTAPPAHGVTSAPDTRPAP

GSTAPPAHGVTSAPDTRPAPGSTAPPAHGVTSAPDTRPAPGSTAPPAHGVTSAPDTRPAPGSTAPPAH

GVTSAPDTRPAPGSTAPPAHGVTSAPDTRPAPGSTAPPAHGVTSAPDTRPAPGSTAPPAHGVTSAPDT

RPAPGSTAPPAHGVTSAPDTRPAPGSTAPPAHGVTSAPDTRPAPGSTAPPAHGVTSAPDTRPAPGSTA

PPAHGVTSAPDTRPAPGSTAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAPDTRPAPGSTAPPAHGVTSAPDTRPAP

GSTAPPAHGVTSAPDTRPAPGSTAPPAHGVTSAPDTRPAPGSTAPPAHGVTSAPDTRPAPGSTAPPAH

GVTSAPDTRPAPGSTAPPAHGVTSAPDTRPAPGSTAPPAHGVTSAPDTRPAPGSTAPPAHGVTSAPDT

RPAPGSTAPPAHGVTSAPDTRPAPGSTAPPAHGVTSAPDTRPAPGSTAPPAHGVTSAPDNRPALGSTA

PPVHNVTSASGSASGSASTLVHNGTSARATTTPASKSTPFSIPSHHSDTPTTLASHSTKTDASSTHHS

SVPPLTSSNHSTSPQLSTGVSFFFLSFHISNLQFNSSLEDPSTDYYQELQRDISEMFLQIYKQGGFLG

LSNIKFRPGSVVVQLTLAFREGTINVHDVETQFNQYKTEAASRYNLTISDVSVSDVPFPFSAQSGAGV
```

-continued

PGWGIALLVLVCVLVALAIVYLIALAVCQCRRKNYGQLDIFPARDTYHPMSEYPTYHTHGRYVPPSST

DRSPYEKVSAGNGGSSLSYTNPAVAAASANL

PSMGFR (SEQ ID NO: 2)

GTINVHDVETQFNQYKTEAASRYNLTISDVSVSDVPFPFSAQSGA

Human NME1
(DNA)

(SEQ ID NO: 3)

atggccaactgtgagcgtaccttcattgcgatcaaaccagatggggtccagcggggtcttgtgggaga gattatcaagcgttttgagcagaaaggattccgccttgttggtctgaaattcatgcaagcttccgaag atcttctcaaggaacactacgttgacctgaaggaccgtccattctttgccggcctggtgaaatacatg cactcagggccggtagttgccatggtctgggaggggctgaatgtggtgaagacgggccgagtcatgct cggggagaccaaccctgcagactccaagcctgggaccatccgtggagacttctgcatacaagttgga ggaacattatacatggcagtgattctgtggagagtgcagagaaggagatcggcttgtggtttcaccct gaggaactggtagattacacgagctgtgctcagaactggatctatgaatga (amino acids)

(SEQ ID NO: 4)

MANCERTFIAIKPDGVQRGLVGEIIKRFEQKGFRLVGLKFMQASEDLLKEHYVDLKDRPFFAGLVKYM

HSGPVVAMVWEGLNVVKTGRVMLGETNPADSKPGTIRGDFCIQVGRNIIHGSDSVESAEKEIGLWFHP

EELVDYTSCAQNWIYE-

Human NME7
(DNA)

(SEQ ID NO: 5)

atgaatcatagtgaaagattcgttttcattgcagagtggtatgatccaaatgcttcacttcttcgacg ttatgagcttttattttacccaggggatggatctgttgaaatgcatgatgtaaagaatcatcgcacct tttaaagcggaccaaatatgataacctgcacttggaagatttatttataggcaacaaagtgaatgtc ttttctcgacaactggtattaattgactatggggatcaatatacagctcgccagctgggcagtaggaa agaaaaaacgctagccctaattaaaccagatgcaatatcaaaggctggagaaataattgaaataataa acaaagctggatttactataaccaaactcaaaatgatgatgctttcaaggaaagaagcattggatttt catgtagatcaccagtcaagacccttttttcaatgagctgatccagtttattacaactggtcctattat tgccatggagattttaagagatgatgctatatgtgaatggaaaagactgctgggacctgcaaactctg gagtggcacgcacagatgcttctgaaagcattagagccctctttggaacagatggcataagaaatgca gcgcatggccctgattcttttgcttctgcggccagagaaatggagttgttttttccttcaagtggagg ttgtgggccggcaaacactgctaaatttactaattgtacctgttgcattgttaaacccccatgctgtca gtgaaggactgttgggaaagatcctgatggctatccgagatgcaggttttgaaatctcagctatgcag atgttcaatatggatcgggttaatgttgaggaattctatgaagtttataaaggagtagtgaccgaata tcatgacatggtgacagaaatgtattctggccccttgtgtagcaatggagattcaacagaataatgcta caaagacatttcgagaattttgtggacctgctgatcctgaaattgcccggcatttacgccctggaact ctcagagcaatctttggtaaaactaagatccagaatgctgttcactgtactgatctgccagaggatgg cctattagaggttcaatacttcttcaagatcttggataattag (amino acids)

(SEQ ID NO: 6)

MNHSERFVFIAEWYDPNASLLRRYELLFYPGDGSVEMHDVKNHRTFLKRTKYDNLHLEDLFIGNKVNV

FSRQLVLIDYGDQYTARQLGSRKEKTLALIKPDAISKAGEIIEIINKAGFTITKLKMMMLSRKEALDF

HVDHQSRPFFNELIQFITTGPIIAMEILRDDAICEWKRLLGPANSGVARTDASESIRALFGTDGIRNA

AHGPDSFASAAREMELFFPSSGGCGPANTAKFTNCTCCIVKPHAVSEGLLGKILMAIRDAGFEISAMQ

-continued

MFNMDRVNVEEFYEVYKGVVTEYHDMVTEMYSGPCVAMEIQQNNATKTFREFCGPADPEIARHLRPGT

LRAIFGKTKIQNAVHCTDLPEDGLLEVQYFFKILDN-

NME7 peptides
NME7A peptide 1 (A domain):
(SEQ ID NO: 7)
MLSRKEALDFHVDHQS

NME7A peptide 2 (A domain):
(SEQ ID NO: 8)
SGVARTDASES

NME7B peptide 1 (B domain):
(SEQ ID NO: 9)
DAGFEISAMQMFNMDRVNVE

NME7B peptide 2 (B domain):
(SEQ ID NO: 10)
EVYKGVVTEYHDMVTE

NME7B peptide 3 (B domain):
(SEQ ID NO: 11)
AIFGKTKIQNAVHCTDLPEDGLLEVQYFF

Mouse E6 Heavy chain variable region sequence:
(DNA)
(SEQ ID NO: 12)
gaggtgaaggtggtggagtctgggggagacttagtgaagcctggagggtccctgaaactctcctgtgt agtctctggattcactttcagtagatatggcatgtcttgggttcgccagactccaggcaagaggctgg agtgggtcgcaaccattagtggtggcggtacttacatctactatccagacagtgtgaaggggcgattc accatctccagagacaatgccaagaacaccctgtacctgcaaatgagcagtctgaagtctgaggacac agccatgtatcactgtacaagggataactacggtaggaactacgactacggtatggactactgggtc aaggaacctcagtcaccgtctcctca (amino acids)
(SEQ ID NO: 13)
EVKVVESGGDLVKPGGSLKLSCVVSGFTFSRYGMSWVRQTPGKRLEWVATISGGGTYIYYPDSVKGRF

TISRDNAKNTLYLQMSSLKSEDTAMYHCTRDNYGRNYDYGMDYWGQGTSVTVSS

Mouse E6 heavy chain variable framework region 1 (FWR1) sequence:
(DNA)
(SEQ ID NO: 14)
gaggtgaaggtggtggagtctgggggagacttagtgaagcctggagggtccctgaaactctcctgtgt agtctct (amino acids)
(SEQ ID NO: 15)
EVKVVESGGDLVKPGGSLKLSCVVSGFTFS Mouse E6 heavy chain variable complementarity determining regions 1
(CDR1) sequence:
(DNA)
(SEQ ID NO: 16)
ggattcactttcagtagatatggcatgtct (amino acids)
(SEQ ID NO: 17)
RYGMS Mouse E6 heavy chain variable framework region 2 (FWR2) sequence:
(DNA)
(SEQ ID NO: 18)
tgggttcgccagactccaggcaagaggctggagtgggtcgca (amino acids)
(SEQ ID NO: 19)
WVRQTPGKRLEWVA Mouse E6 heavy chain variable complementarity determining regions 2
(CDR2) sequence:
(DNA)
(SEQ ID NO: 20)
accattagtggtggcggtacttacatctactatccagacagtgtgaagggg (amino acids)
(SEQ ID NO: 21)
TISGGGTYIYYPDSVKG Mouse E6 heavy chain variable framework region 3 (FWR3) acid
sequence:
(DNA)
(SEQ ID NO: 22)
cgattcaccatctccagagacaatgccaagaacaccctgtacctgcaaatgagcagtctgaagtctga ggacacagccatgtatcactgtacaagg (amino acids)
(SEQ ID NO: 23)
RFTISRDNAKNTLYLQMSSLKSEDTAMYHCTR Mouse E6 heavy chain variable complementarity determining regions 3
(CDR3) sequence:
(DNA)
(SEQ ID NO: 24)
gataactacggtaggaactacgactacggtatggactac (amino acids)
(SEQ ID NO: 25)
DNYGRNYDYGMDY IGHV3-21*03 heavy chain variable region sequence:
(DNA)
(SEQ ID NO: 26)
gaggtgcagctggtggagtctgggggaggcctggtcaagcctggggggtccctgagactctcctgtgc agcctctggattcaccttcagtagctatagcatgaactgggtccgccaggctccagggaaggggctgg agtgggtctcatccattagtagtagtagtagttacatatactacgcagactcagtgaagggccgattc accatctccagagacaacgccaagaactcactgtatctgcaaatgaacagcctgagagccgaggacac ggctgtgtattactgtgcgaga (amino acids)
(SEQ ID NO: 27)
EVQLVESGGGLVKPGGSLRLSCAASGFTFSSYSMNWVRQAPGKGLEWVSSISSSSSYIYYADSVKGRF

TISRDNAKNSLYLQMNSLRAEDTAVYYCAR

IGHV3-21*01 heavy chain variable framework region 1 (FWR1) sequence:
(DNA)
(SEQ ID NO: 28)
gaggtgcagctggtggagtctgggggaggcctggtcaagcctggggggtccctgagactctcctgtgc agcctctggattcaccttcagt (amino acids)
(SEQ ID NO: 29)
EVQLVESGGGLVKPGGSLRLSCAASGFTFS IGHV3-21*01 heavy chain variable complementarity determining regions
1 (CDR1) sequence:
(DNA)
(SEQ ID NO: 30)
agctatagcatgaac (amino acids)
(SEQ ID NO: 31)
SYSMN IGHV3-21*01 heavy chain variable framework region 2 (FWR2) sequence:
(DNA)
(SEQ ID NO: 32)
tgggtccgccaggctccagggaaggggctggagtgggtctca (amino acids)
(SEQ ID NO: 33)
WVRQAPGKGLEWVS IGHV3-21*01 heavy chain variable complementarity determining regions
2 (CDR2) sequence:
(DNA)
(SEQ ID NO: 34)
tccattagtagtagtagtagttacatatactacgcagactcagtgaagggc (amino acids)
(SEQ ID NO: 35)
SISSSSSYIYYADSVKG IGHV3-21*01 heavy chain variable framework region 3 (FWR3) sequence:
(DNA)
(SEQ ID NO: 36)
cgattcaccatctccagagacaacgccaagaactcactgtatctgcaaatgaacagcctgagagccga ggacacggctgtgtattactgtgcgaga (amino acids)
(SEQ ID NO: 37)
RFTISRDNAKNSLYLQMNSLRAEDTAVYYCAR Humanized E6 heavy chain variable region sequence:
(DNA)
(SEQ ID NO: 38)
gaggtgcagctggtggagtctgggggaggcctggtcaagcctggggggtccctgagactctcctgtgc agcctctggattcaccttcagtaggtatggcatgagctgggtccgccaggctccagggaagaggctgg agtgggtctcaaccattagtggcggaggcacctacatatactacccagactcagtgaagggccgattc accatctccagagacaacgccaagaacaccctgtatctgcaaatgaacagcctgagagccgaggacac ggctgtgtattactgtaccagagataactatggccgcaactatgattatggcatggattattggggcc agggcaccctggtgaccgtgagcagc (amino acids)
(SEQ ID NO: 39)
EVQLVESGGGLVKPGGSLRLSCAASGFTFSRYGMSWVRQAPGKRLEWVSTISGGGTYIYYPDSVKGRF

TISRDNAKNTLYLQMNSLRAEDTAVYYCTRDNYGRNYDYGMDYWGQGTLVTVSS

Humanized E6 heavy chain variable framework region 1 (FWR1) acid
sequence:
(DNA)
(SEQ ID NO: 40)
gaggtgcagctggtggagtctgggggaggcctggtcaagcctggggggtccctgagactctcctgtgc agcctctggattcaccttcagt (amino acids)
(SEQ ID NO: 41)
EVQLVESGGGLVKPGGSLRLSCAASGFTFS Humanized E6 heavy chain variable complementarity determining
regions 1 (CDR1) sequence:
(DNA)
(SEQ ID NO: 42)
aggtatggcatgagc (amino acids)
(SEQ ID NO: 43)
RYGMS Humanized E6 heavy chain variable framework region 2 (FWR2) acid
sequence:
(DNA)
(SEQ ID NO: 44)
tgggtccgccaggctccagggaagaggctggagtgggtctca (amino acids)
(SEQ ID NO: 45)
WVRQAPGKRLEWVS -continued Humanized E6 heavy chain variable complementarity determining
regions 2 (CDR2) sequence:
(DNA)

(SEQ ID NO: 46)

accattagtggcggaggcacctacatatactacccagactcagtgaagggc (amino acids)

(SEQ ID NO: 47)

TISGGGTYIYYPDSVKG

Humanized E6 heavy chain variable framework region 3 (FWR3) acid
sequence:
(DNA)

(SEQ ID NO: 48)

cgattcaccatctccagagacaacgccaagaacaccctgtatctgcaaatgaacagcctgagagccga ggacacggctgtgtattactgtaccaga (amino acids)

(SEQ ID NO: 49)

RFTISRDNAKNTLYLQMNSLRAEDTAVYYCTR

Humanized E6 heavy chain variable complementarity determining
regions 3 (CDR3) sequence:
(DNA)

(SEQ ID NO: 50)

gataactatggccgcaactatgattatggcatggattat (amino acids)

(SEQ ID NO: 51)

DNYGRNYDYGMDY

Humanized E6 IgG2 heavy chain synthesized by Genescript:
(DNA)

(SEQ ID NO: 52)

gaattctaagcttgggccaccatggaactggggctccgctgggttttccttgttgctattttagaagg tgtccagtgtgaggtgcagctggtggagtctgggggaggcctggtcaagcctggggggtccctgagac tctcctgtgcagcctctggattcaccttcagtaggtatggcatgagctgggtccgccaggctccaggg aagaggctggagtgggtctcaaccattagtggcggaggcacctacatatactacccagactcagtgaa gggccgattcaccatctccagagacaacgccaagaacaccctgtatctgcaaatgaacagcctgagag ccgaggacacggctgtgtattactgtaccagagataactatggccgcaactatgattatggcatggat tattggggccagggcaccctggtgaccgtgagcagcgcctccaccaagggcccatcggtcttccccct ggcgccctgctccaggagcacctccgagagcacagccgccctgggctgcctggtcaaggactacttcc ccgaaccggtgacggtgtcgtggaactcaggcgctctgaccagcggcgtgcacaccttcccagctgtc ctacagtcctcaggactctactccctcagcagcgtggtgaccgtgccctccagcaacttcggcaccca gacctacacctgcaacgtagatcacaagcccagcaacaccaaggtggacaagacagttgagcgcaaat gttgtgtcgagtgcccaccgtgcccagcaccacctgtggcaggaccgtcagtcttcctcttccccccca aaacccaaggacaccctcatgatctcccggacccctgaggtcacgtgcgtggtggtggacgtgagcca cgaagaccccgaggtccagttcaactggtacgtggacggcgtggaggtgcataatgccaagacaaagc cacgggaggagcagttcaacagcacgttccgtgtggtcagcgtcctcaccgttgtgcaccaggactgg ctgaacggcaaggagtacaagtgcaaggtctccaacaaaggcctcccagcccccatcgagaaaaccat ctccaaaaccaaagggcagccccgagaaccacaggtgtacaccctgcccccatcccgggaggagatga ccaagaaccaggtcagcctgacctgcctggtcaaaggcttctaccccagcgacatcgccgtggagtgg gagagcaatgggcagccggagaacaactacaagaccacacctcccatgctggactccgacggctcctt cttcctctacagcaagctcaccgtggacaagagcaggtggcagcaggggaacgtcttctcatgctccg tgatgcatgaggctctgcacaaccactacacgcagaagagcctctccctgtctccgggtaaatagtaa gtttaaactctaga (amino acids)

(SEQ ID NO: 53)
EF*AWATMELGLRWVFLVAILEGVQCEVQLVESGGGLVKPGGSLRLSCAASGFTFSRYGMSWVRQAPG

KRLEWVSTISGGGTYIYYPDSVKGRFTISRDNAKNTLYLQMNSLRAEDTAVYYCTRDNYGRNYDYGMD

YWGQGTLVTVSSASTKGPSVFPLAPCSRSTSESTAALGCLVKDYFPEPVTVSWNSGALTSGVHTFPAV

LQSSGLYSLSSVVTVPSSNFGTQTYTCNVDHKPSNTKVDKTVERKCCVECPPCPAPPVAGPSVFLFPP

KPKDTLMISRTPEVTCVVVDVSHEDPEVQFNWYVDGVEVHNAKTKPREEQFNSTFRVVSVLTVVHQDW

LNGKEYKCKVSNKGLPAPIEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEALHNHYTQKSLSLSPGK**

V*TLX

Human IgG2 heavy chain constant region sequence:
(DNA)

(SEQ ID NO: 54)
gcctccaccaagggcccatcggtcttccccctggcgcctgctccaggagcacctccgagagcacagc cgccctgggctgcctggtcaaggactactccccgaaccggtgacgcgtgtcgtggaactcaggcgctc tgaccagcggcgtgcacaccttcccagctgtcctacagtcctcaggactctactccctcagcagcgtg gtgaccgtgccctccagcaacttcggcacccagacctacacctgcaacgtagatcacaagcccagcaa caccaaggtggacaagacagttgagcgcaaatgttgtgtcgagtgcccaccgtgcccagcaccacctg tggcaggaccgtcagtcttcctcttccccccaaaacccaaggacaccctcatgatctcccggacccct gaggtcacgtgcgtggtggtggacgtgagccacgaagaccccgaggtccagttcaactggtacgtgga cggcgtggaggtgcataatgccaagacaaagccacgggaggagcagttcaacagcacgttccgtgtgg tcagcgtcctcaccgttgtgcaccaggactggctgaacggcaaggagtacaagtgcaaggtctccaac aaaggcctcccagcccccatcgagaaaaccatctccaaaaccaaagggcagccccgagaaccacaggt gtacaccctgcccccatcccgggaggagatgaccaagaaccaggtcagcctgacctgcctggtcaaag gcttctaccccagcgacatcgccgtggagtgggagagcaatgggcagccggagaacaactacaagacc acacctcccatgctggactccgacggctccttcttcctctacagcaagctcaccgtggacaagagcag gtggcagcaggggaacgtcttctcatgctccgtgatgcatgaggctctgcacaaccactacacgcaga agagcctctccctgtctccgggtaaatag (amino acids)

(SEQ ID NO: 55)
ASTKGPSVFPLAPCSRSTSESTAALGCLVKDYFPEPVTVSWNSGALTSGVHTFPAVLQSSGLYSLSSV

VTVPSSNFGTQTYTCNVDHKPSNTKVDKTVERKCCVECPPCPAPPVAGPSVFLFPPKPKDTLMISRTP

EVTCVVVDVSHEDPEVQFNWYVDGVEVHNAKTKPREEQFNSTFRVVSVLTVVHQDWLNGKEYKCKVSN

KGLPAPIEKTISKTKGQPREPQVYTLPPSREEMTKNQVSLTCLVKGFYPSDIAVEWESNGQPENNYKT

TPPMLDSDGSFFLYSKLTVDKSRWQQGNVFSCSVMHEALHNHYTQKSLSLSPGK

Humanized E6 IgG1 heavy chain sequence:
(DNA)

(SEQ ID NO: 56)
gaggtgcagctggtggagtctgggggaggcctggtcaagcctggggggtccctgagactctcctgtgc agcctctggattcaccttcagtaggtatggcatgagctgggtccgccaggctccagggaagaggctgg agtgggtctcaaccattagtggcggaggcacctacatatactacccagactcagtgaagggccgattc accatctccagagacaacgccaagaacccactgtatctgcaaatgaacagcctgagagccgaggacac ggctgtgtattactgtcccagagataactatggccgcaactatgattatggcatggattattggggcc agggcacccctggtgaccgtgagcagcgctagcaccaagggcccatcggtcttccccctggcaccctcc tccaagagcacctctggggggcacagcggccctgggctgcctggtcaaggactacttccccgaaccggt -continued

```
gacggtgtcgtggaactcaggcgcccgaccagcggcgtgcacaccttcccggctgtcctacagtcct caggactctactccctcagcagcgtggtgacagtgccctccagcagcttgggcacccagacctacatc tgcaacgtgaatcacaagcccagcaacaccaaggtggacaagaaagttgagcccaaatcttgtgacaa aactcacacatgcccaccgtgcccagcacctgaactcctggggggaccgtcagtcttcctcttccccc caaaacccaaggacaccctcatgatctcccggacccctgaggtcacatgcgtggtggtggacgtgagc cacgaagaccctgaggtcaagttcaactggtacgtggacggcgtggaggtgcataatgccaagacaaa gccgcgggaggagcagtacaacagcacgtaccgtgtggtcagcgtcctcaccgtcctgcaccaggact ggctgaatggcaaggagtacaagtgcaaggtctccaacaaagcccctcccagccccatcgagaaaacc atctccaaagccaaagggcagccccgagaaccacaggtgtacaccctgcccccatcccgggaggagat gaccaagaaccaggtcagcctgacctgcctggtcaaaggcttctatcccagcgacatcgccgtggagt gggagagcaatgggcagccggagaacaactacaagaccacgcctcccgtgctggactccgacggctcc ttcttcctctacagcaagctcaccgtggacaagagcaggtggcagcaggggaacgtcttctcatgctc cgtgatgcatgaggctctgcacaaccactacacgcagaagagcctctccctgtctccgggtaaatgat aa
```

(amino acids)

(SEQ ID NO: 57)

EVQLVESGGGLVKPGGSLRLSCAASGFTFSRYGMSWVRQAPGKRLEWVSTISGGGTYIYYPDSVKGRF

TISRDNAKNPLYLQMNSLRAEDTAVYYCPRDNYGRNYDYGMDYWGQGTLVTVSSASTKGPSVFPLAPS

SKSTSGGTAALGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGKEYKCKVSNKALPAPIEKT

ISKAKGQPREPQVYTLPPSREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK**

Human IgG1 heavy chain constant region sequence:
(DNA)

(SEQ ID NO: 58)

```
gctagcaccaagggcccatcggtcttccccctggcaccctcctccaagagcacctctgggggcacagc ggccctgggctgcctggtcaaggactacttccccgaaccggtgacggtgtcgtggaactcaggcgccc tgaccagcggcgtgcacaccttcccggctgtcctacagtcctcaggactctactccctcagcagcgtg gtgacagtgccctccagcagcttgggcacccagacctacatctgcaacgtgaatcacaagcccagcaa caccaaggtggacaagaaagttgagcccaaatcttgtgacaaaactcacacatgcccaccgtgcccag cacctgaactcctggggggaccgtcagtcttcctcttccccccaaaacccaaggacaccctcatgatc tcccggacccctgaggtcacatgcgtggtggtggacgtgagccacgaagaccctgaggtcaagttcaa ctggtacgtggacggcgtggaggtgcataatgccaagacaaagccgcgggaggagcagtacaacagca cgtaccgtgtggtcagcgtcctcaccgtcctgcaccaggactggctgaatggcaaggagtacaagtgc aaggtctccaacaaagcccctcccagccccatcgagaaaaccatctccaaagccaaagggcagccccg agaaccacaggtgtacaccctgcccccatcccgggaggagatgaccaagaaccaggtcagcctgacct gcctggtcaaaggcttctatcccagcgacatcgccgtggagtgggagagcaatgggcagccggagaac aactacaagaccacgcctcccgtgctggactccgacggctccttcttcctctacagcaagctcaccgt ggacaagagcaggtggcagcaggggaacgtcttctcatgctccgtgatgcatgaggctctgcacaacc actacacgcagaagagcctctccctgtctccgggtaaatgataa
```

-continued (amino acids)

(SEQ ID NO: 59)
ASTKGPSVFPLAPSSKSTSGGTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGKEYKC

KVSNKALPAPIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPGK**

Human IgG1 heavy chain constant region gBLOCK#1 sequence:
(DNA)

(SEQ ID NO: 60)
atggcatggattattggggccagggcaccctggtgaccgtgagcagcgctagcaccaagggcccatcg gtcttccccctggcaccctcctccaagagcacctctgggggcacagcggccctgggctgcctggtcaa ggactacttccccgaaccggtgacggtgtcgtggaactcaggcgccctgaccagcggcgtgcacacct tcccggctgtcctacagtcctcaggactctactccctcagcagcgtggtgacagtgccctccagcagc ttgggcacccagacctacatctgcaacgtgaatcacaagcccagcaacaccaaggtggacaagaaagt tgagcccaaatcttgtgacaaaactcacacatgcccaccgtgcccagcacctgaactcctggggggac cgtcagtcttcctcttccccccaaaacccaaggacacccctcatgatctcccggacccctgaggtcaca tgcgtggtggtggacgtgagccacgaagaccctgaggtcaagttcaactggtacgtggacggcgtgga ggtgcataatgccaag Human IgG1 heavy chain constant region gBLOCK#2 sequence:
(DNA)

(SEQ ID NO: 61)
tacgtggacggcgtggaggtgcataatgccaagacaaagccgcgggaggagcagtacaacagcacgta ccgtgtggtcagcgtcctcaccgtcctgcaccaggactggctgaatggcaaggagtacaagtgcaagg tctccaacaaagcccttcccagccccatcgagaaaaccatctccaaagccaaagggcagccccgagaa ccacaggtgtacaccctgcccccatcccgggaggagatgaccaagaaccaggtcagcctgacctgcct ggtcaaaggcttctatcccagcgacatcgccgtggagtgggagagcaatgggcagccggagaacaact acaagaccacgcctcccgtgctggactccgacggctccttcttcctctacagcaagctcaccgtggac aagagcaggtggcagcaggggaacgtcttctcatgctccgtgatgcatgaggctctgcacaaccacta cacgcagaagagcctctccctgtctccgggtaaatgataagtttaaacccgctgatcagcctcgactg tgccttctagttg E6 heavy chain variable region overlapping sequence:
(DNA)

(SEQ ID NO: 62)
atggcatggattattggggccagggcaccct

IgG1 heavy chain constant region overlapping region sequence:
(DNA)

(SEQ ID NO: 63)
tacgtggacggcgtggaggtgcataatgccaag pCDNA3.1 V5 and pSECTag2 overlapping sequence:
(DNA)

(SEQ ID NO: 64)
ccgctgatcagcctcgactgtgccttctagttg

Mouse E6 Light Chain variable region sequence:
(DNA)

(SEQ ID NO: 65)
caaattgttctcacccagtctccagcaatcatgtctgcatctccaggggaggaggtcaccct aacctgcagtgccacctcaagtgtaagttacatacactggttccagcagaggccaggcactt ctcccaaactctggatttatagcacatccaacctggcttctggagtccctgttcgcttcagt ggcagtggatatgggacctcttactctctcacaatcagccgaatggaggctgaagatgctgc -continued
```
cacttattactgccagcaaaggagtagttccccattcacgttcggctcggggacaaagttgg aaataaaa
```

(amino acids)

(SEQ ID NO: 66)

QIVLTQSPAIMSASPGEEVTLTCSATSSVSYIHWFQQRPGTSPKLWIYSTSNLASGVPVRFSGSGYGT

SYSLTISRMEAEDAATYYCQQRSSSPFTFGSGTKLEIK

Mouse E6 light chain variable framework region 1 (FWR1) sequence:
(DNA)

(SEQ ID NO: 67)
```
caaattgttctcacccagtctccagcaatcatgtctgcatctccaggggaggaggtcaccctaacctg c
```

(amino acids)

(SEQ ID NO: 68)

QIVLTQSPAIMSASPGEEVTLTC

Mouse E6 light chain variable complementarity determining regions 1
(CDR1) sequence:
(DNA)

(SEQ ID NO: 69)

AGTGCCACCTCAAGTGTAAGTTACATACAC (amino acids)
SATSSVSYIH (SEQ ID NO: 70)

Mouse E6 light chain variable framework region 2 (FWR2) sequence:
(DNA)

(SEQ ID NO: 71)

tggttccagcagaggccaggcacttctcccaaactctggatttat (amino acids)

(SEQ ID NO: 72)

WFQQRPGTSPKLWIY

Mouse E6 light chain variable complementarity determining regions 2
(CDR2) sequence:
(DNA)

(SEQ ID NO: 73)

agcacatccaacctggcttct (amino acids)
STSNLAS (SEQ ID NO: 74)

Mouse E6 light chain variable framework region 3 (FWR3) sequence:
(DNA)

(SEQ ID NO: 75)
```
ggagtccctgttcgcttcagtggcagtggatatgggacctcttactctctcacaatcagccgaatgga ggctgaagatgctgccacttattactgc
```

(amino acids)

(SEQ ID NO: 76)

GVPVRFSGSGYGTSYSLTISRMEAEDAATYYC

Mouse E6 light chain variable complementarity determining regions 3
(CDR3) sequence:
(DNA)

(SEQ ID NO: 77)

cagcaaaggagtagttccccattcacg (amino acids)

(SEQ ID NO: 78)

QQRSSSPFT

IGKV3-11*02 light chain variable region sequence:
(DNA)

(SEQ ID NO: 79)
```
gaaattgtgttgacacagtctccagccaccctgtctttgtctccaggggaaagagccaccctctcctg cagggccagtcagagtgttagcagctacttagcctggtaccaacagaaacctggccaggctcccaggc tcctcatctatgatgcatccaacagggccactggcatcccagccaggttcagtggcagtgggtctggg
``` agagacttcactctcaccatcagcagcctagagcctgaagattttgcagtttattactgtcagcagcg tagcaactggcctcc (amino acids)
(SEQ ID NO: 80)
EIVLTQSPATLSLSPGERATLSCRASQSVSSYLAWYQQKPGQAPRLLIYDASNRATGIPA

RFSGSGSGRDFTLTISSLEPEDFAVYYCQQRSNWPP

IGKV3-11*02 light chain variable framework region 1 (FWR1) acid
sequence:
(DNA)
(SEQ ID NO: 81)
gaaattgtgttgacacagtctccagccaccctgtctttgtctccaggggaaagagccaccctctcctg c (amino acids)
(SEQ ID NO: 82)
EIVLTQSPATLSLSPGERATLSC IGKV3-11*02 light chain variable complementarity determining regions
1 (CDR1) sequence:
(DNA)
(SEQ ID NO: 83)
agggccagtcagagtgttagcagctacttagcc (amino acids)
(SEQ ID NO: 84)
RASQSVSSYLA IGKV3-11*02 light chain variable framework region 2 (FWR2) sequence:
(DNA)
(SEQ ID NO: 85)
tggtaccaacagaaacctggccaggctcccaggctcctcatctat (amino acids)
(SEQ ID NO: 86)
WYQQKPGQAPRLLIY IGKV3-11*02 light chain variable complementarity determining regions
2 (CDR2) sequence:
(DNA)
(SEQ ID NO: 87)
gatgcatccaacagggccact (amino acids)
(SEQ ID NO: 88)
DASNRAT IGKV3-11*02 light chain variable framework region 3 (FWR3) sequence:
(DNA)
(SEQ ID NO: 89)
ggcatcccagccaggttcagtggcagtgggtctgggagagacttcactctcaccatcagcagcctaga gcctgaagattttgcagtttattactgt (amino acids)
(SEQ ID NO: 90)
GIPARFSGSGSGTDFTLTISSLEPEDFAVYYC IGKV3-11*02 light chain variable complementarity determining
regions3 (CDR3) sequence:
(DNA)
(SEQ ID NO: 91)
cagcagcgtagcaactggcctcc (amino acids)
(SEQ ID NO: 92)
QQRSNWPP Humanized E6 light chain variable region sequence:
(DNA)
(SEQ ID NO: 93)
gaaattgtgttgacacagtctccagccaccctgtctttgtctccaggggaaagagccaccctcacctg cagcgccaccagcagtgttagctacatccactggtaccaacagaggcctggccagagccccaggctcc -continued

```
tcatctatagcacctccaacctggccagcggcatcccagccaggttcagtggcagtgggtctgggagc gactacactctcaccatcagcagcctagagcctgaagattttgcagtttattactgtcagcagcgtag cagctccccttttcacctttggcagcggcaccaaagtggaaattaaa
```

(amino acids)

(SEQ ID NO: 94)
EIVLTQSPATLSLSPGERATLTCSATSSVSYIHWYQQRPGQSPRLLIYSTSNLASGIPARFSGSGSGS

DYTLTISSLEPEDFAVYYCQQRSSSPFTFGSGTKVEIK

Humanized E6 light chain variable framework region 1 (FWR1) acid
sequence:
(DNA)

(SEQ ID NO: 95)
```
gaaattgtgttgacacagtctccagccaccctgtctttgtctccaggggaaagagccaccctcacctg c
```

(amino acids)

(SEQ ID NO: 96)
EIVLTQSPATLSLSPGERATLTC

Humanized E6 light chain variable complementarity determining
regions 1 (CDR1) sequence:
(DNA)

(SEQ ID NO: 97)
agcgccaccagcagtgttagctacatccac (amino acids)

(SEQ ID NO: 98)
SATSSVSYIH

Humanized E6 heavy light variable framework region 2 (FWR2) acid
sequence:
(DNA)

(SEQ ID NO: 99)
tggtaccaacagaggcctggccagagccccaggctcctcatctat (amino acids)

(SEQ ID NO: 100)
WYQQRPGQSPRLLIY

Humanized E6 light chain variable complementarity determining
regions 2 (CDR2) sequence:
(DNA)

(SEQ ID NO: 101)
agcacctccaacctggccagc (amino acids)

(SEQ ID NO: 102)
STSNLAS

Humanized E6 light chain variable framework region 3 (FWR3) acid
sequence:
(DNA)

(SEQ ID NO: 103)
```
ggcatcccagccaggttcagtggcagtgggtctgggagcgactacactctcaccatcagcagcctaga gcctgaagattttgcagtttattactgt
```

(amino acids)

(SEQ ID NO: 104)
GIPARFSGSGSGSDYTLTISSLEPEDFAVYYC

Humanized E6 light chain variable complementarity determining
regions 3 (CDR3) sequence:
(DNA)

(SEQ ID NO: 105)
cagcagcgtagcagctccccttttcacc (amino acids)

(SEQ ID NO: 106)
QQRSSSPFT

-continued

Humanized E6 Kappa light chain synthesized by Genescript:
(DNA)
(SEQ ID NO: 107)
gaattctaagcttgggccaccatggaagcccagcgcagcttctcttcctcctgctactctggctccc agataccactggagaaattgtgttgacacagtctccagccaccctgtctttgtctccaggggaaagag ccaccctcacctgcagcgccaccagcagtgttagctacatccactggtaccaacagaggcctggccag agccccaggctcctcatctatagcacctccaacctggccagcggcatcccagccaggttcagtggcag tgggtctgggagcgactacactctcaccatcagcagcctagagcctgaagattttgcagtttattact gtcagcagcgtagcagctccccctttcacctttggcagcggcaccaaagtggaaattaaaaggacggtg gctgcaccatctgtcttcatcttcccgccatctgatgagcagttgaaatctggaactgcctctgttgt gtgcctgctgaataacttctatcccagagaggccaaagtacagtggaaggtggataacgccctccaat cgggtaactcccaggagagtgtcacagagcaggacagcaaggacagcacctacagcctcagcagcacc ctgacgctgagcaaagcagactacgagaaacacaaagtctacgcctgcgaagtcacccatcagggcct gagctcgcccgtcacaaagagcttcaacaggggagagtgttagtaagtttaaactctaga (amino acids)
(SEQ ID NO: 108)
EF*AWATMEAPAQLLFLLLLWLPDTTGEIVLTQSPATLSLSPGERATLTCSATSSVSYIHWYQQRPGQ

SPRLLIYSTSNLASGIPARFSGSGSGSDYTLTISSLEPEDFAVYYCQQRSSSPFTFGSGTKVEIKRTV

AAPSVFIFPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC**V*TLX

Human Kappa light chain constant region sequence:
(DNA)
(SEQ ID NO: 109)
aggacggtggctgcaccatctgtcttcatcttcccgccatctgatgagcagttgaaatctggaactgc ctctgttgtgtgcctgctgaataacttctatcccagagaggccaaagtacagtggaaggtggataacg ccctccaatcgggtaactcccaggagagtgtcacagagcaggacagcaaggacagcacctacagcctc agcagcaccctgacgctgagcaaagcagactacgagaaacacaaagtctacgcctgcgaagtcaccca tcagggcctgagctcgcccgtcacaaagagcttcaacaggggagagtgttag (amino acids)
(SEQ ID NO: 110)
RTVAAPSVFIFPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC

Humanized E6 lambda light chain sequence:
(DNA)
(SEQ ID NO: 111)
gaaattgtgttgacacagtctccagccaccctgtctttgtctccaggggaaagagccaccctcacctg cagcgccaccagcagtgttagctacatccactggtaccaacagaggcctggccagagccccaggctcc tcatctatagcacctccaacctggccagcggcatcccagccaggttcagtggcagtgggtctgggagc gactacactctcaccatcagcagcctagagcctgaagattttgcagtttattactgtcagcagcgtag cagctccccctttcacctttggcagcggcaccaaagtggaaattaaaggtcagcccaaggctgcccct cggtcactctgttcccgccctcctctgaggagcttcaagccaacaaggccacactggtgtgtctcata agtgacttctacccgggagccgtgacagtggcctggaaggcagatagcagccccgtcaaggcggagt ggagaccaccacaccctccaaacaaagcaacaacaagtacgcggccagcagctatctgagcctgacgc ctgagcagtggaagtcccacagaagctacagctgccaggtcacgcatgaagggagcaccgtggagaag acagtggcccctacagaatgttcatagtaa (amino acids)

(SEQ ID NO: 112)
EIVLTQSPATLSLSPGERATLTCSATSSVSYIHWYQQRPGQSPRLLIYSTSNLASGIPARFSGSGSG
SDYTLTISSLEPEDFAVYYCQQRSSSPFTFGSGTKVEIKGQPKAAPSVTLFPPSSEELQANKATLVCLI
SDFYPGAVTVAWKADSSPVKAGVETTTPSKQSNNKYAASSYLSLTPEQWKSHRSYSCQVTHEGSTVEK
TVAPTECS**

Humanized lambda light chain constant region sequence:
(DNA)

(SEQ ID NO: 113)
ggtcagcccaaggctgccccctcggtcactctgttcccgccctcctctgaggagcttcaagccaacaa
ggccacactggtgtgtctcataagtgacttctacccgggagccgtgacagtggcctggaaggcagata
gcagccccgtcaaggcgggagtggagaccaccacaccctccaaacaaagcaacaacaagtacgcggcc
agcagctatctgagcctgacgcctgagcagtggaagtcccacagaagctacagctgccaggtcacgca
tgaagggagcaccgtggagaagacagtggcccctacagaatgttcatagtaa (amino acids)

(SEQ ID NO: 114)
GQPKAAPSVTLFPPSSEELQANKATLVCLISDFYPGAVTVAWKADSSPVKAGVETTTPSKQSNNKYAA
SSYLSLTPEQWKSHRSYSCQVTHEGSTVEKTVAPTECS**

Human lambda light chain constant region gBLOCK#3 sequence:
(DNA)

(SEQ ID NO: 115)
agcgccaccagcagtgttagctacatccactggtaccaacagaggcctggccagagccccaggctcct
catctatagcacctccaacctggccagcggcatcccagccaggttcagtggcagtgggtctgggagcg
actacactctcaccatcagcagcctagagcctgaagattttgcagtttattactgtcagcagcgtagc
agctccccttttcacctttggcagcggcaccaaagtggaaattaaaggtcagcccaaggctgccccctc
ggtcactctgttcccgccctcctctgaggagcttcaagccaacaaggccacactggtgtgtctcataa
gtgacttctacccgggagccgtgacagtggcctggaaggcagatagcagccccgtcaaggcgggagtg
gagaccaccacaccctccaaacaaagcaacaacaagtacgcggccagcagctatctgagcctgacgcc
tgagcagtggaagtcccacagaagctacagctgccaggtcacgcatgaagggagcaccgtggagaaga
cagtggcccctacagaatgttcatagtaagtttaaacccgctgatcagcctcgactgtgccttctagt
tg E6 light chain variable region overlapping sequence:
(DNA)

(SEQ ID NO: 116)
agcgccaccagcagtgttagctacatccact pCDNA3.1 V5 and pSECTag2 overlapping sequence:
(DNA)

(SEQ ID NO: 117)
ccgctgatcagcctcgactgtgccttctagttg

Mouse C2 heavy chain variable region sequence:
(DNA)

(SEQ ID NO: 118)
gaggtccagctggaggagtcaggggggaggcttagtgaagcctggagggtccctgaaactctcctgtgc
agcctctggattcactttcagtggctatgccatgtcttgggttcgccagactccggagaagaggctgg
agtgggtcgcaaccattagtagtggtggtacttatatctactatccagacagtgtgaaggggcgattc
accatctccagagacaatgccaagaacaccctgtacctgcaaatgagcagtctgaggtctgaggacac
ggccatgtattactgtgcaagacttgggggggataattactacgaatacttcgatgtctggggcgcag
ggaccacggtcaccgtctcctccgccaaaacgacacccccatctgtctat -continued (amino acids)
(SEQ ID NO: 119)
EVQLEESGGGLVKPGGSLKLSCAASGFTFSGYAMSWVRQTPEKRLEWVATISSGGTYIYYPDSVKGRF

TISRDNAKNTLYLQMSSLRSEDTAMYYCARLGGDNYYEYFDVWGAGTTVTVSSAKTTPPSVY

Mouse C2 heavy chain variable framework region 1 (FWR1) sequence:
(DNA)
(SEQ ID NO: 120)
gaggtccagctggaggagtcagggggaggcttagtgaagcctggagggtccctgaaactctcctgtgc agcctctggattcactttcagt (amino acids)
(SEQ ID NO: 121)
EVQLEESGGGLVKPGGSLKLSCAASGFTFS Mouse C2 heavy chain variable complementarity determining regions 1
(CDR1) sequence:
(DNA)
(SEQ ID NO: 122)
ggctatgccatgtct (amino acids)
(SEQ ID NO: 123)
GYAMS Mouse C2 heavy chain variable framework region 2 (FWR2) sequence:
(DNA)
(SEQ ID NO: 124)
tgggttcgccagactccggagaagaggctggagtgggtcgca (amino acids)
(SEQ ID NO: 125)
WVRQTPEKRLEWVA Mouse C2 heavy chain variable complementarity determining regions 2
(CDR2) sequence:
(DNA)
(SEQ ID NO: 126)
accattagtagtggtggtacttatatctactatccagacagtgtgaagggg (amino acids)
(SEQ ID NO: 127)
TISSGGTYIYYPDSVKG Mouse C2 heavy chain variable framework region 3 (FWR3) sequence:
(DNA)
(SEQ ID NO: 128)
cgattcaccatctccagagacaatgccaagaacaccctgtacctgcaaatgagcagtctgaggtctga ggacacggccatgtattactgtgcaaga (amino acids)
(SEQ ID NO: 129)
RFTISRDNAKNTLYLQMSSLRSEDTAMYYCAR Mouse C2 heavy chain variable complementarity determining regions 3
(CDR3) sequence:
(DNA)
(SEQ ID NO: 130)
cttggggggataattactacgaatacttcgatgtc (amino acids)
(SEQ ID NO: 131)
LGGDNYYEYFDV IGHV3-21*04 heavy chain variable region sequence:
(DNA)
(SEQ ID NO: 132)
gaggtgcagctggtggagtctgggggaggcctggtcaagcctggggggtccctgagactctcctgtgc agcctctggattcaccttcagtagctatagcatgaactgggtccgccaggctccagggaaggggctgg agtgggtctcatccattagtagtagtagtagttacatatactacgcagactcagtgaagggccgattc accatctccagagacaacgccaagaactcactgtatctgcaaatgaacagcctgagagccgaggacac ggccgtgtattactgtgcgaga -continued (amino acids)

(SEQ ID NO: 133)
EVQLVESGGGLVKPGGSLRLSCAASGFTFSSYSMNWVRQAPGKGLEWVSSISSSSSYIYYADSVKGRF

TISRDNAKNSLYLQMNSLRAEDTAVYYCAR

IGHV3-21*04 heavy chain variable framework region 1 (FWR1) sequence:
(DNA)

(SEQ ID NO: 134)
gaggtgcagctggtggagtctgggggaggcctggtcaagcctggggggtccctgagactctcctgtgc agcctctggattcaccttcagt (amino acids)

(SEQ ID NO: 135)
EVQLVESGGGLVKPGGSLRLSCAASGFTFS

IGHV3-21*04 heavy chain variable complementarity determining regions
1 (CDR1) sequence:
(DNA)

(SEQ ID NO: 136)
agctatagcatgaac (amino acids)

(SEQ ID NO: 137)
SYSMN

IGHV3-21*04 heavy chain variable framework region 2 (FWR2) sequence:
(DNA)

(SEQ ID NO: 138)
gggtccgccaggctccagggaaggggctggagtgggtctca (amino acids)

(SEQ ID NO: 139)
WVRQAPGKGLEWVS

IGHV3-21*04 heavy chain variable complementarity determining regions
2 (CDR2) sequence:
(DNA)

(SEQ ID NO: 140)
tccattagtagtagtagtagttacatatactacgcagactcagtgaagggc (amino acids)

(SEQ ID NO: 141)
SISSSSSYIYYADSVKG

IGHV3-21*04 heavy chain variable framework region 3 (FWR3) sequence:
(DNA)

(SEQ ID NO: 142)
cgattcaccatctccagagacaacgccaagaactcactgtatctgcaaatgaacagcctgagagccga ggacacggccgtgtattactgtgcgaga (amino acids)

(SEQ ID NO: 143)
RFTISRDNAKNSLYLQMNSLRAEDTAVYYCAR

Humanized C2 heavy chain variable region sequence:
(DNA)

(SEQ ID NO: 144)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttgggggggataattactacgaatacttcgatgtctggggcaaag ggaccacggtcaccgtctcctcc (amino acids)

(SEQ ID NO: 145)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSS

Humanized C2 heavy chain variable framework region 1 (FWR1)
sequence:
(DNA)
(SEQ ID NO: 146)
gaggtgcagctggtggagtctgggggaggcctggtcaagcctggggggtccctgagactctcctgtgc agcctctggattcaccttcagt (amino acids)
(SEQ ID NO: 147)
EVQLVESGGGLVKPGGSLRLSCAASGFTFS Humanized C2 heavy chain variable complementarity determining
regions 1 (CDR1) sequence:
(DNA)
(SEQ ID NO: 148)
ggctatgccatgagc (amino acids)
(SEQ ID NO: 149)
GYAMS Humanized C2 heavy chain variable framework region 2 (FWR2)
sequence:
(DNA)
(SEQ ID NO: 150)
tgggtccgccaggctccagggaaggggctggagtgggtctcaa (amino acids)
(SEQ ID NO: 151)
WVRQAPGKGLEWVS Humanized C2 heavy chain variable complementarity determining
regions 2 (CDR2) sequence:
(DNA)
(SEQ ID NO: 152)
accattagtagtggcggaacctacatatactaccccgactcagtgaagggc (amino acids)
(SEQ ID NO: 153)
TISSGGTYIYYPDSVKG Humanized C2 heavy chain variable framework region 3 (FWR3)
sequence:
(DNA)
(SEQ ID NO: 154)
cgattcaccatctccagagacaacgccaagaactcactgtatctgcaaatgaacagcctgagagccga ggacacggccgtgtattactgtgcgaga (amino acids)
(SEQ ID NO: 155)
RFTISRDNAKNSLYLQMNSLRAEDTAVYYCAR Humanized C2 heavy chain variable complementarity determining
regions 3 (CDR3) sequence:
(DNA)
(SEQ ID NO: 156)
cttggggggataattactacgaatacttcgatgtc (amino acids)
(SEQ ID NO: 157)
LGGDNYYEYFDV Humanized C2 IgG1 heavy chain sequence
(DNA)
(SEQ ID NO: 157)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttggggggataattactacgaatacttcgatgtctggggcaaag ggaccacggtcaccgtctcctccgctagcaccaagggcccatcggtcttccccctggcaccctcctcc aagagcacctctggggggcacagcggccctgggctgcctggtcaaggactacttccccgaaccggtgac -continued

```
ggtgtcgtggaactcaggcgccctgaccagcggcgtgcacaccttcccggctgtcctacagtcctcag gactctactccctcagcagcgtggtgacagtgccctccagcagcttgggcacccagacctacatctgc aacgtgaatcacaagcccagcaacaccaaggtggacaagaaagttgagcccaaatcttgtgacaaaac tcacacatgcccaccgtgcccagcacctgaactcctggggggaccgtcagtcttcctcttccccccaa aacccaaggacaccctcatgatctcccggacccctgaggtcacatgcgtggtggtggacgtgagccac gaagaccctgaggtcaagttcaactggtacgtggacggcgtggaggtgcataatgccaagacaaagcc gcgggaggagcagtacaacagcacgtaccgtgtggtcagcgtcctcaccgtcctgcaccaggactggc tgaatggcaaggagtacaagtgcaaggtctccaacaaagccctcccagcccccatcgagaaaaccatc tccaaagccaaagggcagccccgagaaccacaggtgtacaccctgcccccatcccgggaggagatgac caagaaccaggtcagcctgacctgcctggtcaaaggcttctatcccagcgacatcgccgtggagtggg agagcaatgggcagccggagaacaactacaagaccacgcctcccgtgctggactccgacggctccttc ttcctctacagcaagctcaccgtggacaagagcaggtggcagcaggggaacgtcttctcatgctccgt gatgcatgaggctctgcacaaccactacacgcagaagagcctctccctgtctccgggtaaatgataa
```

(amino acids)

(SEQ ID NO: 158)
```
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSASTKGPSVFPLAPSS

KSTSGGTAALGCLVKDYFPEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESNGQPENNYKTTPPVLDSDGSF

FLYSKLTVDKSRWQQGNVFSCSVMHEALHNHYTQKSLSLSPGK**
```

Humanized C2 gBLOCK#4 sequence:
(DNA)

(SEQ ID NO: 160)
```
actcactatagggagacccaagctggctagttaagcttgggccaccatggagacagacacactcctgc tatgggtactgctgctctgggttccaggttccactggtgacgaggtgcagctggtggagtctggggga ggcctggtcaagcctggggggtccctgagactctcctgtgcagcctctggattcaccttcagtggcta tgccatgagctgggtccgccaggctccagggaaggggctggagtgggtctcaaccattagtagtggcg gaacctacatatactaccccgactcagtgaagggccgattcaccatctccagagacaacgccaagaac tcactgtatctgcaaatgaacagcctgagagccgaggacacggccgtgtattactgtgcgagacttgg gggggataattactacgaatacttcgatgtctggggcaaagggaccacggtcaccgtctcctccgcta gcaccaagggcccatcggtcttccccctggcaccctcctccaagagcacctctggggcacagcggcc ctgggctgcctggtcaaggactacttccccgaaccggtgacggtgtcgtggaactcaggcgccctgac cagc
``` pCDNA3.1 V5 overlapping sequence:
(DNA)

(SEQ ID NO: 161)
```
actcactatagggagacccaagctggctagtt
```

Human IgG1 constant region overlapping sequence:
(DNA)

(SEQ ID NO: 162)
```
gacggtgtcgtggaactcaggcgccctgaccagc
```

Humanized C2 IgG2 heavy chain sequence
(DNA)
(SEQ ID NO: 163)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttggggggataattactacgaatacttcgatgtctggggcaaag ggaccacggtcaccgtctcctccgcctccaccaagggcccatcggtcttccccctggcgccctgctcc aggagcacctccgagagcacagccgccctgggctgcctggtcaaggactacttccccgaaccggtgac ggtgtcgtggaactcaggcgctctgaccagcggcgtgcacaccttcccagctgtcctacagtcctcag gactctactccctcagcagcgtggtgaccgtgccctccagcaacttcggcacccagacctacacctgc aacgtagatcacaagcccagcaacaccaaggtggacaagacagttgagcgcaaatgttgtgtcgagtg cccaccgtgcccagcaccacctgtggcaggaccgtcagtcttcctcttccccccaaaacccaaggaca ccctcatgatctcccggacccctgaggtcacgtgcgtggtggtggacgtgagccacgaagaccccgag gtccagttcaactggtacgtggacggcgtggaggtgcataatgccaagacaaagccacgggaggagca gttcaacagcacgttccgtgtggtcagcgtcctcaccgttgtgcaccaggactggctgaacggcaagg agtacaagtgcaaggtctccaacaaaggcctcccagcccccatcgagaaaaccatctccaaaaccaaa gggcagccccgagaaccacaggtgtacaccctgcccccatcccgggaggagatgaccaagaaccaggt cagcctgacctgcctggtcaaaggcttctaccccagcgacatcgccgtggagtgggagagcaatgggc agccggagaacaactacaagaccacacctcccatgctggactccgacggctccttcttcctctacagc aagctcaccgtggacaagagcaggtggcagcaggggaacgtcttctcatgctccgtgatgcatgaggc tctgcacaaccactacacgcagaagagcctctccctgtctccgggtaaatagtaa (amino acids)
(SEQ ID NO: 164)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSASTKGPSVFPLAPCS

RSTSESTAALGCLVKDYFPEPVTVSWNSGALTSGVHTFPAVLQSSGLYSLSSVVTVPSSNFGTQTYTC

NVDHKPSNTKVDKTVERKCCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCKVSNKGLPAPIEKTISKTK

GQPREPQVYTLPPSREEMTKNQVSLTCLVKGFYPSDIAVEWESNGQPENNYKTTPPMLDSDGSFFLYS

KLTVDKSRWQQGNVFSCSVMHEALHNHYTQKSLSLSPGK**

Humanized C2 gBLOCK#5 sequence:
(DNA)
(SEQ ID NO: 165)
tgctctgggttccaggttccactggtgacgcggcccagccggccgaggtgcagctggtggagtctggg ggaggcctggtcaagcctggggggtccctgagactctcctgtgcagcctctggattcaccttcagtgg ctatgccatgagctgggtccgccaggctccagggaaggggctggagtgggtctcaaccattagtagtg gcggaacctacatatactaccccgactcagtgaagggccgattcaccatctccagagacaacgccaag aactcactgtatctgcaaatgaacagcctgagagccgaggacacggccgtgtattactgtgcgagact tggggggataattactacgaatacttcgatgtctggggcaaagggaccacggtcaccgtctcctccg cctccaccaagggcccatcggtcttccccctggcgccctgctccaggagcacctccgagagcacagcc gccctgggctgcctggtcaaggactacttccccgaaccggtgacggtgtcgtggaactcaggcgctct gacca

```
pSEC Tag2 overlapping sequence:
(DNA)
                                                             (SEQ ID NO: 166)
tgctctgggttccaggttccactggtgacgc Human IgG2 constant region overlapping sequence:
(DNA)
                                                             (SEQ ID NO: 167)
gacggtgtcgtggaactcaggcgctctgacca Mouse C2 light chain variable region sequence:
(DNA)
                                                             (SEQ ID NO: 168)
gacattgtgatcacacagtctacagcttccttaggtgtatctctggggcagagggccaccatctcatg cagggccagcaaaagtgtcagtacatctggctatagttatatgcactggtaccaacagagaccaggac agccacccaaactcctcatctatcttgcatccaacctagaatctggggtccctgccaggttcagtggc agtgggtctgggacagacttcacccctcaacatccatcctgtggaggaggaggatgctgcaacctatta ctgtcagcacagtagggagcttccgttcacgttcggaggggggaccaagctggagataaaacgggctg atgctgcaccaactgtatcc (amino acids)
                                                             (SEQ ID NO: 169)
DIVITQSTASLGVSLGQRATISCRASKSVSTSGYSYMHWYQQRPGQPPKLLIYLASNLESGVPARFSG

SGSGTDFTLNIHPVEEEDAATYYCQHSRELPFTFGGGTKLEIKRADAAPTVS

Mouse C2 light chain variable framework region 1 (FWR1) sequence:
(DNA)
                                                             (SEQ ID NO: 170)
gacattgtgatcacacagtctacagcttccttaggtgtatctctggggcagagggccaccatctcatg c (amino acids)
                                                             (SEQ ID NO: 171)
DIVITQSTASLGVSLGQRATISC Mouse C2 light chain variable complementarity determining regions 1
(CDR1) sequence:
(DNA)
                                                             (SEQ ID NO: 172)
agggccagcaaaagtgtcagtacatctggctatagttatatgcac (amino acids)
                                                             (SEQ ID NO: 173)
RASKSVSTSGYSYMH Mouse C2 light chain variable framework region 2 (FWR2) sequence:
(DNA)
                                                             (SEQ ID NO: 174)
tggtaccaacagagaccaggacagccacccaaactcctcatctat (amino acids)
                                                             (SEQ ID NO: 175)
WYQQRPGQPPKLLIY Mouse C2 light chain variable complementarity determining regions 2
(CDR2) sequence:
(DNA)
                                                             (SEQ ID NO: 176)
cttgcatccaacctagaatc (amino acids)
                                                             (SEQ ID NO: 177)
LASNLES Mouse C2 light chain variable framework region 3 (FWR3) sequence:
(DNA)
                                                             (SEQ ID NO: 178)
tggggtccctgccaggttcagtggcagtgggtctgggacagacttcacccctcaacatccatcctgtgg aggaggaggatgctgcaacctattactgt
```

(amino acids)
(SEQ ID NO: 179)
GVPARFSGSGSGTDFTLNIHPVEEEDAATYYC

Mouse C2 light chain variable complementarity determining regions 3
(CDR3) sequence:
(DNA)
(SEQ ID NO: 180)
cagcacagtagggagcttccgttcacg (amino acids)
(SEQ ID NO: 181)
QHSRELPFT IGKV7-3*01 light chain variable region sequence:
(DNA)
(SEQ ID NO: 182)
gacattgtgctgacccagtctccagcctccttggccgtgtctccaggacagagggccaccatcacctg cagagccagtgagagtgtcagtttcttgggaataaacttaattcactggtatcagcagaaaccaggac aacctcctaaactcctgatttaccaagcatccaataaagacactggggtcccagccaggttcagcggc agtgggtctgggaccgatttcaccctcacaattaatcctgtggaagctaatgatactgcaaattatta ctgtctgcagagtaagaattttcctcccaca (amino acid)
(SEQ ID NO: 183)
DIVLTQSPASLAVSPGQRATITCRASESVSFLGINLIHWYQQKPGQPPKLLIYQASNKDTGVPARFSG

SGSGTDFTLTINPVEANDTANYYCLQSKNFPPT

IGKV7-3*01 light chain variable framework region 1 (FWR1) sequence:
(DNA)
(SEQ ID NO: 184)
gacattgtgctgacccagtctccagcctccttggccgtgtctccaggacagagggccaccatcacctg
c (amino acids)
(SEQ ID NO: 185)
DIVLTQSPASLAVSPGQRATITC IGKV7-3*01 light chain variable complementarity determining regions
1 (CDR1) sequence:
(DNA)
(SEQ ID NO: 186)
agagccagtgagagtgtcagtttcttgggaataaacttaattcac (amino acids)
(SEQ ID NO: 187)
RASESVSFLGINLIH IGKV7-3*01 light chain variable framework region 2 (FWR2) sequence:
(DNA)
(SEQ ID NO: 188)
tggtatcagcagaaaccaggacaacctcctaaactcctgatttac (amino acids)
(SEQ ID NO: 189)
WYQQKPGQPPKLLIY IGKV7-3*01 light chain variable complementarity determining regions
2 (CDR2) sequence:
(DNA)
(SEQ ID NO: 190)
caagcatccaataaagacact (amino acids)
(SEQ ID NO: 191)
QASNKDT IGKV7-3*01 light chain variable framework region 3 (FWR3) sequence:
(DNA)
(SEQ ID NO: 192)
ggggtcccagccaggttcagcggcagtgggtctgggaccgatttcaccctcacaattaatcctgtgga agctaatgatactgcaaattattactgt

```
(amino acids)
                                                       (SEQ ID NO: 193)
GVPARFSGSGSGTDFTLTINPVEANDTANYYC Humanized C2 light chain variable region sequence:
(DNA)
                                                       (SEQ ID NO: 194)
gacattgtgctgacccagtctccagcctccttggccgtgtctccaggacagagggccaccatcacctg cagagccagtaagagtgtcagtaccagcggatactcctacatgcactggtatcagcagaaaccaggac aacctcctaaactcctgatttacctggcatccaatctggagagcggggtcccagccaggttcagcggc agtgggtctgggaccgatttcacccctcacaattaatcctgtggaagctaatgatactgcaaattatta ctgtcagcacagtagggagctgccttttcacattcggcggagggaccaaggtggagatcaaacgaact (amino acids)
                                                       (SEQ ID NO: 195)
DIVLTQSPASLAVSPGQRATITCRASKSVSTSGYSYMHWYQQKPGQPPKLLIYLASNLESGVPARFSG

SGSGTDFTLTINPVEANDTANYYCQHSRELPFTFGGGTKVEIKRT

Humanized C2 light chain variable framework region 1 (FWR1) acid
sequence:
(DNA)
                                                       (SEQ ID NO: 196)
gacattgtgctgacccagtctccagcctccttggccgtgtctccaggacagagggccaccatcacctg c (amino acids)
                                                       (SEQ ID NO: 197)
DIVLTQSPASLAVSPGQRATITC Humanized C2 light chain variable complementarity determining
regions 1 (CDR1) sequence:
(DNA)
                                                       (SEQ ID NO: 198)
agagccagtaagagtgtcagtaccagcggatactcctacatgcac (amino acids)
                                                       (SEQ ID NO: 199)
RASKSVSTSGYSYMH Humanized C2 heavy light variable framework region 2 (FWR2) acid
sequence:
(DNA)
                                                       (SEQ ID NO: 200)
tggtatcagcagaaaccaggacaacctcctaaactcctgatttac (amino acids)
                                                       (SEQ ID NO: 201)
WYQQKPGQPPKLLIY Humanized C2 light chain variable complementarity determining
regions 2 (CDR2) sequence:
(DNA)
                                                       (SEQ ID NO: 202)
ctggcatccaatctggagagc (amino acids)
                                                       (SEQ ID NO: 203)
LASNLES Humanized C2 light chain variable framework region 3 (FWR3) acid
sequence:
(DNA)
                                                       (SEQ ID NO: 204)
ggggtcccagccaggttcagcggcagtgggtctgggaccgatttcacccctcacaattaatcctgtgga agctaatgatactgcaaattattactgt (amino acids)
                                                       (SEQ ID NO: 205)
GVPARFSGSGSGTDFTLTINPVEANDTANYYC
```

Humanized C2 light chain variable complementarity determining regions 3 (CDR3) sequence:
(DNA)

(SEQ ID NO: 206)
cagcacagtagggagctgcctttcaca (amino acids)

(SEQ ID NO: 207)
QHSRELPFT

Humanized C2 light chain variable complementarity determining regions 3 (CDR3) sequence:
(DNA)

(SEQ ID NO: 208)
ctgcagagtaagaattttcctcccaca (amino acids)

(SEQ ID NO: 209)
LQSKNFPPT

Humanized C2 gBLOCK#6 sequence (Kappa light chain in pCDNA3.1 V5):
(DNA)

(SEQ ID NO: 210)
actcactatagggagacccaagctggctagttaagcttgggccaccatggagacagacactcctgc tatgggtactgctgctctgggttccaggttccactggtgacgacattgtgctgacccagtctccagcc tccttggccgtgtctccaggacagagggccaccatcacctgcagagccagtaagagtgtcagtaccag cggatactcctacatgcactggtatcagcagaaaccaggacaacctcctaaactcctgatttacctgg catccaatctggagagcggggtcccagccaggttcagcggcagtgggtctgggaccgatttcaccctc acaattaatcctgtggaagctaatgatactgcaaattattactgtcagcacagtagggagctgccttt cacattcggcggagggaccaaggtggagatcaaacgaactacggtggctgcaccatctgtcttcatct tcccgccatctgatgagcagttgaaatctggaactgcctctgttgtgtgcctgctgaataacttctat cccagagaggccaaagtacagtggaaggtggataacgccctccaatcgggtaactcccaggagagtgt cacagagcaggacagcaaggacagcacctacagcctcagcagcaccctgacgctgagcaaagcagact acgagaaacacaaagtctacgcctgcgaagtcacccatcagggcctgagctcgcccgtcacaaagagc ttcaacaggggagagtgttagtaagtttaaacccgctgatcagcctcgactgtgccttctagttg pCDNA3.1 V5 5' overlapping sequence:
(DNA)

(SEQ ID NO: 211)
actcactatagggagacccaagctggctagtt pCDNA3.1 V5 3' overlapping sequence:
(DNA)

(SEQ ID NO: 212)
ccgctgatcagcctcgactgtgccttctagttg

Humanized C2 gBLOCK#7 sequence (Kappa light chain in pSEC Tag2):
(DNA)

(SEQ ID NO: 213)
tgctctgggttccaggttccactggtgacgcggcccagccggccgacattgtgctgacccagtctcca gcctccttggccgtgtctccaggacagagggccaccatcacctgcagagccagtaagagtgtcagtac cagcggatactcctacatgcactggtatcagcagaaaccaggacaacctcctaaactcctgatttacc tggcatccaatctggagagcggggtcccagccaggttcagcggcagtgggtctgggaccgatttcacc ctcacaattaatcctgtggaagctaatgatactgcaaattattactgtcagcacagtagggagctgcc tttcacattcggcggagggaccaaggtggagatcaaacgaactacggtggctgcaccatctgtcttca tcttcccgccatctgatgagcagttgaaatctggaactgcctctgttgtgtgcctgctgaataacttc tatcccagagaggccaaagtacagtggaaggtggataacgccctccaatcgggtaactcccaggagag tgtcacagagcaggacagcaaggacagcacctacagcctcagcagcaccctgacgctgagcaaagcag actacgagaaacacaaagtctacgcctgcgaagtcacccatcagggcctgagctcgcccgtcacaaag agcttcaacaggggagagtgttagtaagtttaaacccgctgatcagcctcgactgtgccttctagttg pSEC Tag2 5' overlapping sequence:
(DNA)

(SEQ ID NO: 214)

tgctctgggttccaggttccactggtgacgc pSEC Tag2 3' overlapping sequence:
(DNA)

(SEQ ID NO: 215)

ccgctgatcagcctcgactgtgccttctagttg

Humanized C2 gBLOCK#8 sequence (lambda light chain in pCDNA3.1 V5):
(DNA)

(SEQ ID NO: 216)

actcactatagggagacccaagctggctagttaagcttgggccaccatggagacagacacactcctgc tatgggtactgctgctctgggttccaggttccactggtgacgacattgtgctgacccagtctccagcc tccttggccgtgtctccaggacagagggccaccatcacctgcagagccagtaagagtgtcagtaccag cggatactcctacatgcactggtatcagcagaaaccaggacaacctcctaaactcctgatttacctgg catccaatctggagagcggggtcccagccaggttcagcggcagtgggtctgggaccgatttcacccta acaattaatcctgtggaagctaatgatactgcaaattattactgtcagcacagtagggagctgccttt cacattcggcggagggaccaaggtggagatcaaacgaactggtcagcccaaggctgccccctcggtca ctctgttcccgccctcctctgaggagcttcaagccaacaaggccacactggtgtgtctcataagtgac ttctacccgggagccgtgacagtggcctggaaggcagatagcagccccgtcaaggcgggagtggagac caccacaccctccaaacaaagcaacaacaagtacgcggccagcagctatctgagcctgacgcctgagc agtggaagtcccacagaagctacagctgccaggtcacgcatgaagggagcaccgtggagaagacagtg gcccctacagaatgttcatagtaagtttaaacccgctgatcagcctcgactgtgccttctagttg pCDNA3.1 V5 5' overlapping sequence:
(DNA)

(SEQ ID NO: 217)

actcactatagggagacccaagctggctagtt pCDNA3.1 V5 3' overlapping sequence:
(DNA)

(SEQ ID NO: 218)

ccgctgatcagcctcgactgtgccttctagttg

Humanized C2 gBLOCK#9 sequence (lambda light chain in pSEC Tag2):
(DNA)

(SEQ ID NO: 219)

tgctctgggttccaggttccactggtgacgcggcccagccggccgacattgtgctgacccagtctcca gcctccttggccgtgtctccaggacagagggccaccatcacctgcagagccagtaagagtgtcagtac cagcggatactcctacatgcactggtatcagcagaaaccaggacaacctcctaaactcctgatttacc tggcatccaatctggagagcggggtcccagccaggttcagcggcagtgggtctgggaccgatttcacc ctcacaattaatcctgtggaagctaatgatactgcaaattattactgtcagcacagtagggagctgcc tttcacattcggcggagggaccaaggtggagatcaaacgaactggtcagcccaaggctgccccctcgg tcactctgttcccgccctcctctgaggagcttcaagccaacaaggccacactggtgtgtctcataagt gacttctacccgggagccgtgacagtggcctggaaggcagatagcagccccgtcaaggcgggagtgga gaccaccacaccctccaaacaaagcaacaacaagtacgcggccagcagctatctgagcctgacgcctg agcagtggaagtcccacagaagctacagctgccaggtcacgcatgaagggagcaccgtggagaagaca gtggcccctacagaatgttcatagtaagtttaaacccgctgatcagcctcgactgtgccttctagttg -continued pSEC Tag2 5' overlapping sequence:
(DNA)
(SEQ ID NO: 220)
tgctctgggttccaggttccactggtgacgc pSEC Tag2 3' overlapping sequence:
(DNA)
ccgctgatcagcctcgactgtgccttctagttg
(SEQ ID NO: 221)

Murine Ig kappa chain leader sequence
(DNA)
(SEQ ID NO: 222)
atggagacagacacactcctgctatgggtactgctgctctgggttccaggttccactggtgac (amino acids)
(SEQ ID NO: 223)
METDTLLLWVLLLWVPGSTGD Interleukin-2 (IL-2) leader sequence
(DNA)
(SEQ ID NO: 224)
atgtacaggatgcaactcctgtcttgcattgcactaagtcttgcacttgtcacaaacagt (amino acids)
(SEQ ID NO: 225)
MYRMQLLSCIALSLALVTNS CD33 leader sequence
(DNA)
(SEQ ID NO: 226)
atgccttcttctgcttctgcttcctctgctttgggctggagctcttgct (amino acids)
(SEQ ID NO: 227)
MPLLLLLPLLWAGALA IGHV3-21*03 leader sequence
(DNA)
(SEQ ID NO: 228)
atggaactggggctccgctgggttttccttgttgctattttagaaggtgtccagtgt (amino acids)
(SEQ ID NO: 229)
MELGLRWVFLVAILEGVQC IGHV3-11*02 leader sequence
(DNA)
(SEQ ID NO: 230)
atggaagccccagcgcagcttctcttcctcctgctactctggctcccagataccactgga (amino acids)
(SEQ ID NO: 231)
MEAPAQLLFLLLLWLPDTTG Humanized E6 single chain GS3
(DNA)
(SEQ ID NO: 232
gaggtgcagctggtggagtctggggaggcctggtcaagcctggggggtccctgagactctc ctgtgcagcctctggattcaccttcagtaggtatggcatgagctgggtccgccaggctccag ggaagaggctggagtgggtctcaaccattagtggcggaggcacctacatatactacccagac tcagtgaagggccgattcaccatctccagagacaacgccaagaacaccctgtatctgcaaat gaacagcctgagagccgaggacacggctgtgtattactgtaccagagataactatggccgca actatgattatggcatggattattgggccagggcacccctggtgaccgtgagcagcggcggt ggcggatccggcggtggcggatccggcggtggcggatccgaaattgtgttgacacagtctcc agccaccctgtctttgtctccaggggaaagagccaccctcacctgcagcgccaccagcagtg ttagctacatccactggtaccaacagaggcctggccagagcccaggctcctcatctatagc acctccaacctggccagcggcatcccagccaggttcagtggcagtgggtctgggagcgacta -continued cactctcaccatcagcagcctagagcctgaagattttgcagtttattactgtcagcagcgta gcagctccccttttcacctttggcagcggcaccaaagtggaaattaaa (amino acids)

(SEQ ID NO: 233)

EVQLVESGGGLVKPGGSLRLSCAASGFTFSRYGMSWVRQAPGKRLEWVSTISGGGTYIYYPDSVKGRF

TISRDNAKNTLYLQMNSLRAEDTAVYYCTRDNYGRNYDYGMDYWGQGTLVTVSSGGGGSGGGGSGGGG

SEIVLTQSPATLSLSPGERATLTCSATSSVSYIHWYQQRPGQSPRLLIYSTSNLASGIPARFSGSGSG

SDYTLTISSLEPEDFAVYYCQQRSSSPFTFGSGTKVEIK

Humanized E6 single chain IgG1noC
(DNA)

(SEQ ID NO: 234)

gaggtgcagctggtggagtctggggagcctggtcaagcctgggggtccctgagactctcctgtgc agcctctggattcaccttcagtaggtatggcatgagctgggtccgccaggctccagggaagaggctgg agtgggtctcaaccattagtggcggaggcacctacatatactacccagactcagtgaagggccgattc accatctccagagacaacgccaagaacaccctgtatctgcaaatgaacagcctgagagccgaggacac ggctgtgtattactgtaccagagataactatggccgcaactatgattatggcatggattattggggcc agggcacccctggtgaccgtgagcagcgataaaacccatactaaaccgccaaaaccggcgccggaactg ctgggtggtcctggtaccggtgaaattgtgttgacacagtctccagccaccctgtctttgtctccagg ggaaagagccaccctcacctgcagcgccaccagcagtgttagctacatccactggtaccaacagaggc ctggccagagccccaggctcctcatctatagcacctccaacctggccagcggcatcccagccaggttc agtggcagtgggtctgggagcgactacactctcaccatcagcagcctagagcctgaagattttgcagt ttattactgtcagcagcgtagcagctccccttttcacctttggcagcggcaccaaagtggaaattaaa (amino acids)

(SEQ ID NO: 235)

EVQLVESGGGLVKPGGSLRLSCAASGFTFSRYGMSWVRQAPGKRLEWVSTISGGGTYIYYPDSVKGRF

TISRDNAKNTLYLQMNSLRAEDTAVYYCTRDNYGRNYDYGMDYWGQGTLVTVSSDKTHTKPPKPAPEL

LGGPGTGEIVLTQSPATLSLSPGERATLTCSATSSVSYIHWYQQRPGQSPRLLIYSTSNLASGIPARF

SGSGSGSDYTLTISSLEPEDFAVYYCQQRSSSPFTFGSGTKVEIK

Humanized E6 single chain X4 (linker is IgG1 and IgG2 modified hinge
region)
(DNA)

(SEQ ID NO: 236)

gaggtgcagctggtggagtctggggagcctggtcaagcctgggggtccctgagactctcctgtgc agcctctggattcaccttcagtaggtatggcatgagctgggtccgccaggctccagggaagaggctgg agtgggtctcaaccattagtggcggaggcacctacatatactacccagactcagtgaagggccgattc accatctccagagacaacgccaagaacaccctgtatctgcaaatgaacagcctgagagccgaggacac ggctgtgtattactgtaccagagataactatggccgcaactatgattatggcatggattattggggcc agggcacccctggtgaccgtgagcagcgataaaacccatactaaaccgccaaaaccggcgccggaactg ctgggtggtcctggtaccggtactggtggtccgactattaaacctccgaaacctccgaaacctgctcc gaacctgctgggtggtccggaaattgtgttgacacagtctccagccaccctgtctttgtctccagggg aaagagccaccctcacctgcagcgccaccagcagtgttagctacatccactggtaccaacagaggcct ggccagagccccaggctcctcatctatagcacctccaacctggccagcggcatcccagccaggttcag tggcagtgggtctgggagcgactacactctcaccatcagcagcctagagcctgaagattttgcagttt attactgtcagcagcgtagcagctccccttttcacctttggcagcggcaccaaagtggaaattaaa (amino acids)

(SEQ ID NO: 237)

EVQLVESGGGLVKPGGSLRLSCAASGFTFSRYGMSWVRQAPGKRLEWVSTISGGGTYIYYPDSVKGRE

TISRDNAKNTLYLQMNSLRAEDTAVYYCTRDNYGRNYDYGMDYWGQGTLVTVSSDKTHTKPPKPAPEL

LGGPGTGTGGPTIKPPKPPKPAPNLLGGPEIVLTQSPATLSLSPGERATLTCSATSSVSYIHWYQQRP

GQSPRLLIYSTSNLASGIPARFSGSGSGSDYTLTISSLEPEDFAVYYCQQRSSSPFTFGSGTKVEIK

Humanized C2 single chain GS3
(DNA)

(SEQ ID NO: 238)

gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttgggggggataattactacgaatacttcgatgtctggggcaaag ggaccacggtcaccgtctcctccggcggtggcggatccggcggtggcggatccggcggtggcggatcc gacattgtgctgacccagtctccagcctccttggccgtgtctccaggacagagggccaccatcacctg cagagccagtaagagtgtcagtaccagcggatactcctacatgcactggtatcagcagaaaccaggac aacctcctaaactcctgatttacctggcatccaatctggagagcggggtcccagccaggttcagcggc agtgggtctgggaccgatttcaccctcacaattaatcctgtggaagctaatgatactgcaaattatta ctgtcagcacagtagggagctgccttCacattcggcggagggaccaaggtggagatcaaacgaact (amino acids)

(SEQ ID NO: 239)

EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSGGGGSGGGGSGGGGS

DIVLTQSPASLAVSPGQRATITCRASKSVSTSGYSYMHWYQQKPGQPPKLLIYLASNLESGVPARFSG

SGSGTDFTLTINPVEANDTANYYCQHSRELPFTFGGGTKVEIKRT

Humanized C2 single chain IgG (no Cysteine)
(DNA)

(SEQ ID NO: 240)

gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttgggggggataattactacgaatacttcgatgtctggggcaaag ggaccacggtcaccgtctcctccgataaaacccatactaaaccgccaaaaccggcgccggaactgctg ggtggtcctggtaccggtgacattgtgctgacccagtctccagcctccttggccgtgtctccaggaca gagggccaccatcacctgcagagccagtaagagtgtcagtaccagcggatactcctacatgcactggt atcagcagaaaccaggacaacctcctaaactcctgatttacctggcatccaatctggagagcggggtc ccagccaggttcagcggcagtgggtctgggaccgatttcaccctcacaattaatcctgtggaagctaa tgatactgcaaattattactgtcagcacagtagggagctgccttCacattcggcggagggaccaagg tggagatcaaacgaact (amino acids)

(SEQ ID NO: 241)

EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSDKTHTKPPKPAPELL

-continued

GGPGTGDIVLTQSPASLAVSPGQRATITCRASKSVSTSGYSYMHWYQQKPGQPPKLLIYLASNLESGV

PARFSGSGSGTDFTLTINPVEANDTANYYCQHSRELPFTFGGGTKVEIKRT

Humanized C2 single chain X4 (linker is IgG1 and IgG2 modified hinge
region)
(DNA)
(SEQ ID NO: 242)

gaggtgcagctggtggagtctgggggaggcctggtcaagcctggggggtccctgagactctcctgtgc agcctctggattcaccttcagtggctatgccatgagctgggtccgccaggctccaggaaggggctgg agtgggtctcaaccattagtagtggcggaacctacatatactaccccgactcagtgaagggccgattc accatctccagagacaacgccaagaactcactgtatctgcaaatgaacagcctgagagccgaggacac ggccgtgtattactgtgcgagacttggggggataattactacgaatacttcgatgtctggggcaaag ggaccacggtcaccgtctcctccgataaaacccatactaaaccgccaaaaccggcgccggaactgctg ggtggtcctggtaccggtactggtggtccgactattaaacctccgaaacctccgaaacctgctccgaa cctgctgggtggtccggacattgtgctgacccagtctccagcctccttggccgtgtctccaggacaga gggccaccatcacctgcagagccagtaagagtgtcagtaccagcggatactcctacatgcactggtat cagcagaaaccaggacaacctcctaaactcctgatttacctggcatccaatctggagagcggggtccc agccaggttcagcggcagtgggtctgggaccgatttcaccctcacaattaatcctgtggaagctaatg atactgcaaattattactgtcagcacagtagggagctgcctttcacattcggcggagggaccaaggtg gagatcaaacgaact (amino acids)
(SEQ ID NO: 243)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSDKTHTKPPKPAPELL

GGPGTGTGGPTIKPPKPPKPAPNLLGGPDIVLTQSPASLAVSPGQRATITCRASKSVSTSGYSYMHWY

QQKPGQPPKLLIYLASNLESGVPARFSGSGSGTDFTLTINPVEANDTANYYCQHSRELPFTFGGGTKV

EIKRT

Humanized C3 single chain GS3
(DNA)
(SEQ ID NO: 244)
caggttcagctggtgcagtctggagctgaggtgaagaagcctggggcctcagtgaaggtctcctgcaa ggcttctggttacacctttaccgactacgccatgaactgggtgcgacaggcccctggacaagggcttg agtggatgggagtgatcagcaccttcagcggtaacacaaacttcaaccagaagttcaagggcagagtc accatgaccacagacacatccacgagcacagcctacatggagctgaggagcctgagatctgacgacac ggccgtgtattactgtgcgagaagcgactactacggcccatacttcgactactggggccagggcacca ccctgaccgtgtccagcggcggtggcggatccggcggtggcggatccggcggtggcggatccgatatt gtgatgacccagactccactctctctgtccgtcacccctggacagccggcctccatctcctgcaggtc tagtcagaccattgtccatagtaatggaaacacctatttggagtggtacctgcagaagccaggccagt ctccacagctcctgatctataaggtttccaaccggttctctggagtgccagataggttcagtggcagc gggtcagggacagatttcacactgaaaatcagccgggtggaggctgaggatgttggggtttattactg cttccaaggtagccacgtgccttttcaccttcggcggagggaccaaggtggagatcaaacgaact (amino acids)
(SEQ ID NO: 245)
QVQLVQSGAEVKKPGASVKVSCKASGYTFTDYAMNWVRQAPGQGLEWMGVISTFSGNTNFNQKFKGRV tmttdtststaymelrslrsddtavyycarsdyygpyfdywgqgttltvssggggsggggsggggsdi

VMTQTPLSLSVTPGQPASISCRSSQTIVHSNGNTYLEWYLQKPGQSPQLLIYKVSNRFSGVPDRFSGS

GSGTDFTLKISRVEAEDVGVYYCFQGSHVPFTFGGGTKVEIKRT

```
Humanized C3 single chain IgG1 (no Cysteine)
(DNA)
                                                             (SEQ ID NO: 246)
caggttcagctggtgcagtctggagctgaggtgaagaagcctggggcctcagtgaaggtctcctgcaa ggcttctggttacacctttaccgactacgccatgaactgggtgcgacaggcccctggacaagggcttg agtggatgggagtgatcagcaccttcagcggtaacacaaacttcaaccagaagttcaagggcagagtc accatgaccacagacacatccacgagcacagcctacatggagctgaggagcctgagatctgacgacac ggccgtgtattactgtgcgagaagcgactactacggcccatacttcgactactggggccagggcacca ccctgaccgtgtccagcgataaaacccatactaaaccgccaaaaccggcgccggaactgctgggtggt cctggtaccggtgatattgtgatgacccagactccactctctctgtccgtcacccctggacagccggc ctccatctcctgcaggtctagtcagaccattgtccatagtaatggaaacacctatttggagtggtacc tgcagaagccaggccagtctccacagctcctgatctataaggtttccaaccggttctctggagtgcca gataggttcagtggcagcgggtcagggacagatttcacactgaaaatcagccgggtggaggctgagga tgttggggtttattactgcttccaaggtagccacgtgcctttcaccttcggcggagggaccaaggtgg agatcaaacgaact (amino acids)
                                                             (SEQ ID NO: 247)
QVQLVQSGAEVKKPGASVKVSCKASGYTETDYAMNWVRQAPGQGLEWMGVISTFSGNTNFNQKFKGRV

TMTTDTSTSTAYMELRSLRSDDTAVYYCARSDYYGPYFDYWGQGTTLTVSSDKTHTKPPKPAPELLGG

PGTGDIVMTQTPLSLSVTPGQPASISCRSSQTIVHSNGNTYLEWYLQKPGQSPQLLIYKVSNRFSGVP

DRFSGSGSGTDFTLKISRVEAEDVGVYYCFQGSHVPFTFGGGTKVEIKRT

Humanized C3 single chain X4 (linker is IgG1 and IgG2 modified hinge
region)
(DNA)
                                                             (SEQ ID NO: 248)
caggttcagctggtgcagtctggagctgaggtgaagaagcctggggcctcagtgaaggtctcctgcaa ggcttctggttacacctttaccgactacgccatgaactgggtgcgacaggcccctggacaagggcttg agtggatgggagtgatcagcaccttcagcggtaacacaaacttcaaccagaagttcaagggcagagtc accatgaccacagacacatccacgagcacagcctacatggagctgaggagcctgagatctgacgacac ggccgtgtattactgtgcgagaagcgactactacggcccatacttcgactactggggccagggcacca ccctgaccgtgtccagcgataaaacccatactaaaccgccaaaaccggcgccggaactgctgggtggt cctggtaccggtactggtggtccgactattaaacctccgaaacctccgaaacctgctccgaacctgct gggtggtccggatattgtgatgacccagactccactctctctgtccgtcacccctggacagccggcct ccatctcctgcaggtctagtcagaccattgtccatagtaatggaaacacctatttggagtggtacctg cagaagccaggccagtctccacagctcctgatctataaggtttccaaccggttctctggagtgccaga taggttcagtggcagcgggtcagggacagatttcacactgaaaatcagccgggtggaggctgaggatg ttggggtttattactgcttccaaggtagccacgtgcctttcaccttcggcggagggaccaaggtggag atcaaacgaact (amino acids)
                                                             (SEQ ID NO: 249)
QVQLVQSGAEVKKPGASVKVSCKASGYTFTDYAMNWVRQAPGQGLEWMGVISTFSGNTNFNQKFKGRV tmttdtststaymelrslrsddtavyycarsdyygpyfdywgqgttltvssdkthtkppkpapellgg

PGTGTGGPTIKPPKPPKPAPNLLGGPDIVMTQTPLSLSVTPGQPASISCRSSQTIVHSNGNTYLEWYL

QKPGQSPQLLIYKVSNRFSGVPDRFSGSGSGTDFTLKISRVEAEDVGVYYCFQGSHVPFTFGGGTKVE

IKRT
```

-continued

Humanized C8 single chain GS3 (linker is [Gly4Ser1]3)
(DNA)
(SEQ ID NO: 250)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactgggcggcgataactattatgaatattggggcaaagggaccacgg tcaccgtctcctccggcggtggcggatccggcggtggcggatccggcggtggcggatccgacatcgtg atgacccagtctccagactccctggctgtgtctctgggcgagagggccaccatcaactgcagggccag caagagtgttagcaccagcggctacagctacatgcactggtaccagcagaaaccaggacagcctccta agctgctcatttacctggtgtctaacctggaatccggggtccctgaccgattcagtggcagcgggtct gggacagatttcactctcaccatcagcagcctgcaggctgaagatgtggcagtttattactgtcaaca cattcgggaactgaccaggagtgaattcggcggagggaccaaggtggagatcaaacgaact (amino acids)
(SEQ ID NO: 251)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSGGGGSGGGGSGGGGSDIV

MTQSPDSLAVSLGERATINCRASKSVSTSGYSYMHWYQQKPGQPPKLLIYLVSNLESGVPDRFSGSGS

GTDFTLTISSLQAEDVAVYYCQHIRELTRSEFGGGTKVEIKRT

Humanized C8 single chain IgG1 (no Cysteine)
(DNA)
(SEQ ID NO: 252)
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactgggcggcgataactattatgaatattggggcaaagggaccacgg tcaccgtctcctccgataaaacccatactaaaccgccaaaaccggcgccggaactgctgggtggtcct ggtaccggtgacatcgtgatgacccagtctccagactccctggctgtgtctctgggcgagagggccac catcaactgcagggccagcaagagtgttagcaccagcggctacagctacatgcactggtaccagcaga aaccaggacagcctcctaagctgctcatttacctggtgtctaacctggaatccggggtccctgaccga ttcagtggcagcgggtctgggacagatttcactctcaccatcagcagcctgcaggctgaagatgtggc agtttattactgtcaacacattcgggaactgaccaggagtgaattcggcggagggaccaaggtggaga tcaaacgaact (amino acids)
(SEQ ID NO: 253)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSDKTHTKPPKPAPELLGGP

GTGDIVMTQSPDSLAVSLGERATINCRASKSVSTSGYSYMHWYQQKPGQPPKLLIYLVSNLESGVPDR

FSGSGSGTDFTLTISSLQAEDVAVYYCQHIRELTRSEFGGGTKVEIKRT

Humanized C8 single chain X4 (linker is IgG1 and IgG2 modified hinge
region)
(DNA)
(SEQ ID NO: 254)
gaggtgcagctggtggagtctgggggaggcctggtcaagcctggggggtccctgagactctcctgtgc agcctctggattcaccttcagtggctatgccatgagctgggtccgccaggctccagggaaggggctgg -continued agtgggtctcaaccattagtagtggcggaacctacatatactacccagactcagtgaagggccgattc accatctccagagacaacgccaagaactcactgtatctgcaaatgaacagcctgagagccgaggacac ggccgtgtattactgtgcgagactgggcggcgacaattactatgagtattggggcaaagggaccacgg tcaccgtctcctccgataaaacccatactaaaccgccaaaaccggcgccggaactgctgggtggtcct ggtaccggtactggtggtccgactattaaacctccgaaacctccgaaacctgctccgaacctgctggg tggtccggacatcgtgatgacccagtctccagactccctggctgtgtctctgggcgagagggccacca tcaactgcagggccagcaagagtgttagcaccagcggctacagctacatgcactggtaccagcagaaa ccaggacagcctcctaagctgctcatttacctggtgtctaacctggaatccggggtccctgaccgatt cagtggcagcgggtctgggacagatttcactctcaccatcagcagcctgcaggctgaagatgtggcag tttattactgtcaacacattcgggaactgaccaggagtgaattcggcggagggaccaaggtggagatc aaacgaact (amino acids)

(SEQ ID NO: 255)

EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSDKTHTKPPKPAPELLGGP

GTGTGGPTIKPPKPPKPAPNLLGGPDIVMTQSPDSLAVSLGERATINCRASKSVSTSGYSYMHWYQQK

PGQPPKLLIYLVSNLESGVPDRFSGSGSGTDFTLTISSLQAEDVAVYYCQHIRELTRSEFGGGTKVEI

KRT pSECTag2 E6 scFV-FC
(DNA)

(SEQ ID NO: 256)

atggagacagacacactcctgctatgggtactgctgctctgggttccaggttccactggtga cgcggcccagccggccgaggtgcagctggtggagtctggggggaggcctggtcaagcctgggg ggtccctgagactctcctgtgcagcctctggattcaccttcagtaggtatggcatgagctgg gtccgccaggctccagggaagaggctggagtgggtctcaaccattagtggcggaggcaccta catatactacccagactcagtgaagggccgattcaccatctccagagacaacgccaagaaca ccctgtatctgcaaatgaacagcctgagagccgaggacacggctgtgtattactgtaccaga gataactatggccgcaactatgattatggcatggattattggggccagggcaccctggtgac cgtgagcagcggcggtggcggatccggcggtggcggatccggcggtggcggatccgaaattg tgttgacacagtctccagccaccctgtctttgtctccaggggaaagagccaccctcacctgc agcgccaccagcagtgttagctacatccactggtaccaacagaggcctggccagagccccag gctcctcatctatagcacctccaacctggccagcggcatcccagccaggttcagtggcagtg ggtctgggagcgactacactctcaccatcagcagcctagagcctgaagattttgcagtttat tactgtcagcagcgtagcagctcccctttcacctttggcagcggcaccaaagtggaaattaa agagcccaaatcttgtgacaaaactcacacatgcccaccgtgcccagcacctgaactcctgg ggggaccgtcagtcttcctcttccccccaaaacccaaggacaccctcatgatctcccggacc cctgaggtcacatgcgtggtggtggacgtgagccacgaagaccctgaggtcaagttcaactg gtacgtggacggcgtggaggtgcataatgccaagacaaagccgcgggaggagcagtacaaca gcacgtaccgtgtggtcagcgtcctcaccgtcctgcaccaggactggctgaatggcaaggag tacaagtgcaaggtctccaacaaagccctcccagcccccatcgagaaaaccatctccaaagc caaagggcagccccgagaaccacaggtgtacaccctgcccccatcccgggaggagatgacca agaaccaggtcagcctgacctgcctggtcaaaggcttctatcccagcgacatcgccgtggag tgggagagcaatgggcagccggagaacaactacaagaccacgcctcccgtgctggactccga -continued
cggctccttcttcctctacagcaagctcaccgtggacaagagcaggtggcagcaggggaacg tcttctcatgctccgtgatgcatgaggctctgcacaaccactacacgcagaagagcctctcc ctgtctccgggtaaatgataa (amino acids) (SEQ ID NO: 257)

METDTLLLWVLLLWVPGSTGDAAQPAEVQLVESGGGLVKPGGSLRLSCAASGFTFSRYGMSW

VRQAPGKRLEWVSTISGGGTYIYYPDSVKGRFTISRDNAKNTLYLQMNSLRAEDTAVYYCTR

DNYGRNYDYGMDYWGQGTLVTVSSGGGGSGGGGSGGGGSEIVLTQSPATLSLSPGERATLTC

SATSSVSYIHWYQQRPGQSPRLLIYSTSNLASGIPARFSGSGSGSDYTLTISSLEPEDFAVY

YCQQRSSSPFTFGSGTKVEIKEPKSCDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYTQKSLS

LSPGK**

E6 scFC-FC 1 gBLOCk sequence: (SEQ ID NO: 258)
tgctctgggttccaggttccactggtgacgcggcccagccggccgaggtgcagctggtggag tctgggggaggcctggtcaagcctggggggtccctgagactctcctgtgcagcctctggatt caccttcagtaggtatggcatgagctgggtccgccaggctccagggaagaggctggagtggg tctcaaccattagtggcggaggcacctacatatactacccagactcagtgaagggccgattc accatctccagagacaacgccaagaacaccctgtatctgcaaatgaacagcctgagagccga ggacacggctgtgtattactgtaccagagataactatggccgcaactatgattatggcatgg attattggggccagggcaccctggtgaccgtgagcagcggcggtggcggatccggcggtggc ggatccggcggtggcggatccgaaattgtgttgacacagtctccagccaccctgtctttgtc E6 scFC-FC 2 gBLOCk sequence: (SEQ ID NO: 259)
aattgtgttgacacagtctccagccaccctgtctttgtctccaggggaaagagccaccctca cctgcagcgccaccagcagtgttagctacatccactggtaccaacagagagcctggccagagc cccaggctcctcatctatagcacctccaacctggccagcggcatcccagccaggttcagtgg cagtgggtctgggagcgactacactctcaccatcagcagcctagagcctgaagattttgcag tttattactgtcagcagcgtagcagctcccctttcacctttggcagcggcaccaaagtggaa attaaagagcccaaatcttgtgacaaaactcacacatgcccaccgtgcccagcacctgaact cctggggggaccgtcagtcttcctcttccccccaaaacccaaggacaccctcatgatctccc ggacccctgaggtcacatgcgtggtggtggacgtgagccacgaagaccctgaggtcaagttc aactggtacgtggacggcgtggaggtgcataatgccaagacaaagccgcgggaggagcagta caacagcacgtaccgtgtggtcagc pSECTag2 C2 scFV-FC
(DNA) (SEQ ID NO: 260)
atggagacagacacactcctgctatgggtactgctgctctggttccaggttccactggtga cgcggcccagccggccgaggtgcagctggtggagtctgggggaggcctggtcaagcctgggg ggtccctgagactctcctgtgcagcctctggattcaccttcagtggctatgccatgagctgg gtccgccaggctccagggaaggggctggagtgggtctcaaccattagtagtggcggaaccta catatactaccccgactcagtgaagggccgattcaccatctccagagacaacgccaagaact cactgtatctgcaaatgaacagcctgagagccgaggacacggccgtgtattactgtgcgaga -continued cttggggggg ataattactacgaatacttcgatgtctggggcaaagggaccacggtcaccgt ctcctccggcggtggcggatccggcggtggcggatccggcggtggcggatccgacattgtgc tgacccagtctccagcctccttggccgtgtctccaggacagagggccaccatcacctgcaga gccagtaagagtgtcagtaccagcggatactcctacatgcactggtatcagcagaaaccagg acaacctcctaaactcctgatttacctggcatccaatctggagagcggggtcccagccaggt tcagcggcagtgggtctgggaccgatttcaccctcacaattaatcctgtggaagctaatgat actgcaaattattactgtcagcacagtagggagctgcctttcacattcggcggagggaccaa ggtggagatcaaacgaactgagcccaaatcttgtgacaaaactcacacatgcccaccgtgcc cagcacctgaactcctggggggaccgtcagtcttcctcttccccccaaaacccaaggacacc ctcatgatctcccggacccctgaggtcacatgcgtggtggtggacgtgagccacgaagaccc tgaggtcaagttcaactggtacgtggacggcgtggaggtgcataatgccaagacaaagccgc gggaggagcagtacaacagcacgtaccgtgtggtcagcgtcctcaccgtcctgcaccaggac tggctgaatggcaaggagtacaagtgcaaggtctccaacaaagccctcccagcccccatcga gaaaaccatctccaaagccaaagggcagccccgagaaccacaggtgtacaccctgcccccat cccgggaggagatgaccaagaaccaggtcagcctgacctgcctggtcaaaggcttctatccc agcgacatcgccgtggagtgggagagcaatgggcagccggagaacaactacaagaccacgcc tcccgtgctggactccgacggctccttcttcctctacagcaagctcaccgtggacaagagca ggtggcagcaggggaacgtcttctcatgctccgtgatgcatgaggctctgcacaaccactac acgcagaagagcctctccctgtctccgggtaaatgataa (amino acids)

(SEQ ID NO: 261)

METDTLLLWVLLLWVPGSTGDAAQPAEVQLVESGGGLVKPGGSLRLSCAASGFTFSGYAMSW

VRQAPGKGLEWVSTISSGGTYIYYPDSVKGRFTISRDNAKNSLYLQMNSLRAEDTAVYYCAR

LGGDNYYEYFDVWGKGTTVTVSSGGGGSGGGGSGGGGSDIVLTQSPASLAVSPGQRATITCR

ASKSVSTSGYSYMHWYQQKPGQPPKLLIYLASNLESGVPARFSGSGSGTDFTLTINPVEAND

TANYYCQHSRELPFTFGGGTKVEIKRTEPKSCDKTHTCPPCPAPELLGGPSVFLFPPKPKDT

LMISRTPEVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLVKGFYP

SDIAVEWESNGQPENNYKTTPPVLDSDGSFFLYSKLTVDKSRWQQGNVFSCSVMHEALHNHY

TQKSLSLSPGK**

C2 seFV-FC 1 gBLOCk sequence:
(DNA)

(SEQ ID NO: 262)

tgctctgggttccaggttccactggtgacgcggcccagccggccgaggtgcagctggtggag tctgggggaggcctggtcaagcctggggggtccctgagactctcctgtgcagcctctggatt caccttcagtggctatgccatgagctgggtccgccaggctccagggaaggggctggagtggg tctcaaccattagtagtggcggaacctacatatactaccccgactcagtgaagggccgattc accatctccagagacaacgccaagaactcactgtatctgcaaatgaacagcctgagagccga ggacacggccgtgtattactgtgcgagacttgggggggataattactacgaatacttcgatg tctggggcaaagggaccacggtcaccgtctcctccggcggtggcggatccggcggtggcgga tccggcggtggcggatccgacattgtgctgacccagtctccagcctccttggc C2 scFV-FC 2 gBLOCk sequence:
(DNA)

(SEQ ID NO: 263)

cattgtgctgacccagtctccagcctccttggccgtgtctccaggacagagggccaccatca cctgcagagccagtaagagtgtcagtaccagcggatactcctacatgcactggtatcagcag aaaccaggacaacctcctaaactcctgatttacctggcatccaatctggagagcgggtccc agccaggttcagcggcagtgggtctgggaccgatttcaccctcacaattaatcctgtggaag ctaatgatactgcaaattattactgtcagcacagtagggagctgcctttcacattcggcgga gggaccaaggtggagatcaaacgaactgagcccaaatcttgtgacaaaactcacacatgccc accgtgcccagcacctgaactcctggggggaccgtcagtcttcctcttccccccaaaaccca aggacaccctcatgatctcccggacccctgaggtcacatgcgtggtggtggacgtgagccac gaagaccctgaggtcaagttcaactggtacgtggacggcgtggaggtgcataatgccaagac aaagccgcgggaggagcagtacaacagcacgtaccgtgtggtcagc pSECTag2 C3 scFV-FC
(DNA)

(SEQ ID NO: 264)

atggagacagacacactcctgctatgggtactgctgctctgggttccaggttccactggtga cgcggcccagccggcccaggttcagctggtgcagtctggagctgaggtgaagaagcctgggg cctcagtgaaggtctcctgcaaggcttctggttacacctttaccgactacgccatgaactgg gtgcgacaggcccctggacaagggcttgagtggatgggagtgatcagcaccttcagcggtaa cacaaacttcaaccagaagttcaagggcagagtcaccatgaccacagacacatccacgagca cagcctacatggagctgaggagcctgagatctgacgacacggccgtgtattactgtgcgaga agcgactactacggcccatacttcgactactggggccagggcaccaccctgaccgtgtccag cggcggtggcggatccggcggtggcggatccggcggtggcggatccgatattgtgatgaccc agactccactctctctgtccgtcacccctggacagccggcctccatctcctgcaggtctagt cagaccattgtccatagtaatggaaacacctatttggagtggtacctgcagaagccaggcca gtctccacagctcctgatctataaggtttccaaccggttctctggagtgccagataggttca gtggcagcgggtcagggacagatttcacactgaaaatcagccgggtggaggctgaggatgtt ggggtttattactgcttccaaggtagccacgtgccttttaccttcggcggagggaccaaggt ggagatcaaacgaactgagcccaaatcttgtgacaaaactcacacatgcccaccgtgcccag cacctgaactcctggggggaccgtcagtcttcctcttccccccaaaacccaaggacaccctc atgatctcccggacccctgaggtcacatgcgtggtggtggacgtgagccacgaagaccctga ggtcaagttcaactggtacgtggacggcgtggaggtgcataatgccaagacaaagccgcggg aggagcagtacaacagcacgtaccgtgtggtcagcgtcctcaccgtcctgcaccaggactgg ctgaatggcaaggagtacaagtgcaaggtctccaacaaagccctcccagcccccatcgagaa aaccatctccaaagccaaagggcagccccgagaaccacaggtgtacaccctgcccccatccc gggaggagatgaccaagaaccaggtcagcctgacctgcctggtcaaaggcttctatcccagc gacatcgccgtggagtgggagagcaatgggcagccggagaacaactacaagaccacgcctcc cgtgctggactccgacggctccttcttcctctacagcaagctcaccgtggacaagagcaggt ggcagcaggggaacgtcttctcatgctccgtgatgcatgaggctctgcacaaccactacacg cagaagagcctctccctgtctccgggtaaatgataa -continued (amino acids)

(SEQ ID NO: 265)

METDTLLLWVLLLWVPGSTGDAAQPAQVQLVQSGAEVKKPGASVKVSCKASGYTFTDYAMNWVRQAPG

QGLEWMGVISTFSGNTNFNQKFKGRVTMTTDTSTSTAYMELRSLRSDDTAVYYCARSDYYGPYFDYWG

QGTTLTVSSGGGGSGGGGSGGGGSDIVMTQTPLSLSVTPGQPASISCRSSQTIVHSNGNTYLEWYLQK

PGQSPQLLIYKVSNRFSGVPDRFSGSGSGTDFTLKISRVEAEDVGVYYCFQGSHVPFTFGGGTKVEIK

RTEPKSCDKTHTCPPCPAPELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK**

C3 GS scFV FC 1 gBLOCk sequence:
(DNA)

(SEQ ID NO: 266)

tgctctgggttccaggttccactggtgacgcggcccagccggcccaggttcagctggtgcag tctggagctgaggtgaagaagcctggggcctcagtgaaggtctcctgcaaggcttctggtta cacctttaccgactacgccatgaactgggtgcgacaggcccctggacaagggcttgagtgga tgggagtgatcagcaccttcagcggtaacacaaacttcaaccagaagttcaagggcagagtc accatgaccacagacacatccacgagcacagcctacatggagctgaggagcctgagatctga cgacacggccgtgtattactgtgcgagaagcgactactacgcccatacttcgactactggg gccagggcaccaccctgaccgtgtccagcggcggtggcggatccggcggtggcggatccggc ggtggcggatccgatattgtgatgacccagactccactctctctgt C3 scFV FC2 gBLOCk sequence:
(DNA)

(SEQ ID NO: 267)

tattgtgatgacccagactccactctctctgtccgtcacccctggacagccggcctccatct cctgcaggtctagtcagaccattgtccatagtaatggaaacacctatttggagtggtacctg cagaagccaggccagtctccacagctcctgatctataaggttttccaaccggttctctggagt gccagataggttcagtggcagcgggtcaggacagatttcacactgaaaatcagccgggtgg aggctgaggatgttggggtttattactgcttccaaggtagccacgtgccttcaccttcggc ggagggaccaaggtggagatcaaacgaactgagcccaaatcttgtgacaaaactcacacatg cccaccgtgcccagcacctgaactcctggggggaccgtcagtcttcctcttccccccaaaac ccaaggacaccctcatgatctcccggacccctgaggtcacatgcgtggtggtggacgtgagc cacgaagaccctgaggtcaagttcaactggtacgtggacggcgtggaggtgcataatgccaa gacaaagccgcgggaggagcagtacaacagcacgtaccgtgtggtcagc pSECTag2 C8 scFV-FC
(DNA)

(SEQ ID NO: 268)

atggagacagacacactcctgctatgggtactgctgctctgggttccaggttccactggtga cgcggcccagccggccgaggtgcagctggtggagtctgggggaggcctggtcaagcctgggg ggtccctgagactctcctgtgcagcctctggattcaccttcagtggctatgccatgagctgg gtccgccaggctccagggaaggggctggagtgggtctcaaccattagtagtggcggaaccta catatactaccctgactcagtgaagggccgattcaccatctccagagacaacgccaagaact cactgtatctgcaaatgaacagcctgagagccgaggacacggccgtgtattactgtgcgaga ctgggcggcgataactattatgaatattgggcaaagggaccacggtcaccgtctcctccgg cggtggcggatccggcggtggcggatccggcggtggcggatccgacatcgtgatgacccagt -continued

```
ctccagactccctggctgtgtctctgggcgagagggccaccatcaactgcagggccagcaag agtgttagcaccagcggctacagctacatgcactggtaccagcagaaaccaggacagcctcc taagctgctcatttacctggtgtctaacctggaatccggggtccctgaccgattcagtggca gcgggtctgggacagatttcactctcaccatcagcagcctgcaggctgaagatgtggcagtt tattactgtcaacacattcgggaactgaccaggagtgaattcggcggagggaccaaggtgga gatcaaacgaactgagcccaaatcttgtgacaaaactcacacatgcccaccgtgcccagcac ctgaactcctggggggaccgtcagtcttcctcttccccccaaaacccaaggacaccctcatg atctcccggacccctgaggtcacatgcgtggtggtggacgtgagccacgaagaccctgaggt caagttcaactggtacgtggacggcgtggaggtgcataatgccaagacaaagccgcgggagg agcagtacaacagcacgtaccgtgtggtcagcgtcctcaccgtcctgcaccaggactggctg aatggcaaggagtacaagtgcaaggtctccaacaaagccctcccagcccccatcgagaaaac catctccaaagccaaagggcagccccgagaaccacaggtgtacaccctgcccccatcccggg aggagatgaccaagaaccaggtcagcctgacctgcctggtcaaaggcttctatcccagcgac atcgccgtggagtgggagagcaatgggcagccggagaacaactacaagaccacgcctcccgt gctggactccgacggctccttcttcctctacagcaagctcaccgtggacaagagcaggtggc agcaggggaacgtcttctcatgctccgtgatgcatgaggctctgcacaaccactacacgcag aagagcctctccctgtctccgggtaaatgataa
```

(amino acids)

(SEQ ID NO: 269)

```
METDTLLLWVLLLWVPGSTGDAAQPAEVQLVESGGGLVKPGGSLRLSCAASGFTFSGYAMSWVRQAPG

KGLEWVSTISSGGTYIYYPDSVKGRFTISRDNAKNSLYLQMNSLRAEDTAVYYCARLGGDNYYEYWGK

GTTVTVSSGGGGSGGGGSGGGGSDIVMTQSPDSLAVSLGERATINCRASKSVSTSGYSYMHWYQQKPG

QPPKLLIYLVSNLESGVPDRFSGSGSGTDFTLTISSLQAEDVAVYYCQHIRELTRSEFGGGTKVEIKR

TEPKSCDKTHTCPPCPAPELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSKLTVDKSRWQ

QGNVFSCSVMHEALHNHYTQKSLSLSPGK**
```

C8 scFV FC 1 gBLOCk sequence:
(DNA)

(SEQ ID NO: 270)

```
tgctctgggttccaggttccactggtgacgcggcccagccggccgaggtgcagctggtggag tctgggggaggcctggtcaagcctggggggtccctgagactctcctgtgcagcctctggatt caccttcagtggctatgccatgagctgggtccgccaggctccagggaaggggctggagtggg tctcaaccattagtagtggcggaacctacatatactaccctgactcagtgaagggccgattc accatctccagagacaacgccaagaactcactgtatctgcaaatgaacagcctgagagccga ggacacggccgtgtattactgtgcgagactgggcggcgataactattatgaatattggggca aagggaccacggtcaccgtctcctccggcggtggcggatccggcggtggcggatccggcggt ggcggatccgacatcgtgatgacccagtctccagactccctgg
```

C8 ScFV FC2 gBLOCk sequence:
(DNA)

(SEQ ID NO: 271)

```
catcgtgatgacccagtctccagactccctggctgtgtctctgggcgagagggccaccatca actgcagggccagcaagagtgttagcaccagcggctacagctacatgcactggtaccagcag aaaccaggacagcctcctaagctgctcatttacctggtgtctaacctggaatccggggtccc
```

-continued

```
tgaccgattcagtggcagcgggtctgggacagatttcactctcaccatcagcagcctgcagg ctgaagatgtggcagtttattactgtcaacacattcgggaactgaccaggagtgaattcggc ggagggaccaaggtggagatcaaacgaactgagcccaaatcttgtgacaaaactcacacatg cccaccgtgcccagcacctgaactcctggggggaccgtcagtcttcctcttccccccaaaac ccaaggacaccctcatgatctcccggacccctgaggtcacatgcgtggtggtggacgtgagc cacgaagaccctgaggtcaagttcaactggtacgtggacggcgtggaggtgcataatgccaa gacaaagccgcgggaggagcagtacaacagcacgtaccgtgtggtcagc
```

Human IgG1 Fc sequence:
(DNA)

(SEQ ID NO: 272)
```
gagcccaaatcttgtgacaaaactcacacatgcccaccgtgcccagcacctgaactcctgggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagcccccatcgagaaaaccatctccaaagccaaagggcagccccgagaaccacaggtgtacaccctg cccccatcccgggaggagatgaccaagaaccaggtcagcctgacctgcctggtcaaaggcttctatcc cagcgacatcgccgtggagtgggagagcaatgggcagccggagaacaactacaagaccacgcctcccg tgctggactccgacggctccttcttcctctacagcaagctcaccgtggacaagagcaggtggcagcag gggaacgtcttctcatgctccgtgatgcatgaggctctgcacaaccactacacgcagaagagcctctc cctgtctccgggtaaatgataa
```

(amino acids)

(SEQ ID NO: 273)
EPKSCDKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSDGSFFLYSKLTVDKSRWQQ
GNVFSCSVMHEALHNHYTQKSLSLSPGK**

Human IgG1 CH2-CH3 domain sequence:
(DNA)

(SEQ ID NO: 274)
```
ccgtgcccagcacctgaactcctgggggaccgtcagtcttcctcttccccccaaaacccaaggacac cctcatgatctcccggacccctgaggtcacatgcgtggtggtggacgtgagccacgaagaccctgagg tcaagttcaactggtacgtggacggcgtggaggtgcataatgccaagacaaagccgcgggaggagcag tacaacagcacgtaccgtgtggtcagcgtcctcaccgtcctgcaccaggactggctgaatggcaagga gtacaagtgcaaggtctccaacaaagccctcccagcccccatcgagaaaaccatctccaaagccaaag ggcagccccgagaaccacaggtgtacaccctgcccccatcccgggaggagatgaccaagaaccaggtc agcctgacctgcctggtcaaaggcttctatcccagcgacatcgccgtggagtgggagagcaatgggca gccggagaacaactacaagaccacgcctcccgtgctggactccgacggctccttcttcctctacagca agctcaccgtggacaagagcaggtggcagcaggggaacgtcttctcatgctccgtgatgcatgaggct ctgcacaaccactacacgcagaagagcctctccctgtctccgggtaaatgataa
```

(amino acids)

(SEQ ID NO: 275)
PCPAPELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEA
LHNHYTQKSLSLSPGK**

-continued

Human IgG1 CH3 domain sequence:
(DNA)
(SEQ ID NO: 276)
gggcagccccgagaaccacaggtgtacaccctgcccccatcccgggaggagatgaccaagaaccaggt cagcctgacctgcctggtcaaaggcttctatcccagcgacatcgccgtggagtgggagagcaatgggc agccggagaacaactacaagaccacgcctcccgtgctggactccgacggctccttcttcctctacagc aagctcaccgtggacaagagcaggtggcagcaggggaacgtcttctcatgctccgtgatgcatgaggc tctgcacaaccactacacgcagaagagcctctccctgtctccgggtaaatgataa (amino acids)
(SEQ ID NO: 277)
GQPREPQVYTLPPSREEMTKNQVSLTCLVKGFYPSDIAVEWESNGQPENNYKTTPPVLDSDGSFFLYS

KLTVDKSRWQQGNVFSCSVMHEALHNHYTQKSLSLSPGK**

Human IgG1 Fc Y407R sequence:
(DNA)
(SEQ ID NO: 278)
gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagcccccatcgagaaaaccatctccaaagccaaagggcagccccgagaaccacaggtgtacaccctg cccccatcccgggaggagatgaccaagaaccaggtcagcctgacctgcctggtcaaaggcttctatcc cagcgacatcgccgtggagtgggagagcaatgggcagccggagaacaactacaagaccacgcctcccg tgctggactccgacggctccttcttcctcaggagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)
(SEQ ID NO: 279)
EPKSCDKTHTCPPCPAPELLGGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSDGSFFLRSKLTVDKSRWQQ

GNVFSCSVMHEALHNHYTQKSLSLSPGK**

Human IgG1 Fc F405Q sequence:
(DNA)
(SEQ ID NO: 280)
gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagcccccatcgagaaaaccatctccaaagccaaagggcagccccgagaaccacaggtgtacaccctg cccccatcccgggaggagatgaccaagaaccaggtcagcctgacctgcctggtcaaaggcttctatcc cagcgacatcgccgtggagtgggagagcaatgggcagccggagaacaactacaagaccacgcctcccg tgctggactccgacggctccttcctccagctctacagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)

(SEQ ID NO: 281)

EPKSCDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSD

GSFQLYSKLTVDKSRWQQGNVFSCSVMHEALHNHYTQKSLSLSPGK**

Human IgG1 Fc T394D sequence:
(DNA)

(SEQ ID NO: 282)

gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagcccccatcgagaaaaccatctccaaagccaaagggcagccccgagaaccacaggtgtacaccctg cccccatcccgggaggagatgaccaagaaccaggtcagcctgacctgcctggtcaaaggcttctatcc cagcgacatcgccgtggagtgggagagcaatgggcagccggagaacaactacaagaccgaccctcccg tgctggactccgacggctccttcttcctctacagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)

(SEQ ID NO: 283)

EPKSCDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTDPPVLDSD

GSFFLYSKLTVDKSRWQQGNVFSCSVMHEALHNHYTQKSLSLSPGK**

Human IgG1 Fc T366W/L368W sequence:
(DNA)

(SEQ ID NO: 284)

gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagccctcc cagcccccatcgagaaaaccatctccaaagccaaagggcagccccgagaaccacaggtgtacaccctg cccccatcccgggaggagatgaccaagaaccaggtcagcctgtggtgctgggtcaaaggcttctatcc cagcgacatcgccgtggagtgggagagcaatgggcagccggagaacaactacaagaccacgcctcccg tgctggactccgacggctccttcttcctctacagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)

(SEQ ID NO: 285

EPKSCDKTHTCPPCPAPELLGGPSVFLFPPKPKDTLMISRTPEVTCVVVDVSHEDPEVKENW

YVDGVEVHNAKTKPREEQYNSTYRVVSVLTVLHQDWLNGKEYKCKVSNKALPAPIEKTISKA

KGQPREPQVYTLPPSREEMTKNQVSLWCWVKGFYPSDIAVEWESNGQPENNYKTTPPVLDSD

GSFFLYSKLTVDKSRWQQGNVFSCSVMHEALHNHYTQKSLSLSPGK**

-continued

Human IgG1 Fc T364R/L368R sequence:
(DNA)
(SEQ ID NO: 286)
gagcccaaatcttgtgacaaaactcacacatgcccaccgtgcccagcacctgaactcctggggggacc gtcagtcttcctcttccccccaaaacccaaggacaccctcatgatctcccggacccctgaggtcacat gcgtggtggtggacgtgagccacgaagaccctgaggtcaagttcaactggtacgtggacggcgtggag gtgcataatgccaagacaaagccgcgggaggagcagtacaacagcacgtaccgtgtggtcagcgtcct caccgtcctgcaccaggactggctgaatggcaaggagtacaagtgcaaggtctccaacaaagcccctcc cagcccccatcgagaaaaccatctccaaagccaaagggcagccccgagaaccacaggtgtacaccctg cccccatcccgggaggagatgaccaagaaccaggtcaggctgacctgcagggtcaaaggcttctatcc cagcgacatcgccgtggagtgggagagcaatgggcagccggagaacaactacaagaccacgcctcccg tgctggactccgacggctccttcttcctctacagcaagctcaccgtggacaagagcaggtggcagcag gggaacgtcttctcatgctccgtgatgcatgaggctctgcacaaccactacacgcagaagagcctctc cctgtctccgggtaaatgataa (amino acids)
(SEQ ID NO: 287)
EPKSCDKTHTCPPCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVRLTCRVKGFYPSDIAVEWESNGQPENNYKTTPPVLDSD

GSFFLYSKLTVDKSRWQQGNVFSCSVMHEALHNHYTQKSLSLSPGK**

Human IgG1 Fc hingeless sequence:
(DNA)
(SEQ ID NO: 288)
gcacctgaactcctgggggggaccgtcagtcttcctcttccccccaaaacccaaggacaccctcatgat ctcccggacccctgaggtcacatgcgtggtggtggacgtgagccacgaagaccctgaggtcaagttca actggtacgtggacggcgtggaggtgcataatgccaagacaaagccgcgggaggagcagtacaacagc acgtaccgtgtggtcagcgtcctcaccgtcctgcaccaggactggctgaatggcaaggagtacaagtg caaggtctccaacaaagcccctccagcccccatcgagaaaaccatctccaaagccaaagggcagcccc gagaaccacaggtgtacaccctgcccccatcccgggaggagatgaccaagaaccaggtcagcctgacc tgcctggtcaaaggcttctatcccagcgacatcgccgtggagtgggagagcaatgggcagccggagaa caactacaagaccacgcctcccgtgctggactccgacggctccttcttcctctacagcaagctcaccg tggacaagagcaggtggcagcaggggaacgtcttctcatgctccgtgatgcatgaggctctgcacaac cactacacgcagaagagcctctccctgtctccgggtaaatgataa (amino acids)
(SEQ ID NO: 289)
APELLGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSRWQQGNVFSCSVMHEALHN

HYTQKSLSLSPGK**

Human IgG1 G237A FC sequence:
(DNA)
(SEQ ID NO: 290)
gagcccaaatcttgtgacaaaactcacacatgcccaccgtgcccagcacctgaactcctggg ggcccgtcagtcttcctcttccccccaaaacccaaggacaccctcatgatctcccggaccc ctgaggtcacatgcgtggtggtggacgtgagccacgaagaccctgaggtcaagttcaactgg tacgtggacggcgtggaggtgcataatgccaagacaaagccgcgggaggagcagtacaacag cacgtaccgtgtggtcagcgtcctcaccgtcctgcaccaggactggctgaatggcaaggagt -continued

```
acaagtgcaaggtctccaacaaagccctcccagcccccatcgagaaaaccatctccaaagcc aaagggcagccccgagaaccacaggtgtacaccctgcccccatcccgggaggagatgaccaa gaaccaggtcagcctgacctgcctggtcaaaggcttctatcccagcgacatcgccgtggagt gggagagcaatgggcagccggagaacaactacaagaccacgcctcccgtgctggactccgac ggctccttcttcctctacagcaagctcaccgtggacaagagcaggtggcagcaggggaacgt cttctcatgctccgtgatgcatgaggctctgcacaaccactacacgcagaagagcctctcc tgtctccgggtaaa
```

(amino acids) (SEQ ID NO: 291)

```
EPKSCDKTHTCPPCPAPELLGAPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK
```

Human IgG1 L234A/L235A FC sequence:
(DNA) (SEQ ID NO: 292)

```
gagcccaaatcttgtgacaaaactcacacatgcccaccgtgcccagcacctgaagccgcgg gggaccgtcagtcttcctcttccccccaaaacccaaggacaccctcatgatctcccggaccc ctgaggtcacatgcgtggtggtggacgtgagccacgaagaccctgaggtcaagttcaactgg tacgtggacggcgtggaggtgcataatgccaagacaaagccgcgggaggagcagtacaacag cacgtaccgtgtggtcagcgtcctcaccgtcctgcaccaggactggctgaatggcaaggagt acaagtgcaaggtctccaacaaagccctcccagcccccatcgagaaaaccatctccaaagcc aaagggcagccccgagaaccacaggtgtacaccctgcccccatcccgggaggagatgaccaa gaaccaggtcagcctgacctgcctggtcaaaggcttctatcccagcgacatcgccgtggagt gggagagcaatgggcagccggagaacaactacaagaccacgcctcccgtgctggactccgac ggctccttcttcctctacagcaagctcaccgtggacaagagcaggtggcagcaggggaacgt cttctcatgctccgtgatgcatgaggctctgcacaaccactacacgcagaagagcctctcc tgtctccgggtaaa
```

(amino acids) (SEQ ID NO: 293)

```
EPKSCDKTHTCPPCPAPEAAGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK
```

CAR-T E6 CD3z sequence:
(DNA) (SEQ ID NO: 294)

```
atggccctgcccgtgaccgctttgctgctcccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccgggggggcacttacatctattaccccga ctcagtcaaggggagatttaccatttcacgagacaacgctaagaataccctgtatttgcaga tgaattctctgagagcagaggacacagctgtttactattgtacccgcgcaactatggcagg aactacgactacggtatggactattggggacaagggacattggttacagtgagcagtggcgg cggggggcagcggaggaggaggcagcggtggggggggcagcagatagtgctcacgcagtcac ccgcgactctcagtctctcacctggggaacgagctaccctgacgtgctctgctacctcctca
```

-continued

```
gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttggagtgggaccaaggttgaaattaaaacgacaaccccggc ccccagaccaccaacgccagcccccaccatcgccagccaaccctgtctctgagaccagaag cctgtaggcctgccgccggtggagctgtgcacacaagaggactggatttcgcctgtgatatc tacatttgggccccgctcgcaggcacatgtggagtgctcctcctctccctggtgattaccct gtactgccgcgttaagttctcccgatcagccgacgcgcctgcttacaagcagggccagaacc aactgtacaacgagctgaatctcggtagacgggaagagtacgacgtgttggacaaacggaga ggccgcgacccagaaatgggcggcaagcctcgcaggaaaaaccccaggagggactgtacaa tgagttgcagaaagataagatggcagaagcttatagcgagatcggaatgaaggggaagga gacgagggaaaggacacgacggcctttatcagggcctgtccacagcaacaaaagatacgtat gacgccctccatatgcaggcacttccaccacggtgataa
```

(amino acids)

(SEQ ID NO: 295)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKTTTPAPRPPTPAPTIASQPLSLRPEACRPAAGGAVHTRGLDFACDI

YIWAPLAGTCGVLLLSLVITLYCRVKFSRSADAPAYKQGQNQLYNELNLGRREEYDVLDKRR

GRDPEMGGKPRRKNPQEGLYNELQKDKMAEAYSEIGMKGERRRGKGHDGLYQGLSTATKDTY

DALHMQALPPR**
**

CAR-T E6 CD3z gBLOCK sequence:
(DNA)

(SEQ ID NO: 296)

```
tggagctgtgcacacaagaggactggatttcgcctgtgatatctacatttgggccccgctcgcaggca catgtggagtgctcctcctctccctggtgattaccctgtactgccgcgttaagttctcccgatcagcc gacgcgcctgcttacaagcagggccagaaccaactgtacaacgagctgaatctcggtagacgggaaga gtacgacgtgttggacaaacggagaggccgcgacccagaaatgggcggcaagcctcgcaggaaaaacc cccaggagggactgtacaatgagttgcagaaagataagatggcagaagcttatagcgagatcggaatg aaggggaaggagacgagggaaaggacacgacggcctttatcagggcctgtccacagcaacaaaaga tacgtatgacgccctccatatgcaggcacttccaccacggtgataagtttaaacccgctgatcagcct cgactgtgc
```

CAR-T E6 CD28/CD3z sequence:
(DNA)

(SEQ ID NO: 297)

```
atggccctgccgtgaccgctttgctgctccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggcacttacatctattacccga ctcagtcaaggggagatttaccatttcacgagacaacgctaagaataccctgtatttgcaga tgaattctctgagagcagaggacacagctgtttactattgtacccgcgacaactatggcagg aactacgactacggtatggactattggggacaagggacattggttacagtgagcagtggcgg
```

-continued

```
cgggggcagcggaggaggaggcagcggtgggggggcagcgagatagtgctcacgcagtcac ccgcgactctcagtctctcacctggggaacgagctaccctgacgtgctctgctacctcctca gtgtcatatattcactggtatcagcaacggcccgggcagtccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttggggagtgggaccaaggttgaaattaaaacgacaaccccggc ccccagaccaccaacgccagccccaccatcgccagccaaccctgtctctgagaccagaag cctgtaggcctgccgccggtggagctgtgcacacaagaggactggatttcgcctgtgatatc tacatttgggccccgctcgcaggcacatgtggagtgctcctcctctccctggtgattaccct gtactgcagaagcaagcggtctcggctcctgcattctgattacatgaacatgaccccaagaa gaccaggccccaccaggaaacattaccagccctacgctccgccacgcgacttcgctgcctac cggtcccgcgttaagttctcccgatcagccgacgcgcctgcttacaagcagggccagaacca actgtacaacgagctgaatctcggtagacgggaagagtacgacgtgttggacaaacggagag gccgcgacccagaaatgggcggcaagcctcgcaggaaaaaccccaggagggactgtacaat gagttgcagaaagataagatggcagaagcttatagcgagatcggaatgaaggggggaaggag acgagggaaaggacacgacggcctttatcagggcctgtccacagcaacaaaagatacgtatg acgccctccatatgcaggcacttccaccacggtgataa
```

(amino acids)
(SEQ ID NO: 298)

```
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKTTTPAPRPPTPAPTIASQPLSLRPEACRPAAGGAVHTRGLDFACDI

YIWAPLAGTCGVLLLSLVITLYCRSKRSRLLHSDYMNMTPRRPGPTRKHYQPYAPPRDFAAY

RSRVKFSRSADAPAYKQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR**
```

CAR-T E6 CD28/CD3z g BLOCK sequence:
(DNA)
(SEQ ID NO: 299)

```
tggagctgtgcacacaagaggactggatttcgcctgtgatatctacatttgggccccgctcgcaggca catgtggagtgctcctcctctccctggtgattaccctgtactgcagaagcaagcggtctcggctcctg cattctgattacatgaacatgaccccaagaagaccaggccccaccaggaaacattaccagccctacgc tccgccacgcgacttcgctgcctaccggtcccgcgttaagttctcccgatcagccgacgcgcctgctt acaagcagggccagaaccaactgtacaacgagctgaatctcggtagacgggaagagtacgacgtgttg gacaaacggagaggccgcgacccagaaatgggcggcaagcctcgcaggaaaaaccccaggagggact gtacaatgagttgcagaaagataagatggcagaagcttatagcgagatcggaatgaaggggggaagga gacgagggaaaggacacgacggcctttatcagggcctgtccacagcaacaaaagatacgtatgacgcc ctccatatgcaggcacttccaccacggtgataagtttaaacccgctgatcagcctcgactgtgc
```

CAR-T E6 4-1BB/CD3z sequence:
(DNA)
(SEQ ID NO: 300)

```
atggccctgccgtgaccgctttgctgctcccctggcgctgctgctgcacgccgccaggcc agaggtccagctggttgagagtggcggtgggctggttaagcctggcggctccctgcggctga
```

-continued

```
gctgcgccgcgagtggatttactttcagccgatatgggatgagttgggtgcggcaagctccc gggaagaggctggaatgggtctcaacaatctccgggggggcacttacatctattaccccga ctcagtcaaggggagatttaccatttcacgagacaacgctaagaatacccgtatttgcaga tgaattctctgagagcagaggacacagctgtttactattgtacccgcgacaactatggcagg aactacgactacggtatggactattggggacaagggacattggttacagtgagcagtggcgg cgggggcagcggaggaggaggcagcggtggggggggcagcgagatagtgctcacgcagtcac ccgcgactctcagtctctcacctggggaacgagctaccctgacgtgctctgctacctcctca gtgtcatatattcactggtatcagcaacggcccgggcagtccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaaacgacaaccccggc ccccagaccaccaacgccagccccaccatcgccagccaaccccgtctctgagaccagaag cctgtaggcctgccgccggtggagctgtgcacacaagaggactggatttcgcctgtgatatc tacatttgggccccgctcgcaggcacatgtggagtgctcctcctctccctggtgattaccct gtactgcaaaaggggccgcaaaaaactcctttacatttttaagcagccttttatgaggccag tacagacgactcaagaggaagacgggtgctcatgccgctttcctgaggaggaggaaggaggg tgcgaactgcgcgttaagttctcccgatcagccgacgcgcctgcttacaagcagggccagaa ccaactgtacaacgagctgaatctcggtagacgggaagagtacgacgtgttggacaaacgga gaggccgcgacccagaaatgggcggcaagcctcgcaggaaaaaccccaggagggactgtac aatgagttgcagaaagataagatggcagaagcttatagcgagatcggaatgaaggggaaag gagacgagggaaaggacacgacggcctttatcagggcctgtccacagcaacaaaagatacgt atgacgccctccatatgcaggcacttccaccacggtgataa
```

(amino acids)

(SEQ ID NO: 301)
MALPVTALLLLPLALLLHAARPEVQLVESGGGLVKPGGSLRLSCAASGFTFSRYGMSWVRQAPGKRLEW

VSTISGGGTYIYYPDSVKGRFTISRDNAKNTLYLQMNSLRAEDTAVYYCTRDNYGRNYDYGMDYWGQG

TLVTVSSGGGGSGGGGSGGGGSEIVLTQSPATLSLSPGERATLTCSATSSVSYIHWYQQRPGQSPRLL

IYSTSNLASGIPARFSGSGSGSDYTLTISSLEPEDFAVYYCQQRSSSPFTFGSGTKVEIKTTTPAPRP ptpaptiasqplslrpeacrpaaggavhtrgldfacdiyiwaplagtcgvlllslvitlyckrgrkkl

LYIFKQPFMRPVQTTQEEDGCSCRFPEEEEGGCELRVKFSRSADAPAYKQGQNQLYNELNLGRREEYD

VLDKRRGRDPEMGGKPRRKNPQEGLYNELQKDKMAEAYSEIGMKGERRRGKGHDGLYQGLSTATKDTY

DALHMQALPPR**

CAR-T E6 4-1BB/CD3Z gBLOCK sequence:
(DNA)

(SEQ ID NO: 302)
```
tggagctgtgcacacaagaggactggatttcgcctgtgatatctacatttgggccccgctcgcaggca catgtggagtgctcctcctctccctggtgattaccctgtactgcaaaaggggccgcaaaaaactcctt tacattttaagcagccttttatgaggccagtacagacgactcaagaggaagacgggtgctcatgccg ctttcctgaggaggaggaaggagggtgcgaactgcgcgttaagttctcccgatcagccgacgcgcctg cttacaagcagggccagaaccaactgtacaacgagctgaatctcggtagacgggaagagtacgacgtg ttggacaaacggagaggccgcgacccagaaatgggcggcaagcctcgcaggaaaaaccccaggaggg actgtacaatgagttgcagaaagataagatggcagaagcttatagcgagatcggaatgaagggggaaa
```

-continued ggagacgagggaaaggacacgacggcctttatcagggcctgtccacagcaacaaaagatacgtatgac gccctccatatgcaggcacttccaccacggtgataagtttaaacccgctgatcagcctcgactgtgc CAR-T E6 CD28/4-1BB/CD3z sequence:
(DNA)

(SEQ ID NO: 303)

atggccctgccgtgaccgctttgctgctcccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacccctgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtggggggggcagcgagatagtgctcacgcagtcac ccgcgactctcagtctctcacctggggaacgagctaccctgacgtgctctgctacctcctca gtgtcatatattcactggtatcagcaacggcccgggcagtccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaaacgacaaccccggc ccccagaccaccaacgccagcccccaccatcgccagccaacccctgtctctgagaccagaag cctgtaggcctgccgcggtggagctgtgcacacaagaggactggatttcgcctgtgatatc tacatttgggccccgctcgcaggcacatgtggagtgctcctcctctccctggtgattaccct gtactgcagaagcaagcggtctcggctcctgcattctgattacatgaacatgaccccaagaa gaccaggcccccaccaggaaacattaccagccctacgctccgccacgcgacttcgctgcctac cggtccaaaaggggccgcaaaaaactccttttacattttaagcagccttttatgaggccagt acagacgactcaagaggaagacgggtgctcatgccgctttcctgaggaggaggaaggagggt gcgaactgcgcgttaagttctcccgatcagccgacgcgcctgcttacaagcagggccagaac caactgtacaacgagctgaatctcggtagacgggaagagtacgacgtgttggacaaacggag aggccgcgacccagaaatgggcggcaagcctcgcaggaaaaaccccccaggagggactgtaca atgagttgcagaaagataagatggcagaagcttatagcgagatcggaatgaagggggaaagg agacgagggaaaggacacgacggcctttatcagggcctgtccacagcaacaaaagatacgta tgacgccctccatatgcaggcacttccaccacggtgataa (amino acids)

(SEQ ID NO: 304)

MALPVTALLLPLALLLHAARPEVQLVESGGGLVKPGGSLRLSCAASGFTFSRYGMSWVRQAPGKRLEW

VSTISGGGTYIYYPDSVKGRFTISRDNAKNTLYLQMNSLRAEDTAVYYCTRDNYGRNYDYGMDYWGQG

TLVTVSSGGGGSGGGGSGGGGSEIVLTQSPATLSLSPGERATLTCSATSSVSYIHWYQQRPGQSPRLL

IYSTSNLASGIPARFSGSGSGSDYTLTISSLEPEDFAVYYCQQRSSSPFTFGSGTKVEIKTTTPAPRP

PTPAPTIASQPLSLRPEACRPAAGGAVHTRGLDFACDIYIWAPLAGTCGVLLLSLVITLYCRSKRSRL

LHSDYMNMTPRRPGPTRKHYQPYAPPRDFAAYRSKRGRKKLLYIFKQPFMRPVQTTQEEDGCSCRFPE

EEEGGCELRVKFSRSADAPAYKQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR**

CAR-T E6 CD28/4-1BB/CD3z gBLOCK sequence:
(DNA)

(SEQ ID NO: 305)
ataggggagacccaagctggctagttaagcttggtaccgagggccaccatgggccctgcccgtg accgctttgctgctcccctggcgctgctgctgcacgccgccaggccagaggtccagctggt tgagagtggcggtgggctggttaagcctggcggctccctgcggctgagctgcgccgcgagtg gatttactttcagccgatatgggatgagttgggtgcggcaagctcccgggaagaggctggaa tgggtctcaacaatctccggggggggcacttacatctattaccccgactcagtcaaggggag atttaccatttcacgagacaacgctaagaatacccctgtatttgcagatgaattctctgagag cagaggacacagctgtttactattgtacccgcgacaactatggcaggaactacgactacggt atggactattggggacaagggacattggttacagtgagcagtggcggcggggcagcggagg aggaggcagcggtggggggcagcgagatagtgctcacgcagtcacccgcgactctcagtc tctcacctggggaacgagctaccctgacgtgctctgctacctcctcagtgtcatatattcac tggtatcagcaacggcccgggcagtcccctagattgctcatttatagtacctctaatctggc ctcaggtatccctgcacgattttctggatctggttcaggttctgattacaccctcactatct ctagcctggagcctgaagactttgccgtttattactgccagcagaggtctagctccccattc acctttgggagtgggaccaaggttgaaattaaaacgacaaccccggccccccagaccaccaac gccagccccaccatcgccagccaaccctgtctctgagaccagaagcctgtaggcctgccg ccggtggagctgtgcacacaagaggactggattcgcctgtgatatctacatttgggccccg ctcgcaggcacatgtggagtgctcctcctctccctggtgattaccctgtactgcagaagcaa gcggtctcggctcctgcattctgattacatgaacatgaccccaagaagaccaggccccacca ggaaacattaccagccctacgctccgccacgcgacttcgctgcctaccggtccaaaaggggc cgcaaaaaactcctttacatttttaagcagcctttttatgaggccagtacagacgactcaaga ggaagacggtgctcatgccgctttcctgaggaggaggaaggagggtgcgaactgcgcgtta agttctcccgatcagccgacgcgcctgcttacaagcagggccagaaccaactgtacaacgag ctgaatctcggtagacgggaagagtacgacgtgttggacaaacggagaggccgcgacccaga aatgggcggcaagcctcgcaggaaaaaccccaggagggactgtacaatgagttgcagaaag ataagatggcagaagcttatagcgagatcggaatgaaggggaagggagacgagggaagga cacgacggcctttatcagggcctgtccacagcaacaaaagatacgtatgacgccctccatat gcaggcacttccaccacggtgataagtttaaacccgctgatcagcctcgactgtgc CAR-T C2 CD28/4-1BB/CD3z sequence:
(DNA)

(SEQ ID NO: 306)
atggccttgccagtgacggccctgctgctgccattggctcttctgttgcacgctgccaggcctgaagt gcagctcgtagagagtggcggggggactggtgaagcccggtggaagcctcagactcagttgcgccgcct caggtttcacttttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtggggaaagggact accgtgacagttttcaagcggaggaggtggctcaggtggaggcgggtcagggggggaggaagtgatat tgtgctcacacaatccccagcctcccctggctgtgtctcccggccaacgcgctacaattacatgtcggg cctccaaaagcgtgagcaccagcggctacagctacatgcactggtatcaacagaaaccaggacaaccc cccaaactgttgatttatctcgcttcaaacttggagtccggcgtgcctgcgcgcttttcagggagtgg -continued

```
gagcggcacagattttacgctgactatcaaccccgtagaagcaaacgatacagcgaattattattgtc aacattcccgggaactccccttacgttcggcggggggcacaaaggtcgaaattaagagaaccacgaca accccggccccagaccaccaacgccagccccaccatcgccagccaaccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgcaga agcaagcggtctcggctcctgcattctgattacatgaacatgaccccaagaagaccaggcccaccag gaaacattaccagccctacgctccgccacgcgacttcgctgcctaccggtccaaaaggggccgcaaaa aactcctttacatttttaagcagccttttatgaggccagtacagacgactcaagaggaagacgggtgc tcatgccgctttcctgaggaggaggaaggagggtgcgaactgcgcgttaagttctcccgatcagccga cgcgcctgcttacaagcagggccagaaccaactgtacaacgagctgaatctcggtagacgggaagagt acgacgtgttggacaaacggagaggccgcgacccagaaatgggcggcaagcctcgcaggaaaaacccc caggagggactgtacaatgagttgcagaaagataagatggcagaagcttatagcgagatcggaatgaa gggggaaaggagacgagggaaggacacgacggcctttatcagggcctgtccacagcaacaaaagata cgtatgacgccctccatatgcaggcacttccaccacggtgataa
```

(amino acids)

(SEQ ID NO: 307)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYFDVWGKGTTVTVSSGGGGSGGGGSGGGGS

DIVLTQSPASLAVSPGQRATITCRASKSVSTSGYSYMHWYQQKPGQPPKLLIYLASNLESGVPARFSG

SGSGTDFTLTINPVEANDTANYYCQHSRELPFTFGGGTKVEIKRTTTTPAPRPPTPAPTIASQPLSLR

PEACRPAAGGAVHTRGLDFACDIYIWAPLAGTCGVLLLSLVITLYCRSKRSRLLHSDYMNMTPRRPGP

TRKHYQPYAPPRDFAAYRSKRGRKKLLYIFKQPFMRPVQTTQEEDGCSCRFPEEEEGGCELRVKFSRS

ADAPAYKQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR**

CAR-T C2-1 gBLOCK sequence:
(DNA)

(SEQ ID NO: 308)
```
atagggagacccaagctggctagttaagcttggtaccgagggccaccatggccttgccagtgacggcc ctgctgctgccattggctcttctgttgcacgctgccaggcctgaagtgcagctcgtagagagtggcgg gggactggtgaagcccgtggaagcctcagactcagttgcgccgcctcaggtttcacttttcaggtt acgccatgtcctgggtaagacaggcaccggggaaaggactcgagtgggtgtctactatcagctcagga ggcacttatatatattatcctgactctgtaaaaggccgatttacgatttctcgcgacaatgcaaagaa ctccctctacctccaaatgaacagtcttagggcagaagacactgctgtatactattgtgcacgcctcg gcggcgacaactactacgagtactttgacgtgtggggaaagggactaccgtgacagtttcaagcgga ggaggtggctcaggtggaggcgggtcagggggggaggaagtgatattgtgctcacacaatccccagc ctccctggc
```

CAR-T C2-2 gBLOCK sequence:
(DNA)

(SEQ ID NO: 309)
```
aagtgatattgtgctcacacaatccccagcctccctggctgtgtctcccggccaacgcgctacaatta catgtcgggcctccaaaagcgtgagcaccagcggctacagctacatgcactggtatcaacagaaacca ggacaaccccccaaactgttgatttatctcgcttcaaactggagtccggcgtgcctgcgcgcttttc agggagtgggagcggcacagattttacgctgactatcaaccccgtagaagcaaacgatacagcgaatt attattgtcaacattcccgggaactccccttacgttcggcggggcacaaaggtcgaaattaagaga accacgacaaccccggccccagaccaccaacgccagccccaccatcgccagccaaccctgtctct
```

-continued gagaccagaagcctgtaggcctgccgccggtggagctgtgcacacaagaggactggatttcgcctgtg atatctacatttgggccccgctcgcaggcacatgtggagtgc CAR E6 Fc/8/4-1BB/CD3z sequence:
(DNA)
(SEQ ID NO: 310)
atggccctgccgtgaccgctttgctgctcccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacctgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaagagcccaaatcttg tgacaaaactcacacatgcccaccgtgcccagcacctgaactcctggggggaccgtcagtct tcctcttccccccaaaacccaaggacaccctcatgatctcccggacccctgaggtcacatgc gtggtggtggacgtgagccacgaagaccctgaggtcaagttcaactggtacgtggacggcgt ggaggtgcataatgccaagacaaagccgcgggaggagcagtacaacagcacgtaccgtgtgg tcagcgtcctcaccgtcctgcaccaggactggctgaatggcaaggagtacaagtgcaaggtc tccaacaaagccctcccagcccccatcgagaaaaccatctccaaagccaaagggcagccccg agaaccacaggtgtacaccctgcccccatcccgggaggagatgaccaagaaccaggtcagcc tgacctgcctggtcaaaggcttctatcccagcgacatcgccgtggagtgggagagcaatggg cagccggagaacaactacaagaccacgcctcccgtgctggactccgacggctccttcttcct ctacagcaagctcaccgtggacaagagcaggtggcagcaggggaacgtcttctcatgctccg tgatgcatgaggctctgcacaaccactacacgcagaagagcctctccctgtctccgggtaaa atctacatttgggccccgctcgcaggcacatgtggagtgctcctcctctccctggtgattac cctgtactgcaaaaggggccgcaaaaaactcctttacattttaagcagccttttatgaggc cagtacagacgactcaagaggaagacgggtgctcatgccgctttcctgaggaggaggaagga gggtgcgaactgcgcgttaagttctcccgatcagccgacgcgcctgcttacaagcagggcca gaaccaactgtacaacgagctgaatctcggtagacgggaagagtacgacgtgttggacaaac ggagaggccgcgacccagaaatgggcggcaagcctcgcaggaaaaaccccaggagggactg tacaatgagttgcagaaagataagatggcagaagcttatagcgagatcggaatgaaggggga aaggagacgagggaaaggacacgacggcctttatcagggcctgtccacagcaacaaaagata cgtatgacgccctccatatgcaggcacttccaccacggtgataa (amino acids)
(SEQ ID NO: 311)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

-continued

VSYIHWYQQRPGQSPRLLIYSTSNLASGIPARFSGSGSGSDYTLTISSLEPEDFAVYYCQQR
SSSPFTFGSGTKVEIKEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWESNG
QPENNYKTTPPVLDSDGSFFLYSKLTVDKSRWQQGNVFSCSVMHEALHNHYTQKSLSLSPGK
IYIWAPLAGTCGVLLLSLVITLYCKRGRKKLLYIFKQPFMRPVQTTQEEDGCSCRFPEEEEG
GCELRVKFSRSADAPAYKQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR**

E6 CAR pCDH gBLOCK sequence:
(DNA)

(SEQ ID NO: 312)

acgctgttttgacctccatagaagattctagagctagctgtagagcttggtaccgagggcca
ccatggccctgcccgtgaccgctttgctgctccccctggcgctgctgctgcacgccgccagg
ccagaggtccagctggttgagagtggcggtgggctggttaagcctggcggctccctgcggct
gagctgcgccgcgagtggatttactttcagccgatatgggatgagttgggtgcggcaagctc
ccgggaagaggctggaatgggtctcaacaatctccgggggggcacttacatctattacccc
gactcagtcaaggggagatttaccatttcacgagacaacgctaagaataccctgtatttgca
gatgaattctctgagagcagaggacacagctgtttactattgtacccgcgacaactatggca
ggaactacgactacggtatggactattggggacaagggacattggttacagtgagcagtggc
ggcggggcagcggaggaggaggcagcggtggcggaggcagcgagatagtgctcacgcagtc
acccgcgactctcagtctctcacctggggaacgagctaccctgacgtgctctgctacctcct
cagtgtcatatattcactggtatcagcaacggcccgggcagtcccctagattgctcatttat
agtacctctaatctggcctcaggtatccctgc E6 CAR Fc pCDH gBLOCK sequence:
(DNA)

(SEQ ID NO: 313)

agtacctctaatctggcctcaggtatccctgcacgattttctggatctggttcaggttctga
ttacacccctcactatctctagcctggagcctgaagactttgccgtttattactgccagcaga
ggtctagctccccattcacctttgggagtgggaccaaggttgaaattaaagagcccaaatct
tgtgacaaaactcacacatgcccaccgtgcccagcacctgaactcctggggggaccgtcagt
cttcctcttccccccaaaacccaaggacaccctcatgatctcccggacccctgaggtcacat
gcgtggtggtggacgtgagccacgaagaccctgaggtcaagttcaactggtacgtggacggc
gtggaggtgcataatgccaagacaaagccgcgggaggagcagtacaacagcacgtaccgtgt
ggtcagcgtcctcaccgtcctgcaccaggactggctgaatggcaaggagtacaagtgcaagg
tctccaacaaagccctcccagccccatcgagaaaaccatctccaaagccaaagggcagccc
cgagaaccacaggtgtacaccctgcccccatcccgggaggagatgaccaagaaccaggtcag
cctgacctgcctggtcaaaggcttctatcccagcgacatcgccgtggagtgggagagcaatg
ggcagccggagaacaactacaagaccacgcctcccgtgctg E6 CAR 8BB3 pCDH gBLOCK sequence:
(DNA)

(SEQ ID NO: 314)

agaacaactacaagaccacgcctcccgtgctggactccgacggctccttcttcctctacagc
aagctcaccgtggacaagagcaggtggcagcaggggaacgtcttctcatgctccgtgatgca
tgaggctctgcacaaccactacacgcagaagagcctctccctgtctccgggtaaaatctaca
tttgggccccgctcgcaggcacatgtggagtgctcctcctctcccctggtgattaccctgtac

```
tgcaaaagggccgcaaaaaactcctttacattttaagcagccttttatgaggccagtaca gacgactcaagaggaagacgggtgctcatgccgcttcctgaggaggaggaaggagggtgcg aactgcgcgttaagttctcccgatcagccgacgcgcctgcttacaagcagggccagaaccaa ctgtacaacgagctgaatctcggtagacgggaagagtacgacgtgttggacaaacggagagg ccgcgacccagaaatgggcggcaagcctcgcaggaaaaaccccaggagggactgtacaatg agttgcagaaagataagatggcagaagcttatagcgagatcggaatgaaggggggaaggaga cgagggaaggacacgacggccttttatcagggcctgtccacagcaacaaaagatacgtatga cgccctccatatgcaggcacttccaccacggtgataagtttaaacccgctgatcaggcggcc gcgaaggatctgcgatcgctccggtgcccgtcag
```

CAR E6 FcH/8/4-1BB/CD3z sequence:
(DNA)

(SEQ ID NO: 315)

```
atggccctgcccgtgaccgctttgctgctcccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagattaccattcacgagacaacgctaagaataccctgtattcgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttata tacctctaatctggcctcaggtatccctgcacgattttctggatctggttcaggttctgatt acaccctcactatctctagcctggagcctgaagactttgccgtttattactgccagcagagg tctagctcccccattcacctttgggagtgggaccaaggttgaaattaaagcacctgaactcct gggggaccgtcagtcttcctcttccccccaaaacccaaggacaccctcatgatctcccgga cccctgaggtcacatgcgtggtggtggacgtgagccacgaagaccctgaggtcaagttcaac tggtacgtggacggcgtggaggtgcataatgccaagacaaagccgcgggaggagcagtacaa cagcacgtaccgtgtggtcagcgtcctcaccgtcctgcaccaggactggctgaatggcaagg agtacaagtgcaaggtctccaacaaagcccctcccagcccccatcgagaaaaccatctccaaa gccaaagggcagccccgagaaccacaggtgtacaccctgcccccatcccgggaggagatgac caagaaccaggtcagcctgacctgcctggtcaaaggcttctatcccagcgacatcgccgtgg agtgggagagcaatgggcagccggagaacaactacaagaccacgcctcccgtgctggactcc gacggctccttcttcctctacagcaagctcaccgtggacaagagcaggtggcagcagggaa cgtcttctcatgctccgtgatgcatgaggctctgcacaaccactacacgcagaagagcctct ccctgtctccgggtaaaatctacatttgggccccgctcgcaggcacatgtgagtgctcctc ctctcccctggtgattaccctgtactgcaaaagggggccgcaaaaaactccttacattttaa gcagccttttatgaggccagtacagacgactcaagaggaagacgggtgctcatgccgctttc ctgaggaggaggaaggagggtgcgaactgcgcgttaagttctcccgatcagccgacgcgcct gcttacaagcagggccagaaccaactgtacaacgagctgaatctcggtagacgggaagagta cgacgtgttggacaaacggagaggccgcgacccagaaatgggcggcaagcctcgcaggaaaa accccaggagggactgtacaatgagttgcagaaagataagatggcagaagcttatagcgag
```

-continued

```
atcggaatgaaggggggaaaggagacgagggaaaggacacgacggcctttatcagggcctgtc cacagcaacaaaagatacgtatgacgccctccatatgcaggcacttccaccacggtgataa
```

(amino acids)
(SEQ ID NO: 316)

```
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGKIYIWAPLAGTCGVLL

LSLVITLYCKRGRKKLLYIFKQPFMRPVQTTQEEDGCSCRFPEEEEGGCELRVKFSRSADAP

AYKQGQNQLYNELNLGRREEYDVLDKRRGRDPEMGGKPRRKNPQEGLYNELQKDKMAEAYSE

IGMKGERRRGKGHDGLYQGLSTATKDTYDALHMQALPPR**
```

E6 CAR FcH pCDH gBLOCK sequence:
(DNA)
(SEQ ID NO: 317)

```
agtacctctaatctggcctcaggtatccctgcacgattttctggatctggttcaggttctga ttacaccctcactatctctagcctggagcctgaagactttgccgtttattactgccagcaga ggtctagctccccattcacctttggagtgggaccaaggttgaaattaaagcacctgaactc ctgggggaccgtcagtcttcctcttccccccaaaacccaaggacaccctcatgatctcccg gacccctgaggtcacatgcgtggtggtggacgtgagccacgaagaccctgaggtcaagttca actggtacgtggacggcgtggaggtgcataatgccaagacaaagccgcgggaggagcagtac aacagcacgtaccgtgtggtcagcgtcctcaccgtcctgcaccaggactggctgaatggcaa ggagtacaagtgcaaggtctccaacaaagccctcccagcccccatcgagaaaaccatctcca aagccaaagggcagccccgagaaccacaggtgtacaccctgcccccatcccgggaggagatg accaagaaccaggtcagcctgacctgcctggtcaaaggcttctatcccagcgacatcgccgt ggagtgggagagcaatgggcagccggagaacaactacaagaccacgcctcccgtgctg
```

CAR E6 Fc/4/4-1BB/CD3z sequence:
(DNA)
(SEQ ID NO: 318)

```
atggccctgcccgtgaccgctttgctgctccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaataccctgtatttgcaga tgaattctctgagagcagaggacacagctgtttactattgtacccgcgacaactatggcagg aactacgactacggtatggactattggggacaagggacattggttacagtgagcagtggcgg cggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacgcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg
```

-continued

```
tctagctccccattcacctttgggagtgggaccaaggttgaaattaaagagcccaaatcttg tgacaaaactcacacatgcccaccgtgcccagcacctgaactcctggggggaccgtcagtct tcctcttcccccaaaacccaaggacaccctcatgatctcccggacccctgaggtcacatgc gtggtggtggacgtgagccacgaagaccctgaggtcaagttcaactggtacgtggacggcgt ggaggtgcataatgccaagacaaagccgcgggaggagcagtacaacagcacgtaccgtgtgg tcagcgtcctcaccgtcctgcaccaggactggctgaatggcaaggagtacaagtgcaaggtc tccaacaaagcccctcccagcccccatcgagaaaaccatctccaaagccaaagggcagccccg agaaccacaggtgtacaccctgcccccatcccgggaggagatgaccaagaaccaggtcagcc tgacctgcctggtcaaaggcttctatcccagcgacatcgccgtggagtgggagagcaatggg cagccggagaacaactacaagaccacgcctcccgtgctggactccgacggctccttcttcct ctacagcaagctcaccgtggacaagagcaggtggcagcaggggaacgtcttctcatgctccg tgatgcatgaggctctgcacaaccactacacgcagaagagcctctccctgtctccgggtaaa atgggccctgattgtgctggggggcgtcgccggcctcctgcttttcattgggctaggcatctt cttcaaaaggggccgcaaaaaactcctttacattttttaagcagccttttatgaggccagtac agacgactcaagaggaagacgggtgctcatgccgctttcctgaggaggaggaaggagggtgc gaactgcgcgttaagttctcccgatcagccgacgcgcctgcttacaagcagggccagaacca actgtacaacgagctgaatctcggtagacgggaagagtacgacgtgttggacaaacggagag gccgcgacccagaaatgggcggcaagcctcgcaggaaaaaccccaggagggactgtacaat gagttgcagaaagataagatggcagaagcttatagcgagatcggaatgaaggggggaaggag acgagggaaggacacgacggcctttatcagggcctgtccacagcaacaaaagatacgtatg acgccctccatatgcaggcacttccaccacggtgataa
```

(amino acids)

(SEQ ID NO: 319)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQDWLNGKEYKCKV

SNKALPAPIEKTISKAKGQPREPQVYTLPPSREEMTKNQVSLTCLVKGFYPSDIAVEWESNG

QPENNYKTTPPVLDSDGSFFLYSKLTVDKSRWQQGNVFSCSVMHEALHNHYTQKSLSLSPGK

MALIVLGGVAGLLLFIGLGIFFKRGRKKLLYIFKQPFMRPVQTTQEEDGCSCRFPEEEEGGC

ELRVKFSRSADAPAYKQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALPPR**

E6 CAR 44BB3 pCDH gBLOCK sequence:
(DNA)

(SEQ ID NO: 320)

```
agaacaactacaagaccacgcctcccgtgctggactccgacggctccttcttcctctacagc aagctcaccgtggacaagagcaggtggcagcaggggaacgtcttctcatgctccgtgatgca tgaggctctgcacaaccactacacgcagaagagcctctccctgtctccgggtaaaatggccc tgattgtgctggggggcgtcgccggcctcctgcttttcattgggctaggcatcttcttcaaa aggggccgcaaaaaactcctttacattttttaagcagccttttatgaggccagtacagacgac tcaagaggaagacgggtgctcatgccgctttcctgaggaggaggaaggagggtgcgaactgc
```

-continued gcgttaagttctcccgatcagccgacgcgcctgcttacaagcagggccagaaccaactgtac aacgagctgaatctcggtagacgggaagagtacgacgtgttggacaaacggagaggccgcga cccagaaatgggcggcaagcctcgcaggaaaaaccccaggagggactgtacaatgagttgc agaaagataagatggcagaagcttatagcgagatcggaatgaaggggaaaggagacgaggg aaaggacacgacggcctttatcagggcctgtccacagcaacaaaagatacgtatgacgccct ccatatgcaggcacttccaccacggtgataagtttaaacccgctgatcaggcggccgcgaag gatctgcgatcgctccggtgcccgtcag CAR E6 FcH/4/4-1BB/CD3z sequence:
(DNA)

(SEQ ID NO: 321)

atggccctgccgtgaccgctttgctgctcccccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattacccga ctcagtcaaggggagatttaccatttcacgagacaacgctaagaatacc ctgtatttgcaga tgaattctctgagagcagaggacacagctgtttactattgtacccgcgacaactatggcagg aactacgactacggtatggactattggggacaagggacattggttacagtgagcagtggcgg cgggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acacccctcactatctctagcctggagcctgaagactttgccgttattactgccagcagagg tctagctccccattcacctttgggagtgggaccaaggttgaaattaaagcacctgaactcct gggggggaccgtcagtcttcctcttccccccaaaacccaaggacaccctcatgatctcccgga cccctgaggtcacatgcgtggtggtggacgtgagccacgaagaccctgaggtcaagttcaac tggtacgtggacggcgtggaggtgcataatgccaagacaaagccgcgggaggagcagtacaa cagcacgtaccgtgtggtcagcgtcctcaccgtcctgcaccaggactggctgaatggcaagg agtacaagtgcaaggtctccaacaaagcccctcccagcccccatcgagaaaaccatctccaaa gccaaagggcagccccgagaaccacaggtgtacaccctgcccccatcccgggaggagatgac caagaaccaggtcagcctgacctgcctggtcaaaggcttctatcccagcgacatcgccgtgg agtgggagagcaatgggcagccggagaacaactacaagaccacgcctcccgtgctggactcc gacggctccttcttcctctacagcaagctcaccgtggacaagagcaggtggcagcaggggaa cgtcttctcatgctccgtgatgcatgaggctctgcacaaccactacacgcagaagagcctct ccctgtctccgggtaaaatggccctgattgtgctggggggcgtcgccggcctcctgctttc attgggctaggcatcttcttcaaaaggggccgcaaaaaactccttttacatttttaagcagcc ttttatgaggccagtacagacgactcaagaggaagacgggtgctcatgccgctttcctgagg aggaggaaggagggtgcgaactgcgcgttaagttctcccgatcagccgacgcgcctgcttac aagcagggccagaaccaactgtacaacgagctgaatctcggtagacgggaagagtacgacgt gttggacaaacggagaggccgcgacccagaaatgggcggcaagcctcgcaggaaaaaccccc aggagggactgtacaatgagttgcagaaagataagatggcagaagcttatagcgagatcgga atgaaggggaaaggagacgagggaaaggacacgacggcctttatcagggcctgtccacagc aacaaaagatacgtatgacgccctccatatgcaggcacttccaccacggtgataa -continued (amino acids)

(SEQ ID NO: 322)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGKMALIVLGGVAGLLLF

IGLGIFFKRGRKKLLYIFKQPFMRPVQTTQEEDGCSCRFPEEEEGGCELRVKFSRSADAPAY

KQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR**

CAR E6 IgD/8/4-1BB/CD3z sequence:
(DNA)

(SEQ ID NO: 323)

atggccctgccgtgaccgctttgctgctccccctggcgctgctgctgcacgccgcaggccagaggt
ccagctggttgagagtggcggtgggctggttaagcctggcggctccctgcggctgagctgcgccgcga
gtggatttactttcagccgatatgggatgagttgggtgcggcaagctcccgggaagaggctggaatgg
gtctcaacaatctccggggggggcacttacatctattaccccgactcagtcaaggggagatttaccat
ttcacgagacaacgctaagaatacctgtatttgcagatgaattctctgagagcagaggacacagctg
tttactattgtacccgcgacaactatggcaggaactacgactacggtatggactattggggacaaggg
acattggttacagtgagcagtggcggcggggcagcggaggaggaggcagcggtggcggaggcagcga
gatagtgctcacgcagtcacccgcgactctcagtctctcacctggggaacgagctaccctgacgtgct
ctgctacctcctcagtgtcatatattcactggtatcagcaacggcccggcagtcccctagattgctc
atttatagtacctctaatctggcctcaggtatccctgcacgattttctggatctggttcaggttctga
ttacacccctcactatctctagcctggagcctgaagactttgccgtttattactgccagcagaggtcta
gctcccattcacctttgggagtgggaccaaggttgaaattaaagagtctccaaaggcacaggcctcc
tcagtgcccactgcacaaccccaagcagagggcagcctcgccaaggcaaccacagcccagccaccac
ccgtaacacaggaagaggcggcaagagaagaaaaaggagaaggagaaagaggaacaagaagagagag
agacaaagacaccaatctacatttgggccccgctcgcaggcacatgtggagtgctcctcctctccctg
gtgattaccctgtactgcaaaaggggccgcaaaaaactcctttacattttaagcagccttttatgag
gccagtacagacgactcaagaggaagacgggtgctcatgccgctttcctgaggaggaggaaggagggt
gcgaactgcgcgttaagttctcccgatcagccgacgcgcctgcttacaagcagggccagaaccaactg
tacaacgagctgaatctcggtagacgggaagagtacgacgtgttggacaaacggagaggccgcgaccc
agaaatgggcggcaagcctcgcaggaaaaaccccaggagggactgtacaatgagttgcagaaagata
agatggcagaagcttatagcgagatcggaatgaaggggaaaggagacgagggaaaggacacgacggc
ctttatcagggcctgtccacagcaacaaaagatacgtatgacgccctccatatgcaggcacttccacc
acggtgataa (amino acids)

(SEQ ID NO: 324)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

-continued

VSYIHWYQQRPGQSPRLLIYSTSNLASGIPARFSGSGSGSDYTLTISSLEPEDFAVYYCQQR

SSSPFTFGSGTKVEIKESPKAQASSVPTAQPQAEGSLAKATTAPATTRNTGRGGEEKKKEKE

KEEQEERETKTPIYIWAPLAGTCGVLLLSLVITLYCKRGRKKLLYIFKQPFMRPVQTTQEED

GCSCRFPEEEEGGCELRVKFSRSADAPAYKQGQNQLYNELNLGRREEYDVLDKRRGRDPEMG

GKPRRKNPQEGLYNELQKDKMAEAYSEIGMKGERRRGKGHDGLYQGLSTATKDTYDALHMQA

LPPR**

E6 CAR IgD8 pcDH gBLOCK sequence:
(DNA)

(SEQ ID NO: 325)

agtacctctaatctggcctcaggtatccctgcacgattttctggatctggttcaggttctga ttacaccctcactatctctagcctggagcctgaagactttgccgtttattactgccagcaga ggtctagctccccattcacctttgggagtgggaccaaggttgaaattaaagagtctccaaag gcacaggcctcctcagtgcccactgcacaaccccaagcagagggcagcctcgccaaggcaac cacagccccagccaccacccgtaacacaggaagaggcggcgaagagaagaaaaaggagaagg agaaagaggaacaagaagagagagagacaaagacaccaatctacatttgggccccgctcgca ggcacatgtggagtgctcctcctctccctggtgattaccctgtactgcaaaaggggccgcaa aaaactcctttacattttttaagcagccttttatgaggccag E6 CAR BB 3 pCDH gBLOCK sequence:
(DNA)

(SEQ ID NO: 326)

acatttttaagcagccttttatgaggccagtacagacgactcaagaggaagacgggtgctca tgccgctttcctgaggaggaggaaggagggtgcgaactgcgcgttaagttctcccgatcagc cgacgcgcctgcttacaagcagggccagaaccaactgtacaacgagctgaatctcggtagac gggaagagtacgacgtgttggacaaacgagaggccgcgacccagaaatgggcggcaagcct cgcaggaaaaaccccaggagggactgtacaatgagttgcagaaagataagatggcagaagc ttatagcgagatcggaatgaaggggaaaggagacgagggaaaggacacgacggcctttatc agggcctgtccacagcaacaaaagatacgtatgacgccctccatatgcaggcacttccacca cggtgataagtttaaacccgctgatcaggcggccgcgaaggatctgcgatcgctccggtgcc cgtcag CAR E6 IgD/4/4-1BB/CD3z sequence:
(DNA)

(SEQ ID NO: 327)

atggccctgcccgtgaccgctttgctgctccccctggcgctgctgctgcacgccgccaggcc agaggtccagctggttgagagtggcggtgggctggttaagcctggcggctccctgcggctga gctgcgccgcgagtggatttacttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacctgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacgccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaagagtctccaaaggc -continued acaggcctcctcagtgcccactgcacaaccccaagcagagggcagcctcgccaaggcaacca cagccccagccaccacccgtaacacaggaagaggcggcgaagagaagaaaaaggagaaggag aaagaggaacaagaagagagagagacaaagacaccaatggccctgattgtgctgggggcgt cgccggcctcctgcttttcattgggctaggcatcttcttcaaaaggggccgcaaaaaactcc tttacattttttaagcagccttttatgaggccagtacagacgactcaagaggaagacgggtgc tcatgccgctttcctgaggaggaggaaggagggtgcgaactgcgcgttaagttctcccgatc agccgacgcgcctgcttacaagcagggccagaaccaactgtacaacgagctgaatctcggta gacgggaagagtacgacgtgttggacaaacgagaggccgcgacccagaaatgggcggcaag cctcgcaggaaaaaccccaggagggactgtacaatgagttgcagaaagataagatggcaga agcttatagcgagatcggaatgaaggggggaaggagacgagggaaaggacacgacggccttt atcagggcctgtccacagcaacaaaagatacgtatgacgccctccatatgcaggcacttcca ccacggtgataa (amino acids)

(SEQ ID NO: 328)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKESPKAQASSVPTAQPQAEGSLAKATTAPATTRNTGRGGEEKKKEKE

KEEQEERETKTPMALIVLGGVAGLLLFIGLGIFFKRGRKKLLYIFKQPFMRPVQTTQEEDGC

SCRFPEEEEGGCELRVKFSRSADAPAYKQGQNQLYNELNLGRREEYDVLDKRRGRDPEMGGK

PRRKNPQEGLYNELQKDKMAEAYSEIGMKGERRRGKGHDGLYQGLSTATKDTYDALHMQALP

PR**

E6 CAR IgD4 pcDH gBLOCK sequence:
(DNA)

(SEQ ID NO: 329)

agtacctctaatctggcctcaggtatccctgcacgattttctggatctggttcaggttctga ttacaccctcactatctctagcctggagcctgaagactttgccgtttattactgccagcaga ggtctagctccccattcacctttgggagtgggaccaaggttgaaattaaagagtctccaaag gcacaggcctcctcagtgcccactgcacaaccccaagcagagggcagcctcgccaaggcaac cacagccccagccaccacccgtaacacaggaagaggcggcgaagagaagaaaaaggagaagg agaaagaggaacaagaagagagagagacaaagacaccaatggccctgattgtgctgggggc gtcgccggcctcctgcttttcattgggctaggcatcttcttcaaaaggggccgcaaaaaact cctttacattttttaagcagccttttatgaggccag CAR E6 X4/8/4-1BB/CD3z sequence:
(DNA)

(SEQ ID NO: 330)

atggccctgcccgtgaccgctttgctgctcccctggcgctgctgctgcacgccgccaggcc agaggtccagctggttgagagtggcgtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaagggggagatttaccatttcacgagacaacgctaagaataccctgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtggcggaggcagcgagatagtgctcacgcagtcac -continued ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaagacaagacgcacac caagccacctaaaccagctccagaactgctcggaggtcctggcaccggaaccggaggaccta ccatcaaaccacctaagccacctaagcctgctcctaacctgctcggaggacctatctacatt tgggccccgctcgcaggcacatgtggagtgctcctcctctccctggtgattaccctgtactg caaaaggggccgcaaaaaactcctttacattttaagcagccttttatgaggccagtacaga cgactcaagaggaagacgggtgctcatgccgctttcctgaggaggaggaaggagggtgcgaa ctgcgcgttaagttctcccgatcagccgacgcgcctgcttacaagcagggccagaaccaact gtacaacgagctgaatctcggtagacgggaagagtacgacgtgttggacaaacgagaggcc gcgacccagaaatgggcggcaagcctcgcaggaaaaaccccaggagggactgtacaatgag ttgcagaaagataagatggcagaagcttatagcgagatcggaatgaagggggaaggagacg agggaaaggacacgacggcctttatcagggcctgtccacagcaacaaaagatacgtatgacg ccctccatatgcaggcacttccaccacggtgataa (amino acids)

(SEQ ID NO: 331)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKDKTHTKPPKPAPELLGGPGTGTGGPTIKPPKPPKPAPNLLGGPIYI

WAPLAGTCGVLLLSLVITLYCKRGRKKLLYIFKQPFMRPVQTTQEEDGCSCRFPEEEEGGCE

LRVKFSRSADAPAYKQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR**

E6 CAR X48 pCDH gBLOCK sequence:
(DNA)

(SEQ ID NO: 332)

agtacctctaatctggcctcaggtatccctgcacgattttctggatctggttcaggttctga ttacaccctcactatctctagcctggagcctgaagactttgccgtttattactgccagcaga ggtctagctccccattcacctttgggagtgggaccaaggttgaaattaaagacaagacgcac accaagccacctaaaccagctccagaactgctcggaggtcctggcaccggaaccggaggacc taccatcaaaccacctaagccacctaagcctgctcctaacctgctcggaggacctatctaca tttgggccccgctcgcaggcacatgtggagtgctcctcctctccctggtgattaccctgtac tgcaaaaggggccgcaaaaaactcctttacattttaagcagccttttatgaggccag CAR E6 X4/4-1BB/CD3z sequence:
(DNA)

(SEQ ID NO: 333)

atggccctgcccgtgaccgctttgctgctcccctggcgctgctgctgcacgccgccaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattacccga ctcagtcaaggggagatttaccatttcacgagacaacgctaagaatacctgtatttgcaga -continued

```
tgaattctctgagagcagaggacacagctgtttactattgtacccgcgacaactatggcagg aactacgactacggtatggactattggggacaagggacattggttacagtgagcagtggcgg cgggggcagcggaggaggaggcagcggtggcggaggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttggggagtgggaccaaggttgaaattaaagacaagacgcacac caagccacctaaaccagctccagaactgctcggaggtcctggcaccggaaccggaggaccta ccatcaaaccacctaagccacctaagcctgctcctaacctgctcggaggacctatggccctg attgtgctggggggcgtcgccggcctcctgcttttcattgggctaggcatcttcttcaaaag gggccgcaaaaaactcctttacattttttaagcagccttttatgaggccagtacagacgactc aagaggaagacgggtgctcatgccgctttcctgaggaggaggaaggagggtgcgaactgcgc gttaagttctcccgatcagccgacgcgcctgcttacaagcagggccagaaccaactgtacaa cgagctgaatctcggtagacgggaagagtacgacgtgttggacaaacggagaggccgcgacc cagaaatgggcggcaagcctcgcaggaaaaaccccaggagggactgtacaatgagttgcag aaagataagatggcagaagcttatagcgagatcggaatgaaggggggaaaggagacgagggaa aggacacgacggcctttatcagggcctgtccacagcaacaaaagatacgtatgacgccctcc atatgcaggcacttccaccacggtgataa
```

(amino acids)
(SEQ ID NO: 334)
```
MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKDKTHTKPPKPAPELLGGPGTGTGGPTIKPPKPPKPAPNLLGGPMAL

IVLGGVAGLLLFIGLGIFFKRGRKKLLYIFKQPFMRPVQTTQEEDGCSCRFPEEEEGGCELR

VKFSRSADAPAYKQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR**
```

E6 CAR X44 pCDH gBLOCK sequence:
(DNA)
(SEQ ID NO: 335)
```
agtacctctaatctggcctcaggtatccctgcacgattttctggatctggttcaggttctga ttacaccctcactatctctagcctggagcctgaagactttgccgtttattactgccagcaga ggtctagctccccattcacctttggggagtgggaccaaggttgaaattaaagacaagacgcac accaagccacctaaaccagctccagaactgctcggaggtcctggcaccggaaccggaggacc taccatcaaaccacctaagccacctaagcctgctcctaacctgctcggaggacctatggccc tgattgtgctggggggcgtcgccggcctcctgcttttcattgggctaggcatcttcttcaaa aggggccgcaaaaaactcctttacattttttaagcagccttttatgaggccag
```

CAR E6 8+4/4/4-1BB/CD3z sequence:
(DNA)
(SEQ ID NO: 336)
```
atggccctgccccgtgaccgctttgctgctcccctggcgctgctgctgcacgccgccaggcc agaggtccagctggttgagagtggcggtgggctggttaagcctggcggctccctgcggctga gctgcgccgcgagtggatttacttcagccgatatgggatgagttgggtgcggcaagctccc
```

```
gggaagaggctggaatgggtctcaacaatctccggggggggcacttacatctattaccccga
ctcagtcaaggggagatttaccatttcacgagacaacgctaagaatacccgtatttgcaga
tgaattctctgagagcagaggacacagctgtttactattgtacccgcgacaactatggcagg
aactacgactacggtatggactattggggacaagggacattggttacagtgagcagtggcgg
cgggggcagcggaggaggaggcagcggtggcggaggcagcgagatagtgctcacgcagtcac
ccgcgactctcagtctctcacctggggaacgagctaccctgacgtgctctgctacctcctca
gtgtcatatattcactggtatcagcaacggcccgggcagtcccctagattgctcatttatag
tacctctaatctggcctcaggtatccctgcacgattttctggatctggttcaggttctgatt
acaccctcactatctctagcctggagcctgaagactttgccgtttattactgccagcagagg
tctagctccccattcacctttgggagtgggaccaaggttgaaattaaaacgacaaccccggc
ccccagaccaccaacgccagcccccaccatcgccagccaacccctgtctctgagaccagaag
cctgtaggcctgccgccggtggagctgtgcacacaagaggactggatttcgcctgtgatatg
gccctgattgtgctgggggcgtcgccggcctcctgcttttcattgggctaggcatcttctt
caaaaggggccgcaaaaaactcctttacattttttaagcagccttttatgaggccagtacaga
cgactcaagaggaagacgggtgctcatgccgctttcctgaggaggaggaaggagggtgcgaa
ctgcgcgttaagttctcccgatcagccgacgcgcctgcttacaagcagggccagaaccaact
gtacaacgagctgaatctcggtagacgggaagagtacgacgtgttggacaaacggagaggcc
gcgacccagaaatgggcggcaagcctcgcaggaaaaaccccaggagggactgtacaatgag
ttgcagaaagataagatggcagaagcttatagcgagatcggaatgaaggggggaaaggagacg
agggaaaggacacgacggcctttatcagggcctgtccacagcaacaaaagatacgtatgacg
ccctccatatgcaggcacttccaccacggtgataa
(amino acids)
                                                        (SEQ ID NO: 337)
MALPVTALLLPLALLLHAARPEVQLVESGGGLVKPGGSLRLSCAASGFTFSRYGMSWVRQAP
GKRLEWVSTISGGGTYIYYPDSVKGRFTISRDNAKNTLYLQMNSLRAEDTAVYYCTRDNYGR
NYDYGMDYWGQGTLVTVSSGGGGSGGGGSGGGGSEIVLTQSPATLSLSPGERATLTCSATSS
VSYIHWYQQRPGQSPRLLIYSTSNLASGIPARFSGSGSGSDYTLTISSLEPEDFAVYYCQQR
SSSPFTFGSGTKVEIKTTTPAPRPPTPAPTIASQPLSLRPEACRPAAGGAVHTRGLDFACDM
ALIVLGGVAGLLLFIGLGIFFKRGRKKLLYIFKQPFMRPVQTTQEEDGCSCRFPEEEEGGCE
LRVKFSRSADAPAYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR**
E6 CAR CD844 pCDH gBLOCK sequence:
(DNA)
                                                        (SEQ ID NO: 338)
agtacctctaatctggcctcaggtatccctgcacgattttctggatctggttcaggttctga
ttacaccctcactatctctagcctggagcctgaagactttgccgtttattactgccagcaga
ggtctagctccccattcacctttgggagtgggaccaaggttgaaattaaaacgacaaccccg
gcccccagaccaccaacgccagcccccaccatcgccagccaacccctgtctctgagaccaga
agcctgtaggcctgccgccggtggagctgtgcacacaagaggactggatttcgcctgtgata
tggccctgattgtgctgggggcgtcgccggcctcctgcttttcattgggctaggcatcttc
ttcaaaaggggccgcaaaaaactcctttacattttttaagcagccttttatgaggccag
```

-continued

Humanized C2 scFV sequence in CAR:
(DNA)
(SEQ ID NO: 339)
gagggccaccatggccttgccagtgacggccctgctgctgccattggctcttctgttgcacgctgcca ggcctgaagtgcagctcgtagagagtggcgggggactggtgaagcccggtggaagcctcagactcagt tgcgccgcctcaggttttcattttttcaggttacgccatgtcctgggtaagacaggcaccggggaaagg actcgagtgggtgtctactatcagctcaggaggcacttatatatattatcctgactctgtaaaaggcc gatttacgatttctcgcgacaatgcaaagaactccctctacctccaaatgaacagtcttagggcagaa gacactgctgtatactattgtgcacgcctcggcggcgacaactactacgagtactttgacgtgtgggg gaaagggactaccgtgacagtttcaagcggaggaggtggctcaggtggaggcgggtcaggggggggag gaagtgatattgtgctcacacaatccccagcctcctggctgtgtctcccggccaacgcgctacaatt acatgtcgggcctccaaaagcgtgagcaccagcggctacagctacatgcactggtatcaacagaaacc aggacaaccccccaaactgttgatttatctcgcttcaaacttggagtccggcgtgcctgcgcgctttt cagggagtgggagcggcacagattttacgctgactatcaaccccgtagaagcaaacgatacagcgaat tattattgtcaacattcccgggaactccccttttacgttcggcggggggcacaaaggtcgaaattaagag aacc (amino acids)
(SEQ ID NO: 340)
EVQLVESGGGLVKPGGSLRLSCAASGFTFSGYAMSWVRQAPGKGLEWVSTISSGGTYIYYPD

SVKGRFTISRDNAKNSLYLQMNSLRAEDTAVYYCARLGGDNYYEYFDVWGKGTTVTVSSGGG

GSGGGGSGGGGSDIVLTQSPASLAVSPGQRATITCRASKSVSTSGYSYMHWYQQKPGQPPKL

LIYLASNLESGVPARFSGSGSGTDFTLTINPVEANDTANYYCQHSRELPFTFGGGTKVEIKR

T

Humanized E6 SCFV sequence in CAR:
(DNA)
(SEQ ID NO: 341)
gaggtccagctggttgagagtggcggtgggctggttaagcctggcggctccctgcggctgag ctgcgccgcgagtggatttactttcagccgatatgggatgagttgggtgcggcaagctccg ggaagaggctggaatgggtctcaacaatctccggggggggcacttacatctattaccccgac tcagtcaaggggagatttaccatttcacgagacaacgctaagaatacccctgtatttgcagat gaattctctgagagcagaggacacagctgtttactattgtacccgcgacaactatggcagga actacgactacggtatggactattggggacaagggacattggttacagtgagcagtggcggc ggggcagcggaggaggaggcagcggtggggggggcagcgagatagtgctcacgcagtcacc cgcgactctcagtctctcacctggggaacgagctaccctgacgtgctctgctacctcctcag tgtcatatattcactggtatcagcaacggcccgggcagtcccctagattgctcatttatagt acctctaatctggcctcaggtatccctgcacgattttctggatctggttcaggttctgatta caccctcactatctctagcctggagcctgaagactttgccgtttattactgccagcagaggt ctagctccccattcaccttttgggagtgggaccaaggttgaaattaaa (amino acids)
(SEQ ID NO: 342)
EVQLVESGGGLVKPGGSLRLSCAASGFTFSRYGMSWVRQAPGKRLEWVSTISGGGTYIYYPD

SVKGRFTISRDNAKNTLYLQMNSLRAEDTAVYYCTRDNYGRNYDYGMDYWGQGTLVTVSSGG

GGSGGGGSGGGGSEIVLTQSPATLSLSPGERATLTCSATSSVSYIHWYQQRPGQSPRLLIYS

TSNLASGIPARFSGSGSGSDYTLTISSLEPEDFAVYYCQQRSSSPFTFGSGTKVEIK

-continued

CD8 leader sequence:
(DNA)
(SEQ ID NO: 343)
atggccctgcccgtgaccgctttgctgctccccctggcgctgctgctgcacgccgccaggcc a (amino acids)
(SEQ ID NO: 344)
MALPVTALLLPLALLLHAARP CD8 hinge domain sequence:
(DNA)
(SEQ ID NO: 345)
acgacaaccccggcccccagaccaccaacgccagcccccaccatcgccagccaacccctgtc tctgagaccagaagcctgtaggcctgccgccggtggagctgtgcacacaagaggactggatt tcgcctgtgat (amino acids)
(SEQ ID NO: 346)
TTTPAPRPPTPAPTIASQPLSLRPEACRPAAGGAVHTRGLDFACD CD4 hinge domain sequence:
(DNA)
(SEQ ID NO: 347)
tcgggacaggtcctgctggaatccaacatcaaggttctgcccacatggtccaccccggtgca gcca (amino acids)
(SEQ ID NO: 348)
SGQVLLESNIKVLPTWSTPVQP CD28 hinge domain sequence:
(DNA)
(SEQ ID NO: 349)
aaacacctttgtccaagtcccctatttcccggaccttctaagccc (amino acids)
(SEQ ID NO: 350)
KHLCPSPLFPGPSKP CD8+CD4 hinge domain sequence:
(DNA)
(SEQ ID NO: 351)
acgacaaccccggcccccagaccaccaacgccagcccccaccatcgccagccaacccctgtc tctgagaccagaagcctgtaggcctgccgccggtggagctgtgcacacaagaggactggatt tcgcctgtgattcgggacaggtcctgctggaatccaacatcaaggttctgcccacatggtcc accccggtgcagcca (amino acids)
(SEQ ID NO: 352)
TTTPAPRPPTPAPTIASQPLSLRPEACRPAAGGAVHTRGLDFACDSGQVLLESNIKVLPTWS

TPVQP

CD8+CD28 hinge domain sequence:
(DNA)
(SEQ ID NO: 353)
acgacaaccccggcccccagaccaccaacgccagcccccaccatcgccagccaacccctgtc tctgagaccagaagcctgtaggcctgccgccggtggagctgtgcacacaagaggactggatt tcgcctgtgataaacacctttgtccaagtcccctatttcccggaccttctaagccc (amino acids)
(SEQ ID NO: 354)
TTTPAPRPPTPAPTIASQPLSLRPEACRPAAGGAVHTRGLDFACDKHLCPSPLFPGPSKP -continued CD28+CD4 hinge domain sequence:
(DNA)
(SEQ ID NO: 355)
aaacacctttgtccaagtcccctatttcccggaccttctaagccctcgggacaggtcctgct ggaatccaacatcaaggttctgcccacatggtccaccccggtgcagcca (amino acids)
(SEQ ID NO: 356)
KHLCPSPLFPGPSKPSGQVLLESNIKVLPTWSTPVQP Human IgD hinge domain sequence:
(DNA)
(SEQ ID NO: 357)
gagtctccaaaggcacaggcctcctcagtgcccactgcacaaccccaagcagagggcagcct cgccaaggcaaccacagccccagccaccacccgtaacacaggaagaggcggcgaagagaaga aaaaggagaaggagaaagaggaacaagaagagagagagacaaagacacca (amino acids)
(SEQ ID NO: 358)
ESPKAQASSVPTAQPQAEGSLAKATTAPATTRNTGRGGEEKKKEKEKEEQEERETKTP X4 linker (IgG1 and IgG2 modified hinge region) sequence:
(DNA)
(SEQ ID NO: 359)
gacaagacgcacaccaagccacctaaaccagctccagaactgctcggaggtcctggcaccgg aaccggaggacctaccatcaaaccacctaagccacctaagcctgctcctaacctgctcggag gacct (amino acids)
(SEQ ID NO: 360)
DKTHTKPPKPAPELLGGPGTGTGGPTIKPPKPPKPAPNLLGGP CD3 zeta transmembrane domain sequence:
(DNA)
(SEQ ID NO: 361)
ctctgctacctgctggatggaatcctcttcatctatggtgtcattctcactgccttgttcct g (amino acids)
(SEQ ID NO: 362)
LCYLLDGILFIYGVILTALFL CD8 transmembrane domain sequence:
(DNA)
(SEQ ID NO: 363)
atctacatttgggccccgctcgcaggcacatgtggagtgctcctcctctccctggtgattac cctgtactgc (amino acids)
(SEQ ID NO: 364)
IYIWAPLAGTCGVLLLSLVITLYC CD4 transmembrane domain sequence:
(DNA)
(SEQ ID NO: 365)
atggccctgattgtgctggggggcgtcgccggcctcctgcttttcattgggctaggcatctt cttc (amino acids)
(SEQ ID NO: 366)
MALIVLGGVAGLLLFIGLGIFF CD28 transmembrane domain sequence:
(DNA)
(SEQ ID NO: 367)
ttttgggtgctggtggtggttggtggagtcctggcttgctatagcttgctagtaacagtggc ctttattatttttctgggtg (amino acids)
(SEQ ID NO: 3 68)
FWVLVVVGGVLACYSLLVTVAFIIFWV -continued 4-1BB transmembrane domain sequence:
(DNA)
(SEQ ID NO: 369)
atcatctccttctttcttgcgctgacgtcgactgcgttgctcttcctgctgttcttcctcac gctccgtttctctgttgtt (amino acids)
(SEQ ID NO: 370)
IISFFLALTSTALLFLLFFLTLRFSVV OX40 transmembrane domain sequence:
(DNA)
(SEQ ID NO: 371)
gttgccgccatcctgggcctgggcctggtgctggggctgctgggccccctggccatcctgct ggccctgtacctgctc (amino acids)
(SEQ ID NO: 372)
VAAILGLGLVLGLLGPLAILLALYLL CD3 zeta domain sequence:
(DNA)
(SEQ ID NO: 373)
cgcgttaagttctcccgatcagccgacgcgcctgcttacaagcagggccagaaccaactgta caacgagctgaatctcggtagacgggaagagtacgacgtgttggacaaacggagaggccgcg acccagaaatgggcggcaagcctcgcaggaaaaaccccagggaggactgtacaatgagttg cagaaagataagatggcagaagcttatagcgagatcggaatgaaggggaaggagacgagg gaaaggacacgacggcctttatcagggcctgtccacagcaacaaaagatacgtatgacgccc tccatatgcaggcacttccaccacgg (amino acids)
(SEQ ID NO: 374)
RVKFSRSADAPAYKQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

CD3 zeta domain variant sequence:
(DNA)
(SEQ ID NO: 375)
agagtgaagttcagcaggagcgcagacgcccccgcgtaccagcagggccagaaccagctcta taacgagctcaatctaggacgaagagaggagtacgatgttttggacaagagacgtggccggg accctgagatggggggaaagccgagaaggaagaaccctcaggaaggcctgtacaatgaactg cagaaagataagatggcggaggcctacagtgagattgggatgaaaggcgagcgccggaggg caaggggcacgatggcctttaccagggtctcagtacagccaccaaggacacctacgacgccc ttcacatgcaggccctgccccctcgc (amino acids)
(SEQ ID NO: 376)
RVKFSRSADAPAYQQGQNQLYNELNLGRREEYDVLDKRRGRDPEMGGKPRRKNPQEGLYNEL

QKDKMAEAYSEIGMKGERRRGKGHDGLYQGLSTATKDTYDALHMQALPPR

CD28 domain sequence:
(DNA)
(SEQ ID NO: 377)
agaagcaagcggtctcggctcctgcattctgattacatgaacatgaccccaagaagaccagg ccccaccaggaaacattaccagccctacgctccgccacgcgacttcgctgcctaccggtcc (amino acids)
(SEQ ID NO: 378)
RSKRSRLLHSDYMNMTPRRPGPTRKHYQPYAPPRDFAAYRS -continued 4-1BB domain sequence:
(DNA)
(SEQ ID NO: 379)
aaaagggggccgcaaaaaactcctttacatttttaagcagccttttatgaggccagtacagac gactcaagaggaagacgggtgctcatgccgctttcctgaggaggaggaaggagggtgcgaac tg (amino acids)
(SEQ ID NO: 380)
KRGRKKLLYIFKQPFMRPVQTTQEEDGCSCRFPEEEEGGCEL OX40 domain sequence:
(DNA)
(SEQ ID NO: 381)
cggagggaccagaggctgcccccgatgcccacaagcccctggggaggcagtttccggac ccccatccaagaggagcaggccgacgcccactccaccctggccaagatc (amino acids)
(SEQ ID NO: 382)
RRDQRLPPDAHKPPGGGSFRTPIQEEQADAHSTLAKI Humanized anti CD3 scFV clone 12F6 (VH-VL) sequence:
(DNA)
(SEQ ID NO: 383)
caggtgcagctggtgcagagcggaggtggagtggtccaacctggaagatctctgagactgag ctgtaaggctagcgggtacacgttcacatcttacacgatgcactgggtgaggcaagccccg gtaagggcctggaatggatcggatatataaaccccagctcagggtataccaaatataatcag aagttcaaagatcggttcacgatttctgctgataaaagtaagtccaccgctttcctgcagat ggactcactcaggccagaagatactggtgtttatttctgtgcaaggtggcaggactacgacg tgtactttgactattgggggcaggggacgcctgtaacagtatcaagcggcggtggcggatcc ggcggtggcggatccggcggtggcggatccgatattcagatgacccagagcccgagcagcct gagcgcgagcgtgggcgatcgcgtgaccatgacctgccgcgcgagcagcagcgtgagctata tgcattggtatcagcagaccccggggcaaagcgccgaaaccgtggatttatgcgaccagcaac ctggcgagcggcgtgccgagccgctttagcggcagcggcagcggcaccgattataccctgac cattagcagcctgcagccggaagatattgcgacctattattgccagcagtggagcagcaacc cgccgaccttttggccagggcaccaaactgcagattacccgc (amino acids)
(SEQ ID NO: 384)
QVQLVQSGGGVVQPGRSLRLSCKASGYTFTSYTMHWVRQAPGKGLEWIGYINPSSGYTKYNQ

KFKDRFTISADKSKSTAFLQMDSLRPEDTGVYFCARWQDYDVYFDYWGQGTPVTVSSGGGGS

GGGGSGGGGSDIQMTQSPSSLSASVGDRVTMTCRASSSVSYMHWYQQTPGKAPKPWIYATSN

LASGVPSRFSGSGSGTDYTLTISSLQPEDIATYYCQQWSSNPPTFGQGTKLQITR

Humanized anti CD3 scFV clone 12F6 (VL-VH) sequence:
(DNA)
(SEQ ID NO: 385)
gatattcagatgacccagagcccgagcagcctgagcgcgagcgtgggcgatcgcgtgaccat gacctgccgcgcgagcagcagcgtgagctatatgcattggtatcagcagaccccggggcaaag cgccgaaaccgtggatttatgcgaccagcaacctggcgagcggcgtgccgagccgctttagc ggcagcggcagcggcaccgattataccctgaccattagcagcctgcagccggaagatattgc gacctattattgccagcagtggagcagcaacccgccgaccttttggccagggcaccaaactgc agattacccgcggcggtggcggatccggcggtggcggatccggcggtggcggatcccaggtg cagctggtgcagagcggaggtggagtggtccaacctggaagatctctgagactgagctgtaa ggctagcgggtacacgttcacatcttacacgatgcactgggtgaggcaagccccggtaagg -continued

```
gcctggaatggatcggatatataaaccccagctcagggtataccaaatataatcagaagttc aaagatcggttcacgatttctgctgataaaagtaagtccaccgcttttcctgcagatggactc actcaggccagaagatactggtgtttatttctgtgcaaggtggcaggactacgacgtgtact ttgactattgggggcaggggacgcctgtaacagtatcaagc
```

(amino acids) (SEQ ID NO: 386)

```
DIQMTQSPSSLSASVGDRVTMTCRASSSVSYMHWYQQTPGKAPKPWIYATSNLASGVPSRFS
GSGSGTDYTLTISSLQPEDIATYYCQQWSSNPPTFGQGTKLQITRGGGGSGGGGSGGGGSQV
QLVQSGGGWQPGRSLRLSCKASGYTFTSYTMHWVRQAPGKGLEWIGYINPSSGYTKYNQKF
KDRFTISADKSKSTAFLQMDSLRPEDTGVYFCARWQDYDVYFDYWGQGTPVTVSS
```

Humanized anti CD3 scFV clone OKT3 (VH-VL) sequence:
(DNA) (SEQ ID NO: 387)

```
caggtgcagctggtgcagagcggaggcggagtggtgcagcctggaagaagcctgcgcctgag ctgcaaagcgagcggctataccttacccgctataccatgcattgggtgcgccaggcgccgg gcaaaggcctggaatggattggctatattaacccgagccgcggctataccaactataaccag aaagtgaaagatcgctttaccattagcaccgataaaagcaaaagcaccgcgtttctgcagat ggatagcctgcgcccggaagataccgcggtgtattattgcgcgcgctattatgatgatcatt attgcctggattattggggccagggcaccacccctgaccgtgagcagcggcggtggcggatcc ggcggtggcggatccggcggtggcggatccgatattcagatgacccagagcccgagcagcct gagcgcgagcgtgggcgatcgcgtgaccattacctgcagcgcgagcagcagcgtgagctata tgaactggtatcagcagaccccgggcaaagcgccgaaacgctggatttatgataccagcaaa ctggcgagcggcgtgccgagccgctttagcggcagcggcagcggcaccgattatacctttac cattagcagcctgcagccggaagatattgcgacctattattgccagcagtggagcagcaacc cgtttacctttggccagggcaccaaactgcagattacccgc
```

(amino acids) (SEQ ID NO: 388)

```
QVQLVQSGGGVVQPGRSLRLSCKASGYTFTRYTMHWVRQAPGKGLEWIGYINPSRGYTNYNQ
KVKDRFTISTDKSKSTAFLQMDSLRPEDTAVYYCARYYDDHYCLDYWGQGTTLTVSSGGGGS
GGGGSGGGGSDIQMTQSPSSLSASVGDRVTITCSASSSVSYMNWYQQTPGKAPKRWIYDTSK
LASGVPSRFSGSGSGTDYTFTISSLQPEDIATYYCQQWSSNPFTFGQGTKLQITR
```

Humanized anti CD3 scFV clone OKT3 (VH-VL) sequence:
(DNA) (SEQ ID NO: 389)

```
gatattcagatgacccagagcccgagcagcctgagcgcgagcgtgggcgatcgcgtgaccat tacctgcagcgcgagcagcagcgtgagctatatgaactggtatcagcagaccccgggcaaag cgccgaaacgctggatttatgataccagcaaactggcgagcggcgtgccgagccgctttagc ggcagcggcagcggcaccgattatacctttaccattagcagcctgcagccggaagatattgc gacctattattgccagcagtggagcagcaacccgtttacctttggccagggcaccaaactgc agattacccgcggcggtggcggatccggcggtggcggatccggcggtggcggatcccaggtg cagctggtgcagagcggaggcggagtggtgcagcctggaagaagcctgcgcctgagctgcaa agcgagcggctataccttacccgctataccatgcattgggtgcgccaggcgccgggcaaag gcctggaatggattggctatattaacccgagccgcggctataccaactataaccagaaagtg aaagatcgctttaccattagcaccgataaaagcaaaagcaccgcgtttctgcagatggatag cctgcgcccggaagataccgcggtgtattattgcgcgcgctattatgatgatcattattgcc tggattattggggccagggcaccacccctgaccgtgagcagc
```

-continued (amino acids) (SEQ ID NO: 390)

DIQMTQSPSSLSASVGDRVTITCSASSSVSYMNWYQQTPGKAPKRWIYDTSKLASGVPSRFS

GSGSGTDYTFTISSLQPEDIATYYCQQWSSNPFTFGQGTKLQITRGGGGSGGGGSGGGGSQV

QLVQSGGGVVQPGRSLRLSCKASGYTFTRYTMHWVRQAPGKGLEWIGYINPSRGYTNYNQKV

KDRFTISTDKSKSTAFLQMDSLRPEDTAVYYCARYYDDHYCLDYWGQGTTLTVSS

HumanizeE6 scFV (VH-VL) sequence:
(DNA) (SEQ ID NO: 391)

gaggtgcagctggtggagtctgggggaggcctggtcaagcctggggggtccctgagactctc ctgtgcagcctctggattcaccttcagtaggtatggcatgagctgggtccgccaggctccag ggaagaggctggagtgggtctcaaccattagtggcggaggcacctacatatactacccagac tcagtgaagggccgattcaccatctccagagacaacgccaagaacaccctgtatctgcaaat gaacagcctgagagccgaggacacggctgtgtattactgtaccagagataactatggccgca actatgattatggcatggattattggggccagggcaccctggtgaccgtgagcagcggcggt ggcggatccggcggtggcggatccggcggtggcggatccgaaattgtgttgacacagtctcc agccaccctgtctttgtctccaggggaaagagccaccctcacctgcagcgccaccagcagtg ttagctacatccactggtaccaacagaggcctggccagagccccaggctcctcatctatagc acctccaacctggccagcggcatcccagccaggttcagtggcagtgggtctgggagcgacta cactctcaccatcagcagcctagagcctgaagattttgcagtttattactgtcagcagcgta gcagctccccttttaccttTggcagcggcaccaaagtggaaattaaa (amino acids) (SEQ ID NO: 392)

EVQLVESGGGLVKPGGSLRLSCAASGFTFSRYGMSWVRQAPGKRLEWVSTISGGGTYIYYPD

SVKGRFTISRDNAKNTLYLQMNSLRAEDTAVYYCTRDNYGRNYDYGMDYWGQGTLVTVSSGG

GGSGGGGSGGGGSEIVLTQSPATLSLSPGERATLTCSATSSVSYIHWYQQRPGQSPRLLIYS

TSNLASGIPARFSGSGSGSDYTLTISSLEPEDFAVYYCQQRSSSPETFGSGTKVEIK

HumanizeE6 scFV (VL-VH) sequence:
(DNA) (SEQ ID NO: 393)

gaaattgtgttgacacagtctccagccaccctgtctttgtctccaggggaaagagccaccct cacctgcagcgccaccagcagtgttagctacatccactggtaccaacagaggcctggccaga gccccaggctcctcatctatagcacctccaacctggccagcggcatcccagccaggttcagt ggcagtgggtctgggagcgactacactctcaccatcagcagcctagagcctgaagattttgc agtttattactgtcagcagcgtagcagctccccttttaccttTggcagcggcaccaaagtgg aaattaaaggcggtggcggatccggcggtggcggatccggcggtggcggatccgaggtgcag ctggtggagtctgggggaggcctggtcaagcctggggggtccctgagactctcctgtgcagc ctctggattcaccttcagtaggtatggcatgagctgggtccgccaggctccaggaagaggc tggagtgggtctcaaccattagtggcggaggcacctacatatactacccagactcagtgaag ggccgattcaccatctccagagacaacgccaagaacaccctgtatctgcaaatgaacagcct gagagccgaggacacggctgtgtattactgtaccagagataactatggccgcaactatgatt atggcatggattattggggccagggcaccctggtgaccgtgagcagc (amino acids) (SEQ ID NO: 394)

EIVLTQSPATLSLSPGERATLTCSATSSVSYIHWYQQRPGQSPRLLIYSTSNLASGIPARES

GSGSGSDYTLTISSLEPEDFAVYYCQQRSSSPFTFGSGTKVEIKGGGGSGGGGSGGGGSEVQ

LVESGGGLVKPGGSLRLSCAASGFTFSRYGMSWVRQAPGKRLEWVSTISGGGTYIYYPDSVK

GRFTISRDNAKNTLYLQMNSLRAEDTAVYYCTRDNYGRNYDYGMDYWGQGTLVTVSS

HumanizeC2 scFV (VH-VL) sequence:
(DNA)
(SEQ ID NO: 395)

gaggtgcagctggtggagtctgggggaggcctggtcaagcctggggggtccctgagactctc ctgtgcagcctctggattcaccttcagtggctatgccatgagctgggtccgccaggctccag ggaaggggctggagtgggtctcaaccattagtagtggcggaacctacatatactaccccgac tcagtgaagggccgattcaccatctccagagacaacgccaagaactcactgtatctgcaaat gaacagcctgagagccgaggacacggccgtgtattactgtgcgagacttgggggggataatt actacgaatacttcgatgtctggggcaaagggaccacggtcaccgtctcctccggcggtggc ggatccggcggtggcggatccggcggtggcggatccgacattgtgctgacccagtctccagc ctccttggccgtgtctccaggacagagggccaccatcacctgcagagccagtaagagtgtca gtaccagcggatactcctacatgcactggtatcagcagaaaccaggacaacctcctaaactc ctgatttacctggcatccaatctggagagcggggtcccagccaggttcagcggcagtgggtc tgggaccgatttcaccctcacaattaatcctgtggaagctaatgatactgcaaattattact gtcagcacagtagggagctgccttt cacattcggcggagggaccaaggtggagatcaaacga act (amino acids)
(SEQ ID NO: 396)

EVQLVESGGGLVKPGGSLRLSCAASGFTFSGYAMSWVRQAPGKGLEWVSTISSGGTYIYYPD

SVKGRFTISRDNAKNSLYLQMNSLRAEDTAVYYCARLGGDNYYEYFDVWGKGTTVTVSSGGG

GSGGGGSGGGGSDIVLTQSPASLAVSPGQRATITCRASKSVSTSGYSYMHWYQQKPGQPPKL

LIYLASNLESGVPARFSGSGSGTDFTLTINPVEANDTANYYCQHSRELPFTFGGGTKVEIKR

T

HumanizeE6 scFV (VL-VH) sequence:
(DNA)
(SEQ ID NO: 397)

gacattgtgctgacccagtctccagcctccttggccgtgtctccaggacagagggccaccat cacctgcagagccagtaagagtgtcagtaccagcggatactcctacatgcactggtatcagc agaaaccaggacaacctcctaaactcctgatttacctggcatccaatctggagagcggggtc ccagccaggttcagcggcagtgggtctgggaccgatttcaccctcacaattaatcctgtgga agctaatgatactgcaaattattactgtcagcacagtagggagctgccttt cacattcggcg gagggaccaaggtggagatcaaacgaactggcggtggcggatccggcggtggcggatccggc ggtggcggatccgaggtgcagctggtggagtctgggggaggcctggtcaagcctggggggtc cctgagactctcctgtgcagcctctggattcaccttcagtggctatgccatgagctgggtcc gccaggctccagggaaggggctggagtgggtctcaaccattagtagtggcggaacctacata tactaccccgactcagtgaagggccgattcaccatctccagagacaacgccaagaactcact gtatctgcaaatgaacagcctgagagccgaggacacggccgtgtattactgtgcgagacttg gggggataattactacgaatacttcgatgtctggggcaaagggaccacggtcaccgtctcc tcc (amino acids)
(SEQ ID NO: 398)

DIVLTQSPASLAVSPGQRATITCRASKSVSTSGYSYMHWYQQKPGQPPKLLIYLASNLESGV

PARFSGSGSGTDFTLTINPVEANDTANYYCQHSRELPFTFGGGTKVEIKRTGGGGSGGGGSG

```
GGGSEVQLVESGGGLVKPGGSLRLSCAASGFTFSGYAMSWVRQAPGKGLEWVSTISSGGTYI

YYPDSVKGRFTISRDNAKNSLYLQMNSLRAEDTAVYYCARLGGDNYYEYFDVWGKGTTVTVS

S
```

G₄S₁ linker sequence:
(DNA)
(SEQ ID NO: 399)
ggcggtggcggatcc (amino acids)
(SEQ ID NO: 400)
GGGGS

[G₄S₁] × 3 linker sequence:
(DNA)
(SEQ ID NO: 401)
ggcggtggcggatccggcggtggcggatccggcggtggcggatcc (amino acids)
(SEQ ID NO: 402)
GGGGSGGGGSGGGGS 8 aa GS linker sequence:
(DNA)
(SEQ ID NO: 403)
ggcggttccggcggtggatccgga (amino acids)
(SEQ ID NO: 404)
GGSGGGSG 12 aa GS linker sequence:
(DNA)
(SEQ ID NO: 405)
ggcggttccggcggtggatccggcggtggcggatccgga (amino acids)
(SEQ ID NO: 406)
GGSGGGSGGGSG 13 aa GS linker sequence:
(DNA)
(SEQ ID NO: 407)
ggcggtggatccggcggtggcggatccggcggtggatcc (amino acids)
(SEQ ID NO: 408)
GGGSGGGGSGGGS 22 aa GS linker sequence:
(DNA)
(SEQ ID NO: 409)
ggcggtggaagcggcggtggcggatccggcagcggcggaagcggcggtggcggatccggcgg tgga (amino acids)
(SEQ ID NO: 4110)
GGGSGGGGSGSGGSGGGGSGGG 24 aa GS linker sequence:
(DNA)
(SEQ ID NO: 411)
ggcggttccggcggtggatccggcggtggcggatccggaggcggttccggcggtggatccgg cggtggcggatccgga (amino acids)
(SEQ ID NO: 412)
GGSGGGSGGGSGGGSGGGSGGGSG Mouse C3 Heavy chain variable region sequence:
(DNA)
(SEQ ID NO: 413)
caggtccagctgcagcagtctgggcctgagctggtgaggcctggggtctcagtgaagatttcctgcaa gggttccggctacagattcactgattatgctatgaactgggtgaagcagagtcatgcaaagagtctag -continued agtggattggagttattagtactttctctggtaatacaaacttcaaccagaagtttaagggcaaggcc acaatgactgtagacaaatcctccagcacagcctatatggaacttgccagattgacatctgaggattc tgccatgtattactgtgcaagatcggattactacggcccatactttgactactggggccaaggcacca ctctcacagtctcctca (amino acids)
(SEQ ID NO: 414)
QVQLQQSGPELVRPGVSVKISCKGSGYRFTDYAMNWVKQSHAKSLEWIGVISTFSGNTNFNQKFKGKA

TMTVDKSSSTAYMELARLTSEDSAMYYCARSDYYGPYFDYWGQGTTLTVSS

Mouse C3 heavy chain variable framework region 1 (FWR1) sequence:
(DNA)
(SEQ ID NO: 415)
caggtccagctgcagcagtctgggcctgagctggtgaggcctggggtctcagtgaagatttcctgcaa gggttccggctacagattcact (amino acids)
(SEQ ID NO: 416)
QVQLQQSGPELVRPGVSVKISCKGSGYRFT Mouse C3 heavy chain variable complementarity determining regions 1
(CDR1) sequence:
(DNA)
(SEQ ID NO: 417)
gattatgctatgaac (amino acids)
(SEQ ID NO: 418)
DYAMN Mouse C3 heavy chain variable framework region 2 (FWR2) sequence:
(DNA)
(SEQ ID NO: 419)
tgggtgaagcagagtcatgcaaagagtctagagtggattgga (amino acids)
(SEQ ID NO: 420)
WVKQSHAKSLEWIG Mouse C3 heavy chain variable complementarity determining regions 2
(CDR2) sequence:
(DNA)
(SEQ ID NO: 421)
gttattagtactttctctggtaatacaaacttcaaccagaagtttaagggc (amino acids)
(SEQ ID NO: 422)
VISTFSGNTNFNQKFKG Mouse C3 heavy chain variable framework region 3 (FWR3) acid
sequence:
(DNA)
(SEQ ID NO: 423)
aaggccacaatgactgtagacaaatcctccagcacagcctatatggaacttgccagattgacatctga ggattctgccatgtattactgtgcaaga (amino acids)
(SEQ ID NO: 424)
KATMTVDKSSSTAYMELARLTSEDSAMYYCAR Mouse C3 heavy chain variable complementarity determining regions 3
(CDR3) sequence:
(DNA)
(SEQ ID NO: 425)
tcggattactacggcccatactttgactac (amino acids)
(SEQ ID NO: 426)
SDYYGPYFDY IGHV1-18*04 heavy chain variable region sequence:
(DNA)
(SEQ ID NO: 427)
caggttcagctggtgcagtctggagctgaggtgaagaagcctggggcctcagtgaaggtctc ctgcaaggcttctggttacacctttaccagctacggtatcagctgggtgcgacaggcccctg gacaagggcttgagtggatgggatggatcagcgcttacaatggtaacacaaactatgcacag aagctccagggcagagtcaccatgaccacagacacatccacgagcacagcctacatggagct gaggagcctgagatctgacgacacggccgtgtattactgtgcgagaga (amino acids)
(SEQ ID NO: 428)
QVQLVQSGAEVKKPGASVKVSCKASGYTFTSYGISWVRQAPGQGLEWMGWISAYNGNTNYAQKLQGRV

TMTTDTSTSTAYMELRSLRSDDTAVYYCAR

IGHV1-18*04 heavy chain variable framework region 1 (FWR1) sequence:
(DNA)
(SEQ ID NO: 429)
caggttcagctggtgcagtctggagctgaggtgaagaagcctggggcctcagtgaaggtctcctgcaa ggcttctggttacacctttacc (amino acids)
(SEQ ID NO: 430)
QVQLVQSGAEVKKPGASVKVSCKASGYTFT IGHV1-18*04 heavy chain variable complementarity determining regions
1 (CDR1) sequence:
(DNA)
(SEQ ID NO: 431)
agctacggtatcagc (amino acids)
(SEQ ID NO: 432)
SYGIS IGHV1-18*04 heavy chain variable framework region 2 (FWR2) sequence:
(DNA)
(SEQ ID NO: 433)
tgggtgcgacaggcccctggacaagggcttgagtggatggga (amino acids)
(SEQ ID NO: 434)
WVRQAPGQGLEWMG IGHV1-18*04 heavy chain variable complementarity determining regions
2 (CDR2) sequence:
(DNA)
(SEQ ID NO: 435)
tggatcagcgcttacaatggtaacacaaactatgcacagaagctccagggc (amino acids)
(SEQ ID NO: 436)
WISAYNGNTNYAQKLQG IGHV1-18*04 heavy chain variable framework region 3 (FWR3) sequence:
(DNA)
(SEQ ID NO: 437)
agagtcaccatgaccacagacacatccacgagcacagcctacatggagctgaggagcctgagatctga cgacacggccgtgtattactgtgcgaga (amino acids)
(SEQ ID NO: 438)
RVTMTTDTSTSTAYMELRSLRSDDTAVYYCAR Humanized C3 heavy chain variable region sequence:
(DNA)
(SEQ ID NO: 439)
caggttcagctggtgcagtctggagctgaggtgaagaagcctggggcctcagtgaaggtctcctgcaa ggcttctggttacacctttaccgactacgccatgaactgggtgcgacaggcccctggacaagggcttg agtggatgggagtgatcagcacccttcagcggtaacacaaacttcaaccagaagttcaagggcagagtc accatgaccacagacacatccacgagcacagcctacatggagctgaggagcctgagatctgacgacac -continued ggccgtgtattactgtgcgagaagcgactactacggcccatacttcgactactggggccagggcacca ccctgaccgtgtccagc (amino acids)
(SEQ ID NO: 440)
QVQLVQSGAEVKKPGASVKVSCKASGYTFTDYAMNWVRQAPGQGLEWMGVISTFSGNTNFNQKFKGRV

TMTTDTSTSTAYMELRSLRSDDTAVYYCARSDYYGPYFDYWGQGTTLTVSS

Humanized C3 heavy chain variable framework region 1 (FWR1) acid
sequence:
(DNA)
(SEQ ID NO: 441)
caggttcagctggtgcagtctggagctgaggtgaagaagcctggggcctcagtgaaggtctcctgcaa ggcttctggttacacctttacc (amino acids)
(SEQ ID NO: 442)
QVQLVQSGAEVKKPGASVKVSCKASGYTFT Humanized C3 heavy chain variable complementarity determining
regions 1 (CDR1) sequence:
(DNA)
(SEQ ID NO: 443)
gactacgccatgaac (amino acids)
(SEQ ID NO: 444)
DYAMN Humanized C3 heavy chain variable framework region 2 (FWR2) acid
sequence:
(DNA)
(SEQ ID NO: 445)
tgggtgcgacaggcccctggacaagggcttgagtggatggga (amino acids)
(SEQ ID NO: 446)
WVRQAPGQGLEWMG Humanized C3 heavy chain variable complementarity determining
regions 2 (CDR2) sequence:
(DNA)
(SEQ ID NO: 447)
gtgatcagcaccttcagcggtaacacaaacttcaaccagaagttcaagggc (amino acids)
(SEQ ID NO: 448)
VISTFSGNTNFNQKFKG Humanized C3 heavy chain variable framework region 3 (FWR3) acid
sequence:
(DNA)
(SEQ ID NO: 449)
agagtcaccatgaccacagacacatccacgagcacagcctacatggagctgaggagcctgagatctga cgacacggccgtgtattactgtgcgaga (amino acids)
(SEQ ID NO: 450)
RVTMTTDTSTSTAYMELRSLRSDDTAVYYCAR Humanized C3 heavy chain variable complementarity determining
regions 3 (CDR3) sequence:
(DNA)
(SEQ ID NO: 451)
agcgactactacggcccatacttcgactac (amino acids)
(SEQ ID NO: 452)
SDYYGPYFDY Humanized C3 IgG1 heavy chain sequence
(DNA)
(SEQ ID NO: 453)
caggttcagctggtgcagtctggagctgaggtgaagaagcctggggcctcagtgaaggtctcctgcaa ggcttctggttacacctttaccgactacgccatgaactgggtgcgacaggcccctggacaagggcttg -continued

```
agtggatgggagtgatcagcaccttcagcggtaacacaaacttcaaccagaagttcaagggcagagtc accatgaccacagacacatccacgagcacagcctacatggagctgaggagcctgagatctgacgacac ggccgtgtattactgtgcgagaagcgactactacggcccatacttcgactactggggccagggcacca cccctgaccgtgtccagcgctagcaccaagggcccatcggtcttccccctggcaccctcctccaagagc acctctgggggcacagcggccctgggctgcctggtcaaggactacttccccgaaccggtgacggtgtc gtggaactcaggcgccctgaccagcggcgtgcacaccttcccggctgtcctacagtcctcaggactct actccctcagcagcgtggtgacagtgccctccagcagcttgggcacccagacctacatctgcaacgtg aatcacaagcccagcaacaccaaggtggacaagaaagttgagcccaaatcttgtgacaaaactcacac atgcccaccgtgcccagcacctgaactcctggggggaccgtcagtcttcctcttccccccaaaaccca aggacaccctcatgatctcccggacccctgaggtcacatgcgtggtggtggacgtgagccacgaagac cctgaggtcaagttcaactggtacgtggacggcgtggaggtgcataatgccaagacaaagccgcggga ggagcagtacaacagcacgtaccgtgtggtcagcgtcctcaccgtcctgcaccaggactggctgaatg gcaaggagtacaagtgcaaggtctccaacaaagcccttccagcccccatcgagaaaaccatctccaaa gccaaagggcagccccgagaaccacaggtgtacaccctgcccccatcccgggaggagatgaccaagaa ccaggtcagcctgacctgcctggtcaaaggcttctatcccagcgacatcgccgtggagtgggagagca atgggcagccggagaacaactacaagaccacgcctcccgtgctggactccgacggctccttcttcctc tacagcaagctcaccgtggacaagagcaggtggcagcaggggaacgtcttctcatgctccgtgatgca tgaggctctgcacaaccactacacgcagaagagcctctccctgtctccgggtaaatgataa
```

(amino acids)

(SEQ ID NO: 454)

```
QVQLVQSGAEVKKPGASVKVSCKASGYTFTDYAMNWVRQAPGQGLEWMGVISTFSGNTNFNQKFKGRV

TMTTDTSTSTAYMELRSLRSDDTAVYYCARSDYYGPYFDYWGQGTTLTVSSASTKGPSVFPLAPSSKS

TSGGTAALGCLVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKCKVSNKALPAPIEKTISK

AKGQPREPQVYTLPPSREEMTKNQVSLTCLVKGFYPSDIAVEWESNGQPENNYKTTPPVLDSDGSFFL

YSKLTVDKSRWQQGNVFSCSVMHEALHNHYTQKSLSLSPGK**
```

Humanized C3 IgG2 heavy chain sequence
(DNA)

(SEQ ID NO: 455)

```
caggttcagctggtgcagtctggagctgaggtgaagaagcctggggcctcagtgaaggtctcctgcaa ggcttctggttacaccttaccgactacgccatgaactgggtgcgacaggcccctggacaagggcttg agtggatgggagtgatcagcaccttcagcggtaacacaaacttcaaccagaagttcaagggcagagtc accatgaccacagacacatccacgagcacagcctacatggagctgaggagcctgagatctgacgacac ggccgtgtattactgtgcgagaagcgactactacggcccatacttcgactactggggccagggcacca cccctgaccgtgtccagcgcctccaccaagggcccatcggtcttccccctggcgccctgctccaggagc acctccgagagcacagccgccctgggctgcctggtcaaggactacttccccgaaccggtgacggtgtc gtggaactcaggcgctctgaccagcggcgtgcacaccttcccagctgtcctacagtcctcaggactct actccctcagcagcgtggtgaccgtgccctccagcaacttcggcacccagacctacacctgcaacgta gatcacaagcccagcaacaccaaggtggacaagacagttgagcgcaaatgttgtgtcgagtgcccacc gtgcccagcaccacctgtggcaggaccgtcagtcttcctcttccccccaaaacccaaggacaccctca tgatctcccggacccctgaggtcacgtgcgtggtggtggacgtgagccacgaagaccccgaggtccag ttcaactggtacgtggacggcgtggaggtgcataatgccaagacaaagccacgggaggagcagttcaa
```

-continued cagcacgttccgtgtggtcagcgtcctcaccgttgtgcaccaggactggctgaacggcaaggagtaca agtgcaaggtctccaacaaaggcctcccagcccccatcgagaaaaccatctccaaaaccaaagggcag ccccgagaaccacaggtgtacaccctgcccccatcccgggaggagatgaccaagaaccaggtcagcct gacctgcctggtcaaaggcttctaccccagcgacatcgccgtggagtgggagagcaatgggcagccgg agaacaactacaagaccacacctcccatgctggactccgacggctccttcttcctctacagcaagctc accgtggacaagagcaggtggcagcaggggaacgtcttctcatgctccgtgatgcatgaggctctgca caaccactacacgcagaagagcctctccctgtctccgggtaaatagtaa (amino acids)

(SEQ ID NO: 456)
QVQLVQSGAEVKKPGASVKVSCKASGYTFTDYAMNWVRQAPGQGLEWMGVISTFSGNTNFNQKFKGRV tmttdtststaymelrslrsddtavyycarsdyygpyfdywgqgttltvssastkgpsvfplapcsrs

TSESTAALGCLVKDYFPEPVTVSWNSGALTSGVHTFPAVLQSSGLYSLSSVVTVPSSNFGTQTYTCNV

DHKPSNTKVDKTVERKCCVECPPCPAPPVAGPSVFLFPPKPKDTLMISRTPEVTCVVVDVSHEDPEVQ

FNWYVDGVEVHNAKTKPREEQFNSTFRVVSVLTVVHQDWLNGKEYKCKVSNKGLPAPIEKTISKTKGQ

PREPQVYTLPPSREEMTKNQVSLTCLVKGFYPSDIAVEWESNGQPENNYKTTPPMLDSDGSFFLYSKL

TVDKSRWQQGNVFSCSVMHEALHNHYTQKSLSLSPGK**

Humanized C3 heavy chain IgG1 gBLOCK sequence:
(DNA)

(SEQ ID NO: 457)
tgctctgggttccaggttccactggtgacgcggcccagccggcccaggttcagctggtgcagtctgga gctgaggtgaagaagcctggggcctcagtgaaggtctcctgcaaggcttctggttacaccttaccga ctacgccatgaactgggtgcgacaggcccctggacaagggcttgagtggatgggagtgatcagcacct tcagcggtaacacaaacttcaaccagaagttcaagggcagagtcaccatgaccacagacacatccacg agcacagcctacatggagctgaggagcctgagatctgacgacacggccgtgtattactgtgcgagaag cgactactacggcccatacttcgactactggggccagggcaccaccctgaccgtgtccagcgctagca ccaagggcccatcggtcttccccctggcaccctcctccaagagcacctctgggggcacagcggccctg ggctgcctggtcaaggactacttccccgaaccggtgacggtgtcgtggaactcaggcgccctgaccag
c Mouse C3 Light Chain variable region sequence:
(DNA)

(SEQ ID NO: 458)
gatgttttgatgacccaaactccactctccctgcctgtcagtcttggagatcaagcctccatctcttg cagatctagtcagaccattgtacatagtaatggaaacacctatttagaatggtacctgcagaaaccag gccagtctccaaagctcctgatctacaaagtttccaaccgattttctggggtcccagacaggttcagt ggcagtggatcagggacagatttcacactcaagatcaacagagtggaggctgaggatctgggagttta ttactgctttcaaggttcacatgttccattcacgttcggctcggggacaaagttggaaataaaa (amino acids)

(SEQ ID NO: 459)
DVLMTQTPLSLPVSLGDQASISCRSSQTIVHSNGNTYLEWYLQKPGQSPKLLIYKVSNRFSGVPDRFS

GSGSGTDFTLKINRVEAEDLGVYYCFQGSHVPFTFGSGTKLEIK

Mouse C3 light chain variable framework region 1 (FWR1) sequence:
(DNA)

(SEQ ID NO: 460)
gatgttttgatgacccaaactccactctccctgcctgtcagtcttggagatcaagcctccatctcttg
c

```
(amino acids)
                                                      (SEQ ID NO: 461)
DVLMTQTPLSLPVSLGDQASISC Mouse C3 light chain variable complementarity determining regions 1
(CDR1) sequence:
(DNA)
                                                      (SEQ ID NO: 462)
agatctagtcagaccattgtacatagtaatggaaacacctatttagaa (amino acids)
                                                      (SEQ ID NO: 463)
RSSQTIVHSNGNTYLE Mouse C3 light chain variable framework region 2 (FWR2) sequence:
(DNA)
                                                      (SEQ ID NO: 464)
tggtacctgcagaaaccaggccagtctccaaagctcctgatctac (amino acids)
                                                      (SEQ ID NO: 465)
WYLQKPGQSPKLLIY Mouse C3 light chain variable complementarity determining regions 2
(CDR2) sequence:
(DNA)
                                                      (SEQ ID NO: 466)
aaagtttccaaccgatttcct (amino acids)
                                                      (SEQ ID NO: 467)
KVSNRFS Mouse C3 light chain variable framework region 3 (FWR3) sequence:
(DNA)
                                                      (SEQ ID NO: 468)
ggggtcccagacaggttcagtggcagtggatcagggacagatttcacactcaagatcaacagagtgga ggctgaggatctgggagtttattactgc (amino acids)
                                                      (SEQ ID NO: 469)
GVPDRFSGSGSGTDFTLKINRVEAEDLGVYYC Mouse C3 light chain variable complementarity determining regions 3
(CDR3) sequence:
(DNA)
                                                      (SEQ ID NO: 470)
tttcaaggttcacatgttccattcacg (amino acids)
                                                      (SEQ ID NO: 471)
FQGSHVPFT IGKV2-29*03 light chain variable region sequence:
(DNA)
                                                      (SEQ ID NO: 472)
gatattgtgatgacccagactccactctctctgtccgtcacccctggacagccggcctccatctcctg caagtctagtcagagcctcctgcatagtgatggaaagacctatttgtattggtacctgcagaagccag gccagtctccacagctcctgatctatgaagtttccagccggttctctggagtgccagataggttcagt ggcagcgggtcagggacagatttcacactgaaaatcagccgggtggaggctgaggatgttggggttta ttactgcatgcaaggtatacaccttcct (amino acids)
                                                      (SEQ ID NO: 473)
DIVMTQTPLSLSVTPGQPASISCKSSQSLLHSDGKTYLYWYLQKPGQSPQLLIYEVSSRFSGVPDRFS

GSGSGTDFTLKISRVEAEDVGVYYCMQGIHLP
```

-continued

IGKV2-29*03 light chain variable framework region 1 (FWR1) acid
sequence:
(DNA)
(SEQ ID NO: 474)
gatattgtgatgacccagactccactctctctgtccgtcaccctggacagccggcctccatctcctg c (amino acids)
(SEQ ID NO: 475)
DIVMTQTPLSLSVTPGQPAS1SC IGKV2-29*03 light chain variable complementarity determining regions
1 (CDR1) sequence:
(DNA)
(SEQ ID NO: 476)
aagtctagtcagagcctcctgcatagtgatggaaagacctatttgtat (amino acids)
(SEQ ID NO: 477)
KSSQSLLHSDGKTYLY IGKV2-29*03 light chain variable framework region 2 (FWR2) sequence:
(DNA)
(SEQ ID NO: 478)
tggtacctgcagaagccaggccagtctccacagctcctgatctat (amino acids)
(SEQ ID NO: 479)
WYLQKPGQSPQLLIY IGKV2-29*03 light chain variable complementarity determining regions
2 (CDR2) sequence:
(DNA)
(SEQ ID NO: 480)
gaagtttccagccggttc (amino acids)
(SEQ ID NO: 481)
EVSSRFS IGKV2-29*03 light chain variable framework region 3 (FWR3) sequence:
(DNA)
(SEQ ID NO: 482)
ggagtgccagataggttcagtggcagcgggtcagggacagatttcacactgaaaatcagccgggtgga ggctgaggatgttggggtttattactgc (amino acids)
(SEQ ID NO: 483)
GVPDRFSGSGSGTDFTLKISRVEAEDVGVYYC IGKV2-29*03 light chain variable complementarity determining
regions3 (CDR3) sequence:
(DNA)
(SEQ ID NO: 484)
atgcaaggtatacaccttcct (amino acids)
(SEQ ID NO: 485)
MQGIHLP Humanized C3 light chain variable region sequence:
(DNA)
(SEQ ID NO: 486)
gatattgtgatgacccagactccactctctctgtccgtcaccctggacagccggcctccat ctcctgcaggtctagtcagaccattgtccatagtaatggaaacacctatttggagtggtacc tgcagaagccaggccagtctccacagctcctgatctataaggtttccaaccggttctctgga gtgccagataggttcagtggcagcgggtcagggacagatttcacactgaaaatcagccgggt ggaggctgaggatgttggggtttattactgcttccaaggtagccacgtgcctttcaccttcg gcggagggaccaaggtggagatcaaacgaact (amino acids)
(SEQ ID NO: 487)
DIVMTQTPLSLSVTPGQPASISCRSSQTIVHSNGNTYLEWYLQKPGQSPQLLIYKVSNRFSG

VPDRFSGSGSGTDFTLKISRVEAEDVGVYYCFQGSHVPFTFGGGTKVEIKRT

Humanized C3 light chain variable framework region 1 (FWR1)
acid sequence:
(DNA)
(SEQ ID NO: 488)
gatattgtgatgacccagactccactctctctgtccgtcacccctggacagccggcctccat ctcctgc (amino acids)
(SEQ ID NO: 489)
DIVMTQTPLSLSVTPGQPASISC Humanized C3 light chain variable complementarity determining
regions 1 (CDR1) sequence:
(DNA)
(SEQ ID NO: 490)
ggtctagtcagaccattgtccatagtaatggaaacacctatttggag (amino acids)
(SEQ ID NO: 491)
RSSQTIVHSNGNTYLE Humanized C3 light chain variable framework region 2 (FWR2) acid
sequence:
(DNA)
(SEQ ID NO: 492)
tggtacctgcagaagccaggccagtctccacagctcctgatctat (amino acids)
(SEQ ID NO: 493)
WYLQKPGQSPQLLIY Humanized C3 light chain variable complementarity determining
regions 2 (CDR2) sequence:
(DNA)
(SEQ ID NO: 494)
aaggtttccaaccggttctct (amino acids)
(SEQ ID NO: 495)
KVSNRFS Humanized C3 light chain variable framework region 3 (FWR3) acid
sequence:
(DNA)
(SEQ ID NO: 496)
ggagtgccagataggttcagtggcagcgggtcagggacagatttcacactgaaaatcagccgggtgga ggctgaggatgttggggtttattactgc (amino acids)
GVPDRFSGSGSGTDFTLKISRVEAEDVGVYYC
(SEQ ID NO: 497)

Humanized C3 light chain variable complementarity determining
regions 3 (CDR3) sequence:
(DNA)
(SEQ ID NO: 498)
ttccaaggtagccacgtgcctttcacc (amino acids)
(SEQ ID NO: 499)
FQGSHVPFT Humanized C3 lambda light chain sequence
(DNA)
(SEQ ID NO: 500)
gatattgtgatgacccagactccactctctctgtccgtcacccctggacagccggcctccatctcctg caggtctagtcagaccattgtccatagtaatggaaacacctatttggagtggtacctgcagaagccag gccagtctccacagctcctgatctataaggtttccaaccggttctctggagtgccagataggttcagt ggcagcgggtcagggacagatttcacactgaaaatcagccgggtggaggctgaggatgttggggttta

```
ttactgcttccaaggtagccacgtgcctttcaccttcggcggagggaccaaggtggagatcaaacgaa ctggtcagcccaaggctgccccctcggtcactctgttcccgccctcctctgaggagcttcaagccaac aaggccacactggtgtgtctcataagtgacttctacccgggagccgtgacagtggcctggaaggcaga tagcagccccgtcaaggcgggagtggagaccaccacaccctccaaacaaagcaacaacaagtacgcgg ccagcagctatctgagcctgacgcctgagcagtggaagtcccacagaagctacagctgccaggtcacg catgaagggagcaccgtggagaagacagtggcccctacagaatgttcatagtaa
```

(amino acids)

(SEQ ID NO: 501)
DIVMTQTPLSLSVTPGQPASISCRSSQTIVHSNGNTYLEWYLQKPGQSPQLLIYKVSNRFSGVPDRFS

GSGSGTDFTLKISRVEAEDVGVYYCFQGSHVPFTFGGGTKVEIKRTGQPKAAPSVTLFPPSSEELQAN

KATLVCLISDFYPGAVTVAWKADSSPVKAGVETTTPSKQSNNKYAASSYLSLTPEQWKSHRSYSCQVT

HEGSTVEKTVAPTECS**

Humanized C3 Kappa light chain
(DNA)

(SEQ ID NO: 502)
```
gatattgtgatgacccagactccactctctctgtccgtcacccctggacagccggcctccatctcctg caggtctagtcagaccattgtccatagtaatggaaacacctatttggagtggtacctgcagaagccag gccagtctccacagctcctgatctataaggtttccaaccggttctctggagtgccagataggttcagt ggcagcgggtcagggacagatttcacactgaaaatcagccgggtggaggctgaggatgttgggttta ttactgcttccaaggtagccacgtgcctttcaccttcggcggagggaccaaggtggagatcaaacgaa ctacggtggctgcaccatctgtcttcatcttcccgccatctgatgagcagttgaaatctggaactgcc tctgttgtgtgcctgctgaataacttctatcccagagaggccaaagtacagtggaaggtggataacgc cctccaatcgggtaactcccaggagagtgtcacagagcaggacagcaaggacagcacctacagcctca gcagcaccctgacgctgagcaaagcagactacgagaaacacaaagtctacgcctgcgaagtcacccat cagggcctgagctcgcccgtcacaaagagcttcaacaggggagagtgttagtaa
```

(amino acids)

(SEQ ID NO: 503)
DIVMTQTPLSLSVTPGQPASISCRSSQTIVHSNGNTYLEWYLQKPGQSPQLLIYKVSNRFSGVPDRFS

GSGSGTDFTLKISRVEAEDVGVYYCFQGSHVPFTFGGGTKVEIKRTTVAAPSVFIFPPSDEQLKSGTA

SVVCLLNNFYPREAKVQWKVDNALQSGNSQESVTEQDSKDSTYSLSSTLTLSKADYEKHKVYACEVTH

QGLSSPVTKSFNRGEC**

Humanized C3 Kappa light gBLOCK sequence:
(DNA)

(SEQ ID NO: 504)
```
agctggctaggtaagcttggtaccgagctcggatccacgccaccatggagacagacacactc ctgctatgggtactgctgctctgggttccaggttccactggtgacgatattgtgatgaccca gactccactctctctgtccgtcacccctggacagccggcctccatctcctgcaggtctagtc agaccattgtccatagtaatggaaacacctatttggagtggtacctgcagaagccaggccag tctccacagctcctgatctataaggtttccaaccggttctctggagtgccagataggttcag tggcagcgggtcagggacagatttcacactgaaaatcagccgggtggaggctgaggatgttg ggtttattactgcttccaaggtagccacgtgcctttcaccttcggcggagggaccaaggtg gagatcaaacgaactacggtggctgcaccatctgtcttcatcttcccgccatctgatgagca gttgaaatctggaactgcctctgttgtgtgcctgctgaataacttctatcccagagaggcca aagtacagtggaaggtggataacgccctccaatcgggtaactcccaggagagtgtcacagag caggacagcaaggacagcacctacagcctcagcagcaccctgacgctgagcaaagcagacta
```

-continued

```
cgagaaacacaaagtctacgcctgcgaagtcacccatcagggcctgagctcgcccgtcacaa agagcttcaacaggggagagtgttagtaagtttaaacccgctgatcagcctcgactgtgcct tctagttgc
```

Mouse C8 heavy chain variable region sequence
(DNA)
(SEQ ID NO: 505)
```
gaagtgatggtcgtggaaagcggcggtggtctggtaaagccggggggatcccttaagctttc ttgcgccgcatccgggttcacgttctccggctatgccatgtcctgggtccgacagactcccg aaaagcgcttggaatgggtggccactatctcctccggggggacgtacatctactaccccgac agtgtgaaaggaagatttacaatatctcgcgacaacgcaaaaaataccttgtatcttcaaat gagctccctgcggtcagaggacactgccatgtactattgcgcccgcctgggcggcgacaatt actatgagtat
```

(amino acids)
(SEQ ID NO: 506)
EVMVVESGGGIVKPGGSLKLSCAASGFTFSGYAMSWVRQTPEKRLEWVATISSGGTYIYYPDS
VKGRFTISRDNAKNTLYLQMSSLRSEDTAMYYCARLGGDNYYEY Mouse C8 heavy chain variable complementarity determining region 1
(CDR1) sequence:
(DNA)
(SEQ ID NO: 507)
ggctatgccatgtcc (amino acids)
(SEQ ID NO: 508)
GYAMS Mouse C8 heavy chain variable complementarity determining region 2
(CDR2) sequence:
(DNA)
(SEQ ID NO: 509)
actatctcctccggggggacgtacatctactaccccgacagtgtgaaagga (amino acids)
(SEQ ID NO: 510)
TISSGGTYIYYPDSVKG Mouse C8 heavy chain variable complementarity determining region 3
(CDR3) sequence:
(DNA)
(SEQ ID NO: 511)
ctgggcggcgacaattactatgagtat (amino acids)
(SEQ ID NO: 512)
LGGDNYYEY IGHV3-21*04 heavy chain variable region sequence:
(DNA)
(SEQ ID NO: 513)
```
gaggtgcagctggtggagtctgggggaggcctggtcaagcctggggggtccctgagactctc ctgtgcagcctctggattcaccttcagtagctatagcatgaactgggtccgccaggctccag ggaaggggctggagtgggtctcatccattagtagtagtagtagttacatatactacgcagac tcagtgaagggccgattcaccatctccagagacaacgccaagaactcactgtatctgcaaat gaacagcctgagagccgaggacacggccgtgtattactgtcga
```

(amino acids)
(SEQ ID NO: 514)
EVQLVESGGGLVKPGGSLRLSCAASGFTFSSYSMNWVRQAPGKGLEWVSSISSSSSYIYYADSVKGRF
TISRDNAKNSLYLQMNSLRAEDTAVYYCAR

```
IGHV3-21*04 heavy chain variable framework region 1 (FWR1) sequence:
(DNA)
                                                      (SEQ ID NO: 515)
gaggtgcagctggtggagtctggggGaggcctggtcaagcctggggggtccctgagactctcctgtgc agcctctggattcaccttcagt (amino acids)
                                                      (SEQ ID NO: 516)
EVQLVESGGGLVKPGGSLRLSCAASGFTFS IGHV3-21*04 heavy chain variable complementarity determining regions
1 (CDR1) sequence:
(DNA)
                                                      (SEQ ID NO: 517)
agctatagcatgaac (amino acids)
                                                      (SEQ ID NO: 518)
SYSMN IGHV3-21*04 heavy chain variable framework region 2 (FWR2) sequence:
(DNA)
tgggtccgccaggctccagggaaggggctggagtgggtc
                                                      (SEQ ID NO: 519)

(amino acids)
                                                      (SEQ ID NO: 520)
WVRQAPGKGLEWV IGHV3-21*04 heavy chain variable complementarity determining regions
2 (CDR2) sequence:
(DNA)
                                                      (SEQ ID NO: 521)
tcatccattagtagtagtagtagttacatatactacgcagactcagtgaagggc (amino acids)
                                                      (SEQ ID NO: 522)
SSISSSSSYIYYADSVKG IGHV3-21*04 heavy chain variable framework region 3 (FWR3) sequence:
(DNA)
                                                      (SEQ ID NO: 523)
cgattcaccatctccagagacaacgccaagaactcactgtatctgcaaatgaacagcctgagagccga ggacacggccgtgtattactgtgcga (amino acids)
                                                      (SEQ ID NO: 524)
RFTISRDNAKNSLYLQMNSLRAEDTAVYYCAR Humanized C8 heavy chain variable region sequence:
(DNA)
                                                      (SEQ ID NO: 525)
gaggtgcagctggtggagtctggggGaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactgggcggcgataactattatgaatattggggcaaagggaccacgg tcaccgtctcctcc (amino acids)
                                                      (SEQ ID NO: 526)
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSS

Humanized C8 heavy chain variable framework region 1 (FWR1)
sequence:
(DNA)
                                                      (SEQ ID NO: 527)
gaggtgcagctggtggagtctggggGaggcctggtcaagcctggggggtccctgagactctcctgtgc agcctctggattcaccttcagt
```

-continued (amino acids)

(SEQ ID NO: 528)

EVQLVESGGGLVKPGGSLRLSCAASGFTFS

Humanized C8 heavy chain variable complementarity determining region 1 (CDR1) sequence:
(DNA)

(SEQ ID NO: 529)

ggctatgccatgagc (amino acids)

(SEQ ID NO: 530)

GYAMS

Humanized C8 heavy chain variable framework region 2 (FWR2) sequence:
(DNA)

(SEQ ID NO: 531)

tgggtccgccaggctccagggaaggggctggagtgggtctca (amino acids)

(SEQ ID NO: 532)

WVRQAPGKGLEWVS

Humanized C8 heavy chain variable complementarity determining region 2 (CDR2) sequence:
(DNA)

(SEQ ID NO: 533)

accattagtagtggcggaacctacatatactaccctgactcagtgaagggc (amino acids)

(SEQ ID NO: 534)

TISSGGTYIYYPDSVKG

Humanized C8 heavy chain variable framework region 3 (FWR3) sequence:
(DNA)

(SEQ ID NO: 535)

cgattcaccatctccagagacaacgccaagaactcactgtatctgcaaatgaacagcctgagagccga ggacacggccgtgtattactgtgcgaga (amino acids)

(SEQ ID NO: 536)

RFTISRDNAKNSLYLQMNSLRAEDTAVYYCAR

Humanized C8 heavy chain variable complementarity determining region 3 (CDR3) sequence:
(DNA)

(SEQ ID NO: 537)

ctgggcggcgataactattatgaatat (amino acids)

(SEQ ID NO: 538)

LGGDNYYEY

Humanized C8 IgG1 heavy chain sequence
(DNA)

(SEQ ID NO: 539)

gaggtgcagctggtggagtctggggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactgggcggcgataactattatgaatattggggcaaagggaccacgg tcaccgtctcctcggctagcaccaagggcccatcggtcttccccctggcaccctcctccaagagcacc tctgggggcacagcggccctgggctgcctggtcaaggactacttccccgaaccggtgacggtgtcgtg gaactcaggcgccctgaccagcggcgtgcacaccttcccggctgtcctacagtcctcaggactctact ccctcagcagcgtggtgacagtgccctccagcagcttgggcacccagacctacatctgcaacgtgaat cacaagcccagcaacaccaaggtggacaagaaagttgagcccaaatcttgtgacaaaactcacacatg cccaccgtgcccagcacctgaactcctggggggaccgtcagtcttcctcttccccccaaaacccaagg

```
acaccctcatgatctcccggacccctgaggtcacatgcgtggtggtggacgtgagccacgaagaccct gaggtcaagttcaactggtacgtggacggcgtggaggtgcataatgccaagacaaagccgcgggagga gcagtacaacagcacgtaccgtgtggtcagcgtcctcaccgtcctgcaccaggactggctgaatggca aggagtacaagtgcaaggtctccaacaaagccctcccagcccccatcgagaaaaccatctccaaagcc aaagggcagccccgagaaccacaggtgtacaccctgcccccatcccgggaggagatgaccaagaacca ggtcagcctgacctgcctggtcaaaggcttctatcccagcgacatcgccgtggagtgggagagcaatg ggcagccggagaacaactacaagaccacgcctcccgtgctggactccgacggctccttcttcctctac agcaagctcaccgtggacaagagcaggtggcagcaggggaacgtcttctcatgctccgtgatgcatga ggctctgcacaaccactacacgcagaagagcctctccctgtctccgggtaaatgataa
```

(amino acids)
(SEQ ID NO: 540)

```
EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSASTKGPSVFPLAPSSKST

SGGTAALGCLVKDYFPEPVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDSDGSFFLY

SKLTVDKSRWQQGNVFSCSVMHEALHNHYTQKSLSLSPGK**
```

Humanized C8 IgG2 heavy chain sequence
(DNA)
(SEQ ID NO: 541)

```
gaggtgcagctggtggagtctgggggaggcctggtcaagcctggggggtccctgagactctcctgtgc agcctctggattcaccttcagtggctatgccatgagctgggtccgccaggctccagggaaggggctgg agtgggtctcaaccattagtagtggcggaacctacatatactaccctgactcagtgaagggccgattc accatctccagagacaacgccaagaactcactgtatctgcaaatgaacagcctgagagccgaggacac ggccgtgtattactgtgcgagactggcggcgataactattatgaatattggggcaaagggaccacgg tcaccgtctcctccgcctccaccaagggcccatcggtcttccccctggcgccctgctccaggagcacc tccgagagcacagccgccctgggctgcctggtcaaggactacttccccgaaccggtgacggtgtcgtg gaactcaggcgctctgaccagcggcgtgcacaccttcccagctgtcctacagtcctcaggactctact ccctcagcagcgtggtgaccgtgccctccagcaacttcggcacccagacctacacctgcaacgtagat cacaagcccagcaacaccaaggtggacaagacagttgagcgcaaatgttgtgtcgagtgcccaccgtg cccagcaccacctgtggcaggaccgtcagtcttcctcttccccccaaaacccaaggacaccctcatga tctcccggacccctgaggtcacgtgcgtggtggtggacgtgagccacgaagaccccgaggtccagttc aactggtacgtggacggcgtggaggtgcataatgccaagacaaagccacgggaggagcagttcaacag cacgttccgtgtggtcagcgtcctcaccgttgtgcaccaggactggctgaacggcaaggagtacaagt gcaaggtctccaacaaaggcctcccagcccccatcgagaaaaccatctccaaaaccaaagggcagccc cgagaaccacaggtgtacaccctgcccccatcccgggaggagatgaccaagaaccaggtcagcctgac ctgcctggtcaaaggcttctaccccagcgacatcgccgtggagtgggagagcaatgggcagccggaga acaactacaagaccacacctcccatgctggactccgacggctccttcttcctctacagcaagctcacc gtggacaagagcaggtggcagcaggggaacgtcttctcatgctccgtgatgcatgaggctctgcacaa ccactacacgcagaagagcctctccctgtctccgggtaaatagtaa
```

(amino acids)

(SEQ ID NO: 542)

EVQLVESGGGLVKPGGSLRLSCAASGFTFSGYAMSWVRQAPGKGLEWVSTISSGGTYIYYPDSVKGRF

TISRDNAKNSLYLQMNSLRAEDTAVYYCARLGGDNYYEYWGKGTTVTVSSASTKGPSVFPLAPCSRST

SESTAALGCLVKDYFPEPVTVSWNSGALTSGVHTFPAVLQSSGLYSLSSVVTVPSSNFGTQTYTCNVD

HKPSNTKVDKTVERKCCVECPPCPAPPVAGPSVFLFPPKPKDTLMISRTPEVTCVVVDVSHEDPEVQF

NWYVDGVEVHNAKTKPREEQFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYKTTPPMLDSDGSFFLYSKLT

VDKSRWQQGNVFSCSVMHEALHNHYTQKSLSLSPGK**

Mouse C8 light chain variable region sequence
(DNA)

(SEQ ID NO: 543)

gacatcgtcattacgcagacccctgccagtcttgccgtttctctgggccagagggccactatcagtta cagggcgagtaagtctgtgagtaccagcggctatagttacatgcattggaaccagcagaaaccgggac agccaccacgcctgcttatttatctggtgtctaatcttgagtccggggtgcccgccaggttcagcggc agcggctctgggaccgacttcacactcaacattcatccagtggaagaagaggacgctgctacatacta ctgtcaacacattcgggaactgaccaggagtgaa (amino acids)

(SEQ ID NO: 544)

DIVITQTPASLAVSLGQRATISYRASKSVSTSGYSYMHWNQQKPGQPPRLLIYLVSNLESGV

PARFSGSGSGTDFTLNIHPVEEEDAATYYCQHIRELTRSE

Mouse C8 light chain variable complementarity determining region 1
(CDR1) sequence:
(DNA)

(SEQ ID NO: 545)

agggcgagtaagtctgtgagtaccagcggctatagttacatgcat (amino acids)

(SEQ ID NO: 546)

RASKSVSTSGYSYMH

Mouse C8 light chain variable complementarity determining region 2
(CDR2) sequence:
(DNA)

(SEQ ID NO: 547)

ctggtgtctaatcttgagtcc (amino acids)

(SEQ ID NO: 548)

LVSNLES

Mouse C8 light chain variable complementarity determining region 3
(CDR3) sequence:
(DNA)

(SEQ ID NO: 549)

caacacattcgggaactgaccaggagtgaa (amino acids)

(SEQ ID NO: 550)

QHIRELTRSE

NCBI germline z00023 light chain variable region sequence:
(DNA)

(SEQ ID NO: 551)

gacatcgtgatgacccagtctccagactccctggctgtgtctctgggcgagagggccaccatcaactg caagtccagccagagtgttttatacagctccaacaataagaactacttagcttggtaccagcagaaac caggacagcctcctaagctgctcatttactgggcatctacccgggaatccggggtccctgaccgattc agtggcagcgggtctgggacagatttcactctcaccatcagcagcctgcaggctgaagatgtggcagt ttattactgtcagcaatattatagtactcct

```
(amino acids)
                                                     (SEQ ID NO: 552)
DIVMTQSPDSLAVSLGERATINCKSSQSVLYSSNNKNYLAWYQQKPGQPPKLLIYWASTRESGVPDRF

SGSGSGTDFTLTISSLQAEDVAVYYCQQYYSTP

NCBI germline z00023 light chain variable framework region 1 (FWR1)
acid sequence:
(DNA)
                                                     (SEQ ID NO: 553)
gacatcgtgatgacccagtctccagactccctggctgtgtctctgggcgagagggccaccatcaactg c (amino acids)
                                                     (SEQ ID NO: 554)
DIVMTQSPDSLAVSLGERATINC NCBI germline z00023 light chain variable complementarity
determining regions 1 (CDR1) sequence:
(DNA)
                                                     (SEQ ID NO: 555)
aagtccagccagagtgttttatacagctccaacaataagaactacttagct (amino acids)
                                                     (SEQ ID NO: 556)
KSSQSVLYSSNNKNYLA NCBI germline z00023 light chain variable framework region 2 (FWR2)
sequence:
(DNA)
                                                     (SEQ ID NO: 557)
tggtaccagcagaaaccaggacagcctcctaagctgctcatttac (amino acids)
                                                     (SEQ ID NO: 558)
WYQQKPGQPPKLLIY NCBI germline z00023 light chain variable complementarity
determining regions 2 (CDR2) sequence:
(DNA)
                                                     (SEQ ID NO: 559)
tgggcatctacccgggaatcc (amino acids)
                                                     (SEQ ID NO: 560)
WASTRES NCBI germline z00023 light chain variable framework region 3 (FWR3)
sequence:
(DNA)
                                                     (SEQ ID NO: 561)
ggggtccctgaccgattcagtggcagcgggtctgggacagatttcactctcaccatcagcagcctgca ggctgaagatgtggcagtttattactgt (amino acids)
                                                     (SEQ ID NO: 562)
GVPDRFSGSGSGTDFTLTISSLQAEDVAVYYC NCBI germline z00023 light chain variable complementarity
determining regions3 (CDR3) sequence:
(DNA)
                                                     (SEQ ID NO: 563)
cagcaatattatagtactcct (amino acids)
                                                     (SEQ ID NO: 564)
QQYYSTP Humanized C8 light chain variable region sequence
(DNA)
                                                     (SEQ ID NO: 565)
gacatcgtgatgacccagtctccagactccctggctgtgtctctgggcgagagggccaccat caactgcagggccagcaagagtgttagcaccagcggctacagctacatgcactggtaccagc agaaaccaggacagcctcctaagctgctcatttacctggtgtctaacctggaatccggggtc cctgaccgattcagtggcagcgggtctgggacagatttcactctcaccatcagcagcctgca
```

```
ggctgaagatgtggcagtttattactgtcaacacattcgggaactgaccaggagtgaattcg gcggagggaccaaggtggagatcaaacgaact
```

(amino acids)

(SEQ ID NO: 566)

DIVMTQSPDSLAVSLGERATINCRASKSVSTSGYSYMHWYQQKPGQPPKLLIYLVSNLESGV

PDRFSGSGSGTDFTLTISSLQAEDVAVYYCQHIRELTRSEFGGGTKVEIKRT

Humanized C8 light chain variable framework region 1 (FWR1)
sequence:
(DNA)

(SEQ ID NO: 567)

```
gacatcgtgatgacccagtctccagactccctggctgtgtctctgggcgagagggccaccat caactgc
```

(amino acids)

(SEQ ID NO: 568)

DIVMTQSPDSLAVSLGERATINC

Humanized C8 light chain variable complementarity determining region
1 (CDR1) sequence:
(DNA)

(SEQ ID NO: 569)

```
agggccagcaagagtgttagcaccagcggctacagctacatg
```

(amino acids)

(SEQ ID NO: 570)

RASKSVSTSGYSYM

Humanized C8 light chain variable framework region 2 (FWR2)
sequence:
(DNA)

(SEQ ID NO: 571)

```
cactggtaccagcagaaaccaggacagcctcctaagctgctcatttac
```

(amino acids)

(SEQ ID NO: 572)

HWYQQKPGQPPKLLIY

Humanized C8 light chain variable complementarity determining region
2 (CDR2) sequence:
(DNA)

(SEQ ID NO: 573)

```
ctggtgtctaacctggaatcc
```

(amino acids)

(SEQ ID NO: 574)

LVSNLES

Humanized C8 light chain variable framework region 3 (FWR3)
sequence:
(DNA)

(SEQ ID NO: 575)

```
ggggtccctgaccgattcagtggcagcgggtctgggacagatttcactctcaccatcagcagcctgca ggctgaagatgtggcagtttattactgt
```

(amino acids)

(SEQ ID NO: 576)

GVPDRFSGSGSGTDFTLTISSLQAEDVAVYYC

Humanized C8 light chain variable complementarity determining region
3 (CDR3) sequence:
(DNA)

(SEQ ID NO: 577)

```
caacacattcgggaactgaccaggagtgaa
```

(amino acids)

(SEQ ID NO: 578)

QHIRELTRSE

Humanized C8 Lambda light chain sequence
(DNA)

(SEQ ID NO: 579)

```
gacatcgtgatgacccagtctccagactccctggctgtgtctctgggcgagagggccaccatcaactg cagggccagcaagagtgttagcaccagcggctacagctacatgcactggtaccagcagaaaccaggac
```

-continued agcctcctaagctgctcatttacctggtgtctaacctggaatccggggtccctgaccgattcagtggc agcgggtctgggacagatttcactctcaccatcagcagcctgcaggctgaagatgtggcagtttatta ctgtcaacacattcgggaactgaccaggagtgaattcggcggagggaccaaggtggagatcaaacgaa ctggtcagcccaaggctgcccctcggtcactctgttcccgcctcctctgaggagcttcaagccaac aaggccacactggtgtgtctcataagtgacttctacccgggagccgtgacagtggcctggaaggcaga tagcagccccgtcaaggcgggagtggagaccaccacacctccaaacaaagcaacaacaagtacgcgg ccagcagctatctgagcctgacgcctgagcagtggaagtcccacagaagctacagctgccaggtcacg catgaagggagcaccgtggagaagacagtggcccctacagaatgttcatagtaa (amino acids)

(SEQ ID NO: 580)
DIVMTQSPDSLAVSLGERATINCRASKSVSTSGYSYMHWYQQKPGQPPKLLIYLVSNLESGVPDRFSG

SGSGTDFTLTISSLQAEDVAVYYCQHIRELTRSEFGGGTKVEIKRTGQPKAAPSVTLFPPSSEELQAN

KATLVCLISDFYPGAVTVAWKADSSPVKAGVETTTPSKQSNNKYAASSYLSLTPEQWKSHRSYSCQVT

HEGSTVEKTVAPTECS**

Humanized C8 Kappa light chain sequence
(DNA)

(SEQ ID NO: 581)
gacatcgtgatgacccagtctccagactccctggctgtgtctctgggcgagagggccaccatcaactg cagggccagcaagagtgttagcaccagcggctacagctacatgcactggtaccagcagaaaccaggac agcctcctaagctgctcatttacctggtgtctaacctggaatccggggtccctgaccgattcagtggc agcgggtctgggacagatttcactctcaccatcagcagcctgcaggctgaagatgtggcagtttatta ctgtcaacacattcgggaactgaccaggagtgaattcggcggagggaccaaggtggagatcaaacgaa ctacggtggctgcaccatctgtcttcatcttcccgccatctgatgagcagttgaaatctggaactgcc tctgttgtgtgcctgctgaataacttctatcccagagaggccaaagtacagtggaaggtggataacgc cctccaatcgggtaactcccaggagagtgtcacagagcaggacagcaaggacagcacctacagcctca gcagcaccctgacgctgagcaaagcagactacgagaaacacaaagtctacgcctgcgaagtcacccat cagggcctgagctcgcccgtcacaaagagcttcaacaggggagagtgttagtaa (amino acids)

(SEQ ID NO: 582)
DIVMTQSPDSLAVSLGERATINCRASKSVSTSGYSYMHWYQQKPGQPPKLLIYLVSNLESGVPDRFSG

SGSGTDFTLTISSLQAEDVAVYYCQHIRELTRSEFGGGTKVEIKRTTVAAPSVFIFPPSDEQLKSGTA

SVVCLLNNFYPREAKVQWKVDNALQSGNSQESVTEQDSKDSTYSLSSTLTLSKADYEKHKVYACEVTH

QGLSSPVTKSFNRGEC**

Humanized C8 Kappa light chain gBLOCk sequence:
(DNA)

(SEQ ID NO: 583)
agctggctaggtaagcttggtaccgagctcggatccacgccaccatggagacagacacactcctgcta tgggtactgctgctctgggttccaggttccactggtgacgacatcgtgatgacccagtctccagactc cctggctgtgtctctgggcgagagggccaccatcaactgcagggccagcaagagtgttagcaccagcg gctacagctacatgcactggtaccagcagaaaccaggacagcctcctaagctgctcatttacctggtg tctaacctggaatccggggtccctgaccgattcagtggcagcgggtctgggacagatttcactctcac catcagcagcctgcaggctgaagatgtggcagtttattactgtcaacacattcgggaactgaccagga gtgaattcggcggagggaccaaggtggagatcaaacgaactacggtggctgcaccatctgtcttcatc ttcccgccatctgatgagcagttgaaatctggaactgcctctgttgtgtgcctgctgaataacttcta tcccagagaggccaaagtacagtggaaggtggataacgccctccaatcgggtaactcccaggagagtg -continued tcacagagcaggacagcaaggacagccacctacagcctcagcagcaccctgacgctgagcaaagcagac tacgagaaacacaaagtctacgcctgcgaagtcacccatcagggcctgagctcgcccgtcacaaagag cttcaacaggggagagtgttagtaagtttaaacccgctgatcagcctcgactgtgccttctagttgc CAR-T E6 CD8 sequence:
(DNA)

(SEQ ID NO: 584)

gaggtccagctggttgagagtggcggtgggctggttaagcctggcggctccctgcggctgagctgcgc cgcgagtggatttactttcagccgatatgggatgagttgggtgcggcaagctcccgggaagaggctgg aatgggtctcaacaatctccggggggggcacttacatctattaccccgactcagtcaaggggagattt accatttcacgagacaacgctaagaatacccgtatttgcagatgaattctctgagagcagaggacac agctgtttactattgtacccgcgacaactatggcaggaactacgactacggtatggactattgggac aagggacattggttacagtgagcagtggcggcgggggcagcggaggaggaggcagcggtggggggggc agcgagatagtgctcacgcagtcacccgcgactctcagtctctcacctggggaacgagctaccctgac gtgctctgctacctcctcagtgtcatatattcactggtatcagcaacggcccgggcagtcccctagat tgctcatttatagtacctctaatctggcctcaggtatccctgcacgattttctggatctggttcaggt tctgattacaccctcactatctctagcctggagcctgaagactttgccgtttattactgccagcagag gtctagctccccattcacctttgggagtgggaccaaggttgaaattaaaacgacaaccccggcccca gaccaccaacgccagccccaccatcgccagccaaccctgtctctgagaccagaagcctgtaggcct gccgccggtggagctgtgcacacaagaggactggatttcgcctgtgatatctacatttgggcccgct cgcaggcacatgtggagtgctcctcctctccctggtgattaccctgtactgctgataa (amino acids)

(SEQ ID NO: 585)

EVQLVESGGGLVKPGGSLRLSCAASGFTFSRYGMSWVRQAPGKRLEWVSTISGGGTYIYYPD

SVKGRFTISRDNAKNTLYLQMNSLRAEDTAVYYCTRDNYGRNYDYGMDYWGQTLVTVSSGG

GGSGGGGSGGGGSEIVLTQSPATLSLSPGERATLTCSATSSVSYIHWYQQRPGQSPRLLIYS

TSNLASGIPARFSGSGSGSDYTLTISSLEPEDFAVYYCQQRSSSPFTFGSGTKVEIKTTTPA

PRPPTPAPTIASQPLSLRPEACRPAAGGAVHTRGLDFACDIYIWAPLAGTCGVLLLSLVITL

YC**

CAR-T C2 CD8 sequence:
(DNA)

(SEQ ID NO: 586)

gaagtgcagctcgtagagagtggcggggggactggtgaagcccggtggaagcctcagactcag ttgcgccgcctcaggttttcacttttcaggttacgccatgtcctgggtaagacaggcaccgg ggaaaggactcgagtgggtgtctactatcagctcaggaggcacttatatatattatcctgac tctgtaaaaggccgatttacgatttctcgcgacaatgcaaagaactccctctacctccaaat gaacagtcttagggcagaagacactgctgtatactattgtgcacgcctcggcggcgacaact actacgagtactttgacgtgtgggggaaagggactaccgtgacagtttcaagcggaggaggt ggctcaggtggaggcgggtcagggggggaggaagtgatattgtgctcacacaatccccagc ctccctggctgtgtctcccggccaacgcgctacaattacatgtcgggcctccaaaagcgtga gcaccagcggctacagctacatgcactggtatcaacagaaaccaggacaaccccccaaactg ttgatttatctcgcttcaaacttggagtccggcgtgcctgcgcgcttttcagggagtgggag cggcacagattttacgctgactatcaacccgtagaagcaaacgatacagcgaattattatt gtcaacattcccgggaactccccttacgttcggcggggcacaaaggtcgaaattaagaga accacgacaaccccggcccccagaccaccaacgccagcccccaccatcgccagccaacccct gtctctgagaccagaagcctgtaggcctgccgccggtggagctgtgcacacaagaggactgg -continued atttcgcctgtgatatctacatttgggccccgctcgcaggcacatgtggagtgctcctcctc tccctggtgattaccctgtactgctgataa (amino acids)

(SEQ ID NO: 587)

EVQLVESGGGLVKPGGSLRLSCAASGFTFSGYAMSWVRQAPGKGLEWVSTISSGGTYIYYPD

SVKGRFTISRDNAKNSLYLQMNSLRAEDTAVYYCARLGGDNYYEYFDVWGKGTTVTVSSGGG

GSGGGGSGGGGSDIVLTQSPASLAVSPGQRATITCRASKSVSTSGYSYMHWYQQKPGQPPKL

LIYLASNLESGVPARFSGSGSGTDFTLTINPVEANDTANYYCQHSRELPFTFGGGTKVEIKR

TTTTPAPRPPTPAPTIASQPLSLRPEACRPAAGGAVHTRGLDFACDIYIWAPLAGTCGVLLL

SLVITLYC**

CD8/4-1BB sequence
(DNA)

(SEQ ID NO: 588)

acgacaaccccggcccccagaccaccaacgccagcccccaccatcgccagccaacccctgtc tctgagaccagaagcctgtaggcctgccgccggtggagctgtgcacacaagaggactggatt cgcctgtgatatctacatttgggccccgctcgcaggcacatgtggagtgctcctcctctcc ctggtgattaccctgtactgcaaaaggggccgcaaaaaactcctttacatttttaagcagcc ttttatgaggccagtacagacgactcaagaggaagacgggtgctcatgccgctttcctgagg aggaggaaggagggtgcgaactgtgataa (amino acids)

(SEQ ID NO: 589)

TTTPAPRPPTPAPTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCEL**

CD8/CD28 sequence
(DNA)

(SEQ ID NO: 590)

acgacaaccccggcccccagaccaccaacgccagcccccaccatcgccagccaacccctgtc tctgagaccagaagcctgtaggcctgccgccggtggagctgtgcacacaagaggactggatt cgcctgtgatatctacatttgggccccgctcgcaggcacatgtggagtgctcctcctctcc ctggtgattaccctgtactgcagaagcaagcggtctcggctcctgcattctgattacatgaa catgaccccaagaagaccaggccccaccaggaaacattaccagccctacgctccgccacgcg acttcgctgcctaccggtcctgataa (amino acids)

(SEQ ID NO: 591)

TTTPAPRPPTPAPTIASQPLSLRPEACRPAAGGAVHTRGLDFACDIYIWAPLAGTCGVLLLS

LVITLYCRSKRSRLLHSDYMNMTPRRPGPTRKHYQPYAPPRDFAAYRS**

CD8/CD3z sequence:
(DNA)

(SEQ ID NO: 592)

acgacaaccccggcccccagaccaccaacgccagcccccaccatcgccagccaacccctgtc tctgagaccagaagcctgtaggcctgccgccggtggagctgtgcacacaagaggactggatt cgcctgtgatatctacatttgggccccgctcgcaggcacatgtggagtgctcctcctctcc ctggtgattaccctgtactgccgcgttaagttctcccgatcagccgacgcgcctgcttacaa gcagggccagaaccaactgtacaacgagctgaatctcggtagacgggaagagtacgacgtgt tggacaaacggagaggccgcgacccagaaatgggcggcaagcctcgcaggaaaaaccccag gagggactgtacaatgagttgcagaaagataagatggcagaagcttatagcgagatcggaat gaaggggaaaggagacgagggaaaggacacgacggcctttatcagggcctgtccacagcaa caaaagatacgtatgacgccctccatatgcaggcacttccaccacggtgataa -continued (amino acids) (SEQ ID NO: 593)

TTTPAPRPPTPAPTIASQPLSLRPEACRPAAGGAVHTRGLDFACDIYIWAPLAGTCGVLLLS

LVITLYCRVKFSRSADAPAYKQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALPPR**

CD8/CD28/CD3z sequence:
(DNA) (SEQ ID NO: 594)

acgacaaccccggcccccagaccaccaacgccagcccccaccatcgccagccaacccctgtc tctgagaccagaagcctgtaggcctgccgccggtggagctgtgcacacaagaggactggatt tcgcctgtgatatctacatttgggccccgctcgcaggcacatgtggagtgctcctcctctcc ctggtgattacccctgtactgcagaagcaagcggtctcggctcctgcattctgattacatgaa catgaccccaagaagaccaggccccaccaggaaacattaccagccctacgctccgccacgcg acttcgctgcctaccggtcccgcgttaagttctcccgatcagccgacgcgcctgcttacaag cagggccagaaccaactgtacaacgagctgaatctcggtagacgggaagagtacgacgtgtt ggacaaacggagaggccgcgacccagaaatgggcggcaagcctcgcaggaaaaaccccagg agggactgtacaatgagttgcagaaagataagatggcagaagcttatagcgagatcggaatg aaggggaaggagacgagggaaggacacgacggcctttatcagggcctgtccacagcaac aaaagatacgtatgacgccctccatatgcaggcacttccaccacggtgataa (amino acids) (SEQ ID NO: 595)

TTTPAPRPPTPAPTIASQPLSLRPEACRPAAGGAVHTRGLDFACDIYIWAPLAGTCGVLLLS

LVITLYCRSKRSRLLHSDYMNMTPRRPGPTRKHYQPYAPPRDFAAYRSRVKFSRSADAPAYK

QGQNQLYNELNLGRREEYDVLDKRRGRDPEMGGKPRRKNPQEGLYNELQKDKMAEAYSEIGM

KGERRRGKGHDGLYQGLSTATKDTYDALHMQALPPR**

CD8/4-1BB/CD3z sequence:
(DNA) (SEQ ID NO: 596)

acgacaaccccggcccccagaccaccaacgccagcccccaccatcgccagccaacccctgtc tctgagaccagaagcctgtaggcctgccgccggtggagctgtgcacacaagaggactggatt tcgcctgtgatatctacatttgggccccgctcgcaggcacatgtggagtgctcctcctctcc ctggtgattacccctgtactgcaaaaggggccgcaaaaaaactcctttacattttttaagcagcc ttttatgaggccagtacagacgactcaagaggaagacgggtgctcatgccgctttcctgagg aggaggaaggagggtgcgaactgcgcgttaagttctcccgatcagccgacgcgcctgcttac aagcagggccagaaccaactgtacaacgagctgaatctcggtagacgggaagagtacgacgt gttggacaaacggagaggccgcgacccagaaatgggcggcaagcctcgcaggaaaaacccc aggagggactgtacaatgagttgcagaaagataagatggcagaagcttatagcgagatcgga atgaaggggaaggagacgagggaaggacacgacggcctttatcagggcctgtccacagc aacaaaagatacgtatgacgccctccatatgcaggcacttccaccacggtgataa (amino acids) (SEQ ID NO: 597)

TTTPAPRPPTPAPTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELRVKFSRSADAPAY

KQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR**

CD8/CD28/4-1BB/CD3z sequence:
(DNA)

(SEQ ID NO: 598)

acgacaaccccggcccccagaccaccaacgccagcccccaccatcgccagccaacccctgtc tctgagaccagaagcctgtaggcctgccgccggtggagctgtgcacacaagaggactggatt tcgcctgtgatatctacatttgggccccgctcgcaggcacatgtggagtgctcctcctctcc ctggtgattaccctgtactgcagaagcaagcggtctcggctcctgcattctgattacatgaa catgaccccaagaagaccaggccccaccaggaaacattaccagccctacgctccgccacgcg acttcgctgcctaccggtccaaaaggggccgcaaaaaactcctttacattttttaagcagcct tttatgaggccagtacagacgactcaagaggaagacgggtgctcatgccgctttcctgagga ggaggaaggagggtgcgaactgcgcgttaagttctcccgatcagccgacgcgcctgcttaca agcagggccagaaccaactgtacaacgagctgaatctcggtagacgggaagagtacgacgtg ttggacaaacggagaggccgcgacccagaaatgggcggcaagcctcgcaggaaaaaccccca ggaggactgtacaatgagttgcagaaagataagatggcagaagcttatagcgagatcggaa tgaaggggaaggagacgagggaaaggacacgacggcctttatcagggcctgtccacagca acaaaagatacgtatgacgccctccatatgcaggcacttccaccacggtgataa (amino acids)

(SEQ ID NO: 599)

TTTPAPRPPTPAPTIASQPLSLRPEACRPAAGGAVHTRGLDFACDIYIWAPLAGTCGVLLLS

LVITLYCRSKRSRLLHSDYMNMTPRRPGPTRKHYQPYAPPRDFAAYRSKRGRKKLLYIFKQP

FMRPVQTTQEEDGCSCRFPEEEEGGCELRVKFSRSADAPAYKQGQNQLYNELNLGRREEYDV

LDKRRGRDPEMGGKPRRKNPQEGLYNELQKDKMAEAYSEIGMKGERRRGKGHDGLYQGLSTA

TKDTYDALHMQALPPR**

CAR-T C3 4-1BB/CD3Z sequence:
(DNA)

(SEQ ID NO: 600)

atggccctgcccgtgaccgctttgctgctcccctggcgctgctgctgcacgccgccaggcc acaggttcagctggtgcagtctggagctgaggtgaagaagcctggggcctcagtgaaggtct cctgcaaggcttctggttacaccttaccgactacgccatgaactgggtgcgacaggcccct ggacaagggcttgagtggatgggagtgatcagcaccttcagcggtaacacaaacttcaacca gaagttcaagggcagagtcaccatgaccacagacacatccacgagcacagcctacatggagc tgaggagcctgagatctgacgacacggccgtgtattactgtgcgagaagcgactactacggc ccatacttcgactactggggccagggcaccaccctgaccgtgtccagcggcggtggcggatc cggcggtggcggatccggcggtggcggatccgatattgtgatgacccagactccactctctc tgtccgtcacccctggacagccggcctccatctcctgcaggtctagtcagaccattgtccat agtaatggaaacacctatttggagtggtacctgcagaagccaggccagtctccacagctcct gatctataaggtttccaaccggttctctggagtgccagataggttcagtggcagcgggtcag ggacagatttcacactgaaaatcagccgggtggaggctgaggatgttggggtttattactgc ttccaaggtagccacgtgcctttcaccttcggcggagggaccaaggtggagatcaaacgaac tacgacaaccccggcccccagaccaccaacgccagcccccaccatcgccagccaacccctgt ctctgagaccagaagcctgtaggcctgccgccggtggagctgtgcacacaagaggactggat ttcgcctgtgatatctacatttgggccccgctcgcaggcacatgtggagtgctcctcctctc cctggtgattaccctgtactgcaaaaggggccgcaaaaaactcctttacattttttaagcagc cttttatgaggccagtacagacgactcaagaggaagacgggtgctcatgccgctttcctgag -continued gaggaggaaggagggtgcgaactgcgcgttaagttctcccgatcagccgacgcgcctgctta caagcagggccagaaccaactgtacaacgagctgaatctcggtagacgggaagagtacgacg tgttggacaaacggagaggccgcgacccagaaatgggcggcaagcctcgcaggaaaaacccc caggagggactgtacaatgagttgcagaaagataagatggcagaagcttatagcgagatcgg aatgaaggggaaggagacgagggaaggacacgacggcctttatcagggcctgtccacag caacaaaagatacgtatgacgccctccatatgcaggcacttccaccacggtgataa (amino acids)

(SEQ ID NO: 601)

QVQLVQSGAEVKKPGASVKVSCKASGYTFTDYAMNWVRQAPGQGLEWMGVISTFSGNTNFNQ

KFKGRVTMTTDTSTSTAYMELRSLRSDDTAVYYCARSDYYGPYFDYWGQGTTLTVSSGGGGS

GGGGSGGGGSDIVMTQTPLSLSVTPGQPASISCRSSQTIVHSNGNTYLEWYLQKPGQSPQLL

IYKVSNRFSGVPDRFSGSGSGTDFTLKISRVEAEDVGVYYCFQGSHVPFTFGGGTKVEIKRT

TTTPAPRPPTPAPTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELRVKFSRSADAPAY

KQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR**

C3 CAR gBLOCK 1 sequence:
(DNA)

(SEQ ID NO: 602)

atccacgctgttttgacctccatagaagattctagagctagctgtagagcttggtaccgagg gccaccatggccctgcccgtgaccgctttgctgctccccctggcgctgctgctgcacgccgc caggccacaggttcagctggtgcagtctggagctgaggtgaagaagcctggggcctcagtga aggtctcctgcaaggcttctggttacacctttaccgactacgccatgaactgggtgcgacag gcccctggacaagggcttgagtggatgggagtgatcagcaccttcagcggtaacacaaactt caaccagaagttcaagggcagagtcaccatgaccacagacacatccacgagcacagcctaca tggagctgaggagcctgagatctgacgacacggccgtgtattactgtgcgagaagcgactac tacggcccatacttcgactactggggccagggcaccaccctgaccgtgtccagcggcggtgg cggatccggcggtggcggatccggcggtggcggatccgatattgtgatgacccagactccac tctctctgt C3 CAR gBLOCK 2 sequence:
(DNA)

(SEQ ID NO: 603)

tattgtgatgacccagactccactctctctgtccgtcacccctggacagccggcctccatct cctgcaggtctagtcagaccattgtccatagtaatggaaacacctatttggagtggtacctg cagaagccaggccagtctccacagctcctgatctataaggttttccaaccggttctctggagt gccagataggttcagtggcagcgggtcagggacagatttcacactgaaaatcagccgggtgg aggctgaggatgttggggtttattactgcttccaaggtagccacgtgcctttcaccttcggc ggagggaccaaggtggagatcaaacgaactacgacaaccccggccccagaccaccaacgcc agcccccaccatcgccagccaacccctgtctctgagaccagaagcctgtaggcctgccgccg gtggagctgtgcacacaagaggactggatttcgcctgtgatatctacatttgggccccgctc gcaggcacatgtg E6 scFV gBLOCK 1 sequence:
(DNA)

(SEQ ID NO: 604)

tgctctgggttccaggttccactggtgacgcggcccagccggccgaggtgcagctggtggag tctgggggaggcctggtcaagcctggggggtccctgagactctcctgtgcagcctctggatt -continued cacct tcagtaggtatggcatgagctgggtccgccaggctccagggaagaggctggagtggg tctcaaccattagtggcggaggcacctacatatactacccagactcagtgaagggccgattc accatctccagagacaacgccaagaacaccctgtatctgcaaatgaacagcctgagagcga ggacacggctgtgtattactgtaccagagataactatggccgcaactatgattatggcatgg attattggggccagggcaccctggtgaccgtgagcagcggcggtggcggatccggcggtggc ggatccggcggtggcggatcc E6 scFV gBLOCK 2 sequence:
(DNA)
(SEQ ID NO: 605)
ggcggtggcggatccggcggtggcggatccggcggtggcggatccgaaattgtgttgacaca gtctccagccaccctgtctttgtctccaggggaaagagccaccctcacctgcagcgccacca gcagtgttagctacatccactggtaccaacagaggcctggccagagccccaggctcctcatc tatagcacctccaacctggccagcggcatcccagccaggttcagtggcagtgggtctgggag cgactacactctcaccatcagcagcctagagcctgaagattttgcagtttattactgtcagc agcgtagcagctcccctttcacctttggcagcggcaccaaagtggaaattaaaaccggtcat catcaccatcaccactgataagtttaaacccgctgatcagcctcgactgtgccttctagt CAR-T C2 CD3z sequence:
(DNA)
(SEQ ID NO: 606)
atggccttgccagtgacggccctgctgctgccattggctcttctgttgcacgctgccaggcctgaagt gcagctcgtagagagtggcgggggactggtgaagcccggtggaagcctcagactcagttgcgccgcct caggtttcacttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtgggggaagggact accgtgacagtttcaagcggaggaggtggctcaggtggaggcgggtcaggggggggaggaagtgatat tgtgctcacacaatccccagcctccctggctgtgtctcccggccaacgcgctacaattacatgtcggg cctccaaaagcgtgagcaccagcggctacagctacatgcactggtatcaacagaaaccaggacaaccc cccaaactgttgatttatctcgcttcaaacttggagtccggcgtgcctgcgcgttttcagggagtgg gagcggcacagattttacgctgactatcaaccccgtagaagcaaacgatacagcgaattattattgtc aacattcccgggaactccctttacgttcggcgggggcacaaaggtcgaaattaagagaaccacgaca accccggccccagaccaccaacgccagcccccaccatcgccagccaaccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgccgc gttaagttctcccgatcagccgacgcgcctgcttacaagcagggccagaaccaactgtacaacgagct gaatctcggtagacgggaagagtacgacgtgttggacaaacggagaggccgcgacccagaaatgggcg gcaagcctcgcaggaaaaaccccaggagggactgtacaatgagttgcagaaagataagatggcagaa gcttatagcgagatcggaatgaagggggaaaggagacagggaaaggacacgacggcctttatcaggg cctgtccacagcaacaaaagatacgtatgacgccctccatatgcaggcacttccaccacggtgataa (amino acids)
(SEQ ID NO: 607)
MALPVTALLLPLALLLHAARPEVQLVESGGGLVKPGGSLRLSCAASGFTFSGYAMSWVRQAP

GKGLEWVSTISSGGTYIYYPDSVKGRFTISRDNAKNSLYLQMNSLRAEDTAVYYCARLGGDN

YYEYFDVWGKGTTVTVSSGGGGSGGGGSGGGGSDIVLTQSPASLAVSPGQRATITCRASKSV

STSGYSYMHWYQQKPGQPPKLLIYLASNLESGVPARFSGSGSGTDFTLTINPVEANDTANYY

CQHSRELPFTFGGGTKVEIKRTTTTPAPRPPTPAPTIASQPLSLRPEACRPAAGGAVHTRGL

DFACDIYIWAPLAGTCGVLLLSLVITLYCRVKFSRSADAPAYKQGQNQLYNELNLGRREEYD

VLDKRRGRDPEMGGKPRRKNPQEGLYNELQKDKMAEAYSEIGMKGERRRGKGHDGLYQGLST

ATKDTYDALHMQALPPR**

CAR-T C2 CD28/CD3z sequence:
(DNA)
(SEQ ID NO: 608)

atggccttgccagtgacggccctgctgctgccattggctcttctgttgcacgctgccaggcctgaagt gcagctcgtagagagtggcgggggactggtgaagcccggtggaagcctcagactcagttgcgccgcct caggtttcactttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtggggaaagggact accgtgacagtttcaagcggaggaggtggctcaggtggaggcgggtcaggggggggaggaagtgatat tgtgctcacacaatccccagcctccctggctgtgtctcccggccaacgcgctacaattacatgtcggg cctccaaaagcgtgagcaccagcggctacagctacatgcactggtatcaacagaaaccaggacaaccc cccaaactgttgatttatctcgcttcaaacttggagtccggcgtgcctgcgcgcttttcagggagtgg gagcggcacagattttacgctgactatcaaccccgtagaagcaaacgatacagcgaattattattgtc aacattcccgggaactccccttacgttcggcggggcacaaaggtcgaaattaagagaaccacgaca accccggccccagaccaccaacgccagccccaccatcgccagccaaccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgcaga agcaagcggtctcggctcctgcattctgattacatgaacatgaccccaagaagaccaggccccaccag gaaacattaccagccctacgctccgccacgcgacttcgctgcctaccggtcccgcgttaagttctccc gatcagccgacgcgcctgcttacaagcagggccagaaccaactgtacaacgagctgaatctcggtaga cgggaagagtacgacgtgttggacaaacggagaggccgcgacccagaaatgggcggcaagcctcgcag gaaaaaccccaggagggactgtacaatgagttgcagaaagataagatggcagaagcttatagcgaga tcggaatgaaggggaaggagacgagggaaaggacacgacggccttatcagggcctgtccacagca acaaaagatacgtatgacgccctccatatgcaggcacttccaccacggtgataa (amino acids)
(SEQ ID NO: 609)

MALPVTALLLPLALLLHAARPEVQLVESGGGLVKPGGSLRLSCAASGFTFSGYAMSWVRQAP

GKGLEWVSTISSGGTYIYYPDSVKGRFTISRDNAKNSLYLQMNSLRAEDTAVYYCARLGGDN

YYEYFDVWGKGTTVTVSSGGGGSGGGGSGGGGSDIVLTQSPASLAVSPGQRATITCRASKSV

STSGYSYMHWYQQKPGQPPKLLIYLASNLESGVPARFSGSGSGTDFTLTINPVEANDTANYY

CQHSRELPFTFGGGTKVEIKRTTTTPAPRPPTPAPTIASQPLSLRPEACRPAAGGAVHTRGL

DFACDIYIWAPLAGTCGVLLLSLVITLYCRSKRSRLLHSDYMNMTPRRPGPTRKHYQPYAPP

RDFAAYRSRVKFSRSADAPAYKQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR**

CAR-T C2 4-1BB/CD3Z sequence:
(DNA)
(SEQ ID NO: 610)
atggccttgccagtgacggccctgctgctgccattggctcttctgttgcacgctgccaggcctgaagt gcagctcgtagagagtggcgggggactggtgaagcccggtggaagcctcagactcagttgcgccgcct -continued

```
caggtttcacttttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtggggaaagggact accgtgacagtttcaagcggaggaggtggctcaggtggaggcgggtcaggggggaggaagtgatat tgtgctcacacaatccccagcctccctggctgtgtctcccggccaacgcgctacaattacatgtcggg cctccaaaagcgtgagcaccagcggctacagctacatgcactggtatcaacagaaaccaggacaaccc cccaaaactgttgatttatctcgcttcaaacttggagtccggcgtgcctgcgcgcttttcagggagtgg gagcggcacagattttacgctgactatcaaccccgtagaagcaaacgatacagcgaattattattgtc aacattcccgggaactccccttttacgttcggcgggggcacaaaggtcgaaattaagagaaccacgaca accccggccccagaccaccaacgccagccccaccatcgccagccaaccccgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgcaaa aggggccgcaaaaaactccttacatttttaagcagccttttatgaggccagtacagacgactcaaga ggaagacgggtgctcatgccgctttcctgaggaggaggaaggagggtgcgaactgcgcgttaagttct cccgatcagccgacgcgcctgcttacaagcagggccagaaccaactgtacaacgagctgaatctcggt agacgggaagagtacgacgtgttggacaaacggagaggccgcgacccagaaatgggcggcaagcctcg caggaaaaaccccaggagggactgtacaatgagttgcagaaagataagatggcagaagcttatagcg agatcggaatgaaggggaaaggagacgagggaaaggacacgacggccttatcagggcctgtccaca gcaacaaaagatacgtatgacgccctccatatgcaggcacttccaccacggtgataa
```

(amino acids)

(SEQ ID NO: 611)

MALPVTALLLPLALLLHAARPEVQLVESGGGLVKPGGSLRLSCAASGFTFSGYAMSWVRQAP
GKGLEWVSTISSGGTYIYYPDSVKGRFTISRDNAKNSLYLQMNSLRAEDTAVYYCARLGGDN
YYEYFDVWGKGTTVTVSSGGGGSGGGGSGGGGSDIVLTQSPASLAVSPGQRATITCRASKSV
STSGYSYMHWYQQKPGQPPKLLIYLASNLESGVPARFSGSGSGTDFTLTINPVEANDTANYY
CQHSRELPFTFGGGTKVEIKRTTTTPAPRPPTPAPTIASQPLSLRPEACRPAAGGAVHTRGL
DFACDIYIWAPLAGTCGVLLLSLVITLYCKRGRKKLLYIFKQPFMRPVQTTQEEDGCSCRFP
EEEEGGCELRVKFSRSADAPAYKQGQNQLYNELNLGRREEYDVLDKRRGRDPEMGGKPRRKN
PQEGLYNELQKDKMAEAYSEIGMKGERRRGKGHDGLYQGLSTATKDTYDALHMQALPPR**

CAR-T C2 OX40/CD3z sequence:
(DNA)

(SEQ ID NO: 612)

```
atggccttgccagtgacggccctgctgctgccattggctcttctgttgcacgctgccaggcctgaagt gcagctcgtagagagtggcggggggactggtgaagcccggtggaagcctcagactcagttgcgccgcct caggtttcacttttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtggggaaagggact accgtgacagtttcaagcggaggaggtggctcaggtggaggcgggtcaggggggaggaagtgatat tgtgctcacacaatccccagcctccctggctgtgtctcccggccaacgcgctacaattacatgtcggg cctccaaaagcgtgagcaccagcggctacagctacatgcactggtatcaacagaaaccaggacaaccc cccaaaactgttgatttatctcgcttcaaacttggagtccggcgtgcctgcgcgcttttcagggagtgg
```

-continued

```
gagcggcacagattttacgctgactatcaaccccgtagaagcaaacgatacagcgaattattattgtc aacattcccgggaactccccttttacgttcggcgggggcacaaaggtcgaaattaagagaaccacgaca accccggcccccagaccaccaacgccagccccaccatcgccagccaaccccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgccgg agggaccagaggctgccccccgatgcccacaagcccctgggggaggcagtttccggaccccatcca agaggagcaggccgacgcccactccaccctggccaagatccgcgttaagttctcccgatcagccgacg cgcctgcttacaagcagggccagaaccaactgtacaacgagctgaatctcggtagacgggaagagtac gacgtgttggacaaacggagaggccgcgacccagaaatgggcggcaagcctcgcaggaaaaaccccca ggagggactgtacaatgagttgcagaaagataagatggcagaagcttatagcgagatcggaatgaagg gggaaggagacgagggaaaggacacgacggcctttatcagggcctgtccacagcaacaaaagatacg tatgacgccctccatatgcaggcacttccaccacggtgataa
```

(amino acids)

(SEQ ID NO: 613)

```
MALPVTALLLPLALLLHAARPEVQLVESGGGLVKPGGSLRLSCAASGFTFSGYAMSWVRQAP

GKGLEWVSTISSGGTYIYYPDSVKGRFTISRDNAKNSLYLQMNSLRAEDTAVYYCARLGGDN

YYEYFDVWGKGTTVTVSSGGGGSGGGGSGGGGSDIVLTQSPASLAVSPGQRATITCRASKSV

STSGYSYMHWYQQKPGQPPKLLIYLASNLESGVPARFSGSGSGTDFTLTINPVEANDTANYY

CQHSRELPFTFGGGTKVEIKRTTTTPAPRPPTPAPTIASQPLSLRPEACRPAAGGAVHTRGL

DFACDIYIWAPLAGTCGVLLLSLVITLYCRRDQRLPPDAHKPPGGGSFRTPIQEEQADAHST

LAKIRVKFSRSADAPAYKQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR**
```

CAR-T C2 CD28/OX40/CD3Z sequence:
(DNA)

(SEQ ID NO: 614)

```
atggcccttgccagtgacggccctgctgctgccattggctcttctgttgcacgctgccaggcctgaagt gcagctcgtagagagtggcggggggactggtgaagcccggtggaagcctcagactcagttgcgccgcct caggtttcacttttttcaggttacgccatgtcctgggtaagacaggcaccggggaaaggactcgagtgg gtgtctactatcagctcaggaggcacttatatatattatcctgactctgtaaaaggccgatttacgat ttctcgcgacaatgcaaagaactccctctacctccaaatgaacagtcttagggcagaagacactgctg tatactattgtgcacgcctcggcggcgacaactactacgagtactttgacgtgtgggggaaagggact accgtgacagtttcaagcggaggaggtggctcaggtggaggcgggtcaggggggggaggaagtgatat tgtgctcacacaatccccagcctcccggctgtgtctcccggccaacgcgctacaattacatgtcggg cctccaaaagcgtgagcaccagcggctacagctacatgcactggtatcaacagaaaccaggacaaccc cccaaactgttgatttatctcgcttcaaacttggagtccggcgtgcctgcgcgcttttcagggagtgg gagcggcacagattttacgctgactatcaaccccgtagaagcaaacgatacagcgaattattattgtc aacattcccgggaactccccttttacgttcggcgggggcacaaaggtcgaaattaagagaaccacgaca accccggcccccagaccaccaacgccagccccaccatcgccagccaaccccctgtctctgagaccaga agcctgtaggcctgccgccggtggagctgtgcacacaagaggactggatttcgcctgtgatatctaca tttgggccccgctcgcaggcacatgtggagtgctcctcctctccctggtgattaccctgtactgcaga agcaagcggtctcggctcctgcattctgattacatgaacatgaccccaagaagaccaggccccaccag gaaacattaccagccctacgctccgccacgcgacttcgctgcctaccggtcccggagggaccagaggc tgccccccgatgcccacaagcccctgggggaggcagtttccggaccccatccaagaggagcaggcc
```

-continued

```
gacgcccactccaccctggccaagatccgcgttaagttctcccgatcagccgacgcgcctgcttacaa gcagggccagaaccaactgtacaacgagctgaatctcggtagacgggaagagtacgacgtgttggaca aacggagaggccgcgacccagaaatgggcggcaagcctcgcaggaaaaaccccaggagggactgtac aatgagttgcagaaagataagatggcagaagcttatagcgagatcggaatgaagggggaaggagacg agggaaggacacgacggcctttatcagggcctgtccacagcaacaaaagatacgtatgacgccctcc atatgcaggcacttccaccacggtgataa
```

(amino acids)

(SEQ ID NO: 615)

```
MALPVTALLLPLALLLHAARPEVQLVESGGGLVKPGGSLRLSCAASGFTFSGYAMSWVRQAP

GKGLEWVSTISSGGTYIYYPDSVKGRFTISRDNAKNSLYLQMNSLRAEDTAVYYCARLGGDN

YYEYFDVWGKGTTVTVSSGGGGSGGGGSGGGGSDIVLTQSPASLAVSPGQRATITCRASKSV

STSGYSYMHWYQQKPGQPPKLLIYLASNLESGVPARFSGSGSGTDFTLTINPVEANDTANYY

CQHSRELPFTFGGGTKVEIKRTTTTPAPRPPTPAPTIASQPLSLRPEACRPAAGGAVHTRGL

DFACDIYIWAPLAGTCGVLLLSLVITLYCRSKRSRLLHSDYMNMTPRRPGPTRKHYQPYAPP

RDFAAYRSRRDQRLPPDAHKPPGGGSFRTPIQEEQADAHSTLAKIRVKFSRSADAPAYKQGQ

NQLYNELNLGRREEYDVLDKRRGRDPEMGGKPRRKNPQEGLYNELQKDKMAEAYSEIGMKGE

RRRGKGHDGLYQGLSTATKDTYDALHMQALPPR**
```

CAR-T E6 OX40/CD3z sequence:
(DNA)

(SEQ ID NO: 616)

```
atggccctgccgtgaccgctttgctgctcccctggcgctgctgctgcacgccgccaggcc agaggtccagctggttgagagtggcgtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattaccccga ctcagtcaaggggagatttaccatttcacgagacaacgctaagaatacccctgtatttgcaga tgaattctctgagagcagaggacacagctgtttactattgtacccgcgacaactatggcagg aactacgactacggtatggactattggggacaagggacattggttacagtgagcagtggcgg cggggggcagcggaggaggaggcagcggtgggggggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgatttctggatctggttcaggttctgatt acaccctcactatctctagcctggagcctgaagactttgccgtttattactgccagcagagg tctagctccccattcacctttgggagtgggaccaaggttgaaattaaaacgacaaccccggc ccccagaccaccaacgccagcccccaccatcgccagccaacccctgtctctgagaccagaag cctgtaggcctgccgcggtggagctgtgcacacaagaggactggatttcgcctgtgatatc tacatttgggccccgctcgcaggcacatgtggagtgctcctcctctccctggtgattaccct gtactgccggagggaccagaggctgccccccgatgcccacaagcccctgggggaggcagtt tccggacccccatccaagaggagcaggccgacgcccactccaccctggccaagatccgcgtt aagttctcccgatcagccgacgcgcctgcttacaagcagggccagaaccaactgtacaacga gctgaatctcggtagacgggaagagtacgacgtgttggacaaacggagaggccgcgacccag aaatgggcggcaagcctcgcaggaaaaaccccaggagggactgtacaatgagttgcagaaa gataagatggcagaagcttatagcgagatcggaatgaagggggaaggagacgagggaaagg
```

-continued acacgacggcctttatcagggcctgtccacagcaacaaaagatacgtatgacgccctccata tgcaggcacttccaccacggtgataa (amino acids)

(SEQ ID NO: 617)

MALPVTALLLPLALLLHAARPEVQLVESGGGLVKPGGSLRLSCAASGFTFSRYGMSWVRQAP

GKRLEWVSTISGGGTYIYYPDSVKGRFTISRDNAKNTLYLQMNSLRAEDTAVYYCTRDNYGR

NYDYGMDYWGQGTLVTVSSGGGGSGGGGSGGGGSEIVLTQSPATLSLSPGERATLTCSATSS

VSYIHWYQQRPGQSPRLLIYSTSNLASGIPARFSGSGSGSDYTLTISSLEPEDFAVYYCQQR

SSSPFTFGSGTKVEIKTTTPAPRPPTPAPTIASQPLSLRPEACRPAAGGAVHTRGLDFACDI

YIWAPLAGTCGVLLLSLVITLYCRRDQRLPPDAHKPPGGGSFRTPIQEEQADAHSTLAKIRV

KFSRSADAPAYKQGQNQLYNELNLGRREEYDVLDKRRGRDPEMGGKPRRKNPQEGLYNELQK

DKMAEAYSEIGMKGERRRGKGHDGLYQGLSTATKDTYDALHMQALPPR**

CAR-T E6 CD28/OX40/CD3Z sequence:
(DNA)

(SEQ ID NO: 618)

atggccctgccgtgaccgctttgctgctccccctggcgctgctgctgcacgccgcaggcc agaggtccagctggttgagagtggcggtgggctggttaagcctggcggctccctgcggctga gctgcgccgcgagtggatttactttcagccgatatgggatgagttgggtgcggcaagctccc gggaagaggctggaatgggtctcaacaatctccggggggggcacttacatctattacccga ctcagtcaaggggagatttaccatttcacgagacaacgctaagaatacctgtatttgcaga tgaattctctgagagcagaggacacagctgtttactattgtacccgcgacaactatggcagg aactacgactacggtatggactattggggacaagggacattggttacagtgagcagtggcgg cgggggcagcggaggaggaggcagcggtgggggggcagcgagatagtgctcacgcagtcac ccgcgactctcagtctctcacctggggaacgagctaccctgacgtgctctgctacctcctca gtgtcatatattcactggtatcagcaacggcccgggcagtcccctagattgctcatttatag tacctctaatctggcctcaggtatccctgcacgattttctggatctggttcaggttctgatt acaccctcactatctctagcctggagcctgaagactttgccgtttattactgccagcagagg tctagctccccattcacctttgggagtgggaccaaggttgaaattaaaacgacaaccccggc ccccagaccaccaacgccagcccccaccatcgccagccaaccccctgtctctgagaccagaag cctgtaggcctgccgccggtggagctgtgcacacaagaggactggatttcgcctgtgatatc tacatttgggccccgctcgcaggcacatgtggagtgctcctcctctccctggtgattaccct gtactgcagaagcaagcggtctcggctcctgcattctgattacatgaacatgaccccaagaa gaccaggccccaccaggaaacattaccagccctacgctccgccacgcgacttcgctgcctac cggtcccggagggaccagaggctgccccccgatgcccacaagcccctgggggaggcagttt ccggaccccatccaagaggagcaggccgacgccactccaccctggccaagatccgcgtta agttctcccgatcagccgacgcgcctgcttacaagcagggccagaaccaactgtacaacgag ctgaatctcggtagacgggaagagtacgacgtgttggacaaacgagaggccgcgacccaga aatgggcggcaagcctcgcaggaaaaaccccaggagggactgtacaatgagttgcagaaag ataagatggcagaagcttatagcgagatcggaatgaaggggggaaaggagacgagggaagga cacgacggcctttatcagggcctgtccacagcaacaaaagatacgtatgacgccctccatat gcaggcacttccaccacggtgataa (amino acids)

(SEQ ID NO: 619)

MALPVTALLLPLALLLHAARPEVQLVESGGGLVKPGGSLRLSCAASGFTFSRYGMSWVRQAP
GKRLEWVSTISGGGTYIYYPDSVKGRFTISRDNAKNTLYLQMNSLRAEDTAVYYCTRDNYGR
NYDYGMDYWGQGTLVTVSSGGGGSGGGGSGGGGSEIVLTQSPATLSLSPGERATLTCSATSS
VSYIHWYQQRPGQSPRLLIYSTSNLASGIPARFSGSGSGSDYTLTISSLEPEDFAVYYCQQR
SSSPFTFGSGTKVEIKTTTPAPRPPTPAPTIASQPLSLRPEACRPAAGGAVHTRGLDFACDI
YIWAPLAGTCGVLLLSLVITLYCRSKRSRLLHSDYMNMTPRRPGPTRKHYQPYAPPRDFAAY
RSRRDQRLPPDAHKPPGGGSFRTPIQEEQADAHSTLAKIRVKFSRSADAPAYKQGQNQLYNE
LNLGRREEYDVLDKRRGRDPEMGGKPRRKNPQEGLYNELQKDKMAEAYSEIGMKGERRRGKG
HDGLYQGLSTATKDTYDALHMQALPPR**

MUC1 truncated cytoplasmic sequence
(amino acids)
SNIKFRPGSVVVQLTLAFREGTINVHDVETQFNQYKTEAASRY (SEQ ID NO: 620)

MUC1 truncated cytoplasmic sequence
(amino acids)

(SEQ ID NO: 621)

SVVVQLTLAFREGTINVHDVETQFNQYKTEAASRY

MUC1 truncated cytoplasmic sequence
(amino acids)

(SEQ ID NO: 622)

VQLTLAFREGTINVHDVETQFNQY

MUC1 truncated cytoplasmic sequence
(amino acids)

(SEQ ID NO: 623)

SNIKFRPGSVVVQLTLAFREGTIN

Primers (SEQ ID NO: 624)

attctaagcttgggccaccatggaactg (SEQ ID NO: 625)

tctagagtttaaacttactatttacccggagacagggagag (SEQ ID NO: 626)

agtatggcccagccggccgaggtgcagctggtggagtctgg (SEQ ID NO: 627)

tagaaggcacagtcgaggctgatcag (SEQ ID NO: 628)

attctaagcttgggccaccatggaagc (SEQ ID NO: 629)

tctagagtttaaacttactaacactctcccctgttgaagc (SEQ ID NO: 630)

agtatggcccagccggccgaaattgtgttgacacagtctccag (SEQ ID NO: 631)

tagaaggcacagtcgaggctgatcag (SEQ ID NO: 632)

actgtcatatggaggtgcagctggtggagtctg (SEQ ID NO: 633)

actgtctcgagtttaatttccactttggtgccgctgc (SEQ ID NO: 634)

actgtcatatggaggtgcagctggtggagtctg (SEQ ID NO: 635)

actgtaccggttttaatttccactttggtgccgctgc (SEQ ID NO: 636)

cttcttcctcaggagcaagctcaccgtgg

-continued gagccgtcggagtccagc (SEQ ID NO: 637)

gcacctgaactcctgggg (SEQ ID NO: 638)

tttaatttccactttggtgccg (SEQ ID NO: 639)

cgcggctagcttaagcttggtaccgagggcca (SEQ ID NO: 640)

cgcggcggccgcctgatcagcgggtttaaacttatc (SEQ ID NO: 641)

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1—ELISA Competition with NME1 and NME7

PSMGFR peptide was covalently coupled to BSA using Imject Maleimide activated BSA kit (Thermo Fisher). PSMGFR peptide coupled BSA was diluted to 7.5 ug/mL in 0.1M carbonate/bicarbonate buffer pH 9.6 and 50 uL was added to each well of a 96 well plate. After overnight incubation at 4° C., the plate was wash twice with PBS-T and a 3% BSA solution was added to block remaining binding site on the well. After 1 h at RT the plate was washed twice with PBS-T and NME1 or NME7, diluted in PBS-T+ 1% BSA, was added at saturating concentration. After 1 h at RT the plate was washed 3× with PBS-T and anti-MUC1* antibody (or antibody fragments), diluted in PBS-T+1% BSA, was added (5× molar excess compared to NME1/ NME7). After 1 h at RT the plate was washed 3× with PBS-T and goat anti HisTag-HRP, diluted in PBS-T+1% BSA, was added at 1/10000 dilution. After 1 h at RT the plate was washed 3× with PBS-T and remaining NME1 or NME7 bound to the PSMGFR peptide was measured at 415 nm using a ABTS solution (Thermo Fisher).

Example 2—Humanization of Anti-MUC1* Extracellular Domain Monoclonal Antibodies

We generated humanized antibodies that bind to the extracellular domain of MUC1* by a process called complementarity determining region, 'CDR', grafting. First, homology searches were performed to independently align the heavy chain variable region and light chain variable region nucleotides sequences of mouse monoclonal anti-MUC1* antibody (E6 HC SEQ ID NOS:12-13; LC SEQ ID NOS:65-66 and MN-C2 HC SEQ ID NO:118-119; LC SEQ ID NO: 168-169) against a repertoire of human antibody sequences (IMGT, the international ImMunoGeneTics information system). The sequences with the highest homology were selected. IGHV3-21*01 is a human IgG heavy chain variable region sequence with 82.9% (DNA) and 74.5% (amino acids) identity to Mouse MN-E6 heavy chain variable region. IGKV3-11*02 is a human IgG light chain variable region sequence with 68.8% (DNA) and 61.1% (amino acids) identity to Mouse MN-E6 light chain variable region. IGHV3-21*04 is a human IgG heavy chain variable region sequence with 85% (DNA) and 81.6% (amino acids) identity to Mouse MN-C2 heavy chain variable region. IGKV7-3*01 is a human IgG light chain variable region sequence with 76.9% (DNA) and 71.3% (amino acids) identity to Mouse MN-C2 light chain variable region. Second, a model of the mouse scFv was generated to select and keep the mouse residues important for the stability of the CDR and framework. Finally, CDRs from the human germlines were replaced by the corresponding mouse CDRs.

Humanized MN-E6 I2G2 Heavy Chain Cloning

The Kozak consensus sequence followed by the IGHV3-21*03 leader sequence, the humanized MN-E6 heavy chain variable region and the constant region of human IgG2 was synthesized by our request by GenScript, NJ (SEQ ID NOS:52-53. The cDNA was amplified by polymerase chain reaction (PCR) using the following primer: 5'-AT-TCTAAGCTTGGGCCACCATGGAACTG-3' (SEQ ID NO:624) and 5'-TCTAGAGTTTAAACTTACTATT-TACCCGGAGACAGGGAGAG-3' (SEQ ID NO:625). After digestion with HindIII and PmeI restriction enzymes (New England Biolabs), the purified fragment was cloned into the pCDNA 3.1 V5 vector (Life Technologies) digested with the same restriction enzymes.

Humanized MN-E6 heavy chain cDNA was amplified by polymerase chain reaction (PCR) using the following primer: 5'-AGTATGGCCCAGCCGGCCGAGGTGCAGCTGGTG-GAGTCTGG-3' (SEQ ID NO:626) and 5'-TAGAAGGCACAGTCGAGGCTGATCAG-3' (SEQ ID NO:627). After digestion with SfiI and PmeI restriction enzymes (New England Biolabs), the purified fragment was cloned into the pSECTag2 vector (Life Technologies) digested with the same restriction enzymes.

Humanized MN-E6 Kappa Light Chain Cloning

The Kozak consensus sequence followed by the IGHV3-11*02 leader sequence, the humanized MN-E6 light chain variable region and the constant region of human Kappa light chain was synthesized by our request by GenScript, NJ (SEQ ID NOS: 107-108). The cDNA was amplified by polymerase chain reaction (PCR) using the following primer: 5'-ATTCTAAGCTTGGGCCACCATGGAAGC-3' (SEQ ID NO:628) and 5'-TCTAGAGTTTAAACT-TACTAACACTCTCCCCTGTTGAAGC-3' (SEQ ID NO:629). After digestion with HindIII and PmeI restriction enzymes (New England Biolabs), the purified fragment was cloned into the pCDNA 3.1 V5 vector (Life Technologies) digested with the same restriction enzymes.

Humanized MN-E6 light chain cDNA was amplified by polymerase chain reaction (PCR) using the following primer: 5'-AGTATGGCCCAGCCGGCCGAAAT- TGTGTTGACACAGTCTCCAG-3' (SEQ ID NO:630) and 5'-TAGAAGGCACAGTCGAGGCTGATCAG-3' (SEQ ID NO:631). After digestion with SfiI and PmeI restriction enzymes (New England Biolabs), the purified fragment was cloned into the pSECTag2 vector (Life Technologies) digested with the same restriction enzymes.

Humanized MN-E6 IgG1 Heavy Chain Cloning

Humanized MN-E6 IgG2 constructs (pCDNA 3.1 V5 and pSECTag2) were digested with BstEII and PmeI (New England Biolabs) to remove the IgG2 heavy chain constant region. The vector with humanized MN-E6 heavy chain variable region was purified. Human IgG1 heavy chain constant region was synthesized by our request by IDT, IA (SEq ID NOS: 60-61). Both gBLOCKS and the purified vector with humanized MN-E6 variable region were ligated using the Gibson assembly cloning kit (New England Biolabs).

Humanized MN-E6 Lambda Light Chain Cloning

Humanized MN-E6 kappa light chain constructs (pCDNA 3.1 V5 vector and pSECTag2 vector) were digested with KpnI and PmeI (New England Biolabs) to remove the kappa light chain constant region. The vector with humanized MN-E6 light chain variable region was purified. Human lambda light chain constant region was synthesized by our request by IDT, IA (SEQ ID NO: 115). Both, gBLOCK and the purified vector with humanized MN-E6 light chain variable region were ligated using the Gibson assembly cloning kit (New England Biolabs).

Humanized MN-C2 IgG1 and IgG2 Heavy Chain Cloning

Humanized MN-E6 IgG1 and IgG2 heavy chain in pSECTag2 were digested with SfiI and AgeI to remove the MN-E6 variable region. Humanized MN-E6 IgG1 and IgG2 heavy chain in pCDNA 3.1 V5 were digested with HindIII and AgeI to remove the MN-E6 variable region The vectors with human IgG1 or IgG2 constant region were purified. Humanized MN-C2 heavy chains were synthesized by our request by IDT, IA (SEQ ID NOS:160 and 165). Sequence to be cloned into pCDNA 3.1 V5 contains in 5' the murine Ig kappa chain leader sequence (SEQ ID NO 160). Both, gBLOCK and purified vector with human IgG1 or IgG2 constant region were ligated using the Gibson assembly cloning kit (New England Biolabs).

Humanized MN-C2 Karma/Lambda Light Chain Cloning

Two humanized MN-C2 variable region fused to the kappa light chain constant region and two humanized MN-C2 variable region fused to the lambda light chain constant region were synthesized by our request by IDT, IA (SEQ ID NOS: 210 and 213 and SEQ ID NOS: 216 and 219, respectively). pCDNA 3.1 V5 was digested with HindIII and PmeI restriction enzymes (New England Biolabs) and pSEC Tag2 was digested with SfiI and PmeI restriction enzymes (New England Biolabs). Both plasmids were then purified. SEQ ID NOS: 210 and 216 were ligated into digested pCDNA 3.1 V5 and SEQ ID NOS: 213 and 219 were ligated into digested pSEC Tag2 using the Gibson assembly cloning kit (New England Biolabs).

Humanized C3 IgG1 Heavy Chain Cloning

Humanized E6 IgG1 construct (pSECTag2) was digested with SfiI and AgeI (New England Biolabs) to remove the E6 heavy chain variable region. The vector without humanized E6 heavy chain variable region was purified. Humanized C3 heavy chain variable region was synthesized by our request by IDT, IA (SEQ ID NO:457). gBLOCK and the purified vector were ligated using the Gibson assembly cloning kit (New England Biolabs).

Humanized C3 Kappa Light Chain Cloning pEF V5-His was digested with BamHI and PmeI (New England Biolabs) and purified. Humanized C3 kappa light chain was synthesized by our request by IDT, IA (SEq ID NO:504). Both, gBLOCK and the purified vector were ligated using the Gibson assembly cloning kit (New England Biolabs).

Humanized C8 Kappa Light Chain Cloning pEF V5-His was digested with BamHi and PmeI (New England Biolabs) and purified. Humanized C8 kappa light chain was synthesized by our request by IDT, IA (SEq ID NO:583). Both, gBLOCK and the purified vector were ligated using the Gibson assembly cloning kit (New England Biolabs).

Example 3—Cloning of Humanized scFV of Anti-MUC1* Extracellular Domain Antibodies Humanized E6 scFV Cloning:

pSEC Tag2 was digested with SfiI and PmeI (New England Biolabs) and purified. Humanized E6 scFV gBLOCKS were synthesized by our request by IDT, IA (SEQ ID NOS: 604-605). Both, gBLOCKs and the purified vector were ligated using the Gibson assembly cloning kit (New England Biolabs).

Humanized E6 scFV cDNA was amplified by polymerase chain reaction (PCR) using the following primers: 5-ACTGTCATATGGAGGTGCAGCTGGTGGAGTCTG-3' (SEQ ID NO:632) and 5'-ACTGTCTCGAGTTTAAT-TTCCACTTTGGTGCCGCTGC-3' (SEQ ID NO:633). After digestion with NdeI and XhoI restriction enzymes (New England Biolabs), the purified fragment was cloned into the pET21b vector (Novagen) digested with the same restriction enzymes. Humanized E6 scFV cDNA was cloned 5' of the Histidine Tag for protein purification.

Humanized E6 scFV cDNA was amplified by polymerase chain reaction (PCR) using the following primers: 5-ACTGTCATATGGAGGTGCAGCTGGTGGAGTCTG-3' (SEQ ID NO:634) and 5'-ACTGTACCGGTTTTAAT-TTCCACTTTGGTGCCGCTGC-3' (SEQ ID NO:635). After digestion with NdeI and AgeI restriction enzymes (New England Biolabs), the purified fragment was cloned into a modified pET21b vector (Novagen) digested with the same restriction enzymes. The vector was modified to include the StrepTag2 sequence followed by 2 stop codons 5' of the Histidine Tag. Humanized E6 scFV cDNA was cloned 5' of the StrepTag2 for protein purification.

Humanized E6, C2, C3 and C8 scFV-Fc Cloning

Humanized E6 IgG1 construct (pSECTag2) was digested with SfiI and SacII (New England Biolabs) to remove the E6 heavy chain variable region and part of the IgG1 heavy chain constant region. The vector without humanized E6 heavy chain variable region was purified. Humanized E6, C2, C3 and C8 scFV gBLOCKS were synthesized by our request by IDT, IA (SEQ ID NO:258-259, 262-263, 266-267 and 270-271). E6, C2, C3 and C8 gBLOCKS and the purified vector were ligated using the Gibson assembly cloning kit (New England Biolabs) to assemble the corresponding scFV in frame of the human IgG1 Fc region.

Humanized E6 scFV-Fc Y407R Cloning

Humanized E6 scFV-Fc tyrosine 407 was mutated to an arginine (Y407R) by site directed mutagenesis. The Q5 site directed mutagenesis kit (NEB) was used with the following primers: 5'-CTTCTTCCTCAGGAGCAAGCT-CACCGTGG-3' (SEQ ID NO:636) and 5'-GAGCCGTCG-GAGTCCAGC-3' (SEQ ID NO:637)

Humanized E6 scFV-Fc Hingeless Cloning

Hinge region of humanized E6 scFV-Fc was removed by site directed mutagenesis. The Q5 site directed mutagenesis kit (NEB) was used with the following primers: 5'-GCACCTGAACTCCTGGGG-3' (SEQ ID NO:638) and 5'-TTTAATTTCCACTTTGGTGCCG-3' (SEQ ID NO:639)

Example 4—Cloning of CAR-T of Anti-MUC1* Extracellular Domain antibodies

CAR E6 CD28/4-1BB/CD3z cloning:

pCDNA 3.1 V5 was digested with KpnI and PmeI (New England Biolabs) and purified. Full CAR-T E6 (CD8/CD28/4-1BB/CD3z) gBLOCK was synthesized by our request by IDT, IA (SEq ID NO:305). Both, gBLOCK and the purified vector were ligated using the Gibson assembly cloning kit (New England Biolabs).

Car E6 Cd3z Cloning:

pCDNA 3.1 V5 CAR-T E6 CD8/CD28/4-1BB/CD3z was digested with EcoRV and PmeI (New England Biolabs) to remove cytoplasmic domains. The vector without cytoplasmic domains was purified. CAR-T E6 CD8/CD3z gBLOCK was synthesized by our request by IDT, IA (SEq ID NO:296). Both, gBLOCK and the purified vector were ligated using the Gibson assembly cloning kit (New England Biolabs).

Car E6 Cd28/Cd3z Cloning:

pCDNA 3.1 V5 CAR-T E6 CD8/CD28/4-1BB/CD3z was digested with EcoRV and PmeI (New England Biolabs) to remove cytoplasmic domains. The vector without cytoplasmic domains was purified. CAR-T E6 CD8/CD28/CD3z gBLOCK was synthesized by our request by IDT, IA (SEq ID NO:299). Both, gBLOCK and the purified vector were ligated using the Gibson assembly cloning kit (New England Biolabs).

Car E6 4-1Bb/Cd3z Cloning:

pCDNA 3.1 V5 CAR-T E6 CD8/CD28/4-1BB/CD3z was digested with EcoRV and PmeI (New England Biolabs) to remove cytoplasmic domains. The vector without cytoplasmic domains was purified. CAR-T E6 CD8/4-1BB/CD3z gBLOCK was synthesized by our request by IDT, IA (SEq ID NO:302). Both, gBLOCK and the purified vector were ligated using the Gibson assembly cloning kit (New England Biolabs).

Car C2 Cd28/4-1Bb/Cd3z Cloning:

pCDNA 3.1 V5 CAR-T E6 CD8/CD28/4-1BB/CD3z was digested with KpnI and EcoRV (New England Biolabs) E6 scFV. The vector without E6 scFV was purified. CAR-T C2 gBLOCKs were synthesized by our request by IDT, IA (SEq ID NOS: 308-309). Both, gBLOCKs and the purified vector were ligated using the Gibson assembly cloning kit (New England Biolabs).

CAR Sub-Cloning into Lentiviral Vectors:

All pcDNA 3.1 V5 CAR cDNAs were amplified by polymerase chain reaction (PCR) using the following primers: 5-CGCGGCTAGCTTAAGCTTGGTACCGAGGGCCA-3' (SEQ ID NO:640) and 5'-CGCGGCGGCCGCCTGATCAGCGGGTTTAAACTTATC-3' (SEQ ID NO:641). After digestion with NheI and NotI restriction enzymes (New England Biolabs), the purified fragments were cloned into lentiviral vectors (pCDH-EF1-MCS-IRES GFP and pCDH-CMV-MCS-EF1-copGFP+puro, SBI) digested with the same restriction enzymes.

Car-E6—Fc/8/41Bb/Cd3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 313 and 314). The gBLOCKs and the purified vector were ligated using the Gibson assembly cloning kit (New England Biolabs).

Car-E6—Fch/8/41Bb/Cd3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 317 and 314). The gBLOCKs and the purified vector were ligated using the Gibson assembly cloning kit (New England Biolabs).

Car-E6-Fc-4-41Bb-Cd3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 313 and 320). The gBLOCKs and the purified vector were ligated using the Gibson assembly cloning kit (New England Biolabs).

Car-E6 Fch/4/41Bb/Cd3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 317 and 320). The gBLOCKs and the purified vector were ligated using the Gibson assembly cloning kit (New England Biolabs).

Car-E6 12D/8/41Bb/Cd3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 325 and 326). The gBLOCKs and the purified vector were ligated using the Gibson assembly cloning kit (New England Biolabs).

Car-E6 12D/4/41Bb/Cd3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 329 and 326). The gBLOCKs and the purified vector were ligated using the Gibson assembly cloning kit (New England Biolabs).

Car-E6 X4/8/41Bb/Cd3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 332 and 326). The gBLOCKs and the purified vector were ligated using the Gibson assembly cloning kit (New England Biolabs).

Car-E6 X4/4/41Bb/Cd3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 335 and 326). The gBLOCKs and the purified vector were ligated using the Gibson assembly cloning kit (New England Biolabs).

Car E6-8+4-4-41Bb-Cd3z Cloning:

pCDH-CMV-MCS-EF1-copGFP+puro (SBI) was digested with NheI and NotI (New England Biolabs) and the vector was purified. gBLOCKs were synthesized by our request by IDT, IA (SEq ID NOS: 312, 338 and 326). The gBLOCKs and the purified vector were ligated using the Gibson assembly cloning kit (New England Biolabs).

Example 5—Lentivirus Production

HEK 293T cells (ATCC) were used to produce lentivirus. The day prior transfection plates (6 well plate) were coated with poly-D-lysine and cells seeded so that cell density reaches 90-95% at the time of transfection and cultures in a 5% CO2 atmosphere. The next daycells were transfected with Lipofectamine 3000 (life technologies) and Opti-MEM® I Reduced Serum Medium according to the manufacturer instructions (0.75 ug of lentiviral expression vector and 2.25 ug of pPACKH1 packaging mix was used). After 6 h incubation, the media was changed and media containing lentivirus was harvested after 24 and 48 hours. Lentivirus was concentrated with Lenti-X concentrator (Clontech) and titer was calculated using the Lenti-X p@4 Rapid Titer Kit (Clontech). Lentivirus was store at −80 C in single-use aliquots.

Example 6—Lipofectamine Transient Expression

HEK 293T cells (ATCC) were used to test expression of humanized IgG. The night before transfection, cells were passed at ⅓ dilution (6 well plate) and cultures in a 5% CO2 atmosphere. The next day, 1 hour before transfection, the media was change to complete media without antibiotics (DMEM high glucose from ATCC containing 10% fetal calf serum). For transfection, we used Lipofectamine 3000 (life technologies) and Opti-MEM® I Reduced Serum Medium according to the manufacturer instructions. 1.25 ug of the heavy chain construct and 1.25 ug of the light chain construct or 2.5 ug of Fc-fusion constructs was used. After 48h incubation, the media was collected, cleared by centrifugation and used in an ELISA assay to quantify the level of humanized IgG expression and binding to PSMGFR peptide.

Example 7—Polyethylenimine (PEI) Large Scale Transient Expression

HEK 293T cells (ATCC) were used for large scale expression of Fc-fusion protein. The night before transfection, cells were passed ($6.5 \times 10^6$ cells in 150 mm dish) and cultures in a 5% CO2 atmosphere. The next day, 1 hour before transfection, cell were washed once with PBS pH 7.4 and the media was change to complete media without antibiotics (DMEM high glucose from ATCC containing 10% ultra low IgG fetal calf serum). For transfection, we used Polyethylenimine "Max" (PEI "Max", Polysciences) and Opti-MEM® I Reduced Serum Medium (25 ug of Fc-fusion constructs+250 ug of PEI). After 72h incubation, the media was collected and stored at −20° C. or cleared by centrifugation/filtration for purification.

Example 8—Jurkat Cells Lentivirus Transduction

Protocol #1: A 50/50 solution (2 mL) of lentivirus was prepared in fresh media, supplemented with 8 ug/mL of polybrene and added to a well of a 6 well plate. Jurkat E6-1 cells (ATCC, TIB-152) were pelleted at 1200 rpm for 5 min at RT and resuspended in fresh media (RPMI containing 10% fetal calf serum and 1% penicillin/streptomycin/amphotericin b). Cells were counted and add $2 \times 10^5$ cells to the well containing the virus+Polybrene solution. Incubate for 24-48h and add fresh media and/or split the cells. After 72h, start growing cells with antibiotic selection (puromycin).

Protocol #2: Jurkat E6-1 cells (ATCC, TIB-152) were pelleted at 1200 rpm for 5 min at RT and resuspended in fresh media (RPMI containing 10% fetal calf serum and 1% penicillin/streptomycin/amphotericin b) at $2.5 \times 10^5$ cells/mL. Add 2 mL of cells to a 15 mL sterile conical tube, add 1× of Transdux infection reagent (1×, SBI) and lentivirus. Mix gently and incubate at RT for 20 min. Centrifuge cells at 1900 rpm for 30 min at 32° C., remove supernatant, resuspend cells in 2 mL of fresh media and transfer cells to a well of a 6 well plate. Inspect cells for GFP expression after 48h.

Example 9—T Cells Lentivirus Transduction

Highly purified T cells (AllCells) were pelleted at 200×g for 5 min at RT and resuspended at $1 \times 10^6$ cells/mL in fresh media (RPMI1640 containing 10% fetal calf serum and 1% penicillin/streptomycin). Add CD3/CD28 activator Dynabeads (Thermo Fisher, 25 uL for $1 \times 10^6$ cells) and seed 24 well plate with 1 mL of cells and add IL2 (Thermo Fisher). Monitor cells daily and split cells if needed. The day before the transduction coat a plate with Retronectin (Takara) and store it overnight at 4° C. The next, remove the Retronectin solution add a blocking solution (2% BSA in PBS) and incubate 30 min at RT. Remove BSA solution add PBS until cells are ready. Collect activated T cells and resuspend them at $0.5 \times 10^6$ cells/mL in fresh media. Add 1 mL of cells to the retronectin treated plate, 1 mL of lentivirus solution and IL2. Cells were spinoculated by centrifugation of the pate at 1000×g for 90 min at RT. The plate was return to the incubator overnight. Next, remove 1 mL of media, add 1 mL of virus and repeat spinoculation. Monitor cells and split them if necessary at a density of $0.5-1 \times 10^6$ cells/mL. T cells can be used for cytokine release assay or cytotoxicity assay 48h post transduction.

Example 10—IL2 Detection

IL-2 secretion in media was measured using a human IL-2 ELISA kit (Thermo Fisher). Plates were coated with and anti-IL-2 antibody (coating antibody, 1/100 in PBS). After overnight incubation at 4° C., the plate was wash 3 times with PBS-T and a 4% BSA solution was added to block remaining binding site on the well. After 1 h at RT the plate was washed once with PBS-T and conditioned media (CM) and IL-2 standard diluted in PBS+4% BSA, was added. After 2h at RT the plate was washed 3× with PBS-T and anti-human IL-2 (detection antibody) diluted in PBS+4% BSA (1/100), was added. After 2h at RT the plate was washed 5× with PBS-T and Streptavidin-HRP (1/400) was added. After 30 min at RT, the plate was washed 7× with PBS-T (soak 1 min each wash) and substrate solution was added. The reaction was stopped after 20 min by adding the stop solution and absorbance was read at 450 nm (minus absorbance at 550 nm) within 30 min of stopping.

Example 11—IFN-γ Detection

IFN-γ secretion in media was measured using a human IFN-γ ELISA kit (Biolegend). Plates were coated with and anti-IFN-γ antibody (capture antibody, 1× in coating buffer). After overnight incubation at 4° C., the plate was washed 4 times with PBS-T and blocking solution was added to block remaining binding site on the well. After 1 h at RT (shaking at 500 rpm) the plate was washed 4 times with PBS-T and conditioned media (CM) and IFN-γ standard, was added. After 2h at RT with shaking, the plate was washed 4 times with PBS-T and detection antibody (lx), was added. After 1 h at RT with shaking, the plate was washed 4 times with PBS-T and Avidin-HRP (1×) was added. After 30 min at RT with shaking, the plate was washed 5 times with PBS-T (soak 1 min each wash) and TMB substrate solution was added. The reaction was stopped after 20 min by adding the stop solution and absorbance was read at 450 nm (minus absorbance at 570 nm) within 15 min of stopping.

Example 12—CAR T Cytotoxicity Assay

Human T cells were isolated from whole blood according to standard protocols. The T cells were then separately transduced twice with lenti virus bearing the CAR constructs, wherein the CAR constructs bear a GFP tag. Following 2-3 days of culture in RPMI 10% FBS and IL-2, the cells were stained with F(ab')2 to label surface expression of MN-E6, MN-C2, MN-C3 and MN-C8. Cells were then sorted by flow cytometry for Fab-positive, GFP-positive cells. That means that the double positive population had a CAR inserted and that the CAR exposed the correct antibody fragment. The CAR T cells were then ready to be mixed with the MUC1* negative control cells or the target MUC1* positive cancer cells.

The target cells were prepared as follows: Harvest target cells and resuspend cells in serum-free medium containing 15 uM of CMTMr dye (Cell Tracker Orange, 5-and-6-4-chloromethyl benzoyl amino tetramethylrhodamine, Thermo Fisher) at $1\text{-}1.5 \times 10^6$ cells/mL. Incubate 30 min under growth conditions appropriate to particular cell type. Wash in culture media and transfer stained cells to a new tube and incubate the cells 60 min in media. Wash 2 more times in culture media to get rid of all excess dye. Set up the assay in 24 well plates with 0.5 ml media total volume. Resuspend the target cells (and control target cells) so that there are always 20,000 cells per well (20,000 cells/250 ul). Plate 250 ul in each well. Add 250 ul of the T cells so that the ratio of T cell: target cells=20:1, 10:1, 5:1 or 1:1. Analyse cells after 24 h and 72h. For suspension target cells, take off the 0.5 ml media from the well and place in tube, wash the well with 0.5 ml media or PBS. For adherent target cells, take off the 0.5 ml media from the well and place in tube, wash the well with 0.5 ml PBS. Add the PBS to the same tube and add 120 ul trypsin to the well. Incubate for 4 min then add 0.5 ml media to neutralize trypsin and place that in the tube as well. Spin cells and resuspend pellet in 100 ul FACS buffer. Spin cells again. Resuspend cells in 100 ul buffer+5 ul anti-CD3 antibody, for 30 min on ice (to stain T cells). After 30 min, wash stained cells 2× with FACS buffer and resuspend in 250 ul buffer. Run the cells through the filter cap of the FACS tube. 10 min prior to analysis, add 10 ul 7AAD dye to each tube and analyze with Fortessa under the Cytotoxicity template.

Example 13—ELISA Expression Level of Humanized IgG

Figure 9:
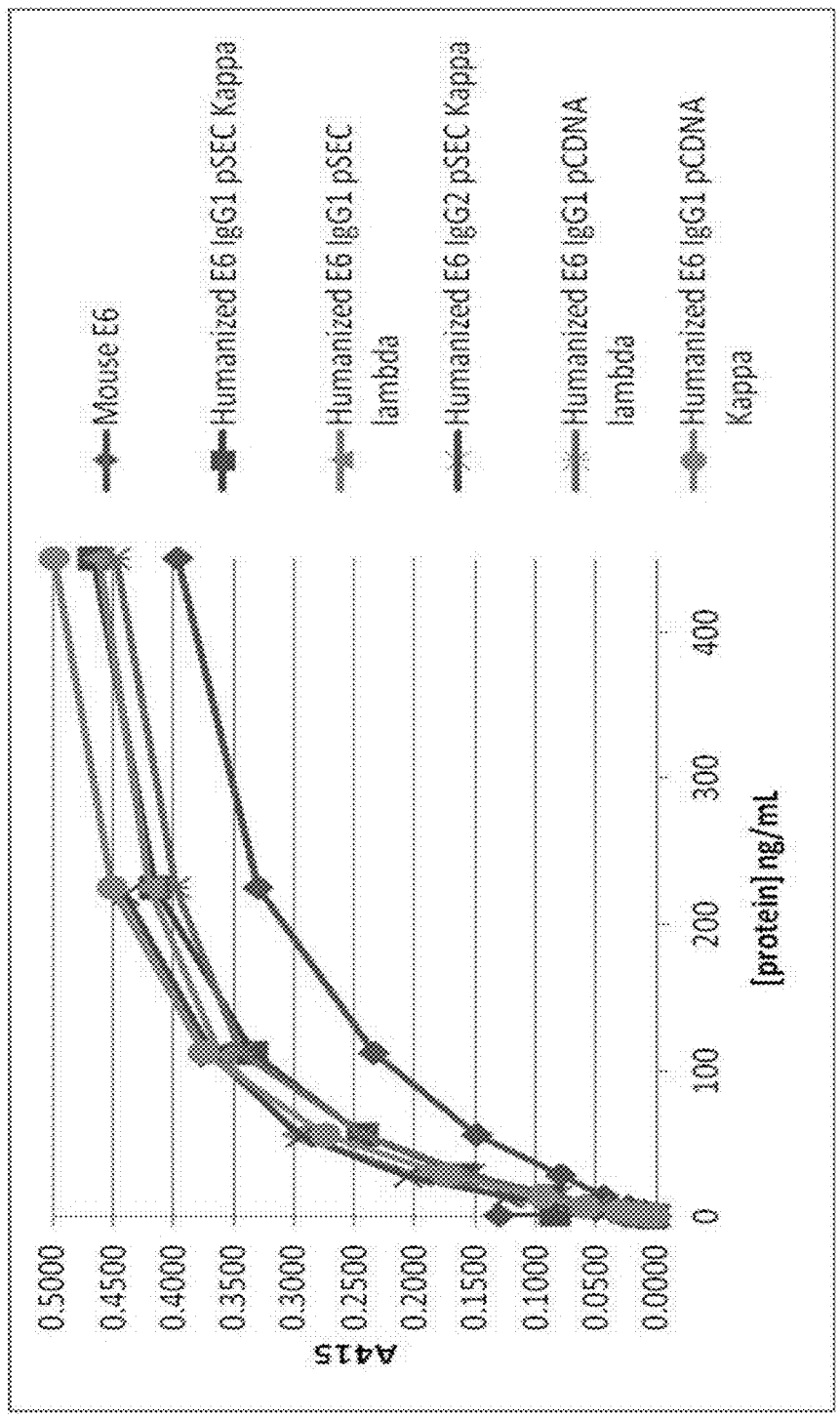
FIG. 9 is a graph of an ELISA assay comparing the binding of the parent mouse MN-E6 antibody to the humanized versions of the MN-E6 antibody to a surface presenting the PSMGFR peptide derived from the MUC1* extracellular domain.
Figure 11:
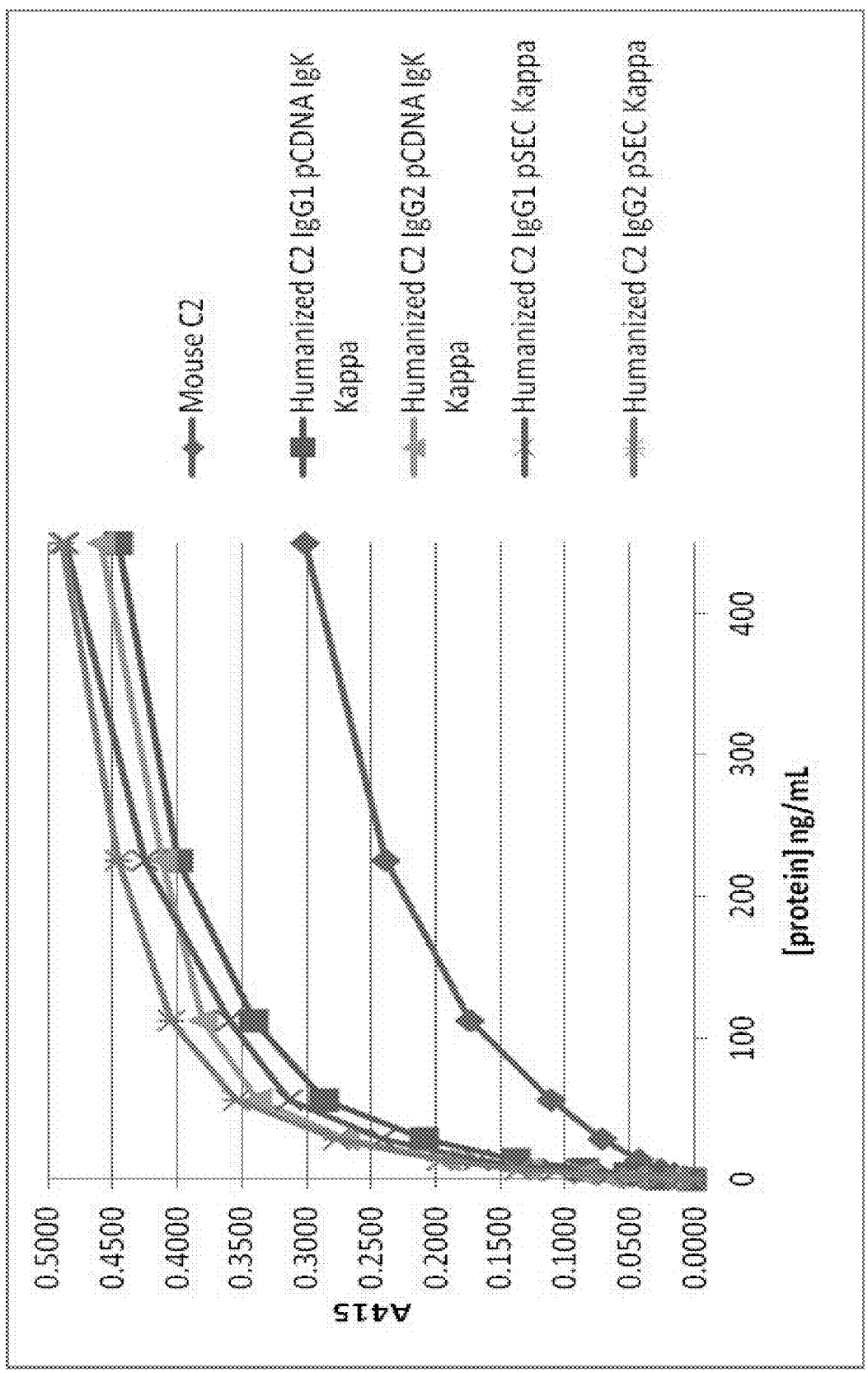
FIG. 11 is a graph of an ELISA assay comparing the binding of the parent mouse MN-C2 antibody to the humanized versions of the MN-C2 antibody to a surface presenting the PSMGFR peptide derived from the MUC1* extracellular domain.
Figure 12:
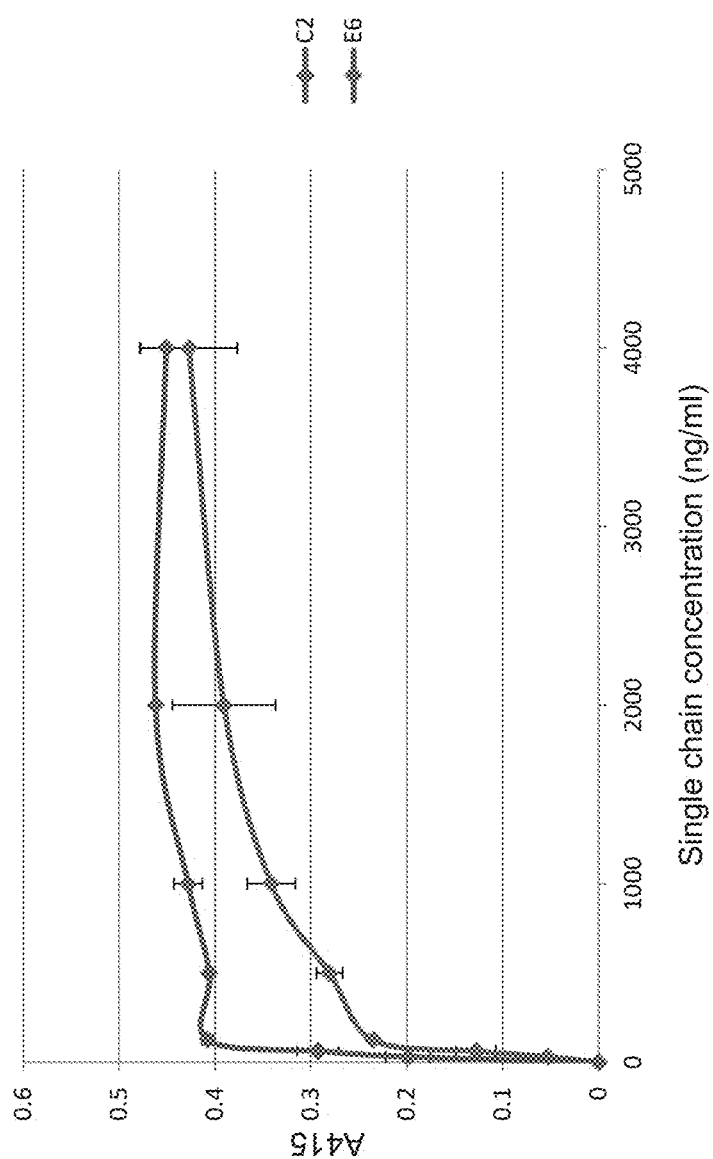
FIG. 12 is a graph of an ELISA assay showing binding of humanized single chain (scFv) MN-C2 and MN-E6 antibodies binding to a surface presenting the PSMGFR peptide derived from the MUC1* extracellular domain.

Goat Anti-human Fc specific antibody was diluted to 5 ug/mL in 0.1M carbonate/bicarbonate buffer pH 9.6 and 50 uL was added to each well of a 96 well plate. After overnight incubation at 4° C., the plate was wash twice with PBS-T and a 3% BSA solution was added to block remaining binding site on the well. After 1 h at RT the plate was washed twice with PBS-T and conditioned media (CM), diluted in PBS-T+1% BSA, was added at different concentrations. Also, purified human IgG (life technologies), diluted in PBS-T+1% BSA, was added at different concentrations to make a standard curve for determination of the expression level of the humanized IgG or Fc-fusion protein. After 1 h at RT the plate was washed 3× with PBS-T and anti-human (H+L) HRP (life technologies) diluted in PBS-T+1% BSA, was added at $\frac{1}{2500}$. After 1 h at RT the plate was washed 3× with PBS-T and binding of human IgG and humanized IgG was measured at 415 nm using a ABTS solution (ThermoFisher) (FIG. 9 (MN-E6) and FIG. 11 (MN-C2)).

Figure 8:
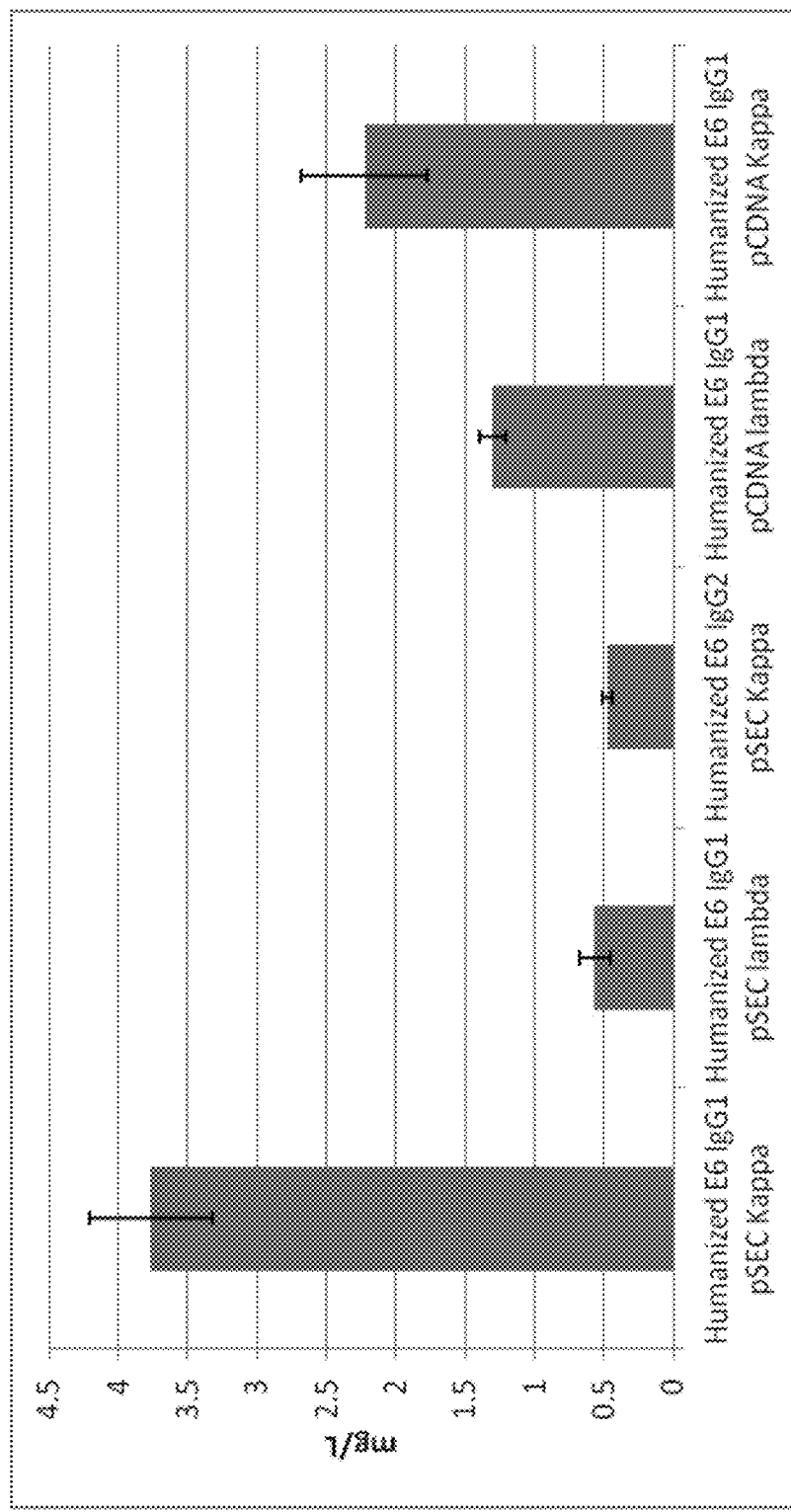
FIG. 8 is a graph of an ELISA assay showing differing levels of expression of humanized MN-E6 anti-MUC1* antibody depending on whether the light chain was kappa or lambda and whether the variable portion was fused to a human IgG1 or IgG2.

Example 14—ELISA Humanized IgG Binding to PSMGFR Peptide of the MUC1* Extracellular Domain A synthetic peptide of sequence PSMGFR was covalently coupled to BSA using Imject Maleimide activated BSA kit (Thermo Fisher). PSMGFR coupled BSA was diluted to 7.5 ug/mL in 0.1M carbonate/bicarbonate buffer pH 9.6 and 50 uL was added to each well of a 96 well plate. After overnight incubation at 4° C., the plate was wash twice with PBS-T and a 3% BSA solution was added to block remaining binding site on the well. After 1 h at RT the plate was washed twice with PBS-T and conditioned media (CM), diluted in PBS-T+1% BSA, was added at different concentrations. At the same time corresponding mouse IgG was diluted in PBS-T+1% BSA and added at different concentrations as binding control. After 1 h at RT the plate was washed 3× with PBS-T and anti-human (H+L) HRP (life technologies) diluted in PBS-T+1% BSA, was added at $\frac{1}{5000}$ to detect binding of humanized IgG. Anti-Mouse HRP (life technologies) diluted in PBS-T+1% BSA, was added at $\frac{1}{2500}$ to detect binding of mouse IgG. After 1 h at RT the plate was washed 3× with PBS-T and binding was measured at 415 nm using a ABTS solution (ThermoFisher) (FIG. 8 (MN-E6) and FIG. 10 (MN-C2)).

Example 15—Stable Cell Lines Generation

CHO-K1 cells (ATCC) were used to create stable cell lines expressing high level of humanized IgG. HEK293 cells (ATCC) were used to create stable cell lines expressing high level of Fc-fusion proteins. The night before transfection, cells were passed at $\frac{1}{3}$ dilution (6 well plate) and cultures in a 5% CO2 atmosphere. The next day, 1 hour before transfection, the media was change to complete media without antibiotics (F12K or DMEM containing 10% fetal calf serum). For transfection, we used Lipofectamine 3000 (life technologies) and Opti-MEM® I Reduced Serum Medium according to the manufacturer instructions. 1.25 ug of the heavy chain construct and 1.25 ug of the light chain construct or 2.5 ug of Fc-fusion constructs was used. After 24h, cells were trypsinized and plated into a T75 flask (in F12K or DMEM containing 10% fetal calf serum). After 24 h, cells were trypsinized, diluted to 100 cells/mL and 1000 cells/mL in F12K or DMEM containing 10% FCS and selection agent (Zeocin for pSECTag2 or G418 for pCDNA 3.1 V5), plated in 96 well plate (100 uL per well) and cultures in a 5% CO2 atmosphere. After 2-3 weeks, the culture media from single clones were collected, cleared by centrifugation and used in an ELISA assay to quantify the level of humanized IgG expression and binding to PSMGFR peptide. The clones with the highest expression and PSMGFR binding were expanded for large scale expression.

Example 16—Scfv Expression pET21b E6 scFV plasmid (with HisTag or StrepTagII) was transformed into Shuffle T7 express competent cells (NEB). TB broth (Terrific broth) was inoculated with $\frac{1}{100}$ of an overnight culture (LB broth-30° C.-200 rpm) and cultured at 30° C./200 rpm. When OD600 reached ~1, temperature was reduced to 20° C. and growth was continued. After 2h, recombinant protein expression was induced with 0.2 mM Isopropyl-O-D-thio-galactoside (IPTG, Gold Biotechnology) and culture was stopped after 22h. After harvesting the cells by centrifugation (6000 rpm for 10 min at 4° C.), cell pellet was resuspended with running buffer. For Histag protein buffer was: 50 mM Tris pH8.0, 300 mM NaCl and 5 mM imidazole. For StrepTagII protein buffer was 100 mM Tris pH 8.0 and 150 mM NaCl.

Example 17—His Tag EscFV Purification

MgCl2 (0.5 mM), DNAse (0.5 ug/mL, Sigma), PMSF (1 mM, Gold Bitotechnology) and BugBuster (1×, Novagen) was added. Cell suspension was incubated on a rotating platform for 20 min at RT. Insoluble cell debris was removed by centrifugation (20000 rpm for 30 min at 4° C.). The cleared lysate was then applied to a Ni-NTA column (Qiagen) equilibrated with the running buffer. The column was washed before eluting the protein off the column with the running buffer supplemented with 495 mM imidazole. The protein was further purified by size exclusion chromatography (Superdex 200). The fractions containing the protein were pooled, aliquoted and stored at −80° C.

Example 18—StrepTagII EscFV Purification

MgCl2 (0.5 mM), DNAse (0.5 ug/mL, Sigma), PMSF (1 mM, Gold Bitotechnology) and BugBuster (1×, Novagen) was added. Cell suspension was incubated on a rotating platform for 20 min at RT. Insoluble cell debris was removed by centrifugation (20000 rpm for 30 min at 4° C.). The cleared lysate was then applied to a Strep-Tactin column (IBA) equilibrated with the running buffer. The column was washed before eluting the protein off the column with the running buffer supplemented with 5 mM d-Desthiobiotin. The protein was further purified by size exclusion chromatography (Superdex 200). The fractions containing the protein were pooled, aliquoted and stored at −80° C.

Example 19—Humanize IgG/Fc-Fusion Purification

Condition media (from transient transfection or stable cell line) was collected, cleared by centrifugation and filtered (0.2 um). The media was then loaded on a protein A (Genscript) or CaptureSelect FcXL (Thermo Fisher) and the protein purified according to manufacturer instructions using acid condition for elution. The eluted protein was then dialyzed against PBS pH 7.4 and further purified by size exclusion chromatography (Superdex 200). The fractions containing the protein were pooled, aliquoted and stored at −80° C.

Example 20—Immunohistochemistry

Human tissue specimens were purchased from Biomax. The tissues were either normal or cancerous as determined by a board certified pathologist. Tissues were anonymized but were labeled with a number, tissue type, stage of cancer and if available, a TNM tumor grading designation. TNM grading is as follows: T is primary tumor. Tx is primary tumor cannot be assessed. TO is no evidence of a tumor. This is carcinoma in situ, intraepithelial or invasion of lamina propia. T1 is tumor invades submucosa. T2 is tumor invades muscularis propia. T3 is tumor invades through muscularis propia into subserosa or into non-peritonealized pericolic or perirectal tissues. T4 is tumor directly invades other organs or structures and/or perforate visceral peritoneum. N is regional lymph nodes. NO is no regional lymph node metastasis. N1 is metastasis in 1 to 3 regional lymph nodes. N2 is metastatic in 4 or more regional lymph nodes. M is for distant metastasis. M0 means no distant metastasis. M1 is distant metastasis.

Tissues were stained with a primary anti-MUC1* antibody mouse monoclonal MN-C2, MN-E6, humanized MN-E6 scFv-Fc, or humanized MN-E6 scFv-Fc-biotin. If the primary were a mouse monoclonal antibody, then the secondary antibody used was a rabbit anti-mouse HRP-conjugated antibody. If the primary were a humanized antibody, then the secondary was a goat-anti-human HRP conjugated antibody. If the primary were a biotinylated antibody, then the secondary was a streptavidin HRP conjugated antibody.

Tissue specimens were de-paraffinized using xylene and ethanol according to standard protocols. An antigen retrieval procedure was used for some tissues which involved 10 mM Sodium Citrate-0.05% Tween pH 6 buffer (pre boil buffer, keep warm) boil 10', cool down 20' in rice cooker, then rinse cold tap water 5 minutes then two 5 min. washes in TBS. Tissues were blocked for 1 hr at RT in 10% NGS plus 5% BSA in TBS. If the primary antibody used was humanized MN-E6scFv, which was conjugated to biotin so that it could be visualized by a secondary antibody, the tissues were pre-blocked with an avidin solution then a biotin solution. Primary antibodies were incubated with tissues overnight at 4 degrees C. in 1% BSA-TBS with gentle orbital rotation. Tissues were rinsed with TBS-T for 5 minutes with gentle rocking. For HRP-conjugate detection only, mounted tissues were incubated in 3% $H_2O_2$ in TBS for 15 minutes at RT. For tissues incubated with biotinylated primary antibodies, they were then bathed in StreptAvidin for 10 min with Streptavidin-HRP label (Biocare Cat #: HP604 G, H, L), then washed 3 times for 5 minutes at RT in TBS-T with gentle rocking. They were then developed with chromogen (DAB—1 mL diluent; 1 drop DAB substrate) for 5 minutes at RT, then rinsed with running tap water for 5 minutes. They were then counterstained for 1 second hematoxylin then brief dip in 0.08% $NH_4OH$ 'bluing reagent' followed by 5 minutes in running water. Tissues were then dehydrated and mounted with Cytoseal XYL (1 drop/section) and coverslipped.

All of the references cited herein are incorporated by reference in their entirety.

Those skilled in the art will recognize, or be able to ascertain using no more than routine experimentation, many equivalents to the specific embodiments of the invention specifically described herein.

The invention claimed is:

1. A polypeptide comprising an anti-MUC1* antibody fragment, wherein the anti-MUC1* antibody fragment comprises a heavy chain variable region and a light chain variable region that have complementarity determining regions (CDRs) in the heavy chain variable region and the light chain variable region as follows:
CDR1 heavy chain SEQ ID NO: 123,
CDR1 light chain SEQ ID NO: 173,
CDR2 heavy chain SEQ ID NO: 127,
CDR2 light chain SEQ ID NO: 177,
CDR3 heavy chain SEQ ID NO: 131, and
CDR3 light chain SEQ ID NO: 181;
wherein the heavy chain variable region comprises an amino acid sequence that has at least 90% sequence identity to SEQ ID NO: 145 and the light chain variable region comprises an amino acid sequence that has at least 90% sequence identity to SEQ ID NO: 195; and
wherein the polypeptide binds to a receptor on an immune cell.

2. The polypeptide of claim 1, wherein the heavy chain variable region comprises an amino acid sequence that has at least 95% sequence identity to SEQ ID NO: 145 and the light chain variable region comprises an amino acid sequence that has at least 95% sequence identity to SEQ ID NO: 195.

3. The polypeptide of claim 1, wherein the heavy chain variable region comprises an amino acid sequence that has at least 98% sequence identity to SEQ ID NO: 145 and the light chain variable region comprises an amino acid sequence that has at least 98% sequence identity to SEQ ID NO: 195.

4. The polypeptide of claim 1, wherein the heavy chain variable region comprises the amino acid sequence according to SEQ ID NO: 145 and the light chain variable region comprises the amino acid sequence according to SEQ ID NO: 195.

5. The polypeptide of claim 1, wherein the heavy chain variable region and a light chain variable region are connected by a linker.

6. The polypeptide of claim 5, wherein the linker comprises the amino acid sequence according to SEQ ID NO: 402.

7. The polypeptide of claim 1, wherein the anti-MUC1* antibody fragment comprises a single chain variable fragment (scFv).

8. The polypeptide of claim 7, wherein the scFv comprises an amino acid sequence that has at least 90% sequence identity to any one of SEQ ID NOs: 239, 241, 243, 396, or 398.

9. The polypeptide of claim 7, wherein the scFv comprises an amino acid sequence that has at least 95% sequence identity to any one of SEQ ID NOs: 239, 241, 243, 396, or 398.

10. The polypeptide of claim 7, wherein the scFv comprises an amino acid sequence that has at least 98% sequence identity to any one of SEQ ID NOs: 239, 241, 243, 396, or 398.

11. The polypeptide of claim 7, wherein the scFv comprises an amino acid sequence according to any one of SEQ ID NOs: 239, 241, 243, 396, or 398.

12. The polypeptide of claim 7, wherein the scFv is selected for its ability to bind to a MUC1* peptide, wherein the MUC1* peptide comprises the amino acid sequence of SEQ ID NO: 2, SEQ ID NO: 620, or SEQ ID NO: 621.

13. The polypeptide of claim 7, wherein the scFv is selected for its ability to bind to a MUC1* positive cancer or a MUC1* transfected cell.

14. The polypeptide of claim 13, wherein the MUC1* positive cancer cell comprises MUC1* positive breast cancer cells.

15. The polypeptide of claim 13, wherein the MUC1* positive cancer cell comprises MUC1* positive prostate cancer cells.

16. The polypeptide of claim 7, wherein the scFv is selected for its ability to inhibit growth of MUC1* positive cancer cells.

17. The polypeptide of claim 16, wherein the MUC1* positive cancer cells comprise MUC1* positive breast cancer cells.

18. The polypeptide of claim 1, wherein the immune cell comprises a T cell.

19. The polypeptide of claim 18, wherein the receptor on the immune cell comprises CD3.

20. The polypeptide of claim 19, wherein the polypeptide further comprises an amino acid sequence with at least 90% sequence identity to SEQ ID NO: 390 or SEQ ID NO: 388.

21. The polypeptide of claim 19, wherein the polypeptide further comprises an amino acid sequence with at least 95% sequence identity to SEQ ID NO: 390 or SEQ ID NO: 388.

22. The polypeptide of claim 19, wherein the polypeptide further comprises an amino acid sequence with at least 98% sequence identity to SEQ ID NO: 390 or SEQ ID NO: 388.

23. The polypeptide of claim 19, wherein the polypeptide further comprises the amino acid sequence of SEQ ID NO: 390 or SEQ ID NO: 388.

24. The polypeptide of claim 1, wherein the polypeptide comprises an amino acid sequence with at least 95% sequence identity to SEQ ID NO: 239 and an amino acid sequence with at least 95% sequence identity to SEQ ID NO: 390.

25. The polypeptide of claim 1, wherein the polypeptide comprises an amino acid sequence with at least 95% sequence identity to SEQ ID NO: 239 and an amino acid sequence with at least 95% sequence identity to SEQ ID NO: 388.

26. The polypeptide of claim 1, wherein the polypeptide comprises an amino acid sequence with at least 95% sequence identity to SEQ ID NO: 398 and an amino acid sequence with at least 95% sequence identity to SEQ ID NO: 388.

27. The polypeptide of claim 1, wherein the polypeptide comprises the amino acid sequence of SEQ ID NO: 239, the amino acid sequence of SEQ ID NO: 400, and the amino acid sequence of SEQ ID NO: 390.

28. The polypeptide of claim 1, wherein the polypeptide comprises the amino acid sequence of SEQ ID NO: 239, the amino acid sequence of SEQ ID NO: 400, and the amino acid sequence of SEQ ID NO: 388.

29. The polypeptide of claim 1, wherein the polypeptide comprises the amino acid sequence of SEQ ID NO: 398, the amino acid sequence of SEQ ID NO: 400, and the amino acid sequence of SEQ ID NO: 388.

* * * * *

SEQUENCE LISTING

```
Sequence total quantity: 643
SEQ ID NO: 1            moltype = AA  length = 1255
FEATURE                 Location/Qualifiers
REGION                  1..1255
                        note = MUC1 Receptor
source                  1..1255
```

```
                    mol_type = protein
                    organism = synthetic construct
SEQUENCE: 1
MTPGTQSPFF  LLLLLTVLTV  VTGSGHASST  PGGEKETSAT  QRSSVPSSTE  KNAVSMTSSV    60
LSSHSPGSGS  STTQGQDVTL  APATEPASGS  AATWGQDVTS  VPVTRPALGS  TTPPAHDVTS   120
APDNKPAPGS  TAPPAHGVTS  APDTRPAPGS  TAPPAHGVTS  APDTRPAPGS  TAPPAHGVTS   180
APDTRPAPGS  TAPPAHGVTS  APDTRPAPGS  TAPPAHGVTS  APDTRPAPGS  TAPPAHGVTS   240
APDTRPAPGS  TAPPAHGVTS  APDTRPAPGS  TAPPAHGVTS  APDTRPAPGS  TAPPAHGVTS   300
APDTRPAPGS  TAPPAHGVTS  APDTRPAPGS  TAPPAHGVTS  APDTRPAPGS  TAPPAHGVTS   360
APDTRPAPGS  TAPPAHGVTS  APDTRPAPGS  TAPPAHGVTS  APDTRPAPGS  TAPPAHGVTS   420
APDTRPAPGS  TAPPAHGVTS  APDTRPAPGS  TAPPAHGVTS  APDTRPAPGS  TAPPAHGVTS   480
APDTRPAPGS  TAPPAHGVTS  APDTRPAPGS  TAPPAHGVTS  APDTRPAPGS  TAPPAHGVTS   540
APDTRPAPGS  TAPPAHGVTS  APDTRPAPGS  TAPPAHGVTS  APDTRPAPGS  TAPPAHGVTS   600
APDTRPAPGS  TAPPAHGVTS  APDTRPAPGS  TAPPAHGVTS  APDTRPAPGS  TAPPAHGVTS   660
APDTRPAPGS  TAPPAHGVTS  APDTRPAPGS  TAPPAHGVTS  APDTRPAPGS  TAPPAHGVTS   720
APDTRPAPGS  TAPPAHGVTS  APDTRPAPGS  TAPPAHGVTS  APDTRPAPGS  TAPPAHGVTS   780
APDTRPAPGS  TAPPAHGVTS  APDTRPAPGS  TAPPAHGVTS  APDTRPAPGS  TAPPAHGVTS   840
APDTRPAPGS  TAPPAHGVTS  APDTRPAPGS  TAPPAHGVTS  APDTRPAPGS  TAPPAHGVTS   900
APDTRPAPGS  TAPPAHGVTS  APDTRPAPGS  TAPPAHGVTS  APDNRPALGS  TAPPVHNVTS   960
ASGSASGSAS  TLVHNGTSAR  ATTTPASKST  PFSIPSHHSD  TPTTLASHST  KTDASSTHHS  1020
SVPPLTSSNH  STSPQLSTGV  SFFFLSFHIS  NLQFNSSLED  PSTDYYQELQ  RDISEMFLQI  1080
YKQGGFLGLS  NIKFRPGSVV  VQLTLAFREG  TINVHDVETQ  FNQYKTEAAS  RYNLTISDVS  1140
VSDVPFPFSA  QSGAGVPGWG  IALLVLVCVL  VALAIVYLIA  LAVCQCRRKN  YGQLDIFPAR  1200
DTYHPMSEYP  TYHTHGRYVP  PSSTDRSPYE  KVSAGNGGSS  LSYTNPAVAA  ASANL       1255

SEQ ID NO: 2           moltype = AA   length = 45
FEATURE                Location/Qualifiers
REGION                 1..45
                       note = PSMGFR
source                 1..45
                       mol_type = protein
                       organism = synthetic construct
SEQUENCE: 2
GTINVHDVET  QFNQYKTEAA  SRYNLTISDV  SVSDVPFPFS  AQSGA                     45

SEQ ID NO: 3           moltype = DNA  length = 459
FEATURE                Location/Qualifiers
misc_feature           1..459
                       note = Human NME1
source                 1..459
                       mol_type = other DNA
                       organism = synthetic construct
SEQUENCE: 3
atggccaact  gtgagcgtac  cttcattgcg  atcaaaccag  atggggtcca  gcggggtctt    60
gtgggagaga  ttatcaagcg  ttttgagcag  aaaggattcc  gccttgttgg  tctgaaattc   120
atgcaagctt  ccgaagatct  tctcaaggaa  cactacgttg  acctgaagga  ccgtccattc   180
tttgccggcc  tggtgaaata  catgcactca  gggccggtag  ttgccatggt  ctgggagggg   240
ctgaatgtgg  tgaagacggg  ccgagtcatg  ctcggggaga  ccaaccctgc  agactccaag   300
cctgggacca  tccgtggaga  cttctgcata  caagttggca  ggaacattat  acatggcagt   360
gattctgtgg  agagtgcaga  gaaggagatc  ggcttgtggt  tccaccctga  ggaactggta   420
gattacacga  gctgtgctca  gaactggatc  tatgaatga                            459

SEQ ID NO: 4           moltype = AA   length = 152
FEATURE                Location/Qualifiers
REGION                 1..152
                       note = Human NME1
source                 1..152
                       mol_type = protein
                       organism = synthetic construct
SEQUENCE: 4
MANCERTFIA  IKPDGVQRGL  VGEIIKRFEQ  KGFRLVGLKF  MQASEDLLKE  HYVDLKDRPF    60
FAGLVKYMHS  GPVVAMVWEG  LNVVKTGRVM  LGETNPADSK  PGTIRGDFCI  QVGRNIIHGS   120
DSVESAEKEI  GLWFHPEELV  DYTSCAQNWI  YE                                   152

SEQ ID NO: 5           moltype = DNA  length = 1131
FEATURE                Location/Qualifiers
misc_feature           1..1131
                       note = Human NME7
source                 1..1131
                       mol_type = other DNA
                       organism = synthetic construct
SEQUENCE: 5
atgaatcata  gtgaaagatt  cgttttcatt  gcagagtggt  atgatccaaa  tgcttcactt    60
cttcgacgtt  atgagctttt  attttaccca  ggggatggat  ctgttgaaat  gcatgatgta   120
aagaatcatc  gcacctttt   aaagcggacc  aaatatgata  acctgcactt  ggaagattta   180
tttataggca  acaaagtgaa  tgtcttttct  cgacaactgg  tattaattga  ctatggggat   240
caatatacag  ctcgccagct  gggcagtagg  aagaaaaaa   cgctagccct  aattaaacca   300
gatgcaatat  caaaggctgg  agaaataatt  gaaataataa  acaaagctgg  atttactata   360
accaaactca  aatgatgat   gctttcaagg  aaagaagcat  tggattttca  tgtagatcac   420
```

-continued

```
cagtcaagac cctttttcaa tgagctgatc cagtttatta caactggtcc tattattgcc    480
atggagattt taagagatga tgctatatgt gaatggaaaa gactgctggg acctgcaaac    540
tctggagtgg cacgcacaga tgcttctgaa agcattagag ccctctttgg aacagatggc    600
ataagaaatg cagcgcatgg ccctgattct tttgcttctg cggccagaga aatggagttg    660
tttttccctt caagtggagg ttgtgggccg gcaaacactg ctaaatttac taattgtacc    720
tgttgcattg ttaaacccca tgctgtcagt gaaggactgt tgggaaagat cctgatggct    780
atccgagatg caggttttga aatctcagct atgcagatgt tcaatatgga tcgggttaat    840
gttgaggaat tctatgaagt ttataaagga gtagtgaccg aatatcatga catggtgaca    900
gaaatgtatt ctggcccttg tgtagcaatg gagattcaac agaataatgc tacaaagaca    960
tttcgagaat tttgtggacc tgctgatcct gaaattgccc ggcatttacg ccctggaact   1020
ctcagagcaa tctttggtaa aactaagatc cagaatgctg ttcactgtac tgatctgcca   1080
gaggatggcc tattagaggt tcaatacttc ttcaagatct tggataatta g            1131
```

```
SEQ ID NO: 6            moltype = AA  length = 376
FEATURE                 Location/Qualifiers
REGION                  1..376
                        note = Human NME7
source                  1..376
                        mol_type = protein
                        organism = synthetic construct
SEQUENCE: 6
MNHSERFVFI AEWYDPNASL LRRYELLFYP GDGSVEMHDV KNHRTFLKRT KYDNLHLEDL    60
FIGNKVNVFS RQLVLIDYGD QYTARQLGSR KEKTLALIKP DAISKAGEII EIINKAGFTI   120
TKLKMMMLSR KEALDFHVDH QSRPFFNELI QFITTGPIIA MEILRDDAIC EWKRLLGPAN   180
SGVARTDASE SIRALFGTDG IRNAAHGPDS FASAAREMEL FFPSSGGCGP ANTAKFTNCT   240
CCIVKPHAVS EGLLGKILMA IRDAGFEISA MQMFNMDRVN VEEFYEVYKG VVTEYHDMVT   300
EMYSGPCVAM EIQQNNATKT FREFCGPADP EIARHLRPGT LRAIFGKTKI QNAVHCTDLP   360
EDGLLEVQYF FKILDN                                                  376
```

```
SEQ ID NO: 7            moltype = AA  length = 16
FEATURE                 Location/Qualifiers
REGION                  1..16
                        note = NME7 peptide 1 (A domain)
source                  1..16
                        mol_type = protein
                        organism = synthetic construct
SEQUENCE: 7
MLSRKEALDF HVDHQS                                                   16
```

```
SEQ ID NO: 8            moltype = AA  length = 11
FEATURE                 Location/Qualifiers
REGION                  1..11
                        note = NME7A peptide 2 (A domain)
source                  1..11
                        mol_type = protein
                        organism = synthetic construct
SEQUENCE: 8
SGVARTDASE S                                                        11
```

```
SEQ ID NO: 9            moltype = AA  length = 20
FEATURE                 Location/Qualifiers
REGION                  1..20
                        note = NME7B peptide 1 (B domain)
source                  1..20
                        mol_type = protein
                        organism = synthetic construct
SEQUENCE: 9
DAGFEISAMQ MFNMDRVNVE                                               20
```

```
SEQ ID NO: 10           moltype = AA  length = 16
FEATURE                 Location/Qualifiers
REGION                  1..16
                        note = NME7B peptide 2 (B domain)
source                  1..16
                        mol_type = protein
                        organism = synthetic construct
SEQUENCE: 10
EVYKGVVTEY HDMVTE                                                   16
```

```
SEQ ID NO: 11           moltype = AA  length = 29
FEATURE                 Location/Qualifiers
REGION                  1..29
                        note = NME7B peptide 3 (B domain)
source                  1..29
                        mol_type = protein
                        organism = synthetic construct
SEQUENCE: 11
AIFGKTKIQN AVHCTDLPED GLLEVQYFF                                     29
```

-continued

```
SEQ ID NO: 12            moltype = DNA  length = 366
FEATURE                  Location/Qualifiers
misc_feature             1..366
                         note = Mouse E6 Heavy chain variable region sequence
source                   1..366
                         mol_type = other DNA
                         organism = synthetic construct
SEQUENCE: 12
gaggtgaagg tggtggagtc tgggggagac ttagtgaagc ctggagggtc cctgaaactc   60
tcctgtgtag tctctggatt cactttcagt agatatggca tgtcttgggt tcgccagact  120
ccaggcaaga ggctggagtg ggtcgcaacc attagtggtg gcgtactta catctactat   180
ccagacagtg tgaaggggcg attcaccatc tccagagaca atgccaagaa caccctgtac  240
ctgcaaatga gcagtctgaa gtctgaggac acagccatgt atcactgtac aagggataac  300
tacggtagga actacgacta cggtatggac tactggggtc aaggaacctc agtcaccgtc  360
tcctca                                                             366

SEQ ID NO: 13            moltype = AA   length = 122
FEATURE                  Location/Qualifiers
REGION                   1..122
                         note = Mouse E6 Heavy chain variable region sequence
source                   1..122
                         mol_type = protein
                         organism = synthetic construct
SEQUENCE: 13
EVKVVESGGD LVKPGGSLKL SCVVSGFTFS RYGMSWVRQT PGKRLEWVAT ISGGGTYIYY   60
PDSVKGRFTI SRDNAKNTLY LQMSSLKSED TAMYHCTRDN YGRNYDYGMD YWGQGTSVTV  120
SS                                                                 122

SEQ ID NO: 14            moltype = DNA  length = 75
FEATURE                  Location/Qualifiers
misc_feature             1..75
                         note = Mouse E6 heavy chain variable framework region 1
                         (FWR1) sequence
source                   1..75
                         mol_type = other DNA
                         organism = synthetic construct
SEQUENCE: 14
gaggtgaagg tggtggagtc tgggggagac ttagtgaagc ctggagggtc cctgaaactc   60
tcctgtgtag tctct                                                   75

SEQ ID NO: 15            moltype = AA   length = 30
FEATURE                  Location/Qualifiers
REGION                   1..30
                         note = Mouse E6 heavy chain variable framework region 1
                         (FWR1) sequence
source                   1..30
                         mol_type = protein
                         organism = synthetic construct
SEQUENCE: 15
EVKVVESGGD LVKPGGSLKL SCVVSGFTFS                                    30

SEQ ID NO: 16            moltype = DNA  length = 30
FEATURE                  Location/Qualifiers
misc_feature             1..30
                         note = Mouse E6 heavy chain variable complementarity
                         determining regions1 (CDR1) sequence
source                   1..30
                         mol_type = other DNA
                         organism = synthetic construct
SEQUENCE: 16
ggattcactt tcagtagata tggcatgtct                                    30

SEQ ID NO: 17            moltype = AA   length = 5
FEATURE                  Location/Qualifiers
REGION                   1..5
                         note = Mouse E6 heavy chain variable complementarity
                         determining regions1 (CDR1) sequence
source                   1..5
                         mol_type = protein
                         organism = synthetic construct
SEQUENCE: 17
RYGMS                                                               5

SEQ ID NO: 18            moltype = DNA  length = 42
FEATURE                  Location/Qualifiers
misc_feature             1..42
                         note = Mouse E6 heavy chain variable framework region 2
                         (FWR2) sequence
source                   1..42
```

```
                        mol_type = other DNA
                        organism = synthetic construct
SEQUENCE: 18
tgggttcgcc agactccagg caagaggctg gagtgggtcg ca                         42

SEQ ID NO: 19           moltype = AA  length = 14
FEATURE                 Location/Qualifiers
REGION                  1..14
                        note = Mouse E6 heavy chain variable framework region 2
                        (FWR2) sequence
source                  1..14
                        mol_type = protein
                        organism = synthetic construct
SEQUENCE: 19
WVRQTPGKRL EWVA                                                        14

SEQ ID NO: 20           moltype = DNA  length = 51
FEATURE                 Location/Qualifiers
misc_feature            1..51
                        note = Mouse E6 heavy chain variable complementarity
                        determining regions2 (CDR2) sequence
source                  1..51
                        mol_type = other DNA
                        organism = synthetic construct
SEQUENCE: 20
accattagtg gtggcggtac ttacatctac tatccagaca gtgtgaaggg g               51

SEQ ID NO: 21           moltype = AA  length = 17
FEATURE                 Location/Qualifiers
REGION                  1..17
                        note = Mouse E6 heavy chain variable complementarity
                        determining regions2 (CDR2) sequence
source                  1..17
                        mol_type = protein
                        organism = synthetic construct
SEQUENCE: 21
TISGGGTYIY YPDSVKG                                                     17

SEQ ID NO: 22           moltype = DNA  length = 96
FEATURE                 Location/Qualifiers
misc_feature            1..96
                        note = Mouse E6 heavy chain variable framework region 3
                        (FWR3) acidsequence
source                  1..96
                        mol_type = other DNA
                        organism = synthetic construct
SEQUENCE: 22
cgattcacca tctccagaga caatgccaag aacaccctgt acctgcaaat gagcagtctg      60
aagtctgagg acacagccat gtatcactgt acaagg                                96

SEQ ID NO: 23           moltype = AA  length = 32
FEATURE                 Location/Qualifiers
REGION                  1..32
                        note = Mouse E6 heavy chain variable framework region 3
                        (FWR3) acidsequence
source                  1..32
                        mol_type = protein
                        organism = synthetic construct
SEQUENCE: 23
RFTISRDNAK NTLYLQMSSL KSEDTAMYHC TR                                    32

SEQ ID NO: 24           moltype = DNA  length = 39
FEATURE                 Location/Qualifiers
misc_feature            1..39
                        note = Mouse E6 heavy chain variable complementarity
                        determining regions3 (CDR3) sequence
source                  1..39
                        mol_type = other DNA
                        organism = synthetic construct
SEQUENCE: 24
gataactacg gtaggaacta cgactacggt atggactac                             39

SEQ ID NO: 25           moltype = AA  length = 13
FEATURE                 Location/Qualifiers
REGION                  1..13
                        note = Mouse E6 heavy chain variable complementarity
                        determining regions3 (CDR3) sequence
source                  1..13
                        mol_type = protein
```

```
                        organism = synthetic construct
SEQUENCE: 25
DNYGRNYDYG MDY                                                    13

SEQ ID NO: 26           moltype = DNA  length = 294
FEATURE                 Location/Qualifiers
misc_feature            1..294
                        note = IGHV3-21*03 heavy chain variable region sequence
source                  1..294
                        mol_type = other DNA
                        organism = synthetic construct
SEQUENCE: 26
gaggtgcagc tggtggagtc tgggggaggc ctggtcaagc ctgggggtc cctgagactc     60
tcctgtgcag cctctggatt caccttcagt agctatagca tgaactgggt ccgccaggct   120
ccagggaagg ggctggagtg ggtctcatcc attagtagta gtagtagtta catatactac   180
gcagactcag tgaagggccg attcaccatc tccagagaca acgccaagaa ctcactgtat   240
ctgcaaatga acagcctgag agccgaggac acggctgtgt attactgtgc gaga         294

SEQ ID NO: 27           moltype = AA  length = 98
FEATURE                 Location/Qualifiers
REGION                  1..98
                        note = IGHV3-21*03 heavy chain variable region sequence
source                  1..98
                        mol_type = protein
                        organism = synthetic construct
SEQUENCE: 27
EVQLVESGGG LVKPGGSLRL SCAASGFTFS SYSMNWVRQA PGKGLEWVSS ISSSSSYIYY     60
ADSVKGRFTI SRDNAKNSLY LQMNSLRAED TAVYYCAR                             98

SEQ ID NO: 28           moltype = DNA  length = 90
FEATURE                 Location/Qualifiers
misc_feature            1..90
                        note = IGHV3-21*01 heavy chain variable framework region 1
                        (FWR1) sequence
source                  1..90
                        mol_type = other DNA
                        organism = synthetic construct
SEQUENCE: 28
gaggtgcagc tggtggagtc tgggggaggc ctggtcaagc ctgggggtc cctgagactc     60
tcctgtgcag cctctggatt caccttcagt                                     90

SEQ ID NO: 29           moltype = AA  length = 30
FEATURE                 Location/Qualifiers
REGION                  1..30
                        note = IGHV3-21*01 heavy chain variable framework region 1
                        (FWR1) sequence
source                  1..30
                        mol_type = protein
                        organism = synthetic construct
SEQUENCE: 29
EVQLVESGGG LVKPGGSLRL SCAASGFTFS                                     30

SEQ ID NO: 30           moltype = DNA  length = 15
FEATURE                 Location/Qualifiers
misc_feature            1..15
                        note = IGHV3-21*01 heavy chain variable complementarity
                        determiningregions 1 (CDR1) sequence
source                  1..15
                        mol_type = other DNA
                        organism = synthetic construct
SEQUENCE: 30
agctatagca tgaac                                                     15

SEQ ID NO: 31           moltype = AA  length = 5
FEATURE                 Location/Qualifiers
REGION                  1..5
                        note = IGHV3-21*01 heavy chain variable complementarity
                        determiningregions 1 (CDR1) sequence
source                  1..5
                        mol_type = protein
                        organism = synthetic construct
SEQUENCE: 31
SYSMN                                                                 5

SEQ ID NO: 32           moltype = DNA  length = 42
FEATURE                 Location/Qualifiers
misc_feature            1..42
                        note = IGHV3-21*01 heavy chain variable framework region 2
                        (FWR2) sequence
```

```
source                    1..42
                          mol_type = other DNA
                          organism = synthetic construct
SEQUENCE: 32
tgggtccgcc aggctccagg gaaggggctg gagtgggtct ca                            42

SEQ ID NO: 33             moltype = AA  length = 14
FEATURE                   Location/Qualifiers
REGION                    1..14
                          note = IGHV3-21*01 heavy chain variable framework region 2
                          (FWR2) sequence
source                    1..14
                          mol_type = protein
                          organism = synthetic construct
SEQUENCE: 33
WVRQAPGKGL EWVS                                                           14

SEQ ID NO: 34             moltype = DNA  length = 51
FEATURE                   Location/Qualifiers
misc_feature              1..51
                          note = IGHV3-21*01 heavy chain variable complementarity
                          determiningregions 2 (CDR2) sequence
source                    1..51
                          mol_type = other DNA
                          organism = synthetic construct
SEQUENCE: 34
tccattagta gtagtagtag ttacatatac tacgcagact cagtgaaggg c                  51

SEQ ID NO: 35             moltype = AA  length = 17
FEATURE                   Location/Qualifiers
REGION                    1..17
                          note = IGHV3-21*01 heavy chain variable complementarity
                          determiningregions 2 (CDR2) sequence
source                    1..17
                          mol_type = protein
                          organism = synthetic construct
SEQUENCE: 35
SISSSSSYIY YADSVKG                                                        17

SEQ ID NO: 36             moltype = DNA  length = 96
FEATURE                   Location/Qualifiers
misc_feature              1..96
                          note = IGHV3-21*01 heavy chain variable framework region 3
                          (FWR3) sequence
source                    1..96
                          mol_type = other DNA
                          organism = synthetic construct
SEQUENCE: 36
cgattcacca tctccagaga caacgccaag aactcactgt atctgcaaat gaacagcctg         60
agagccgagg acacggctgt gtattactgt gcgaga                                   96

SEQ ID NO: 37             moltype = AA  length = 32
FEATURE                   Location/Qualifiers
REGION                    1..32
                          note = IGHV3-21*01 heavy chain variable framework region 3
                          (FWR3) sequence
source                    1..32
                          mol_type = protein
                          organism = synthetic construct
SEQUENCE: 37
RFTISRDNAK NSLYLQMNSL RAEDTAVYYC AR                                       32

SEQ ID NO: 38             moltype = DNA  length = 366
FEATURE                   Location/Qualifiers
misc_feature              1..366
                          note = Humanized E6 heavy chain variable region sequence
source                    1..366
                          mol_type = other DNA
                          organism = synthetic construct
SEQUENCE: 38
gaggtgcagc tggtggagtc tgggggaggc ctggtcaagc ctgggggtc cctgagactc          60
tcctgtgcag cctctggatt caccttcagt aggtatggca tgagctgggt ccgccaggct         120
ccagggaaga ggctggagtg ggtctcaacc attagtggcg aggcaccta catatactac          180
ccagactcag tgaagggccg attcaccatc tccagagaca cgccaagaa caccctgtat          240
ctgcaaatga acagcctgag agccgaggac acggctgtgt attactgtac cagagataac         300
tatggccgca actatgatta tggcatggat tattggggcc agggcaccct ggtgaccgtg         360
agcagc                                                                    366

SEQ ID NO: 39             moltype = AA  length = 122
```

```
                                -continued

FEATURE                 Location/Qualifiers
REGION                  1..122
                        note = Humanized E6 heavy chain variable region sequence
source                  1..122
                        mol_type = protein
                        organism = synthetic construct
SEQUENCE: 39
EVQLVESGGG LVKPGGSLRL SCAASGFTFS RYGMSWVRQA PGKRLEWVST ISGGGTYIYY    60
PDSVKGRFTI SRDNAKNTLY LQMNSLRAED TAVYYCTRDN YGRNYDYGMD YWGQGTLVTV   120
SS                                                                  122

SEQ ID NO: 40           moltype = DNA  length = 90
FEATURE                 Location/Qualifiers
misc_feature            1..90
                        note = Humanized E6 heavy chain variable framework region 1
                         (FWR1) acidsequence
source                  1..90
                        mol_type = other DNA
                        organism = synthetic construct
SEQUENCE: 40
gaggtgcag tggtggagtc tgggggaggc ctggtcaagc ctggggggtc cctgagactc    60
tcctgtgcag cctctggatt caccttcagt                                    90

SEQ ID NO: 41           moltype = AA  length = 30
FEATURE                 Location/Qualifiers
REGION                  1..30
                        note = Humanized E6 heavy chain variable framework region 1
                         (FWR1) acidsequence
source                  1..30
                        mol_type = protein
                        organism = synthetic construct
SEQUENCE: 41
EVQLVESGGG LVKPGGSLRL SCAASGFTFS                                    30

SEQ ID NO: 42           moltype = DNA  length = 15
FEATURE                 Location/Qualifiers
misc_feature            1..15
                        note = Humanized E6 heavy chain variable complementarity
                         determiningregions 1 (CDR1) sequence
source                  1..15
                        mol_type = other DNA
                        organism = synthetic construct
SEQUENCE: 42
aggtatggca tgagc                                                    15

SEQ ID NO: 43           moltype = AA  length = 5
FEATURE                 Location/Qualifiers
REGION                  1..5
                        note = Humanized E6 heavy chain variable complementarity
                         determiningregions 1 (CDR1) sequence
source                  1..5
                        mol_type = protein
                        organism = synthetic construct
SEQUENCE: 43
RYGMS                                                                5

SEQ ID NO: 44           moltype = DNA  length = 42
FEATURE                 Location/Qualifiers
misc_feature            1..42
                        note = Humanized E6 heavy chain variable framework region 2
                         (FWR2) acidsequence
source                  1..42
                        mol_type = other DNA
                        organism = synthetic construct
SEQUENCE: 44
tgggtccgcc aggctccagg gaagaggctg gagtgggtct ca                       42

SEQ ID NO: 45           moltype = AA  length = 14
FEATURE                 Location/Qualifiers
REGION                  1..14
                        note = Humanized E6 heavy chain variable framework region 2
                         (FWR2) acidsequence
source                  1..14
                        mol_type = protein
                        organism = synthetic construct
SEQUENCE: 45
WVRQAPGKRL EWVS                                                     14

SEQ ID NO: 46           moltype = DNA  length = 51
```

```
FEATURE                 Location/Qualifiers
misc_feature            1..51
                        note = Humanized E6 heavy chain variable complementarity
                        determiningregions 2 (CDR2) sequence
source                  1..51
                        mol_type = other DNA
                        organism = synthetic construct
SEQUENCE: 46
accattagtg gcggaggcac ctacatatac tacccagact cagtgaaggg c              51

SEQ ID NO: 47           moltype = AA  length = 17
FEATURE                 Location/Qualifiers
REGION                  1..17
                        note = Humanized E6 heavy chain variable complementarity
                        determiningregions 2 (CDR2) sequence
source                  1..17
                        mol_type = protein
                        organism = synthetic construct
SEQUENCE: 47
TISGGGTYIY YPDSVKG                                                    17

SEQ ID NO: 48           moltype = DNA  length = 96
FEATURE                 Location/Qualifiers
misc_feature            1..96
                        note = Humanized E6 heavy chain variable framework region 3
                        (FWR3) acidsequence
source                  1..96
                        mol_type = other DNA
                        organism = synthetic construct
SEQUENCE: 48
cgattcacca tctccagaga caacgccaag aaccccctgt atctgcaaat gaacagcctg     60
agagccgagg acacggctgt gtattactgt accaga                               96

SEQ ID NO: 49           moltype = AA  length = 32
FEATURE                 Location/Qualifiers
REGION                  1..32
                        note = Humanized E6 heavy chain variable framework region 3
                        (FWR3) acidsequence
source                  1..32
                        mol_type = protein
                        organism = synthetic construct
SEQUENCE: 49
RFTISRDNAK NTLYLQMNSL RAEDTAVYYC TR                                   32

SEQ ID NO: 50           moltype = DNA  length = 39
FEATURE                 Location/Qualifiers
misc_feature            1..39
                        note = Humanized E6 heavy chain variable complementarity
                        determiningregions 3 (CDR3) sequence
source                  1..39
                        mol_type = other DNA
                        organism = synthetic construct
SEQUENCE: 50
gataactatg gccgcaacta tgattatggc atggattat                            39

SEQ ID NO: 51           moltype = AA  length = 13
FEATURE                 Location/Qualifiers
REGION                  1..13
                        note = Humanized E6 heavy chain variable complementarity
                        determiningregions 3 (CDR3) sequence
source                  1..13
                        mol_type = protein
                        organism = synthetic construct
SEQUENCE: 51
DNYGRNYDYG MDY                                                        13

SEQ ID NO: 52           moltype = DNA  length = 1442
FEATURE                 Location/Qualifiers
misc_feature            1..1442
                        note = Humanized E6 IgG2 heavy chain synthesized by
                        Genescript
source                  1..1442
                        mol_type = other DNA
                        organism = synthetic construct
SEQUENCE: 52
gaattctaag cttgggccac catggaactg gggctccgct gggttttcct tgttgctatt     60
ttagaaggtg tccagtgtga ggtgcagctg gtggagtctg ggggaggcct ggtcaagcct    120
ggggggtccc tgagactctc ctgtgcagcc tctggattca ccttcagtag gtatggcatg    180
agctgggtcc gccaggctcc agggaagagg ctggagtggg tctcaaccat tagtggcgga   240
```

-continued

```
ggcaccetaca tatactaccc agactcagtg aagggccgat tcaccatctc cagagacaac   300
gccaagaaca ccctgtatct gcaaatgaac agcctgagag ccgaggacac ggctgtgtat   360
tactgtacca gagataacta tggccgcaac tatgattatg gcatggatta ttggggccag   420
ggcaccctgg tgaccgtgag cagcgcctcc accaagggcc catcggtctt ccccctggcg   480
ccctgctcca ggagcacctc cgagagcaca gcggccctgg gctgcctggt caaggactac   540
ttccccgaac cggtgacggt gtcgtggaac tcaggcgctc tgaccagcgg cgtgcacacc   600
ttcccagctg tcctacagtc ctcaggactc tactccctca gcagcgtggt gaccgtgccc   660
tccagcaact cggcaccca gacctacacc tgcaacgtag atcacaagcc cagcaacacc   720
aaggtggaca gacagttga gcgcaaatgt tgtgtcgagt gcccaccgtg cccagcacca   780
cctgtggcag gaccgtcagt cttcctcttc cccccaaaac ccaaggacac cctcatgatc   840
tcccggaccc ctgaggtcac gtgcgtggtg gtggacgtga gccacgaaga ccccgaggtc   900
cagttcaact ggtacgtgga cggcgtggag gtgcataatg ccaagacaaa gccacgggag   960
gagcagttca acagcacgtt ccgtgtggtc agcgtcctca ccgttgtgca ccaggactgg  1020
ctgaacggca aggagtacaa gtgcaaggtc tccaacaaag gcctcccagc ccccatcgag  1080
aaaaccatct ccaaaaccaa agggcagccc cgagaaccac aggtgtacac cctgcccca  1140
tcccgggagg agatgaccaa gaaccaggtc agcctgacct gcctggtcaa aggcttctac  1200
cccagcgaca tcgccgtgga gtgggagagc aatgggcagc cggagaacaa ctacaagacc  1260
acacctccca tgctggactc cgacggctcc ttcttcctct acagcaagct caccgtggac  1320
aagagcaggt ggcagcaggg gaacgtcttc tcatgctccg tgatgcatga ggctctgcac  1380
aaccactaca cgcagaagag cctctccctg tctccgggta aatagtaagt ttaaactcta  1440
ga                                                                1442
```

SEQ ID NO: 53          moltype = AA   length = 477
FEATURE                Location/Qualifiers
REGION                 1..477
                       note = Humanized E6 IgG2 heavy chain synthesized by
                         Genescript
SITE                   477
                       note = misc_feature - Xaa can be any naturally occurring
                         amino acid
source                 1..477
                       mol_type = protein
                       organism = synthetic construct
SEQUENCE: 53
```
EFAWATMELG LRWVFLVAIL EGVQCEVQLV ESGGGLVKPG GSLRLSCAAS GFTFSRYGMS   60
WVRQAPGKRL EWVSTISGGG TYIYYPDSVK GRFTISRDNA KNTLYLQMNS LRAEDTAVYY  120
CTRDNYGRNY DYGMDYWGQG TLVTVSSAST KGPSVFPLAP CSRSTSESTA ALGCLVKDYF  180
PEPVTVSWNS GALTSGVHTF PAVLQSSGLY SLSSVVTVPS SNFGTQTYTC NVDHKPSNTK  240
VDKTVERKCC VECPPCPAPP VAGPSVFLFP PKPKDTLMIS RTPEVTCVVV DVSHEDPEVQ  300
FNWYVDGVEV HNAKTKPREE QFNSTFRVVS VLTVVHQDWL NGKEYKCKVS NKGLPAPIEK  360
TISKTKGQPR EPQVYTLPPS REEMTKNQVS LTCLVKGFYP SDIAVEWESN GQPENNYKTT  420
PPMLDSDGSF FLYSKLTVDK SRWQQGNVFS CSVMHEALHN HYTQKSLSLS PGKVTLX     477
```

SEQ ID NO: 54          moltype = DNA   length = 981
FEATURE                Location/Qualifiers
misc_feature           1..981
                       note = Human IgG2 heavy chain constant region sequence
source                 1..981
                       mol_type = other DNA
                       organism = synthetic construct
SEQUENCE: 54
```
gcctccacca agggcccatc ggtcttcccc ctggcgccct gctccaggag cacctccgag   60
agcacagccg ccctgggctg cctggtcaag gactacttcc ccgaaccggt gacggtgtcg  120
tggaactcag gcgctctgac cagcggcgtg cacaccttcc cagctgtcct acagtcctca  180
ggactctact ccctcagcag cgtggtgacc gtgccctcca gcaacttcgg cacccagacc  240
tacacctgca acgtagatca caagcccagc aacaccaagg tggacaagac agttgagcgc  300
aaatgttgtg tcgagtgccc accgtgccca gcaccacctg tggcaggacc gtcagtcttc  360
ctcttccccc caaaacccaa ggacaccctc atgatctccc ggacccctga ggtcacgtgc  420
gtggtggtgg acgtgagcca cgaagacccc gaggtccagt tcaactggta cgtggacggc  480
gtggaggtgc ataatgccaa gacaaagcca cggaggagc agttcaacag cacgttccgt  540
gtggtcagcg tcctcaccgt tgtgcaccag gactggctga acggcaagga gtacaagtgc  600
aaggtctcca acaaaggcct cagcccccc atcgagaaaa ccatctccaa aaccaaaggg  660
cagccccgag aaccacaggt gtacaccctg cccccatccc gggaggagat gaccaagaac  720
caggtcagcc tgacctgcct ggtcaaaggc ttctacccca gcgacatcgc cgtggagtgg  780
gagagcaatg gcagccgga gaacaactac aagaccacac tcccatgct ggactccgac  840
ggctccttct tcctctacag caagctcacc gtggacaaga gcaggtggca gcaggggaac  900
gtcttctcat gctccgtgat gcatgaggct ctgcacaacc actacacgca gaagagcctc  960
tccctgtctc cgggtaaata g                                            981
```

SEQ ID NO: 55          moltype = AA   length = 326
FEATURE                Location/Qualifiers
REGION                 1..326
                       note = Human IgG2 heavy chain constant region sequence
source                 1..326
                       mol_type = protein
                       organism = synthetic construct
SEQUENCE: 55
```
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF  120
```

```
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                       326

SEQ ID NO: 56           moltype = DNA   length = 1362
FEATURE                 Location/Qualifiers
misc_feature            1..1362
                        note = Humanized E6 IgG1 heavy chain sequence
source                  1..1362
                        mol_type = other DNA
                        organism = synthetic construct
SEQUENCE: 56
gaggtgcagc tggtggagtc tgggggaggc ctggtcaagc ctgggggtc cctgagactc      60
tcctgtgcag cctctggatt caccttcagt aggtatggca tgagctgggt ccgccaggct    120
ccagggaaga ggctggagtg ggtctcaacc attagtggcg gaggcaccta catatactac    180
ccagactcag tgaaggggcg attcaccatc tccagagaca cgccaagaa cccactgtat    240
ctgcaaatga acagcctgag agccgaggac acggctgtgt attactgtcc cagagataac    300
tatggccgca actatgatta tggcatggat tattgggggcc agggcaccct ggtgaccgtg    360
agcagcgcta gcaccaaggg cccatcggtc ttccccctgg caccctcctc caagagcacc    420
tctgggggca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgacagtgc cctccagcag cttgggcacc    600
cagacctaca tctgcaacgt gaatcacaag cccagcaaca ccaaggtgga caagaaagtt    660
gagcccaaat cttgtgacaa aactcacaca tgcccaccgt gcccagcacc tgaactcctg    720
gggggaccgt cagtcttcct cttccccca aaacccaagg acaccctcat gatctccng    780
accctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga caactacaa gaccacgcct   1200
cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga gagcctctcc cctgtctccg ggtaaatgat aa                      1362

SEQ ID NO: 57           moltype = AA   length = 452
FEATURE                 Location/Qualifiers
REGION                  1..452
                        note = Humanized E6 IgG1 heavy chain sequence
source                  1..452
                        mol_type = protein
                        organism = synthetic construct
SEQUENCE: 57
EVQLVESGGG LVKPGGSLRL SCAASGFTFS RYGMSWVRQA PGKRLEWVST ISGGGTYIYY     60
PDSVKGRFTI SRDNAKNPLY LQMNSLRAED TAVYYCPRDN YGRNYDYGMD YWQGTLVTV    120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 58           moltype = DNA   length = 996
FEATURE                 Location/Qualifiers
misc_feature            1..996
                        note = Human IgG1 heavy chain constant region sequence
source                  1..996
                        mol_type = other DNA
                        organism = synthetic construct
SEQUENCE: 58
gctagcacca agggcccatc ggtcttcccc ctggcaccct cctccaagag cacctctggg      60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgaca gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tgataa                               996
```

```
SEQ ID NO: 59            moltype = AA   length = 330
FEATURE                  Location/Qualifiers
REGION                   1..330
                         note = Human IgG1 heavy chain constant region sequence
source                   1..330
                         mol_type = protein
                         organism = synthetic construct
SEQUENCE: 59
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 60            moltype = DNA   length = 560
FEATURE                  Location/Qualifiers
misc_feature             1..560
                         note = Human IgG1 heavy chain constant region gBLOCK#1
                         sequence
source                   1..560
                         mol_type = other DNA
                         organism = synthetic construct
SEQUENCE: 60
atggcatgga ttattggggc cagggcaccc tggtgaccgt gagcagcgct agcaccaagg    60
gcccatcggt cttccccctg gcaccctcct ccaagagcac ctctgggggc acagcggccc   120
tgggctgcct ggtcaaggac tacttccccg aaccggtgac ggtgtcgtgg aactcaggcg   180
ccctgaccag cggcgtgcac accttcccgg ctgtcctaca gtcctcagga ctctactccc   240
tcagcagcgt ggtgacagtg ccctccagca gcttgggcac ccagacctac atctgcaacg   300
tgaatcacaa gcccagcaac accaaggtgg acaagaaagt tgagcccaaa tcttgtgaca   360
aaactcacac atgcccaccg tgcccagcac ctgaactcct ggggggaccg tcagtcttcc   420
tcttcccccc aaaacccaag gacaccctca tgatctcccg gacccctgag gtcacatgcg   480
tggtggtgga cgtgagccac gaagaccctg aggtcaagtt caactggtac gtggacggcg   540
tggaggtgca taatgccaag                                              560

SEQ ID NO: 61            moltype = DNA   length = 557
FEATURE                  Location/Qualifiers
misc_feature             1..557
                         note = Human IgG1 heavy chain constant region gBLOCK#2
                         sequence
source                   1..557
                         mol_type = other DNA
                         organism = synthetic construct
SEQUENCE: 61
tacgtggacg gcgtggaggt gcataatgcc aagacaaagc cgcgggagga gcagtacaac    60
agcacgtacc gtgtggtcag cgtcctcacc gtcctgcacc aggactggct gaatggcaag   120
gagtacaagt gcaaggtctc caacaaagcc ctcccagccc ccatcgagaa aaccatctcc   180
aaagccaaag ggcagccccg agaaccacag gtgtacaccc tgcccccatc ccgggaggag   240
atgaccaaga accaggtcag cctgacctgc ctggtcaaag gcttctatcc cagcgacatc   300
gccgtggagt gggagagcaa tgggcagccg gagaacaact acaagaccac gcctcccgtg   360
ctggactccg acggctcctt cttcctctac agcaagctca ccgtggacaa gagcaggtgg   420
cagcagggga acgtcttctc atgctccgtg atgcatgagg ctctgcacaa ccactacacg   480
cagaagagcc tctccctgtc tccgggtaaa tgataagttt aaacccgctg atcagcctcg   540
actgtgcctt ctagttg                                                 557

SEQ ID NO: 62            moltype = DNA   length = 31
FEATURE                  Location/Qualifiers
misc_feature             1..31
                         note = E6 heavy chain variable region overlapping sequence
source                   1..31
                         mol_type = other DNA
                         organism = synthetic construct
SEQUENCE: 62
atggcatgga ttattggggc cagggcaccc t                                  31

SEQ ID NO: 63            moltype = DNA   length = 33
FEATURE                  Location/Qualifiers
misc_feature             1..33
                         note = IgG1 heavy chain constant region overlapping region
                         sequence
source                   1..33
                         mol_type = other DNA
                         organism = synthetic construct
SEQUENCE: 63
tacgtggacg gcgtggaggt gcataatgcc aag                                33

SEQ ID NO: 64            moltype = DNA   length = 33
FEATURE                  Location/Qualifiers
```

| | | |
|---|---|---|
| misc_feature | 1..33 | |
| | note = pCDNA3.1 V5 and pSECTag2 overlapping sequence | |
| source | 1..33 | |
| | mol_type = other DNA | |
| | organism = synthetic construct | |

SEQUENCE: 64
```
ccgctgatca gcctcgactg tgccttctag ttg                              33
```

| | | |
|---|---|---|
| SEQ ID NO: 65 | moltype = DNA  length = 318 | |
| FEATURE | Location/Qualifiers | |
| misc_feature | 1..318 | |
| | note = Mouse E6 Light Chain variable region sequence | |
| source | 1..318 | |
| | mol_type = other DNA | |
| | organism = synthetic construct | |

SEQUENCE: 65
```
caaattgttc tcacccagtc tccagcaatc atgtctgcat ctccagggga ggaggtcacc  60
ctaacctgca gtgccacctc aagtgtaagt tacatacact ggttccagca gaggccaggc 120
acttctccca aactctggat ttatagcaca tccaacctgg cttctggagt ccctgttcgc 180
ttcagtggca gtggatatgg gacctcttac tctctcacaa tcagccgaat ggaggctgaa 240
gatgctgcca cttattactg ccagcaaagg agtagttccc cattcacgtt cggctcgggg 300
acaaagttgg aaataaaa                                              318
```

| | | |
|---|---|---|
| SEQ ID NO: 66 | moltype = AA  length = 106 | |
| FEATURE | Location/Qualifiers | |
| REGION | 1..106 | |
| | note = Mouse E6 Light Chain variable region sequence | |
| source | 1..106 | |
| | mol_type = protein | |
| | organism = synthetic construct | |

SEQUENCE: 66
```
QIVLTQSPAI MSASPGEEVT LTCSATSSVS YIHWFQQRPG TSPKLWIYST SNLASGVPVR  60
FSGSGYGTSY SLTISRMEAE DAATYYCQQR SSSPFTFGSG TKLEIK               106
```

| | | |
|---|---|---|
| SEQ ID NO: 67 | moltype = DNA  length = 69 | |
| FEATURE | Location/Qualifiers | |
| misc_feature | 1..69 | |
| | note = Mouse E6 light chain variable framework region 1 (FWR1) sequence | |
| source | 1..69 | |
| | mol_type = other DNA | |
| | organism = synthetic construct | |

SEQUENCE: 67
```
caaattgttc tcacccagtc tccagcaatc atgtctgcat ctccagggga ggaggtcacc  60
ctaacctgc                                                         69
```

| | | |
|---|---|---|
| SEQ ID NO: 68 | moltype = AA  length = 23 | |
| FEATURE | Location/Qualifiers | |
| REGION | 1..23 | |
| | note = Mouse E6 light chain variable framework region 1 (FWR1) sequence | |
| source | 1..23 | |
| | mol_type = protein | |
| | organism = synthetic construct | |

SEQUENCE: 68
```
QIVLTQSPAI MSASPGEEVT LTC                                         23
```

| | | |
|---|---|---|
| SEQ ID NO: 69 | moltype = DNA  length = 30 | |
| FEATURE | Location/Qualifiers | |
| misc_feature | 1..30 | |
| | note = Mouse E6 light chain variable complementarity determining regions1 (CDR1) sequence | |
| source | 1..30 | |
| | mol_type = other DNA | |
| | organism = synthetic construct | |

SEQUENCE: 69
```
agtgccacct caagtgtaag ttacatacac                                  30
```

| | | |
|---|---|---|
| SEQ ID NO: 70 | moltype = AA  length = 10 | |
| FEATURE | Location/Qualifiers | |
| REGION | 1..10 | |
| | note = Mouse E6 light chain variable complementarity determining regions1 (CDR1) sequence | |
| source | 1..10 | |
| | mol_type = protein | |
| | organism = synthetic construct | |

SEQUENCE: 70
```
SATSSVSYIH                                                        10
```

```
SEQ ID NO: 71              moltype = DNA  length = 45
FEATURE                    Location/Qualifiers
misc_feature               1..45
                           note = Mouse E6 light chain variable framework region 2
                           (FWR2) sequence
source                     1..45
                           mol_type = other DNA
                           organism = synthetic construct
SEQUENCE: 71
tggttccagc agaggccagg cacttctccc aaactctgga tttat              45

SEQ ID NO: 72              moltype = AA  length = 15
FEATURE                    Location/Qualifiers
REGION                     1..15
                           note = Mouse E6 light chain variable framework region 2
                           (FWR2) sequence
source                     1..15
                           mol_type = protein
                           organism = synthetic construct
SEQUENCE: 72
WFQQRPGTSP KLWIY                                               15

SEQ ID NO: 73              moltype = DNA  length = 21
FEATURE                    Location/Qualifiers
misc_feature               1..21
                           note = Mouse E6 light chain variable complementarity
                           determining regions2 (CDR2) sequence
source                     1..21
                           mol_type = other DNA
                           organism = synthetic construct
SEQUENCE: 73
agcacatcca acctggcttc t                                        21

SEQ ID NO: 74              moltype = AA  length = 7
FEATURE                    Location/Qualifiers
REGION                     1..7
                           note = Mouse E6 light chain variable complementarity
                           determining regions2 (CDR2) sequence
source                     1..7
                           mol_type = protein
                           organism = synthetic construct
SEQUENCE: 74
STSNLAS                                                        7

SEQ ID NO: 75              moltype = DNA  length = 96
FEATURE                    Location/Qualifiers
misc_feature               1..96
                           note = Mouse E6 light chain variable framework region 3
                           (FWR3) sequence
source                     1..96
                           mol_type = other DNA
                           organism = synthetic construct
SEQUENCE: 75
ggagtccctg ttcgcttcag tggcagtgga tatgggacct cttactctct cacaatcagc  60
cgaatggagg ctgaagatgc tgccacttat tactgc                           96

SEQ ID NO: 76              moltype = AA  length = 32
FEATURE                    Location/Qualifiers
REGION                     1..32
                           note = Mouse E6 light chain variable framework region 3
                           (FWR3) sequence
source                     1..32
                           mol_type = protein
                           organism = synthetic construct
SEQUENCE: 76
GVPVRFSGSG YGTSYSLTIS RMEAEDAATY YC                            32

SEQ ID NO: 77              moltype = DNA  length = 27
FEATURE                    Location/Qualifiers
misc_feature               1..27
                           note = Mouse E6 light chain variable complementarity
                           determining regions3 (CDR3) sequence
source                     1..27
                           mol_type = other DNA
                           organism = synthetic construct
SEQUENCE: 77
cagcaaagga gtagttcccc attcacg                                  27

SEQ ID NO: 78              moltype = AA  length = 9
```

```
FEATURE                 Location/Qualifiers
REGION                  1..9
                        note = Mouse E6 light chain variable complementarity
                         determining regions3 (CDR3) sequence
source                  1..9
                        mol_type = protein
                        organism = synthetic construct
SEQUENCE: 78
QQRSSSPFT                                                                  9

SEQ ID NO: 79           moltype = DNA  length = 287
FEATURE                 Location/Qualifiers
misc_feature            1..287
                        note = IGKV3-11*02 light chain variable region sequence
source                  1..287
                        mol_type = other DNA
                        organism = synthetic construct
SEQUENCE: 79
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggagagac ttcactctca ccatcagcag cctagagcct   240
gaagattttg cagtttatta ctgtcagcag cgtagcaact ggcctcc                 287

SEQ ID NO: 80           moltype = AA  length = 96
FEATURE                 Location/Qualifiers
REGION                  1..96
                        note = IGKV3-11*02 light chain variable region sequence
source                  1..96
                        mol_type = protein
                        organism = synthetic construct
SEQUENCE: 80
EIVLTQSPAT LSLSPGERAT LSCRASQSVS SYLAWYQQKP GQAPRLLIYD ASNRATGIPA    60
RFSGSGSGRD FTLTISSLEP EDFAVYYCQQ RSNWPP                              96

SEQ ID NO: 81           moltype = DNA  length = 69
FEATURE                 Location/Qualifiers
misc_feature            1..69
                        note = IGKV3-11*02 light chain variable framework region 1
                         (FWR1) acidsequence
source                  1..69
                        mol_type = other DNA
                        organism = synthetic construct
SEQUENCE: 81
gaaattgtgt tgacacagtc tccagccacc ctgtctttgt ctccagggga aagagccacc    60
ctctcctgc                                                            69

SEQ ID NO: 82           moltype = AA  length = 23
FEATURE                 Location/Qualifiers
REGION                  1..23
                        note = IGKV3-11*02 light chain variable framework region 1
                         (FWR1) acidsequence
source                  1..23
                        mol_type = protein
                        organism = synthetic construct
SEQUENCE: 82
EIVLTQSPAT LSLSPGERAT LSC                                            23

SEQ ID NO: 83           moltype = DNA  length = 33
FEATURE                 Location/Qualifiers
misc_feature            1..33
                        note = IGKV3-11*02 light chain variable complementarity
                         determiningregions 1 (CDR1) sequence
source                  1..33
                        mol_type = other DNA
                        organism = synthetic construct
SEQUENCE: 83
agggccagtc agagtgttag cagctactta gcc                                 33

SEQ ID NO: 84           moltype = AA  length = 11
FEATURE                 Location/Qualifiers
REGION                  1..11
                        note = IGKV3-11*02 light chain variable complementarity
                         determiningregions 1 (CDR1) sequence
source                  1..11
                        mol_type = protein
                        organism = synthetic construct
SEQUENCE: 84
RASQSVSSYL A                                                         11
```

```
SEQ ID NO: 85           moltype = DNA  length = 45
FEATURE                 Location/Qualifiers
misc_feature            1..45
                        note = IGKV3-11*02 light chain variable framework region 2
                        (FWR2) sequence
source                  1..45
                        mol_type = other DNA
                        organism = synthetic construct
SEQUENCE: 85
tggtaccaac agaaacctgg ccaggctccc aggctcctca tctat                           45

SEQ ID NO: 86           moltype = AA   length = 15
FEATURE                 Location/Qualifiers
REGION                  1..15
                        note = IGKV3-11*02 light chain variable framework region 2
                        (FWR2) sequence
source                  1..15
                        mol_type = protein
                        organism = synthetic construct
SEQUENCE: 86
WYQQKPGQAP RLLIY                                                            15

SEQ ID NO: 87           moltype = DNA  length = 21
FEATURE                 Location/Qualifiers
misc_feature            1..21
                        note = IGKV3-11*02 light chain variable complementarity
                        determiningregions 2 (CDR2) sequence
source                  1..21
                        mol_type = other DNA
                        organism = synthetic construct
SEQUENCE: 87
gatgcatcca acagggccac t                                                     21

SEQ ID NO: 88           moltype = AA   length = 7
FEATURE                 Location/Qualifiers
REGION                  1..7
                        note = IGKV3-11*02 light chain variable complementarity
                        determiningregions 2 (CDR2) sequence
source                  1..7
                        mol_type = protein
                        organism = synthetic construct
SEQUENCE: 88
DASNRAT                                                                      7

SEQ ID NO: 89           moltype = DNA  length = 96
FEATURE                 Location/Qualifiers
misc_feature            1..96
                        note = IGKV3-11*02 light chain variable framework region 3
                        (FWR3) sequence
source                  1..96
                        mol_type = other DNA
                        organism = synthetic construct
SEQUENCE: 89
ggcatcccag ccaggttcag tggcagtggg tctgggagag acttcactct caccatcagc           60
agcctagagc ctgaagattt tgcagtttat tactgt                                     96

SEQ ID NO: 90           moltype = AA   length = 32
FEATURE                 Location/Qualifiers
REGION                  1..32
                        note = IGKV3-11*02 light chain variable framework region 3
                        (FWR3) sequence
source                  1..32
                        mol_type = protein
                        organism = synthetic construct
SEQUENCE: 90
GIPARFSGSG SGTDFTLTIS SLEPEDFAVY YC                                         32

SEQ ID NO: 91           moltype = DNA  length = 23
FEATURE                 Location/Qualifiers
misc_feature            1..23
                        note = IGKV3-11*02 light chain variable complementarity
                        determiningregions3 (CDR3) sequence
source                  1..23
                        mol_type = other DNA
                        organism = synthetic construct
SEQUENCE: 91
cagcagcgta gcaactggcc tcc                                                   23
```

```
SEQ ID NO: 92              moltype = AA   length = 8
FEATURE                    Location/Qualifiers
REGION                     1..8
                           note = IGKV3-11*02 light chain variable complementarity
                             determiningregions3 (CDR3) sequence
source                     1..8
                           mol_type = protein
                           organism = synthetic construct
SEQUENCE: 92
QQRSNWPP                                                                   8

SEQ ID NO: 93              moltype = DNA   length = 318
FEATURE                    Location/Qualifiers
misc_feature               1..318
                           note = Humanized E6 light chain variable region sequence
source                     1..318
                           mol_type = other DNA
                           organism = synthetic construct
SEQUENCE: 93
gaaattgtgt tgacacagtc tccagccacc ctgtctttgt ctccagggga aagagccacc     60
ctcacctgca gcgccaccag cagtgttagc tacatccact ggtaccaaca gaggcctggc    120
cagagcccca ggctcctcat ctatagcacc tccaacctgg ccagcggcat cccagccagg    180
ttcagtggca gtgggtctgg gagcgactac actctcacca tcagcagcct agagcctgaa    240
gattttgcag tttattactg tcagcagcgt agcagctccc ctttcacctt tggcagcggc    300
accaaagtgg aaattaaa                                                  318

SEQ ID NO: 94              moltype = AA   length = 106
FEATURE                    Location/Qualifiers
REGION                     1..106
                           note = Humanized E6 light chain variable region sequence
source                     1..106
                           mol_type = protein
                           organism = synthetic construct
SEQUENCE: 94
EIVLTQSPAT LSLSPGERAT LTCSATSSVS YIHWYQQRPG QSPRLLIYST SNLASGIPAR     60
FSGSGSGSDY TLTISSLEPE DFAVYYCQQR SSSPFTFGSG TKVEIK                   106

SEQ ID NO: 95              moltype = DNA   length = 69
FEATURE                    Location/Qualifiers
misc_feature               1..69
                           note = Humanized E6 light chain variable framework region 1
                             (FWR1) acidsequence
source                     1..69
                           mol_type = other DNA
                           organism = synthetic construct
SEQUENCE: 95
gaaattgtgt tgacacagtc tccagccacc ctgtctttgt ctccagggga aagagccacc     60
ctcacctgc                                                             69

SEQ ID NO: 96              moltype = AA   length = 23
FEATURE                    Location/Qualifiers
REGION                     1..23
                           note = Humanized E6 light chain variable framework region 1
                             (FWR1) acidsequence
source                     1..23
                           mol_type = protein
                           organism = synthetic construct
SEQUENCE: 96
EIVLTQSPAT LSLSPGERAT LTC                                             23

SEQ ID NO: 97              moltype = DNA   length = 30
FEATURE                    Location/Qualifiers
misc_feature               1..30
                           note = Humanized E6 light chain variable complementarity
                             determiningregions 1 (CDR1) sequence
source                     1..30
                           mol_type = other DNA
                           organism = synthetic construct
SEQUENCE: 97
agcgccacca gcagtgttag ctacatccac                                      30

SEQ ID NO: 98              moltype = AA   length = 10
FEATURE                    Location/Qualifiers
REGION                     1..10
                           note = Humanized E6 light chain variable complementarity
                             determiningregions 1 (CDR1) sequence
source                     1..10
                           mol_type = protein
                           organism = synthetic construct
```

```
SEQUENCE: 98
SATSSVSYIH                                                              10

SEQ ID NO: 99           moltype = DNA  length = 45
FEATURE                 Location/Qualifiers
misc_feature            1..45
                        note = Humanized E6 heavy light variable framework region 2
                        (FWR2) acidsequence
source                  1..45
                        mol_type = other DNA
                        organism = synthetic construct
SEQUENCE: 99
tggtaccaac agaggcctgg ccagagcccc aggctcctca tctat           45

SEQ ID NO: 100          moltype = AA  length = 15
FEATURE                 Location/Qualifiers
REGION                  1..15
                        note = Humanized E6 heavy light variable framework region 2
                        (FWR2) acidsequence
source                  1..15
                        mol_type = protein
                        organism = synthetic construct
SEQUENCE: 100
WYQQRPGQSP RLLIY                                                        15

SEQ ID NO: 101          moltype = DNA  length = 21
FEATURE                 Location/Qualifiers
misc_feature            1..21
                        note = Humanized E6 light chain variable complementarity
                        determiningregions 2 (CDR2) sequence
source                  1..21
                        mol_type = other DNA
                        organism = synthetic construct
SEQUENCE: 101
agcacctcca acctggccag c                                                 21

SEQ ID NO: 102          moltype = AA  length = 7
FEATURE                 Location/Qualifiers
REGION                  1..7
                        note = Humanized E6 light chain variable complementarity
                        determiningregions 2 (CDR2) sequence
source                  1..7
                        mol_type = protein
                        organism = synthetic construct
SEQUENCE: 102
STSNLAS                                                                  7

SEQ ID NO: 103          moltype = DNA  length = 96
FEATURE                 Location/Qualifiers
misc_feature            1..96
                        note = Humanized E6 light chain variable framework region 3
                        (FWR3) acidsequence
source                  1..96
                        mol_type = other DNA
                        organism = synthetic construct
SEQUENCE: 103
ggcatcccag ccaggttcag tgcagtgggt tctgggagcg actacactct caccatcagc       60
agcctagagc ctgaagattt tgcagtttat tactgt                                 96

SEQ ID NO: 104          moltype = AA  length = 32
FEATURE                 Location/Qualifiers
REGION                  1..32
                        note = Humanized E6 light chain variable framework region 3
                        (FWR3) acidsequence
source                  1..32
                        mol_type = protein
                        organism = synthetic construct
SEQUENCE: 104
GIPARFSGSG SGSDYTLTIS SLEPEDFAVY YC                                     32

SEQ ID NO: 105          moltype = DNA  length = 27
FEATURE                 Location/Qualifiers
misc_feature            1..27
                        note = Humanized E6 light chain variable complementarity
                        determiningregions 3 (CDR3) sequence
source                  1..27
                        mol_type = other DNA
                        organism = synthetic construct
SEQUENCE: 105
```

```
cagcagcgta gcagctcccc tttcacc                                             27
```

SEQ ID NO: 106          moltype = AA   length = 9
FEATURE                 Location/Qualifiers
REGION                  1..9
                        note = Humanized E6 light chain variable complementarity
                         determiningregions 3 (CDR3) sequence
source                  1..9
                        mol_type = protein
                        organism = synthetic construct
SEQUENCE: 106
```
QQRSSSPFT                                                                  9
```

SEQ ID NO: 107          moltype = DNA   length = 740
FEATURE                 Location/Qualifiers
misc_feature            1..740
                        note = Humanized E6 Kappa light chain synthesized by
                         Genescript
source                  1..740
                        mol_type = other DNA
                        organism = synthetic construct
SEQUENCE: 107
```
gaattctaag cttgggccac catggaagcc ccagcgcagc ttctcttcct cctgctactc    60
tggctcccag ataccactgg agaaattgtg ttgacacagt ctccagccac cctgtctttg   120
tctccagggg aaagagccac cctcacctgc agcgccacca gcagtgttag ctacatccac   180
tggtaccaac agaggcctgg ccagagcccc aggctcctca tctatagcac ctccaacctg   240
gccagcggca tcccagccag gttcagtggc agtgggtctg ggagcgacta cactctcacc   300
atcagcagcc tagagcctga agattttgca gtttattact gtcagcagcg tagcagctcc   360
cctttcacct ttggcagcgg caccaaagtg gaaattaaaa ggacggtggc tgcaccatct   420
gtcttcatct tcccgccatc tgatgagcag ttgaaatctg gaactgcctc tgttgtgtgc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga acacaaagt ctacgcctgc   660
gaagtcaccc atcagggcct gagctcgccc gtcacaaaga gcttcaacag gggagagtgt   720
tagtaagttt aaactctaga                                                740
```

SEQ ID NO: 108          moltype = AA   length = 243
FEATURE                 Location/Qualifiers
REGION                  1..243
                        note = Humanized E6 Kappa light chain synthesized by
                         Genescript
SITE                    243
                        note = misc_feature - Xaa can be any naturally occurring
                         amino acid
source                  1..243
                        mol_type = protein
                        organism = synthetic construct
SEQUENCE: 108
```
EFAWATMEAP AQLLFLLLLW LPDTTGEIVL TQSPATLSLS PGERATLTCS ATSSVSYIHW    60
YQQRPGQSPR LLIYSTSNLA SGIPARFSGS GSGSDYTLTI SSLEPEDFAV YYCQQRSSSP   120
FTFGSGTKVE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGECV   240
TLX                                                                   243
```

SEQ ID NO: 109          moltype = DNA   length = 324
FEATURE                 Location/Qualifiers
misc_feature            1..324
                        note = Human Kappa light chain constant region sequence
source                  1..324
                        mol_type = other DNA
                        organism = synthetic construct
SEQUENCE: 109
```
aggacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttag                                           324
```

SEQ ID NO: 110          moltype = AA   length = 107
FEATURE                 Location/Qualifiers
REGION                  1..107
                        note = Human Kappa light chain constant region sequence
source                  1..107
                        mol_type = protein
                        organism = synthetic construct
SEQUENCE: 110
```
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107
```

```
SEQ ID NO: 111          moltype = DNA  length = 642
FEATURE                 Location/Qualifiers
misc_feature            1..642
                        note = Humanized E6 lambda light chain sequence
source                  1..642
                        mol_type = other DNA
                        organism = synthetic construct
SEQUENCE: 111
gaaattgtgt tgacacagtc tccagccacc ctgtctttgt ctccagggga aagagccacc    60
ctcacctgca gcgccaccag cagtgttagc tacatccact ggtaccaaca gaggcctggc   120
cagagcccca ggctcctcat ctatagcacc tccaacctgg ccagcggcat cccagccagg   180
ttcagtggca gtgggtctgg agcgactac actctcacca tcagcagcct agagcctgaa    240
gattttgcag tttattactg tcagcagcgt agcagctccc ctttcacctt tggcagcggc   300
accaaagtgg aaattaaagg tcagcccaag gctgccccct cggtcactct gttcccgccc   360
tcctctgagg agcttcaagc caacaaggcc acactggtgt gtctcataag tgacttctac   420
ccgggagccg tgacagtggc ctggaaggca gatagcagcc ccgtcaaggc gggagtggag   480
accaccacac cctccaaaca aagcaacaac aagtacgcgg ccagcagcta tctgagcctg   540
acgcctgagc agtggaagtc ccacagaagc tacagcgcc aggtcacgca tgaagggagc    600
accgtggaga agacagtggc ccctacagaa tgttcatagt aa                     642

SEQ ID NO: 112          moltype = AA  length = 212
FEATURE                 Location/Qualifiers
REGION                  1..212
                        note = Humanized E6 lambda light chain sequence
source                  1..212
                        mol_type = protein
                        organism = synthetic construct
SEQUENCE: 112
EIVLTQSPAT LSLSPGERAT LTCSATSSVS YIHWYQQRPG QSPRLLIYST SNLASGIPAR    60
FSGSGSGSDY TLTISSLEPE DFAVYYCQQR SSSPFTFGSG TKVEIKGQPK AAPSVTLFPP   120
SSEELQANKA TLVCLISDFY PGAVTVAWKA DSSPVKAGVE TTTPSKQSNN KYAASSYLSL   180
TPEQWKSHRS YSCQVTHEGS TVEKTVAPTE CS                                 212

SEQ ID NO: 113          moltype = DNA  length = 324
FEATURE                 Location/Qualifiers
misc_feature            1..324
                        note = Humanized lambda light chain constant region sequence
source                  1..324
                        mol_type = other DNA
                        organism = synthetic construct
SEQUENCE: 113
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcggggagtgg agaccaccac ccctccaaa    180
caaagcaaca acaagtacgc ggccagcagc tatctgagcc tgacgcctga gcagtggaag   240
tcccacagaa gctacagctg ccaggtcacg catgaaggga gcaccgtgga agacagtg     300
gccccctacag aatgttcata gtaa                                         324

SEQ ID NO: 114          moltype = AA  length = 106
FEATURE                 Location/Qualifiers
REGION                  1..106
                        note = Humanized lambda light chain constant region sequence
source                  1..106
                        mol_type = protein
                        organism = synthetic construct
SEQUENCE: 114
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 115          moltype = DNA  length = 614
FEATURE                 Location/Qualifiers
misc_feature            1..614
                        note = Human lambda light chain constant region gBLOCK#3
                          sequence
source                  1..614
                        mol_type = other DNA
                        organism = synthetic construct
SEQUENCE: 115
agcgccacca gcagtgttag ctacatccac tggtaccaac agaggcctgg ccagagcccc    60
aggctcctca tctatagcac ctccaacctg gccagcggca tcccagccag gttcagtggc   120
agtgggtctg gagcgactac cactctcacc atcagcagcc tagagcctga gattttgca    180
gtttattact gtcagcagcg tagcagctcc ctttcacct tggcagcgg caccaaagtg     240
gaaattaaag gtcagcccaa ggctgccccc tcggtcactc tgttcccgcc ctcctctga    300
gagcttcaag ccaacaaggc cacactggtg tgtctcataa gtgacttcta cccgggagcc   360
gtgacagtgg cctggaaggc agatagcagc cccgtcaagg cggggagtgga gaccaccaca   420
ccctccaaac aaagcaacaa caagtacgcg gccagcagct atctgagcct gacgcctgag   480
cagtggaagt cccacagaag ctacagctgc caggtcacgc atgaagggag caccgtggag   540
aagacagtgg cccctacaga atgttcatag taagtttaaa cccgctgatc agcctcgact   600
```

```
gtgccttcta gttg                                                      614

SEQ ID NO: 116           moltype = DNA  length = 31
FEATURE                  Location/Qualifiers
misc_feature             1..31
                         note = E6 light chain variable region overlapping sequence
source                   1..31
                         mol_type = other DNA
                         organism = synthetic construct
SEQUENCE: 116
agcgccacca gcagtgttag ctacatccac t                                    31

SEQ ID NO: 117           moltype = DNA  length = 33
FEATURE                  Location/Qualifiers
misc_feature             1..33
                         note = pCDNA3.1 V5 and pSECTag2 overlapping sequence
source                   1..33
                         mol_type = other DNA
                         organism = synthetic construct
SEQUENCE: 117
ccgctgatca gcctcgactg tgccttctag ttg                                  33

SEQ ID NO: 118           moltype = DNA  length = 390
FEATURE                  Location/Qualifiers
misc_feature             1..390
                         note = Mouse C2 heavy chain variable region sequence
source                   1..390
                         mol_type = other DNA
                         organism = synthetic construct
SEQUENCE: 118
gaggtccagc tggaggagtc agggggaggc ttagtgaagc ctggagggtc cctgaaactc      60
tcctgtgcag cctctggatt cactttcagt ggctatgcca tgtcttgggt tcgccagact     120
ccggagaaga ggctggagtg ggtcgcaacc attagtagtg gtggtactta tatctactat     180
ccagacagtg tgaaggggcg attcaccatc tccagagaa atgccaagaa caccctgtac      240
ctgcaaatga gcagtctgag gtctgaggac acggccatgt attactgtgc aagacttggg    300
ggggataatt actacgaata cttcgatgtc tggggcgcag ggaccacggt caccgtctcc    360
tccgccaaaa cgacaccccc atctgtctat                                     390

SEQ ID NO: 119           moltype = AA  length = 130
FEATURE                  Location/Qualifiers
REGION                   1..130
                         note = Mouse C2 heavy chain variable region sequence
source                   1..130
                         mol_type = protein
                         organism = synthetic construct
SEQUENCE: 119
EVQLEESGGG LVKPGGSLKL SCAASGFTFS GYAMSWVRQT PEKRLEWVAT ISSGGTYIYY      60
PDSVKGRFTI SRDNAKNTLY LQMSSLRSED TAMYYCARLG GDNYYEYFDV WGAGTTVTVS    120
SAKTTPPSVY                                                           130

SEQ ID NO: 120           moltype = DNA  length = 90
FEATURE                  Location/Qualifiers
misc_feature             1..90
                         note = Mouse C2 heavy chain variable framework region 1
                         (FWR1) sequence
source                   1..90
                         mol_type = other DNA
                         organism = synthetic construct
SEQUENCE: 120
gaggtccagc tggaggagtc agggggaggc ttagtgaagc ctggagggtc cctgaaactc      60
tcctgtgcag cctctggatt cactttcagt                                      90

SEQ ID NO: 121           moltype = AA  length = 30
FEATURE                  Location/Qualifiers
REGION                   1..30
                         note = Mouse C2 heavy chain variable framework region 1
                         (FWR1) sequence
source                   1..30
                         mol_type = protein
                         organism = synthetic construct
SEQUENCE: 121
EVQLEESGGG LVKPGGSLKL SCAASGFTFS                                      30

SEQ ID NO: 122           moltype = DNA  length = 15
FEATURE                  Location/Qualifiers
misc_feature             1..15
                         note = Mouse C2 heavy chain variable complementarity
                         determining regions1 (CDR1) sequence
source                   1..15
```

```
                        mol_type = other DNA
                        organism = synthetic construct
SEQUENCE: 122
ggctatgcca tgtct                                                      15

SEQ ID NO: 123          moltype = AA  length = 5
FEATURE                 Location/Qualifiers
REGION                  1..5
                        note = Mouse C2 heavy chain variable complementarity
                         determining regions1 (CDR1) sequence
source                  1..5
                        mol_type = protein
                        organism = synthetic construct
SEQUENCE: 123
GYAMS                                                                  5

SEQ ID NO: 124          moltype = DNA  length = 42
FEATURE                 Location/Qualifiers
misc_feature            1..42
                        note = Mouse C2 heavy chain variable framework region 2
                         (FWR2) sequence
source                  1..42
                        mol_type = other DNA
                        organism = synthetic construct
SEQUENCE: 124
tgggttcgcc agactccgga gaagaggctg gagtgggtcg ca                         42

SEQ ID NO: 125          moltype = AA  length = 14
FEATURE                 Location/Qualifiers
REGION                  1..14
                        note = Mouse C2 heavy chain variable framework region 2
                         (FWR2) sequence
source                  1..14
                        mol_type = protein
                        organism = synthetic construct
SEQUENCE: 125
WVRQTPEKRL EWVA                                                        14

SEQ ID NO: 126          moltype = DNA  length = 51
FEATURE                 Location/Qualifiers
misc_feature            1..51
                        note = Mouse C2 heavy chain variable complementarity
                         determining regions2 (CDR2) sequence
source                  1..51
                        mol_type = other DNA
                        organism = synthetic construct
SEQUENCE: 126
accattagta gtggtggtac ttatatctac tatccagaca gtgtgaaggg g               51

SEQ ID NO: 127          moltype = AA  length = 17
FEATURE                 Location/Qualifiers
REGION                  1..17
                        note = Mouse C2 heavy chain variable complementarity
                         determining regions2 (CDR2) sequence
source                  1..17
                        mol_type = protein
                        organism = synthetic construct
SEQUENCE: 127
TISSGGTYIY YPDSVKG                                                     17

SEQ ID NO: 128          moltype = DNA  length = 96
FEATURE                 Location/Qualifiers
misc_feature            1..96
                        note = Mouse C2 heavy chain variable framework region 3
                         (FWR3) sequence
source                  1..96
                        mol_type = other DNA
                        organism = synthetic construct
SEQUENCE: 128
cgattcacca tctccagaga caatgccaag aacaccctgt acctgcaaat gagcagtctg      60
aggtctgagg acacggccat gtattactgt gcaaga                                96

SEQ ID NO: 129          moltype = AA  length = 32
FEATURE                 Location/Qualifiers
REGION                  1..32
                        note = Mouse C2 heavy chain variable framework region 3
                         (FWR3) sequence
source                  1..32
                        mol_type = protein
```

```
                            organism = synthetic construct
SEQUENCE: 129
RFTISRDNAK NTLYLQMSSL RSEDTAMYYC AR                            32

SEQ ID NO: 130          moltype = DNA  length = 36
FEATURE                 Location/Qualifiers
misc_feature            1..36
                        note = Mouse C2 heavy chain variable complementarity
                         determining regions3 (CDR3) sequence
source                  1..36
                        mol_type = other DNA
                        organism = synthetic construct
SEQUENCE: 130
cttgggggggg ataattacta cgaatacttc gatgtc                       36

SEQ ID NO: 131          moltype = AA  length = 12
FEATURE                 Location/Qualifiers
REGION                  1..12
                        note = Mouse C2 heavy chain variable complementarity
                         determining regions3 (CDR3) sequence
source                  1..12
                        mol_type = protein
                        organism = synthetic construct
SEQUENCE: 131
LGGDNYYEYF DV                                                  12

SEQ ID NO: 132          moltype = DNA  length = 294
FEATURE                 Location/Qualifiers
misc_feature            1..294
                        note = IGHV3-21*04 heavy chain variable region sequence
source                  1..294
                        mol_type = other DNA
                        organism = synthetic construct
SEQUENCE: 132
gaggtgcagc tggtggagtc tggggggaggc ctggtcaagc ctggggggtc cctgagactc  60
tcctgtgcag cctctggatt caccttcagt agctatagca tgaactgggt ccgccaggct  120
ccagggaagg ggctggagtg ggtctcatcc attagtagta gtagtagtta catatactac  180
gcagactcag tgaagggccg attcaccatc tccagagaca acgccaagaa ctcactgtat  240
ctgcaaatga acagcctgag agccgaggac acggccgtgt attactgtgc gaga        294

SEQ ID NO: 133          moltype = AA  length = 98
FEATURE                 Location/Qualifiers
REGION                  1..98
                        note = IGHV3-21*04 heavy chain variable region sequence
source                  1..98
                        mol_type = protein
                        organism = synthetic construct
SEQUENCE: 133
EVQLVESGGG LVKPGGSLRL SCAASGFTFS SYSMNWVRQA PGKGLEWVSS ISSSSSYIYY   60
ADSVKGRFTI SRDNAKNSLY LQMNSLRAED TAVYYCAR                          98

SEQ ID NO: 134          moltype = DNA  length = 90
FEATURE                 Location/Qualifiers
misc_feature            1..90
                        note = IGHV3-21*04 heavy chain variable framework region 1
                         (FWR1) sequence
source                  1..90
                        mol_type = other DNA
                        organism = synthetic construct
SEQUENCE: 134
gaggtgcagc tggtggagtc tggggggaggc ctggtcaagc ctggggggtc cctgagactc  60
tcctgtgcag cctctggatt caccttcagt                                   90

SEQ ID NO: 135          moltype = AA  length = 30
FEATURE                 Location/Qualifiers
REGION                  1..30
                        note = IGHV3-21*04 heavy chain variable framework region 1
                         (FWR1) sequence
source                  1..30
                        mol_type = protein
                        organism = synthetic construct
SEQUENCE: 135
EVQLVESGGG LVKPGGSLRL SCAASGFTFS                                   30

SEQ ID NO: 136          moltype = DNA  length = 15
FEATURE                 Location/Qualifiers
misc_feature            1..15
                        note = IGHV3-21*04 heavy chain variable complementarity
                         determiningregions 1 (CDR1) sequence
```

```
source                  1..15
                        mol_type = other DNA
                        organism = synthetic construct
SEQUENCE: 136
agctatagca tgaac                                                            15

SEQ ID NO: 137          moltype = AA  length = 5
FEATURE                 Location/Qualifiers
REGION                  1..5
                        note = IGHV3-21*04 heavy chain variable complementarity
                        determiningregions 1 (CDR1) sequence
source                  1..5
                        mol_type = protein
                        organism = synthetic construct
SEQUENCE: 137
SYSMN                                                                        5

SEQ ID NO: 138          moltype = DNA  length = 41
FEATURE                 Location/Qualifiers
misc_feature            1..41
                        note = IGHV3-21*04 heavy chain variable framework region 2
                        (FWR2)sequence
source                  1..41
                        mol_type = other DNA
                        organism = synthetic construct
SEQUENCE: 138
gggtccgcca ggctccaggg aaggggctgg agtgggtctc a                                41

SEQ ID NO: 139          moltype = AA  length = 14
FEATURE                 Location/Qualifiers
REGION                  1..14
                        note = IGHV3-21*04 heavy chain variable framework region 2
                        (FWR2)sequence
source                  1..14
                        mol_type = protein
                        organism = synthetic construct
SEQUENCE: 139
WVRQAPGKGL EWVS                                                             14

SEQ ID NO: 140          moltype = DNA  length = 51
FEATURE                 Location/Qualifiers
misc_feature            1..51
                        note = IGHV3-21*04 heavy chain variable complementarity
                        determiningregions 2 (CDR2) sequence
source                  1..51
                        mol_type = other DNA
                        organism = synthetic construct
SEQUENCE: 140
tccattagta gtagtagtag ttacatatac tacgcagact cagtgaaggg c                    51

SEQ ID NO: 141          moltype = AA  length = 17
FEATURE                 Location/Qualifiers
REGION                  1..17
                        note = IGHV3-21*04 heavy chain variable complementarity
                        determiningregions 2 (CDR2) sequence
source                  1..17
                        mol_type = protein
                        organism = synthetic construct
SEQUENCE: 141
SISSSSSYIY YADSVKG                                                          17

SEQ ID NO: 142          moltype = DNA  length = 96
FEATURE                 Location/Qualifiers
misc_feature            1..96
                        note = IGHV3-21*04 heavy chain variable framework region 3
                        (FWR3)sequence
source                  1..96
                        mol_type = other DNA
                        organism = synthetic construct
SEQUENCE: 142
cgattcacca tctccagaga caacgccaag aactcactgt atctgcaaat gaacagcctg           60
agagccgagg acacggccgt gtattactgt gcgaga                                     96

SEQ ID NO: 143          moltype = AA  length = 32
FEATURE                 Location/Qualifiers
REGION                  1..32
                        note = IGHV3-21*04 heavy chain variable framework region 3
                        (FWR3)sequence
source                  1..32
```

```
                        mol_type = protein
                        organism = synthetic construct
SEQUENCE: 143
RFTISRDNAK NSLYLQMNSL RAEDTAVYYC AR                          32

SEQ ID NO: 144          moltype = DNA  length = 363
FEATURE                 Location/Qualifiers
misc_feature            1..363
                        note = Humanized C2 heavy chain variable region sequence
source                  1..363
                        mol_type = other DNA
                        organism = synthetic construct
SEQUENCE: 144
gaggtgcagc tggtggagtc tgggggaggc ctggtcaagc ctggggggtc cctgagactc   60
tcctgtgcag cctctggatt caccttcagt ggctatgcca tgagctgggt ccgccaggct  120
ccagggaagg gctggagtg gtctcaacc attagtagtg gcggaaccta catatactac  180
cccgactcag tgaagggccg attcaccatc tccagagaca cgccaagaa ctcactgtat  240
ctgcaaatga acagcctgag agccgaggac acggccgtgt attactgtgc gagacttggg  300
ggggataatt actacgaata cttcgatgtc tggggcaaag ggaccacggt caccgtctcc  360
tcc                                                                363

SEQ ID NO: 145          moltype = AA  length = 121
FEATURE                 Location/Qualifiers
REGION                  1..121
                        note = Humanized C2 heavy chain variable region sequence
source                  1..121
                        mol_type = protein
                        organism = synthetic construct
SEQUENCE: 145
EVQLVESGGG LVKPGGSLRL SCAASGFTFS GYAMSWVRQA PGKGLEWVST ISSGGTYIYY   60
PDSVKGRFTI SRDNAKNSLY LQMNSLRAED TAVYYCARLG GDNYYEYFDV WGKGTTVTVS  120
S                                                                  121

SEQ ID NO: 146          moltype = DNA  length = 90
FEATURE                 Location/Qualifiers
misc_feature            1..90
                        note = Humanized C2 heavy chain variable framework region 1
                         (FWR1) sequence
source                  1..90
                        mol_type = other DNA
                        organism = synthetic construct
SEQUENCE: 146
gaggtgcagc tggtggagtc tgggggaggc ctggtcaagc ctggggggtc cctgagactc   60
tcctgtgcag cctctggatt caccttcagt                                    90

SEQ ID NO: 147          moltype = AA  length = 30
FEATURE                 Location/Qualifiers
REGION                  1..30
                        note = Humanized C2 heavy chain variable framework region 1
                         (FWR1) sequence
source                  1..30
                        mol_type = protein
                        organism = synthetic construct
SEQUENCE: 147
EVQLVESGGG LVKPGGSLRL SCAASGFTFS                             30

SEQ ID NO: 148          moltype = DNA  length = 15
FEATURE                 Location/Qualifiers
misc_feature            1..15
                        note = Humanized C2 heavy chain variable complementarity
                         determiningregions 1 (CDR1) sequence
source                  1..15
                        mol_type = other DNA
                        organism = synthetic construct
SEQUENCE: 148
ggctatgcca tgagc                                             15

SEQ ID NO: 149          moltype = AA  length = 5
FEATURE                 Location/Qualifiers
REGION                  1..5
                        note = Humanized C2 heavy chain variable complementarity
                         determiningregions 1 (CDR1) sequence
source                  1..5
                        mol_type = protein
                        organism = synthetic construct
SEQUENCE: 149
GYAMS                                                        5

SEQ ID NO: 150          moltype = DNA  length = 43
```

```
FEATURE                 Location/Qualifiers
misc_feature            1..43
                        note = Humanized C2 heavy chain variable framework region 2
                        (FWR2)sequence
source                  1..43
                        mol_type = other DNA
                        organism = synthetic construct
SEQUENCE: 150
tgggtccgcc aggctccagg gaagggggctg gagtgggtct caa                   43

SEQ ID NO: 151          moltype = AA  length = 14
FEATURE                 Location/Qualifiers
REGION                  1..14
                        note = Humanized C2 heavy chain variable framework region 2
                        (FWR2)sequence
source                  1..14
                        mol_type = protein
                        organism = synthetic construct
SEQUENCE: 151
WVRQAPGKGL EWVS                                                    14

SEQ ID NO: 152          moltype = DNA  length = 51
FEATURE                 Location/Qualifiers
misc_feature            1..51
                        note = Humanized C2 heavy chain variable complementarity
                        determiningregions 2 (CDR2) sequence
source                  1..51
                        mol_type = other DNA
                        organism = synthetic construct
SEQUENCE: 152
accattagta gtggcggaac ctacatatac taccccgact cagtgaaggg c            51

SEQ ID NO: 153          moltype = AA  length = 17
FEATURE                 Location/Qualifiers
REGION                  1..17
                        note = Humanized C2 heavy chain variable complementarity
                        determiningregions 2 (CDR2) sequence
source                  1..17
                        mol_type = protein
                        organism = synthetic construct
SEQUENCE: 153
TISSGGTYIY YPDSVKG                                                 17

SEQ ID NO: 154          moltype = DNA  length = 96
FEATURE                 Location/Qualifiers
misc_feature            1..96
                        note = Humanized C2 heavy chain variable framework region 3
                        (FWR3)sequence
source                  1..96
                        mol_type = other DNA
                        organism = synthetic construct
SEQUENCE: 154
cgattcacca tctccagaga caacgccaag aactcactgt atctgcaaat gaacagcctg   60
agagccgagg acacggccgt gtattactgt gcgaga                            96

SEQ ID NO: 155          moltype = AA  length = 32
FEATURE                 Location/Qualifiers
REGION                  1..32
                        note = Humanized C2 heavy chain variable framework region 3
                        (FWR3)sequence
source                  1..32
                        mol_type = protein
                        organism = synthetic construct
SEQUENCE: 155
RFTISRDNAK NSLYLQMNSL RAEDTAVYYC AR                                32

SEQ ID NO: 156          moltype = DNA  length = 36
FEATURE                 Location/Qualifiers
misc_feature            1..36
                        note = Humanized C2 heavy chain variable complementarity
                        determiningregions 3 (CDR3) sequence
source                  1..36
                        mol_type = other DNA
                        organism = synthetic construct
SEQUENCE: 156
cttgggggggg ataattacta cgaatacttc gatgtc                           36

SEQ ID NO: 157          moltype = AA  length = 12
FEATURE                 Location/Qualifiers
```

| REGION | 1..12 |
| --- | --- |
| | note = Humanized C2 heavy chain variable complementarity determiningregions 3 (CDR3) sequence |
| source | 1..12 |
| | mol_type = protein |
| | organism = synthetic construct |

SEQUENCE: 157
LGGDNYYEYF DV                                                                12

| SEQ ID NO: 158 | moltype = DNA  length = 1359 |
| --- | --- |
| FEATURE | Location/Qualifiers |
| misc_feature | 1..1359 |
| | note = Humanized C2 IgG1 heavy chain sequence |
| source | 1..1359 |
| | mol_type = other DNA |
| | organism = synthetic construct |

SEQUENCE: 158
```
gaggtgcagc tggtggagtc tgggggaggc ctggtcaagc ctggggggtc cctgagactc   60
tcctgtgcag cctctggatt caccttcagt ggctatgcca tgagctgggt ccgccaggct  120
ccagggaagg gctggagtg gtctcaacc attagtagtg gcgaaccta catatactac  180
cccgactcag tgaaggccg attcaccatc tccagagaca cgccaagaa ctcactgtat  240
ctgcaaatga acagcctgag agccgaggac acggccgtgt attactgtgc gagacttggg  300
gggataatt actacgaata cttcgatgtc tggggcaaag gaccacggtc caccgtctcc  360
tccgctagca ccaagggccc atcggtcttc cccctggcac cctcctccaa gagcacctct  420
gggggcacag cggccctggg ctgcctggtc aaggactact ccccgaacc ggtgacggtg  480
tcgtggaact caggcgccct gaccagcggc gtgcacacct tcccggctgt cctacagtcc  540
tcaggactct actccctcag cagcgtggtg acagtgccct ccagcagctt gggcacccag  600
acctacatct gcaacgtgaa tcacaagccc agcaacacca aggtggacaa gaaagttgag  660
cccaaatctt gtgacaaaac tcacacatgc ccaccgtgcc cagcacctga actcctgggg  720
ggaccgtcag tcttcctctt ccccccaaaa cccaaggaca cccctcatga tctcccggacc  780
cctgaggtca catgcgtggt ggtggacgtg agccacgaag accctgaggt caagttcaac  840
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcaaggt ctccaacaaa gcccctccag ccccccatcga gaaaaccatc 1020
tccaaagcca aagggcagcc ccgagaacca caggtgtaca ccctgccccc atcccgggag 1080
gagatgacca agaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tacagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaatgataa                         1359
```

| SEQ ID NO: 159 | moltype = AA  length = 451 |
| --- | --- |
| FEATURE | Location/Qualifiers |
| REGION | 1..451 |
| | note = Humanized C2 IgG1 heavy chain sequence |
| source | 1..451 |
| | mol_type = protein |
| | organism = synthetic construct |

SEQUENCE: 159
```
EVQLVESGGG LVKPGGSLRL SCAASGFTFS GYAMSWVRQA PGKGLEWVST ISSGGTYIYY   60
PDSVKGRFTI SRDNAKNSLY LQMNSLRAED TAVYYCARLG GDNYYEYFDV WGKGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451
```

| SEQ ID NO: 160 | moltype = DNA  length = 616 |
| --- | --- |
| FEATURE | Location/Qualifiers |
| misc_feature | 1..616 |
| | note = Humanized C2 gBLOCK#4 sequence |
| source | 1..616 |
| | mol_type = other DNA |
| | organism = synthetic construct |

SEQUENCE: 160
```
actcactata gggagaccca agctggctag ttaagcttgg gccaccatgg agacagacac   60
actcctgcta tgggtactgc tgctctgggt tccaggttcc actggtgacg aggtgcagct  120
ggtggagtct gggggaggcc tggtcaagcc tggggggtc ctgagactct cctgtgcagc  180
ctctggattc accttcagtg gctatgccat gagctgggtc cgccaggctc agggaaggg  240
gctggagtgg gtctcaacca ttagtagtgg cggaacctac atatactacc ccgactcagt  300
gaaggccga ttcaccatct ccagagacaa cgccaagaac tcactgtatc tgcaaatgaa  360
cagcctgaga gccgaggaca cggccgtgta ttactgtgcg agacttgggg gggataatta  420
ctacgaatac ttcgatgtct ggggcaaagg gaccacggtc accgtctcct ccgctagcac  480
caagggccca tcggtcttcc ccctggcacc ctcctccaag agcacctctg ggggacagc  540
ggccctgggc tgcctggtca aggactactt ccccgaaccg gtgacggtgt cgtggaactc  600
aggcgccctg accagc                                                  616
```

| SEQ ID NO: 161 | moltype = DNA  length = 32 |
| --- | --- |

```
FEATURE                 Location/Qualifiers
misc_feature            1..32
                        note = pCDNA3.1 V5 overlapping sequence
source                  1..32
                        mol_type = other DNA
                        organism = synthetic construct
SEQUENCE: 161
actcactata gggagaccca agctggctag tt                                        32

SEQ ID NO: 162          moltype = DNA  length = 34
FEATURE                 Location/Qualifiers
misc_feature            1..34
                        note = Human IgG1 constant region overlapping sequence
source                  1..34
                        mol_type = other DNA
                        organism = synthetic construct
SEQUENCE: 162
gacggtgtcg tggaactcag gcgccctgac cagc                                      34

SEQ ID NO: 163          moltype = DNA  length = 1347
FEATURE                 Location/Qualifiers
misc_feature            1..1347
                        note = Humanized C2 IgG2 heavy chain sequence
source                  1..1347
                        mol_type = other DNA
                        organism = synthetic construct
SEQUENCE: 163
gaggtgcagc tggtggagtc tgggggaggc ctggtcaagc ctggggggtc cctgagactc           60
tcctgtgcag cctctggatt caccttcagt ggctatgcca tgagctgggt ccgccaggct          120
ccagggaagg ggctggagtg ggtctcaacc attagtagtg gcggaaccta catatactac          180
cccgactcag tgaagggccg attcaccatc tccagagaca acgccaagaa ctcactgtat          240
ctgcaaatga acagcctgag agccgaggac acggccgtgt attactgtgc gagacttggg          300
ggggataatt actacgaata cttcgatgtc tggggcaaag ggaccacggt caccgtctcc          360
tccgcctcca ccaagggccc atcggtcttc cccctggcgc cctgctccag gagcacctcc          420
gagagcacag ccgccctggg ctgcctggtc aaggactact tccccgaacc ggtgacggtg          480
tcgtggaact caggcgctct gaccagcggc gtgcacacct tcccagctgt cctacagtcc          540
tcaggactct actccctcag cagcgtggtg accgtgccct ccagcaactt cggcacccag          600
acctacacct gcaacgtaga tcacaagccc agcaacacca aggtggacaa gacagttgag          660
cgcaaatgtt gtgtcgagtg cccaccgtgc ccagcaccac ctgtggcagg accgtcagtc          720
ttcctcttcc ccccaaaacc caaggacacc ctcatgatct cccggacccc tgaggtcacg          780
tgcgtggtgg tggacgtgag ccacgaagac cccgaggtcc agttcaactg gtacgtggac          840
ggcgtggagg tgcataatgc caagacaaag ccacgggagg agcagttcaa cagcacgttc          900
cgtgtggtca gcgtcctcac cgttgtgcac caggactggc tgaacggcaa ggagtacaag          960
tgcaaggtct ccaacaaagg cctcccagcc cccatcgaga aaaccatctc caaaaccaaa         1020
gggcagcccc gagaaccaca ggtgtacacc ctgcccccat cccgggagga gatgaccaag         1080
aaccaggtca gcctgacctg cctggtcaaa ggcttctacc ccagcgacat cgccgtggag         1140
tgggagagca atgggcagcc ggagaacaac tacaagacca cacctcccat gctggactcc         1200
gacggctcct tcttcctcta cagcaagctc accgtggaca agagcaggtg gcagcagggg         1260
aacgtcttct catgctccgt gatgcatgag gctctgcaca accactacac gcagaagagc         1320
ctctccctgt ctccgggtaa atagtaa                                             1347

SEQ ID NO: 164          moltype = AA  length = 447
FEATURE                 Location/Qualifiers
REGION                  1..447
                        note = Humanized C2 IgG2 heavy chain sequence
source                  1..447
                        mol_type = protein
                        organism = synthetic construct
SEQUENCE: 164
EVQLVESGGG LVKPGGSLRL SCAASGFTFS GYAMSWVRQA PGKGLEWVST ISSGGTYIYY           60
PDSVKGRFTI SRDNAKNSLY LQMNSLRAED TAVYYCARLG GDNYYEYFDV WGKGTTVTVS          120
SASTKGPSVF PLAPCSRSTS ESTAALGCLV KDYFPEPVTV SWNSGALTSG VHTFPAVLQS          180
SGLYSLSSVV TVPSSNFGTQ TYTCNVDHKP SNTKVDKTVE RKCCVECPPC PAPPVAGPSV          240
FLFPPKPKDT LMISRTPEVT CVVVDVSHED PEVQFNWYVD GVEVHNAKTK PREEQFNSTF          300
RVVSVLTVVH QDWLNGKEYK CKVSNKGLPA PIEKTISKTK GQPREPQVYT LPPSREEMTK          360
NQVSLTCLVK GFYPSDIAVE WESNGQPENN YKTTPPMLDS DGSFFLYSKL TVDKSRWQQG          420
NVFSCSVMHE ALHNHYTQKS LSLSPGK                                             447

SEQ ID NO: 165          moltype = DNA  length = 549
FEATURE                 Location/Qualifiers
misc_feature            1..549
                        note = Humanized C2 gBLOCK#5 sequence
source                  1..549
                        mol_type = other DNA
                        organism = synthetic construct
SEQUENCE: 165
tgctctgggt tccaggttcc actggtgacg cggcccagcc ggccgaggtg cagctggtgg           60
agtctggggg aggcctggtc aagcctgggg ggtccctgag actctcctgt gcagcctctg          120
gattcacctt cagtggctat gccatgagct gggtccgcca ggctccaggg aaggggctgg          180
```

```
agtgggtctc aaccattagt agtggcggaa cctacatata ctaccccgac tcagtgaagg    240
gccgattcac catctccaga gacaacgcca agaactcact gtatctgcaa atgaacagcc    300
tgagagccga ggacacggcc gtgtattact gtgcgagact tgggggggat aattactacg    360
aatacttcga tgtctggggc aaagggacca cggtcaccgt ctcctccgcc tccaccaagg    420
gcccatcggt cttccccctg gcgccctgct ccaggagcac ctcgagagc acagccgccc     480
tgggctgcct ggtcaaggac tacttccccg aaccggtgac ggtgtcgtgg aactcaggcg    540
ctctgacca                                                           549
```

```
SEQ ID NO: 166          moltype = DNA   length = 31
FEATURE                 Location/Qualifiers
misc_feature            1..31
                        note = pSEC Tag2 overlapping sequence
source                  1..31
                        mol_type = other DNA
                        organism = synthetic construct
SEQUENCE: 166
tgctctgggt tccaggttcc actggtgacg c                                   31

SEQ ID NO: 167          moltype = DNA   length = 32
FEATURE                 Location/Qualifiers
misc_feature            1..32
                        note = Human IgG2 constant region overlapping sequence
source                  1..32
                        mol_type = other DNA
                        organism = synthetic construct
SEQUENCE: 167
gacggtgtcg tggaactcag gcgctctgac ca                                  32

SEQ ID NO: 168          moltype = DNA   length = 360
FEATURE                 Location/Qualifiers
misc_feature            1..360
                        note = Mouse C2 light chain variable region sequence
source                  1..360
                        mol_type = other DNA
                        organism = synthetic construct
SEQUENCE: 168
gacattgtga tcacacagtc tacagcttcc ttaggtgtat ctctggggca gagggccacc    60
atctcatgca gggccagcaa aagtgtcagt acatctggct atagttatat gcactggtac    120
caacagagac caggacagcc acccaaactc ctcatctatc ttgcatccaa cctagaatct    180
ggggtccctg ccaggttcag tggcagtggg tctgggacag acttcaccct caacatccat    240
cctgtggagg aggaggatgc tgcaacctat tactgtcagc acagtaggga gcttccgttc    300
acgttcggag gggggaccaa gctggagata aaacgggctg atgctgcacc aactgtatcc    360

SEQ ID NO: 169          moltype = AA    length = 120
FEATURE                 Location/Qualifiers
REGION                  1..120
                        note = Mouse C2 light chain variable region sequence
source                  1..120
                        mol_type = protein
                        organism = synthetic construct
SEQUENCE: 169
DIVITQSTAS LGVSLGQRAT ISCRASKSVS TSGYSMHWY QQRPGQPPKL LIYLASNLES     60
GVPARFSGSG SGTDFTLNIH PVEEEDAATY YCQHSRELPF TFGGGTKLEI KRADAAPTVS    120

SEQ ID NO: 170          moltype = DNA   length = 69
FEATURE                 Location/Qualifiers
misc_feature            1..69
                        note = Mouse C2 light chain variable framework region 1
                        (FWR1) sequence
source                  1..69
                        mol_type = other DNA
                        organism = synthetic construct
SEQUENCE: 170
gacattgtga tcacacagtc tacagcttcc ttaggtgtat ctctggggca gagggccacc    60
atctcatgc                                                           69

SEQ ID NO: 171          moltype = AA    length = 23
FEATURE                 Location/Qualifiers
REGION                  1..23
                        note = Mouse C2 light chain variable framework region 1
                        (FWR1) sequence
source                  1..23
                        mol_type = protein
                        organism = synthetic construct
SEQUENCE: 171
DIVITQSTAS LGVSLGQRAT ISC                                            23

SEQ ID NO: 172          moltype = DNA   length = 45
FEATURE                 Location/Qualifiers
```

```
misc_feature            1..45
                        note = Mouse C2 light chain variable complementarity
                         determining regions1 (CDR1) sequence
source                  1..45
                        mol_type = other DNA
                        organism = synthetic construct
SEQUENCE: 172
agggccagca aaagtgtcag tacatctggc tatagttata tgcac                45

SEQ ID NO: 173          moltype = AA  length = 15
FEATURE                 Location/Qualifiers
REGION                  1..15
                        note = Mouse C2 light chain variable complementarity
                         determining regions1 (CDR1) sequence
source                  1..15
                        mol_type = protein
                        organism = synthetic construct
SEQUENCE: 173
RASKSVSTSG YSYMH                                                 15

SEQ ID NO: 174          moltype = DNA  length = 45
FEATURE                 Location/Qualifiers
misc_feature            1..45
                        note = Mouse C2 light chain variable framework region 2
                         (FWR2) sequence
source                  1..45
                        mol_type = other DNA
                        organism = synthetic construct
SEQUENCE: 174
tggtaccaac agagaccagg acagccaccc aaactcctca tctat                45

SEQ ID NO: 175          moltype = AA  length = 15
FEATURE                 Location/Qualifiers
REGION                  1..15
                        note = Mouse C2 light chain variable framework region 2
                         (FWR2) sequence
source                  1..15
                        mol_type = protein
                        organism = synthetic construct
SEQUENCE: 175
WYQQRPGQPP KLLIY                                                 15

SEQ ID NO: 176          moltype = DNA  length = 20
FEATURE                 Location/Qualifiers
misc_feature            1..20
                        note = Mouse C2 light chain variable complementarity
                         determining regions2 (CDR2) sequence
source                  1..20
                        mol_type = other DNA
                        organism = synthetic construct
SEQUENCE: 176
cttgcatcca acctagaatc                                            20

SEQ ID NO: 177          moltype = AA  length = 7
FEATURE                 Location/Qualifiers
REGION                  1..7
                        note = Mouse C2 light chain variable complementarity
                         determining regions2 (CDR2) sequence
source                  1..7
                        mol_type = protein
                        organism = synthetic construct
SEQUENCE: 177
LASNLES                                                          7

SEQ ID NO: 178          moltype = DNA  length = 97
FEATURE                 Location/Qualifiers
misc_feature            1..97
                        note = Mouse C2 light chain variable framework region 3
                         (FWR3) sequence
source                  1..97
                        mol_type = other DNA
                        organism = synthetic construct
SEQUENCE: 178
tggggtccct gccaggttca gtggcagtgg gtctgggaca gacttcaccc tcaacatcca 60
tcctgtggag gaggaggatg ctgcaaccta ttactgt                         97

SEQ ID NO: 179          moltype = AA  length = 32
FEATURE                 Location/Qualifiers
REGION                  1..32
```

```
                     note = Mouse C2 light chain variable framework region 3
                       (FWR3) sequence
source               1..32
                     mol_type = protein
                     organism = synthetic construct
SEQUENCE: 179
GVPARFSGSG SGTDFTLNIH PVEEEDAATY YC                                     32

SEQ ID NO: 180       moltype = DNA   length = 27
FEATURE              Location/Qualifiers
misc_feature         1..27
                     note = Mouse C2 light chain variable complementarity
                       determining regions3 (CDR3) sequence
source               1..27
                     mol_type = other DNA
                     organism = synthetic construct
SEQUENCE: 180
cagcacagta gggagcttcc gttcacg                                           27

SEQ ID NO: 181       moltype = AA    length = 9
FEATURE              Location/Qualifiers
REGION               1..9
                     note = Mouse C2 light chain variable complementarity
                       determining regions3 (CDR3) sequence
source               1..9
                     mol_type = protein
                     organism = synthetic construct
SEQUENCE: 181
QHSRELPFT                                                                9

SEQ ID NO: 182       moltype = DNA   length = 303
FEATURE              Location/Qualifiers
misc_feature         1..303
                     note = IGKV7-3*01 light chain variable region sequence
source               1..303
                     mol_type = other DNA
                     organism = synthetic construct
SEQUENCE: 182
gacattgtgc tgacccagtc tccagcctcc ttggccgtgt ctccaggaca gagggccacc       60
atcacctgca gagccagtga gagtgtcagt ttcttgggaa taaacttaat tcactgtat       120
cagcagaaac caggacaacc tcctaaactc ctgatttacc aagcatccaa taaagacact      180
ggggtcccag ccaggttcag cggcagtggg tctgggaccg atttcaccct cacaattaat      240
cctgtggaag ctaatgatac tgcaaattat tactgtctgc agagtaagaa ttttcctccc      300
aca                                                                    303

SEQ ID NO: 183       moltype = AA    length = 101
FEATURE              Location/Qualifiers
REGION               1..101
                     note = IGKV7-3*01 light chain variable region sequence
source               1..101
                     mol_type = protein
                     organism = synthetic construct
SEQUENCE: 183
DIVLTQSPAS LAVSPGQRAT ITCRASESVS FLGINLIHWY QQKPGQPPKL LIYQASNKDT       60
GVPARFSGSG SGTDFTLTIN PVEANDTANY YCLQSKNFPP T                          101

SEQ ID NO: 184       moltype = DNA   length = 69
FEATURE              Location/Qualifiers
misc_feature         1..69
                     note = IGKV7-3*01 light chain variable framework region 1
                       (FWR1) sequence
source               1..69
                     mol_type = other DNA
                     organism = synthetic construct
SEQUENCE: 184
gacattgtgc tgacccagtc tccagcctcc ttggccgtgt ctccaggaca gagggccacc       60
atcacctgc                                                               69

SEQ ID NO: 185       moltype = AA    length = 23
FEATURE              Location/Qualifiers
REGION               1..23
                     note = IGKV7-3*01 light chain variable framework region 1
                       (FWR1) sequence
source               1..23
                     mol_type = protein
                     organism = synthetic construct
SEQUENCE: 185
DIVLTQSPAS LAVSPGQRAT ITC                                               23
```

| | |
|---|---|
| SEQ ID NO: 186 | moltype = DNA  length = 45 |
| FEATURE | Location/Qualifiers |
| misc_feature | 1..45 |
| | note = IGKV7-3*01 light chain variable complementarity determiningregions 1 (CDR1) sequence |
| source | 1..45 |
| | mol_type = other DNA |
| | organism = synthetic construct |

SEQUENCE: 186
agagccagtg agagtgtcag tttcttggga ataaacttaa ttcac                                45

| | |
|---|---|
| SEQ ID NO: 187 | moltype = AA  length = 15 |
| FEATURE | Location/Qualifiers |
| REGION | 1..15 |
| | note = IGKV7-3*01 light chain variable complementarity determiningregions 1 (CDR1) sequence |
| source | 1..15 |
| | mol_type = protein |
| | organism = synthetic construct |

SEQUENCE: 187
RASESVSFLG INLIH                                                                 15

| | |
|---|---|
| SEQ ID NO: 188 | moltype = DNA  length = 45 |
| FEATURE | Location/Qualifiers |
| misc_feature | 1..45 |
| | note = IGKV7-3*01 light chain variable framework region 2 (FWR2)sequence |
| source | 1..45 |
| | mol_type = other DNA |
| | organism = synthetic construct |

SEQUENCE: 188
tggtatcagc agaaaccagg acaacctcct aaactcctga tttac                                45

| | |
|---|---|
| SEQ ID NO: 189 | moltype = AA  length = 15 |
| FEATURE | Location/Qualifiers |
| REGION | 1..15 |
| | note = IGKV7-3*01 light chain variable framework region 2 (FWR2)sequence |
| source | 1..15 |
| | mol_type = protein |
| | organism = synthetic construct |

SEQUENCE: 189
WYQQKPGQPP KLLIY                                                                 15

| | |
|---|---|
| SEQ ID NO: 190 | moltype = DNA  length = 21 |
| FEATURE | Location/Qualifiers |
| misc_feature | 1..21 |
| | note = IGKV7-3*01 light chain variable complementarity determiningregions 2 (CDR2) sequence |
| source | 1..21 |
| | mol_type = other DNA |
| | organism = synthetic construct |

SEQUENCE: 190
caagcatcca ataaagacac t                                                          21

| | |
|---|---|
| SEQ ID NO: 191 | moltype = AA  length = 7 |
| FEATURE | Location/Qualifiers |
| REGION | 1..7 |
| | note = IGKV7-3*01 light chain variable complementarity determiningregions 2 (CDR2) sequence |
| source | 1..7 |
| | mol_type = protein |
| | organism = synthetic construct |

SEQUENCE: 191
QASNKDT                                                                          7

| | |
|---|---|
| SEQ ID NO: 192 | moltype = DNA  length = 96 |
| FEATURE | Location/Qualifiers |
| misc_feature | 1..96 |
| | note = IGKV7-3*01 light chain variable framework region 3 (FWR3)sequence |
| source | 1..96 |
| | mol_type = other DNA |
| | organism = synthetic construct |

SEQUENCE: 192
ggggtcccag ccaggttcag cggcagtggg tctgggaccg atttcaccct cacaattaat               60
cctgtggaag ctaatgatac tgcaaattat tactgt                                         96

| | |
|---|---|
| SEQ ID NO: 193 | moltype = AA  length = 32 |

-continued

```
FEATURE                 Location/Qualifiers
REGION                  1..32
                        note = IGKV7-3*01 light chain variable framework region 3
                        (FWR3)sequence
source                  1..32
                        mol_type = protein
                        organism = synthetic construct
SEQUENCE: 193
GVPARFSGSG SGTDFTLTIN PVEANDTANY YC                                  32

SEQ ID NO: 194          moltype = DNA  length = 339
FEATURE                 Location/Qualifiers
misc_feature            1..339
                        note = Humanized C2 light chain variable region sequence
source                  1..339
                        mol_type = other DNA
                        organism = synthetic construct
SEQUENCE: 194
gacattgtgc tgacccagtc tccagcctcc ttggccgtgt ctccaggaca gagggccacc   60
atcacctgca gagccagtaa gagtgtcagt accagcggat actcctacat gcactggtat  120
cagcagaaac aggacaaacc tcctaaactc ctgatttacc tggcatccaa tctggagagc  180
ggggtcccag ccaggttcag cggcagtggg tctgggacag atttcaccct cacaattaat  240
cctgtggaag ctaatgatac tgcaaattat tactgtcagc acagtaggga gctgcctttc  300
acattcggcg agggaccaa ggtggagatc aaacgaact                           339

SEQ ID NO: 195          moltype = AA  length = 113
FEATURE                 Location/Qualifiers
REGION                  1..113
                        note = Humanized C2 light chain variable region sequence
source                  1..113
                        mol_type = protein
                        organism = synthetic construct
SEQUENCE: 195
DIVLTQSPAS LAVSPGQRAT ITCRASKSVS TSGYSYMHWY QQKPGQPPKL LIYLASNLES    60
GVPARFSGSG SGTDFTLTIN PVEANDTANY YCQHSRELPF TFGGGTKVEI KRT          113

SEQ ID NO: 196          moltype = DNA  length = 69
FEATURE                 Location/Qualifiers
misc_feature            1..69
                        note = Humanized C2 light chain variable framework region 1
                        (FWR1) acidsequence
source                  1..69
                        mol_type = other DNA
                        organism = synthetic construct
SEQUENCE: 196
gacattgtgc tgacccagtc tccagcctcc ttggccgtgt ctccaggaca gagggccacc   60
atcacctgc                                                           69

SEQ ID NO: 197          moltype = AA  length = 23
FEATURE                 Location/Qualifiers
REGION                  1..23
                        note = Humanized C2 light chain variable framework region 1
                        (FWR1) acidsequence
source                  1..23
                        mol_type = protein
                        organism = synthetic construct
SEQUENCE: 197
DIVLTQSPAS LAVSPGQRAT ITC                                            23

SEQ ID NO: 198          moltype = DNA  length = 45
FEATURE                 Location/Qualifiers
misc_feature            1..45
                        note = Humanized C2 light chain variable complementarity
                        determiningregions 1 (CDR1) sequence
source                  1..45
                        mol_type = other DNA
                        organism = synthetic construct
SEQUENCE: 198
agagccagta agagtgtcag taccagcgga tactcctaca tgcac                    45

SEQ ID NO: 199          moltype = AA  length = 15
FEATURE                 Location/Qualifiers
REGION                  1..15
                        note = Humanized C2 light chain variable complementarity
                        determiningregions 1 (CDR1) sequence
source                  1..15
                        mol_type = protein
                        organism = synthetic construct
SEQUENCE: 199
```

```
RASKSVSTSG YSYMH                                                 15

SEQ ID NO: 200          moltype = DNA   length = 45
FEATURE                 Location/Qualifiers
misc_feature            1..45
                        note = Humanized C2 heavy light variable framework region 2
                        (FWR2) acidsequence
source                  1..45
                        mol_type = other DNA
                        organism = synthetic construct
SEQUENCE: 200
tggtatcagc agaaaccagg acaacctcct aaactcctga tttac               45

SEQ ID NO: 201          moltype = AA    length = 15
FEATURE                 Location/Qualifiers
REGION                  1..15
                        note = Humanized C2 heavy light variable framework region 2
                        (FWR2) acidsequence
source                  1..15
                        mol_type = protein
                        organism = synthetic construct
SEQUENCE: 201
WYQQKPGQPP KLLIY                                                 15

SEQ ID NO: 202          moltype = DNA   length = 21
FEATURE                 Location/Qualifiers
misc_feature            1..21
                        note = Humanized C2 light chain variable complementarity
                        determiningregions 2 (CDR2) sequence
source                  1..21
                        mol_type = other DNA
                        organism = synthetic construct
SEQUENCE: 202
ctggcatcca atctggagag c                                          21

SEQ ID NO: 203          moltype = AA    length = 7
FEATURE                 Location/Qualifiers
REGION                  1..7
                        note = Humanized C2 light chain variable complementarity
                        determiningregions 2 (CDR2) sequence
source                  1..7
                        mol_type = protein
                        organism = synthetic construct
SEQUENCE: 203
LASNLES                                                          7

SEQ ID NO: 204          moltype = DNA   length = 96
FEATURE                 Location/Qualifiers
misc_feature            1..96
                        note = Humanized C2 light chain variable framework region 3
                        (FWR3) acidsequence
source                  1..96
                        mol_type = other DNA
                        organism = synthetic construct
SEQUENCE: 204
ggggtcccag ccaggttcag cggcagtggg tctgggaccg atttcaccct cacaattaat 60
cctgtggaag ctaatgatac tgcaaattat tactgt                          96

SEQ ID NO: 205          moltype = AA    length = 32
FEATURE                 Location/Qualifiers
REGION                  1..32
                        note = Humanized C2 light chain variable framework region 3
                        (FWR3) acidsequence
source                  1..32
                        mol_type = protein
                        organism = synthetic construct
SEQUENCE: 205
GVPARFSGSG SGTDFTLTIN PVEANDTANY YC                              32

SEQ ID NO: 206          moltype = DNA   length = 27
FEATURE                 Location/Qualifiers
misc_feature            1..27
                        note = Humanized C2 light chain variable complementarity
                        determiningregions 3 (CDR3) sequence
source                  1..27
                        mol_type = other DNA
                        organism = synthetic construct
SEQUENCE: 206
cagcacagta gggagctgcc tttcaca                                    27
```

```
SEQ ID NO: 207          moltype = AA   length = 9
FEATURE                 Location/Qualifiers
REGION                  1..9
                        note = Humanized C2 light chain variable complementarity
                         determiningregions 3 (CDR3) sequence
source                  1..9
                        mol_type = protein
                        organism = synthetic construct
SEQUENCE: 207
QHSRELPFT                                                                  9

SEQ ID NO: 208          moltype = DNA   length = 27
FEATURE                 Location/Qualifiers
misc_feature            1..27
                        note = Humanized C2 light chain variable complementarity
                         determiningregions 3 (CDR3) sequence
source                  1..27
                        mol_type = other DNA
                        organism = synthetic construct
SEQUENCE: 208
ctgcagagta agaattttcc tcccaca                                              27

SEQ ID NO: 209          moltype = AA   length = 9
FEATURE                 Location/Qualifiers
REGION                  1..9
                        note = Humanized C2 light chain variable complementarity
                         determiningregions 3 (CDR3) sequence
source                  1..9
                        mol_type = protein
                        organism = synthetic construct
SEQUENCE: 209
LQSKNFPPT                                                                  9

SEQ ID NO: 210          moltype = DNA   length = 813
FEATURE                 Location/Qualifiers
misc_feature            1..813
                        note = Humanized C2 gBLOCK#6 sequence (Kappa light chain in
                         pCDNA3.1 V5)
source                  1..813
                        mol_type = other DNA
                        organism = synthetic construct
SEQUENCE: 210
actcactata gggagaccca agctggctag ttaagcttgg gccaccatgg agacagacac           60
actcctgcta tgggtactgc tgctctgggt tccaggttcc actggtgacg acattgtgct          120
gacccagtct ccagcctcct tggccgtgtc tccaggacag agggccacca tcacctgcag          180
agccagtaag agtgtcagta ccagcggata ctcctacatg cactggtatc agcagaaacc          240
aggacaacct cctaaactcc tgatttacct ggcatccaat ctggagagcg ggtcccagc           300
caggttcagc ggcagtgggt ctgggaccga tttcaccctc acaattaatc ctgtggaagc          360
taatgatact gcaaattatt actgtcagca cagtagggag ctgcctttca cattcggcgg          420
agggaccaag gtggagatca acgaactac ggtggctgca ccatctgtct tcatcttccc          480
gccatctgat gagcagttga aatctggaac tgcctctgtt gtgtgcctgc tgaataactt          540
ctatcccaga gaggccaaag tacagtggaa ggtggataac gccctccaat cgggtaactc          600
ccaggagagt gtcacagagc aggacagcaa ggacagcacc tacagcctca gcagcaccct          660
gacgctgagc aaagcagact acgagaaaca caaagtctac gcctgcgaag tcacccatca          720
gggcctgagc tcgcccgtca caaagagctt caacagggga gagtgttagt aagtttaaac          780
ccgctgatca gcctcgactg tgccttctag ttg                                      813

SEQ ID NO: 211          moltype = DNA   length = 32
FEATURE                 Location/Qualifiers
misc_feature            1..32
                        note = pCDNA3.1 V5 5' overlapping sequence
source                  1..32
                        mol_type = other DNA
                        organism = synthetic construct
SEQUENCE: 211
actcactata gggagaccca agctggctag tt                                        32

SEQ ID NO: 212          moltype = DNA   length = 33
FEATURE                 Location/Qualifiers
misc_feature            1..33
                        note = pCDNA3.1 V5 3' overlapping sequence
source                  1..33
                        mol_type = other DNA
                        organism = synthetic construct
SEQUENCE: 212
ccgctgatca gcctcgactg tgccttctag ttg                                       33

SEQ ID NO: 213          moltype = DNA   length = 748
```

```
FEATURE              Location/Qualifiers
misc_feature         1..748
                     note = Humanized C2 gBLOCK#7 sequence (Kappa light chain in
                       pSEC Tag2)
source               1..748
                     mol_type = other DNA
                     organism = synthetic construct
SEQUENCE: 213
tgctctgggt tccaggttcc actggtgacg cggcccagcc ggccgacatt gtgctgaccc   60
agtctccagc ctccttggcc gtgtctccag gacagagggc caccatcacc tgcagagcca  120
gtaagagtgt cagtaccagc ggatactcct acatgcactg gtatcagcag aaaccaggac  180
aacctcctaa actcctgatt tacctggcat ccaatctgga gagcggggtc ccagccaggt  240
tcagcggcag tgggtctggg accgatttca ccctcacaat taatcctgtg aagctaatg   300
atactgcaaa ttattactgt cagcacagta gggagctgcc tttcacattc ggcggaggga  360
ccaaggtgga gatcaaacga actacgtggg ctgcaccatc tgtcttcatc ttcccgccat  420
ctgatgagca gttgaaatct ggaactgcct ctgttgtgtg cctgctgaat aacttctatc  480
ccagagaggc caaagtacag tggaaggtgg ataacgccct ccaatcgggt aactcccagg  540
agagtgtcac agagcaggac agcaaggaca gcacctacag cctcagcagc accctgacgc  600
tgagcaaagc agactacgag aaacacaaag tctacgcctg cgaagtcacc catcagggcc  660
tgagctcgcc cgtcacaaag agcttcaaca gggagagtg ttagtaagtt taaacccgct   720
gatcagcctc gactgtgcct tctagttg                                     748

SEQ ID NO: 214       moltype = DNA length = 31
FEATURE              Location/Qualifiers
misc_feature         1..31
                     note = pSEC Tag2 5' overlapping sequence
source               1..31
                     mol_type = other DNA
                     organism = synthetic construct
SEQUENCE: 214
tgctctgggt tccaggttcc actggtgacg c                                  31

SEQ ID NO: 215       moltype = DNA length = 33
FEATURE              Location/Qualifiers
misc_feature         1..33
                     note = pSEC Tag2 3' overlapping sequence
source               1..33
                     mol_type = other DNA
                     organism = synthetic construct
SEQUENCE: 215
ccgctgatca gcctcgactg tgccttctag ttg                                33

SEQ ID NO: 216       moltype = DNA length = 813
FEATURE              Location/Qualifiers
misc_feature         1..813
                     note = Humanized C2 gBLOCK#8 sequence (lambda light chain
                       in pCDNA3.1V5)
source               1..813
                     mol_type = other DNA
                     organism = synthetic construct
SEQUENCE: 216
actcactata gggagaccca agctggctag ttaagcttgg gccaccatgg agacagacac    60
actcctgcta tgggtactgc tgctctgggt tccaggttcc actggtgacg acattgtgct  120
gacccagtct ccagcctcct ggccgtgtc tccaggacag agggccacca tcacctgcag   180
agccagtaag agtgtcagta ccagcggata ctcctacatg cactggtatc agcagaaacc  240
aggacaacct cctaaactcc tgatttacct ggcatccaat ctggagagcg gggtcccagc  300
caggttcagc ggcagtgggt ctgggaccga tttcaccctc acaattaatc ctgtggaagc  360
taatgatact gcaaattatt actgtcagca cagtagggag ctgcctttca cattcggcgg  420
agggaccaag gtggagatca aacgaactgt ggctgcacca tctgtcttca tcttcccgcc  480
atctgatgag cagttgaaat ctggaactgc ctctgttgtg tgcctgctga ataacttcta  540
tcccagagag gccaaagtac agtggaaggt ggataacgcc ctccaatcgg gtaactccca  600
ggagagtgtc acagagcagg acagcaagga cagcacctac agcctcagca gcaccctgac  660
gctgagcctg acgcctgagc agtggaagtc cacagaagc tacagctgcc aggtcacgca   720
tgaagggagc accgtggaga gacagtggc cctacagaa tgttcatagt aagtttaaac   780
ccgctgatca gcctcgactg tgccttctag ttg                                813

SEQ ID NO: 217       moltype = DNA length = 32
FEATURE              Location/Qualifiers
misc_feature         1..32
                     note = pCDNA3.1 V5 5' overlapping sequence
source               1..32
                     mol_type = other DNA
                     organism = synthetic construct
SEQUENCE: 217
actcactata gggagaccca agctggctag tt                                  32

SEQ ID NO: 218       moltype = DNA length = 33
FEATURE              Location/Qualifiers
misc_feature         1..33
```

```
                        note = pCDNA3.1 V5 3' overlapping sequence
source                  1..33
                        mol_type = other DNA
                        organism = synthetic construct
SEQUENCE: 218
ccgctgatca gcctcgactg tgccttctag ttg                                       33

SEQ ID NO: 219          moltype = DNA  length = 748
FEATURE                 Location/Qualifiers
misc_feature            1..748
                        note = Humanized C2 gBLOCK#9 sequence (lambda light chain
                         in pSEC Tag2)
source                  1..748
                        mol_type = other DNA
                        organism = synthetic construct
SEQUENCE: 219
tgctctgggt tccaggttcc actggtgacg cggcccagcc ggccgacatt gtgctgaccc           60
agtctccagc ctccttggcc gtgtctccag gacagagggc caccatcacc tgcagagcca          120
gtaagagtgt cagtaccagc ggatactcct acatgcactg gtatcagcag aaaccaggac          180
aacctcctaa actcctgatt tacctggcat ccaatctgga gagcggggtc ccagccaggt          240
tcagcggcag tgggtctggg accgatttca ccctcacaat taatcctgtg aagctaatg           300
atactgcaaa ttattactgt cagcacagta gggagctgcc tttcacattc ggcggaggga          360
ccaaggtgga gatcaaacga actggtcagc caaggctgc ccctcggtc actctgttcc            420
cgccctcctc tgaggagctt caagccaaca aggccacact ggtgtgtctc ataagtgact          480
tctacccggg agccgtgaca gtggcctgga aggcagatag cagccccgtc aaggcgggag          540
tggagaccac cacaccctcc aaacaaagca caacaagtc cgcggccagc agctatctga          600
gcctgacgcc tgagcagtgg aagtcccaca gaagctacag ctgccaggtc acgcatgaag          660
ggagcaccgt ggagaagaca gtggcccta cagaatgttc atagtaagtt taaacccgct          720
gatcagcctc gactgtgcct tctagttg                                              748

SEQ ID NO: 220          moltype = DNA  length = 31
FEATURE                 Location/Qualifiers
misc_feature            1..31
                        note = pSEC Tag2 5' overlapping sequence
source                  1..31
                        mol_type = other DNA
                        organism = synthetic construct
SEQUENCE: 220
tgctctgggt tccaggttcc actggtgacg c                                         31

SEQ ID NO: 221          moltype = DNA  length = 33
FEATURE                 Location/Qualifiers
misc_feature            1..33
                        note = pSEC Tag2 3' overlapping sequence
source                  1..33
                        mol_type = other DNA
                        organism = synthetic construct
SEQUENCE: 221
ccgctgatca gcctcgactg tgccttctag ttg                                       33

SEQ ID NO: 222          moltype = DNA  length = 63
FEATURE                 Location/Qualifiers
misc_feature            1..63
                        note = Murine Ig kappa chain leader sequence
source                  1..63
                        mol_type = other DNA
                        organism = synthetic construct
SEQUENCE: 222
atggagacag acacactcct gctatgggta ctgctgctct gggttccagg ttccactggt           60
gac                                                                         63

SEQ ID NO: 223          moltype = AA  length = 21
FEATURE                 Location/Qualifiers
REGION                  1..21
                        note = Murine Ig kappa chain leader sequence
source                  1..21
                        mol_type = protein
                        organism = synthetic construct
SEQUENCE: 223
METDTLLLWV LLLWVPGSTG D                                                    21

SEQ ID NO: 224          moltype = DNA  length = 60
FEATURE                 Location/Qualifiers
misc_feature            1..60
                        note = Interleukin-2 (IL-2) leader sequence
source                  1..60
                        mol_type = other DNA
                        organism = synthetic construct
SEQUENCE: 224
```

```
atgtacagga tgcaactcct gtcttgcatt gcactaagtc ttgcacttgt cacaaacagt    60

SEQ ID NO: 225          moltype = AA   length = 20
FEATURE                 Location/Qualifiers
REGION                  1..20
                        note = Interleukin-2 (IL-2) leader sequence
source                  1..20
                        mol_type = protein
                        organism = synthetic construct
SEQUENCE: 225
MYRMQLLSCI ALSLALVTNS                                                20

SEQ ID NO: 226          moltype = DNA   length = 48
FEATURE                 Location/Qualifiers
misc_feature            1..48
                        note = CD33 leader sequence
source                  1..48
                        mol_type = other DNA
                        organism = synthetic construct
SEQUENCE: 226
atgcctcttc tgcttctgct tcctctgctt tgggctggag ctcttgct                 48

SEQ ID NO: 227          moltype = AA   length = 16
FEATURE                 Location/Qualifiers
REGION                  1..16
                        note = CD33 leader sequence
source                  1..16
                        mol_type = protein
                        organism = synthetic construct
SEQUENCE: 227
MPLLLLLPLL WAGALA                                                    16

SEQ ID NO: 228          moltype = DNA   length = 57
FEATURE                 Location/Qualifiers
misc_feature            1..57
                        note = IGHV3-21*03 leader sequence
source                  1..57
                        mol_type = other DNA
                        organism = synthetic construct
SEQUENCE: 228
atggaactgg ggctccgctg ggttttcctt gttgctattt tagaaggtgt ccagtgt       57

SEQ ID NO: 229          moltype = AA   length = 19
FEATURE                 Location/Qualifiers
REGION                  1..19
                        note = IGHV3-21*03 leader sequence
source                  1..19
                        mol_type = protein
                        organism = synthetic construct
SEQUENCE: 229
MELGLRWVFL VAILEGVQC                                                 19

SEQ ID NO: 230          moltype = DNA   length = 60
FEATURE                 Location/Qualifiers
misc_feature            1..60
                        note = IGHV3-11*02 leader sequence
source                  1..60
                        mol_type = other DNA
                        organism = synthetic construct
SEQUENCE: 230
atggaagccc cagcgcagct tctcttcctc ctgctactct ggctcccaga taccactgga    60

SEQ ID NO: 231          moltype = AA   length = 20
FEATURE                 Location/Qualifiers
REGION                  1..20
                        note = IGHV3-11*02 leader sequence
source                  1..20
                        mol_type = protein
                        organism = synthetic construct
SEQUENCE: 231
MEAPAQLLFL LLLWLPDTTG                                                20

SEQ ID NO: 232          moltype = DNA   length = 729
FEATURE                 Location/Qualifiers
misc_feature            1..729
                        note = Humanized E6 single chain GS3
source                  1..729
                        mol_type = other DNA
                        organism = synthetic construct
```

-continued

```
SEQUENCE: 232
gaggtgcagc tggtggagtc tggggggaggc ctggtcaagc ctggggggtc cctgagactc    60
tcctgtgcag cctctggatt caccttcagt aggtatggca tgagctgggt ccgccaggct   120
ccagggaaga ggctggagtg ggtctcaacc attagtggcg gaggcaccta catatactac   180
ccagactcag tgaagggccg attcaccatc tccagagaca cgccaagaa caccctgtat    240
ctgcaaatga acagcctgag agccgaggac acggctgtgt attactgtac cagagataac   300
tatgccgca actatgatta tggcatggat tattgggggcc agggcaccct ggtgaccgtg    360
agcagcggcg gtggcggatc cggcggtggc ggatccggcg gtggcggatc cgaaattgtg   420
ttgacacagt ctccagccac cctgtctttg tctccagggg aaagagccac cctcacctgc   480
agcgccacca gcagtgttag ctacatccac tggtaccaac agaggcctgg ccagagcccc   540
aggctcctca tctatagcac ctccaacctg gccagcggca tcccagccag gttcagtggc   600
agtgggtctg ggagcgacta cactctcacc atcagcagcc tagagcctga agattttgca   660
gtttattact gtcagcagcg tagcagctcc cctttcacct ttggcagcgg caccaaagtg   720
gaaattaaa                                                           729

SEQ ID NO: 233          moltype = AA  length = 243
FEATURE                 Location/Qualifiers
REGION                  1..243
                        note = Humanized E6 single chain GS3
source                  1..243
                        mol_type = protein
                        organism = synthetic construct
SEQUENCE: 233
EVQLVESGGG LVKPGGSLRL SCAASGFTFS RYGMSWVRQA PGKRLEWVST ISGGGTYIYY    60
PDSVKGRFTI SRDNAKNTLY LQMNSLRAED TAVYYCTRDN YGRNYDYGMD YWGQGTLVTV   120
SSGGGGSGGG GSGGGGSEIV LTQSPATLSL SPGERATLTC SATSSVSYIH WYQQRPGQSP   180
RLLIYSTSNL ASGIPARFSG SGSGSDYTLT ISSLEPEDFA VYYCQQRSSS PFTFGSGTKV   240
EIK                                                                 243

SEQ ID NO: 234          moltype = DNA  length = 747
FEATURE                 Location/Qualifiers
misc_feature            1..747
                        note = Humanized E6 single chain IgG1noC
source                  1..747
                        mol_type = other DNA
                        organism = synthetic construct
SEQUENCE: 234
gaggtgcagc tggtggagtc tggggggaggc ctggtcaagc ctggggggtc cctgagactc    60
tcctgtgcag cctctggatt caccttcagt aggtatggca tgagctgggt ccgccaggct   120
ccagggaaga ggctggagtg ggtctcaacc attagtggcg gaggcaccta catatactac   180
ccagactcag tgaagggccg attcaccatc tccagagaca cgccaagaa caccctgtat    240
ctgcaaatga acagcctgag agccgaggac acggctgtgt attactgtac cagagataac   300
tatgccgca actatgatta tggcatggat tattgggggcc agggcaccct ggtgaccgtg    360
agcagcgata aaacccatac taaaccgcca aaaccggcgc cggaactgct gggtggtcct   420
ggtaccggtg aaattgtgtt gacacagtct ccagccaccc tgtctttgtc tccaggggaa   480
agagccaccc tcacctgcag cgccaccagc agtgttagc acatccactg gtaccaacag    540
aggcctggcc agagccccag gctcctcatc tatagcacct ccaacctggc cagcggcatc   600
ccagccaggt tcagtggcag tgggtctggg agcgactaca ctctcaccat cagcagccta   660
gagcctgaag attttgcagt ttattactgt cagcagcgta gcagctcccc tttcaccttt   720
ggcagcggca ccaaagtgga aattaaa                                       747

SEQ ID NO: 235          moltype = AA  length = 249
FEATURE                 Location/Qualifiers
REGION                  1..249
                        note = Humanized E6 single chain IgG1noC
source                  1..249
                        mol_type = protein
                        organism = synthetic construct
SEQUENCE: 235
EVQLVESGGG LVKPGGSLRL SCAASGFTFS RYGMSWVRQA PGKRLEWVST ISGGGTYIYY    60
PDSVKGRFTI SRDNAKNTLY LQMNSLRAED TAVYYCTRDN YGRNYDYGMD YWGQGTLVTV   120
SSDKTHTKPP KPAPELLGGP GTGEIVLTQS PATLSLSPGE RATLTCSATS SVSYIHWYQQ   180
RPGQSPRLLI YSTSNLASGI PARFSGSGSG SDYTLTISSL EPEDFAVYYC QQRSSSPFTF   240
GSGTKVEIK                                                           249

SEQ ID NO: 236          moltype = DNA  length = 813
FEATURE                 Location/Qualifiers
misc_feature            1..813
                        note = Humanized E6 single chain X4 (linker is IgG1 and
                        IgG2 modifiedhinge region)
source                  1..813
                        mol_type = other DNA
                        organism = synthetic construct
SEQUENCE: 236
gaggtgcagc tggtggagtc tggggggaggc ctggtcaagc ctggggggtc cctgagactc    60
tcctgtgcag cctctggatt caccttcagt aggtatggca tgagctgggt ccgccaggct   120
ccagggaaga ggctggagtg ggtctcaacc attagtggcg gaggcaccta catatactac   180
ccagactcag tgaagggccg attcaccatc tccagagaca cgccaagaa caccctgtat    240
ctgcaaatga acagcctgag agccgaggac acggctgtgt attactgtac cagagataac   300
```

```
tatggccgca actatgatta tggcatggat tattgggccc agggcaccct ggtgaccgtg    360
agcagcgata aaacccatac taaaccgcca aaaccggcgc cggaactgct gggtggtcct    420
ggtaccggta ctggtggtcc gactattaaa cctccgaaac ctccgaaacc tgctccgaac    480
ctgctgggtg tccggaaat tgtgttgaca cagtctccag ccaccctgtc tttgtctcca    540
ggggaaagag ccaccctcac ctgcagcgcc accagcagtg ttagctacat ccactggtac    600
caacagaggc ctggccagag ccccaggctc ctcatctata gcacctccaa cctggccagc    660
ggcatcccag ccaggttcag tggcagtggg tctgggagcg actacactct caccatcagc    720
agcctagagc ctgaagattt tgcagtttat tactgtcagc agcgtagcag ctcccctttc    780
acctttggca gcggcaccaa agtggaaatt aaa                                 813

SEQ ID NO: 237          moltype = AA   length = 271
FEATURE                 Location/Qualifiers
REGION                  1..271
                        note = Humanized E6 single chain X4 (linker is IgG1 and
                        IgG2 modifiedhinge region)
source                  1..271
                        mol_type = protein
                        organism = synthetic construct
SEQUENCE: 237
EVQLVESGGG LVKPGGSLRL SCAASGFTFS RYGMSWVRQA PGKRLEWVST ISGGGTYIYY    60
PDSVKGRFTI SRDNAKNTLY LQMNSLRAED TAVYYCTRDN YGRNYDYGMD YWGQGTLVTV    120
SSDKTHTKPP KPAPELLGGP GTGTGGPTIK PPKPPKPAPN LLGGPEIVLT QSPATLSLSP    180
GERATLTCSA TSSVSYIHWY QQRPGQSPRL LIYSTSNLAS GIPARFSGSG SGSDYTLTIS    240
SLEPEDFAVY YCQQRSSSPF TFGSGTKVEI K                                    271

SEQ ID NO: 238          moltype = DNA   length = 747
FEATURE                 Location/Qualifiers
misc_feature            1..747
                        note = Humanized C2 single chain GS3
source                  1..747
                        mol_type = other DNA
                        organism = synthetic construct
SEQUENCE: 238
gaggtgcagc tggtggagtc tgggggaggc ctggtcaagc ctgggggtc cctgagactc     60
tcctgtgcag cctctggatt caccttcagt ggctatgcca tgagctgggt ccgccaggct    120
ccagggaagg gctggagtg gtctcaacc attagtagtg gcggaaccta catatactac     180
cccgactcag tgaagggccg attcaccatc tccagagaca cgccaagaa ctcactgtat    240
ctgcaaatga acagcctgag agccgaggac acggccgtgt attactgtgc gagacttggg    300
ggggataatt actacgaata cttcgatgtc tggggcaagt ggaccacggt caccgtctcc    360
tccggcggtg gcggatccgg cggtggcgga tccggcggtg gcggatccga cattgtgctg    420
acccagtctc cagcctcctt ggccgtgtct ccaggacaga gggccaccat cacctgcaga    480
gccagtaaga gtgtcagtac cagcggatac tcctacatgc actggtatca gcagaaacca    540
ggacaacctc ctaaactcct gatttacctg gcatccaatc tggagaggcgg ggtcccgagc    600
aggttcagcg gcagtgggtc tgggaccgat ttcacccctca caattaatcc tgtgaagct    660
aatgatactg caaattatta ctgtcagcac agtagggagc tgcctttcac attcggcgga    720
gggaccaagg tggagatcaa acgaact                                         747

SEQ ID NO: 239          moltype = AA   length = 249
FEATURE                 Location/Qualifiers
REGION                  1..249
                        note = Humanized C2 single chain GS3
source                  1..249
                        mol_type = protein
                        organism = synthetic construct
SEQUENCE: 239
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYFDV WGKGTTVTVS    120
SGGGGSGGGG SGGGGSDIVL TQSPASLAVS PGQRATITCR ASKSVSTSGY SYMHWYQQKP    180
GQPPKLLIYL ASNLESGVPA RFSGSGSGTD FTLTINPVEA NDTANYYCQH SRELPFTFGG    240
GTKVEIKRT                                                             249

SEQ ID NO: 240          moltype = DNA   length = 765
FEATURE                 Location/Qualifiers
misc_feature            1..765
                        note = Humanized C2 single chain IgG (no Cysteine)
source                  1..765
                        mol_type = other DNA
                        organism = synthetic construct
SEQUENCE: 240
gaggtgcagc tggtggagtc tgggggaggc ctggtcaagc ctgggggtc cctgagactc     60
tcctgtgcag cctctggatt caccttcagt ggctatgcca tgagctgggt ccgccaggct    120
ccagggaagg gctggagtg gtctcaacc attagtagtg gcggaaccta catatactac     180
cccgactcag tgaagggccg attcaccatc tccagagaca cgccaagaa ctcactgtat    240
ctgcaaatga acagcctgag agccgaggac acggccgtgt attactgtgc gagacttggg    300
ggggataatt actacgaata cttcgatgtc tggggcaaag gaccacggt caccgtctcc    360
tccgataaaa cccatactaa accgccaaaa ccggcgccgg aactgctggg tggtcctggt    420
accggtgaca ttgtgctgac ccagtctcca gcctccttgg ccgtgtctcc aggacagagg    480
gccaccatca cctgcagagc cagtaagagt gtcagtacca gcggatactc ctacatgcac    540
tggtatcagc agaaaccagg acaacctcct aaactctga tttacctggc atccaatctg    600
```

```
gagagcgggg tcccagccag gttcagcggc agtgggtctg ggaccgattt caccctcaca    660
attaatcctg tggaagctaa tgatactgca aattattact gtcagcacag tagggagctg    720
cctttcacat tcggcggagg gaccaaggtg gagatcaaac gaact                    765
```

```
SEQ ID NO: 241              moltype = AA  length = 255
FEATURE                     Location/Qualifiers
REGION                      1..255
                            note = Humanized C2 single chain IgG (no Cysteine)
source                      1..255
                            mol_type = protein
                            organism = synthetic construct
SEQUENCE: 241
EVQLVESGGG LVKPGGSLRL SCAASGFTFS GYAMSWVRQA PGKGLEWVST ISSGGTYIYY     60
PDSVKGRFTI SRDNAKNSLY LQMNSLRAED TAVYYCARLG GDNYYEYFDV WGKGTTVTVS    120
SDKTHTKPPK PAPELLGGPG TGDIVLTQSP ASLAVSPGQR ATITCRASKS VSTSGYSYMH    180
WYQQKPGQPP KLLIYLASNL ESGVPARFSG SGSGTDFTLT INPVEANDTA NYYCQHSREL    240
PFTFGGGTKV EIKRT                                                     255
```

```
SEQ ID NO: 242              moltype = DNA  length = 831
FEATURE                     Location/Qualifiers
misc_feature                1..831
                            note = Humanized C2 single chain X4 (linker is IgG1 and
                            IgG2 modifiedhinge region)
source                      1..831
                            mol_type = other DNA
                            organism = synthetic construct
SEQUENCE: 242
gaggtgcagc tggtggagtc tgggggaggc ctggtcaagc ctgggggtc cctgagactc      60
tcctgtgcag cctctggatt caccttcagt ggctatgcca tgagctgggt ccgccaggct    120
ccagggaagg ggctggagtg ggtctcaacc attagtggtg gcgaaccta catatactac     180
cccgactcag tgaagggccg attcaccatc tccagagaca acgccaagaa ctcactgtat    240
ctgcaaatga acagcctgag agccgaggac acggccgtgt attactgtgc gagacttggg    300
gggataatt actacgaata cttcgatgtc tggggcaaag ggaccacggt caccgtctcc    360
tccgataaaa cccatactaa accgccaaaa ccggcgccgg aactgctggg tggtcctggt    420
accggtactg tggtccgac tattaaacct ccgaaacctc cgaaacctgc tccgaacctg    480
ctgggtggtc cggacattgt gctgacccag tctccagcct ccttggccgt gtctccagga    540
cagagggcca ccatcacctg cagagccagt aagagtgtca gtaccagcgg atactcctac    600
atgcactggt atcagcagaa accaggacaa cctcctaaac tcctgattta cctggcatcc    660
aatctggaga gcggggtccc agccaggttc agcggcagtg ggtctgggac cgatttcacc    720
ctcacaatta tcctgtggaa agctaatgat actgcaaatt attactgtca gcacagtagg    780
gagctgcctt tcacattcgg cggagggacc aaggtggaga tcaaacgaac t             831
```

```
SEQ ID NO: 243              moltype = AA  length = 277
FEATURE                     Location/Qualifiers
REGION                      1..277
                            note = Humanized C2 single chain X4 (linker is IgG1 and
                            IgG2 modifiedhinge region)
source                      1..277
                            mol_type = protein
                            organism = synthetic construct
SEQUENCE: 243
EVQLVESGGG LVKPGGSLRL SCAASGFTFS GYAMSWVRQA PGKGLEWVST ISSGGTYIYY     60
PDSVKGRFTI SRDNAKNSLY LQMNSLRAED TAVYYCARLG GDNYYEYFDV WGKGTTVTVS    120
SDKTHTKPPK PAPELLGGPG TGTGGPTIKP KPPKPAPNL LGGPDIVLTQ SPASLAVSPG     180
QRATITCRAS KSVSTSGYSY MHWYQQKPGQ PPKLLIYLAS NLESGVPARF SGSGSGTDFT    240
LTINPVEAND TANYYCQHSR ELPFTFGGGT KVEIKRT                             277
```

```
SEQ ID NO: 244              moltype = DNA  length = 744
FEATURE                     Location/Qualifiers
misc_feature                1..744
                            note = Humanized C3 single chain GS3
source                      1..744
                            mol_type = other DNA
                            organism = synthetic construct
SEQUENCE: 244
caggttcagc tggtgcagtc tggagctgag gtgaagaagc tgggcctc agtgaaggtc       60
tcctgcaagg cttctggtta cacctttacc gactacgcca tgaactgggt gcgacaggcc    120
cctggacaag ggcttgagtg gatgggagtg atcagcacct tcagcggtaa cacaaacttc    180
aaccagaagt tcaagggcag agtcaccatg accacagaca catccacgag cacagcctac    240
atggagctga ggagcctgag atctgacgac acggccgtgt attactgtgc gagaagcgac    300
tactacggcc atacttcga ctactggggc cagggcacca cctgaccgt gtccagcggc     360
ggtggcggat ccggcggtgg cggatccggc ggtggcggat ccgatattgt gatgacccag    420
actccactct ctctgtccgt caccctggga cagccggcct ccatcctg caggtctagt     480
cagaccattg tccatagtaa tggaaacacc tatttggagt ggtacctgca gaagccaggc    540
cagtctccac agctcctgat ctataaggtt tccaaccggt tctctggagt gccagatagg    600
ttcagtggca gcgggtcagg gacagatttc acactgaaaa tcagccgggt ggaggctgag    660
gatgttgggg tttattactg cttccaaggt agccacgtgc ctttcacctt cggcggaggg    720
accaaggtgg agatcaaacg aact                                           744
```

```
SEQ ID NO: 245          moltype = AA  length = 248
FEATURE                 Location/Qualifiers
REGION                  1..248
                        note = Humanized C3 single chain GS3
source                  1..248
                        mol_type = protein
                        organism = synthetic construct
SEQUENCE: 245
QVQLVQSGAE VKKPGASVKV SCKASGYTFT DYAMNWVRQA PGQGLEWMGV ISTFSGNTNF    60
NQKFKGRVTM TTDTSTSTAY MELRSLRSDD TAVYYCARSD YYGPYFDYWG QGTTLTVSSG   120
GGGSGGGGSG GGGSDIVMTQ TPLSLSVTPG QPASISCRSS QTIVHSNGNT YLEWYLQKPG   180
QSPQLLIYKV SNRFSGVPDR FSGSGSGTDF TLKISRVEAE DVGVYYCFQG SHVPFTFGGG   240
TKVEIKRT                                                           248

SEQ ID NO: 246          moltype = DNA  length = 762
FEATURE                 Location/Qualifiers
misc_feature            1..762
                        note = Humanized C3 single chain IgG1 (no Cysteine)
source                  1..762
                        mol_type = other DNA
                        organism = synthetic construct
SEQUENCE: 246
caggttcagc tggtgcagtc tggagctgag gtgaagaagc ctggggcctc agtgaaggtc    60
tcctgcaagg cttctggtta cacctttacc gactacgcca tgaactgggt gcgacaggcc   120
cctggacaag gcttgagtg gatgggagtg atcagcacct tcagcggtaa cacaaacttc   180
aaccagaagt tcaagggcag agtcaccatg accacagaca tccacgag cacagcctac   240
atggagctga ggagcctgag atctgacgac acggccgtgt attactgtgc gagaagcgac   300
tactacggcc catacttcga ctactggggc cagggcacca ccctgaccgt gtccagcgat   360
aaaacccata ctaaaccgcc aaaaccggcg ccggaactgc tggtggtcc tggtaccggt   420
gatattgtga tgacccagac tccactctct gtgtccgtca cccctggaca gccggcctcc   480
atctcctgca ggtctagtca gaccattgtc catagtaatg gaaacaccta tttggagtgg   540
tacctgcaga agccaggcca gtctccacag ctcctgatct ataaggtttc aaccggttc   600
tctggagtgc cagataggtt cagtggcagc gggtcaggga cagatttcac actgaaaatc   660
agccgggtgg aggctgagga tgttggggtt tattactgct tccaaggtag ccacgtgcct   720
ttcaccttcg gcggagggac caaggtggag atcaaacgaa ct                      762

SEQ ID NO: 247          moltype = AA  length = 254
FEATURE                 Location/Qualifiers
REGION                  1..254
                        note = Humanized C3 single chain IgG1 (no Cysteine)
source                  1..254
                        mol_type = protein
                        organism = synthetic construct
SEQUENCE: 247
QVQLVQSGAE VKKPGASVKV SCKASGYTFT DYAMNWVRQA PGQGLEWMGV ISTFSGNTNF    60
NQKFKGRVTM TTDTSTSTAY MELRSLRSDD TAVYYCARSD YYGPYFDYWG QGTTLTVSSD   120
KTHTKPPKPA PELLGGPGTG DIVMTQTPLS LSVTPGQPAS ISCRSSQTIV HSNGNTYLEW   180
YLQKPGQSPQ LLIYKVSNRF SGVPDRFSGS GSGTDFTLKI SRVEAEDVGV YYCFQGSHVP   240
FTFGGGTKVE IKRT                                                    254

SEQ ID NO: 248          moltype = DNA  length = 828
FEATURE                 Location/Qualifiers
misc_feature            1..828
                        note = Humanized C3 single chain X4 (linker is IgG1 and
                        IgG2 modifiedhinge region)
source                  1..828
                        mol_type = other DNA
                        organism = synthetic construct
SEQUENCE: 248
caggttcagc tggtgcagtc tggagctgag gtgaagaagc ctggggcctc agtgaaggtc    60
tcctgcaagg cttctggtta cacctttacc gactacgcca tgaactgggt gcgacaggcc   120
cctggacaag gcttgagtg gatgggagtg atcagcacct tcagcggtaa cacaaacttc   180
aaccagaagt tcaagggcag agtcaccatg accacagaca tccacgag cacagcctac   240
atggagctga ggagcctgag atctgacgac acggccgtgt attactgtgc gagaagcgac   300
tactacggcc catacttcga ctactggggc cagggcacca ccctgaccgt gtccagcgat   360
aaaacccata ctaaaccgcc aaaaccggcg ccggaactgc tggtggtcc tggtaccggt   420
actggtggtc cgactattaa acctccgaaa cctccgaaac tgctccgaa cctgctgggt   480
ggtccggata ttgtgatgac ccagactcca ctctctgtct ccgtcacccc tggacagccg   540
gcctccatct cctgcaggtc tagtcagacc attgtccata gtaatggaaa cacctatttg   600
gagtggtacc tgcagaagcc aggccagtct ccacagctcc tgatctataa ggtttcaac   660
cggttctctg gagtgccaga taggttcagt ggcagcgggt cagggacaga tttcacactg   720
aaaatcagcc gggtggaggc tgaggatgtt ggggtttatt actgcttcca aggtagccac   780
gtgcctttca ccttcggcgg agggaccaag gtggagatca aacgaact                828

SEQ ID NO: 249          moltype = AA  length = 276
FEATURE                 Location/Qualifiers
REGION                  1..276
                        note = Humanized C3 single chain X4 (linker is IgG1 and
                        IgG2 modifiedhinge region)
```

```
source                      1..276
                            mol_type = protein
                            organism = synthetic construct
SEQUENCE: 249
QVQLVQSGAE VKKPGASVKV SCKASGYTFT DYAMNWVRQA PGQGLEWMGV ISTFSGNTNF    60
NQKFKGRVTM TTDTSTSTAY MELRSLRSDD TAVYYCARSD YYGPYFDYWG QGTTLTVSSD   120
KTHTKPPKPA PELLGGPGTG TGGPTIKPPK PPKPAPNLLG GPDIVMTQTP LSLSVTPGQP   180
ASISCRSSQT IVHSNGNTYL EWYLQKPGQS PQLLIYKVSN RFSGVPDRFS GSGSGTDFTL   240
KISRVEAEDV GVYYCFQGSH VPFTFGGGTK VEIKRT                             276

SEQ ID NO: 250              moltype = DNA  length = 741
FEATURE                     Location/Qualifiers
misc_feature                1..741
                            note = Humanized C8 single chain GS3 (linker is [Gly4Ser1]3)
source                      1..741
                            mol_type = other DNA
                            organism = synthetic construct
SEQUENCE: 250
gaggtgcagc tggtggagtc tgggggaggc ctggtcaagc ctgggggtc cctgagactc     60
tcctgtgcag cctctggatt caccttcagt ggctatgcca tgagctgggt ccgccaggct   120
ccagggaagg ggctggagtg ggtctcaacc attagtagtg gcggaaccta catatactac   180
cctgactcag tgaagggccg attcaccatc tccagagaca acgccaagaa ctcactgtat   240
ctgcaaatga acagcctgag agccgaggac acggccgtgt attactgtgc gagactgggc   300
ggcgataact attatgaata ttggggcaaa gggaccacgg tcaccgtctc ctccggcggt   360
ggcggatccg gcggtggcgg atccggcggt ggcggatccg acatcgtgat gacccagtct   420
ccagactccc tggctgtgtc tctgggcgag agggccacca tcaactgcag ggccaag      480
agtgttagca ccagcggcta cagctacatg cactggtacc agcagaaacc aggacagcct   540
cctaagctgc tcatttacct ggtgtctaac ctggaatccg gggtccctga ccgattcagt   600
ggcagcgggt ctgggacaga tttcactctc accatcagca gcctgcaggc tgaagatgtg   660
gcagtttatt actgtcaaca cattcggaa ctgaccagga gtgaattcgg cggagggacc    720
aagttggaga tcaaacgaac t                                             741

SEQ ID NO: 251              moltype = AA  length = 247
FEATURE                     Location/Qualifiers
REGION                      1..247
                            note = Humanized C8 single chain GS3 (linker is [Gly4Ser1]3)
source                      1..247
                            mol_type = protein
                            organism = synthetic construct
SEQUENCE: 251
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYWGK GTTVTVSSGG   120
GGSGGGGSGG GGSDIVMTQS PDSLAVSLGE RATINCRASK SVSTSGYSYM HWYQQKPGQP   180
PKLLIYLVSN LESGVPDRFS GSGSGTDFTL TISSLQAEDV AVYYCQHIRE LTRSEFGGGT   240
KVEIKRT                                                             247

SEQ ID NO: 252              moltype = DNA  length = 759
FEATURE                     Location/Qualifiers
misc_feature                1..759
                            note = Humanized C8 single chain IgG1 (no Cysteine)
source                      1..759
                            mol_type = other DNA
                            organism = synthetic construct
SEQUENCE: 252
gaggtgcagc tggtggagtc tgggggaggc ctggtcaagc ctgggggtc cctgagactc     60
tcctgtgcag cctctggatt caccttcagt ggctatgcca tgagctgggt ccgccaggct   120
ccagggaagg ggctggagtg ggtctcaacc attagtagtg gcggaaccta catatactac   180
cctgactcag tgaagggccg attcaccatc tccagagaca acgccaagaa ctcactgtat   240
ctgcaaatga acagcctgag agccgaggac acggccgtgt attactgtgc gagactgggc   300
ggcgataact attatgaata ttggggcaaa gggaccacgg tcaccgtctc ctccgataaa   360
acccatacta aaccgccaaa accggcgccg gaactgctgg gtggtcctgg taccggtgac   420
atcgtgatga cccagtctcc agactccctg gctgtgtctc tgggcgagag ggccaccatc   480
aactgcaggg ccagcaagag tgttagcacc agcggctaca gctacatgca ctggtaccag   540
cagaaaccag gacagcctcc taagctgctc atttacctgt gtctaacct ggaatccggt    600
gtccctgacc gattcagtgg cagcgggtct gggacagatt tcactctcac catcagcagc   660
ctgcaggctg aagatgtggc agtttattac tgtcaacaca ttcgggaact gaccaggagt   720
gaattcggcg agggaccaa ggtggagatc aaacgaact                           759

SEQ ID NO: 253              moltype = AA  length = 253
FEATURE                     Location/Qualifiers
REGION                      1..253
                            note = Humanized C8 single chain IgG1 (no Cysteine)
source                      1..253
                            mol_type = protein
                            organism = synthetic construct
SEQUENCE: 253
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYWGK GTTVTVSSDK   120
THTKPPKPAP ELLGGPGTGD IVMTQSPDSL AVSLGERATI NCRASKSVST SGYSYMHWYQ   180
```

-continued

```
QKPGQPPKLL IYLVSNLESG VPDRFSGSGS GTDFTLTISS LQAEDVAVYY CQHIRELTRS   240
EFGGGTKVEI KRT                                                      253

SEQ ID NO: 254           moltype = DNA  length = 825
FEATURE                  Location/Qualifiers
misc_feature             1..825
                         note = Humanized C8 single chain X4 (linker is IgG1 and
                         IgG2 modifiedhinge region)
source                   1..825
                         mol_type = other DNA
                         organism = synthetic construct
SEQUENCE: 254
gaggtgcagc tggtggagtc tgggggaggc ctggtcaagc ctggggggtc cctgagactc    60
tcctgtgcag cctctggatt caccttcagt ggctatgcca tgggggtggg ccgccaggct   120
ccagggaagg ggctggagtg ggtctcaacc attagtagtg gcggaaccta catatactac   180
ccagactcag tgaagggccg attcaccatc tccagagaca acgccaagaa ctcactgtat   240
ctgcaaatga acagcctgag agccgaggac acggccgtgt attactgtgc gagactgggc   300
ggcgacaatt actatgagta ttggggcaaa gggaccacgg tcaccgtctc ctccgataaa   360
acccatacta aaccgccaaa accggcgccg gaactgctgg gtggtcctgg taccggtact   420
ggtggtccga ctattaaacc tccgaaacct ccgaaacctg ctccgaacct gctgggtggt   480
ccggacatcg tgatgaccca gtctccagac tccctggctg tgtctctggg cgagagggcc   540
accatcaact gcagggccag caagagtgtt agcaccagtg gctacagcta catgcactgg   600
taccagcaga aaccaggaca gcctcctaag ctgctcattt acctggtgtc taacctggaa   660
tccggggtcc ctgaccgatt cagtggcagc gggtctggga cagatttcac tctcaccatc   720
agcagcctgc aggctgaaga tgtggcagtt tattactgtc aacacattcg ggaactgacc   780
aggagtgaat tcggcggagg gaccaaggtg gagatcaaac gaact                   825

SEQ ID NO: 255           moltype = AA  length = 275
FEATURE                  Location/Qualifiers
REGION                   1..275
                         note = Humanized C8 single chain X4 (linker is IgG1 and
                         IgG2 modifiedhinge region)
source                   1..275
                         mol_type = protein
                         organism = synthetic construct
SEQUENCE: 255
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYWGK GTTVTVSSDK   120
THTKPPKPAP ELLGGPGTGT GGPTIKPPKP PKPAPNLLGG PDIVMTQSPD SLAVSLGERA   180
TINCRASKSV STSGYSYMHW YQQKPGQPPK LLIYLVSNLE SGVPDRFSGS GSGTDFTLTI   240
SSLQAEDVAV YYCQHIRELT RSEFGGGTKV EIKRT                              275

SEQ ID NO: 256           moltype = DNA  length = 1509
FEATURE                  Location/Qualifiers
misc_feature             1..1509
                         note = pSECTag2 E6 scFV-FC
source                   1..1509
                         mol_type = other DNA
                         organism = synthetic construct
SEQUENCE: 256
atggagacag acacactcct gctatgggta ctgctgctct ggttccagg ttcactggt     60
gacgcggccc agccgccga ggtgcagctg gtggagtctg ggggaggcct ggtcaagcct   120
gggggtccc tgagactctc ctgtgcagcc tctggattca ccttcagtag gtatggcatg   180
agctgggtcc gccaggctcc agggaagagg ctggagtggg tctcaaccat tagtggcgga   240
ggcacctaca tatactaccc agactcagtg aagggccgtt caccatctc cagagacaac   300
gccaagaaca ccctgtatct gcaaatgaac agcctgagag ccgaggacac ggctgtgtat   360
tactgtacca gagataacta tggccgcaac tatgattatg catggatta ttggggccag   420
ggcacccctgg tgaccgtgag cagcggcggt ggcggatccg gcggtggcgg atccggcggt   480
ggcggatccg aaattgtgtt gacacagtct ccagccaccc tgtctttgtc tccagggaa   540
agagccaccc tcacctgcag cgccaccagc agtgttagct acatcactg gtaccaacag   600
aggcctggcc agagcccag gctcctcatc tatagcacct ccaacctggc cagcggcatc   660
ccagccaggt tcagtggcag tgggtctggg acgactaca ctctcaccat cagcagccta   720
gagcctgaag attttgcagt ttattactgt cagcagcgta gcagctcccc ttcaccttt   780
ggccagggga ccaaagtgga aattaaaag cccaaatctt gtgacaaaac tcacacatgc   840
ccaccgtgcc cagcacctga actcctggg ggaccgtcag tcttcctctt ccccccaaaa   900
cccaaggaca ccctcatgat ctcccggacc cctgaggtca catgcgtgtg gtggacgtg   960
agccacgaag accctgaggt caagttcaac tggtacgtgg acggcgtgga ggtgcataat  1020
gccaagacaa agccgcggga ggagcagtac aacagcacgt accgtgtgg tcagcgtcct  1080
ccgtcctgc accaggactg gctgaatggc aaggagtaca agtgcaaggt ctccaacaaa  1140
gccctcccag cccccatcga gaaaaccatc tccaaagcca agggcagcc cgagaaccca  1200
caggtgtaca ccctgccccc atcccgggag gagatgacca gaaccaggtc cagcctgacc  1260
tgcctggtca aaggcttcta tcccagcgac atcgccgtgg agtgggagag caatgggcag  1320
ccggagaaca actacaagac cacgcctccc gtgctggact ccgacggctc cttcttcctc  1380
tacagcaagc tcaccgtgga caagagcagg tggcagcagg ggaacgtctt ctcatgctcc  1440
gtgatgcatg aggctctgca caaccactac acgcagaaga gcctctccct gtctccgggt  1500
aaatgataa                                                          1509

SEQ ID NO: 257           moltype = AA  length = 501
FEATURE                  Location/Qualifiers
```

| REGION | 1..501 |
| --- | --- |
| | note = pSECTag2 E6 scFV-FC |
| source | 1..501 |
| | mol_type = protein |
| | organism = synthetic construct |

SEQUENCE: 257

```
METDTLLLWV LLLWVPGSTG DAAQPAEVQL VESGGGLVKP GGSLRLSCAA SGFTFSRYGM  60
SWVRQAPGKR LEWVSTISGG GTYIYYPDSV KGRFTISRDN AKNTLYLQMN SLRAEDTAVY 120
YCTRDNYGRN YDYGMDYWGQ GTLVTVSSGG GGSGGGGSGG GGSEIVLTQS PATLSLSPGE 180
RATLTCSATS SVSYIHWYQQ RPGQSPRLLI YSTSNLASGI PARFSGSGSG SDYTLTISSL 240
EPEDFAVYYC QQRSSSPFTF GSGTKVEIKE PKSCDKTHTC PPCPAPELLG GPSVFLFPPK 300
PKDTLMISRT PEVTCVVVDV SHEDPEVKFN WYVDGVEVHN AKTKPREEQY NSTYRVVSVL 360
TVLHQDWLNG KEYKCKVSNK ALPAPIEKTI SKAKGQPREP QVYTLPPSRE EMTKNQVSLT 420
CLVKGFYPSD IAVEWESNGQ PENNYKTTPP VLDSDGSFFL YSKLTVDKSR WQQGNVFSCS 480
VMHEALHNHY TQKSLSLSPG K                                          501
```

| SEQ ID NO: 258 | moltype = DNA   length = 496 |
| --- | --- |
| FEATURE | Location/Qualifiers |
| misc_feature | 1..496 |
| | note = E6 scFC-FC 1 gBLOCk sequence |
| source | 1..496 |
| | mol_type = other DNA |
| | organism = synthetic construct |

SEQUENCE: 258

```
tgctctgggt tccaggttcc actggtgacg cggcccagcc ggccgaggtg cagctggtgg  60
agtctgggg aggcctggtc aagcctgggg gtccctgag actctcctgt gcagctctg  120
gattcacctt cagtaggtat ggcatgagct gggtccgcca ggctccaggg aagaggctgg 180
agtgggtctc aaccattagt ggcggaggca cctacatata ctaccagac tcagtgaagg 240
gccgattcac catctccaga gacaacgcca agaacaccct gtatctgcaa atgaacagcc 300
tgagagccga ggacacggct gtgtattact gtaccagga taactatggc cgcaactatg 360
attatggcat ggattattgg ggccagggca cctggtgac cgtgagcagc gcggtggcc 420
gatccggcgg tggcggatcc ggcggtggcg gatccgaaat tgtgttgaca cagtctccag 480
ccaccctgtc tttgtc                                                496
```

| SEQ ID NO: 259 | moltype = DNA   length = 583 |
| --- | --- |
| FEATURE | Location/Qualifiers |
| misc_feature | 1..583 |
| | note = E6 scFC-FC 2 gBLOCk sequence |
| source | 1..583 |
| | mol_type = other DNA |
| | organism = synthetic construct |

SEQUENCE: 259

```
aattgtgttg acacagtctc cagccaccct gtctttgtct ccaggggaaa gagccaccct  60
cacctgcagc gccaccagca gtgttagcta catccactgg taccaacaga ggcctggcca 120
gagcccagg ctcctcatct atagcacctc caacctggcc agcggcatcc cagccaggtt 180
cagtggcagt gggtctggga cgactacac tctcaccatc agcagcctag agcctgaaga 240
ttttgcagtt tattactgtc agcagcgtag cagctccctt tcaccttttg gcagcggcac 300
caaagtggaa attaaagagc ccaaatcttg tgacaaaact cacacatgcc caccgtgccc 360
agcacctgaa ctcctggggg gaccgtcagt cttcctcttc cccccaaaac ccaaggacac 420
cctcatgatc tcccggaccc ctgaggtcac atgcgtggtg gtggacgtga gccacgaaga 480
ccctgaggtc aagttcaact ggtacgtgga cggcgtggag gtgcataatg ccaagacaaa 540
gccgcgggag gagcagtaca acagcacgta ccgtgtggtc agc                  583
```

| SEQ ID NO: 260 | moltype = DNA   length = 1527 |
| --- | --- |
| FEATURE | Location/Qualifiers |
| misc_feature | 1..1527 |
| | note = pSECTag2 C2 scFV-FC |
| source | 1..1527 |
| | mol_type = other DNA |
| | organism = synthetic construct |

SEQUENCE: 260

```
atggagacag acacactcct gctatgggta ctgctgctct gggttccagg ttccactggt  60
gacgcggccc agccggccga ggtgcagctg gtggagtctg ggggaggcct ggtcaagcct 120
ggggggtccc tgagactctc ctgtgcagcc tctggattca ccttcagtag ctatgccatg 180
agctgggtcc gccaggctcc agggaagggg ctggagtggg tctcaaccat tagtagtggc 240
ggaacctaca tatactaccc cgactcagtg aagggccgat tcaccatctc cagagacaac 300
gccaagaact cactgtatct gcaaatgaac agcctgagag ccgaggacac ggccgtgtat 360
tactgtgcga gacttggggg ggataattac tacgaatact tcgatgtctg ggggcaaggg 420
accacggtca ccgtctcctc cggcggtggc ggatccggcg gtggcggatc cggcggtggc 480
ggatccgaca ttgtgctgac ccagtctcca gcctccttgg ccgtgtctcc aggacagagg 540
gccaccatca cctgcagagc cagtaagagt gtcagtacca gcggatactc ctacatgcac 600
tggtatcagc agaaaccagg acaacctcct aaactcctga tttacctggc atccaatctg 660
gagagcgggg tcccagccag gttcagcggc agtgggtctg gaccgatttt caccctcaca 720
attaatcctg tggaatctaa tgatactgca aattattact gtcagcacag tagggagctg 780
cctttcacat cggcggagg gaccaaggtg gagatcaaac gaactgagcc caaatctgt 840
gacaaaactc acacatgccc accgtgccca gcacctgaac tcctgggggg accgtcagtc 900
ttcctcttcc ccccaaaacc caaggacacc ctcatgatct cccggacccc tgaggtcaca 960
tgcgtggtgg tggacgtgag ccacgaagac cctgaggtca agttcaactg gtacgtggac 1020
ggcgtggagg tgcataatgc caagacaaag ccgcgggagg agcagtacaa cagcacgtac 1080
```

```
cgtgtggtca gcgtcctcac cgtcctgcac caggactggc tgaatggcaa ggagtacaag  1140
tgcaaggtct ccaacaaagc cctcccagcc cccatcgaga aaaccatctc caaagccaaa  1200
gggcagcccc gagaaccaca ggtgtacacc ctgcccccat cccgggagga gatgaccaag  1260
aaccaggtca gcctgacctg cctggtcaaa ggcttctatc ccagcgacat cgccgtggag  1320
tgggagagca atgggcagcc ggagaacaac tacaagacca cgcctcccgt gctggactcc  1380
gacggctcct tcttcctcta cagcaagctc accgtggaca gagcaggtg gcagcagggg  1440
aacgtcttct catgctccgt gatgcatgag gctctgcaca accactacac gcagaagagc  1500
ctctccctgt ctccgggtaa atgataa                                      1527

SEQ ID NO: 261          moltype = AA   length = 507
FEATURE                 Location/Qualifiers
REGION                  1..507
                        note = pSECTag2 C2 scFV-FC
source                  1..507
                        mol_type = protein
                        organism = synthetic construct
SEQUENCE: 261
METDTLLLWV LLLWVPGSTG DAAQPAEVQL VESGGGLVKP GGSLRLSCAA SGFTFSGYAM   60
SWVRQAPGKG LEWVSTISSG GTYIYYPDSV KGRFTISRDN AKNSLYLQMN SLRAEDTAVY  120
YCARLGGDNY YEYFDVWGKG TTVTVSSGGG GSGGGGSGGG GSDIVLTQSP ASLAVSPGQR  180
ATITCRASKS VSTSGYSYMH WYQQKPGQPP KLLIYLASNL ESGVPARFSG SGSGTDFTLT  240
INPVEANDTA NYYCQHSREL PFTFGGGTKV EIKRTEPKSC DKTHTCPPCP APELLGGPSV  300
FLFPPKPKDT LMISRTPEVT CVVVDVSHED PEVKFNWYVD GVEVHNAKTK PREEQYNSTY  360
RVVSVLTVLH QDWLNGKEYK CKVSNKALPA PIEKTISKAK GQPREPQVYT LPPSREEMTK  420
NQVSLTCLVK GFYPSDIAVE WESNGQPENN YKTTPPVLDS DGSFFLYSKL TVDKSRWQQG  480
NVFSCSVMHE ALHNHYTQKS LSLSPGK                                     507

SEQ ID NO: 262          moltype = DNA   length = 487
FEATURE                 Location/Qualifiers
misc_feature            1..487
                        note = C2 scFV-FC 1 gBLOCk sequence
source                  1..487
                        mol_type = other DNA
                        organism = synthetic construct
SEQUENCE: 262
tgctctgggt tccaggttcc actggtgacg cggcccagcc ggccgaggtg cagctggtgg   60
agtctggggg aggcctggtc aagcctgggg ggtccctgag actctcctgt gcagcctctg  120
gattcacctt cagtggctat gccatgagct gggtccgcca ggctccaggg aaggggctgg  180
agtgggtctc aaccattagt agtggcgaa cctacatata ctaccccgac tcagtgaagg  240
gccgattcac catctccaga gacaacgcca agaactcact gtatctgcaa atgaacagcc  300
tgagagccga ggacacggcc gtgtattact gtgcgagact tgggggggat aattactacg  360
aatacttcga tgtctggggc aaagggacca cggtcaccgt ctcctccggc ggtggcggat  420
ccggcggtgg cggatccggc ggtggcggat ccgacattgt gctgacccag tctccagcct  480
ccttggc                                                           487

SEQ ID NO: 263          moltype = DNA   length = 604
FEATURE                 Location/Qualifiers
misc_feature            1..604
                        note = C2 scFV-FC 2 gBLOCk sequence
source                  1..604
                        mol_type = other DNA
                        organism = synthetic construct
SEQUENCE: 263
cattgtgctg acccagtctc cagcctcctt ggccgtgtct ccaggacaga gggccaccat   60
cacctgcaga gccagtaaga gtgtcagtac cagcggatac tcctacatgc actggtatca  120
gcagaaacca ggacaacctc ctaaactcct gatttacctg gcatccaatc tggagagcgg  180
ggtcccagcc aggtttcagcg gcagtgggtc tgggaccgat ttcacccta caattaatcc  240
tgtggaagct aatgatactg caaattatta ctgtcagcac agtagggagc tgcctttcac  300
attcggcgga gggaccaagg tggagatcaa acgaactgag cccaaatctt gtgacaaaac  360
tcacacatgc ccaccgtgcc cagcacctga actcctgggg ggaccgtcag tcttcctctt  420
ccccccaaaa cccaaggaca cctcatgat ctccccggacc cctgaggtca catgcgtggt  480
ggtggacgtg agccacgaag accctgaggt caagttcaac tggtacgtgg acggcgtgga  540
ggtgcataat gccaagacaa agccgcggga ggagcagtac aacagcacgt accgtgtggt  600
cagc                                                              604

SEQ ID NO: 264          moltype = DNA   length = 1524
FEATURE                 Location/Qualifiers
misc_feature            1..1524
                        note = pSECTag2 C3 scFV-FC
source                  1..1524
                        mol_type = other DNA
                        organism = synthetic construct
SEQUENCE: 264
atggagacag acacactcct gctatgggta ctgctgctct gggttccagg ttccactggt   60
gacgcggccc agccggccca ggttcagctg gtgcagtctg gagctgaggt gaagaagcct  120
ggggcctcag tgaaggtctc ctgcaaggct tctggttaca cctttaccga ctacgccatg  180
aactgggtgc gacaggcccc tggacaaggg cttgagtgga tgggagtgat cagcaccttc  240
agcggtaaca caaacttcaa ccagaagttc aagggcagag tcaccatgac cacagacaca  300
tccacgagca cagcctacat ggagctgagg agcctgagat ctgacgacac ggccgtgtat  360
```

```
tactgtgcga gaagcgacta ctacggccca tacttcgact actggggcca gggcaccacc    420
ctgaccgtgt ccagcggcgg tggcggatcc ggcggtggcg gatccggcgg tgcggatcc     480
gatattgtga tgacccagac tccactctct ctgtccgtca ccctggaca gccgcctcc      540
atctcctgca ggtctagtca gaccattgtc catagtaatg gaaacaccta tttggagtgg    600
tacctgcaga agccaggcca gtctccacag ctcctgatct ataaggtttc aaccggttc     660
tctggagtgc cagataggtt cagtggcagc gggtcaggga cagatttcac actgaaaatc    720
agccgggtgg aggctgagga tgttggggtt tattactgct tccaaggtag ccacgtgcct    780
ttcaccttcg gcggagggac caaggtggag atcaaacgaa ctgagcccaa atcttgtgac    840
aaaactcaca catgcccacc gtgcccagca cctgaactcc tggggggacc gtcagtcttc    900
ctcttcccc  caaaacccaa ggacaccctc atgatctccc ggacccctga ggtcacatgc    960
gtggtggtgg acgtgagcca cgaagaccct gaggtcaagt tcaactggta cgtggacggc   1020
gtggaggtgc ataatgccaa gacaaagccg cgggaggagc agtacaacag cacgtaccgt   1080
gtggtcagcg tcctcaccgt cctgcaccag gactggctga atggcaagga gtacaagtgc   1140
aaggtctcca acaaagccct cccagccccc atcgagaaaa ccatctccaa agccaaaggg   1200
cagccccgag aaccacaggt gtacaccctg cccccatccc gggaggagat gaccaagaac   1260
caggtcagcc tgacctgcct ggtcaaaggc ttctatccca gcgacatcgc cgtggagtgg   1320
gagagcaatg ggcagccgga gaacaactac aagaccacgc tcccgtgct ggactccgac    1380
ggctccttct tcctctacag caagctcacc gtggacaaga gcaggtggca gcaggggaac   1440
gtcttctcat gctccgtgat gcatgaggct ctgcacaacc actacacgca gaagagcctc   1500
tccctgtctc cgggtaaatg ataa                                          1524

SEQ ID NO: 265          moltype = AA   length = 506
FEATURE                 Location/Qualifiers
REGION                  1..506
                        note = pSECTag2 C3 scFV-FC
source                  1..506
                        mol_type = protein
                        organism = synthetic construct
SEQUENCE: 265
METDTLLLWV LLLWVPGSTG DAAQPAQVQL VQSGAEVKKP GASVKVSCKA SGYTFTDYAM     60
NWVRQAPGQG LEWMGVISTF SGNTNFNQKF KGRVTMTTDT STSTAYMELR SLRSDDTAVY   120
YCARSDYYGP YFDYWGQGTT LTVSSGGGGS GGGGSGGGGS DIVMTQTPLS LSVTPGQPAS   180
ISCRSSQTIV HSNGNTYLEW YLQKPGQSPQ LLIYKVSNRF SGVPDRFSGS GSGTDFTLKI   240
SRVEAEDVGV YYCFQGSHVP FTFGGGTKVE IKRTEPKSCD KTHTCPPCPA PELLGGPSVF   300
LFPPKPKDTL MISRTPEVTC VVVDVSHEDP EVKFNWYVDG VEVHNAKTKP REEQYNSTYR   360
VVSVLTVLHQ DWLNGKEYKC KVSNKALPAP IEKTISKAKG QPREPQVYTL PPSREEMTKN   420
QVSLTCLVKG FYPSDIAVEW ESNGQPENNY KTTPPVLDSD GSFFLYSKLT VDKSRWQQGN   480
VFSCSVMHEA LHNHYTQKSL SLSPGK                                       506

SEQ ID NO: 266          moltype = DNA   length = 480
FEATURE                 Location/Qualifiers
misc_feature            1..480
                        note = C3 GS scFV FC 1 gBLOCk sequence
source                  1..480
                        mol_type = other DNA
                        organism = synthetic construct
SEQUENCE: 266
tgctctgggt tccaggttcc actggtgacg cggcccagcc ggcccaggtt cagctggtgc     60
agtctggage tgaggtgaag aagcctgggg cctcagtgaa ggtctcctgc aaggcttctg    120
gttacacctt taccgactac gccatgaact gggtgcgaca ggcccctgga caagggcttg    180
agtggatggg agtgatcagc accttcagcg gtaacacaaa cttcaaccag aagttcaagg    240
gcagagtcac catgaccaca gacacatcca cgagcacaga ctacatggag ctgaggagcc    300
tgagatctga cgacacggcc gtgtattact gtgcgagaag cgactactac ggcccatact    360
cgactactgg gccagggc accaccctga ccgtgtccag cggcggtggc ggatccggcg    420
gtggcggatc cggcggtggc ggatccgata ttgtgatgac ccagactcca ctctctctgt    480

SEQ ID NO: 267          moltype = DNA   length = 607
FEATURE                 Location/Qualifiers
misc_feature            1..607
                        note = C3 scFV FC2 gBLOCk sequence
source                  1..607
                        mol_type = other DNA
                        organism = synthetic construct
SEQUENCE: 267
tattgtgatg acccagactc cactctctct gtccgtcacc cctggacagc cggcctccat     60
ctcctgcagg tctagtcaga ccattgtcca tagtaatgga aacacctatt tggagtggta   120
cctgcagaag ccaggccagt ctccacagct cctgatctat aaggtttcaa ccgttctc     180
tggagtgcca gataggttca gtggcagcgg gtcagggaca gatttcacac tgaaaatcag   240
ccgggtggag gctgaggatg ttggggttta ttactgcttc caaggtagcc acgtgccttt   300
caccttcggc ggagggacca aggtggagat caaacgaact gagcccaaat cttgtgacaa   360
aactcacaca tgcccaccgt gcccagcacc tgaactcctg gggggaccgt cagtcttcct   420
cttcccccca aaacccaagg acaccctcat gatctcccgg acccctgagg tcacatgcgt   480
ggtggtggac gtgagccacg aagaccctga ggtcaagttc aactggtacg tggacggcgt   540
ggaggtgcat aatgccaaga caaagccgcg ggaggagcag tacaacagca cgtaccgtgt   600
ggtcagc                                                            607

SEQ ID NO: 268          moltype = DNA   length = 1521
FEATURE                 Location/Qualifiers
misc_feature            1..1521
```

|  | note = pSECTag2 C8 scFV-FC | |
| --- | --- | --- |
| source | 1..1521 | |
|  | mol_type = other DNA | |
|  | organism = synthetic construct | |

SEQUENCE: 268

```
atggagacag acacactcct gctatgggta ctgctgctct ggggttccagg ttccactggt    60
gacgcggccc agccggccga ggtgcagctg gtggagtctg ggggaggcct ggtcaagcct   120
ggggggtccc tgagactctc ctgtgcagcc tctggattca ccttcagtgg ctatgccatg   180
agctgggtcc gccaggctcc agggaagggg ctggagtggg tctcaaccat tagtagtggc   240
ggaacctaca tatactaccc tgactcagtg aagggccgat tcaccatctc cagagacaac   300
gccaagaact cactgtatct gcaaatgaac agcctgagag ccgaggacac ggccgtgtat   360
tactgtgcga gactgggcgg cgataactat atgaatatt  ggggcaaagg gaccacggtc   420
accgtctcct ccggcggtgg cggatccggc ggtggcggat ccgcggtgg cggatccgac   480
atcgtgatga cccagtctcc agactccctg gctgtgtctc tgggcgagag ggccaccatc   540
aactgcaggg ccagcaagag tgttagcacc agcggctaca gctacatgca ctggtaccag   600
cagaaaccag gacagcctcc taagctgctc atttacctgg tgtctaacct ggaatccggg   660
gtccctgacc gattcagtgg cagcgggtct gggacagatt tcactctcac catcagcagc   720
ctgcaggctg aagatgtggc agtttattac tgtcaacaca ttcggaact gaccaggagt   780
gaattcggcg gagggaccaa ggtggagatc aaacgaactg agcccaaatc ttgtgacaaa   840
actcacacat gcccaccgtg cccagcacct gaactcctgg ggggaccgtc agtcttcctc   900
ttccccccaa aacccaagga caccctcatg atctcccgga ccctgaggt cacatgcgtg    960
gtggtggacg tgagccacga agaccctgag gtcaagttca actggtacgt ggacggcgtg  1020
gaggtgcata atgccaagac aaagccgcgg gaggagcagt acaacagcac gtaccgtgtg  1080
gtcagcgtcc tcaccgtcct gcaccaggac tggctgaatg gcaaggagta caagtgcaag  1140
gtctccaaca aagccctccc agcccccatc gagaaaacca tctccaaagc caaagggcag  1200
ccccgagaac cacaggtgta caccctgccc ccatcccggg aggagatgac caagaaccag  1260
gtcagcctga cctgcctggt caaaggcttc tatcccagcg acatcgccgt ggagtgggag  1320
agcaatgggc agccggagaa caactacaag accacgcctc ccgtgctgga ctccgacggc  1380
tccttcttcc tctacagcaa gctcaccgtg gacaagagca ggtggcagca ggggaacgtc  1440
ttctcatgct ccgtgatgca tgaggctctg cacaaccact acacgcagaa gagcctctcc  1500
ctgtctccgg gtaaatgata a                                             1521
```

| SEQ ID NO: 269 | moltype = AA  length = 505 |
| --- | --- |
| FEATURE | Location/Qualifiers |
| REGION | 1..505 |
|  | note = pSECTag2 C8 scFV-FC |
| source | 1..505 |
|  | mol_type = protein |
|  | organism = synthetic construct |

SEQUENCE: 269

```
METDTLLLWV LLLWVPGSTG DAAQPAEVQL VESGGGLVKP GGSLRLSCAA SGFTFSGYAM    60
SWVRQAPGKG LEWVSTISSG GTYIYYPDSV KGRFTISRDN AKNSLYLQMN SLRAEDTAVY   120
YCARLGGDNY YEYWGKGTTV TVSSGGGGSG GGGSGGGGSD IVMTQSPDSL AVSLGERATI   180
NCRASKSVST SGYSYMHWYQ QKPGQPPKLL IYLVSNLESG VPDRFSGSGS GTDFTLTISS   240
LQAEDVAVYY CQHIRELTRS EFGGGTKVEI KRTEPKSCDK THTCPPCPAP ELLGGPSVFL   300
FPPKPKDTLM ISRTPEVTCV VVDVSHEDPE VKFNWYVDGV EVHNAKTKPR EEQYNSTYRV   360
VSVLTVLHQD WLNGKEYKCK VSNKALPAPI EKTISKAKGQ PREPQVYTLP PSREEMTKNQ   420
VSLTCLVKGF YPSDIAVEWE SNGQPENNYK TTPPVLDSDG SFFLYSKLTV DKSRWQQGNV   480
FSCSVMHEAL HNHYTQKSLS LSPGK                                         505
```

| SEQ ID NO: 270 | moltype = DNA  length = 477 |
| --- | --- |
| FEATURE | Location/Qualifiers |
| misc_feature | 1..477 |
|  | note = C8 scFV FC 1 gBLOCk sequence |
| source | 1..477 |
|  | mol_type = other DNA |
|  | organism = synthetic construct |

SEQUENCE: 270

```
tgctctgggt tccaggttcc actggtgacg cggcccagcc ggccgaggtg cagctggtgg    60
agtctggggg aggcctggtc aagcctgggg ggtccctgag actctcctgt gcagcctctg   120
gattcacctt cagtggctat gccatgagct gggtccgcca ggctcaggg aagggcctgg   180
agtgggtctc aaccattagt agtggcggaa cctacatata ctaccctgac tcagtgaagg   240
gccgattcac catctccaga gacaacgcca agaactcact gtatctgcaa atgaacagcc   300
tgagagccga ggacacggcc gtgtattact gtgcgagact gggcggcgat aactattatg   360
aatattgggg caaagggacc acggtcaccg tctcctccgg cggtggcgga tccggcggtg   420
gcggatccgg cggtggcgga tccgacatct gatgaccca gtctccagac tccctgg      477
```

| SEQ ID NO: 271 | moltype = DNA  length = 607 |
| --- | --- |
| FEATURE | Location/Qualifiers |
| misc_feature | 1..607 |
|  | note = C8 scFV FC2 gBLOCk sequence |
| source | 1..607 |
|  | mol_type = other DNA |
|  | organism = synthetic construct |

SEQUENCE: 271

```
catcgtgatg acccagtctc cagactccct ggctgtgtct ctgggcgaga gggccaccat    60
caactgcagg gccagcaaga gtgttagcac cagcggctac agctacatgc actggtacca   120
gcagaaacca ggacagcctc ctaagctgct catttacctg gtgtctaacc tggaatccgg   180
ggtccctgac cgattcagtg gcagcgggtc tgggacagat tcactctca ccatcagcag   240
```

```
cctgcaggct gaagatgtgg cagtttatta ctgtcaacac attcgggaac tgaccaggag   300
tgaattcggc ggagggacca aggtggagat caaacgaact gagcccaaat cttgtgacaa   360
aactcacaca tgcccaccgt gcccagcacc tgaactcctg gggggaccgt cagtcttcct   420
cttccccca aaacccaagg acaccctcat gatctcccgg acccctgagg tcacatgcgt   480
ggtggtggac gtgagccacg aagaccctga ggtcaagttc aactggtacg tggacggcgt   540
ggaggtgcat aatgccaaga caaagccgcg ggaggagcag tacaacagca cgtaccgtgt   600
ggtcagc                                                             607

SEQ ID NO: 272           moltype = DNA  length = 702
FEATURE                  Location/Qualifiers
misc_feature             1..702
                         note = Human IgG1 Fc sequence
source                   1..702
                         mol_type = other DNA
                         organism = synthetic construct
SEQUENCE: 272
gagcccaaat cttgtgacaa aactcacaca tgcccaccgt gcccagcacc tgaactcctg    60
gggggaccgt cagtcttcct cttccccca aaacccaagg acaccctcat gatctcccgg   120
acccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccgtcc tgcaccagga ctggctgaat   300
ggcaaggagt acaagtgcaa ggtctccaac aaagccctcc cagcccccat cgagaaaacc   360
atctccaaag ccaaagggca gccccgagaa ccacaggtgt acaccctgcc cccatcccgg   420
gaggagatga ccaagaacca ggtcagcctg acctgcctgg tcaaaggctt ctatcccagc   480
gacatcgccg tggagtggga gagcaatggg cagccggaga caactacaa gaccacgcct   540
cccgtgctgg actccgacgg ctccttcttc ctctacagca agctcaccgt ggacaagagc   600
aggtggcagc aggggaacgt cttctcatgc tccgtgatgc atgaggctct gcacaaccac   660
tacacgcaga gagcctctc cctgtctccg ggtaaatgat aa                      702

SEQ ID NO: 273           moltype = AA   length = 232
FEATURE                  Location/Qualifiers
REGION                   1..232
                         note = Human IgG1 Fc sequence
source                   1..232
                         mol_type = protein
                         organism = synthetic construct
SEQUENCE: 273
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 274           moltype = DNA  length = 666
FEATURE                  Location/Qualifiers
misc_feature             1..666
                         note = Human IgG1 CH2-CH3 domain sequence
source                   1..666
                         mol_type = other DNA
                         organism = synthetic construct
SEQUENCE: 274
ccgtgcccag cacctgaact cctgggggga ccgtcagtct tcctcttccc cccaaaaccc    60
aaggacaccc tcatgatctc ccggacccct gaggtcacat gcgtggtggt ggacgtgagc   120
cacgaagacc ctgaggtcaa gttcaactgg tacgtggacg gcgtggaggt gcataatgcc   180
aagacaaagc cgcgggagga gcagtacaac agcacgtacc gtgtggtcag cgtcctcacc   240
gtcctgcacc aggactggct gaatggcaag gagtacaagt gcaaggtctc caacaaagcc   300
ctcccagccc ccatcgagaa aaccatctcc aaagccaaag gcagccccg agaaccacag   360
gtgtacaccc tgcccccatc ccgggaggag atgaccaaga accaggtcag cctgacctgc   420
ctggtcaaag gcttctatcc cagcgacatc gccgtggagt gggagagcaa tgggcagccg   480
gagaacaact acaagaccac gcctcccgtg ctggactccg acggctcctt cttcctctac   540
agcaagctca ccgtggacaa gagcaggtgg cagcagggga acgtcttctc atgctccgtg   600
atgcatgagg ctctgcacaa ccactacacg cagaagagcc tctccctgtc tccgggtaaa   660
tgataa                                                              666

SEQ ID NO: 275           moltype = AA   length = 220
FEATURE                  Location/Qualifiers
REGION                   1..220
                         note = Human IgG1 CH2-CH3 domain sequence
source                   1..220
                         mol_type = protein
                         organism = synthetic construct
SEQUENCE: 275
PCPAPELLGG PSVFLFPPKP KDTLMISRTP EVTCVVVDVS HEDPEVKFNW YVDGVEVHNA    60
KTKPREEQYN STYRVVSVLT VLHQDWLNGK EYKCKVSNKA LPAPIEKTIS KAKGQPREPQ   120
VYTLPPSREE MTKNQVSLTC LVKGFYPSDI AVEWESNGQP ENNYKTTPPV LDSDGSFFLY   180
SKLTVDKSRW QQGNVFSCSV MHEALHNHYT QKSLSLSPGK                         220

SEQ ID NO: 276           moltype = DNA  length = 327
FEATURE                  Location/Qualifiers
misc_feature             1..327
```

```
                       note = Human IgG1 CH3 domain sequence
source                 1..327
                       mol_type = other DNA
                       organism = synthetic construct
SEQUENCE: 276
gggcagcccc gagaaccaca ggtgtacacc ctgcccccat cccgggagga gatgaccaag   60
aaccaggtca gcctgacctg cctggtcaaa ggcttctatc ccagcgacat cgccgtggag  120
tgggagagca atgggcagcc ggagaacaac tacaagacca cgcctcccgt gctggactcc  180
gacggctcct tcttcctcta cagcaagctc accgtggaca agagcaggtg gcagcagggg  240
aacgtcttct catgctccgt gatgcatgag gctctgcaca accactacac gcagaagagc  300
ctctccctgt ctccgggtaa atgataa                                     327

SEQ ID NO: 277         moltype = AA  length = 107
FEATURE                Location/Qualifiers
REGION                 1..107
                       note = Human IgG1 CH3 domain sequence
source                 1..107
                       mol_type = protein
                       organism = synthetic construct
SEQUENCE: 277
GQPREPQVYT LPPSREEMTK NQVSLTCLVK GFYPSDIAVE WESNGQPENN YKTTPPVLDS   60
DGSFFLYSKL TVDKSRWQQG NVFSCSVMHE ALHNHYTQKS LSLSPGK                107

SEQ ID NO: 278         moltype = DNA  length = 702
FEATURE                Location/Qualifiers
misc_feature           1..702
                       note = Human IgG1 Fc Y407R sequence
source                 1..702
                       mol_type = other DNA
                       organism = synthetic construct
SEQUENCE: 278
gagcccaaat cttgtgacaa aactcacaca tgcccaccgt gcccagcacc tgaactcctg   60
gggggaccgt cagtcttcct cttccccca aaacccaagg acaccctcat gatctcccgg   120
accccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
ggcaaggagt acaagtgcaa ggtctccaac aaagccctcc cagcccccat cgagaaaacc  360
atctccaaag ccaaagggca gccccgagaa ccacaggtgt acaccctgcc cccatcccgg  420
gaggagatga ccaagaacca ggtcagcctg acctgcctgg tcaaaggctt ctatcccagc  480
gacatcgccg tggagtggga gagcaatggg cagccggaga caactacaa gaccacgcct  540
cccgtgctgg actccgacgg ctccttcttc ctcaggagca agctcaccgt ggacaagagc  600
aggtggcagc aggggaacgt cttctcatgc tccgtgatgc atgaggctct gcacaaccac  660
tacacgcaga gagcctctc cctgtctccg ggtaaatgat aa                     702

SEQ ID NO: 279         moltype = AA  length = 232
FEATURE                Location/Qualifiers
REGION                 1..232
                       note = Human IgG1 Fc Y407R sequence
source                 1..232
                       mol_type = protein
                       organism = synthetic construct
SEQUENCE: 279
EPKSCDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LRSKLTVDKS RWQQGNVFSC SVMHEALHNH YTQKSLSLSP GK          232

SEQ ID NO: 280         moltype = DNA  length = 702
FEATURE                Location/Qualifiers
misc_feature           1..702
                       note = Human IgG1 Fc F405Q sequence
source                 1..702
                       mol_type = other DNA
                       organism = synthetic construct
SEQUENCE: 280
gagcccaaat cttgtgacaa aactcacaca tgcccaccgt gcccagcacc tgaactcctg   60
gggggaccgt cagtcttcct cttccccca aaacccaagg acaccctcat gatctcccgg   120
accccctgagg tcacatgcgt ggtggtggac gtgagccacg aagaccctga ggtcaagttc  180
aactggtacg tggacggcgt ggaggtgcat aatgccaaga caaagccgcg ggaggagcag  240
tacaacagca cgtaccgtgt ggtcagcgtc ctcaccgtcc tgcaccagga ctggctgaat  300
ggcaaggagt acaagtgcaa ggtctccaac aaagccctcc cagcccccat cgagaaaacc  360
atctccaaag ccaaagggca gccccgagaa ccacaggtgt acaccctgcc cccatcccgg  420
gaggagatga ccaagaacca ggtcagcctg acctgcctgg tcaaaggctt ctatcccagc  480
gacatcgccg tggagtggga gagcaatggg cagccggaga caactacaa gaccacgcct  540
cccgtgctgg actccgacgg ctccttccag ctctacagca agctcaccgt ggacaagagc  600
aggtggcagc aggggaacgt cttctcatgc tccgtgatgc atgaggctct gcacaaccac  660
tacacgcaga gagcctctc cctgtctccg ggtaaatgat aa                     702

SEQ ID NO: 281         moltype = AA  length = 232
```

```
FEATURE                 Location/Qualifiers
REGION                  1..232
                        note = Human IgG1 Fc F405Q sequence
source                  1..232
                        mol_type = protein
                        organism = synthetic construct
SEQUENCE: 281
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFQ LYSKLTVDKS RWQQGNVFSC SVMHEALHNH YTQKSLSLSP GK           232

SEQ ID NO: 282          moltype = DNA   length = 702
FEATURE                 Location/Qualifiers
misc_feature            1..702
                        note = Human IgG1 Fc T394D sequence
source                  1..702
                        mol_type = other DNA
                        organism = synthetic construct
SEQUENCE: 282
gagcccaaat cttgtgacaa aactcacaca tgcccaccgt gcccagcacc tgaactcctg    60
gggggaccgt cagtcttcct cttccccccc aaaacccaag gacaccctca tgatctcccg   120
accccctgag gtcacatgcg tggtggtgga cgtgagccac gaagaccctg aggtcaagtt   180
caactggtac gtggacggcg tggaggtgca taatgccaag acaaagccgc gggaggagca   240
gtacaacagc acgtaccgtg tggtcagcgt ctcaccgtcc tgcaccagga ctggctgaat   300
ggcaaggagt acaagtgcaa ggtctccaac aaagccctcc cagccccat cgagaaaacc   360
atctccaaag ccaaagggca gccccgagaa ccacaggtgt acaccctgcc cccatcccgg   420
gaggagatga ccaagaacca ggtcagcctg acctgcctgg tcaaaggctt ctatcccagc   480
gacatcgccg tggagtggga gagcaatggg cagccggaga caactacaa gaccgaccct   540
cccgtgctgg actccgacgg ctccttcttc tctacagca agctcaccgt ggacaagagc   600
aggtggcagc aggggaacgt cttctcatgc tccgtgatgc atgaggctct gcacaaccac   660
tacacgcaga gagcctctc cctgtctccg ggtaaatgat aa                      702

SEQ ID NO: 283          moltype = AA    length = 232
FEATURE                 Location/Qualifiers
REGION                  1..232
                        note = Human IgG1 Fc T394D sequence
source                  1..232
                        mol_type = protein
                        organism = synthetic construct
SEQUENCE: 283
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTDP   180
PVLDSDGSFF LYSKLTVDKS RWQQGNVFSC SVMHEALHNH YTQKSLSLSP GK           232

SEQ ID NO: 284          moltype = DNA   length = 702
FEATURE                 Location/Qualifiers
misc_feature            1..702
                        note = Human IgG1 Fc T366W/L368W sequence
source                  1..702
                        mol_type = other DNA
                        organism = synthetic construct
SEQUENCE: 284
gagcccaaat cttgtgacaa aactcacaca tgcccaccgt gcccagcacc tgaactcctg    60
gggggaccgt cagtcttcct cttccccccc aaaacccaag gacaccctca tgatctcccg   120
accccctgag gtcacatgcg tggtggtgga cgtgagccac gaagaccctg aggtcaagtt   180
caactggtac gtggacggcg tggaggtgca taatgccaag acaaagccgc gggaggagca   240
gtacaacagc acgtaccgtg tggtcagcgt ctcaccgtcc tgcaccagga ctggctgaat   300
ggcaaggagt acaagtgcaa ggtctccaac aaagccctcc cagccccat cgagaaaacc   360
atctccaaag ccaaagggca gccccgagaa ccacaggtgt acaccctgcc cccatcccgg   420
gaggagatga ccaagaacca ggtcagcctg tggtgctggg tcaaaggctt ctatcccagc   480
gacatcgccg tggagtggga gagcaatggg cagccggaga caactacaa gaccacgcct   540
cccgtgctgg actccgacgg ctccttcttc tctacagca agctcaccgt ggacaagagc   600
aggtggcagc aggggaacgt cttctcatgc tccgtgatgc atgaggctct gcacaaccac   660
tacacgcaga gagcctctc cctgtctccg ggtaaatgat aa                      702

SEQ ID NO: 285          moltype = AA    length = 232
FEATURE                 Location/Qualifiers
REGION                  1..232
                        note = Human IgG1 Fc T366W/L368W sequence
source                  1..232
                        mol_type = protein
                        organism = synthetic construct
SEQUENCE: 285
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL WCWVKGFYPS DIAVEWESNG QPENNYKTTP   180
PVLDSDGSFF LYSKLTVDKS RWQQGNVFSC SVMHEALHNH YTQKSLSLSP GK           232
```

```
SEQ ID NO: 286          moltype = DNA   length = 702
FEATURE                 Location/Qualifiers
misc_feature            1..702
                        note = Human IgG1 Fc T364R/L368R sequence
source                  1..702
                        mol_type = other DNA
                        organism = synthetic construct
SEQUENCE: 286
gagcccaaat cttgtgacaa aactcacaca tgcccaccgt gcccagcacc tgaactcctg     60
gggggaccgt cagtcttcct cttcccccca aaacccaagg acaccctcat gatctcccgg    120
acccctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaaagggca gccccgagaa ccacaggtgt acaccctgcc cccatcccgg    420
gaggagatga ccaagaacca ggtcaggctg acctgcaggg tcaaaggctt ctatcccagc    480
gacatcgccg tggagtggga gcaatggag cagccggaca acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaatgat aa                       702

SEQ ID NO: 287          moltype = AA   length = 232
FEATURE                 Location/Qualifiers
REGION                  1..232
                        note = Human IgG1 Fc T364R/L368R sequence
source                  1..232
                        mol_type = protein
                        organism = synthetic construct
SEQUENCE: 287
EPKSCDKTHT CPPCPAPELL GGPSVFLFPP KPKDTLMISR TPEVTCVVVD VSHEDPEVKF     60
NWYVDGVEVH NAKTKPREEQ YNSTYRVVSV LTVLHQDWLN GKEYKCKVSN KALPAPIEKT    120
ISKAKGQPRE PQVYTLPPSR EEMTKNQVRL TCRVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 288          moltype = DNA   length = 657
FEATURE                 Location/Qualifiers
misc_feature            1..657
                        note = Human IgG1 Fc hingeless sequence
source                  1..657
                        mol_type = other DNA
                        organism = synthetic construct
SEQUENCE: 288
gcacctgaac tcctgggggg accgtcagtc ttcctcttcc ccccaaaacc caaggacacc     60
ctcatgatct cccggacccc tgaggtcaca tgcgtggtgg tggacgtgag ccacgaagac    120
cctgaggtca agttcaactg gtacgtggac ggcgtggagg tgcataatgc caagacaaag    180
ccgcgggagg agcagtacaa cagcacgtac cgtgtggtca gcgtcctcac cgtcctgcac    240
caggactggc tgaatggcaa ggagtacaag tgcaaggtct ccaacaaagc cctcccagcc    300
cccatcgaga aaccatctc caagccaaa gggcagcccc gagaaccaca ggtgtacacc    360
ctgccccat cccgggagga gatgaccaag aaccaggtca gcctgacctg cctggtcaaa    420
ggcttctatc ccagcgacat cgccgtggag tgggagagcaatgggcagcc ggagaaccaa    480
tacaagacca cgcctcccgt gctggactcc gacggctcct tcttcctcta cagcaagctc    540
accgtggaca gcaggtg gcagcagggg aacgtcttct catgctccgt gatgcatgag    600
gctctgcaca accactacac gcagaagagc ctctccctgt ctccgggtaa atgataa       657

SEQ ID NO: 289          moltype = AA   length = 217
FEATURE                 Location/Qualifiers
REGION                  1..217
                        note = Human IgG1 Fc hingeless sequence
source                  1..217
                        mol_type = protein
                        organism = synthetic construct
SEQUENCE: 289
APELLGGPSV FLFPPKPKDT LMISRTPEVT CVVVDVSHED PEVKFNWYVD GVEVHNAKTK     60
PREEQYNSTY RVVSVLTVLH QDWLNGKEYK CKVSNKALPA PIEKTISKAK GQPREPQVYT    120
LPPSREEMTK NQVSLTCLVK GFYPSDIAVE WESNGQPENN YKTTPPVLDS DGSFFLYSKL    180
TVDKSRWQQG NVFSCSVMHE ALHNHYTQKS LSLSPGK                             217

SEQ ID NO: 290          moltype = DNA   length = 696
FEATURE                 Location/Qualifiers
misc_feature            1..696
                        note = Human IgG1 G237A FC sequence
source                  1..696
                        mol_type = other DNA
                        organism = synthetic construct
SEQUENCE: 290
gagcccaaat cttgtgacaa aactcacaca tgcccaccgt gcccagcacc tgaactcctg     60
gggcccccgt cagtcttcct cttcccccca aaacccaagg acaccctcat gatctcccgg    120
acccctgagg tcacatgcgt ggtggtggac gtgagccacg aagaccctga ggtcaagttc    180
```

```
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaaagggca gccccgagaa ccacaggtgt acaccctgcc cccatcccgg    420
gaggagatga ccaagaacca ggtcagcctg acctgcctgg tcaaaggctt ctatcccagc    480
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaa                              696

SEQ ID NO: 291          moltype = AA   length = 232
FEATURE                 Location/Qualifiers
REGION                  1..232
                        note = Human IgG1 G237A FC sequence
source                  1..232
                        mol_type = protein
                        organism = synthetic construct
SEQUENCE: 291
EPKSCDKTHT CPPCPAPELL GAPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPSR EEMTKNQVSL TCLVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 292          moltype = DNA   length = 696
FEATURE                 Location/Qualifiers
misc_feature            1..696
                        note = Human IgG1 L234A/L235A FC sequence
source                  1..696
                        mol_type = other DNA
                        organism = synthetic construct
SEQUENCE: 292
gagcccaaat cttgtgacaa aactcacaca tgcccaccgt gcccagcacc tgaagccgcc    60
gggggaccgt cagtcttcct cttccccccca aaacccaagg acaccctcat gatctcccgg    120
acccctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaaagggca gccccgagaa ccacaggtgt acaccctgcc cccatcccgg    420
gaggagatga ccaagaacca ggtcagcctg acctgcctgg tcaaaggctt ctatcccagc    480
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaa                              696

SEQ ID NO: 293          moltype = AA   length = 232
FEATURE                 Location/Qualifiers
REGION                  1..232
                        note = Human IgG1 L234A/L235A FC sequence
source                  1..232
                        mol_type = protein
                        organism = synthetic construct
SEQUENCE: 293
EPKSCDKTHT CPPCPAPEAA GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT    120
ISKAKGQPRE PQVYTLPPSR EEMTKNQVSL TCLVKGFYPS DIAVEWESNG QPENNYKTTP    180
PVLDSDGSFF LYSKLTVDKS RWQQGNVFSC SVMHEALHNH YTQKSLSLSP GK            232

SEQ ID NO: 294          moltype = DNA   length = 1341
FEATURE                 Location/Qualifiers
misc_feature            1..1341
                        note = CAR-T E6 CD3z sequence
source                  1..1341
                        mol_type = other DNA
                        organism = synthetic construct
SEQUENCE: 294
atggccctgc ccgtgaccgc tttgctgctc cccctggcgc tgctgctgca cgccgccagg    60
ccagaggtcc agctggttga gagtggcggt gggctggtta agcctggcgg ctccctgcgg    120
ctgagctgcg ccgcgagtgg atttactttc agcgatatg gatgagttg ggtgcggcaa    180
gctcccggga gaggctgga atgggtctca acaatcgtat gggggggcac ttacatctat    240
taccccgact cagtcaaggg gagatttacc atttcacgag acaacgctaa gaataccctg    300
tatttgcaga tgaattctct gagagcagag gacacagctg tttactattg tacccgcgac    360
aactatggca ggaactacga ctacggtatg gactattggg gacaaggac attggttaca    420
gtgagcagtg cggcggggg cagcggagga ggaggcagcg gtgggggggg cagcgagata    480
gtgctcacgc agtcacccgc gactctcagt ctctccggg gggaacagc taccctgacg    540
tgctctgcta cctcctcagt gtcatatatt cactggtatc agcaacgcc cgggcagtcc    600
cctagattgc tcatttatag tacctctaat ctggcctcag gtatccctgc acgattttct    660
ggatctggtt caggttctga ttacacctc atatctcta gcctggagcc tgaagacttt    720
gccgtttatt actgccagca gagtctagc tccccattca cctttgggag tgggaccaag    780
gttgaaatta aacgacaac cccggccccc agaccaccaa cgccagcccc caccatcgcc    840
```

```
agccaacccc tgtctctgag accagaagcc tgtaggcctg ccgccggtgg agctgtgcac    900
acaagaggac tggatttcgc ctgtgatatc tacatttggg ccccgctcgc aggcacatgt    960
ggagtgctcc tcctctccct ggtgattacc ctgtactgcc gcgttaagtt ctcccgatca   1020
gccgacgcgc tgcttacaa gcagggccag aaccaactgt acaacgagct gaatctcggt   1080
agacgggaag agtacgacgt gttggacaaa cggagagcgc gcgacccaga aatgggcggc   1140
aagcctcgca ggaaaaaccc ccaggaggga ctgtacaatg agttgcagaa agataagatg   1200
gcagaagctt atagcgagat cggaatgaag ggggaaagga gacgaggaa aggacacgac   1260
ggcctttatc agggcctgtc cacagcaaca aaagatacgt atgacgccct ccatatgcag   1320
gcacttccac cacggtgata a                                             1341

SEQ ID NO: 295           moltype = AA  length = 445
FEATURE                  Location/Qualifiers
REGION                   1..445
                         note = CAR-T E6 CD3z sequence
source                   1..445
                         mol_type = protein
                         organism = synthetic construct
SEQUENCE: 295
MALPVTALLL PLALLLHAAR PEVQLVESGG GLVKPGGSLR LSCAASGFTF SRYGMSWVRQ     60
APGKRLEWVS TISGGGTYIY YPDSVKGRFT ISRDNAKNTL YLQMNSLRAE DTAVYYCTRD    120
NYGRNYDYGM DYWGQGTLVT VSSGGGGSGG GGSGGGGSEI VLTQSPATLS LSPGERATLT    180
CSATSSVSYI HWYQQRPGQS PRLLIYSTSN LASGIPARFS GSGSGSDYTL TISSLEPEDF    240
AVYYCQQRSS SPFTFGSGTK VEIKTTTPAP RPPTPAPTIA SQPLSLRPEA CRPAAGGAVH    300
TRGLDFACDI YIWAPLAGTC GVLLLSLVIT LYCRVKFSRS ADAPAYKQGQ NQLYNELNLG    360
RREEYDVLDK RRGRDPEMGG KPRRKNPQEG LYNELQKDKM AEAYSEIGMK GERRRGKGHD    420
GLYQGLSTAT KDTYDALHMQ ALPPR                                          445

SEQ ID NO: 296           moltype = DNA  length = 485
FEATURE                  Location/Qualifiers
misc_feature             1..485
                         note = CAR-T E6 CD3z gBLOCK sequence
source                   1..485
                         mol_type = other DNA
                         organism = synthetic construct
SEQUENCE: 296
tggagctgtg cacacaagag gactggattt cgcctgtgat atctacattt ggccccgct     60
cgcaggcaca tgtggagtgc tcctcctctc cctggtgatt accctgtact gccgcgttaa   120
gttctcccga tcagccgacg cgcctgctta caagcagggc cagaaccaac tgtacaacga   180
gctgaatctc ggtagacggg aagagtacga cgtgttggac aaacggagag ccgacccag   240
agaaatgggc ggcaagcctc gcaggaaaaa ccccaggag gactgtaca atgagttgca   300
gaaagataag atggcagaag cttatagcga gatcggaatg aaggggaaa ggagacgagg   360
gaaaggacac gacggccttt atcagggcct gtccacagca acaaaagata cgtatgacgc   420
cctccatatg caggcacttc caccacgtg ataagttta acccgctgat cagcctcgac   480
tgtgc                                                               485

SEQ ID NO: 297           moltype = DNA  length = 1464
FEATURE                  Location/Qualifiers
misc_feature             1..1464
                         note = CAR-T E6 CD28/CD3z sequence
source                   1..1464
                         mol_type = other DNA
                         organism = synthetic construct
SEQUENCE: 297
atggccctgc ccgtgaccgc tttgctgctc cccctggcgc tgctgctgca cgccgccagg     60
ccagaggtcc agctggttga gagtggcggt gggctggtta agcctggcgg ctccctgcgg    120
ctgagctgcg ccgcgagtgg atttactttc agccgatatg ggatgagttg ggtgcgccaa    180
gctcccggga gaggctggaa tgggtctca acaatctccg ggggggggcac ttacatctat    240
taccccgact cagtcaaggg gagatttacc atttcacgag acaacgctaa gaataccctg    300
tatttgcaga tgaattctct gagagcagag gacacagctg tttactattg tacccgcgac    360
aactatggca ggaactacga ctacggtatg gactattgga acaagggac attggttaca    420
gtgagcagtg gcggcggggg cagcggagga ggaggcagcg gtgggggggg cagcgagata    480
gtgctcacgc agtcacccgc gactctcagt ctctcacctg ggaacgagc tacccctacg    540
tgctctgcta cctcctcagt gtcatatatt cactggtatc agcaacggcc cggcagtcc    600
cctagattgc tcatttatag tacctctaat ctggcctcag gtatccctgc acgatttct    660
ggatctggtt caggttctga ttacaccctc actatctcta gcctggagcc tgaagacttt    720
gccgtttatt actgccagca gaggtctagc tcccccatta ccctttggga gtgggaccaag    780
gttgaaatta aaacgacaac cccggccccc agaccaccaa cgccagcccc caccatcgcc    840
agccaacccc tgtctctgag accagaagcc tgtaggcctg ccgccggtgg agctgtgcac    900
acaagaggac tggatttcgc ctgtgatatc tacatttggg ccccgctcgc aggcacatgt    960
ggagtgctcc tcctctccct ggtgattacc ctgtactgca gaagcaagcg gtctcggctc   1020
ctgcattctg attacatgaa catgaccccca gaagaccag ccccaccag aaacattac   1080
cagccctacg ctccgccacg cgacttcgct gcctaccggt cccgcgttaa gttctcccga   1140
tcagccgacg cgcctgctta caagcagggc cagaaccaac tgtacaacga gctgaatctc   1200
ggtagacggg aagagtacga cgtgttggac aaacggagag ccgacccaga aatgggcggc   1260
aagcctcgca ggaaaaaccc ccaggaggga ctgtacaatg agttgcaga aagataag   1320
atggcagaag cttatagcga gatcggaatg aaggggaaa ggagacgagg gaaaggacac   1380
gacggccttt atcagggcct gtccacagca acaaaagata cgtatgacgc cctccatatg   1440
caggcacttc caccacggtg ataa                                           1464
```

```
SEQ ID NO: 298            moltype = AA   length = 486
FEATURE                   Location/Qualifiers
REGION                    1..486
                          note = CAR-T E6 CD28/CD3z sequence
source                    1..486
                          mol_type = protein
                          organism = synthetic construct
SEQUENCE: 298
MALPVTALLL PLALLLHAAR PEVQLVESGG GLVKPGGSLR LSCAASGFTF SRYGMSWVRQ     60
APGKRLEWVS TISGGGTYIY YPDSVKGRFT ISRDNAKNTL YLQMNSLRAE DTAVYYCTRD    120
NYGRNYDYGM DYWGQGTLVT VSSGGGGSGG GGSGGGGSEI VLTQSPATLS LSPGERATLT    180
CSATSSVSYI HWYQQRPGQS PRLLIYSTSN LASGIPARFS GSGSGSDYTL TISSLEPEDF    240
AVYYCQQRSS SPFTFGSGTK VEIKTTTPAP RPPTPAPTIA SQPLSLRPEA CRPAAGGAVH    300
TRGLDFACDI YIWAPLAGTC GVLLLSLVIT LYCRSKRSRL LHSDYMNMTP RRPGPTRKHY    360
QPYAPPRDFA AYRSRVKFSR SADAPAYKQG QNQLYNELNL GRREEYDVLD KRRGRDPEMG    420
GKPRRKNPQE GLYNELQKDK MAEAYSEIGM KGERRRGKGH DGLYQGLSTA TKDTYDALHM    480
QALPPR                                                               486

SEQ ID NO: 299            moltype = DNA   length = 608
FEATURE                   Location/Qualifiers
misc_feature              1..608
                          note = CAR-T E6 CD28/CD3z g BLOCK sequence
source                    1..608
                          mol_type = other DNA
                          organism = synthetic construct
SEQUENCE: 299
tggagctgtg cacacaagag gactggattt cgcctgtgat atctacattt gggccccgct     60
cgcaggcaca tgtggagtgc tcctcctctc cctggtgatt accctgtact gcagaagcaa    120
gcggtctcgg ctcctgcatt ctgattacat gaacatgacc ccaagaagac caggcccac     180
caggaaacat taccagcct acgctccgcc acgcgacttc gctgcctacc ggtcccgcgt    240
taagttctcc cgatcagccg acgcgcctgc ttacaagcag gccagaacc aactgtacaa     300
cgagctgaat ctcggtagac gggaagagta cgacgtgttg acaaacgga gaggccgcga     360
cccagaaatg ggcggcaagc ctcgcaggaa aaaccccag gagggactgt acaatgagtt     420
gcagaaagat aagatggcag aagcttatag cgagatcgga atgaagggg aaggagacg     480
agggaaagga cacgacggcc tttatcaggg cctgtccaca gcaacaaaag atacgtatga    540
cgccctccat atgcaggcac ttccaccacg gtgataagtt taaacccgct gatcagcctc    600
gactgtgc                                                             608

SEQ ID NO: 300            moltype = DNA   length = 1467
FEATURE                   Location/Qualifiers
misc_feature              1..1467
                          note = CAR-T E6 4-1BB/CD3z sequence
source                    1..1467
                          mol_type = other DNA
                          organism = synthetic construct
SEQUENCE: 300
atggccctgc ccgtgaccgc tttgctgctc cccctggcgc tgctgctgca cgccgccagg     60
ccagaggtcc agctggttga gagtggcggt gggctggtta agcctggcgg ctccctgcgg    120
ctgagctgcg ccgcgagtgg atttactttc agccgatatg gatgagttg ggtgcggcaa     180
gctcccggga gaggctggaa atgggtctca acaatctccg ggggggcac ttacatctat     240
tacccgacta cagtcaaggg agatttacc atttcacgag acaacgctaa gaataccctg    300
tatttgcaga tgaattctct gagagcagag gacacagctg tttactattg tacccgcgac    360
aactatggca gaactacga ctacggtatg gactattggg gacaaggac attggttaca    420
gtgagcagtg gcggcgggg cagcggagga ggaggcagcg gtgggggggg cagcgagata    480
gtgctcacgc agtcacccgc gactctcagt ctctcacctg gggaacgagc taccctgacg    540
tgctctgcta cctcctcagt gtcatatatt cactggtatc agcaacggcc cgggcagtcc    600
cctagattgc tcatttatag tacctctaat ctggcctcag gtatccctgc acgattttct    660
ggatctggtt caggttctga ttacacccct actatctcta gcctggagcc tgaagacttt    720
gccgtttatt actgccagca gaggtctagc tccccattca ccttggggag tgggaccaag    780
gttgaaatta aaacgacaac cccggccccc agaccaccaa cgccagccc caccatcgcc    840
agccaacccc tgtctctgag accagaagcc tgtaggcctg ccgccggtgg agctgtgcac    900
acaagaggac tggatttcgc ctgtgatatc tacatttggg cccgctcgc aggcacatgt    960
ggagtgctcc tcctctccct ggtgattacc ctgtactgca aagggggccg caaaaaactc   1020
ctttacattt ttaagcagcc ttttatgagg ccagtacaga ctcaagagga ggacggcagt   1080
tgctcatgcc gctttcctga ggaggaggaa ggagggtgcg aactgcgcgt taagttctcc   1140
cgatcagccg acgcgcctgc ttacaagcag gccagaacc aactgtacaa cgagctgaat   1200
ctcggtagac gggaagagta cgacgtgttg acaaacgga gaggccgcga cccagaaatg   1260
ggcggcaagc ctcgcaggaa aaaccccag gagggactgt acaatgagtt gcagaaagat   1320
aagatggcag aagcttatag cgagatcgga atgaagggg aaggagacg agggaaagga   1380
cacgacggcc tttatcaggg cctgtccaca gcaacaaaag atacgtatga cgccctccat   1440
atgcaggcac ttccaccacg gtgataa                                       1467

SEQ ID NO: 301            moltype = AA   length = 487
FEATURE                   Location/Qualifiers
REGION                    1..487
                          note = CAR-T E6 4-1BB/CD3z sequence
source                    1..487
                          mol_type = protein
                          organism = synthetic construct
```

```
SEQUENCE: 301
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DWGQGTLVT VSSGGGGSGG GGSGGGGSEI VLTQSPATLS LSPGERATLT    180
CSATSSVSYI HWYQQRPGQS PRLLIYSTSN LASGIPARFS GSGSGSDYTL TISSLEPEDF   240
AVYYCQQRSS SPFTFGSGTK VEIKTTTPAP RPPTPAPTIA SQPLSLRPEA CRPAAGGAVH   300
TRGLDFACDI YIWAPLAGTC GVLLLSLVIT LYCKRGRKKL LYIFKQPFMR PVQTTQEEDG   360
CSCRFPEEEE GGCELRVKFS RSADAPAYKQ GQNQLYNELN LGRREEYDVL DKRRGRDPEM   420
GGKPRRKNPQ EGLYNELQKD KMAEAYSEIG MKGERRRGKG HDGLYQGLST ATKDTYDALH   480
MQALPPR                                                              487

SEQ ID NO: 302              moltype = DNA   length = 611
FEATURE                     Location/Qualifiers
misc_feature                1..611
                            note = CAR-T E6 4-1BB/CD3z gBLOCK sequence
source                      1..611
                            mol_type = other DNA
                            organism = synthetic construct
SEQUENCE: 302
tggagctgtg cacacaagag gactggattt cgcctgtgat atctacattt gggccccgct    60
cgcaggcaca tgtggagtgc tcctcctctc cctggtgatt accctgtact gcaaaagggg   120
ccgcaaaaaa ctcctttaca ttttttaagca gccttttatg aggccagtac agacgactca   180
agaggaagac gggtgctcat gccgctttcc tgaggaggag gaaggagggt gcgaactgcg   240
cgttaagttc tcccgatcag ccgacgcgcc tgcttacaag cagggccaga accaactgta   300
caacgagctg aatctcggta gacgggaaga gtacgacgtg ttggacaaac ggagaggccg   360
cgacccagaa atgggcggca agcctcgcag gaaaaacccc caggaggac tgtacaatga    420
gttgcagaaa gataagatgg cagaagctta tagcgagatc ggaatgaagg gggaaggag    480
acgagggaaa ggacacgacg gcctttatca gggcctgtcc acagcaacaa aagatacgta   540
tgacgccctc catatgcagg cacttccacc acggtgataa gtttaaaccc gctgatcagc   600
ctcgactgtg c                                                        611

SEQ ID NO: 303              moltype = DNA   length = 1590
FEATURE                     Location/Qualifiers
misc_feature                1..1590
                            note = CAR-T E6 CD28/4-1BB/CD3z sequence
source                      1..1590
                            mol_type = other DNA
                            organism = synthetic construct
SEQUENCE: 303
atggccctgc ccgtgaccgc tttgctgctc cccctggcgc tgctgctgca cgccgccagg    60
ccagaggtcc agctggttga gagtggcggt gggctggtta gcctggcgg ctccctgcgg   120
ctgagctgcg ccgcgagtgg atttactttc agccgatatg gatgagttg ggtgcggcaa    180
gctcccggga agaggctgga atgggtctca acaatcctgg gggggcac ttacatctat     240
taccccgact cagtcaaggg gagatttacc atttcacgag acaacgctaa gaatacctg    300
tatttgcaga tgaattctct gagagcagag gacacagctg tttactattg tacccgcgac   360
aactatggca ggaactacga ctacggtatg gactattggg gacaagggac attggttaca   420
gtgagcagtg gcggcggggg cagcggagga ggaggcagcg gtggggggag cagcgagata   480
gtgctcacgc agtcacccgc gactctcagt ctctcacctg ggaacgagc tacccctacg    540
tgctctgcta cctcctcagt gtcatatatt cactggtatc agcaacgcc cgggcagtcc    600
cctagattgc tcatttatag tacctctaat ctggcctcag gtatcccgc acgatttct    660
ggatctgtt caggttctga ttacaccctc actatctctc gcctggagcc tgaagacttt   720
gccgtttatt actgccagca gaggtctagc tccccattca cctttgggag tgggaccaag   780
gttgaaatta aaacgacaac cccggccccc agaccaccaa cgccagcccc caccatcgcc    840
agccaacccc tgtctctgag accagaagcc tgtaggcctg ccgccggtgg agctgtgcac   900
acaagaggac tggatttcgc ctgtgatatc tacatttgg ccccgctcg gcaggcacatg    960
ggagtgctcc tcctctccct ggtgattacc ctgtactgca aagcaagcg gtctcggctc   1020
ctgcattctg attacatgaa catgaccca agaagaccag gccccaccag gaaacattac   1080
cagccctacg ctccgccacg cgacttcgct gcctaccggt ccaaaagggg ccgcaaaaaa   1140
ctcctttaca ttttttaagca gccttttatg aggccagtac agacgactca agaggaagac   1200
gggtgctcat gccgctttcc tgaggaggag gaaggagggt gcgaactgcg cgttaagttc   1260
tcccgatcag ccgacgcgcc tgcttacaag cagggccaga accaactgta caacgagctg   1320
aatctcggta gacgggaaga gtacgacgtg ttggacaaac ggagaggccg cgacccagaa   1380
atgggcggca agcctcgcag gaaaaacccc caggaggac tgtacaatga gttgcagaaa   1440
gataagatgg cagaagctta tagcgagatc ggaatgaagg gggaaggag acgagggaaa   1500
ggacacgacg gcctttatca gggcctgtcc acagcaacaa aagatacgta tgacgccctc   1560
catatgcagg cacttccacc acggtgataa                                    1590

SEQ ID NO: 304              moltype = AA   length = 528
FEATURE                     Location/Qualifiers
REGION                      1..528
                            note = CAR-T E6 CD28/4-1BB/CD3z sequence
source                      1..528
                            mol_type = protein
                            organism = synthetic construct
SEQUENCE: 304
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DWGQGTLVT VSSGGGGSGG GGSGGGGSEI VLTQSPATLS LSPGERATLT    180
CSATSSVSYI HWYQQRPGQS PRLLIYSTSN LASGIPARFS GSGSGSDYTL TISSLEPEDF   240
```

```
AVYYCQQRSS SPFTFGSGTK VEIKTTTPAP RPPTPAPTIA SQPLSLRPEA CRPAAGGAVH  300
TRGLDFACDI YIWAPLAGTC GVLLLSLVIT LYCRSKRSRL LHSDYMNMTP RRPGPTRKHY  360
QPYAPPRDFA AYRSKRGRKK LLYIFKQPFM RPVQTTQEED GCSCRFPEEE EGGCELRVKF  420
SRSADAPAYK QGQNQLYNEL NLGRREEYDV LDKRRGRDPE MGGKPRRKNP QEGLYNELQK  480
DKMAEAYSEI GMKGERRRGK GHDGLYQGLS TATKDTYDAL HMQALPPR              528

SEQ ID NO: 305          moltype = DNA   length = 1668
FEATURE                 Location/Qualifiers
misc_feature            1..1668
                        note = CAR-T E6 CD28/4-1BB/CD3z gBLOCK sequence
source                  1..1668
                        mol_type = other DNA
                        organism = synthetic construct
SEQUENCE: 305
ataggagac  ccaagctggc  tagttaagct  tggtaccgag  ggccaccatg  gccctgcccg    60
tgaccgcttt  gctgctcccc  ctggcgctgc  tgctgcacgc  cgccaggcca  gaggtccagc   120
tggttgagag  tggcggtggg  ctggttaagc  ctggcggctc  cctgcggctg  agctgcgccg   180
cgagtggatt  tactttcagc  cgatatggga  tgagttgggt  gcggcaagct  gcgggaaga    240
ggctggaatg  ggtctcaaca  atctccgggg  ggggcactta  catctattac  ccgactcag    300
tcaagggga   atttaccatt  tcacgagaca  acgctaagaa  tacccgtgtat  ttgcagatga   360
attctctgag  agcagaggac  acagctgttt  actattgtac  ccgcgacaac  tatggcagga   420
actacgacta  cggtatggac  tattgggac  aaggggacatt  ggttacagtg  gcagtgggg    480
gcggggggcag  cggaggagga  ggcagcggtg  ggggggggcag  cgagatagtg  ctcacgcagt   540
cacccgcgac  tctcagtctc  tcacctgggg  aacgagctac  cctgacgtgc  tctgctacct   600
cctcagtgtc  atatattcac  tggtatcagc  aacggcccgg  gcagtccct   agattgctca   660
tttatagtac  ctctaatctg  gcctcaggta  tccctgcacg  attttctgga  tctggttcag   720
gttctgatta  caccctcact  atctctagcc  tggagcctga  agactttgcc  gtttattact   780
gccagcagag  gtctagctcc  ccattcacct  ttgggagtgg  gaccaaggtt  gaaattaaaa   840
cgacaacccc  ggccccagaa  ccaccaacgc  cagcccccac  catcgccagc  caacccctgt   900
ctctgagacc  agaagcctgt  aggcctgccg  ccggtggac  tgtgcacaca  agaggactgg   960
atttcgcctg  tgatatctac  atttgggccc  cgctcgcagg  cacatgtgga  gtgctcctcc  1020
tctccctggt  gattaccctg  tactgcagaa  gcaagcggtc  tcggctcctg  cattctgatt  1080
acatgaacat  gaccccaaga  agaccaggcc  ccaccaggaa  acattaccag  ccctacgctc  1140
cgccacgcga  cttcgctgcc  taccggtcca  aaaggggccg  caaaaaactc  ctttacattt  1200
ttaagcagcc  ttttatgagg  ccagtacaga  cgactcaaga  ggaagacggg  tgctcatgcc  1260
gctttcctga  ggaggaggaa  ggagggtgcg  aactgcgcgt  taagttctcc  cgatcagccg  1320
acgcgcctgc  ttacaagcag  ggccagaacc  aactgtacaa  cgagctgaat  ctcggtagac  1380
gggaagagta  cgacgtgttg  gacaaacgga  gaggccgcga  cccagaaatg  gcggcaagc   1440
ctcgcaggaa  aaaccccag  gagggactgt  acaatgagtt  gcaagaaagat  aagatggcag   1500
aagcttatag  cgagatcgga  atgaagggg   aaaggagacg  agggaaagga  cacgacggcc   1560
tttatcaggg  cctgtccaca  gcaacaaaag  atacgtatga  cgccctccat  atgcaggcac   1620
ttccaccacg  gtgataagtt  taaacccgct  gatcagcctc  gactgtgc                1668

SEQ ID NO: 306          moltype = DNA   length = 1608
FEATURE                 Location/Qualifiers
misc_feature            1..1608
                        note = CAR-T C2 CD28/4-1BB/CD3z sequence
source                  1..1608
                        mol_type = other DNA
                        organism = synthetic construct
SEQUENCE: 306
atggccttgc  cagtgacggc  cctgctgctg  ccattggctc  ttctgttgca  cgctgccagg    60
cctgaagtgc  agctcgtaga  gagtggcggg  ggactggtga  agcccggtgg  aagcctcaga   120
ctcagttgcg  ccgcctcagg  tttcactttt  tcaggttacg  ccatgtcctg  ggtaagacag   180
gcaccgggga  aaggactcga  gtgggtgtct  actatcagct  caggaggcac  ttatatatat   240
tatcctgact  ctgtaaaagg  ccgatttacg  atttctcgcg  acaatgcaaa  gaactccctc   300
taccctccaaa  tgaacagtct  tagggcagaa  gacactgctg  tatactattg  tgcacgcctc   360
ggcggcgaca  actactacga  gtactttgac  gtgtggggga  aagggactac  cgtgacagtt   420
tcaagcggag  gaggtggctc  aggtggaggc  gggtcagggg  ggagggaag   tgatattgtg   480
ctcacacaat  ccccagcctc  cctggctgtg  tctcccgggc  aacgcgctac  aattacatgt   540
cgggcctcca  aaagcgtgag  caccagcggc  tacagctaca  tgcactggta  tcaacagaaa   600
ccaggacaac  cccccaaaact  gttgatttat  ctcgcttcaa  acttggagtc  cggcgtgcct   660
gcgcgctttt  caggagtgg   gagcggcaca  gattttacgc  tgactatcaa  ccccgtagaa   720
gcaaacgata  cagcgaatta  ttattgtcaa  cattcccggg  aactccccctt  tacgtcggc   780
gggggcacaa  aggtcgaaat  taagagaacc  acgacaaccc  cggccccag   accaccaacg   840
ccagccccca  ccatcgccag  ccaacccctg  tctctgagac  cagaagcctg  taggcctgcc   900
gccggtggac  tgtgcacac   aagaggactg  gatttcgcct  gtgatatcta  catttgggcc   960
ccgctcgcag  gcacatgtgg  agtgctcctc  ctctccctgg  tgattaccct  gtactgcaga  1020
agcaagcggt  ctcggctcct  gcattctgat  tacatgaact  tgaccccaag  aagaccagg   1080
cccaccagga  acattaccag  ccctacgct   ccgccacgcg  acttcgctgc  ctaccggtcc  1140
aaaaggggcc  gcaaaaaact  cctttacatt  tttaagcagc  cttttatgag  gccagtacag  1200
acgactcaag  aggaagacgg  gtgctcatgc  cgctttcctg  aggaggagga  aggagggtgc  1260
gaactgcgcg  ttaagttctc  ccgatcagcc  gacgcgcctg  cttacaagca  gggccagaac  1320
caactgtaca  acgagctgaa  tctcggtaga  cgggaagagt  acgacgtgtt  gacaaacgg   1380
agaggccgcg  acccagaaat  gggcggcaag  cctcgcagga  aaaaccccca  ggagggactg  1440
tacaatgagt  tgcagaaaga  taagatggca  gaagcttata  gcgagatcgg  aatgaagggg  1500
gaaaggagac  gagggaaagg  acacgacggc  ctttatcagg  gcctgtccac  agcaacaaaa  1560
gatacgtatg  acgccctcca  tatgcaggca  cttccaccac  ggtgataa              1608
```

```
SEQ ID NO: 307              moltype = AA   length = 513
FEATURE                     Location/Qualifiers
REGION                      1..513
                            note = CAR-T C2 CD28/4-1BB/CD3z sequence
source                      1..513
                            mol_type = protein
                            organism = synthetic construct
SEQUENCE: 307
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYFDV WGKGTTVTVS   120
SGGGGSGGGG SGGGGSDIVL TQSPASLAVS PGQRATITCR ASKSVSTSGY SYMHWYQQKP   180
GQPPKLLIYL ASNLESGVPA RFSGSGSGTD FTLTINPVEA NDTANYYCQH SRELPFTFGG   240
GTKVEIKRTT TTPAPRPPTP APTIASQPLS LRPEACRPAA GGAVHTRGLD FACDIYIWAP   300
LAGTCGVLLL SLVITLYCRS KRSRLLHSDY MNMTPRRPGP TRKHYQPYAP PRDFAAYRSK   360
RGRKKLLYIF KQPFMRPVQT TQEEDGCSCR FPEEEEGGCE LRVKFSRSAD APAYKQGQNQ   420
LYNELNLGRR EEYDVLDKRR GRDPEMGGKP RRKNPQEGLY NELQKDKMAE AYSEIGMKGE   480
RRRGKGHDGL YQGLSTATKD TYDALHMQAL PPR                                513

SEQ ID NO: 308              moltype = DNA   length = 553
FEATURE                     Location/Qualifiers
misc_feature                1..553
                            note = CAR-T C2-1 gBLOCK sequence
source                      1..553
                            mol_type = other DNA
                            organism = synthetic construct
SEQUENCE: 308
atagggagac ccaagctggc tagttaagct tggtaccgag ggccaccatg gccttgccag    60
tgacggccct gctgctgcca ttggctcttc tgttgcacgc tgccaggcct gaagtgcagc   120
tcgtagagag tggcggggga ctggtgaagc ccggtgaaag cctcagactc agttgcgccg   180
cctcaggttt cacttttca ggttacgcca tgtcctggtc aagacaggca ccggggaaag   240
gactcgagtg ggtgtctact atcagctcag gaggcactta tatatattat cctgactctg   300
taaaaggccg atttacgatt tctcgcgaca atgcaaagaa ctccctctac tccaaatgaa   360
acagtcttag gcagaagac actgctgtat actattgtgc acgcctcggc ggcgacaact   420
actacgagta ctttgacgtg tggggaaag ggactaccgt gacagtttca gcggaggag   480
gtggctcagg tggaggcggg tcaggggggg gaggaagtga tattgtgctc acacaatccc   540
cagcctcct ggc                                                       553

SEQ ID NO: 309              moltype = DNA   length = 518
FEATURE                     Location/Qualifiers
misc_feature                1..518
                            note = CAR-T C2-2 gBLOCK sequence
source                      1..518
                            mol_type = other DNA
                            organism = synthetic construct
SEQUENCE: 309
aagtgatatt gtgctcacac aatccccagc ctccctggct gtgtctcccg gccaacgcgc    60
tacaattaca tgtcgggcct ccaaaagcgt gagcaccagc ggctacagct acatgcactg   120
gtatcaacag aaaccaggac aacccccaa actgttgatt tatctcgctt caaacttgga   180
gtccggcgtg cctgcgcgct tttcaggag tgggagcggc acagattta cgctgactat   240
caaccccgta gaagcaaacg atacagcgaa ttattattgt caacattccc gggaactccc   300
ctttcgttc ggcgggggca caaaggtcga aattaagaga accacgacaa ccccgacctc   360
cagaccacca acgccagccc ccaccatcgc cagccaaccc ctgtctctga accagaagc   420
ctgtaggcct gccgccggtg gagctgtgca cacaagagga ctggatttcg cctgtgatat   480
ctacatttgg gccccgctcg caggcacatg tggagtgc                           518

SEQ ID NO: 310              moltype = DNA   length = 2028
FEATURE                     Location/Qualifiers
misc_feature                1..2028
                            note = CAR E6 Fc/8/4-1BB/CD3z sequence
source                      1..2028
                            mol_type = other DNA
                            organism = synthetic construct
SEQUENCE: 310
atggccctgc ccgtgaccgc tttgctgctc cccctggcgc tgctgctgca cgccgccagg    60
ccagaggtcc agctggttga gagtggcggt gggctggtta gcctggcgg ctccctgcgg   120
ctgagctgcg ccgcgagtgg atttactttc agccgatatg ggatgagttg ggtgcggcaa   180
gctcccggga gaggctgga atgggtctca acaatctccg gggggggcac ttacatctat   240
taccccgact cagtcaaggg gagatttacc atttcacgag acaacgctaa gaataccgta   300
tatttgcaga tgaattctct gagagcagag gacacagcgt ttactattg taccccgcga   360
aactatggca ggaactacga ctacggtatg gactattggg gacaagggac attggttaca   420
gtgagcagtg gcgcggggg cagcggagga ggaggcagcg gtgcggagg cagcgagata   480
gtgctcacgc agtcacccgc gactctcagt ctctcacctg ggaacgagc taccctgacg   540
tgctctgcta cctcctcagt gcatatatt cactggtatc agcaacggcc cggcagtcc   600
cctagaacta tcatttatag tacctctaat ctggcctcag gtatccctgc acgattttct   660
ggatctggtt caggttctga ttacaccctc actatctcta gcctggagcc tgaagacttt   720
gccgtttatt actgccagca gaggtctagc tccccattca cctttgggag tgggaccaag   780
gttgaaatta agagcccaa atcttgtgac aaaactcaca catgcccacc gtgcccagca   840
cctgaactcc tggggggacc gtcagtcttc ctcttcccc caaaacccaa ggacaccctc   900
atgatctccc ggacccctga ggtcacatgc gtggtggtgg acgtgagcca cgaagaccct   960
```

```
gaggtcaagt tcaactggta cgtggacggc gtggaggtgc ataatgccaa gacaaagccg   1020
cgggaggagc agtacaacag cacgtaccgt gtggtcagcg tcctcaccgt cctgcaccag   1080
gactggctga atggcaagga gtacaagtgc aaggtctcca acaaagccct cccagccccc   1140
atcgagaaaa ccatctccaa agccaaaggg cagccccgag aaccacaggt gtacaccctg   1200
cccccatccc gggaggagat gaccaagaac caggtcagcc tgacctgcct ggtcaaaggc   1260
ttctatccca gcgacatcgc cgtggagtgg gagagcaatg ggcagccgga gaacaactac   1320
aagaccacgc ctcccgtgct ggactccgac ggctccttct tcctctacag caagctcacc   1380
gtggacaaga gcaggtggca gcaggggaac gtcttctcat gctccgtgat gcatgaggct   1440
ctgcacaacc actacacgca gaagagcctc tccctgtctc cgggtaaaat ctacatttgg   1500
gccccgctcg caggcacatg tggagtgctc ctcctctccc tggtgattac cctgtactgc   1560
aaaaggggcc gcaaaaaact cctttacatt tttaagcagc cttttatgag gccagtacag   1620
acgactcaag aggaagacgg tgtgctcatg cgctttcctg aggaggagga aggagggtgc   1680
gaactgcgcg ttaagttctc ccgatcagcc gacgcgcctg cttacaagca gggccagaac   1740
caactgtaca acgagctgaa tctcggtaga cgggaagagt acgacgtgtt ggacaaacgg   1800
agaggccgcg acccagaaat gggcggcaag cctcgcagga aaaaccccca ggagggactg   1860
tacaatgagt tgcagaaaga taagatggca gaagcttata gcgagatcgg aatgaagggg   1920
gaaaggagac gagggaaagg cacgacggcc tttatcagg gcctgtccac agcaacaaaa   1980
gatacgtatg acgccctcca tatgcaggca cttccaccac ggtgataa             2028

SEQ ID NO: 311              moltype = AA   length = 674
FEATURE                     Location/Qualifiers
REGION                      1..674
                            note = CAR E6 Fc/8/4-1BB/CD3z sequence
source                      1..674
                            mol_type = protein
                            organism = synthetic construct
SEQUENCE: 311
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKEPKSCD KTHTCPPCPA PELLGGPSVF LFPPKPKDTL   300
MISRTPEVTC VVVDVSHEDP EVKFNWYVDG VEVHNAKTKP REEQYNSTYR VVSVLTVLHQ   360
DWLNGKEYKC KVSNKALPAP IEKTISKAKG QPREPQVYTL PPSREEMTKN QVSLTCLVKG   420
FYPSDIAVEW ESNGQPENNY KTTPPVLDSD GSFFLYSKLT VDKSRWQQGN VFSCSVMHEA   480
LHNHYTQKSL SLSPGKIYIW APLAGTCGVL LLSLVITLYC KRGRKKLLYI FKQPFMRPVQ   540
TTQEEDGCSC RFPEEEEGGC ELRVKFSRSA DAPAYKQGQN QLYNELNLGR REEYDVLDKR   600
RGRDPEMGGK PRRKNPQEGL YNELQKDKMA EAYSEIGMKG ERRRGKGHDG LYQGLSTATK   660
DTYDALHMQA LPPR                                                    674

SEQ ID NO: 312              moltype = DNA   length = 714
FEATURE                     Location/Qualifiers
misc_feature                1..714
                            note = E6 CAR pCDH gBLOCK sequence
source                      1..714
                            mol_type = other DNA
                            organism = synthetic construct
SEQUENCE: 312
acgctgtttt gacctccata gaagattcta gagctagctg tagagcttgg taccgagggc    60
caccatggcc ctgcccgtga ccgctttgct gctccccctg cgctgctgc tgcacgccgc   120
caggccagag gtccagctgg ttgagagtgg cggtggggtg gttaagcctg gcggctccc   180
gcggctgagc tgcgccgcga gtggatttac tttcagccga tatgggatga gttgggtgcg   240
gcaagctccc gggaagaggc tggaatgggt ctcaacaatc tccggggggg gcacttacat   300
ctattacccc gactcagtca aggggagatt taccatttca cgagacaacg ctaagaatac   360
cctgtatttg cagatgaatt ctctgagagc agaggacaca gctgtttact attgtacccg   420
cgacaactat ggcaggaact acgactacgg tatggactat tggggacaag gacattggt   480
tacagtgagc agtggcggcg ggggcagcgg aggaggaggc agcggtggcg gaggcagcga   540
gatagtgctc acgcagtcac ccgcgactct cagtctctca cctggggaac gagctaccct   600
gacgtgctct gctacctcct cagtgtcata tattcactgg tatcagcaac ggcccgggca   660
gtcccctaga ttgctcattt atagtacctc taatctggcc tcaggtatcc ctgc          714

SEQ ID NO: 313              moltype = DNA   length = 723
FEATURE                     Location/Qualifiers
misc_feature                1..723
                            note = E6 CAR Fc pCDH gBLOCK sequence
source                      1..723
                            mol_type = other DNA
                            organism = synthetic construct
SEQUENCE: 313
agtacctcta atctggcctc aggtatccct gcacgatttt ctggatctgg ttcaggttct    60
gattacaccc tcactatctc tagcctggag cctgaagact ttgccgttta ttactgccag   120
cagaggtcta gctccccatt caccttgg agtgggacca aggttgaaat taagagccc   180
aaatcttgtg acaaaactca cacatgccca ccgtgcccag cacctgaact cctgggggga   240
ccgtcagtct tcctcttccc cccaaaaccc aaggacaccc tcatgatctc ccggacccct   300
gaggtcacat gcgtggtggt ggacgtgagc cacgaagacc ctgaggtcaa gttcaactgg   360
tacgtggacg gcgtggaggt gcataatgcc aagacaaagc cgcgggagga gcagtacaac   420
agcacgtacc gtgtggtcag cgtcctcacc gtcctgcacc aggactggct gaatggcaag   480
gagtacaagt gcaaggtctc caacaaagcc ctcccagccc ccatcgagaa aaccatctcc   540
aaagccaaag gcagcccg agaaccacag gtgtacaccc tgcccccatc ccgggaggag   600
```

```
atgaccaaga accaggtcag cctgacctgc ctggtcaaag gcttctatcc cagcgacatc   660
gccgtggagt gggagagcaa tgggcagccg agaacaact  acaagaccac gcctcccgtg   720
ctg                                                                 723
```

| SEQ ID NO: 314 | moltype = DNA  length = 778 |
|---|---|
| FEATURE | Location/Qualifiers |
| misc_feature | 1..778 |
|  | note = E6 CAR 8BB3 pCDH gBLOCK sequence |
| source | 1..778 |
|  | mol_type = other DNA |
|  | organism = synthetic construct |

```
SEQUENCE: 314
agaacaacta caagaccacg cctcccgtgc tggactccga cggctccttc ttcctctaca   60
gcaagctcac cgtggacaag agcaggtggc agcagggga  cgtcttctca tgctccgtga  120
tgcatgaggc tctgcacaac cactacacg  agaagagcct ctccctgtct ccgggtaaaa  180
tctacatttg ggccccgctc gcaggcacat gtggagtgct cctcctctcc ctggtgatta  240
ccctgtactg caaaaggggc cgcaaaaaac tccttacat  ttttaagcag cctttatga   300
ggccagtaca gacgactcaa gaggaagacg ggtgctcatg ccgctttcct gaggaggagg  360
aaggagggtg cgaactgcgc gttaagttct cccgatcagc cgacgcgcct gcttacaagc  420
agggccagaa ccaactgtac aacgagctga atctcggtag acgggaagag tacgacgtgt  480
tggacaaacg gagaggccgc gacccagaaa tgggcggcaa gcctcgcagg aaaaaccccc  540
aggaggact  gtacaatgag ttgcagaaag ataagatgcg agaagcttat agcgagatcg  600
gaatgaaggg ggaaggagag cgagggaaag gacacgacgg cctttatcag ggcctgtcca  660
cagcaacaaa agatacgtat gacgcctcc  atatgcaggc acttccacca cggtgataag  720
tttaaacccg ctgatcaggc ggccgcgaag gatctgcgat cgctccggtg cccgtcag   778
```

| SEQ ID NO: 315 | moltype = DNA  length = 1983 |
|---|---|
| FEATURE | Location/Qualifiers |
| misc_feature | 1..1983 |
|  | note = CAR E6 FcH/8/4-1BB/CD3z sequence |
| source | 1..1983 |
|  | mol_type = other DNA |
|  | organism = synthetic construct |

```
SEQUENCE: 315
atggccctgc ccgtgaccgc tttgctgctc cccctggcgc tgctgctgca cgccgccagg    60
ccagaggtcc agctggttga gagtggcggg gggctggtta agcctggcgg ctccctgcgg   120
ctgagctgcg ccgcgagtgg atttactttc agccgatatg gcatgagttg ggtgcggcaa   180
gctcccggga gaggctgga  atgggtctca acaatctccg ggggggggcac ttacatctat   240
taccccgact cagtcaaggg gagatttacc atttcacgag acaacgctaa gaataccctg   300
tatttgcaga tgaattctct gagagcagag acacagctg  tttactattg tacccgcgac   360
aactatggca ggaactacga ctacggtatg gactattggg gacaagggac attggttaca   420
gtgagcagtg gcggcggggg cagcggagga ggaggcagcg gtggcggagg cagcgagata   480
gtgctcacgc agtcacccgc gactctcagt ctctcacctg gggaacagca taccctgagg   540
tgctctgcta cctcctcagt gtcatatatt cactggtatc agcaacgcgcc cgggcagtcc   600
cctagattgc tcatttatag tacctctaat ctggcctcag gtatccctgc acgattttct   660
ggatctggtt caggttctga ttacaccctc actatctcta gcctggagcc tgaagacttt   720
gccgttttatt actgccagca gaggtctagc tccccattca ctttgggag  tgggaccaag   780
gttgaaatta agcacctga  actcctgggg ggaccgtcag tcttcctctt ccccccaaaa   840
cccaaggaca ccctcatgat ctcccggacc cctgaggtca catgcgtggt ggtggacgtg   900
agccacgaag accctgaggt caagttcaac tggtacgtgg acggcgtgga ggtgcataat   960
gccaagacaa agccgcggga ggagcagtac aacagcacgt accgtgtgt  cagcgtcctc  1020
accgtcctgc accaggactg gctgaatggc aaggagtaca agtgcaaggt ctccaacaaa  1080
gcctcccag  ccccatcga gaaaaccatc tccaaagcca agggcagcc  ccgagaacca  1140
caggtgtaca cctgcccccc atcccgggag gagatgacca gaaccaggt cagcctgacc  1200
tgcctggtca aaggcttcta tcccagcgac atcgccgtgg agtgggagag caatgggcag  1260
ccggagaaca actacaagac cacgcctccc gtgctggact ccgacggctc cttcttcctc  1320
tacagcaagc tcaccgtgga caagagcagg tggcagcagg ggaacgtctt catgctccc   1380
gtgatgcatg aggctctgca caaccactac acgcagaaga gcctctccct gtctccgggt  1440
aaaatctaca tttgggcccc gctcgcaggc acatgtggag tgctcctcct ccctggtgtt  1500
attaccctgt actgcaaaag gggccgcaaa aaactccttt acatttttaa gcagcctttt  1560
atgaggccag tacagacgac tcaagaggaa gacgggtgct catgccgctt tcctgaggag  1620
gaggaaggag gggtgcgaac tgcgcgttaag ttctcccgat cagccgacgc gcctgcttac  1680
aagcagggcc agaaccaact gtacaacgag ctgaatctcg gtagacggga agagtacgac  1740
gtgttggaca aacggagagg ccgcgaccca gaaatgggcg gcaagcctcg caggaaaaac  1800
ccccaggagg gactgtacaa tgagttgcag aaagataaga tggcagaagc ttatagcgag  1860
atcggaatga agggggaaag gagacgaggg aaaggacacg acggccttta tcagggcctg  1920
tccacagcaa caaaagatac gtatgacgcc ctccatatgc aggcacttcc accacggtga  1980
taa                                                                1983
```

| SEQ ID NO: 316 | moltype = AA  length = 659 |
|---|---|
| FEATURE | Location/Qualifiers |
| REGION | 1..659 |
|  | note = CAR E6 FcH/8/4-1BB/CD3z sequence |
| source | 1..659 |
|  | mol_type = protein |
|  | organism = synthetic construct |

```
SEQUENCE: 316
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
```

```
NYGRNYDYGM DYWGQGTLVT VSSGGGGSGG GGSGGGGSEI VLTQSPATLS LSPGERATLT  180
CSATSSVSYI HWYQQRPGQS PRLLIYSTSN LASGIPARFS GSGSGSDYTL TISSLEPEDF  240
AVYYCQQRSS SPFTFGSGTK VEIKAPELLG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRE EMTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
KIYIWAPLAG TCGVLLLSLV ITLYCKRGRK KLLYIFKQPF MRPVQTTQEE DGCSCRFPEE  540
EEGGCELRVK FSRSADAPAY KQGQNQLYNE LNLGRREEYD VLDKRRGRDP EMGGKPRRKN  600
PQEGLYNELQ KDKMAEAYSE IGMKGERRRG KGHDGLYQGL STATKDTYDA LHMQALPPR   659

SEQ ID NO: 317         moltype = DNA  length = 678
FEATURE                Location/Qualifiers
misc_feature           1..678
                       note = E6 CAR FcH pCDH gBLOCK sequence
source                 1..678
                       mol_type = other DNA
                       organism = synthetic construct
SEQUENCE: 317
agtacctcta atctggcctc aggtatccct gcacgatttt ctggatctgg ttcaggttct    60
gattacaccc tcactatctc tagcctggag cctgaagact ttgccgttta ttactgccag   120
cagaggtcta gctccccatt caccttttggg agtgggacca aggttgaaat taaagcacct   180
gaactcctgg ggggaccgtc agtcttcctc ttcccccaaa aacccaagga caccctcatg   240
atctcccgga cccctgaggt cacatgcgtg gtggtggacg tgagccacga agaccctgag   300
gtcaagttca actggtacgt ggacggcgtg gaggtgcata atgccaagac aaagccgcgg   360
gaggagcagt acaacagcac gtaccgtgtg gtcagcgtcc tcaccgtcct gcaccaggac   420
tggctgaatg gcaaggagta caagtgcaag gtctccaaca aagccctccc agcccccatc   480
gagaaaacca tctccaaagc caaagggcag ccccgagaac cacaggtgta caccctgccc   540
ccatcccggg aggagatgac caagaaccag gtcagcctga cctgcctggt caaaggcttc   600
tatcccagca acatcgccgt ggagtgggag agcaatgggc agccggagaa caactacaag   660
accacgcctc ccgtgctg                                                  678

SEQ ID NO: 318         moltype = DNA  length = 2022
FEATURE                Location/Qualifiers
misc_feature           1..2022
                       note = CAR E6 Fc/4/4-1BB/CD3z sequence
source                 1..2022
                       mol_type = other DNA
                       organism = synthetic construct
SEQUENCE: 318
atggccctgc ccgtgaccgc tttgctgctc ccctggcgc tgctgctgca cgccgccagg    60
ccagaggtcc agctggttga gagtggcggt gggctggtta gcctggcgg ctccctgcgg   120
ctgagctgcg ccgcgagtgg atttactttc agccgatatg gatgagttg ggtgcggcaa   180
gctcccggga agaggctgga atgggtctca acaatcgtag gggggggcac ttacatctat   240
taccccgact cagtcaaggg gagatttacc atttcacgag acaacgctaa gaatacccctg   300
tatttgcaga tgaattctct gagagcagag gacacagctg tttactattg taccgcgac    360
aactatggca ggaactacga ctacggtatg gactattggg gacaagggac attggttaca   420
gtgagcagtg gcggcggggg cagcggagga ggaggcagcg gtggcggagg cagcgagata   480
gtgctcacgc agtcacccgc gactctcagt ctctcacctg ggaacgagc tacccctgacg   540
tgctctgcta cctcctcagt gtcatatatt cactggtatc agcaacgcc cgggcagtcc   600
cctagattgc tcatttatag tacctctaat ctggcctcag gtatccctgc acgatttct   660
ggatctggtt caggttctga ttacaccctc actatctcta gcctggagc tgaagactct   720
gccgtttatt actgccagca gaggtctagc tccccatttca cctttgggag tgggaccaag   780
gttgaaatta agagccccaa atcttgtgac aaaactcaca catgcccacc gtgcccagca   840
cctgaactcc tgggggggac cgtcagtctt ctcttcccc caaaacccaa ggacaccctc   900
atgatctccc ggacccctga ggtcacatgc gtggtggtgga cgtgagccac gaagacccct   960
gaggtcaagt tcaactggta cgtggacggc gtggaggtgc ataatgccaa gacaaagccg  1020
cgggaggagc agtacaacag cacgtaccgt gtggtcagcg tcctcaccgt cctgcaccag  1080
gactggctga atggcaagga gtacaagtgc aaggtctcca acaaagccct cccagccccc  1140
atcgagaaaa ccatctccaa agccaaaggg cagccccgag aaccacaggt gtacaccctg  1200
cccccatccc gggaggagat gaccaagaac caggtcagcc tgacctgcct ggtcaaaggc  1260
ttctatccca gcgacatcgc cgtggagtgg gagagcaatg ggcagccgga gaacaactac  1320
aagaccacgc ctcccgtgct ggactccgac ggctccttct tcctctacag caagctcacc  1380
gtggacaaga gcaggtggca gcagggggaac gtcttctcat gctccgtgat gcatgaggct  1440
ctgcacaacc actacacgca gaagagcctc tccctgtctc cgggtaaaat ggccctgatt  1500
gtgctggggg gcgtcgccgg cctcctgctt ttcattgggc taggcatctt cttcaaaagg  1560
ggccgcaaaa aactccttta catttttaag cagccttttta tgaggccagt acagacgact  1620
caagaggaag acggtgctc atgccgcttt cctgaggagg aggaaggagg tgcgaactg  1680
cgcgttaagt tctccgatc agccgacgcg cctgcttaca agcagggcca gaaccaactg  1740
tacaacgac tgaatctcgg tagacggaaa gagtacgacg tgttggacaa acggaggagc  1800
cgcgacccag aaatgggcgg caagcctcgc aggaaaaacc cccaggaggg actgtacaat  1860
gagttgcaga agataagat ggcagaagct tatagcgaga tcggaatgaa gggggaaagg  1920
agacgaggga aggacacgga cggctttat cagggcctgt ccacagcaac aaaagatacg  1980
tatgacgccc tccatatgca ggcacttcca ccacggtgat aa                     2022

SEQ ID NO: 319         moltype = AA  length = 672
FEATURE                Location/Qualifiers
REGION                 1..672
                       note = CAR E6 Fc/4/4-1BB/CD3z sequence
source                 1..672
```

```
                        mol_type = protein
                        organism = synthetic construct
SEQUENCE: 319
MALPVTALLL PLALLLHAAR PEVQLVESGG GLVKPGGSLR LSCAASGFTF SRYGMSWVRQ     60
APGKRLEWVS TISGGGTYIY YPDSVKGRFT ISRDNAKNTL YLQMNSLRAE DTAVYYCTRD    120
NYGRNYDYGM DYWGQGTLVT VSSGGGGSGG GGSGGGGSEI VLTQSPATLS LSPGERATLT    180
CSATSSVSYI HWYQQRPGQS PRLLIYSTSN LASGIPARFS GSGSGSDYTL TISSLEPEDF    240
AVYYCQQRSS SPFTFGSGTK VEIKEPKSCD KTHTCPPCPA PELLGGPSVF LFPPKPKDTL    300
MISRTPEVTC VVVDVSHEDP EVKFNWYVDG VEVHNAKTKP REEQYNSTYR VVSVLTVLHQ    360
DWLNGKEYKC KVSNKALPAP IEKTISKAKG QPREPQVYTL PPSREEMTKN QVSLTCLVKG    420
FYPSDIAVEW ESNGQPENNY KTTPPVLDSD GSFFLYSKLT VDKSRWQQGN VFSCSVMHEA    480
LHNHYTQKSL SLSPGKMALI VLGGVAGLLL FIGLGIFFKR GRKKLLYIFK QPFMRPVQTT    540
QEEDGCSCRF PEEEEGGCEL RVKFSRSADA PAYKQGQNQL YNELNLGRRE EYDVLDKRRG    600
RDPEMGGKPR RKNPQEGLYN ELQKDKMAEA YSEIGMKGER RRGKGHDGLY QGLSTATKDT    660
YDALHMQALP PR                                                       672

SEQ ID NO: 320          moltype = DNA  length = 772
FEATURE                 Location/Qualifiers
misc_feature            1..772
                        note = E6 CAR 44BB3 pCDH gBLOCK sequence
source                  1..772
                        mol_type = other DNA
                        organism = synthetic construct
SEQUENCE: 320
agaacaacta caagaccacg cctcccgtgc tggactccga cggctccttc ttcctctaca     60
gcaagctcac cgtggacaag agcaggtggc agcaggggaa cgtcttctca tgctccgtga    120
tgcatgaggc tctgcacaac cactacacgc agaagagcct ctccctgtct ccgggtaaaa    180
tggccctgat tgtgctgggg ggcgtcgccg gcctcctgct tttcattggg ctaggcatct    240
tcttcaaaag gggccgcaaa aaactccttt acatttttaa gcagcctttt atgaggccag    300
tacagacgac tcaagaggaa gacggctgct catgccgctt tcctgaggag gaggaaggag    360
ggtgcgaact gcgcgttaag ttctcccgat cagccgacgc gcctgcttac aagcagggcc    420
agaaccaact gtacaacgag ctgaatctcg gtagacggga agagtacgac gtgttggaca    480
aacggagagg ccgcgaccca gaaatgggcg gcaagcctcg caggaaaaac ccccaggagg    540
gactgtacaa tgagttgcag aaagataaga tggcagaagc ttatagcgag atcggaatga    600
aggggaaag gagacgaggg aaaggacacg acggccttta tcagggcctg tccacagcaa    660
caaaagatac gtatgacgcc ctccatatgc aggcacttcc accacggtga taagtttaaa    720
cccgctgatc aggcggccgc gaaggatctg cgatcgctcc ggtgcccgtc ag           772

SEQ ID NO: 321          moltype = DNA  length = 1977
FEATURE                 Location/Qualifiers
misc_feature            1..1977
                        note = CAR E6 FcH/4/4-1BB/CD3z sequence
source                  1..1977
                        mol_type = other DNA
                        organism = synthetic construct
SEQUENCE: 321
atggccctgc ccgtgaccgc tttgctgctc cccctggcgc tgctgctgca cgccgccagg     60
ccagaggtcc agctggttga gagtggcggg gggctggtta gcctggcgg ctccctgcgg    120
ctgagctgcg ccgcgagtgg atttactttc agccgatatg ggatgagttg ggtgcggcaa    180
gctcccggga gaggctggaa atgggtctca acaatctccg gggggggcac ttacatctat    240
tacccgact cagtcaaggg gagatttacc atttcacgag acaacgctaa gaataccctg    300
tatttgcaga tgaattctct gagagcagag gacacagctg tttactattg taccgcgac    360
aactatggca ggaactacga ctacggtatg gactattggg gacaaggac attggttaca    420
gtgagcagtg gcggcggggg cagcggagga ggaggcagcg gtggcggagg cagcgagata    480
gtgctcacgc agtcaccgc gactctcagt ctctcacctg gggaacgagc taccctgacg    540
tgctctgcta cctcctcagt gtcatatatt cactggtatc agcaacggcc cgggcagtcc    600
cctagattgc tcatttatag tacctctaat ctggcctcag gtatccctgc acgattttct    660
ggatctggtt caggttctga ttacacccto actatctcta gcctggagcc tgaagacttt    720
gccgtttatt actgccagca gaggtctagc tccccattca ccttttgggag tgggaccaag    780
gttgaaatta aagcacctga actcctgggg ggaccgtcag tcttcctctt cccccccaaa    840
cccaaggaca ccctcatgat ctcccggacc cctgaggtca catgcgtggt ggtggacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca agtgcaaggt ctccaacaaa   1080
gccctcccag cccccatcga gaaaaccatc tccaaagcca agggcagcc ccgagaacca   1140
caggtgtaca ccctgccccc atccggggag gagatgacca gaaccaggt cagcctgacc   1200
tgcctggtca aaggcttcta tcccagcgac atcgccgtgg agtgggagag caatgggcag   1260
ccggagaaca actacaagac cacgcctccc gtgctggact ccgacggctc cttcttcctc   1320
tacagcaagc tcaccgtgga caagagcagg tggcagcagg ggaacgtctt ctcatgctcc   1380
gtgatgcatg aggctctgca caaccactac acgcagaaga gcctctccct gtctccgggt   1440
aaaatggccc tgattgtgct ggggggcgtc gccggcctcc tgcttttcat tgggctaggc   1500
atcttcttca aaaggggccg caaaaaactc tttacattt taagcagcc ttttatgagg   1560
ccagtacaga cgactcaaga ggaagacggg tgctcatgcc gctttcctga ggaggaggaa   1620
ggagggtgcg aactgcgcgt taagttctcc cgatcagccg acgcgcctgc ttacaagcag   1680
ggccagaacc aactgtacaa cgagctgaat ctcggtagac gggaagagta cgacgtgttg   1740
gacaaacgga gaggccgcga cccagaaatg ggcggcaagc ctcgcaggaa aaaccccag   1800
gagggactgt acaatgagtt gcagaaagat aagatggcag aagcttatag cgagatcgga   1860
atgaaggggg aaaggagacg agggaaagga cacgacggcc tttatcaggg cctgtccaca   1920
gcaacaaaag tacgtatga cgccctccat atgcaggcac ttccaccacg gtgataa       1977
```

```
SEQ ID NO: 322            moltype = AA  length = 657
FEATURE                   Location/Qualifiers
REGION                    1..657
                          note = CAR E6 FcH/4/4-1BB/CD3z sequence
source                    1..657
                          mol_type = protein
                          organism = synthetic construct
SEQUENCE: 322
MALPVTALLL PLALLLHAAR PEVQLVESGG GLVKPGGSLR LSCAASGFTF SRYGMSWVRQ  60
APGKRLEWVS TISGGGTYIY YPDSVKGRFT ISRDNAKNTL YLQMNSLRAE DTAVYYCTRD 120
NYGRNYDYGM DWGQGTLVT VSSGGGGSGG GGSGGGGSEI VLTQSPATLS LSPGERATLT 180
CSATSSVSYI HWYQQRPGQS PRLLIYSTSN LASGIPARFS GSGSGSDYTL TISSLEPEDF 240
AVYYCQQRSS SPFTFGSGTK VEIKAPELLG GPSVFLFPPK PKDTLMISRT PEVTCVVVDV 300
SHEDPEVKFN WYVDGVEVHN AKTKPREEQY NSTYRVVSVL TVLHQDWLNG KEYKCKVSNK 360
ALPAPIEKTI SKAKGQPREP QVYTLPPSRE EMTKNQVSLT CLVKGFYPSD IAVEWESNGQ 420
PENNYKTTPP VLDSDGSFFL YSKLTVDKSR WQQGNVFSCS VMHEALHNHY TQKSLSLSPG 480
KMALIVLGGV AGLLLFIGLG IFFKRGRKKL LYIFKQPFMR PVQTTQEEDG CSCRFPEEEE 540
GGCELRVKFS RSADAPAYKQ GQNQLYNELN LGRREEYDVL DKRRGRDPEM GGKPRRKNPQ 600
EGLYNELQKD KMAEAYSEIG MKGERRRGKG HDGLYQGLST ATKDTYDALH MQALPPR    657

SEQ ID NO: 323            moltype = DNA  length = 1506
FEATURE                   Location/Qualifiers
misc_feature              1..1506
                          note = CAR E6 IgD/8/4-1BB/CD3z sequence
source                    1..1506
                          mol_type = other DNA
                          organism = synthetic construct
SEQUENCE: 323
atggccctgc ccgtgaccgc tttgctgctc cccctggcgc tgctgctgca cgccgccagg   60
ccagaggtcc agctggttga gagtggcggt gggctggtta agcctggcgg ctccctgcgg  120
ctgagctgcg ccgcgagtgg atttactttc agccgatatg ggatgagttg ggtgcggcaa  180
gctcccggga gaggctggaa atgggtctca acaatctccg gggggggcac ttacatctat  240
taccccgact cagtcaaggg gagatttacc atttcacgag acaacgctaa gaatacgctc  300
tatttgcaga tgaattctct gagagcagag gacacagctg tttactattg taccgcgcga  360
aactatggca ggaactacga ctacggtatg gactattggg gacaagggac attggttaca  420
gtgagcagtg gcggcggggg cagcggagga ggaggcagcg gtggcggagg cagcgagata  480
gtgctcacgc agtcacccgc gactctcagt ctctcacctg gggaacgagc taccctgacg  540
tgctctgcta cctcctcagt gtcatatatt cactggtatc agcaacggcc cgggcagtcc  600
cctagattgc tcatttatag tacctctaat ctggcctcag gtatccctgc acgattttct  660
ggatctggtt caggttctga ttacaccctc actatctcta gcctggagcc tgaagacttt  720
gccgtttatt actgccagca gaggtctagc tccccattca cctttgggag tgggaccaag  780
gttgaaatta aagagtctcc aaaggcacag gcctcctcag tgccccactgc acaacccaa  840
gcagagggca gcctcgccaa ggcaaccaca gccccagcca ccaccgtaa cacaggaaga  900
ggcggcgaag agaagaaaaa ggagaaggag aagaggaac aagaagagag agacaaag    960
acaccaatct acatttgggc cccgctgca ggcacatgtg gagtgctcct cctctccctg 1020
gtgattaccc tgtactgcaa aagggggccgc aaaaaactcc tttacatttt taagcagcct 1080
tttatgaggc cagtacagac gactcaagag gaagacgggt gctcatgccg ctttcctgag 1140
gaggaggaag gaggtgcgga actgcgcgtt aagttctccc gatcagccga cgcgcctgct 1200
tacaagcagg gccagaacca actgtacaac gagctgaatc tcggtagacg ggaagagtac 1260
gacgtgttgg acaaacggag aggccgcgac ccagaaatgg gcggcaagcc tcgcaggaaa 1320
aaccccagg agggactgta caatgagttg cagaaagata gatggcaga agcttatagc 1380
gagatcggaa tgaaggggga aaggagacga gggaaggac acgacggcct ttatcagggc 1440
ctgtccacag caacaaaaga tacgtatgac gcctccata tgcaggcact tccaccacgg 1500
tgataa                                                            1506

SEQ ID NO: 324            moltype = AA  length = 500
FEATURE                   Location/Qualifiers
REGION                    1..500
                          note = CAR E6 IgD/8/4-1BB/CD3z sequence
source                    1..500
                          mol_type = protein
                          organism = synthetic construct
SEQUENCE: 324
MALPVTALLL PLALLLHAAR PEVQLVESGG GLVKPGGSLR LSCAASGFTF SRYGMSWVRQ  60
APGKRLEWVS TISGGGTYIY YPDSVKGRFT ISRDNAKNTL YLQMNSLRAE DTAVYYCTRD 120
NYGRNYDYGM DWGQGTLVT VSSGGGGSGG GGSGGGGSEI VLTQSPATLS LSPGERATLT 180
CSATSSVSYI HWYQQRPGQS PRLLIYSTSN LASGIPARFS GSGSGSDYTL TISSLEPEDF 240
AVYYCQQRSS SPFTFGSGTK VEIKESPKAQ ASSVPTAQPQ AEGSLAKATT APATTRNTGR 300
GGEEKKKEKE KEEQEERETK TPIYIWAPLA GTCGVLLLSL VITLYCKRGR KKLLYIFKQP 360
FMRPVQTTQE EDGCSCRFPE EEEGGCELRV KFSRSADAPA YKQGQNQLYN ELNLGRREEY 420
DVLDKRRGRD PEMGGKPRRK NPQEGLYNEL QKDKMAEAYS EIGMKGERRR GKGHDGLYQG 480
LSTATKDTYD ALHMQALPPR                                             500

SEQ ID NO: 325            moltype = DNA  length = 475
FEATURE                   Location/Qualifiers
misc_feature              1..475
                          note = E6 CAR IgD8 pcDH gBLOCK sequence
source                    1..475
```

```
                         mol_type = other DNA
                         organism = synthetic construct
SEQUENCE: 325
agtacctcta atctggcctc aggtatccct gcacgatttt ctggatctgg ttcaggttct      60
gattacaccc tcactatctc tagcctggag cctgaagact ttgccgttta ttactgccag     120
cagaggtcta gctccccatt cacctttggg agtgggacca aggttgaaat taaagagtct     180
ccaaaggcac aggcctcctc agtgccact gcacaacccc aagcagaggg cagcctcgcc      240
aaggcaacca cagccccagc caccaccgt aacacaggaa gaggcggcga agagaagaaa      300
aaggagaagg agaaagagga acaagaagag agagagacaa agacaccaat ctacatttgg     360
gccccgctcg caggcacatg tggagtgctc ctcctctccc tggtgattac cctgtactgc     420
aaaaggggcc gcaaaaaact cctttacatt tttaagcagc cttttatgag gccag          475

SEQ ID NO: 326         moltype = DNA   length = 502
FEATURE                Location/Qualifiers
misc_feature           1..502
                       note = E6 CAR BB 3 pCDH gBLOCK sequence
source                 1..502
                       mol_type = other DNA
                       organism = synthetic construct
SEQUENCE: 326
acattttaa gcagcctttt atgaggccag tacagacgac tcaagaggaa gacgggtgct       60
catgcgcctt tcctgaggag gaggaaggag ggtgcgaagt gcgcgttaag ttctcccgat     120
cagccgacgc gcctgcttac aagcaggggc agaaccaact gtacaacgag ctgaatctcg     180
gtagacggga agagtacgac gtgttggaca acggagagg ccgcgaccca gaaatgggcg      240
gcaagcctcg caggaaaaac ccccaggagg gactgtacaa tgagttgcag aaagataaga     300
tggcagaagc ttatagcgag atcggaatga agggggaagg gagacgaggg aaaggacacg     360
acggcctttta tcagggcctg tccacacaa caaaagatac gtatgacgcc ctccatatgc     420
aggcacttcc accacggtga taagtttaaa cccgctgatc aggcggccgc gaaggatctg     480
cgatcgctcc ggtgcccgtc ag                                              502

SEQ ID NO: 327         moltype = DNA   length = 1500
FEATURE                Location/Qualifiers
misc_feature           1..1500
                       note = CAR E6 IgD/4/4-1BB/CD3z sequence
source                 1..1500
                       mol_type = other DNA
                       organism = synthetic construct
SEQUENCE: 327
atggccctgc ccgtgaccgc tttgctgctc cccctggcgc tgctgctgca cgccgccagg      60
ccagaggtcc agctggttga gagtggcggt gggctggtta agcctggcgg ctccctgcgg     120
ctgagctgcg ccgcgagtgg atttactttc agccgatatg gatgagttg ggtgcggcaa      180
gctcccggga gaggctggaa atgggtctca acaatctccg ggggggcac ttacatctat      240
taccccgact cagtcaaggg gagatttacc atttcacgag acaacgctaa gaataccctg     300
tatttgcaga tgaattctct gagagcagag gacacagctg tttactattg taccgcgac     360
aactatggca gaactacga ctacggtatg gactattggg gacaaggac attggttaca      420
gtgagcagtg gcggcgggg cagcggagga ggaggcagcg gtggcggagg cagcgagata     480
gtgctcacgc agtcacccgc gactctcagt tctcaccgg ggaaccagct caccctgacg      540
tgctctgcta cctcctcagt gtcatatatt cactggtatc agcaacggcc cgggcagtcc     600
cctagattgc tcatttatag tacctctaat ctggcctcag gtatccctgc acgattttct     660
ggatctggtt caggttctga ttacacccte actatctca gcctggagcc tgaagacttt      720
gccgtttatt actgccagca gaggtctagc tccccattca cctttgggag tgggaccaag     780
gttgaaatta aagagtctcc aaaggcacag gcctcctcag tgcccactgc acaacccca      840
gcagagggca gcctcgccaa ggcaaccaca gccccagcca ccaccgtaa cacaggaaga      900
ggcggcgaag aagaaaaa ggagaaggag aagaggaac aagaagagag agacaaag         960
acaccaatgg ccctgattgt gctggggggc gtcgccgcc tcctgcttt cattgggcta     1020
ggcatcttct tcaaaagggg ccgcaaaaaa ctcctttaca ttttttaagca gccttttatg    1080
aggccagtac agacgactca agaggaagac gggtgctcat gccgctttcc tgaggaggag    1140
gaaggagggt gcgaactgcg cgttaagttc tcccgatcag ccgacgcgcc tgcttacaag    1200
cagggccaga accaactgta caacgagctg aatctcggta gacggaaga gtacgacgtg    1260
ttggacaaac ggagaggccg cgacccagaa atgggcgca agcctcgcag gaaaaaccc     1320
caggaggac tgtacaatga gttgcagaaa gataagatgg cagaagctta tagcgagatc    1380
ggaatgaagg gggaaggag acgagggaaa ggacacgacg gcctttatca gggcctgtcc    1440
acagcaacaa aagatacgta tgacgccctc catatgcagg cacttccacc acggtgataa    1500

SEQ ID NO: 328         moltype = AA    length = 498
FEATURE                Location/Qualifiers
REGION                 1..498
                       note = CAR E6 IgD/4/4-1BB/CD3z sequence
source                 1..498
                       mol_type = protein
                       organism = synthetic construct
SEQUENCE: 328
MALPVTALLL PLALLLHAAR PEVQLVESGG GLVKPGGSLR LSCAASGFTF SRYGMSWVRQ      60
APGKRLEWVS TISGGGTYIY YPDSVKGRFT ISRDNAKNTL YLQMNSLRAE DTAVYYCTRD     120
NYGRNYDYGM DYWGQGTLVT VSSGGGGSGG GGSGGGGSEI VLTQSPATLS LSPGERATLT     180
CSATSSVSYI HWYQQRPGQS PRLLIYSTSN LASGIPARFS GSGSGSDYTL TISSLEPEDF     240
AVYYCQQRSS SPFTFGSGTK VEIKESPKAQ ASSVPTAQPQ AEGSLAKATT APATTRNTGR     300
GGEEKKKEKE KEEQEERETK TPMALIVLGG VAGLLLFIGL GIFFKRGRKK LLYIFKQPFM     360
RPVQTTQEED GCSCRFPEEE EGGCELRVKF SRSADAPAYK QGQNQLYNEL NLGRREEYDV     420
```

```
LDKRRGRDPE MGGKPRRKNP QEGLYNELQK DKMAEAYSEI GMKGERRRGK GHDGLYQGLS    480
TATKDTYDAL HMQALPPR                                                 498

SEQ ID NO: 329           moltype = DNA  length = 469
FEATURE                  Location/Qualifiers
misc_feature             1..469
                         note = E6 CAR IgD4 pcDH gBLOCK sequence
source                   1..469
                         mol_type = other DNA
                         organism = synthetic construct
SEQUENCE: 329
agtacctcta atctggcctc aggtatccct gcacgatttt ctggatctgg ttcaggttct    60
gattacaccc tcactatctc tagcctggag cctgaagact ttgccgttta ttactgccag    120
cagaggtcta gctccccatt cacctttggg agtgggacaa aggttgaaat taaagagtct    180
ccaaaggcac aggcctcctc agtgcccact gcacaacccc aagcagaggg cagcctcgcc    240
aaggcaacca cagccccagc caccacccgt aacacaggaa gaggcggcga agagaagaaa    300
aaggagaagg agaaagagga acaagaagag agagagacaa agacaccaat ggccctgatt    360
gtgctggggg gcgtcgccgg cctcctgctt ttcattgggc taggcatctt cttcaaaagg    420
ggccgcaaaa aactccttta catttttaag cagccttttn tgaggccag                469

SEQ ID NO: 330           moltype = DNA  length = 1461
FEATURE                  Location/Qualifiers
misc_feature             1..1461
                         note = CAR E6 X4/8/4-1BB/CD3z sequence
source                   1..1461
                         mol_type = other DNA
                         organism = synthetic construct
SEQUENCE: 330
atggccctgc ccgtgaccgc tttgctgctc cccctggcgc tgctgctgca cgccgccagg    60
ccagaggtcc agctggttga gagtggcggt gggctggtta agcctggcgg ctccctgcgg    120
ctgagctgcg ccgcgagtgg atttactttc agccgatatg ggatgagttg ggtgcggcaa    180
gctcccggga gaggctgga tgggtctca acaatctccg ggggggggcac ttacatctat    240
taccccgact cagtcaaggg gagatttacc atttcacgag acaacgctaa gaatacctg     300
tatttgcaga tgaattctct gagagcagag gacacagctg tttactattg tacccgcga    360
aactatggca ggaactacga ctacggtatg gactattggg gacaagggac attggttaca    420
gtgagcagtg gcggcggggg cagcggagga ggaggcagcg gtggcggagg cagcgagata    480
gtgctcacgc agtcacccgc gactctcagt ctctcacctg ggaacgagc taccctgacg    540
tgctctgcta cctcctcagt gtcatatatt cactggtatc agcaacggcc cgggcagtcc    600
cctagattgc tcatttatag tacctctaat ctggcctcag gtatccctgc acgatttct    660
ggatctggtt caggttctga ttacaccctc actatctcta gcctggagcc tgaagactt    720
gccgtttatt actgccagca gaggtctagc tccccattca cctttgggag tgggaccaag    780
gttgaaatta agacaagac gcacaccaag ccacctaaac cagctccaga actgctcgga    840
ggtcctggca ccggaaccgg aggacctacc atcaaaccac ctaagccact taagcctgcc    900
cctaacctgc tcgaggacc tatctacatt tgggccccgc tcgcaggcac atgtggagtg    960
ctcctcctct ccctggtgat taccctgtac tgcaaaaggg gccgcaaaaa actcctttac   1020
attttaaagc agccttttat gaggccagta cagacgact aagaggaaga cggtgctca    1080
tgccgctttc ctgaggagga ggaaggaggg tgcgaactgc gcgttaagtt ctccccgatca   1140
gccgacgcgc ctgcttacaa gcagggccaa aaccaactgt acaacgagct gaatctcggt   1200
agacgggaag agtacgacgt gttggacaaa cggagaggcc gcgacccaga aatgggcggc   1260
aagcctcgca ggaaaacacc caggaggga ctgtacaatg agttcagaa agataagatg    1320
gcagaagctt atagcgagat cggaatgaag ggggaaagga gacgagggaa aggacacgac   1380
ggcctttatc agggctgtc cacagcaaca aaagatacgt atgacgccct ccatatgcag   1440
gcacttccac cacggtgata a                                             1461

SEQ ID NO: 331           moltype = AA  length = 485
FEATURE                  Location/Qualifiers
REGION                   1..485
                         note = CAR E6 X4/8/4-1BB/CD3z sequence
source                   1..485
                         mol_type = protein
                         organism = synthetic construct
SEQUENCE: 331
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKDKTHTK PPKAPELLG GPGTGTGGPT IKPPKPPKPA   300
PNLLGGPIYI WAPLAGTCGV LLLSVITLY CKRGRKKLLY IFKQPFMRPV QTTQEEDGCS   360
CRFPEEEEGG CELRVKFSRS ADAPAYKQGQ NQLYNELNLG RREEYDVLDK RRGRDPEMGG   420
KPRRKNPQEG LYNELQKDKM AEAYSEIGMK GERRRGKGHD GLYQGLSTAT KDTYDALHMQ   480
ALPPR                                                               485

SEQ ID NO: 332           moltype = DNA  length = 430
FEATURE                  Location/Qualifiers
misc_feature             1..430
                         note = E6 CAR X48 pCDH gBLOCK sequence
source                   1..430
                         mol_type = other DNA
                         organism = synthetic construct
```

```
SEQUENCE: 332
agtacctcta atctggcctc aggtatccct gcacgatttt ctggatctgg ttcaggttct    60
gattacaccc tcactatctc tagcctggag cctgaagact ttgccgttta ttactgccag   120
cagaggtcta gctccccatt cacctttggg agtgggacca aggttgaaat aaagacaag    180
acgcacacca agccacctaa accagctcca gaactgctcg gaggtcctgg caccggaacc   240
ggaggaccta ccatcaaacc acctaagcca cctaagcctg ctcctaacct gctcggagga   300
cctatctaca tttgggcccc gctcgcaggc acatgtggag tgctcctcct ctccctggtg   360
attaccctgt actgcaaaag gggccgcaaa aaactccttt acatttttaa gcagccttt    420
atgaggccag                                                          430

SEQ ID NO: 333           moltype = DNA  length = 1455
FEATURE                  Location/Qualifiers
misc_feature             1..1455
                         note = CAR E6 X4/4-1BB/CD3z sequence
source                   1..1455
                         mol_type = other DNA
                         organism = synthetic construct
SEQUENCE: 333
atggccctgc ccgtgaccgc tttgctgctc cccctggcgc tgctgctgca cgccgccagg    60
ccagaggtcc agctggttga gagtggcggt gggctggtta gcctggcgg ctccctgcgg   120
ctgagctgcg ccgcgagtgg atttactttc agccgatatg ggatgagttg ggtgcggcaa   180
gctcccggga agaggctgga atgggtctca acaatctccg gggggggcac ttacatctat   240
taccccgact cagtcaaggg gagatttacc atttcacgag acaacgctaa gaataccctg   300
tatttgcaga tgaattctct gagagcagag gacacagctg tttactattg taccccgcgac  360
aactatggca ggaactacga ctacggtatg gactattggg acaagggac attggttaca    420
gtgagcagtg gcggcggggg cagcggagga ggaggcggcg gtggcggagg cagcgagata   480
gtgctcacgc agtcacccgc gactctcagt ctctcacctg ggaacgagc taccctgacg    540
tgctctgcta cctcctcagt gtcatatatt cactggtatc agcaacgcc cgggcagtcc   600
cctagattgc tcatttatag tacctctaat ctggcctcag gtatccctgc acgattttct   660
ggatctggtt caggttctga ttacaccctc actatctcgc ctgagcc tgaagacttt     720
gccgtttatt actgccagca gaggtctagc tccccattca cctttgggag tgggaccaag   780
gttgaaatta agacaagac gcacaccaag ccacctaaac agctccaga actgctcgga    840
ggtcctggca ccggaaccgg aggacctacc atcaaaccac ctaagccacc taagcctgct   900
cctaacctgc tcggaggacc tatgccctg attgtgctgg ggggcgtcgc cggcctcctg   960
cttttcattg gctaggcat cttcttcaaa aggggccgca aaaaactcct ttacattttt  1020
aagcagcctt ttatgaggcc agtacagacg actcaagagg aagacgggtg tcatgccgc  1080
tttcctgagg aggaggaagg agggtgcgaa ctgcgcgtta agttctcccg atcagccgac  1140
gcgcctgctt acaagcaggg ccagaaccaa ctgtacaacg agctgaatct cggtagacgg  1200
gaagatacg acgtgttgga caagcggaga ggccgcgacc cagaaatggg cggcaagcct  1260
cgcaggaaaa accccaggaa gggactgtac aatgagttgc agaaagataa gatggcagaa  1320
gcttatagcg agatcggaat gaaggggaa aggagacgag ggaaaggaca cgacggcctt  1380
tatcagggcc tgtccacagc aacaaagat acgtatgacg ccctccatat gcaggcactt  1440
ccaccacggt gataa                                                  1455

SEQ ID NO: 334           moltype = AA  length = 483
FEATURE                  Location/Qualifiers
REGION                   1..483
                         note = CAR E6 X4/4-1BB/CD3z sequence
source                   1..483
                         mol_type = protein
                         organism = synthetic construct
SEQUENCE: 334
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKDKTHTK PPKPAPELLG GPGTGTGGPT IKPPKPPKPA   300
PNLLGGPMAL IVLGGVAGLL LFIGLGIFFK RGRKKLLYIF KQPFMRPVQT TQEEDGCSCR   360
FPEEEEGGCE LRVKFSRSAD APAYKQGQNQ LYNELNLGRR EEYDVLDKRR GRDPEMGGKP   420
RRKNPQEGLY NELQKDKMAE AYSEIGMKGE RRRGKGHDGL YQGLSTATKD TYDALHMQAL   480
PPR                                                                 483

SEQ ID NO: 335           moltype = DNA  length = 424
FEATURE                  Location/Qualifiers
misc_feature             1..424
                         note = E6 CAR X44 pCDH gBLOCK sequence
source                   1..424
                         mol_type = other DNA
                         organism = synthetic construct
SEQUENCE: 335
agtacctcta atctggcctc aggtatccct gcacgatttt ctggatctgg ttcaggttct    60
gattacaccc tcactatctc tagcctggag cctgaagact ttgccgttta ttactgccag   120
cagaggtcta gctccccatt cacctttggg agtgggacca aggttgaaat aaagacaag    180
acgcacacca agccacctaa accagctcca gaactgctcg gaggtcctgg caccggaacc   240
ggaggaccta ccatcaaacc acctaagcca cctaagcctg ctcctaacct gctcggagga   300
cctatgcccc tgattgtgct ggggggcgtc gccggcctcc tgcttttcat gggctaggc    360
atcttcttca aagggggccg caaaaaactc tttacatttt ttaagcagcc ttttatgagg   420
ccag                                                                424
```

```
SEQ ID NO: 336         moltype = DNA   length = 1461
FEATURE                Location/Qualifiers
misc_feature           1..1461
                       note = CAR E6 8+4/4/4-1BB/CD3z sequence
source                 1..1461
                       mol_type = other DNA
                       organism = synthetic construct
SEQUENCE: 336
atggccctgc ccgtgaccgc tttgctgctc cccctggcgc tgctgctgca cgccgccagg   60
ccagaggtcc agctggttga gagtggcggt gggctggtta agcctggcgg ctccctgcgg  120
ctgagctgcg ccgcgagtgg atttactttc agccgtatatg ggatgagttg ggtgcggcaa  180
gctcccggga gaggctggaa tgggtctca acaatctccg gggggggcac ttacatctat  240
taccccgact cagtcaaggg gagatttacc atttcacgag acaacgctaa gaataccctg  300
tatttgcaga tgaattctct gagagcagag gacacagtca tttactattg taccgccga  360
aactatggca ggaactacga ctacggtatg gactattggg gacaagggac attggttaca  420
gtgagcagtg gcggcggggg cagcggagga ggaggcagcg gtggcggagg cagcgagata  480
gtgctcacgc agtcacccgc gactctcagt ctctcacctg gggaacgagc taccctgacg  540
tgctctgcta cctcctcagt gtcatatatt cactggtatc agcaacggcc cggtcagtcc  600
cctagattgc tcatttatag tacctctaat ctggcctcag gtatccctgc acgatttctc  660
ggatctggtt caggttctga ttacaccctc actatctcta gcctggagcc tgaagacttt  720
gccgtttatt actgccagca gagtctagc tcccccattca ccttgggag tgggaccaag  780
gttgaaatta aaacgacaac cccggccccc agaccaccaa ctccagccc caccatcgct  840
agccaacccc tgtctctgag accaaagcc tgtaggcctg ccgccggtgg agctgtgcac  900
acaagaggac tggatttcgc ctgtgatatg gccctgattg tgctggggggg cgtcgccggc  960
ctcctgcttt tcattgggct aggcatcttc ttcaaaaggg gccgcaaaaa actcctttac 1020
atttttaagc agcctttttat gaggccagta cagacgactc aagaggaaga cgggtgctca 1080
tgccgctttc ctgaggagga ggaaggaggg tgcgaactgc gcgttaagtt ctcccgatca 1140
gccgacgcgc ctgcttacaa gcaggcag aaccaactgt acaacgagct gaatctcggt 1200
agacgggaag agtacgacgt gttggacaaa cggagaggc cgcacccaga atgggcggc 1260
aagcctcgca ggaaaaaccc caggaggga ctgtacatgg agttgcagaa agataagatg 1320
gcagaagctt atagcgagat cggaatgaag ggggaaggga gacgaggaa aggacacgac 1380
ggcctttatc agggcctgtc cacagcaaca aaagatacgt atgacgccct ccatatgcag 1440
gcacttccac cacggtgata a                                           1461

SEQ ID NO: 337         moltype = AA   length = 485
FEATURE                Location/Qualifiers
REGION                 1..485
                       note = CAR E6 8+4/4/4-1BB/CD3z sequence
source                 1..485
                       mol_type = protein
                       organism = synthetic construct
SEQUENCE: 337
MALPVTALLL PLALLLHAAR PEVQLVESGG GLVKPGGSLR LSCAASGFTF SRYGMSWVRQ   60
APGKRLEWVS TISGGGTYIY YPDSVKGRFT ISRDNAKNTL YLQMNSLRAE DTAVYYCTRD  120
NYGRNYDYGM DYWGQGTLVT VSSGGGGSGG GGSGGGGSEI VLTQSPATLS LSPGERATLT  180
CSATSSVSYI HWYQQRPGQS PRLLIYSTSN LASGIPARFS GSGSGSDYTL TISSLEPEDF  240
AVYYCQQRSS SPFTFGSGTK VEIKTTTPAP RPPTPAPTIA SQPLSLRPEA CRPAAGGAVH  300
TRGLDFACDM ALIVLGGVAG LLLFIGLGIF FKRGRKKLLY IFKQPFMRPV QTTQEEDGCS  360
CRFPEEEEGG CELRVKFSRS ADAPAYKQGQ NQLYNELNLG RREEYDVLDK RRGRDPEMGG  420
KPRRKNPQEG LYNELQKDKM AEAYSEIGMK GERRRGKGHD GLYQGLSTAT KDTYDALHMQ  480
ALPPR                                                              485

SEQ ID NO: 338         moltype = DNA   length = 430
FEATURE                Location/Qualifiers
misc_feature           1..430
                       note = E6 CAR CD844 pCDH gBLOCK sequence
source                 1..430
                       mol_type = other DNA
                       organism = synthetic construct
SEQUENCE: 338
agtacctcta atctggcctc aggtatccct gcacgatttt ctggatctgg ttcaggttct   60
gattacaccc tcactatctc tagcctggag cctgaagact tgccgtttta ttactgccag  120
cagaggtcta gctccccatt caccttttgg agtgggacca aggttgaaat taaaacgaca  180
accccggccc ccagaccacc aacgccagcc ccaccatcgc ctgtctctg  240
agaccagaag cctgtaggcc tgccgccggt ggagctgtgc acacaagagg actgattttc  300
gcctgtgata tggcccctgat tgtgctgggg ggcgtcgccg gctcctgct tttcattggg  360
ctaggcatct tcttcaaaag ggcccgcaaa aaactccttt acattttaa gcagcctttt  420
atgaggccag                                                         430

SEQ ID NO: 339         moltype = DNA   length = 820
FEATURE                Location/Qualifiers
misc_feature           1..820
                       note = Humanized C2 scFV sequence in CAR
source                 1..820
                       mol_type = other DNA
                       organism = synthetic construct
SEQUENCE: 339
gagggccacc atggccttgc cagtgacggc cctgctgctg ccattggctc ttctgttgca   60
cgctgccagg cctgaagtgc agctcgtaga gagtggcggt ggactggtga agcccggtgg  120
```

```
aagcctcaga ctcagttgcg ccgcctcagg tttcactttt tcaggttacg ccatgtcctg   180
ggtaagacag gcaccgggga aaggactcga gtgggtgtct actatcagct caggaggcac   240
ttatatatat tatcctgact ctgtaaaagg ccgatttacg atttctcgcg acaatgcaaa   300
gaactccctc tacctccaaa tgaacagtct tagggcagaa gacactgctg tatactattg   360
tgcacgcctc ggcggcgaca actactacga gtactttgac gtgtggggga aagggactac   420
cgtgacagtt tcaagcggag gaggtggctc aggtggaggc gggtcagggg ggggaggaag   480
tgatattgtg ctcacacaat ccccagcctc cctggctgtg tctcccggcc aacgcgctac   540
aattacatgt cgggcctcca aaagcgtgag caccagcggc tacagctaca tgcactggta   600
tcaacagaaa ccaggacaac cccccaaact gttgatttat ctcgcttcaa acttggagtc   660
cggcgtgcct gcgcggcttt cagggagtgg gagcggcaca gatttttacg tgactatcaa   720
ccccgtagaa gcaaacgata cagcgaatta ttattgtcaa cattcccggg aactccccttt  780
tacgttcggc gggggcacaa aggtcgaaat taagagaacc                         820

SEQ ID NO: 340           moltype = AA   length = 249
FEATURE                  Location/Qualifiers
REGION                   1..249
                         note = Humanized C2 scFV sequence in CAR
source                   1..249
                         mol_type = protein
                         organism = synthetic construct
SEQUENCE: 340
EVQLVESGGG LVKPGGSLRL SCAASGFTFS GYAMSWVRQA PGKGLEWVST ISSGGTYIYY   60
PDSVKGRFTI SRDNAKNSLY LQMNSLRAED TAVYYCARLG GDNYYEYFDV WGKGTTVTVS  120
SGGGGSGGGG SGGGGSDIVL TQSPASLAVS PGQRATITCR ASKSVSTSGY SYMHWYQQKP  180
GQPPKLLIYL ASNLESGVPA RFSGSGSGTD FTLTINPVEA NDTANYYCQH SRELPFTFGG  240
GTKVEIKRT                                                          249

SEQ ID NO: 341           moltype = DNA   length = 729
FEATURE                  Location/Qualifiers
misc_feature             1..729
                         note = Humanized E6 scFV sequence in CAR
source                   1..729
                         mol_type = other DNA
                         organism = synthetic construct
SEQUENCE: 341
gaggtccagc tggttgagag tggcggtggg ctggttaagc ctggcggctc cctgcggctg    60
agctgcgccg cgagtggatt tactttcagc cgatatggga tgagttgggt gcggcaagct   120
cccgggaaga ggctggaatg ggtctcaaca atctccgggg ggggcactta catctattac   180
cccgactcag tcaaggggag atttaccatt tcacgagaca acgctaagaa tacctgtat    240
ttgcagatga attctctgag agcagaggac acagctgttt actattgtac ccgcgacaac   300
tatggcagga actacgacta cggtatggac tattggggac aagggacatt ggttacagtg   360
agcagtggcg gcggggcag cggaggagga ggcagcggtg ggggggggcag cgagatagtg   420
ctcacgcagt caccccgcac tctcagtctc tcacctggga acgagctac cctgacgtgc    480
tctgctacct cctcagtgtc atatattcac tggtatcagc aacggccggg cagtccctt    540
agattgctca tttatagtac ctctaatctg gcctcaggta tccctgcacg attttctgga   600
tctggttcag gttctgatta caccctcact atctctagcc tggagcctga agactttgcc   660
gtttattact gccagcagag gtctagctcc ccattcacct ttgggagtgg gaccaaggtt   720
gaaattaaa                                                          729

SEQ ID NO: 342           moltype = AA   length = 243
FEATURE                  Location/Qualifiers
REGION                   1..243
                         note = Humanized E6 scFV sequence in CAR
source                   1..243
                         mol_type = protein
                         organism = synthetic construct
SEQUENCE: 342
EVQLVESGGG LVKPGGSLRL SCAASGFTFS RYGMSWVRQA PGKRLEWVST ISGGGTYIYY    60
PDSVKGRFTI SRDNAKNTLY LQMNSLRAED TAVYYCTRDN YGRNYDYGMD YWGQGTLVTV   120
SSGGGGSGGG GSGGGGSEIV LTQSPATLSL SPGERATLTC SATSSVSYIH WYQQRPGQSP   180
RLLIYSTSNL ASGIPARFSG SGSGSDYTLT ISSLEPEDFA VYYCQQRSSS PFTFGSGTKV   240
EIK                                                                243

SEQ ID NO: 343           moltype = DNA   length = 63
FEATURE                  Location/Qualifiers
misc_feature             1..63
                         note = CD8 leader sequence
source                   1..63
                         mol_type = other DNA
                         organism = synthetic construct
SEQUENCE: 343
atggccctgc ccgtgaccgc tttgctgctc ccctggcgc tgctgctgca cgccgccagg     60
cca                                                                 63

SEQ ID NO: 344           moltype = AA   length = 21
FEATURE                  Location/Qualifiers
REGION                   1..21
                         note = CD8 leader sequence
source                   1..21
```

```
                        mol_type = protein
                        organism = synthetic construct
SEQUENCE: 344
MALPVTALLL PLALLLHAAR P                                         21

SEQ ID NO: 345          moltype = DNA   length = 135
FEATURE                 Location/Qualifiers
misc_feature            1..135
                        note = CD8 hinge domain sequence
source                  1..135
                        mol_type = other DNA
                        organism = synthetic construct
SEQUENCE: 345
acgacaaccc cggcccccag accaccaacg ccagccccca ccatcgccag ccaacccctg    60
tctctgagac cagaagcctg taggcctgcc gccggtggag ctgtgcacac aagaggactg   120
gatttcgcct gtgat                                                   135

SEQ ID NO: 346          moltype = AA    length = 45
FEATURE                 Location/Qualifiers
REGION                  1..45
                        note = CD8 hinge domain sequence
source                  1..45
                        mol_type = protein
                        organism = synthetic construct
SEQUENCE: 346
TTTPAPRPPT PAPTIASQPL SLRPEACRPA AGGAVHTRGL DFACD                   45

SEQ ID NO: 347          moltype = DNA   length = 66
FEATURE                 Location/Qualifiers
misc_feature            1..66
                        note = CD4 hinge domain sequence
source                  1..66
                        mol_type = other DNA
                        organism = synthetic construct
SEQUENCE: 347
tcgggacagg tcctgctgga atccaacatc aaggttctgc ccacatggtc caccccggtg    60
cagcca                                                              66

SEQ ID NO: 348          moltype = AA    length = 22
FEATURE                 Location/Qualifiers
REGION                  1..22
                        note = CD4 hinge domain sequence
source                  1..22
                        mol_type = protein
                        organism = synthetic construct
SEQUENCE: 348
SGQVLLESNI KVLPTWSTPV QP                                            22

SEQ ID NO: 349          moltype = DNA   length = 45
FEATURE                 Location/Qualifiers
misc_feature            1..45
                        note = CD28 hinge domain sequence
source                  1..45
                        mol_type = other DNA
                        organism = synthetic construct
SEQUENCE: 349
aaacaccttt gtccaagtcc cctatttccc ggaccttcta agccc                   45

SEQ ID NO: 350          moltype = AA    length = 15
FEATURE                 Location/Qualifiers
REGION                  1..15
                        note = CD28 hinge domain sequence
source                  1..15
                        mol_type = protein
                        organism = synthetic construct
SEQUENCE: 350
KHLCPSPLFP GPSKP                                                    15

SEQ ID NO: 351          moltype = DNA   length = 201
FEATURE                 Location/Qualifiers
misc_feature            1..201
                        note = CD8+CD4 hinge domain sequence
source                  1..201
                        mol_type = other DNA
                        organism = synthetic construct
SEQUENCE: 351
acgacaaccc cggcccccag accaccaacg ccagccccca ccatcgccag ccaacccctg    60
tctctgagac cagaagcctg taggcctgcc gccggtggag ctgtgcacac aagaggactg   120
gatttcgcct gtgattcggg acaggtcctg ctggaatcca acatcaaggt tctgcccaca   180
```

```
tggtccaccc cggtgcagcc a                                              201

SEQ ID NO: 352          moltype = AA  length = 67
FEATURE                 Location/Qualifiers
REGION                  1..67
                        note = CD8+CD4 hinge domain sequence
source                  1..67
                        mol_type = protein
                        organism = synthetic construct
SEQUENCE: 352
TTTPAPRPPT PAPTIASQPL SLRPEACRPA AGGAVHTRGL DFACDSGQVL LESNIKVLPT    60
WSTPVQP                                                              67

SEQ ID NO: 353          moltype = DNA  length = 180
FEATURE                 Location/Qualifiers
misc_feature            1..180
                        note = CD8+CD28 hinge domain sequence
source                  1..180
                        mol_type = other DNA
                        organism = synthetic construct
SEQUENCE: 353
acgacaaccc cggcccccag accaccaacg ccagccccca ccatcgccag ccaacccctg    60
tctctgagac cagaagcctg taggcctgcc gccggtggag ctgtgcacac aagaggactg   120
gatttcgcct gtgataaaca cctttgtcca agtccctat ttcccggacc ttctaagccc    180

SEQ ID NO: 354          moltype = AA  length = 60
FEATURE                 Location/Qualifiers
REGION                  1..60
                        note = CD8+CD28 hinge domain sequence
source                  1..60
                        mol_type = protein
                        organism = synthetic construct
SEQUENCE: 354
TTTPAPRPPT PAPTIASQPL SLRPEACRPA AGGAVHTRGL DFACDKHLCP SPLFPGPSKP    60

SEQ ID NO: 355          moltype = DNA  length = 111
FEATURE                 Location/Qualifiers
misc_feature            1..111
                        note = CD28+CD4 hinge domain sequence
source                  1..111
                        mol_type = other DNA
                        organism = synthetic construct
SEQUENCE: 355
aaacaccttt gtccaagtcc cctatttccc ggaccttcta agccctcggg acaggtcctg    60
ctggaatcca acatcaaggt tctgcccaca tggtccaccc cggtgcagcc a             111

SEQ ID NO: 356          moltype = AA  length = 37
FEATURE                 Location/Qualifiers
REGION                  1..37
                        note = CD28+CD4 hinge domain sequence
source                  1..37
                        mol_type = protein
                        organism = synthetic construct
SEQUENCE: 356
KHLCPSPLFP GPSKPSGQVL LESNIKVLPT WSTPVQP                              37

SEQ ID NO: 357          moltype = DNA  length = 174
FEATURE                 Location/Qualifiers
misc_feature            1..174
                        note = Human IgD hinge domain sequence
source                  1..174
                        mol_type = other DNA
                        organism = synthetic construct
SEQUENCE: 357
gagtctccaa aggcacaggc ctcctcagtg cccactgcac aacccaagc agagggcagc     60
ctcgccaagg caaccacagc cccagccacc acccgtaaca caggaagagg cggcgaagag   120
aagaaaaagg agaaggagaa agaggaacaa gaagagagag agacaaagac acca         174

SEQ ID NO: 358          moltype = AA  length = 58
FEATURE                 Location/Qualifiers
REGION                  1..58
                        note = Human IgD hinge domain sequence
source                  1..58
                        mol_type = protein
                        organism = synthetic construct
SEQUENCE: 358
ESPKAQASSV PTAQPQAEGS LAKATTAPAT TRNTGRGGEE KKKEKEKEEQ EERETKTP       58

SEQ ID NO: 359          moltype = DNA  length = 129
```

```
FEATURE                 Location/Qualifiers
misc_feature            1..129
                        note = X4 linker (IgG1 and IgG2 modified hinge region)
                        sequence
source                  1..129
                        mol_type = other DNA
                        organism = synthetic construct
SEQUENCE: 359
gacaagacgc acaccaagcc acctaaacca gctccagaac tgctcggagg tcctggcacc    60
ggaaccggag gacctaccat caaaccacct aagccaccta agcctgctcc taacctgctc   120
ggaggacct                                                           129

SEQ ID NO: 360          moltype = AA  length = 43
FEATURE                 Location/Qualifiers
REGION                  1..43
                        note = X4 linker (IgG1 and IgG2 modified hinge region)
                        sequence
source                  1..43
                        mol_type = protein
                        organism = synthetic construct
SEQUENCE: 360
DKTHTKPPKP APELLGGPGT GTGGPTIKPP KPPKPAPNLL GGP                       43

SEQ ID NO: 361          moltype = DNA  length = 63
FEATURE                 Location/Qualifiers
misc_feature            1..63
                        note = CD3 zeta transmembrane domain sequence
source                  1..63
                        mol_type = other DNA
                        organism = synthetic construct
SEQUENCE: 361
ctctgctacc tgctggatgg aatcctcttc atctatggtg tcattctcac tgccttgttc    60
ctg                                                                  63

SEQ ID NO: 362          moltype = AA  length = 21
FEATURE                 Location/Qualifiers
REGION                  1..21
                        note = CD3 zeta transmembrane domain sequence
source                  1..21
                        mol_type = protein
                        organism = synthetic construct
SEQUENCE: 362
LCYLLDGILF IYGVILTALF L                                              21

SEQ ID NO: 363          moltype = DNA  length = 72
FEATURE                 Location/Qualifiers
misc_feature            1..72
                        note = CD8 transmembrane domain sequence
source                  1..72
                        mol_type = other DNA
                        organism = synthetic construct
SEQUENCE: 363
atctacattt gggccccgct cgcaggcaca tgtggagtgc tcctcctctc cctggtgatt    60
accctgtact gc                                                        72

SEQ ID NO: 364          moltype = AA  length = 24
FEATURE                 Location/Qualifiers
REGION                  1..24
                        note = CD8 transmembrane domain sequence
source                  1..24
                        mol_type = protein
                        organism = synthetic construct
SEQUENCE: 364
IYIWAPLAGT CGVLLLSLVI TLYC                                           24

SEQ ID NO: 365          moltype = DNA  length = 66
FEATURE                 Location/Qualifiers
misc_feature            1..66
                        note = CD4 transmembrane domain sequence
source                  1..66
                        mol_type = other DNA
                        organism = synthetic construct
SEQUENCE: 365
atggccctga ttgtgctggg gggcgtcgcc ggcctcctgc ttttcattgg gctaggcatc    60
ttcttc                                                               66

SEQ ID NO: 366          moltype = AA  length = 22
FEATURE                 Location/Qualifiers
REGION                  1..22
```

```
                        note = CD4 transmembrane domain sequence
source                  1..22
                        mol_type = protein
                        organism = synthetic construct
SEQUENCE: 366
MALIVLGGVA GLLLFIGLGI FF                                            22

SEQ ID NO: 367          moltype = DNA  length = 81
FEATURE                 Location/Qualifiers
misc_feature            1..81
                        note = CD28 transmembrane domain sequence
source                  1..81
                        mol_type = other DNA
                        organism = synthetic construct
SEQUENCE: 367
ttttgggtgc tggtggtggt tggtggagtc ctggcttgct atagcttgct agtaacagtg   60
gcctttatta ttttctgggt g                                             81

SEQ ID NO: 368          moltype = AA  length = 27
FEATURE                 Location/Qualifiers
REGION                  1..27
                        note = CD28 transmembrane domain sequence
source                  1..27
                        mol_type = protein
                        organism = synthetic construct
SEQUENCE: 368
FWVLVVVGGV LACYSLLVTV AFIIFWV                                       27

SEQ ID NO: 369          moltype = DNA  length = 81
FEATURE                 Location/Qualifiers
misc_feature            1..81
                        note = 4-1BB transmembrane domain sequence
source                  1..81
                        mol_type = other DNA
                        organism = synthetic construct
SEQUENCE: 369
atcatctcct tctttcttgc gctgacgtcg actgcgttgc tcttcctgct gttcttcctc   60
acgctccgtt tctctgttgt t                                             81

SEQ ID NO: 370          moltype = AA  length = 27
FEATURE                 Location/Qualifiers
REGION                  1..27
                        note = 4-1BB transmembrane domain sequence
source                  1..27
                        mol_type = protein
                        organism = synthetic construct
SEQUENCE: 370
IISFFLALTS TALLFLLFFL TLRFSVV                                       27

SEQ ID NO: 371          moltype = DNA  length = 78
FEATURE                 Location/Qualifiers
misc_feature            1..78
                        note = OX40 transmembrane domain sequence
source                  1..78
                        mol_type = other DNA
                        organism = synthetic construct
SEQUENCE: 371
gttgccgcca tcctgggcct gggcctggtg ctggggctgc tgggcccct ggccatcctg    60
ctggccctgt acctgctc                                                 78

SEQ ID NO: 372          moltype = AA  length = 26
FEATURE                 Location/Qualifiers
REGION                  1..26
                        note = OX40 transmembrane domain sequence
source                  1..26
                        mol_type = protein
                        organism = synthetic construct
SEQUENCE: 372
VAAILGLGLV LGLLGPLAIL LALYLL                                        26

SEQ ID NO: 373          moltype = DNA  length = 336
FEATURE                 Location/Qualifiers
misc_feature            1..336
                        note = CD3 zeta domain sequence
source                  1..336
                        mol_type = other DNA
                        organism = synthetic construct
SEQUENCE: 373
cgcgttaagt tctcccgatc agccgacgcg cctgcttaca agcagggcca gaaccaactg   60
```

```
tacaacgagc tgaatctcgg tagacgggaa gagtacgacg tgttggacaa acggagaggc    120
cgcgacccag aaatgggcgg caagcctcgc aggaaaaacc cccaggaggg actgtacaat    180
gagttgcaga aagataagat ggcagaagct tatagcgaga tcggaatgaa ggggaaagg     240
agacgaggga aaggacacga cggcctttat cagggcctgt ccacagcaac aaaagatacg    300
tatgacgccc tccatatgca ggcacttcca ccacgg                              336
```

```
SEQ ID NO: 374          moltype = AA  length = 112
FEATURE                 Location/Qualifiers
REGION                  1..112
                        note = CD3 zeta domain sequence
source                  1..112
                        mol_type = protein
                        organism = synthetic construct
SEQUENCE: 374
RVKFSRSADA PAYKQGQNQL YNELNLGRRE EYDVLDKRRG RDPEMGGKPR RKNPQEGLYN     60
ELQKDKMAEA YSEIGMKGER RRGKGHDGLY QGLSTATKDT YDALHMQALP PR            112

SEQ ID NO: 375          moltype = DNA  length = 336
FEATURE                 Location/Qualifiers
misc_feature            1..336
                        note = CD3 zeta domain variant sequence
source                  1..336
                        mol_type = other DNA
                        organism = synthetic construct
SEQUENCE: 375
agagtgaagt tcagcaggag cgcagacgcc cccgcgtacc agcagggcca gaaccagctc     60
tataacgagc tcaatctagg acgaagagag gagtacgatg ttttggacaa gagacgtggc    120
cgggaccctg agatggggg aaagccgaga aggaagaacc ctcaggaagg cctgtacaat    180
gaactgcaga aagataagat ggcggaggcc tacagtgaga ttgggatgaa aggcgagcgc    240
cggagggca agggggcacga tggcctttac cagggtctca gtacagccac caaggacacc   300
tacgacgccc ttcacatgca ggccctgccc cctcgc                              336

SEQ ID NO: 376          moltype = AA  length = 112
FEATURE                 Location/Qualifiers
REGION                  1..112
                        note = CD3 zeta domain variant sequence
source                  1..112
                        mol_type = protein
                        organism = synthetic construct
SEQUENCE: 376
RVKFSRSADA PAYQQGQNQL YNELNLGRRE EYDVLDKRRG RDPEMGGKPR RKNPQEGLYN     60
ELQKDKMAEA YSEIGMKGER RRGKGHDGLY QGLSTATKDT YDALHMQALP PR            112

SEQ ID NO: 377          moltype = DNA  length = 123
FEATURE                 Location/Qualifiers
misc_feature            1..123
                        note = CD28 domain sequence
source                  1..123
                        mol_type = other DNA
                        organism = synthetic construct
SEQUENCE: 377
agaagcaagc ggtctcggct cctgcattct gattacatga acatgacccc aagaagacca     60
ggccccacca ggaaacatta ccagccctac gctccgccac gcgacttcgc tgcctaccgg    120
tcc                                                                  123

SEQ ID NO: 378          moltype = AA  length = 41
FEATURE                 Location/Qualifiers
REGION                  1..41
                        note = CD28 domain sequence
source                  1..41
                        mol_type = protein
                        organism = synthetic construct
SEQUENCE: 378
RSKRSRLLHS DYMNMTPRRP GPTRKHYQPY APPRDFAAYR S                         41

SEQ ID NO: 379          moltype = DNA  length = 126
FEATURE                 Location/Qualifiers
misc_feature            1..126
                        note = 4-1BB domain sequence
source                  1..126
                        mol_type = other DNA
                        organism = synthetic construct
SEQUENCE: 379
aaaaggggc gcaaaaaact cctttacatt tttaagcagc cttttatgag gccagtacag      60
acgactcaag aggaagacgg gtgctcatgc cgctttcctg aggaggagga aggagggtgc    120
gaactg                                                              126

SEQ ID NO: 380          moltype = AA  length = 42
FEATURE                 Location/Qualifiers
```

```
REGION                  1..42
                        note = 4-1BB domain sequence
source                  1..42
                        mol_type = protein
                        organism = synthetic construct
SEQUENCE: 380
KRGRKKLLYI FKQPFMRPVQ TTQEEDGCSC RFPEEEEGGC EL                      42

SEQ ID NO: 381          moltype = DNA  length = 111
FEATURE                 Location/Qualifiers
misc_feature            1..111
                        note = OX40 domain sequence
source                  1..111
                        mol_type = other DNA
                        organism = synthetic construct
SEQUENCE: 381
cggagggacc agaggctgcc ccccgatgcc cacaagcccc tggggggagg cagtttccgg   60
accccccatcc aagaggagca ggccgacgcc cactccaccc tggccaagat c          111

SEQ ID NO: 382          moltype = AA  length = 37
FEATURE                 Location/Qualifiers
REGION                  1..37
                        note = OX40 domain sequence
source                  1..37
                        mol_type = protein
                        organism = synthetic construct
SEQUENCE: 382
RRDQRLPPDA HKPPGGGSFR TPIQEEQADA HSTLAKI                            37

SEQ ID NO: 383          moltype = DNA  length = 723
FEATURE                 Location/Qualifiers
misc_feature            1..723
                        note = Humanized anti CD3 scFV clone 12F6 (VH-VL) sequence
source                  1..723
                        mol_type = other DNA
                        organism = synthetic construct
SEQUENCE: 383
caggtgcagc tggtgcagag cggaggtgga gtggtccaac ctggaagatc tctgagactg   60
agctgtaagg ctagcgggta cacgttcaca tcttacacga tgcactgggt gaggcaagcc  120
cccggtaagg gcctggaatg gatcggatat ataaacccca gctcagggta taccaaatat  180
aatcagaagt tcaaagatcg gttcacgatt tctgctgata aaagtaagtc caccgctttc  240
ctgcagatgg actcactcag gccagaagat actggtgttt atttctgtgc aaggtggcag  300
gactacgacg tgtactttga ctattggggg caggggcagc tgtaacagt atcaagcggc  360
ggtggcggat ccggcggtgg cggatccggc ggtggcggat ccgatattca gatgacccag  420
agcccgagca gcctgagcgc gagcgtgggc gatcgcgtga ccatgacctg ccgcgcgagc  480
agcagcgtga gctatatgca ttggtatcag cagaccccgg gcaaagcgcc gaaaccgtgg  540
atttatgcga ccagcaacct ggcgagcggc gtgccgagcc gctttagcgg cagcggcagc  600
ggcaccgatt ataccctgac cattagcagc ctgcagccgg aagatattgc gacctattat  660
tgccagcagt ggagcagcaa cccgccgacc tttggccagg gcaccaaact gcagattacc  720
cgc                                                                723

SEQ ID NO: 384          moltype = AA  length = 241
FEATURE                 Location/Qualifiers
REGION                  1..241
                        note = Humanized anti CD3 scFV clone 12F6 (VH-VL) sequence
source                  1..241
                        mol_type = protein
                        organism = synthetic construct
SEQUENCE: 384
QVQLVQSGGG VVQPGRSLRL SCKASGYTFT SYTMHWVRQA PGKGLEWIGY INPSSGYTKY   60
NQKFKDRFTI SADKSKSTAF LQMDSLRPED TGVYFCARWQ DYDVYFDYWG QGTPVTVSSG  120
GGGSGGGGSG GGGSDIQMTQ SPSSLSASVG DRVTMTCRAS SSVSYMHWYQ QTPGKAPKPW  180
IYATSNLASG VPSRFSGSGS GTDYTLTISS LQPEDIATYY CQQWSSNPPT FGQGTKLQIT  240
R                                                                 241

SEQ ID NO: 385          moltype = DNA  length = 723
FEATURE                 Location/Qualifiers
misc_feature            1..723
                        note = Humanized anti CD3 scFV clone 12F6 (VL-VH) sequence
source                  1..723
                        mol_type = other DNA
                        organism = synthetic construct
SEQUENCE: 385
gatattcaga tgacccagag cccgagcagc ctgagcgcga gcgtgggcga tcgcgtgacc   60
atgacctgcc gcgcgagcag cagcgtgagc tatatgcatt ggtatcagca gaccccgggc  120
aaagcgccga aaccgtggat ttatgcgacc agcaacctgg cgagcggcgt gccgagccgc  180
tttagcggca gcggcagcgg caccgattat accctgacca ttagcagcct gcagccggaa  240
gatattgcga cctattattg ccagcagtgg agcagcaacc cgccgacctt tggccagggc  300
accaaactgc agattacccg cggcggtggc ggatccggcg gtggcggatc cggcggtggc  360
```

```
ggatcccagg tgcagctggt gcagagcgga ggtggagtgg tccaacctgg aagatctctg   420
agactgagct gtaaggctag cgggtacacg ttcacatctt acacgatgca ctgggtgagg   480
caagccccg  gtaagggcct ggaatggatc ggatatataa accccagctc agggtatacc   540
aaatataatc agaagttcaa agatcggttc acgatttctg ctgataaaag taagtccacc   600
gctttcctgc agatggactc actcaggcca gaagatactg gtgtttattt ctgtgcaagg   660
tggcaggact acgacgtgta cttttgactat tgggggcagg gacgcctgt  aacagtatca   720
agc                                                                 723

SEQ ID NO: 386            moltype = AA   length = 241
FEATURE                   Location/Qualifiers
REGION                    1..241
                          note = Humanized anti CD3 scFV clone 12F6 (VL-VH) sequence
source                    1..241
                          mol_type = protein
                          organism = synthetic construct
SEQUENCE: 386
DIQMTQSPSS LSASVGDRVT MTCRASSSVS YMHWYQQTPG KAPKPWIYAT SNLASGVPSR    60
FSGSGSGTDY TLTISSLQPE DIATYYCQQW SSNPPTFGQG TKLQITRGGG GSGGGGSGGG   120
GSQVQLVQSG GGVVQPGRSL RLSCKASGYT FTSYTMHWVR QAPGKGLEWI GYINPSSGYT   180
KYNQKFKDRF TISADKSKST AFLQMDSLRP EDTGVYFCAR WQDYDVYFDY WGQGTPVTVS   240
S                                                                  241

SEQ ID NO: 387            moltype = DNA   length = 723
FEATURE                   Location/Qualifiers
misc_feature              1..723
                          note = Humanized anti CD3 scFV clone OKT3 (VH-VL) sequence
source                    1..723
                          mol_type = other DNA
                          organism = synthetic construct
SEQUENCE: 387
caggtgcagc tggtgcagag cggaggcgga gtggtgcagc ctggaagaag cctgcgcctg    60
agctgcaaag cgagcggcta ccctttacc  cgctatacca tgcattgggt gcgccaggcg   120
ccgggcaaag gcctggaatg gattggctat attaacccga gccgcggcta taccaactat   180
aaccagaaag tgaaagatcg ctttaccatt agcaccgata aaagcaaaag caccgcgttt   240
ctgcagatgg atagcctgcg cccggaagat accgcggtgt attattgcgc gcgctattat   300
gatgatcatt attgcctgga ttattgggggc agggcacca cccgaccgt  gagcagcggc   360
ggtggcggat ccggcggtgg cggatccggc ggtggcggat ccgatattca gatgacccag   420
agcccgagca gcctgagcgc gagcgtgggc gatcgcgtga ccattacctg cagcgcgagc   480
agcagcgtga gctatatgaa ctggtatcag cagacccccg gcaaagcgcc gaaacgctgg   540
atttatgata ccagcaaact ggcgagcggc gtgccgagcc gctttagcgg cagcggcagc   600
ggcaccgatt ataccttac  cattagcagc ctgcagccgg aagatattgc gacctattat   660
tgccagcagt ggagcagcaa cccgtttacc tttggccagg gcaccaaact gcagattacc   720
cgc                                                                723

SEQ ID NO: 388            moltype = AA   length = 241
FEATURE                   Location/Qualifiers
REGION                    1..241
                          note = Humanized anti CD3 scFV clone OKT3 (VH-VL) sequence
source                    1..241
                          mol_type = protein
                          organism = synthetic construct
SEQUENCE: 388
QVQLVQSGGG VVQPGRSLRL SCKASGYTFT RYTMHWVRQA PGKGLEWIGY INPSRGYTNY    60
NQKVKDRFTI STDKSKSTAF LQMDSLRPED TAVYYCARYY DDHYCLDYWG QGTTLTVSSG   120
GGGSGGGGSG GGGSDIQMTQ SPSSLSASVG DRVTITCSAS SSVSYMNWYQ QTPGKAPKRW   180
IYDTSKLASG VPSRFSGSGS GTDYTFTISS LQPEDIATYY CQQWSSNPFT FGQGTKLQIT   240
R                                                                  241

SEQ ID NO: 389            moltype = DNA   length = 723
FEATURE                   Location/Qualifiers
misc_feature              1..723
                          note = Humanized anti CD3 scFV clone OKT3 (VH-VL) sequence
source                    1..723
                          mol_type = other DNA
                          organism = synthetic construct
SEQUENCE: 389
gatattcaga tgacccagag cccgagcagc ctgagcgcga gcgtgggcga tcgcgtgacc    60
attacctgca gcgcgagcag cagcgtgagc tatatgaact ggtatcagca gaccccgggc   120
aaagcgccga aacgctggat ttatgatacc agcaaactgg cgagcggcgt gccgagcgc   180
tttagcggca gcggcagcgg caccgattat acctttacca ttagcagcct gcagccggaa   240
gatattgcga cctattattg ccagcagtgg agcagcaacc cgtttacctt tggccagggc   300
accaaactgc agattacccg cggcggtggc ggatccggcg gtggcggatc cggcggtggc   360
ggatcccagg tgcagctggt gcagagcgga ggcggagtgg tgcagcctgg aagaagcctg   420
cgcctgagct gcaaagcgag cggctatacc tttaccgc   ataccatgca ttgggtgcgc   480
caggcgccgg gcaaaggcct ggaatggatt ggctatatta acccgagccg cggctatacc   540
aactataacc agaaagtgaa agatcgcttt accattagca ccgataaaag caaaagcacc   600
gcgtttctgc agatggatag cctgcgcccg gaagataccg cggtgtatta ttgcgcgcgc   660
tattatgatg atcattattg cctggattat tgggggcagg gcaccaccct gaccgtgagc   720
agc                                                                723
```

```
SEQ ID NO: 390          moltype = AA   length = 241
FEATURE                 Location/Qualifiers
REGION                  1..241
                        note = Humanized anti CD3 scFV clone OKT3 (VH-VL) sequence
source                  1..241
                        mol_type = protein
                        organism = synthetic construct
SEQUENCE: 390
DIQMTQSPSS LSASVGDRVT ITCSASSSVS YMNWYQQTPG KAPKRWIYDT SKLASGVPSR    60
FSGSGSGTDY TFTISSLQPE DIATYYCQQW SSNPFTFGQG TKLQITRGGG GSGGGGSGGG   120
GSQVQLVQSG GGVVQPGRSL RLSCKASGYT FTRYTMHWVR QAPGKGLEWI GYINPSRGYT   180
NYNQKVKDRF TISTDKSKST AFLQMDSLRP EDTAVYYCAR YYDDHYCLDY WGQGTTLTVS   240
S                                                                  241

SEQ ID NO: 391          moltype = DNA   length = 729
FEATURE                 Location/Qualifiers
misc_feature            1..729
                        note = HumanizeE6 scFV (VH-VL) sequence
source                  1..729
                        mol_type = other DNA
                        organism = synthetic construct
SEQUENCE: 391
gaggtgcagc tggtggagtc tgggggaggc ctggtcaagc ctgggggtc cctgagactc     60
tcctgtgcag cctctggatt caccttcagt aggtatggca tgagctgggt ccgccaggct   120
ccagggaaga ggctggagtg gtctcaacc attagtggta gaggcaccta catatactac    180
ccagactcag tgaagggccg attcaccatc tccagagaca cgccaagaa caccctgtat    240
ctgcaaatga acagcctgag agccgaggac acggctgtgt attactgtac cagagataac   300
tatggccgca actatgatta tggcatggat tattggggcc agggcaccct ggtgaccgtg   360
agcagcggcg gtggcggatc cggcggtggc ggatccggcg gtggcggatc cgaaattaaa   420
ttgacacagt ctccagccac cctgtctttg tctccagggg aaagagccac cctcacctgc   480
agcgccacca gcagtgttag ctacatccac tggtaccaac agaggcctgg ccagagcccc   540
aggctcctca tctatagcac ctccaacctg gccagcggga tcccagccag gttcagtggc   600
agtgggtctg ggagcgacta cactctcacc atcagcagcc tagagcctga agattttgca   660
gtttattact gtcagcagcg tagcagctcc ctttcacctt tggcagcgg caccaaagtg    720
gaaattaaa                                                          729

SEQ ID NO: 392          moltype = AA   length = 243
FEATURE                 Location/Qualifiers
REGION                  1..243
                        note = HumanizeE6 scFV (VH-VL) sequence
source                  1..243
                        mol_type = protein
                        organism = synthetic construct
SEQUENCE: 392
EVQLVESGGG LVKPGGSLRL SCAASGFTFS RYGMSWVRQA PGKRLEWVST ISGGGTYIYY    60
PDSVKGRFTI SRDNAKNTLY LQMNSLRAED TAVYYCTRDN YGRNYDYGMD YWGQGTLVTV   120
SSGGGGSGGG GSGGGGSEIV LTQSPATLSL SPGERATLTC SATSSVSYIH WYQQRPGQSP   180
RLLIYSTSNL ASGIPARFSG SGSGSDYTLT ISSLEPEDFA VYYCQQRSSS PFTFGSGTKV   240
EIK                                                                243

SEQ ID NO: 393          moltype = DNA   length = 729
FEATURE                 Location/Qualifiers
misc_feature            1..729
                        note = HumanizeE6 scFV (VL-VH) sequence
source                  1..729
                        mol_type = other DNA
                        organism = synthetic construct
SEQUENCE: 393
gaaattgtgt tgacacagtc tccagccacc ctgtctttgt ctccagggga aagagccacc    60
ctcacctgca gcgccaccag cagtgttagc tacatccact ggtaccaaca gaggcctggc   120
cagagcccca ggctcctcat ctatagcacc tccaacctgg ccagcggcat cccagccagg   180
ttcagtggca gtgggtctgg gagcgactac actctcacca tcagcagcct agagcctgaa   240
gattttgcag tttattactg tcagcagcgt agcagctcc ctttcacctt tggcagcgg    300
accaaagtgg aaattaaagg cggtggcgga tccggcggtg gcggatccgg cggtggcgga   360
tccgaggtgc agctggtgga gtctggggga ggcctggtca agcctggggg gtccctgaga   420
ctctcctgtg cagcctctgg attcaccttc agtaggtatg gcatgagctg ggtccgccag   480
gctccaggga gaggctgga gtgggtctca accattagtg gcggaggcac ctacatatac    540
tacccagact cagtgaaggg ccgattcacc atctccagag acaacgccaa gaacaccctg   600
tatctgcaaa tgaacagcct gagagccgag gacacggctg tgtattactg taccagagat   660
aactatggcc gcaactatga ttatggcatg gattattggg gccagggcac cctggtgacc   720
gtgagcagc                                                          729

SEQ ID NO: 394          moltype = AA   length = 243
FEATURE                 Location/Qualifiers
REGION                  1..243
                        note = HumanizeE6 scFV (VL-VH) sequence
source                  1..243
                        mol_type = protein
```

```
                         organism = synthetic construct
SEQUENCE: 394
EIVLTQSPAT  LSLSPGERAT  LTCSATSSVS  YIHWYQQRPG  QSPRLLIYST  SNLASGIPAR   60
FSGSGSGSDY  TLTISSLEPE  DFAVYYCQQR  SSSPFTFGSG  TKVEIKGGGG  SGGGGSGGGG  120
SEVQLVESGG  GLVKPGGSLR  LSCAASGFTF  SRYGMSWVRQ  APGKRLEWVS  TISGGGTYIY  180
YPDSVKGRFT  ISRDNAKNTL  YLQMNSLRAE  DTAVYYCTRN  NYGRNYDYGM  DYWGQGTLVT  240
VSS                                                                    243

SEQ ID NO: 395          moltype = DNA  length = 747
FEATURE                 Location/Qualifiers
misc_feature            1..747
                        note = HumanizeC2 scFV (VH-VL) sequence
source                  1..747
                        mol_type = other DNA
                        organism = synthetic construct
SEQUENCE: 395
gaggtgcagc tggtggagtc tgggggaggc ctggtcaagc ctgggggtc cctgagactc    60
tcctgtgcag cctctggatt cacccttcagt ggctatgcca tgagctgggt ccgccaggct   120
ccagggaagg ggctggagtg gtctcaacc attagtagtg gcggaaccta catatactac   180
cccgactcag tgaagggccg attcaccatc tccagagaca acgccaagaa ctcactgtat   240
ctgcaaatga acagcctgag agccgaggac acggccgtgt attactgtgc gagacttggg   300
ggataattt actacgaata cttcgatgtc tggggccagg gaaccacggt caccgtctcc   360
tccggcggtg gcggatccgg cggtggcgga tccggcggtg gcgatccga cattgtgctg   420
acccagtctc cagcctcctt ggccgtgtct ccaggacaga gggccaccat cacctgcaga   480
gccagtaaga gtgtcagtac cagcggatac tcctacatgc actggtatca gcagaaacca   540
ggacaacctc ctaaactcct gatttacctg gcatcaactc tggagagcgg ggtcccagc   600
aggttcagcg gcagtgggtc tgggaccgat ttcaccctca caattaatcc tgtggaagct   660
aatgatactg caaattatta ctgtcagcac agtagggagc tgccttttcac attcggcgga   720
gggaccaagg tggagatcaa acgaact                                        747

SEQ ID NO: 396          moltype = AA  length = 249
FEATURE                 Location/Qualifiers
REGION                  1..249
                        note = HumanizeC2 scFV (VH-VL) sequence
source                  1..249
                        mol_type = protein
                        organism = synthetic construct
SEQUENCE: 396
EVQLVESGGG  LVKPGGSLRL  SCAASGFTFS  GYAMSWVRQA  PGKGLEWVST  ISSGGTYIYY   60
PDSVKGRFTI  SRDNAKNSLY  LQMNSLRAED  TAVYYCARLG  GDNYYEYFDV  WGKGTTVTVS  120
SGGGGSGGGG  SGGGGSDIVL  TQSPASLAVS  PGQRATITCR  ASKSVSTSGY  SYMHWYQQKP  180
GQPPKLLIYL  ASNLESGVPA  RFSGSGSGTD  FTLTINPVEA  NDTANYYCQH  SRELPFTFGG  240
GTKVEIKRT                                                              249

SEQ ID NO: 397          moltype = DNA  length = 747
FEATURE                 Location/Qualifiers
misc_feature            1..747
                        note = HumanizeE6 scFV (VL-VH) sequence
source                  1..747
                        mol_type = other DNA
                        organism = synthetic construct
SEQUENCE: 397
gacattgtgc tgacccagtc tccagcctcc ttggccgtgt ctccaggaca gagggccacc    60
atcacctgca gagccagtaa gagtgtcagt accagcggat actcctacat gcactggtat   120
cagcagaaac caggacaacc tcctaaactc tgatttacc tggcatccaa tctggagagc   180
ggggtcccag ccaggttcag cggcagtggg tctgggaccg atttcaccct cacaattaat   240
cctgtggaag ctaatgatac tgcaaattat tactgtcagc acagtaggga gctgcctttc   300
acattcggcg gagggaccaa ggtggagatc aaacgaactg cggtggcgg atccggcggt   360
ggcggatccg gcggtggcgg atccgaggtg cagctggtgg agtcgggggg aggcctggtc   420
aagcctgggg gttcctgag actctcctgt gcagcctctg gattcacctt cagtggctat   480
gccatgagct gggtccgcca ggctccaggg aaggggctgg agtgggtctc aaccattagt   540
agtggcggaa cctacatata ctaccccgac tcagtgaagg gccgattcac catctccaga   600
gacaacgcca agaactcact gtatctgcaa atgaacagcc tgagagccga ggacacggcc   660
gtgtattact gtgcgagact tggggggat aattactacg aatacttcga tgtctggggc   720
aaagggacca cggtcaccgt ctcctcc                                        747

SEQ ID NO: 398          moltype = AA  length = 249
FEATURE                 Location/Qualifiers
REGION                  1..249
                        note = HumanizeE6 scFV (VL-VH) sequence
source                  1..249
                        mol_type = protein
                        organism = synthetic construct
SEQUENCE: 398
DIVLTQSPAS  LAVSPGQRAT  ITCRASKSVS  TSGYSYMHWY  QQKPGQPPKL  LIYLASNLES   60
GVPARFSGSG  SGTDFTLTIN  PVEANDTANY  YCQHSRELPF  TFGGGTKVEI  KRTGGGGSGG  120
GGSGGGGSEV  QLVESGGGLV  KPGGSLRLSC  AASGFTFSGY  AMSWVRQAPG  KGLEWVSTIS  180
SGGTYIYYPD  SVKGRFTISR  DNAKNSLYLQ  MNSLRAEDTA  VYYCARLGGD  NYYEYFDVWG  240
KGTTVTVSS                                                              249
```

```
SEQ ID NO: 399          moltype = DNA  length = 15
FEATURE                 Location/Qualifiers
misc_feature            1..15
                        note = G4S1 linker sequence
source                  1..15
                        mol_type = other DNA
                        organism = synthetic construct
SEQUENCE: 399
ggcggtggcg gatcc                                                          15

SEQ ID NO: 400          moltype = AA  length = 5
FEATURE                 Location/Qualifiers
REGION                  1..5
                        note = G4S1 linker sequence
source                  1..5
                        mol_type = protein
                        organism = synthetic construct
SEQUENCE: 400
GGGGS                                                                      5

SEQ ID NO: 401          moltype = DNA  length = 45
FEATURE                 Location/Qualifiers
misc_feature            1..45
                        note = [G4S1]x3 linker sequence
source                  1..45
                        mol_type = other DNA
                        organism = synthetic construct
SEQUENCE: 401
ggcggtggcg gatccggcgg tggcggatcc ggcggtggcg gatcc                          45

SEQ ID NO: 402          moltype = AA  length = 15
FEATURE                 Location/Qualifiers
REGION                  1..15
                        note = [G4S1]x3 linker sequence
source                  1..15
                        mol_type = protein
                        organism = synthetic construct
SEQUENCE: 402
GGGGSGGGGS GGGGS                                                          15

SEQ ID NO: 403          moltype = DNA  length = 24
FEATURE                 Location/Qualifiers
misc_feature            1..24
                        note = 8 aa GS linker sequence
source                  1..24
                        mol_type = other DNA
                        organism = synthetic construct
SEQUENCE: 403
ggcggttccg gcggtggatc cgga                                                24

SEQ ID NO: 404          moltype = AA  length = 8
FEATURE                 Location/Qualifiers
REGION                  1..8
                        note = 8 aa GS linker sequence
source                  1..8
                        mol_type = protein
                        organism = synthetic construct
SEQUENCE: 404
GGSGGGSG                                                                   8

SEQ ID NO: 405          moltype = DNA  length = 39
FEATURE                 Location/Qualifiers
misc_feature            1..39
                        note = 12 aa GS linker sequence
source                  1..39
                        mol_type = other DNA
                        organism = synthetic construct
SEQUENCE: 405
ggcggttccg gcggtggatc cggcggtggc ggatccgga                                39

SEQ ID NO: 406          moltype = AA  length = 12
FEATURE                 Location/Qualifiers
REGION                  1..12
                        note = 12 aa GS linker sequence
source                  1..12
                        mol_type = protein
                        organism = synthetic construct
SEQUENCE: 406
```

```
GGSGGGSGGG SG                                                              12

SEQ ID NO: 407         moltype = DNA  length = 39
FEATURE                Location/Qualifiers
misc_feature           1..39
                       note = 13 aa GS linker sequence
source                 1..39
                       mol_type = other DNA
                       organism = synthetic construct
SEQUENCE: 407
ggcggtggat ccggcggtgg cggatccggc ggtggatcc                                 39

SEQ ID NO: 408         moltype = AA  length = 13
FEATURE                Location/Qualifiers
REGION                 1..13
                       note = 13 aa GS linker sequence
source                 1..13
                       mol_type = protein
                       organism = synthetic construct
SEQUENCE: 408
GGGSGGGGSG GGS                                                             13

SEQ ID NO: 409         moltype = DNA  length = 66
FEATURE                Location/Qualifiers
misc_feature           1..66
                       note = 22 aa GS linker sequence
source                 1..66
                       mol_type = other DNA
                       organism = synthetic construct
SEQUENCE: 409
ggcggtggaa gcggcggtgg cggatccggc agcggcggaa gcggcggtgg cggatccggc          60
ggtgga                                                                     66

SEQ ID NO: 410         moltype = AA  length = 22
FEATURE                Location/Qualifiers
REGION                 1..22
                       note = 22 aa GS linker sequence
source                 1..22
                       mol_type = protein
                       organism = synthetic construct
SEQUENCE: 410
GGGSGGGGSG SGGSGGGGSG GG                                                   22

SEQ ID NO: 411         moltype = DNA  length = 78
FEATURE                Location/Qualifiers
misc_feature           1..78
                       note = 24 aa GS linker sequence
source                 1..78
                       mol_type = other DNA
                       organism = synthetic construct
SEQUENCE: 411
ggcggttccg gcggtggatc cggcggtggc ggatccggag gcggttccgg cggtggatcc          60
ggcggtggcg gatccgga                                                        78

SEQ ID NO: 412         moltype = AA  length = 24
FEATURE                Location/Qualifiers
REGION                 1..24
                       note = 24 aa GS linker sequence
source                 1..24
                       mol_type = protein
                       organism = synthetic construct
SEQUENCE: 412
GGSGGGSGGG SGGGSGGGSG GGSG                                                 24

SEQ ID NO: 413         moltype = DNA  length = 357
FEATURE                Location/Qualifiers
misc_feature           1..357
                       note = Mouse C3 Heavy chain variable region sequence
source                 1..357
                       mol_type = other DNA
                       organism = synthetic construct
SEQUENCE: 413
caggtccagc tgcagcagtc tgggcctgag ctggtgaggc ctggggtctc agtgaagatt          60
tcctgcaagg gttccggcta cagattcact gattatgcta tgaactgggt gaagcagagt         120
catgcaaaga gtctagagtg gattggagtt attagtactt tctctggtaa tacaaacttc         180
aaccagaagt ttaagggcaa ggccacaatg actgtagaca atcctccag cacagcctat          240
atggaacttg ccagattgac atctgaggat tctgccatgt attactgtgc aagatcggat         300
tactacggcc catactttga ctactggggc caaggcacca ctctcacagt ctcctca           357
```

```
SEQ ID NO: 414            moltype = AA    length = 119
FEATURE                   Location/Qualifiers
REGION                    1..119
                          note = Mouse C3 Heavy chain variable region sequence
source                    1..119
                          mol_type = protein
                          organism = synthetic construct
SEQUENCE: 414
QVQLQQSGPE LVRPGVSVKI SCKGSGYRFT DYAMNWVKQS HAKSLEWIGV ISTFSGNTNF    60
NQKFKGKATM TVDKSSSTAY MELARLTSED SAMYYCARSD YYGPYFDYWG QGTTLTVSS    119

SEQ ID NO: 415            moltype = DNA    length = 90
FEATURE                   Location/Qualifiers
misc_feature              1..90
                          note = Mouse C3 heavy chain variable framework region 1
                          (FWR1) sequence
source                    1..90
                          mol_type = other DNA
                          organism = synthetic construct
SEQUENCE: 415
caggtccagc tgcagcagtc tgggcctgag ctggtgaggc ctggggtctc agtgaagatt    60
tcctgcaagg gttccggcta cagattcact                                    90

SEQ ID NO: 416            moltype = AA    length = 30
FEATURE                   Location/Qualifiers
REGION                    1..30
                          note = Mouse C3 heavy chain variable framework region 1
                          (FWR1) sequence
source                    1..30
                          mol_type = protein
                          organism = synthetic construct
SEQUENCE: 416
QVQLQQSGPE LVRPGVSVKI SCKGSGYRFT                                    30

SEQ ID NO: 417            moltype = DNA    length = 15
FEATURE                   Location/Qualifiers
misc_feature              1..15
                          note = Mouse C3 heavy chain variable complementarity
                          determining regions1 (CDR1) sequence
source                    1..15
                          mol_type = other DNA
                          organism = synthetic construct
SEQUENCE: 417
gattatgcta tgaac                                                    15

SEQ ID NO: 418            moltype = AA    length = 5
FEATURE                   Location/Qualifiers
REGION                    1..5
                          note = Mouse C3 heavy chain variable complementarity
                          determining regions1 (CDR1) sequence
source                    1..5
                          mol_type = protein
                          organism = synthetic construct
SEQUENCE: 418
DYAMN                                                               5

SEQ ID NO: 419            moltype = DNA    length = 42
FEATURE                   Location/Qualifiers
misc_feature              1..42
                          note = Mouse C3 heavy chain variable framework region 2
                          (FWR2) sequence
source                    1..42
                          mol_type = other DNA
                          organism = synthetic construct
SEQUENCE: 419
tgggtgaagc agagtcatgc aaagagtcta gagtggattg ga                      42

SEQ ID NO: 420            moltype = AA    length = 14
FEATURE                   Location/Qualifiers
REGION                    1..14
                          note = Mouse C3 heavy chain variable framework region 2
                          (FWR2) sequence
source                    1..14
                          mol_type = protein
                          organism = synthetic construct
SEQUENCE: 420
WVKQSHAKSL EWIG                                                     14

SEQ ID NO: 421            moltype = DNA    length = 51
```

| FEATURE | Location/Qualifiers |
|---|---|
| misc_feature | 1..51<br>note = Mouse C3 heavy chain variable complementarity determining regions2 (CDR2) sequence |
| source | 1..51<br>mol_type = other DNA<br>organism = synthetic construct |

SEQUENCE: 421
```
gttattagta ctttctctgg taatacaaac ttcaaccaga agtttaaggg c        51
```

| SEQ ID NO: 422 | moltype = AA  length = 17 |
|---|---|
| FEATURE | Location/Qualifiers |
| REGION | 1..17<br>note = Mouse C3 heavy chain variable complementarity determining regions2 (CDR2) sequence |
| source | 1..17<br>mol_type = protein<br>organism = synthetic construct |

SEQUENCE: 422
```
VISTFSGNTN FNQKFKG                                               17
```

| SEQ ID NO: 423 | moltype = DNA  length = 96 |
|---|---|
| FEATURE | Location/Qualifiers |
| misc_feature | 1..96<br>note = Mouse C3 heavy chain variable framework region 3 (FWR3) acidsequence |
| source | 1..96<br>mol_type = other DNA<br>organism = synthetic construct |

SEQUENCE: 423
```
aaggccacaa tgactgtaga caaatcctcc agcacagcct atatggaact tgccagattg   60
acatctgagg attctgccat gtattactgt gcaaga                            96
```

| SEQ ID NO: 424 | moltype = AA  length = 32 |
|---|---|
| FEATURE | Location/Qualifiers |
| REGION | 1..32<br>note = Mouse C3 heavy chain variable framework region 3 (FWR3) acidsequence |
| source | 1..32<br>mol_type = protein<br>organism = synthetic construct |

SEQUENCE: 424
```
KATMTVDKSS STAYMELARL TSEDSAMYYC AR                              32
```

| SEQ ID NO: 425 | moltype = DNA  length = 30 |
|---|---|
| FEATURE | Location/Qualifiers |
| misc_feature | 1..30<br>note = Mouse C3 heavy chain variable complementarity determining regions3 (CDR3) sequence |
| source | 1..30<br>mol_type = other DNA<br>organism = synthetic construct |

SEQUENCE: 425
```
tcggattact acggcccata ctttgactac                                 30
```

| SEQ ID NO: 426 | moltype = AA  length = 10 |
|---|---|
| FEATURE | Location/Qualifiers |
| REGION | 1..10<br>note = Mouse C3 heavy chain variable complementarity determining regions3 (CDR3) sequence |
| source | 1..10<br>mol_type = protein<br>organism = synthetic construct |

SEQUENCE: 426
```
SDYYGPYFDY                                                       10
```

| SEQ ID NO: 427 | moltype = DNA  length = 296 |
|---|---|
| FEATURE | Location/Qualifiers |
| misc_feature | 1..296<br>note = IGHV1-18*04 heavy chain variable region sequence |
| source | 1..296<br>mol_type = other DNA<br>organism = synthetic construct |

SEQUENCE: 427
```
caggttcagc tggtgcagtc tggagctgag gtgaagaagc ctggggcctc agtgaaggtc   60
tcctgcaagg cttctggtta cacctttacc agctacggta tcagctgggt gcgacaggcc  120
cctggacaag gccttgagtg gatgggatgg atcagcgctt acaatggtaa cacaaactat  180
gcacagaagc tccagggcag agtcaccatg accacagaca catccacgag cacagcctac  240
atggagctga ggagcctgag atctgacgac acggccgtgt attactgtgc gagaga       296
```

```
SEQ ID NO: 428           moltype = AA   length = 98
FEATURE                  Location/Qualifiers
REGION                   1..98
                         note = IGHV1-18*04 heavy chain variable region sequence
source                   1..98
                         mol_type = protein
                         organism = synthetic construct
SEQUENCE: 428
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCAR                            98

SEQ ID NO: 429           moltype = DNA   length = 90
FEATURE                  Location/Qualifiers
misc_feature             1..90
                         note = IGHV1-18*04 heavy chain variable framework region 1
                         (FWR1) sequence
source                   1..90
                         mol_type = other DNA
                         organism = synthetic construct
SEQUENCE: 429
caggttcagc tggtgcagtc tggagctgag gtgaagaagc ctggggcctc agtgaaggtc    60
tcctgcaagg cttctggtta caccttacc                                      90

SEQ ID NO: 430           moltype = AA   length = 30
FEATURE                  Location/Qualifiers
REGION                   1..30
                         note = IGHV1-18*04 heavy chain variable framework region 1
                         (FWR1) sequence
source                   1..30
                         mol_type = protein
                         organism = synthetic construct
SEQUENCE: 430
QVQLVQSGAE VKKPGASVKV SCKASGYTFT                                     30

SEQ ID NO: 431           moltype = DNA   length = 15
FEATURE                  Location/Qualifiers
misc_feature             1..15
                         note = IGHV1-18*04 heavy chain variable complementarity
                         determiningregions 1 (CDR1) sequence
source                   1..15
                         mol_type = other DNA
                         organism = synthetic construct
SEQUENCE: 431
agctacggta tcagc                                                     15

SEQ ID NO: 432           moltype = AA   length = 5
FEATURE                  Location/Qualifiers
REGION                   1..5
                         note = IGHV1-18*04 heavy chain variable complementarity
                         determiningregions 1 (CDR1) sequence
source                   1..5
                         mol_type = protein
                         organism = synthetic construct
SEQUENCE: 432
SYGIS                                                                 5

SEQ ID NO: 433           moltype = DNA   length = 42
FEATURE                  Location/Qualifiers
misc_feature             1..42
                         note = IGHV1-18*04 heavy chain variable framework region 2
                         (FWR2) sequence
source                   1..42
                         mol_type = other DNA
                         organism = synthetic construct
SEQUENCE: 433
tgggtgcgac aggcccctgg acaagggctt gagtggatgg ga                       42

SEQ ID NO: 434           moltype = AA   length = 14
FEATURE                  Location/Qualifiers
REGION                   1..14
                         note = IGHV1-18*04 heavy chain variable framework region 2
                         (FWR2) sequence
source                   1..14
                         mol_type = protein
                         organism = synthetic construct
SEQUENCE: 434
WVRQAPGQGL EWMG                                                      14
```

```
SEQ ID NO: 435              moltype = DNA  length = 51
FEATURE                     Location/Qualifiers
misc_feature                1..51
                            note = IGHV1-18*04 heavy chain variable complementarity
                            determiningregions 2 (CDR2) sequence
source                      1..51
                            mol_type = other DNA
                            organism = synthetic construct
SEQUENCE: 435
tggatcagcg cttacaatgg taacacaaac tatgcacaga agctccaggg c            51

SEQ ID NO: 436              moltype = AA  length = 17
FEATURE                     Location/Qualifiers
REGION                      1..17
                            note = IGHV1-18*04 heavy chain variable complementarity
                            determiningregions 2 (CDR2) sequence
source                      1..17
                            mol_type = protein
                            organism = synthetic construct
SEQUENCE: 436
WISAYNGNTN YAQKLQG                                                  17

SEQ ID NO: 437              moltype = DNA  length = 96
FEATURE                     Location/Qualifiers
misc_feature                1..96
                            note = IGHV1-18*04 heavy chain variable framework region 3
                            (FWR3)sequence
source                      1..96
                            mol_type = other DNA
                            organism = synthetic construct
SEQUENCE: 437
agagtcacca tgaccacaga cacatccacg agcacagcct acatggagct gaggagcctg   60
agatctgacg acacggccgt gtattactgt gcgaga                             96

SEQ ID NO: 438              moltype = AA  length = 32
FEATURE                     Location/Qualifiers
REGION                      1..32
                            note = IGHV1-18*04 heavy chain variable framework region 3
                            (FWR3)sequence
source                      1..32
                            mol_type = protein
                            organism = synthetic construct
SEQUENCE: 438
RVTMTTDTST STAYMELRSL RSDDTAVYYC AR                                 32

SEQ ID NO: 439              moltype = DNA  length = 357
FEATURE                     Location/Qualifiers
misc_feature                1..357
                            note = Humanized C3 heavy chain variable region sequence
source                      1..357
                            mol_type = other DNA
                            organism = synthetic construct
SEQUENCE: 439
caggttcagc tggtgcagtc tggagctgag gtgaagaagc ctggggcctc agtgaaggtc   60
tcctgcaagg cttctggtta cacctttacc gactacgcta tgaactgggt gcgacaggcc  120
cctggacaag gcttgagtg gatgggagtg atcagcacct tcagcggtaa cacaaacttc   180
aaccagaagt tcaagggcag agtcaccatg accacagaca catccacgag cacagcctac   240
atggagctga ggagcctgag atctgacgac acggccgtgt attactgtgc gagagcgac    300
tactacggcc catacttcga ctactggggc cagggcacca ccctgaccgt gtccagc      357

SEQ ID NO: 440              moltype = AA  length = 119
FEATURE                     Location/Qualifiers
REGION                      1..119
                            note = Humanized C3 heavy chain variable region sequence
source                      1..119
                            mol_type = protein
                            organism = synthetic construct
SEQUENCE: 440
QVQLVQSGAE VKKPGASVKV SCKASGYTFT DYAMNWVRQA PGQGLEWMGV ISTFSGNTNF   60
NQKFKGRVTM TTDTSTSTAY MELRSLRSDD TAVYYCARSD YYGPYFDYWG QGTTLTVSS   119

SEQ ID NO: 441              moltype = DNA  length = 90
FEATURE                     Location/Qualifiers
misc_feature                1..90
                            note = Humanized C3 heavy chain variable framework region 1
                            (FWR1) acidsequence
source                      1..90
                            mol_type = other DNA
                            organism = synthetic construct
```

```
SEQUENCE: 441
caggttcagc tggtgcagtc tggagctgag gtgaagaagc ctggggcctc agtgaaggtc    60
tcctgcaagg cttctggtta caccttttacc                                    90

SEQ ID NO: 442           moltype = AA   length = 30
FEATURE                  Location/Qualifiers
REGION                   1..30
                         note = Humanized C3 heavy chain variable framework region 1
                         (FWR1) acidsequence
source                   1..30
                         mol_type = protein
                         organism = synthetic construct
SEQUENCE: 442
QVQLVQSGAE VKKPGASVKV SCKASGYTFT                                     30

SEQ ID NO: 443           moltype = DNA   length = 15
FEATURE                  Location/Qualifiers
misc_feature             1..15
                         note = Humanized C3 heavy chain variable complementarity
                         determiningregions 1 (CDR1) sequence
source                   1..15
                         mol_type = other DNA
                         organism = synthetic construct
SEQUENCE: 443
gactacgcca tgaac                                                     15

SEQ ID NO: 444           moltype = AA   length = 5
FEATURE                  Location/Qualifiers
REGION                   1..5
                         note = Humanized C3 heavy chain variable complementarity
                         determiningregions 1 (CDR1) sequence
source                   1..5
                         mol_type = protein
                         organism = synthetic construct
SEQUENCE: 444
DYAMN                                                                 5

SEQ ID NO: 445           moltype = DNA   length = 42
FEATURE                  Location/Qualifiers
misc_feature             1..42
                         note = Humanized C3 heavy chain variable framework region 2
                         (FWR2) acidsequence
source                   1..42
                         mol_type = other DNA
                         organism = synthetic construct
SEQUENCE: 445
tgggtgcgac aggcccctgg acaagggctt gagtggatgg ga                       42

SEQ ID NO: 446           moltype = AA   length = 14
FEATURE                  Location/Qualifiers
REGION                   1..14
                         note = Humanized C3 heavy chain variable framework region 2
                         (FWR2) acidsequence
source                   1..14
                         mol_type = protein
                         organism = synthetic construct
SEQUENCE: 446
WVRQAPGQGL EWMG                                                      14

SEQ ID NO: 447           moltype = DNA   length = 51
FEATURE                  Location/Qualifiers
misc_feature             1..51
                         note = Humanized C3 heavy chain variable complementarity
                         determiningregions 2 (CDR2) sequence
source                   1..51
                         mol_type = other DNA
                         organism = synthetic construct
SEQUENCE: 447
gtgatcagca ccttcagcgg taacacaaac ttcaaccaga agttcaaggg c              51

SEQ ID NO: 448           moltype = AA   length = 17
FEATURE                  Location/Qualifiers
REGION                   1..17
                         note = Humanized C3 heavy chain variable complementarity
                         determiningregions 2 (CDR2) sequence
source                   1..17
                         mol_type = protein
                         organism = synthetic construct
SEQUENCE: 448
```

VISTFSGNTN FNQKFKG                                                                17

SEQ ID NO: 449           moltype = DNA   length = 96
FEATURE                  Location/Qualifiers
misc_feature             1..96
                         note = Humanized C3 heavy chain variable framework region 3
                         (FWR3) acidsequence
source                   1..96
                         mol_type = other DNA
                         organism = synthetic construct
SEQUENCE: 449
agagtcacca tgaccacaga cacatccacg agcacagcct acatggagct gaggagcctg    60
agatctgacg acacggccgt gtattactgt gcgaga                              96

SEQ ID NO: 450           moltype = AA    length = 32
FEATURE                  Location/Qualifiers
REGION                   1..32
                         note = Humanized C3 heavy chain variable framework region 3
                         (FWR3) acidsequence
source                   1..32
                         mol_type = protein
                         organism = synthetic construct
SEQUENCE: 450
RVTMTTDTST STAYMELRSL RSDDTAVYYC AR                                  32

SEQ ID NO: 451           moltype = DNA   length = 30
FEATURE                  Location/Qualifiers
misc_feature             1..30
                         note = Humanized C3 heavy chain variable complementarity
                         determiningregions 3 (CDR3) sequence
source                   1..30
                         mol_type = other DNA
                         organism = synthetic construct
SEQUENCE: 451
agcgactact acggcccata cttcgactac                                     30

SEQ ID NO: 452           moltype = AA    length = 10
FEATURE                  Location/Qualifiers
REGION                   1..10
                         note = Humanized C3 heavy chain variable complementarity
                         determiningregions 3 (CDR3) sequence
source                   1..10
                         mol_type = protein
                         organism = synthetic construct
SEQUENCE: 452
SDYYGPYFDY                                                           10

SEQ ID NO: 453           moltype = DNA   length = 1353
FEATURE                  Location/Qualifiers
misc_feature             1..1353
                         note = Humanized C3 IgG1 heavy chain sequence
source                   1..1353
                         mol_type = other DNA
                         organism = synthetic construct
SEQUENCE: 453
caggttcagc tggtgcagtc tggagctgag gtgaagaagc ctggggcctc agtgaaggtc    60
tcctgcaagg cttctggtta cacctttacc gactacgcca tgaactgggt gcgacaggcc   120
cctggacaag ggcttgagtg gatgggagtg atcagcacct tcagcggtaa cacaaacttc   180
aaccagaagt tcaagggcag agtcaccatg accacagaca tccacgagca cagcctac    240
atggagctga ggagcctgag atctgacgac acggccgtgt attactgtgc gagaagcgac   300
tactacggcc catacttcga ctactgggc cagggcacca ccctgaccgt gtccagcgct   360
agcaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgacagtg ccctccagca gcttgggcac ccagacctac   600
atctgcaacg tgaatcacaa gcccagcaac accaaggtgg acaagaaagt tgagcccaaa   660
tcttgtgaca aaactcacac atgcccaccg tgcccagcac ctgaactcct ggggggaccg   720
tcagtcttcc tcttccccc aaaacccaag gacaccctca tgatctcccg gacccctgag   780
gtcacatgcg tggtggtgga cgtgagccac gaagaccctg aggtcaagtt caactggtac   840
gtggacggcg tggaggtgca taatgccaag acaaagccgc gggaggagca gtacaacagc   900
acgtaccgtg tggtcagcgt cctcaccgtc ctgcaccagg actggctgaa tggcaaggag   960
tacaagtgca aggtctccaa caaagccctc cagcccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg catgaggctc tgcacaacca ctacacgcag  1320
aagagcctct ccctgtctcc gggtaaatga taa                                1353

```
SEQ ID NO: 454            moltype = AA   length = 449
FEATURE                   Location/Qualifiers
REGION                    1..449
                          note = Humanized C3 IgG1 heavy chain sequence
source                    1..449
                          mol_type = protein
                          organism = synthetic construct
SEQUENCE: 454
QVQLVQSGAE VKKPGASVKV SCKASGYTFT DYAMNWVRQA PGQGLEWMGV ISTFSGNTNF   60
NQKFKGRVTM TTDTSTSTAY MELRSLRSDD TAVYYCARSD YYGPYFDYWG QGTTLTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 455            moltype = DNA   length = 1341
FEATURE                   Location/Qualifiers
misc_feature              1..1341
                          note = Humanized C3 IgG2 heavy chain sequence
source                    1..1341
                          mol_type = other DNA
                          organism = synthetic construct
SEQUENCE: 455
caggttcagc tggtgcagtc tggagctgag gtgaagaagc ctggggcctc agtgaaggtc    60
tcctgcaagg cttctggtta cacctttacc gactacgcca tgaactgggt gcgacaggcc   120
cctggacaag gcttgagtg gatgggagtg atcagcacct tcagcggtaa cacaaacttc   180
aaccagaagt tcaagggcag agtcaccatg accacagaca tccacgag cacagcctac     240
atggagctga ggagcctgag atctgacgac acggccgtgt attactgtgc gagaagcgac   300
tactacggcc catacttcga ctactgggc cagggcacca ccctgaccgt gtccagcgac    360
tccaccaagg gcccatcggt cttccccctg gcgccctgct ccaggagcac ctccgagagc   420
acagccgccc tgggctgcct ggtcaaggac tacttccccg aaccggtgac ggtgtcgtgg   480
aactcaggcg ctctgaccag cggcgtgcac accttcccag ctgtcctaca gtcctcagga   540
ctctactccc tcagcagcgt ggtgaccgtg ccctccagca cttcggcgtg ccagacctac   600
acctgcaacg tagatcacaa gcccagcaac accaaggtgg acaagacagt tgagcgcaaa   660
tgttgtgtcg agtgcccacc gtgcccagca ccacctgtgg caggaccgtc agtcttcctc   720
ttccccccaa aacccaagga caccctcatg atctccggga ccctgaggt cacgtgcgtg     780
gtggtggacg tgagccacga agaccccgag gtccagttca actggtacgt ggacggcgtg   840
gaggtgcata atgccaagac aaagccacgg gaggagcagt tcaacagcac gttccgtgtg   900
gtcagcgtcc tcaccgttgt gcaccaggac tggctgaacg gcaaggagta caagtgcaag   960
gtctccaaca aaggcctccc agcccccatc gagaaaacca tctccaaaac caaagggcag  1020
ccccgagaac cacaggtgta cacctgccc ccatcccggg aggagatgac caagaaccag   1080
gtcagcctga cctgcctggt caaaggcttc taccccagcg acatcgccgt ggagtgggag   1140
agcaatgggc agccggagaa caactacaag accacacctc ccatgctgga ctccgacggc  1200
tccttcttcc tctacagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gtaaatagta a                                            1341

SEQ ID NO: 456            moltype = AA   length = 445
FEATURE                   Location/Qualifiers
REGION                    1..445
                          note = Humanized C3 IgG2 heavy chain sequence
source                    1..445
                          mol_type = protein
                          organism = synthetic construct
SEQUENCE: 456
QVQLVQSGAE VKKPGASVKV SCKASGYTFT DYAMNWVRQA PGQGLEWMGV ISTFSGNTNF   60
NQKFKGRVTM TTDTSTSTAY MELRSLRSDD TAVYYCARSD YYGPYFDYWG QGTTLTVSSA  120
STKGPSVFPL APCSRSTSES TAALGCLVKD YFPEPVTVSW NSGALTSGVH TFPAVLQSSG  180
LYSLSSVVTV PSSNFGTQTY TCNVDHKPSN TKVDKTVERK CCVECPPCPA PPVAGPSVFL  240
FPPKPKDTLM ISRTPEVTCV VVDVSHEDPE VQFNWYVDGV EVHNAKTKPR EEQFNSTFRV  300
VSVLTVVHQD WLNGKEYKCK VSNKGLPAPI EKTISKTKGQ PREPQVYTLP PSREEMTKNQ  360
VSLTCLVKGF YPSDIAVEWE SNGQPENNYK TTPPMLDSDG SFFLYSKLTV DKSRWQQGNV  420
FSCSVMHEAL HNHYTQKSLS LSPGK                                        445

SEQ ID NO: 457            moltype = DNA   length = 545
FEATURE                   Location/Qualifiers
misc_feature              1..545
                          note = Humanized C3 heavy chain IgG1 gBLOCK sequence
source                    1..545
                          mol_type = other DNA
                          organism = synthetic construct
SEQUENCE: 457
tgctctgggt tccaggttcc actggtgacg cggcccagcc ggcccaggtt cagctggtgc    60
agtctggagc tgaggtgaag aagcctgggg cctcagtgaa ggtctcctgc aaggcttctg   120
gttacacctt taccgactac gccatgaact gggtgcgaca ggcccctgga caagggcttg   180
agtggatggg agtgatcagc accttcagcg gtaacacaaa cttcaaccag aagttcaagg   240
gcagagtcac catgaccaca gacacatcca cgagcacagc ctacatggag ctgaggagcc   300
```

```
tgagatctga cgacacggcc gtgtattact gtgcgagaag cgactactac ggcccatact    360
tcgactactg gggccagggc accaccctga ccgtgtccag cgctagcacc aagggcccat    420
cggtcttccc cctggcaccc tcctccaaga gcacctctgg gggcacagcg gccctgggct    480
gcctggtcaa ggactacttc cccgaaccgg tgacggtgtc gtggaactca ggcgccctga    540
ccagc                                                                545

SEQ ID NO: 458            moltype = DNA   length = 336
FEATURE                   Location/Qualifiers
misc_feature              1..336
                          note = Mouse C3 Light Chain variable region sequence
source                    1..336
                          mol_type = other DNA
                          organism = synthetic construct
SEQUENCE: 458
gatgttttga tgacccaaac tccactctcc ctgcctgtca gtcttggaga tcaagcctcc     60
atctcttgca gatctagtca gaccattgta catagtaatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
aacagagtgg aggctgagga tctgggagtt tattactgct ttcaaggttc acatgttcca    300
ttcacgttcg gctcggggac aaagttggaa ataaaa                              336

SEQ ID NO: 459            moltype = AA   length = 112
FEATURE                   Location/Qualifiers
REGION                    1..112
                          note = Mouse C3 Light Chain variable region sequence
source                    1..112
                          mol_type = protein
                          organism = synthetic construct
SEQUENCE: 459
DVLMTQTPLS LPVSLGDQAS ISCRSSQTIV HSNGNTYLEW YLQKPGQSPK LLIYKVSNRF     60
SGVPDRFSGS GSGTDFTLKI NRVEAEDLGV YYCFQGSHVP FTFGSGTKLE IK            112

SEQ ID NO: 460            moltype = DNA   length = 69
FEATURE                   Location/Qualifiers
misc_feature              1..69
                          note = Mouse C3 light chain variable framework region 1
                            (FWR1) sequence
source                    1..69
                          mol_type = other DNA
                          organism = synthetic construct
SEQUENCE: 460
gatgttttga tgacccaaac tccactctcc ctgcctgtca gtcttggaga tcaagcctcc     60
atctcttgc                                                             69

SEQ ID NO: 461            moltype = AA   length = 23
FEATURE                   Location/Qualifiers
REGION                    1..23
                          note = Mouse C3 light chain variable framework region 1
                            (FWR1) sequence
source                    1..23
                          mol_type = protein
                          organism = synthetic construct
SEQUENCE: 461
DVLMTQTPLS LPVSLGDQAS ISC                                              23

SEQ ID NO: 462            moltype = DNA   length = 48
FEATURE                   Location/Qualifiers
misc_feature              1..48
                          note = Mouse C3 light chain variable complementarity
                            determining regions1 (CDR1) sequence
source                    1..48
                          mol_type = other DNA
                          organism = synthetic construct
SEQUENCE: 462
agatctagtc agaccattgt acatagtaat ggaaacacct atttagaa                   48

SEQ ID NO: 463            moltype = AA   length = 16
FEATURE                   Location/Qualifiers
REGION                    1..16
                          note = Mouse C3 light chain variable complementarity
                            determining regions1 (CDR1) sequence
source                    1..16
                          mol_type = protein
                          organism = synthetic construct
SEQUENCE: 463
RSSQTIVHSN GNTYLE                                                      16

SEQ ID NO: 464            moltype = DNA   length = 45
FEATURE                   Location/Qualifiers
```

```
misc_feature                1..45
                            note = Mouse C3 light chain variable framework region 2
                            (FWR2) sequence
source                      1..45
                            mol_type = other DNA
                            organism = synthetic construct
SEQUENCE: 464
tggtacctgc agaaaccagg ccagtctcca aagctcctga tctac              45

SEQ ID NO: 465              moltype = AA   length = 15
FEATURE                     Location/Qualifiers
REGION                      1..15
                            note = Mouse C3 light chain variable framework region 2
                            (FWR2) sequence
source                      1..15
                            mol_type = protein
                            organism = synthetic construct
SEQUENCE: 465
WYLQKPGQSP KLLIY                                                15

SEQ ID NO: 466              moltype = DNA   length = 21
FEATURE                     Location/Qualifiers
misc_feature                1..21
                            note = Mouse C3 light chain variable complementarity
                            determining regions2 (CDR2) sequence
source                      1..21
                            mol_type = other DNA
                            organism = synthetic construct
SEQUENCE: 466
aaagtttcca accgattttc t                                         21

SEQ ID NO: 467              moltype = AA   length = 7
FEATURE                     Location/Qualifiers
REGION                      1..7
                            note = Mouse C3 light chain variable complementarity
                            determining regions2 (CDR2) sequence
source                      1..7
                            mol_type = protein
                            organism = synthetic construct
SEQUENCE: 467
KVSNRFS                                                          7

SEQ ID NO: 468              moltype = DNA   length = 96
FEATURE                     Location/Qualifiers
misc_feature                1..96
                            note = Mouse C3 light chain variable framework region 3
                            (FWR3) sequence
source                      1..96
                            mol_type = other DNA
                            organism = synthetic construct
SEQUENCE: 468
ggggtcccag acaggttcag tggcagtgga tcagggacag atttcacact caagatcaac   60
agagtggagg ctgaggatct gggagtttat tactgc                             96

SEQ ID NO: 469              moltype = AA   length = 32
FEATURE                     Location/Qualifiers
REGION                      1..32
                            note = Mouse C3 light chain variable framework region 3
                            (FWR3) sequence
source                      1..32
                            mol_type = protein
                            organism = synthetic construct
SEQUENCE: 469
GVPDRFSGSG SGTDFTLKIN RVEAEDLGVY YC                              32

SEQ ID NO: 470              moltype = DNA   length = 27
FEATURE                     Location/Qualifiers
misc_feature                1..27
                            note = Mouse C3 light chain variable complementarity
                            determining regions3 (CDR3) sequence
source                      1..27
                            mol_type = other DNA
                            organism = synthetic construct
SEQUENCE: 470
tttcaaggtt cacatgttcc attcacg                                   27

SEQ ID NO: 471              moltype = AA   length = 9
FEATURE                     Location/Qualifiers
REGION                      1..9
```

|  |  |  |
|---|---|---|
| | note = Mouse C3 light chain variable complementarity<br>determining regions3 (CDR3) sequence | |
| source | 1..9<br>mol_type = protein<br>organism = synthetic construct | |
| SEQUENCE: 471 | | |
| FQGSHVPFT | | 9 |
| | | |
| SEQ ID NO: 472<br>FEATURE<br>misc_feature | moltype = DNA length = 300<br>Location/Qualifiers<br>1..300<br>note = IGKV2-29*03 light chain variable region sequence | |
| source | 1..300<br>mol_type = other DNA<br>organism = synthetic construct | |
| SEQUENCE: 472 | | |
| gatattgtga tgacccagac tccactctct ctgtccgtca cccctggaca gccggcctcc | | 60 |
| atctcctgca agtctagtca gagcctcctg catagtgatg gaaagaccta tttgtattgg | | 120 |
| tacctgcaga agccaggcca gtctccacac ctcctgatct atgaagtttc cagccggttc | | 180 |
| tctggagtgc cagataggtt cagtggcagc gggtcaggga cagatttcac actgaaaatc | | 240 |
| agccgggtgg aggctgagga tgttggggtt tattactgca tgcaaggtat acaccttcct | | 300 |
| | | |
| SEQ ID NO: 473<br>FEATURE<br>REGION | moltype = AA length = 100<br>Location/Qualifiers<br>1..100<br>note = IGKV2-29*03 light chain variable region sequence | |
| source | 1..100<br>mol_type = protein<br>organism = synthetic construct | |
| SEQUENCE: 473 | | |
| DIVMTQTPLS LSVTPGQPAS ISCKSSQSLL HSDGKTYLYW YLQKPGQSPQ LLIYEVSSRF | | 60 |
| SGVPDRFSGS GSGTDFTLKI SRVEAEDVGV YYCMQGIHLP | | 100 |
| | | |
| SEQ ID NO: 474<br>FEATURE<br>misc_feature | moltype = DNA length = 69<br>Location/Qualifiers<br>1..69<br>note = IGKV2-29*03 light chain variable framework region 1<br>(FWR1) acidsequence | |
| source | 1..69<br>mol_type = other DNA<br>organism = synthetic construct | |
| SEQUENCE: 474 | | |
| gatattgtga tgacccagac tccactctct ctgtccgtca cccctggaca gccggcctcc | | 60 |
| atctcctgc | | 69 |
| | | |
| SEQ ID NO: 475<br>FEATURE<br>REGION | moltype = AA length = 23<br>Location/Qualifiers<br>1..23<br>note = IGKV2-29*03 light chain variable framework region 1<br>(FWR1) acidsequence | |
| source | 1..23<br>mol_type = protein<br>organism = synthetic construct | |
| SEQUENCE: 475 | | |
| DIVMTQTPLS LSVTPGQPAS ISC | | 23 |
| | | |
| SEQ ID NO: 476<br>FEATURE<br>misc_feature | moltype = DNA length = 49<br>Location/Qualifiers<br>1..49<br>note = IGKV2-29*03 light chain variable complementarity<br>determiningregions 1 (CDR1) sequence | |
| source | 1..49<br>mol_type = other DNA<br>organism = synthetic construct | |
| SEQUENCE: 476 | | |
| aagtctagtc agagcctcct gcatagtgat ggaaagacct atttsgtat | | 49 |
| | | |
| SEQ ID NO: 477<br>FEATURE<br>REGION | moltype = AA length = 16<br>Location/Qualifiers<br>1..16<br>note = IGKV2-29*03 light chain variable complementarity<br>determiningregions 1 (CDR1) sequence | |
| source | 1..16<br>mol_type = protein<br>organism = synthetic construct | |
| SEQUENCE: 477 | | |
| KSSQSLLHSD GKTYLY | | 16 |
| | | |
| SEQ ID NO: 478 | moltype = DNA length = 45 | |

```
FEATURE                 Location/Qualifiers
misc_feature            1..45
                        note = IGKV2-29*03 light chain variable framework region 2
                        (FWR2)sequence
source                  1..45
                        mol_type = other DNA
                        organism = synthetic construct
SEQUENCE: 478
tggtacctgc agaagccagg ccagtctcca cagctcctga tctat              45

SEQ ID NO: 479          moltype = AA  length = 15
FEATURE                 Location/Qualifiers
REGION                  1..15
                        note = IGKV2-29*03 light chain variable framework region 2
                        (FWR2)sequence
source                  1..15
                        mol_type = protein
                        organism = synthetic construct
SEQUENCE: 479
WYLQKPGQSP QLLIY                                               15

SEQ ID NO: 480          moltype = DNA  length = 18
FEATURE                 Location/Qualifiers
misc_feature            1..18
                        note = IGKV2-29*03 light chain variable complementarity
                        determiningregions 2 (CDR2) sequence
source                  1..18
                        mol_type = other DNA
                        organism = synthetic construct
SEQUENCE: 480
gaagtttcca gccggttc                                            18

SEQ ID NO: 481          moltype = AA  length = 7
FEATURE                 Location/Qualifiers
REGION                  1..7
                        note = IGKV2-29*03 light chain variable complementarity
                        determiningregions 2 (CDR2) sequence
source                  1..7
                        mol_type = protein
                        organism = synthetic construct
SEQUENCE: 481
EVSSRFS                                                        7

SEQ ID NO: 482          moltype = DNA  length = 96
FEATURE                 Location/Qualifiers
misc_feature            1..96
                        note = IGKV2-29*03 light chain variable framework region 3
                        (FWR3)sequence
source                  1..96
                        mol_type = other DNA
                        organism = synthetic construct
SEQUENCE: 482
ggagtgccag ataggttcag tgcagcgggt caggacag atttcacact gaaaatcagc    60
cgggtggagg ctgaggatgt tggggtttat tactgc                           96

SEQ ID NO: 483          moltype = AA  length = 32
FEATURE                 Location/Qualifiers
REGION                  1..32
                        note = IGKV2-29*03 light chain variable framework region 3
                        (FWR3)sequence
source                  1..32
                        mol_type = protein
                        organism = synthetic construct
SEQUENCE: 483
GVPDRFSGSG SGTDFTLKIS RVEAEDVGVY YC                             32

SEQ ID NO: 484          moltype = DNA  length = 21
FEATURE                 Location/Qualifiers
misc_feature            1..21
                        note = IGKV2-29*03 light chain variable complementarity
                        determiningregions3 (CDR3) sequence
source                  1..21
                        mol_type = other DNA
                        organism = synthetic construct
SEQUENCE: 484
atgcaaggta tacaccttcc t                                        21

SEQ ID NO: 485          moltype = AA  length = 7
FEATURE                 Location/Qualifiers
```

| | |
|---|---|
| REGION | 1..7<br>note = IGKV2-29*03 light chain variable complementarity determiningregions3 (CDR3) sequence |
| source | 1..7<br>mol_type = protein<br>organism = synthetic construct |

SEQUENCE: 485
MQGIHLP                                                              7

| | |
|---|---|
| SEQ ID NO: 486 | moltype = DNA  length = 342 |
| FEATURE | Location/Qualifiers |
| misc_feature | 1..342<br>note = Humanized C3 light chain variable region sequence |
| source | 1..342<br>mol_type = other DNA<br>organism = synthetic construct |

SEQUENCE: 486
gatattgtga tgacccagac tccactctct ctgtccgtca cccctggaca gccggcctcc   60
atctcctgca ggtctagtca gaccattgtc catagtaatg gaaacaccta tttggagtgg  120
tacctgcaga agccaggcca gtctccacag ctcctgatct ataaggtttc caaccggttc  180
tctggagtgc cagataggtt cagtggcagc gggtcaggga cagatttcac actgaaaatc  240
agccgggtgg aggctgagga tgttggggtt tattactgct tccaaggtag ccacgtgcct  300
ttcaccttcg gcggagggac caaggtggag atcaaacgaa ct                     342

| | |
|---|---|
| SEQ ID NO: 487 | moltype = AA  length = 114 |
| FEATURE | Location/Qualifiers |
| REGION | 1..114<br>note = Humanized C3 light chain variable region sequence |
| source | 1..114<br>mol_type = protein<br>organism = synthetic construct |

SEQUENCE: 487
DIVMTQTPLS LSVTPGQPAS ISCRSSQTIV HSNGNTYLEW YLQKPGQSPQ LLIYKVSNRF   60
SGVPDRFSGS GSGTDFTLKI SRVEAEDVGV YYCFQGSHVP FTFGGGTKVE IKRT        114

| | |
|---|---|
| SEQ ID NO: 488 | moltype = DNA  length = 69 |
| FEATURE | Location/Qualifiers |
| misc_feature | 1..69<br>note = Humanized C3 light chain variable framework region 1 (FWR1) acidsequence |
| source | 1..69<br>mol_type = other DNA<br>organism = synthetic construct |

SEQUENCE: 488
gatattgtga tgacccagac tccactctct ctgtccgtca cccctggaca gccggcctcc   60
atctcctgc                                                           69

| | |
|---|---|
| SEQ ID NO: 489 | moltype = AA  length = 23 |
| FEATURE | Location/Qualifiers |
| REGION | 1..23<br>note = Humanized C3 light chain variable framework region 1 (FWR1) acidsequence |
| source | 1..23<br>mol_type = protein<br>organism = synthetic construct |

SEQUENCE: 489
DIVMTQTPLS LSVTPGQPAS ISC                                            23

| | |
|---|---|
| SEQ ID NO: 490 | moltype = DNA  length = 47 |
| FEATURE | Location/Qualifiers |
| misc_feature | 1..47<br>note = Humanized C3 light chain variable complementarity determiningregions 1 (CDR1) sequence |
| source | 1..47<br>mol_type = other DNA<br>organism = synthetic construct |

SEQUENCE: 490
ggtctagtca gaccattgtc catagtaatg gaaacaccta tttggag                  47

| | |
|---|---|
| SEQ ID NO: 491 | moltype = AA  length = 16 |
| FEATURE | Location/Qualifiers |
| REGION | 1..16<br>note = Humanized C3 light chain variable complementarity determiningregions 1 (CDR1) sequence |
| source | 1..16<br>mol_type = protein<br>organism = synthetic construct |

SEQUENCE: 491
RSSQTIVHSN GNTYLE                                                    16

```
SEQ ID NO: 492          moltype = DNA  length = 45
FEATURE                 Location/Qualifiers
misc_feature            1..45
                        note = Humanized C3 light chain variable framework region 2
                        (FWR2) acidsequence
source                  1..45
                        mol_type = other DNA
                        organism = synthetic construct
SEQUENCE: 492
tggtacctgc agaagccagg ccagtctcca cagctcctga tctat               45

SEQ ID NO: 493          moltype = AA  length = 15
FEATURE                 Location/Qualifiers
REGION                  1..15
                        note = Humanized C3 light chain variable framework region 2
                        (FWR2) acidsequence
source                  1..15
                        mol_type = protein
                        organism = synthetic construct
SEQUENCE: 493
WYLQKPGQSP QLLIY                                                15

SEQ ID NO: 494          moltype = DNA  length = 21
FEATURE                 Location/Qualifiers
misc_feature            1..21
                        note = Humanized C3 light chain variable complementarity
                        determiningregions 2 (CDR2) sequence
source                  1..21
                        mol_type = other DNA
                        organism = synthetic construct
SEQUENCE: 494
aaggtttcca accggttctc t                                         21

SEQ ID NO: 495          moltype = AA  length = 7
FEATURE                 Location/Qualifiers
REGION                  1..7
                        note = Humanized C3 light chain variable complementarity
                        determiningregions 2 (CDR2) sequence
source                  1..7
                        mol_type = protein
                        organism = synthetic construct
SEQUENCE: 495
KVSNRFS                                                         7

SEQ ID NO: 496          moltype = DNA  length = 96
FEATURE                 Location/Qualifiers
misc_feature            1..96
                        note = Humanized C3 light chain variable framework region 3
                        (FWR3) acidsequence
source                  1..96
                        mol_type = other DNA
                        organism = synthetic construct
SEQUENCE: 496
ggagtgccag ataggttcag tggcagcggg tcaggacag atttcacact gaaaatcagc 60
cgggtggagg ctgaggatgt tggggtttat tactgc                         96

SEQ ID NO: 497          moltype = AA  length = 32
FEATURE                 Location/Qualifiers
REGION                  1..32
                        note = Humanized C3 light chain variable framework region 3
                        (FWR3) acidsequence
source                  1..32
                        mol_type = protein
                        organism = synthetic construct
SEQUENCE: 497
GVPDRFSGSG SGTDFTLKIS RVEAEDVGVY YC                             32

SEQ ID NO: 498          moltype = DNA  length = 27
FEATURE                 Location/Qualifiers
misc_feature            1..27
                        note = Humanized C3 light chain variable complementarity
                        determiningregions 3 (CDR3) sequence
source                  1..27
                        mol_type = other DNA
                        organism = synthetic construct
SEQUENCE: 498
ttccaaggta gccacgtgcc tttcacc                                   27
```

| SEQ ID NO: 499 | moltype = AA length = 9 |
| --- | --- |
| FEATURE | Location/Qualifiers |
| REGION | 1..9 |
| | note = Humanized C3 light chain variable complementarity determiningregions 3 (CDR3) sequence |
| source | 1..9 |
| | mol_type = protein |
| | organism = synthetic construct |

SEQUENCE: 499
FQGSHVPFT 9

| SEQ ID NO: 500 | moltype = DNA length = 666 |
| --- | --- |
| FEATURE | Location/Qualifiers |
| misc_feature | 1..666 |
| | note = Humanized C3 lambda light chainsequence |
| source | 1..666 |
| | mol_type = other DNA |
| | organism = synthetic construct |

SEQUENCE: 500
```
gatattgtga tgacccagac tccactctct ctgtccgtca cccctggaca gccggcctcc   60
atctcctgca ggtctagtca gaccattgtc catagtaatg gaaacaccta tttggagtgg  120
tacctgcaga agccaggcca gtctccacag ctcctgatct ataaggtttc aaccggttc   180
tctggagtgc cagataggtt cagtggcagc gggtcaggga cagatttcac actgaaaatc  240
agccgggtgg aggctgagga tgttggggtt tattactgct tccaaggtag ccacgtgcct  300
ttcaccttcg gcggagggac caaggtggag atcaaacgaa ctggtcagcc caaggctgcc  360
ccctcggtca ctctgttccc gccctcctct gaggagcttc aagccaacaa ggccacactg  420
gtgtgtctct aagtgacttc taccccggga gccgtgacag tggcctgaa ggcagatagc  480
agccccgtca aggcgggagt ggagaccacc acacccctcca aacaaagcaa caacaagtac  540
gcggccagca gctatctgag cctgacgcct gagcagtgga agtcccacag aagctacagc  600
tgccaggtca cgcatgaagg gagcaccgtg agaagacag tggcccctac agaatgttca  660
tagtaa                                                              666
```

| SEQ ID NO: 501 | moltype = AA length = 220 |
| --- | --- |
| FEATURE | Location/Qualifiers |
| REGION | 1..220 |
| | note = Humanized C3 lambda light chainsequence |
| source | 1..220 |
| | mol_type = protein |
| | organism = synthetic construct |

SEQUENCE: 501
```
DIVMTQTPLS LSVTPGQPAS ISCRSSQTIV HSNGNTYLEW YLQKPGQSPQ LLIYKVSNRF   60
SGVPDRFSGS GSGTDFTLKI SRVEAEDVGV YYCFQGSHVP FTGGGTKVE IKRTGQPKAA   120
PSVTLFPPSS EELQANKATL VCLISDFYPG AVTVAWKADS SPVKAGVETT TPSKQSNNKY  180
AASSYLSLTP EQWKSHRSYS CQVTHEGSTV EKTVAPTECS                          220
```

| SEQ ID NO: 502 | moltype = DNA length = 666 |
| --- | --- |
| FEATURE | Location/Qualifiers |
| misc_feature | 1..666 |
| | note = Humanized C3 Kappa light chain |
| source | 1..666 |
| | mol_type = other DNA |
| | organism = synthetic construct |

SEQUENCE: 502
```
gatattgtga tgacccagac tccactctct ctgtccgtca cccctggaca gccggcctcc   60
atctcctgca ggtctagtca gaccattgtc catagtaatg gaaacaccta tttggagtgg  120
tacctgcaga agccaggcca gtctccacag ctcctgatct ataaggtttc aaccggttc   180
tctggagtgc cagataggtt cagtggcagc gggtcaggga cagatttcac actgaaaatc  240
agccgggtgg aggctgagga tgttggggtt tattactgct tccaaggtag ccacgtgcct  300
ttcaccttcg gcggagggac caaggtggag atcaaacgaa ctacggtggc tgcaccatct  360
gtcttcatct tcccgccatc tgatgagcag ttgaaatctg gaactgcctc tgttgtgtgc  420
ctgctgaata acttctatcc cagagaggcc aaagtacagt ggaaggtgga taacgccctc  480
caatcgggta actcccagga gagtgtcaca gagcaggaca gcaaggacag cacctacagc  540
ctcagcagca ccctgacgct gagcaaagca gactacgaga aacacaaagt ctacgcctgc  600
gaagtcaccc atcagggcct gagctcgccc gtcacaaaga gcttcaacag gggagagtgt  660
tagtaa                                                              666
```

| SEQ ID NO: 503 | moltype = AA length = 220 |
| --- | --- |
| FEATURE | Location/Qualifiers |
| REGION | 1..220 |
| | note = Humanized C3 Kappa light chain |
| source | 1..220 |
| | mol_type = protein |
| | organism = synthetic construct |

SEQUENCE: 503
```
DIVMTQTPLS LSVTPGQPAS ISCRSSQTIV HSNGNTYLEW YLQKPGQSPQ LLIYKVSNRF   60
SGVPDRFSGS GSGTDFTLKI SRVEAEDVGV YYCFQGSHVP FTGGGTKVE IKRTTVAAPS   120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                          220
```

```
SEQ ID NO: 504              moltype = DNA  length = 815
FEATURE                     Location/Qualifiers
misc_feature                1..815
                            note = Humanized C3 Kappa light gBLOCK sequence
source                      1..815
                            mol_type = other DNA
                            organism = synthetic construct
SEQUENCE: 504
agctggctag gtaagcttgg taccgagctc ggatccacgc caccatggag acagacacac    60
tcctgctatg ggtactgctg ctctgggttc caggttccac tggtgacgat attgtgatga   120
cccagactcc actctctctg tccgtcaccc ctggacagcc ggcctccatc tcctgcaggt   180
ctagtcagac cattgtccat agtaatggaa acacctattt ggagtggtac ctgcagaagc   240
caggccagtc tccacagctc ctgatctata aggtttccaa ccggttctct ggagtgccag   300
ataggttcag tggcagcggg tcagggacag atttcacact gaaaatcagc cgggtggagg   360
ctgaggatgt tggggtttat tactgctttc aaggtagcca cgtgcctttc accttcggcg   420
gagggaccaa ggtggagatc aaacgaacta cggtggctgc accatctgtc ttcatcttcc   480
cgccatctga tgagcagttg aaatctggaa ctgcctctgt tgtgtgcctg ctgaataact   540
tctatcccag agaggccaaa gtacagtgga aggtggataa cgccctccaa tcgggtaact   600
cccaggagag tgtcacagag caggacagca aggacagcac ctacagcctc agcagcaccc   660
tgacgctgag caaagcagac tacgagaaac acaaagtcta cgcctgcgaa gtcacccatc   720
agggcctgag ctcgcccgtc acaaagagct tcaacagggg agagtgttag taagtttaaa   780
cccgctgatc agcctcgact gtgccttcta gttgc                              815

SEQ ID NO: 505              moltype = DNA  length = 321
FEATURE                     Location/Qualifiers
misc_feature                1..321
                            note = Mouse C8 heavy chain variable region sequence
source                      1..321
                            mol_type = other DNA
                            organism = synthetic construct
SEQUENCE: 505
gaagtgatgg tcgtggaaag cggcggtggt ctggtaaagc cgggggggatc ccttaagctt    60
tcttgcgccg catccgggtt cacgttctcc ggctatgcca tgtcctgggt ccgacagact   120
cccgaaaagc gcttggaatg ggtggccact atctcctccg gggggacgta catctactac   180
cccgacagtg tgaaaggaag atttacaata tctcgcgaca acgcaaaaaa taccttgtat   240
cttcaaatga gctccctgcg gtcagaggac actgccatgt actattgcgc ccgcctgggc   300
ggcgacaatt actatgagta t                                              321

SEQ ID NO: 506              moltype = AA  length = 107
FEATURE                     Location/Qualifiers
REGION                      1..107
                            note = Mouse C8 heavy chain variable region sequence
source                      1..107
                            mol_type = protein
                            organism = synthetic construct
SEQUENCE: 506
EVMVVESGGG LVKPGGSLKL SCAASGFTFS GYAMSWVRQT PEKRLEWVAT ISSGGTYIYY    60
PDSVKGRFTI SRDNAKNTLY LQMSSLRSED TAMYYCARLG GDNYYEY                 107

SEQ ID NO: 507              moltype = DNA  length = 15
FEATURE                     Location/Qualifiers
misc_feature                1..15
                            note = Mouse C8 heavy chain variable complementarity
                            determining region1 (CDR1) sequence
source                      1..15
                            mol_type = other DNA
                            organism = synthetic construct
SEQUENCE: 507
ggctatgcca tgtcc                                                      15

SEQ ID NO: 508              moltype = AA  length = 5
FEATURE                     Location/Qualifiers
REGION                      1..5
                            note = Mouse C8 heavy chain variable complementarity
                            determining region1 (CDR1) sequence
source                      1..5
                            mol_type = protein
                            organism = synthetic construct
SEQUENCE: 508
GYAMS                                                                  5

SEQ ID NO: 509              moltype = DNA  length = 51
FEATURE                     Location/Qualifiers
misc_feature                1..51
                            note = Mouse C8 heavy chain variable complementarity
                            determining region2 (CDR2) sequence
source                      1..51
                            mol_type = other DNA
                            organism = synthetic construct
```

```
SEQUENCE: 509
actatctcct ccgggggac gtacatctac taccccgaca gtgtgaaagg a                51

SEQ ID NO: 510         moltype = AA  length = 17
FEATURE                Location/Qualifiers
REGION                 1..17
                       note = Mouse C8 heavy chain variable complementarity
                       determining region2 (CDR2) sequence
source                 1..17
                       mol_type = protein
                       organism = synthetic construct
SEQUENCE: 510
TISSGGTYIY YPDSVKG                                                     17

SEQ ID NO: 511         moltype = DNA  length = 27
FEATURE                Location/Qualifiers
misc_feature           1..27
                       note = Mouse C8 heavy chain variable complementarity
                       determining region3 (CDR3) sequence
source                 1..27
                       mol_type = other DNA
                       organism = synthetic construct
SEQUENCE: 511
ctgggcggcg acaattacta tgagtat                                          27

SEQ ID NO: 512         moltype = AA  length = 9
FEATURE                Location/Qualifiers
REGION                 1..9
                       note = Mouse C8 heavy chain variable complementarity
                       determining region3 (CDR3) sequence
source                 1..9
                       mol_type = protein
                       organism = synthetic construct
SEQUENCE: 512
LGGDNYYEY                                                              9

SEQ ID NO: 513         moltype = DNA  length = 292
FEATURE                Location/Qualifiers
misc_feature           1..292
                       note = IGHV3-21*04 heavy chain variable region sequence
source                 1..292
                       mol_type = other DNA
                       organism = synthetic construct
SEQUENCE: 513
gaggtgcagc tggtggagtc tgggggaggc ctggtcaagc ctgggggtc cctgagactc       60
tcctgtgcag cctctggatt caccttcagt agctatagca tgaactgggt ccgccaggct      120
ccagggaagg ggctgagtg ggtctcatcc attagtagta gtagttta catatactac         180
gcagactcag tgaagggccg attcaccatc tccagagaca acgccaagaa ctcactgtat      240
ctgcaaatga acagcctgag agccgaggac acggccgtgt attactgtgc ga              292

SEQ ID NO: 514         moltype = AA  length = 98
FEATURE                Location/Qualifiers
REGION                 1..98
                       note = IGHV3-21*04 heavy chain variable region sequence
source                 1..98
                       mol_type = protein
                       organism = synthetic construct
SEQUENCE: 514
EVQLVESGGG LVKPGGSLRL SCAASGFTFS SYSMNWVRQA PGKGLEWVSS ISSSSSYIYY      60
ADSVKGRFTI SRDNAKNSLY LQMNSLRAED TAVYYCAR                              98

SEQ ID NO: 515         moltype = DNA  length = 90
FEATURE                Location/Qualifiers
misc_feature           1..90
                       note = IGHV3-21*04 heavy chain variable framework region 1
                       (FWR1) sequence
source                 1..90
                       mol_type = other DNA
                       organism = synthetic construct
SEQUENCE: 515
gaggtgcagc tggtggagtc tgggggaggc ctggtcaagc ctgggggtc cctgagactc       60
tcctgtgcag cctctggatt caccttcagt                                       90

SEQ ID NO: 516         moltype = AA  length = 30
FEATURE                Location/Qualifiers
REGION                 1..30
                       note = IGHV3-21*04 heavy chain variable framework region 1
                       (FWR1) sequence
source                 1..30
```

```
                        mol_type = protein
                        organism = synthetic construct
SEQUENCE: 516
EVQLVESGGG LVKPGGSLRL SCAASGFTFS                                      30

SEQ ID NO: 517          moltype = DNA  length = 15
FEATURE                 Location/Qualifiers
misc_feature            1..15
                        note = IGHV3-21*04 heavy chain variable complementarity
                        determiningregions 1 (CDR1) sequence
source                  1..15
                        mol_type = other DNA
                        organism = synthetic construct
SEQUENCE: 517
agctatagca tgaac                                                      15

SEQ ID NO: 518          moltype = AA  length = 5
FEATURE                 Location/Qualifiers
REGION                  1..5
                        note = IGHV3-21*04 heavy chain variable complementarity
                        determiningregions 1 (CDR1) sequence
source                  1..5
                        mol_type = protein
                        organism = synthetic construct
SEQUENCE: 518
SYSMN                                                                  5

SEQ ID NO: 519          moltype = DNA  length = 39
FEATURE                 Location/Qualifiers
misc_feature            1..39
                        note = IGHV3-21*04 heavy chain variable framework region 2
                        (FWR2)sequence
source                  1..39
                        mol_type = other DNA
                        organism = synthetic construct
SEQUENCE: 519
tgggtccgcc aggctccagg gaaggggctg gagtgggtc                            39

SEQ ID NO: 520          moltype = AA  length = 13
FEATURE                 Location/Qualifiers
REGION                  1..13
                        note = IGHV3-21*04 heavy chain variable framework region 2
                        (FWR2)sequence
source                  1..13
                        mol_type = protein
                        organism = synthetic construct
SEQUENCE: 520
WVRQAPGKGL EWV                                                        13

SEQ ID NO: 521          moltype = DNA  length = 54
FEATURE                 Location/Qualifiers
misc_feature            1..54
                        note = IGHV3-21*04 heavy chain variable complementarity
                        determiningregions 2 (CDR2) sequence
source                  1..54
                        mol_type = other DNA
                        organism = synthetic construct
SEQUENCE: 521
tcatccatta gtagtagtag tagttacata tactacgcag actcagtgaa gggc           54

SEQ ID NO: 522          moltype = AA  length = 18
FEATURE                 Location/Qualifiers
REGION                  1..18
                        note = IGHV3-21*04 heavy chain variable complementarity
                        determiningregions 2 (CDR2) sequence
source                  1..18
                        mol_type = protein
                        organism = synthetic construct
SEQUENCE: 522
SSISSSSSYI YYADSVKG                                                   18

SEQ ID NO: 523          moltype = DNA  length = 94
FEATURE                 Location/Qualifiers
misc_feature            1..94
                        note = IGHV3-21*04 heavy chain variable framework region 3
                        (FWR3)sequence
source                  1..94
                        mol_type = other DNA
                        organism = synthetic construct
```

```
SEQUENCE: 523
cgattcacca tctccagaga caacgccaag aactcactgt atctgcaaat gaacagcctg    60
agagccgagg acacggccgt gtattactgt gcga                                94

SEQ ID NO: 524          moltype = AA   length = 32
FEATURE                 Location/Qualifiers
REGION                  1..32
                        note = IGHV3-21*04 heavy chain variable framework region 3
                        (FWR3)sequence
source                  1..32
                        mol_type = protein
                        organism = synthetic construct
SEQUENCE: 524
RFTISRDNAK NSLYLQMNSL RAEDTAVYYC AR                                  32

SEQ ID NO: 525          moltype = DNA   length = 354
FEATURE                 Location/Qualifiers
misc_feature            1..354
                        note = Humanized C8 heavy chain variable region sequence
source                  1..354
                        mol_type = other DNA
                        organism = synthetic construct
SEQUENCE: 525
gaggtgcagc tggtggagtc tgggggaggc ctggtcaagc ctggggggtc cctgagactc    60
tcctgtgcag cctctggatt caccttcagt ggctatgcca tgagctgggt ccgccaggct   120
ccagggaagg ggctggagtg ggtctcaacc attagtagtg gcggaaccta catatactac   180
cctgactcag tgaagggccg attcaccatc tccagagaca acgccaagaa ctcactgtat   240
ctgcaaatga acagcctgag agccgaggac acggccgtgt attactgtgc gagactgggc   300
ggcgataact attatgaata ttggggcaaa gggaccacgg tcaccgtctc ctcc         354

SEQ ID NO: 526          moltype = AA   length = 118
FEATURE                 Location/Qualifiers
REGION                  1..118
                        note = Humanized C8 heavy chain variable region sequence
source                  1..118
                        mol_type = protein
                        organism = synthetic construct
SEQUENCE: 526
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYWGK GTTVTVSS     118

SEQ ID NO: 527          moltype = DNA   length = 90
FEATURE                 Location/Qualifiers
misc_feature            1..90
                        note = Humanized C8 heavy chain variable framework region 1
                        (FWR1)sequence
source                  1..90
                        mol_type = other DNA
                        organism = synthetic construct
SEQUENCE: 527
gaggtgcagc tggtggagtc tgggggaggc ctggtcaagc ctggggggtc cctgagactc    60
tcctgtgcag cctctggatt caccttcagt                                     90

SEQ ID NO: 528          moltype = AA   length = 30
FEATURE                 Location/Qualifiers
REGION                  1..30
                        note = Humanized C8 heavy chain variable framework region 1
                        (FWR1)sequence
source                  1..30
                        mol_type = protein
                        organism = synthetic construct
SEQUENCE: 528
EVQLVESGGG LVKPGGSLRL SCAASGFTFS                                     30

SEQ ID NO: 529          moltype = DNA   length = 15
FEATURE                 Location/Qualifiers
misc_feature            1..15
                        note = Humanized C8 heavy chain variable complementarity
                        determiningregion 1 (CDR1) sequence
source                  1..15
                        mol_type = other DNA
                        organism = synthetic construct
SEQUENCE: 529
ggctatgcca tgagc                                                     15

SEQ ID NO: 530          moltype = AA   length = 5
FEATURE                 Location/Qualifiers
REGION                  1..5
                        note = Humanized C8 heavy chain variable complementarity
```

```
                              determiningregion 1 (CDR1) sequence
source                        1..5
                              mol_type = protein
                              organism = synthetic construct
SEQUENCE: 530
GYAMS                                                                   5

SEQ ID NO: 531                moltype = DNA  length = 42
FEATURE                       Location/Qualifiers
misc_feature                  1..42
                              note = Humanized C8 heavy chain variable framework region 2
                              (FWR2)sequence
source                        1..42
                              mol_type = other DNA
                              organism = synthetic construct
SEQUENCE: 531
tgggtccgcc aggctccagg gaaggggctg gagtgggtct ca                          42

SEQ ID NO: 532                moltype = AA   length = 14
FEATURE                       Location/Qualifiers
REGION                        1..14
                              note = Humanized C8 heavy chain variable framework region 2
                              (FWR2)sequence
source                        1..14
                              mol_type = protein
                              organism = synthetic construct
SEQUENCE: 532
WVRQAPGKGL EWVS                                                        14

SEQ ID NO: 533                moltype = DNA   length = 51
FEATURE                       Location/Qualifiers
misc_feature                  1..51
                              note = Humanized C8 heavy chain variable complementarity
                              determiningregion 2 (CDR2) sequence
source                        1..51
                              mol_type = other DNA
                              organism = synthetic construct
SEQUENCE: 533
accattagta gtggcggaac ctacatatac taccctgact cagtgaaggg c                51

SEQ ID NO: 534                moltype = AA   length = 17
FEATURE                       Location/Qualifiers
REGION                        1..17
                              note = Humanized C8 heavy chain variable complementarity
                              determiningregion 2 (CDR2) sequence
source                        1..17
                              mol_type = protein
                              organism = synthetic construct
SEQUENCE: 534
TISSGGTYIY YPDSVKG                                                     17

SEQ ID NO: 535                moltype = DNA   length = 96
FEATURE                       Location/Qualifiers
misc_feature                  1..96
                              note = Humanized C8 heavy chain variable framework region 3
                              (FWR3)sequence
source                        1..96
                              mol_type = other DNA
                              organism = synthetic construct
SEQUENCE: 535
cgattcacca tctccagaga caacgccaag aactcactgt atctgcaaat gaacagcctg       60
agagccgagg acacggccgt gtattactgt gcgaga                                 96

SEQ ID NO: 536                moltype = AA   length = 32
FEATURE                       Location/Qualifiers
REGION                        1..32
                              note = Humanized C8 heavy chain variable framework region 3
                              (FWR3)sequence
source                        1..32
                              mol_type = protein
                              organism = synthetic construct
SEQUENCE: 536
RFTISRDNAK NSLYLQMNSL RAEDTAVYYC AR                                    32

SEQ ID NO: 537                moltype = DNA   length = 27
FEATURE                       Location/Qualifiers
misc_feature                  1..27
                              note = Humanized C8 heavy chain variable complementarity
                              determiningregion 3 (CDR3) sequence
```

```
source                  1..27
                        mol_type = other DNA
                        organism = synthetic construct
SEQUENCE: 537
ctgggcggcg ataactatta tgaatat                                           27

SEQ ID NO: 538          moltype = AA   length = 9
FEATURE                 Location/Qualifiers
REGION                  1..9
                        note = Humanized C8 heavy chain variable complementarity
                         determiningregion 3 (CDR3) sequence
source                  1..9
                        mol_type = protein
                        organism = synthetic construct
SEQUENCE: 538
LGGDNYYEY                                                                9

SEQ ID NO: 539          moltype = DNA   length = 1350
FEATURE                 Location/Qualifiers
misc_feature            1..1350
                        note = Humanized C8 IgG1 heavy chain sequence
source                  1..1350
                        mol_type = other DNA
                        organism = synthetic construct
SEQUENCE: 539
gaggtgcagc tggtggagtc tgggggaggc ctggtcaagc ctggggggtc cctgagactc         60
tcctgtgcag cctctggatt caccttcagt ggctatgcca tgagctgggt ccgccaggct        120
ccagggaagg gctggagtg gtctcaacc attagtagtg gcggaaccta catatactac         180
cctgactcag tgaagggccg attcaccatc tccagagaca cgccaagaa ctcactgtat        240
ctgcaaatga acagcctgag agccgaggac acggccgtgt attactgtgc gagactgggc        300
ggcgataact attatgaata ttggggcaaa gggaccacgg tcaccgtctc ctccgctagc        360
accaagggcc catcggtctt ccccctggca ccctcctcca agagcacctc tgggggcaca        420
gcggccctgg gctgcctggt caaggactac ttccccgaac cggtgacggt gtcgtggaac        480
tcaggcgccc tgaccagcgg cgtgcacacc ttcccggctg tcctacagtc ctcaggactc        540
tactccctca gcagcgtggt gaccgtgccc tccagcagct tgggcaccca gacctacatc        600
tgcaacgtga atcacaagcc cagcaacacc aaggtggaca agaaagttga gcccaaatct        660
tgtgacaaaa ctcacacatg cccaccgtgc ccagcacctg aactcctggg gggaccgtca        720
gtcttcctct tccccccaaa acccaaggac accctcatga tctcccggac ccctgaggtc        780
acatgcgtgg tggtggacgt gagccacgaa gaccctgagg tcaagttcaa ctggtacgtg        840
gacggcgtgg aggtgcataa tgccaagaca aagccgcggg aggagcagta caacagcacg        900
taccgtgtgg tcagcgtcct caccgtcctg caccaggact ggctgaatgg caaggagtac        960
aagtgcaagg tctccaacaa agccctccca gcccccatcg agaaaaccat ctccaaagcc       1020
aaagggcagc cccgagaacc acaggtgtac accctgcccc catcccggga ggatgagctg       1080
aagaaccagg tcagcctgac ctgcctggtc aaaggcttct atcccagcga catcgccgtg       1140
gagtgggaga gcaatgggca gccggagaac aactacaaga ccacgcctcc cgtgctggac       1200
tccgacggct ccttcttcct ctacagcaag ctcaccgtgg acaagagcag gtggcagcag       1260
gggaacgtct tctcatgctc cgtgatgcat gaggctctgc acaaccacta cacgcagaag       1320
agcctctccc tgtctccggg taaatgataa                                       1350

SEQ ID NO: 540          moltype = AA   length = 448
FEATURE                 Location/Qualifiers
REGION                  1..448
                        note = Humanized C8 IgG1 heavy chain sequence
source                  1..448
                        mol_type = protein
                        organism = synthetic construct
SEQUENCE: 540
EVQLVESGGG LVKPGGSLRL SCAASGFTFS GYAMSWVRQA PGKGLEWVST ISSGGTYIYY         60
PDSVKGRFTI SRDNAKNSLY LQMNSLRAED TAVYYCARLG GDNYYEYWGK GTTVTVSSAS        120
TKGPSVFPLA PSSKSTSGGT AALGCLVKDY FPEPVTVSWN SGALTSGVHT FPAVLQSSGL        180
YSLSSVVTVP SSSLGTQTYI CNVNHKPSNT KVDKKVEPKS CDKTHTCPPC PAPELLGGPS        240
VFLFPPKPKD TLMISRTPEV TCVVVDVSHE DPEVKFNWYV DGVEVHNAKT KPREEQYNST        300
YRVVSVLTVL HQDWLNGKEY KCKVSNKALP APIEKTISKA KGQPREPQVY TLPPSREEMT        360
KNQVSLTCLV KGFYPSDIAV EWESNGQPEN NYKTTPPVLD SDGSFFLYSK LTVDKSRWQQ        420
GNVFSCSVMH EALHNHYTQK SLSLSPGK                                         448

SEQ ID NO: 541          moltype = DNA   length = 1338
FEATURE                 Location/Qualifiers
misc_feature            1..1338
                        note = Humanized C8 IgG2 heavy chain sequence
source                  1..1338
                        mol_type = other DNA
                        organism = synthetic construct
SEQUENCE: 541
gaggtgcagc tggtggagtc tgggggaggc ctggtcaagc ctggggggtc cctgagactc         60
tcctgtgcag cctctggatt caccttcagt ggctatgcca tgagctgggt ccgccaggct        120
ccagggaagg gctggagtg gtctcaacc attagtagtg gcggaaccta catatactac         180
cctgactcag tgaagggccg attcaccatc tccagagaca cgccaagaa ctcactgtat        240
ctgcaaatga acagcctgag agccgaggac acggccgtgt attactgtgc gagactgggc        300
```

```
ggcgataact attatgaata ttggggcaaa gggaccacgg tcaccgtctc ctccgcctcc    360
accaagggcc catcggtctt cccccctggcg ccctgctcca ggagcacctc cgagagcaca   420
gccgccctgg gctgcctggt caaggactac ttccccgaac cggtgacggt gtcgtggaac    480
tcaggcgctc tgaccagcgg cgtgcacacc ttcccagctg tcctacagtc ctcaggactc    540
tactccctca gcagcgtggt gaccgtgccc tccagcaact tcggcaccca gacctacacc    600
tgcaacgtag atcacaagcc cagcaacacc aaggtggaca gacagttga gcgcaaatgt     660
tgtgtcgagt gcccaccgtg cccagcacca cctgtggcag gaccgtcagt cttcctcttc    720
cccccaaaac ccaaggacac cctcatgatc tcccggaccc ctgaggtcac gtgcgtggtg    780
gtggacgtga gccacgaaga ccccgaggtc cagttcaact ggtacgtgga cggcgtggag    840
gtgcataatg ccaagacaaa gccacgggag gagcagttca acagcacgtt ccgtgtggtc    900
agcgtcctca ccgttgtgca ccaggactgg ctgaacggca aggagtacaa gtgcaaggtc    960
tccaacaaag gcctcccagc ccccatcgag aaaaccatct ccaaaaccaa agggcagccc   1020
cgagaaccac aggtgtacac cctgccccca tcccgggagg agatgaccaa gaaccaggtc   1080
agcctgacct gcctggtcaa aggcttctac cccagcgaca tcgccgtgga gtgggagagc   1140
aatgggcagc cggagaacaa ctacaagacc acacctccca tgctggactc cgacggctcc   1200
ttcttcctct acagcaagct caccgtggac aagagcaggt ggcagcaggg gaacgtcttc   1260
tcatgctccg tgatgcatga ggctctgcac aaccactaca cgcagaagag cctctccctg   1320
tctccgggta aatagtaa                                                  1338

SEQ ID NO: 542          moltype = AA  length = 444
FEATURE                 Location/Qualifiers
REGION                  1..444
                        note = Humanized C8 IgG2 heavy chain sequence
source                  1..444
                        mol_type = protein
                        organism = synthetic construct
SEQUENCE: 542
EVQLVESGGG LVKPGGSLRL SCAASGFTFS GYAMSWVRQA PGKGLEWVST ISSGGTYIYY    60
PDSVKGRFTI SRDNAKNSLY LQMNSLRAED TAVYYCARLG GDNYYEYWGK GTTVTVSSAS   120
TKGPSVFPLA PCSRSTSEST AALGCLVKDY FPEPVTVSWN SGALTSGVHT FPAVLQSSGL   180
YSLSSVVTVP SSNFGTQTYT CNVDHKPSNT KVDKTVERKC CVECPPCPAP PVAGPSVFLF   240
PPKPKDTLMI SRTPEVTCVV VDVSHEDPEV QFNWYVDGVE VHNAKTKPRE EQFNSTFRVV   300
SVLTVVHQDW LNGKEYKCKV SNKGLPAPIE KTISKTKGQP REPQVYTLPP SREEMTKNQV   360
SLTCLVKGFY PSDIAVEWES NGQPENNYKT TPPMLDSDGS FFLYSKLTVD KSRWQQGNVF   420
SCSVMHEALH NHYTQKSLSL SPGK                                          444

SEQ ID NO: 543          moltype = DNA  length = 306
FEATURE                 Location/Qualifiers
misc_feature            1..306
                        note = Mouse C8 light chain variable region sequence
source                  1..306
                        mol_type = other DNA
                        organism = synthetic construct
SEQUENCE: 543
gacatcgtca ttacgcagac ccctgccagt cttgccgttt ctctgggcca gagggccact    60
atcagttaca gggcgagtaa gtctgtgagt accagcggct atagttacat gcattggaac   120
cagcagaaac cgggacatgcc accacgcctg cttatttatc tggtgtctaa tcttgagtcc   180
ggggtgcccg ccaggttcag cggcagcggc tctgggaccg acttcacact caacattcat   240
ccagtggaag aagaggacgc tgctacatac tactgtcaac acattcggga actgaccagg   300
agtgaa                                                               306

SEQ ID NO: 544          moltype = AA  length = 102
FEATURE                 Location/Qualifiers
REGION                  1..102
                        note = Mouse C8 light chain variable region sequence
source                  1..102
                        mol_type = protein
                        organism = synthetic construct
SEQUENCE: 544
DIVITQTPAS LAVSLGQRAT ISYRASKSVS TSGYSYMHWN QQKPGQPPRL LIYLVSNLES    60
GVPARFSGSG SGTDFTLNIH PVEEEDAATY YCQHIRELTR SE                      102

SEQ ID NO: 545          moltype = DNA  length = 45
FEATURE                 Location/Qualifiers
misc_feature            1..45
                        note = Mouse C8 light chain variable complementarity
                        determining region1 (CDR1) sequence
source                  1..45
                        mol_type = other DNA
                        organism = synthetic construct
SEQUENCE: 545
agggcgagta agtctgtgag taccagcggc tatagttaca tgcat                    45

SEQ ID NO: 546          moltype = AA  length = 15
FEATURE                 Location/Qualifiers
REGION                  1..15
                        note = Mouse C8 light chain variable complementarity
                        determining region1 (CDR1) sequence
source                  1..15
```

```
                         mol_type = protein
                         organism = synthetic construct
SEQUENCE: 546
RASKSVSTSG YSYMH                                                         15

SEQ ID NO: 547           moltype = DNA  length = 21
FEATURE                  Location/Qualifiers
misc_feature             1..21
                         note = Mouse C8 light chain variable complementarity
                          determining region2 (CDR2) sequence
source                   1..21
                         mol_type = other DNA
                         organism = synthetic construct
SEQUENCE: 547
ctggtgtcta atcttgagtc c                                                  21

SEQ ID NO: 548           moltype = AA  length = 7
FEATURE                  Location/Qualifiers
REGION                   1..7
                         note = Mouse C8 light chain variable complementarity
                          determining region2 (CDR2) sequence
source                   1..7
                         mol_type = protein
                         organism = synthetic construct
SEQUENCE: 548
LVSNLES                                                                  7

SEQ ID NO: 549           moltype = DNA  length = 30
FEATURE                  Location/Qualifiers
misc_feature             1..30
                         note = Mouse C8 light chain variable complementarity
                          determining region3 (CDR3) sequence
source                   1..30
                         mol_type = other DNA
                         organism = synthetic construct
SEQUENCE: 549
caacacattc gggaactgac caggagtgaa                                         30

SEQ ID NO: 550           moltype = AA  length = 10
FEATURE                  Location/Qualifiers
REGION                   1..10
                         note = Mouse C8 light chain variable complementarity
                          determining region3 (CDR3) sequence
source                   1..10
                         mol_type = protein
                         organism = synthetic construct
SEQUENCE: 550
QHIRELTRSE                                                               10

SEQ ID NO: 551           moltype = DNA  length = 303
FEATURE                  Location/Qualifiers
misc_feature             1..303
                         note = NCBI germline z00023 light chain variable region
                          sequence
source                   1..303
                         mol_type = other DNA
                         organism = synthetic construct
SEQUENCE: 551
gacatcgtga tgacccagtc tccagactcc ctggctgtgt ctctgggcga gagggccacc        60
atcaactgca agtccagcca gagtgtttta tacagctcca acaataagaa ctacttagct        120
tggtaccagc agaaaccagg acagcctcct aagctgctca tttactgggc atctacccgg        180
gaatccgggg tccctgaccg attcagtggc agcgggtctg ggacagattt cactctcacc        240
atcagcagcc tgcaggctga agatgtggca gtttattact gtcagcaata ttatagtact        300
cct                                                                      303

SEQ ID NO: 552           moltype = AA  length = 101
FEATURE                  Location/Qualifiers
REGION                   1..101
                         note = NCBI germline z00023 light chain variable region
                          sequence
source                   1..101
                         mol_type = protein
                         organism = synthetic construct
SEQUENCE: 552
DIVMTQSPDS LAVSLGERAT INCKSSQSVL YSSNNKNYLA WYQQKPGQPP KLLIYWASTR        60
ESGVPDRFSG SGSGTDFTLT ISSLQAEDVA VYYCQQYYST P                            101

SEQ ID NO: 553           moltype = DNA  length = 69
FEATURE                  Location/Qualifiers
```

```
misc_feature              1..69
                          note = NCBI germline z00023 light chain variable framework
                            region 1(FWR1) acid sequence
source                    1..69
                          mol_type = other DNA
                          organism = synthetic construct
SEQUENCE: 553
gacatcgtga tgacccagtc tccagactcc ctggctgtgt ctctgggcga gagggccacc  60
atcaactgc                                                          69

SEQ ID NO: 554            moltype = AA  length = 23
FEATURE                   Location/Qualifiers
REGION                    1..23
                          note = NCBI germline z00023 light chain variable framework
                            region 1(FWR1) acid sequence
source                    1..23
                          mol_type = protein
                          organism = synthetic construct
SEQUENCE: 554
DIVMTQSPDS LAVSLGERAT INC                                          23

SEQ ID NO: 555            moltype = DNA  length = 51
FEATURE                   Location/Qualifiers
misc_feature              1..51
                          note = NCBI germline z00023 light chain variable
                            complementaritydetermining regions 1 (CDR1) sequence
source                    1..51
                          mol_type = other DNA
                          organism = synthetic construct
SEQUENCE: 555
aagtccagcc agagtgtttt atacagctcc aacaataaga actacttagc t            51

SEQ ID NO: 556            moltype = AA  length = 17
FEATURE                   Location/Qualifiers
REGION                    1..17
                          note = NCBI germline z00023 light chain variable
                            complementaritydetermining regions 1 (CDR1) sequence
source                    1..17
                          mol_type = protein
                          organism = synthetic construct
SEQUENCE: 556
KSSQSVLYSS NNKNYLA                                                 17

SEQ ID NO: 557            moltype = DNA  length = 45
FEATURE                   Location/Qualifiers
misc_feature              1..45
                          note = NCBI germline z00023 light chain variable framework
                            region 2(FWR2) sequence
source                    1..45
                          mol_type = other DNA
                          organism = synthetic construct
SEQUENCE: 557
tggtaccagc agaaaccagg acagcctcct aagctgctca tttac                  45

SEQ ID NO: 558            moltype = AA  length = 15
FEATURE                   Location/Qualifiers
REGION                    1..15
                          note = NCBI germline z00023 light chain variable framework
                            region 2(FWR2) sequence
source                    1..15
                          mol_type = protein
                          organism = synthetic construct
SEQUENCE: 558
WYQQKPGQPP KLLIY                                                   15

SEQ ID NO: 559            moltype = DNA  length = 21
FEATURE                   Location/Qualifiers
misc_feature              1..21
                          note = NCBI germline z00023 light chain variable
                            complementaritydetermining regions 2 (CDR2) sequence
source                    1..21
                          mol_type = other DNA
                          organism = synthetic construct
SEQUENCE: 559
tgggcatcta cccgggaatc c                                            21

SEQ ID NO: 560            moltype = AA  length = 7
FEATURE                   Location/Qualifiers
REGION                    1..7
```

```
                        note = NCBI germline z00023 light chain variable
                           complementaritydetermining regions 2 (CDR2) sequence
source                  1..7
                        mol_type = protein
                        organism = synthetic construct
SEQUENCE: 560
WASTRES                                                                    7

SEQ ID NO: 561          moltype = DNA  length = 96
FEATURE                 Location/Qualifiers
misc_feature            1..96
                        note = NCBI germline z00023 light chain variable framework
                           region 3(FWR3) sequence
source                  1..96
                        mol_type = other DNA
                        organism = synthetic construct
SEQUENCE: 561
ggggtccctg accgattcag tggcagcggg tctgggacag atttcactct caccatcagc       60
agcctgcagg ctgaagatgt ggcagtttat tactgt                                 96

SEQ ID NO: 562          moltype = AA  length = 32
FEATURE                 Location/Qualifiers
REGION                  1..32
                        note = NCBI germline z00023 light chain variable framework
                           region 3(FWR3) sequence
source                  1..32
                        mol_type = protein
                        organism = synthetic construct
SEQUENCE: 562
GVPDRFSGSG SGTDFTLTIS SLQAEDVAVY YC                                       32

SEQ ID NO: 563          moltype = DNA  length = 21
FEATURE                 Location/Qualifiers
misc_feature            1..21
                        note = NCBI germline z00023 light chain variable
                           complementaritydetermining regions3 (CDR3) sequence
source                  1..21
                        mol_type = other DNA
                        organism = synthetic construct
SEQUENCE: 563
cagcaatatt atagtactcc t                                                   21

SEQ ID NO: 564          moltype = AA  length = 7
FEATURE                 Location/Qualifiers
REGION                  1..7
                        note = NCBI germline z00023 light chain variable
                           complementaritydetermining regions3 (CDR3) sequence
source                  1..7
                        mol_type = protein
                        organism = synthetic construct
SEQUENCE: 564
QQYYSTP                                                                    7

SEQ ID NO: 565          moltype = DNA  length = 342
FEATURE                 Location/Qualifiers
misc_feature            1..342
                        note = Humanized C8 light chain variable region sequence
source                  1..342
                        mol_type = other DNA
                        organism = synthetic construct
SEQUENCE: 565
gacatcgtga tgacccagtc tccagactcc ctggctgtgt ctctgggcga gagggccacc       60
atcaactgca gggccagcaa gagtgttagc accagcggct acagctacat gcactggtac      120
cagcagaaac caggacagcc tcctaagctg ctcatttacc tggtgtctaa cctggaatcc      180
ggggtccctg accgattcag tggcagcggg tctgggacag atttcactct caccatcagc      240
agcctgcagg ctgaagatgt ggcagtttat tactgtcaac acattcggga actgaccagg      300
agtgaattcg gcggagggac caaggtggag atcaaacgaa ct                         342

SEQ ID NO: 566          moltype = AA  length = 114
FEATURE                 Location/Qualifiers
REGION                  1..114
                        note = Humanized C8 light chain variable region sequence
source                  1..114
                        mol_type = protein
                        organism = synthetic construct
SEQUENCE: 566
DIVMTQSPDS LAVSLGERAT INCRASKSVS TSGYSYMHWY QQKPGQPPKL LIYLVSNLES        60
GVPDRFSGSG SGTDFTLTIS SLQAEDVAVY YCQHIRELTR SEFGGGTKVE IKRT             114
```

```
SEQ ID NO: 567          moltype = DNA   length = 69
FEATURE                 Location/Qualifiers
misc_feature            1..69
                        note = Humanized C8 light chain variable framework region 1
                        (FWR1)sequence
source                  1..69
                        mol_type = other DNA
                        organism = synthetic construct
SEQUENCE: 567
gacatcgtga tgacccagtc tccagactcc ctggctgtgt ctctgggcga gagggccacc   60
atcaactgc                                                           69

SEQ ID NO: 568          moltype = AA   length = 23
FEATURE                 Location/Qualifiers
REGION                  1..23
                        note = Humanized C8 light chain variable framework region 1
                        (FWR1)sequence
source                  1..23
                        mol_type = protein
                        organism = synthetic construct
SEQUENCE: 568
DIVMTQSPDS LAVSLGERAT INC                                           23

SEQ ID NO: 569          moltype = DNA   length = 42
FEATURE                 Location/Qualifiers
misc_feature            1..42
                        note = Humanized C8 light chain variable complementarity
                        determiningregion 1 (CDR1) sequence
source                  1..42
                        mol_type = other DNA
                        organism = synthetic construct
SEQUENCE: 569
agggccagca agagtgttag caccagcggc tacagctaca tg                      42

SEQ ID NO: 570          moltype = AA   length = 14
FEATURE                 Location/Qualifiers
REGION                  1..14
                        note = Humanized C8 light chain variable complementarity
                        determiningregion 1 (CDR1) sequence
source                  1..14
                        mol_type = protein
                        organism = synthetic construct
SEQUENCE: 570
RASKSVSTSG YSYM                                                     14

SEQ ID NO: 571          moltype = DNA   length = 48
FEATURE                 Location/Qualifiers
misc_feature            1..48
                        note = Humanized C8 light chain variable framework region 2
                        (FWR2)sequence
source                  1..48
                        mol_type = other DNA
                        organism = synthetic construct
SEQUENCE: 571
cactggtacc agcagaaacc aggacagcct cctaagctgc tcatttac                48

SEQ ID NO: 572          moltype = AA   length = 16
FEATURE                 Location/Qualifiers
REGION                  1..16
                        note = Humanized C8 light chain variable framework region 2
                        (FWR2)sequence
source                  1..16
                        mol_type = protein
                        organism = synthetic construct
SEQUENCE: 572
HWYQQKPGQP PKLLIY                                                   16

SEQ ID NO: 573          moltype = DNA   length = 21
FEATURE                 Location/Qualifiers
misc_feature            1..21
                        note = Humanized C8 light chain variable complementarity
                        determiningregion 2 (CDR2) sequence
source                  1..21
                        mol_type = other DNA
                        organism = synthetic construct
SEQUENCE: 573
ctggtgtcta acctggaatc c                                             21

SEQ ID NO: 574          moltype = AA   length = 7
```

| FEATURE | Location/Qualifiers |
|---|---|
| REGION | 1..7 |
| | note = Humanized C8 light chain variable complementarity determiningregion 2 (CDR2) sequence |
| source | 1..7 |
| | mol_type = protein |
| | organism = synthetic construct |

SEQUENCE: 574
LVSNLES                                                                                          7

| SEQ ID NO: 575 | moltype = DNA   length = 96 |
|---|---|
| FEATURE | Location/Qualifiers |
| misc_feature | 1..96 |
| | note = Humanized C8 light chain variable framework region 3 (FWR3)sequence |
| source | 1..96 |
| | mol_type = other DNA |
| | organism = synthetic construct |

SEQUENCE: 575
ggggtccctg accgattcag tggcagcggg tctgggacag atttcactct caccatcagc   60
agcctgcagg ctgaagatgt ggcagtttat tactgt                             96

| SEQ ID NO: 576 | moltype = AA   length = 32 |
|---|---|
| FEATURE | Location/Qualifiers |
| REGION | 1..32 |
| | note = Humanized C8 light chain variable framework region 3 (FWR3)sequence |
| source | 1..32 |
| | mol_type = protein |
| | organism = synthetic construct |

SEQUENCE: 576
GVPDRFSGSG SGTDFTLTIS SLQAEDVAVY YC                                  32

| SEQ ID NO: 577 | moltype = DNA   length = 30 |
|---|---|
| FEATURE | Location/Qualifiers |
| misc_feature | 1..30 |
| | note = Humanized C8 light chain variable complementarity determiningregion 3 (CDR3) sequence |
| source | 1..30 |
| | mol_type = other DNA |
| | organism = synthetic construct |

SEQUENCE: 577
caacacattc gggaactgac caggagtgaa                                     30

| SEQ ID NO: 578 | moltype = AA   length = 10 |
|---|---|
| FEATURE | Location/Qualifiers |
| REGION | 1..10 |
| | note = Humanized C8 light chain variable complementarity determiningregion 3 (CDR3) sequence |
| source | 1..10 |
| | mol_type = protein |
| | organism = synthetic construct |

SEQUENCE: 578
QHIRELTRSE                                                           10

| SEQ ID NO: 579 | moltype = DNA   length = 666 |
|---|---|
| FEATURE | Location/Qualifiers |
| misc_feature | 1..666 |
| | note = Humanized C8 Lambda light chain sequence |
| source | 1..666 |
| | mol_type = other DNA |
| | organism = synthetic construct |

SEQUENCE: 579
gacatcgtga tgacccagtc tccagactcc ctggctgtgt ctctgggcga gagggccacc    60
atcaactgca gggccagcaa gagtgttagc accagcggct acagctacat gcactggtac   120
cagcagaaac aggacagcc tcctaagctg ctcatttacc tggtgtctaa cctgaatcc    180
ggggtccctg accgattcag tggcagcggg tctgggacag atttcactct caccatcagc   240
agcctgcagg ctgaagatgt ggcagtttat tactgtcaac acattcggga actgaccagg   300
agtgaattcg gcggagggac caaggtggag atcaaacgaa ctggtcagcc caaggctgcc   360
ccctcggtca ctctgttccc gcctcctct gaggagcttc aagccaacaa ggccacactg   420
gtgtgtctca taagtgactt ctacccggga gccgtgacag tggcctggaa ggcagatagc   480
agccccgtca aggcgggagt ggagaccacc acaccctcca acaaagcaa caacaagtac   540
gcggccagca gctatctgag cctgacgcct gagcagtgga gtcccacag aagctacagc   600
tgccaggtca cgcatgaagg gagcaccgtg gagaagacag tggcccctac agaatgttca   660
tagtaa                                                              666

| SEQ ID NO: 580 | moltype = AA   length = 220 |
|---|---|
| FEATURE | Location/Qualifiers |
| REGION | 1..220 |

```
                        note = Humanized C8 Lambda light chain sequence
source                  1..220
                        mol_type = protein
                        organism = synthetic construct
SEQUENCE: 580
DIVMTQSPDS LAVSLGERAT INCRASKSVS TSGYSYMHWY QQKPGQPPKL LIYLVSNLES     60
GVPDRFSGSG SGTDFTLTIS SLQAEDVAVY YCQHIRELTR SEFGGGTKVE IKRTGQPKAA    120
PSVTLFPPSS EELQANKATL VCLISDFYPG AVTVAWKADS SPVKAGVETT TPSKQSNNKY    180
AASSYLSLTP EQWKSHRSYS CQVTHEGSTV EKTVAPTECS                          220

SEQ ID NO: 581          moltype = DNA  length = 666
FEATURE                 Location/Qualifiers
misc_feature            1..666
                        note = Humanized C8 Kappa light chain sequence
source                  1..666
                        mol_type = other DNA
                        organism = synthetic construct
SEQUENCE: 581
gacatcgtga tgacccagtc tccagactcc ctggctgtgt ctctgggcga gagggccacc     60
atcaactgca gggccagcaa gagtgttagc accagcggct acagctacat gcactggtac    120
cagcagaaac aggacagcc tcctaagctg ctcatttacc tggtgtctaa cctggaatcc    180
ggggtccctg accgattcag tggcagcggg tctgggacag atttcactct caccatcagc    240
agcctgcagg ctgaagatgt ggcagtttat tactgtcaac acattcggga actgaccagg    300
agtgaattcg gcggagggac caaggtggag atcaaacgaa ctcgtggcc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tagtaa                                                               666

SEQ ID NO: 582          moltype = AA  length = 220
FEATURE                 Location/Qualifiers
REGION                  1..220
                        note = Humanized C8 Kappa light chain sequence
source                  1..220
                        mol_type = protein
                        organism = synthetic construct
SEQUENCE: 582
DIVMTQSPDS LAVSLGERAT INCRASKSVS TSGYSYMHWY QQKPGQPPKL LIYLVSNLES     60
GVPDRFSGSG SGTDFTLTIS SLQAEDVAVY YCQHIRELTR SEFGGGTKVE IKRTTVAAPS    120
VFIFPPSDEQ LKSGTASVVC LLNNFYPREA KVQWKVDNAL QSGNSQESVT EQDSKDSTYS    180
LSSTLTLSKA DYEKHKVYAC EVTHQGLSSP VTKSFNRGEC                          220

SEQ ID NO: 583          moltype = DNA  length = 815
FEATURE                 Location/Qualifiers
misc_feature            1..815
                        note = Humanized C8 Kappa light chain gBLOCk sequence
source                  1..815
                        mol_type = other DNA
                        organism = synthetic construct
SEQUENCE: 583
agctggctag gtaagcttgg taccgagctc ggatccacgc caccatggag acagacacac     60
tcctgctatg ggtactgctg ctctgggttc caggttccac tggtgacgac atcgtgatga    120
cccagtctcc agactccctg gctgtgtctc tgggcgagag ggccaccatc aactgcaggg    180
ccagcaagag tgttagcacc agcggctaca gctacatgca ctggtaccag cagaaaccag    240
gacagcctcc taagctgctc atttacctgg tgtctaacct ggaatccggg gtccctgacc    300
gattcagtgg cagcgggtct gggacagatt tcactctcac catcagcagc ctgcaggctg    360
aagatgtggc agtttattac tgtcaacaca ttcgggagct gaccaggagt gaattcggcg    420
gagggaccaa ggtggagatc aaacgaacta cggtggctgc accatctgtc ttcatcttcc    480
cgccatctga tgagcagttg aaatctggaa ctgcctctgt tgtgtgcctg ctgaataact    540
tctatcccag agaggccaaa gtacagtgga aggtggataa cgcctccaa tcgggtaact    600
cccaggagag tgtcacagag caggacagca aggacagcac ctacagcctc agcagcaccc    660
tgacgctgag caaagcagac tacgagaaac acaaagtcta cgcctgcgaa gtcacccatc    720
agggcctgag ctcgcccgtc acaaagagct tcaacagggg agagtgttag taagtttaaa    780
cccgctgatc agcctcgact gtgccttcta gttgc                               815

SEQ ID NO: 584          moltype = DNA  length = 942
FEATURE                 Location/Qualifiers
misc_feature            1..942
                        note = CAR-T E6 CD8 sequence
source                  1..942
                        mol_type = other DNA
                        organism = synthetic construct
SEQUENCE: 584
gaggtccagc tggttgagag tggcggtggg ctggttaagc ctggcggctc cctgcggctc     60
agctgcgccg cgagtggatt tactttcagc cgatatggga tgagttgggt gcggcaagct    120
cccgggaaga ggctggaatg ggtctcaaca atctccgggg gggcactta catctattac    180
cccgactcag tcaaggggag atttaccatt tcacgagaca cgctaagaa tacccctgta t    240
```

```
ttgcagatga attctctgag agcagaggac acagctgttt actattgtac ccgcgacaac    300
tatggcagga actacgacta cggtatggac tattggggac aagggacatt ggttacagtg    360
agcagtggcg gcgggggcag cggaggagga ggcagcggtg ggggggcag cgagatagtg     420
ctcacgcagt caccccgcgac tctcagtctc tcacctgggg aacgagctac cctgacgtgc   480
tctgctacct cctcagtgtc atatattcac tggtatcagc aacggcccgg gcagtcccct    540
agattgctca tttatagtac ctctaatctg gcctcaggta tccctgcacg attttctgga   600
tctggttcag gttctgatta cacccctcact atctctagcc tggagcctga agactttgcc   660
gtttattact gccagcagag gtctagctcc ccattcacct tgggagtgg gaccaaggtt    720
gaaattaaaa cgacaacccc ggcccccaga ccaccaacgc cagcccccac catcgccagc    780
caacccctgt ctctgagacc agaagcctgt aggcctgcc ccggtggagc tgtgcacaca    840
agaggactgg atttcgcctg tgatatctac atttgggccc cgctcgcagg cacatgtgga   900
gtgctcctcc tctccctggt gattaccctg tactgctgat aa                      942

SEQ ID NO: 585          moltype = AA   length = 312
FEATURE                 Location/Qualifiers
REGION                  1..312
                        note = CAR-T E6 CD8 sequence
source                  1..312
                        mol_type = protein
                        organism = synthetic construct
SEQUENCE: 585
EVQLVESGGG LVKPGGSLRL SCAASGFTFS RYGMSWVRQA PGKRLEWVST ISGGGTYIYY     60
PDSVKGRFTI SRDNAKNTLY LQMNSLRAED TAVYYCTRDN YGRNYDYGMD YWGQGTLVTV    120
SSGGGGSGGG GSGGGGSEIV LTQSPATLSL SPGERATLTC SATSSVSYIH WYQQRPGQSP   180
RLLIYSTSNL ASGIPARFSG SGSGSDYTLT ISSLEPEDFA VYYCQQRSSS PFTFGSGTKV   240
EIKTTTPAPR PPTPAPTIAS QPLSLRPEAC RPAAGGAVHT RGLDFACDIY IWAPLAGTCG   300
VLLLSLVITL YC                                                       312

SEQ ID NO: 586          moltype = DNA   length = 960
FEATURE                 Location/Qualifiers
misc_feature            1..960
                        note = CAR-T C2 CD8 sequence
source                  1..960
                        mol_type = other DNA
                        organism = synthetic construct
SEQUENCE: 586
gaagtgcagc tcgtagagag tggcggggga ctggtgaagc ccgtggaag cctcagactc      60
agttgcgccg cctcaggttt cacttttca ggttacgcca tgtcctgggt aagacaggca    120
ccggggaaag gactcgagtg ggtgtctact atcagctcag gaggcactta tatatattat   180
cctgactctg taaaaggccg atttacgatt ctcgcgaca atgcaaagaa ctccctctac   240
ctccaaatga acagtcttag ggcagaagac actgctgtat actattgtgc acgcctcggc   300
ggcgacaact actacgagta ctttgacgtg tggggaaag gactaccgt gacagtttca    360
agcggaggag gtggctcagg tggaggcggg tcaggggcga gtggaaagtga tattgtgcta   420
acacaatccc cagcctccct ggctgtgtct cccggccaac gcgctacaat acatgtcgg   480
gcctccaaaa gcgtgagcac cagcggctac agctacatgc actggtatca acagaaacca   540
ggacaacccc ccaaactgtt gatttatctc gcttcaaact tggagtccgg cgtgcctgcg   600
cgcttttcag ggagtgggag cggcacagat tttacgctga ctatcaaccc cgtagaagca   660
aacgatacag cgaattatta ttgtcaacat tcccgggaac tccccttac gttcggcggg   720
ggcacaaagg tcgaaattaa agaaccacg acaaccccgg cccccagacc accaacgcca   780
gcccccacca tcgccagcca acccctgtct ctgagaccag aagcctgtag gcctgccgcc   840
ggtggagctg tgcacacaag aggactggat ttcgcctgtg atatctacat ttgggccccg   900
ctcgcaggca catgtgagt gctcctcctc tccctggtga ttaccctgta ctgctgataa   960

SEQ ID NO: 587          moltype = AA   length = 318
FEATURE                 Location/Qualifiers
REGION                  1..318
                        note = CAR-T C2 CD8 sequence
source                  1..318
                        mol_type = protein
                        organism = synthetic construct
SEQUENCE: 587
EVQLVESGGG LVKPGGSLRL SCAASGFTFS GYAMSWVRQA PGKGLEWVST ISSGGTYIYY     60
PDSVKGRFTI SRDNAKNSLY LQMNSLRAED TAVYYCARLG GDNYYEYFDV WGKGTTVTVS   120
SGGGGSGGGG SGGGGSDIVL TQSPASLAVS PGQRATITCR ASKSVSTSGY SYMHWYQQKP   180
GQPPKLLIYL ASNLESGVPA RFSGSGSGTD FTLTINPVEA NDTANYYCQH SRELPFTFGG   240
GTKVEIKRTT TTPAPRPPTP APTIASQPLS LRPEACRPAA GGAVHTRGLD FACDIYIWAP   300
LAGTCGVLLL SLVITLYC                                                 318

SEQ ID NO: 588          moltype = DNA   length = 339
FEATURE                 Location/Qualifiers
misc_feature            1..339
                        note = CD8/4-1BB sequence
source                  1..339
                        mol_type = other DNA
                        organism = synthetic construct
SEQUENCE: 588
acgacaaccc cggcccccag accaccaacg ccagccccca ccatcgccag ccaacccctg     60
tctctgagac cagaagcctg taggcctgcc gccggtggag ctgtgcacac aagaggactg   120
gatttcgcct gtgatatcta catttgggcc ccgctcgcag gcacatgtgg agtgctcctc   180
```

```
ctctccctgg tgattaccct gtactgcaaa aggggccgca aaaaactcct ttacattttt   240
aagcagcctt ttatgaggcc agtacagacg actcaagagg aagacgggtg ctcatgccgc   300
tttcctgagg aggaggaagg agggtgcgaa ctgtgataa                          339

SEQ ID NO: 589          moltype = AA   length = 111
FEATURE                 Location/Qualifiers
REGION                  1..111
                        note = CD8/4-1BB sequence
source                  1..111
                        mol_type = protein
                        organism = synthetic construct
SEQUENCE: 589
TTTPAPRPPT PAPTIASQPL SLRPEACRPA AGGAVHTRGL DFACDIYIWA PLAGTCGVLL    60
LSLVITLYCK RGRKKLLYIF KQPFMRPVQT TQEEDGCSCR FPEEEEGGCE L            111

SEQ ID NO: 590          moltype = DNA   length = 336
FEATURE                 Location/Qualifiers
misc_feature            1..336
                        note = CD8/CD28 sequence
source                  1..336
                        mol_type = other DNA
                        organism = synthetic construct
SEQUENCE: 590
acgacaaccc cggcccccag accaccaacg ccagccccca ccatcgccag ccaacccctg    60
tctctgagac cagaagcctg taggcctgcc gccggtggag ctgtgcacac aagaggactg   120
gatttcgcct gtgatatcta catttgggcc ccgctcgcag gcacatgtgg agtgctcctc   180
ctctccctgg tgattaccct gtactgcaga agcaagcggt ctcggctcct gcattcgat    240
tacatgaaca tgaccccaag aagaccaggc ccaccaggaa acattacca gccctacgct   300
ccgccacgcg acttcgctgc ctaccggtcc tgataa                             336

SEQ ID NO: 591          moltype = AA   length = 110
FEATURE                 Location/Qualifiers
REGION                  1..110
                        note = CD8/CD28 sequence
source                  1..110
                        mol_type = protein
                        organism = synthetic construct
SEQUENCE: 591
TTTPAPRPPT PAPTIASQPL SLRPEACRPA AGGAVHTRGL DFACDIYIWA PLAGTCGVLL    60
LSLVITLYCR SKRSRLLHSD YMNMTPRRPG PTRKHYQPYA PPRDFAAYRS              110

SEQ ID NO: 592          moltype = DNA   length = 549
FEATURE                 Location/Qualifiers
misc_feature            1..549
                        note = CD8/CD3z sequence
source                  1..549
                        mol_type = other DNA
                        organism = synthetic construct
SEQUENCE: 592
acgacaaccc cggcccccag accaccaacg ccagccccca ccatcgccag ccaacccctg    60
tctctgagac cagaagcctg taggcctgcc gccggtggag ctgtgcacac aagaggactg   120
gatttcgcct gtgatatcta catttgggcc ccgctcgcag gcacatgtgg agtgctcctc   180
ctctccctgg tgattaccct gtactgccgc gttaagttct cccgatcagc cgacgcgcct   240
gcttacaagc agggccagaa ccaactgtac aacgagctga atctcggtag acgggaagag   300
tacgacgtgt tggacaaacg gagaggccgc gacccagaaa tgggcggcaa gcctcgcagg   360
aaaaaccccc aggagggact gtacaatgag ttgcagaaaa ataagatggc agaagctat   420
agcgagatcg gaatgaaggg ggaaaggaga cgagggaaag gacacgacgg cctttatcag   480
ggcctgtcca cagcaacaaa agatacgtat gacgccctcc atatgcaggc acttccacca   540
cggtgataa                                                           549

SEQ ID NO: 593          moltype = AA   length = 181
FEATURE                 Location/Qualifiers
REGION                  1..181
                        note = CD8/CD3z sequence
source                  1..181
                        mol_type = protein
                        organism = synthetic construct
SEQUENCE: 593
TTTPAPRPPT PAPTIASQPL SLRPEACRPA AGGAVHTRGL DFACDIYIWA PLAGTCGVLL    60
LSLVITLYCR VKFSRSADAP AYKQGQNQLY NELNLGRREE YDVLDKRRGR DPEMGGKPRR   120
KNPQEGLYNE LQKDKMAEAY SEIGMKGERR RGKGHDGLYQ GLSTATKDTY DALHMQALPP   180
R                                                                   181

SEQ ID NO: 594          moltype = DNA   length = 672
FEATURE                 Location/Qualifiers
misc_feature            1..672
                        note = CD8/CD28/CD3z sequence
source                  1..672
                        mol_type = other DNA
```

```
                              organism = synthetic construct
SEQUENCE: 594
acgacaaccc cggcccccag accaccaacg ccagccccca ccatcgccag ccaacccctg    60
tctctgagac cagaagcctg taggcctgcc gccggtggag ctgtgcacac aagaggactg   120
gatttcgcct gtgatatcta catttgggcc ccgctgcagg gcacatgtgg agtgctcctc   180
ctctccctgg tgattaccct gtactgcaga agcaagcggt ctcggctcct gcattctgat   240
tacatgaaca tgaccccaag aagaccaggc cccaccagga acattacca gccctacgct    300
ccgccacgcg acttcgctgc ctaccggtcc cgcgttaagt tctcccgatc agccgacgcg   360
cctgcttaca agcagggcca gaaccaactg tacaacgagc tgaatctcgg tagacgggaa   420
gagtacgacg tgttggacaa acggagaggc cgcgacccag aaatgggcgg caagcctcgc   480
aggaaaaacc cccaggaggg actgtacaat gagttgcaga agataagat ggcagaagct    540
tatagcgaga tcggaatgaa gggggaaagg agacgaggga aaggacgacg cggcctttat   600
cagggcctgt ccacagcaac aaaagatacg tatgacgccc tccatatgca ggcacttcca   660
ccacggtgat aa                                                       672

SEQ ID NO: 595              moltype = AA   length = 222
FEATURE                     Location/Qualifiers
REGION                      1..222
                              note = CD8/CD28/CD3z sequence
source                      1..222
                              mol_type = protein
                              organism = synthetic construct
SEQUENCE: 595
TTTPAPRPPT PAPTIASQPL SLRPEACRPA AGGAVHTRGL DFACDIYIWA PLAGTCGVLL    60
LSLVITLYCR SKRSRLLHSD YMNMTPRRPG PTRKHYQPYA PPRDFAAYRS RVKFSRSADA   120
PAYKQGQNQL YNELNLGRRE EYDVLDKRRG RDPEMGGKPR RKNPQEGLYN ELQKDKMAEA   180
YSEIGMKGER RRGKGHDGLY QGLSTATKDT YDALHMQALP PR                      222

SEQ ID NO: 596              moltype = DNA   length = 675
FEATURE                     Location/Qualifiers
misc_feature                1..675
                              note = CD8/4-1BB/CD3z sequence
source                      1..675
                              mol_type = other DNA
                              organism = synthetic construct
SEQUENCE: 596
acgacaaccc cggcccccag accaccaacg ccagccccca ccatcgccag ccaacccctg    60
tctctgagac cagaagcctg taggcctgcc gccggtggag ctgtgcacac aagaggactg   120
gatttcgcct gtgatatcta catttgggcc ccgctgcagg gcacatgtgg agtgctcctc   180
ctctccctgg tgattaccct gtactgcaaa aggggccgca aaaaactcct ttacattttt   240
aagcagcctt ttatgaggcc agtacagacg actcaagagg aagacgggtg tcatgccgc    300
tttcctgagg aggaggaagg agggtgcgaa ctgcgcgtta agttctcccg atcagccgac   360
gcgcctgctt acaagcaggg ccagaaccaa ctgtacaacg agctgaatct cggtagacgg   420
gaagagtacg acgtgttgga caaacggaga ggccgcgacc cagaaatggg cggcaagcct   480
cgcaggaaaa accccaggag gggactgtac aatgagttgc agaaagataa gatggcagaa   540
gcttatagcg agatcggaat gaaggggga aggagacgag gaaaggaca cgacggcctt     600
tatcagggcc tgtccacagc aacaaaagat acgtatgacg ccctccatat gcaggcactt   660
ccaccacggt gataa                                                    675

SEQ ID NO: 597              moltype = AA   length = 223
FEATURE                     Location/Qualifiers
REGION                      1..223
                              note = CD8/4-1BB/CD3z sequence
source                      1..223
                              mol_type = protein
                              organism = synthetic construct
SEQUENCE: 597
TTTPAPRPPT PAPTIASQPL SLRPEACRPA AGGAVHTRGL DFACDIYIWA PLAGTCGVLL    60
LSLVITLYCK RGRKKLLYIF KQPFMRPVQT TQEEDGCSCR FPEEEEGGCE LRVKFSRSAD   120
APAYKQGQNQ LYNELNLGRR EEYDVLDKRR GRDPEMGGKP RRKNPQEGLY NELQKDKMAE   180
AYSEIGMKGE RRRGKGHDGL YQGLSTATKD TYDALHMQAL PPR                     223

SEQ ID NO: 598              moltype = DNA   length = 798
FEATURE                     Location/Qualifiers
misc_feature                1..798
                              note = CD8/CD28/4-1BB/CD3z sequence
source                      1..798
                              mol_type = other DNA
                              organism = synthetic construct
SEQUENCE: 598
acgacaaccc cggcccccag accaccaacg ccagccccca ccatcgccag ccaacccctg    60
tctctgagac cagaagcctg taggcctgcc gccggtggag ctgtgcacac aagaggactg   120
gatttcgcct gtgatatcta catttgggcc ccgctgcag gcacatgtgg agtgctcctc    180
ctctccctgg tgattaccct gtactgcaga agcaagcggt ctcggctcct gcattctgat   240
tacatgaaca tgaccccaag aagaccaggc cccaccagga acattacca gccctacgct    300
ccgccacgcg acttcgctgc ctaccggtcc aaaaggggcc gcaaaaaact cctttacatt   360
tttaagcagc cttttatgag gccagtacag acgactcaag aggaagacgg tgctcatgc    420
cgcttccctg aggaggagga aggagggtgc gaactgcgcg ttaagttctc ccgatcagcc   480
gacgcgcctg cttacaagca gggccagaac caactgtaca acgagctgaa tctcggtaga   540
```

```
cgggaagagt acgacgtgtt ggacaaacgg agaggccgcg acccagaaat gggcggcaag   600
cctcgcagga aaaaccccca ggagggactg tacaatgagt tgcagaaaga taagatggca   660
gaagcttata gcgagatcgg aatgaagggg gaaaggagac gagggaaagg acacgacggc   720
ctttatcagg gcctgtccac agcaacaaaa gatacgtatg acgccctcca tatgcaggca   780
cttccaccac ggtgataa                                                 798
```

| | | |
|---|---|---|
| SEQ ID NO: 599 | moltype = AA  length = 264 | |
| FEATURE | Location/Qualifiers | |
| REGION | 1..264 | |
| | note = CD8/CD28/4-1BB/CD3z sequence | |
| source | 1..264 | |
| | mol_type = protein | |
| | organism = synthetic construct | |

```
SEQUENCE: 599
TTTPAPRPPT PAPTIASQPL SLRPEACRPA AGGAVHTRGL DFACDIYIWA PLAGTCGVLL    60
LSLVITLYCR SKRSRLLHSD YMNMTPRRPG PTRKHYQPYA PPRDFAAYRS KRGRKKLLYI   120
FKQPFMRPVQ TTQEEDGCSC RFPEEEEGGC ELRVKFSRSA DAPAYKQGQN QLYNELNLGR   180
REEYDVLDKR RGRDPEMGGK PRRKNPQEGL YNELQKDKMA EAYSEIGMKG ERRRGKGHDG   240
LYQGLSTATK DTYDALHMQA LPPR                                         264
```

| | | |
|---|---|---|
| SEQ ID NO: 600 | moltype = DNA  length = 1482 | |
| FEATURE | Location/Qualifiers | |
| misc_feature | 1..1482 | |
| | note = CAR-T C3 4-1BB/CD3z sequence | |
| source | 1..1482 | |
| | mol_type = other DNA | |
| | organism = synthetic construct | |

```
SEQUENCE: 600
atggccctgc ccgtgaccgc tttgctgctc ccctggcgc tgctgctgca cgccgccagg     60
ccacaggttc agctggtgca gtctggagct gaggtgaaga agcctggggc ctcagtgaag   120
gtctcctgca aggcttctgg ttacaccttt accgactacg ccatgaactg ggtgcgacag   180
gcccctggac aagggcttga gtggatggga gtgatcagca cctcagcgg taacacaaac   240
ttcaaccaga gttcaaggg cagagtcacc atgaccacag acacatccac gagcacagcc   300
tacatggagc tgaggagcct gagatctgac gacacggccg tgtattactg tgcgagaagc   360
gactactacg gcccatactt cgactactgg ggccagggaa ccacccctgac cgtctccagc   420
ggcggtggcg gatccggcgg tggcggatcc ggcggtggcg gatccgatat tgtgatgacc   480
cagactccac tctctctgtc cgtcacccct ggacagccgg cctccatctc ctgcaggtct   540
agtcagacca ttgtccatag taatggaaac acctatttgg agtggtacct gcagaagcca   600
ggccagtctc cacagctcct gatctataag gtttccaacc ggttctctgg agtgccagat   660
aggttcagtg gcagcgggtc aggacagat ttcacactga aaatcagccg ggtggaggct   720
gaggatgttg ggtttattac tgcttccaa ggtagccacg tgcctttcac cttcggcgga   780
gggaccaagt ggagatcaa acgaactacg acaaccccgg ccccccagacc accaacgcca   840
gcccccacca tcgccagcca acccctgtct ctgagaccag aagcctgtag gcctgccgcc   900
ggtggagctg tgcacacaag aggactggat ttcgcctgtg atatctacat ttgggccccg   960
ctcgcaggca catgtggagt gctcctcctc tccctggtga ttacccctgta ctgcaaaagg  1020
ggccgcaaaa aactcctttta catttttaag cagccttta tgaggccagt acagacgact  1080
caagagaaga cgggtgctc atgccgcttt cctgaggagg aggaaggagg tgcgaactg   1140
cgcgttaagt tctcccgatc agccgacgcg cctgcttaca gcagggcca gaaccaactg   1200
tacaacgagc tgaatctcgg tagacgggaa gagtacgacg tgttggacaa acggagaggc   1260
cgcgacccag aaatgggcgg caagcctcgc aggaaaaaacc cccaggaggg actgtacaat  1320
gagttgcaga aagataagat ggcagaagct tatagcgaga tcggaatgaa gggggaaagg   1380
agacgagggaa aggacacgacga cggcttttat cagggcctgt ccacagcaac aaaagatacg  1440
tatgacgccc tccatatgca ggcacttcca ccacggtgat aa                      1482
```

| | | |
|---|---|---|
| SEQ ID NO: 601 | moltype = AA  length = 471 | |
| FEATURE | Location/Qualifiers | |
| REGION | 1..471 | |
| | note = CAR-T C3 4-1BB/CD3z sequence | |
| source | 1..471 | |
| | mol_type = protein | |
| | organism = synthetic construct | |

```
SEQUENCE: 601
QVQLVQSGAE VKKPGASVKV SCKASGYTFT DYAMNWVRQA PGQGLEWMGV ISTFSGNTNF    60
NQKFKGRVTM TTDTSTSTAY MELRSLRSDD TAVYYCARSD YYGPYFDYWG QGTTLTVSSG   120
GGGSGGGGSG GGGSDIVMTQ TPLSLSVTPG QPASISCRSS QTIVHSNGNT YLEWYLQKPG   180
QSPQLLIYKV SNRFSGVPDR FSGSGSGTDF TLKISRVEAE DVGVYYCFQG SHVPFTFGGG   240
TKVEIKRTTT TPAPRPPTPA PTIASQPLSL RPEACRPAAG GAVHTRGLDF ACDIYIWAPL   300
AGTCGVLLLS LVITLYCKRG RKKLLYIFKQ PFMRPVQTTQ EEDGCSCRFP EEEEGGCELR   360
VKFSRSADAP AYKQGQNQLY NELNLGRREE YDVLDKRRGR DPEMGGKPRR KNPQEGLYNE   420
LQKDKMAEAY SEIGMKGERR RGKGHDGLYQ GLSTATKDTY DALHMQALPP R            471
```

| | | |
|---|---|---|
| SEQ ID NO: 602 | moltype = DNA  length = 567 | |
| FEATURE | Location/Qualifiers | |
| misc_feature | 1..567 | |
| | note = C3 CAR gBLOCK 1 sequence | |
| source | 1..567 | |
| | mol_type = other DNA | |
| | organism = synthetic construct | |

```
SEQUENCE: 602
```

```
atccacgctg tttttgacctc catagaagat tctagagcta gctgtagagc ttggtaccga    60
gggccaccat ggccctgccc gtgaccgctg tgctgctccc cctggcgctg ctgctgcacg   120
ccgccaggcc acaggttcag ctggtgcagt ctggagctga ggtgaagaag cctggggcct   180
cagtgaaggt ctcctgcaag gcttctggtt acacctttac cgactacgcc atgaactggg   240
tgcgacaggc ccctggacaa gggcttgagt ggatggggt gatcagcacc ttcagcggta   300
acacaaactt caaccagaag ttcaagggca gagtcaccat gaccacagac acatccacga   360
gcacagccta catggagctg aggagcctga gatctgacga cacggccgtg tattactgtg   420
cgagaagcga ctactacggc ccatacttcg actactgggg ccagggcacc accctgaccg   480
tgtccagcgc cggtggcgga tccggcgtg gcggatccgc cggtggcgga tccgatattg   540
tgatgaccca gactccactc tctctgt                                        567

SEQ ID NO: 603         moltype = DNA   length = 509
FEATURE                Location/Qualifiers
misc_feature           1..509
                       note = C3 CAR gBLOCK 2 sequence
source                 1..509
                       mol_type = other DNA
                       organism = synthetic construct
SEQUENCE: 603
tattgtgatg acccagactc cactctctct gtccgtcacc cctggacagc cggcctccat    60
ctcctgcagg tctagtcaga ccattgtcca tagtaatgga acacctatt tggagtggta   120
cctgcagaag ccaggccagt ctccacagct cctgatctat aaggtttcca accggttctc   180
tggagtgcca gataggttca gtggcagcgg gtcaggcgga gatttcacac tgaaaatcag   240
ccgggtggag gctgaggatg ttgggggttta ttactgcttc caaggtagcc acgtgccttt   300
caccttcggc ggagggacca aggtggagat caaacgaact acgacaaccc cggcccccag   360
accaccaacg ccagccccca ccatcgccag ccaaccctg tctctgagac agaagcctg    420
taggcctgcc gccggtggag ctgtgcacac aagaggactg gatttcgcct gtgatatcta   480
catttgggcc ccgctcgcag gcacatgtg                                     509

SEQ ID NO: 604         moltype = DNA   length = 455
FEATURE                Location/Qualifiers
misc_feature           1..455
                       note = E6 scFV gBLOCK 1 sequence
source                 1..455
                       mol_type = other DNA
                       organism = synthetic construct
SEQUENCE: 604
tgctctgggt tccaggttcc actggtgacg cggcccagcc ggccgaggtg cagctggtgg    60
agtctggggg aggcctggtc aagcctgggg gttcccgag actctcctgt gcagcctctg   120
gattcacctt cagtaggtat ggcatgagct gggtccgcca ggctccaggg aagaggctgg   180
agtgggtctc aaccattagt ggcggaggca cctacatata ctaccagac tcagtgaagg   240
gccgattcac catctccaga gacaacgcca agaacaccct gtatctgcaa atgaacagc   300
tgagagccga ggacacggct gtgtattact gtaccagcga taactatg cgcaactatg   360
attatggcat ggattattgg ggccagggca ccctggtgac cgtgagcagc ggcggtggcg   420
gatccggcgg tggcggatcc ggcggtggcg gatcc                              455

SEQ ID NO: 605         moltype = DNA   length = 432
FEATURE                Location/Qualifiers
misc_feature           1..432
                       note = E6 scFV gBLOCK 2 sequence
source                 1..432
                       mol_type = other DNA
                       organism = synthetic construct
SEQUENCE: 605
ggcggtggcg gatccggcgg tggcggatcc ggcggtggcg gatccgaaat tgtgttgaca    60
cagtctccag ccaccctgtc tttgtctcca ggggaaagag ccaccctcac ctgcagcgcc   120
accagcagtt ttagctacat ccactggtac aacagagggc ctggccagag ccccaggctc   180
ctcatctata gcacctccaa cctggccagc ggcatcccag ccaggttcag tggcagtggg   240
tctgggagcg actacactct caccatcagc agcctagagc tgaagatttt gcagtttat   300
tactgtcagc agcgtagcag ctccccttc acctttggca ggcaccaa agtggaaatt   360
aaaaccggtc atcatcacca tcaccactga taagttaaaa ccgctgatc agcctcgact   420
gtgccttcta gt                                                       432

SEQ ID NO: 606         moltype = DNA   length = 1359
FEATURE                Location/Qualifiers
misc_feature           1..1359
                       note = CAR-T C2 CD3z sequence
source                 1..1359
                       mol_type = other DNA
                       organism = synthetic construct
SEQUENCE: 606
atggccttgc cagtgacggc cctgctgctg ccattggctc ttctgttgca cgctgccagg    60
cctgaagtga agctcgtaga gagtggcggg ggactggtga gcccggtgg aagcctcaga   120
ctcagttgcg ccgcctcagg tttcacttt tcaggttacg ccatgtcctg ggtaagacag   180
gcaccgggga aaggactcga gtgggtgtct actatcagct caggaggcac ttatatat   240
tatcctgact ctgtaaaagg ccgatttacg atttctcgcg acaatgcaaa gaactccctc   300
tacctccaaa tgaacagtct tagggcagaa gacactgctg tatactattg tgcacgcctc   360
ggcggcgaca actactacga gtactttgac gtgtggggga agggactac cgtgacagtt   420
tcaagcggag gaggtggctc aggtggaggc gggtcagggg gggaggaag tgatattgtg   480
```

```
ctcacacaat ccccagcctc cctggctgtg tctcccggcc aacgcgctac aattacatgt    540
cgggcctcca aaagcgtgag caccagcggc tacagctaca tgcactggta tcaacagaaa    600
ccaggacaac cccccaaact gttgatttat ctcgcttcaa acttggagtc cggcgtgcct    660
gcgcgctttt cagggagtgg gagcggcaca gattttacgc tgactatcaa ccccgtagaa    720
gcaaacgata cagcgaatta ttattgtcaa cattcccggg aactcccctt tacgttcggc    780
ggggcacaa aggtcgaaat taagagaacc acgacaaccc cggccccag accaccaacg     840
ccagccccca ccatcgccag caacccctg tctctgagac cagaagcctg taggcctgcc     900
gccggtggag ctgtgcacac aagaggactg gatttcgcct gtgatatcta catttgggcc    960
ccgctcgcag gcacatgtgg agtgctcctc ctctccctgg tgattaccct gtactgccgc   1020
gttaagttct cccgatcagc cgacgcgcct gcttacaagc agggccagaa ccaactggta   1080
aacgagctga atctcggtag acgggaagag tacgacgtgt tggacaaacg agaggccgac   1140
gacccagaaa tgggcggcaa gcctcgcagg aaaaaccccc aggagggact gtacaatgag   1200
ttgcagaaag ataagatggc agaagcttat agcgagatcg gaatgaaggg ggaaaggaga   1260
cgagggaaag gacacgacgg cctttatcag ggcctgtcca cagcaacaaa agatacgtat   1320
gacgccctcc atatgcaggc acttccacca cggtgataa                          1359

SEQ ID NO: 607          moltype = AA  length = 451
FEATURE                 Location/Qualifiers
REGION                  1..451
                        note = CAR-T C2 CD3z sequence
source                  1..451
                        mol_type = protein
                        organism = synthetic construct SEQUENCE: 607
MALPVTALLL PLALLLHAAR PEVQLVESGG GLVKPGGSLR LSCAASGFTF SGYAMSWVRQ    60
APGKGLEWVS TISSGGTYIY YPDSVKGRFT ISRDNAKNSL YLQMNSLRAE DTAVYYCARL   120
GGDNYYEYFD VWGKGTTVTV SSGGGGSGGG GSGGGGSDIV LTQSPASLAV SPGQRATITC   180
RASKSVSTSG YSYMHWYQQK PGQPPKLLIY LASNLESGVP ARFSGSGSGT DFTLTINPVE   240
ANDTANYYCQ HSRELPFTFG GGTKVEIKRT TTTPAPRPPT PAPTIASQPL SLRPEACRPA   300
AGGAVHTRGL DFACDIYIWA PLAGTCGVLL LSLVITLYCR VKFSRSADAP AYKQGQNQLY   360
NELNLGRREE YDVLDKRRGR DPEMGGKPRR KNPQEGLYNE LQKDKMAEAY SEIGMKGERR   420
RGKGHDGLYQ GLSTATKDTY DALHMQALPP R                                  451

SEQ ID NO: 608          moltype = DNA  length = 1482
FEATURE                 Location/Qualifiers
misc_feature            1..1482
                        note = CAR-T C2 CD28/CD3z sequence
source                  1..1482
                        mol_type = other DNA
                        organism = synthetic construct SEQUENCE: 608
atggccttgc cagtgacggc cctgctgctg ccattggctc ttctgttgca cgctgccagg    60
cctgaagtgc agctcgtaga gagtggcggg ggactggtga agcccggtgg aagcctcaga   120
ctcagttgcg ccgcctcagg tttcactttt tcaggttacg ccatgtcctg gtaagacaga   180
gcaccgggga aaggactcga gtgggtgtct actatcagct caggaggcac ttatatatat   240
tatcctgact ctgtaaaagg ccgatttacg atttctcgcg acaatgcaaa gaactccctc   300
tacctccaaa tgaacagtct tagggcagaa gacactgcta tactattatg tgcacgcctc   360
ggcggcgaca actactacga gtactttgac gtgtgggga aagggactac cgtgacagtt   420
tcaagcggag gaggtggctc aggtggaggc gggtcagggg gggaggaag tgatattgtg   480
ctcacacaat ccccagcctc cctggctgtg tctcccggcc aacgcgctac aattacatgt   540
cgggcctcca aaagcgtgag caccagcggc tacagctaca tgcactggta tcaacagaaa   600
ccaggacaac cccccaaact gttgatttat ctcgcttcaa acttggagtc cggcgtgcct   660
gcgcgctttt cagggagtgg gagcggcaca gattttacgc tgactatcaa ccccgtagaa   720
gcaaacgata cagcgaatta ttattgtcaa cattcccggg aactcccctt tacgttcggc   780
ggggcacaa aggtcgaaat taagagaacc acgacaaccc cggccccag accaccaacg    840
ccagccccca ccatcgccag caacccctg tctctgagac cagaagcctg taggcctgcc    900
gccggtggag ctgtgcacac aagaggactg gatttcgcct gtgatatcta catttgggcc   960
ccgctcgcag gcacatgtgg agtgctcctc ctctccctgg tgattaccct gtactgcaga  1020
agcaagcggt ctcggctcct gcattctgat tacatgaaca tgacccaag aagaccaggc  1080
cccaccagga aacattacca gccctacgct ccgccacgcg acttcgctgc ctaccggtcg  1140
cgcgttaagt tctcccgatc agccgacgcg cctgcttaca gcagggccaa gaaccaactg  1200
tacaacgagc tgaatctcgg tagacgggaa gagtacgacg tgttgacaa acggagaggc  1260
cgcgacccag aaatgggcgg caagcctcgc aggaaaaaccc cccaggaggg actgtacaat  1320
gagttgcaga aagataagat ggcagaagct tatagcgaga tcggaatgaa gggggaaagg  1380
agacgaggga aaggacacga cggcctttat cagggcctgt ccacagcaac aaaagatacg  1440
tatgacgccc tccatatgca ggcacttcca ccacggtgat aa                     1482

SEQ ID NO: 609          moltype = AA  length = 492
FEATURE                 Location/Qualifiers
REGION                  1..492
                        note = CAR-T C2 CD28/CD3z sequence
source                  1..492
                        mol_type = protein
                        organism = synthetic construct SEQUENCE: 609
MALPVTALLL PLALLLHAAR PEVQLVESGG GLVKPGGSLR LSCAASGFTF SGYAMSWVRQ    60
APGKGLEWVS TISSGGTYIY YPDSVKGRFT ISRDNAKNSL YLQMNSLRAE DTAVYYCARL   120
GGDNYYEYFD VWGKGTTVTV SSGGGGSGGG GSGGGGSDIV LTQSPASLAV SPGQRATITC   180
RASKSVSTSG YSYMHWYQQK PGQPPKLLIY LASNLESGVP ARFSGSGSGT DFTLTINPVE   240
```

```
ANDTANYYCQ HSRELPFTFG GGTKVEIKRT TTTPAPRPPT PAPTIASQPL SLRPEACRPA    300
AGGAVHTRGL DFACDIYIWA PLAGTCGVLL LSLVITLYCR SKRSRLLHSD YMNMTPRRPG    360
PTRKHYQPYA PPRDFAAYRS RVKFSRSADA PAYKQGQNQL YNELNLGRRE EYDVLDKRRG    420
RDPEMGGKPR RKNPQEGLYN ELQKDKMAEA YSEIGMKGER RRGKGHDGLY QGLSTATKDT    480
YDALHMQALP PR                                                       492

SEQ ID NO: 610          moltype = DNA  length = 1485
FEATURE                 Location/Qualifiers
misc_feature            1..1485
                        note = CAR-T C2 4-1BB/CD3z sequence
source                  1..1485
                        mol_type = other DNA
                        organism = synthetic construct
SEQUENCE: 610
atggccttgc cagtgacggc cctgctgctg ccattggctc ttctgttgca cgctgccagg      60
cctgaagtgc agctcgtaga gagtggcggg ggactggtga agcccggtgg aagcctcaga    120
ctcagttgcg ccgcctcagg tttcactttt tcaggttacg ccatgtcctg ggtaagacag    180
gcaccgggga aaggactcga gtgggtgtct actatcagct caggaggcac ttatatatat    240
tatcctgact ctgtaaaagg ccgatttacg atttctcgcg acaatgcaaa gaactccctc    300
tacctccaaa tgaacagtct tagggcagaa gacactgctg tatactattg cacgcctc      360
ggcggcgaca actactacga gtactttgac gtgtggggga aagggactac cgtgacagtt    420
tcaagcggag gaggtggctc aggtggaggc gggtcagggg gtggaggaag tgatattgtg    480
ctcacacaat cccagcctc cctggctgtg tctcccggcc aacgcgctac aattacatgt    540
cgggcctcca aaagcgtgag caccagcggc tacagctaca tgcactggta tcaacagaaa    600
ccaggacaac cccccaaact gttgatttat ctcgcttcaa acttggagtc cggcgtgcct    660
gcgcgctttt cagggagtgg gagcggcaca gatttttacgc tgactatcaa ccccgtagaa    720
gcaaacgata cagcgaatta ttattgtcaa cattcccggg aactcccctt tacgttcggc    780
gggggcacaa aggtcgaaat taagagaacc acgacaaccc cggcccccag accaccaacg    840
ccagccccca ccatcgccag caacccctg tctctgagac cagaagcctg taggcctgcc    900
gccgtggag ctgtgcacac aaggaggactg gatttcgcct gtgatatcta catttgggcc    960
ccgctcgcag gcacatgtgg agtgctcctc ctctccctgg tgattaccct gtactgcaaa   1020
aggggccgca aaaaactcct ttacattttt aagcagcctt ttatgaggcc agtacagacg   1080
actcaagagg aagacgggtg ctcatgccgc tttcctgagg aggaggaagg agggtgcgaa   1140
ctgcgcgtta agttctcccg atcagccgac gcgcctgctt acaagcaggg ccaaaccaa   1200
ctgtacaacg agctgaatct cggtagacg gaagagtacg acgtgttgga caacgtggaga  1260
ggccgcgacc cagaaatggg cggcaagcct cgcaggaaaa accccaggag gggactgtac  1320
aatgagttgc agaagataa gatgcagaa gcttatagcg agatcggaat gaaggggaa      1380
aggagacgag ggaaaggaca cgacggcctt tatcagggcc tgtccacagc aacaaaagat  1440
acgtatgacg ccctccatat gcaggcactt ccaccacggt gataa                   1485

SEQ ID NO: 611          moltype = AA  length = 493
FEATURE                 Location/Qualifiers
REGION                  1..493
                        note = CAR-T C2 4-1BB/CD3z sequence
source                  1..493
                        mol_type = protein
                        organism = synthetic construct
SEQUENCE: 611
MALPVTALLL PLALLLHAAR PEVQLVESGG GLVKPGGSLR LSCAASGFTF SGYAMSWVRQ     60
APGKGLEWVS TISSGGTYIY YPDSVKGRFT ISRDNAKNSL YLQMNSLRAE DTAVYYCARL   120
GGDNYYEYFD VWGKGTTVTV SSGGGGSGGG GSGGGGSDIV LTQSPASLAV SPGQRATITC   180
RASKSVSTSG YSYMHWYQQK PGQPPKLLIY LASNLESGVP ARFSGSGSGT DFTLTINPVE   240
ANDTANYYCQ HSRELPFTFG GGTKVEIKRT TTTPAPRPPT PAPTIASQPL SLRPEACRPA   300
AGGAVHTRGL DFACDIYIWA PLAGTCGVLL LSLVITLYCK RGRKKLLYIF KQPFMRPVQT   360
TQEEDGCSCR FPEEEEGGCE LRVKFSRSAD APAYKQGQNQ LYNELNLGRR EEYDVLDKRR   420
GRDPEMGGKP RRKNPQEGLY NELQKDKMAE AYSEIGMKGE RRRGKGHDGL YQGLSTATKD   480
TYDALHMQAL PPR                                                     493

SEQ ID NO: 612          moltype = DNA  length = 1470
FEATURE                 Location/Qualifiers
misc_feature            1..1470
                        note = CAR-T C2 OX40/CD3z sequence
source                  1..1470
                        mol_type = other DNA
                        organism = synthetic construct
SEQUENCE: 612
atggccttgc cagtgacggc cctgctgctg ccattggctc ttctgttgca cgctgccagg      60
cctgaagtgc agctcgtaga gagtggcggg ggactggtga agcccggtgg aagcctcaga    120
ctcagttgcg ccgcctcagg tttcactttt tcaggttacg ccatgtcctg ggtaagacag    180
gcaccgggga aaggactcga gtgggtgtct actatcagct caggaggcac ttatatatat    240
tatcctgact ctgtaaaagg ccgatttacg atttctcgcg acaatgcaaa gaactccctc    300
tacctccaaa tgaacagtct tagggcagaa gacactgctg tatactattg cacgcctc      360
ggcggcgaca actactacga gtactttgac gtgtggggga aagggactac cgtgacagtt    420
tcaagcggag gaggtggctc aggtggaggc gggtcagggg gtggaggaag tgatattgtg    480
ctcacacaat cccagcctc cctggctgtg tctcccggcc aacgcgctac aattacatgt    540
cgggcctcca aaagcgtgag caccagcggc tacagctaca tgcactggta tcaacagaaa    600
ccaggacaac cccccaaact gttgatttat ctcgcttcaa acttggagtc cggcgtgcct    660
gcgcgctttt cagggagtgg gagcggcaca gatttttacgc tgactatcaa ccccgtagaa    720
gcaaacgata cagcgaatta ttattgtcaa cattcccggg aactcccctt tacgttcggc    780
```

-continued

```
ggggggcacaa aggtcgaaat taagagaacc acgacaaccc cggccccccag accaccaacg 840
ccagccccca ccatcgccag ccaacccctg tctctgagac cagaagcctg taggcctgcc 900
gccggtggag ctgtgcacac aagaggactg gatttcgcct gtgatatcta catttgggcc 960
ccgctcgcag gcacatgtgg agtgctcctc ctctccctgg tgattaccct gtactgccgc 1020
agggaccaga ggctgccccc cgatgcccac aagcccctg gacggaggcag tttccggacc 1080
cccatccaag aggagcaggc cgacgcccac tccaccctgg ccaagatccg cgttaagttc 1140
tcccgatcag ccgacgcgcc tgcttacaag cagggccaga accaactgta caacgagctg 1200
aatctcggta gacgggaaga gtacgacgtg ttggacaaac ggagaggccg cgacccagaa 1260
atgggcggca agcctcgcag gaaaaacccc caggaggac tgtacaatga gttgcagaaa 1320
gataagatgg cagaagctta tagcgagatc ggaatgaagg gagaaggag acgagggaaa 1380
ggacacgacg gcctttatca gggcctgtcc acagcaacaa aagatacgta tgacgcctc 1440
catatgcagg cacttccacc acggtgataa 1470
```

SEQ ID NO: 613  moltype = AA  length = 488
FEATURE       Location/Qualifiers
REGION        1..488
              note = CAR-T C2 OX40/CD3z sequence
source        1..488
              mol_type = protein
              organism = synthetic construct
SEQUENCE: 613
MALPVTALLL PLALLLHAAR PEVQLVESGG GLVKPGGSLR LSCAASGFTF SGYAMSWVRQ 60
APGKGLEWVS TISSGGTYIY YPDSVKGRFT ISRDNAKNSL YLQMNSLRAE DTAVYYCARL 120
GGDNYYEYFD VWGKGTTVTV SSGGGGSGGG GSGGGGSDIV LTQSPASLAV SPGQRATITC 180
RASKSVSTSG YSYMHWYQQK PGQPPKLLIY LASNLESGVP ARFSGSGSGT DFTLTINPVE 240
ANDTANYYCQ HSRELPFTFG GGTKVEIKRT TTTPAPRPPT PAPTIASQPL SLRPEACRPA 300
AGGAVHTRGL DFACDIYIWA PLAGTCGVLL LSLVITLYCR RDQRLPPDAH KPPGGGSFRT 360
PIQEEQADAH STLAKIRVKF SRSADAPAYK QGQNQLYNEL NLGRREEYDV LDKRRGRDPE 420
MGGKPRRKNP QEGLYNELQK DKMAEAYSEI GMKGERRRGK GHDGLYQGLS TATKDTYDAL 480
HMQALPPR                                                         488

SEQ ID NO: 614  moltype = DNA  length = 1593
FEATURE         Location/Qualifiers
misc_feature    1..1593
                note = CAR-T C2 CD28/OX40/CD3z sequence
source          1..1593
                mol_type = other DNA
                organism = synthetic construct
SEQUENCE: 614
atggccttgc cagtgacggc cctgctgctg ccattggctc ttctgttgca cgctgccagg 60
cctgaagtgc agctcgtaga gagtggcggg ggactggtga agcccggtgg aagcctcaga 120
ctcagttgcg ccgcctcagg tttcactttt tcaggttacg ccatgtcctg ggtaagacag 180
gcaccgggga aaggactcga gtgggtgtct actatcagt caggaggcac ttatatatat 240
tatcctgact ctgtaaaagg ccgatttacg atttctcgcg acaatgcaaa gaactccctc 300
tacctccaaa tgaacagtct tagggcagaa gacactgctg tatactattg tgcacgcctc 360
ggcggcgaca ctactacga gtactttgac gtgtggggga agggactac cgtgacagtt 420
tcaagcggag gaggtggctc aggtggaggc gggtcagggg gggaaggga tgatattgtg 480
ctcacacaat cccagccctc cctggctgtg tctccccggcc aacgcgctac aattacatgt 540
cgggcctcca aaagcgtgag caccagcggc tacagctaca tgcactggta tcaacagaaa 600
ccaggacaac ccccaaaact gttgatttat ctcgcttcaa acttggagtc cggcgtgcct 660
gcgcgctttt cagggagtgg gagcggcaca gattttacgc tgactatcaa ccccgtagaa 720
gcaaacgata cagcgaatta ttattgtcaa cattccgggg aactccctt tacgttcggc 780
gggggcacaa aggtcgaaat taagagaacc acgacaaccc cggccccag accaccaacg 840
ccagccccca ccatcgccag ccaacccctg tctctgagac cagaagcctg taggcctgcc 900
gccggtggag ctgtgcacac aagaggactg gatttcgcct gtgatatcta catttgggcc 960
ccgctcgcag gcacatgtgg agtgctcctc ctctccctgg tgattaccct gtactgcaga 1020
agcaagcggt ctcggctcct gcattctgat tacatgaaca tgaccccaag aagaccaggc 1080
cccaccagga acattacca gccctacgct ccgccacgcg acttcgctgc ctaccggtcc 1140
cggagggacc agaggctgcc ccccgatgcc acaagcccc tgggggagat cagtttccgg 1200
acccccatcc aagaggagca ggccgacgcc cactccaccc tggccaagat ccgcgttaag 1260
ttctcccgat cagccgacgc gcctgcttac aagcagggcc agaaccaact gtacaacgag 1320
ctgaatctcg gtagacggga agagtacgac gtgttggaca acggagagg ccgcgaccca 1380
gaaatgggcg gcaagcctcg caggaaaaac ccccaggagg actgtacaa tgagttgcag 1440
aaagataaga tggcagaagc cttatagcgag atcggaatga aggggaaag gagacgaggg 1500
aaaggacacg acggccttta tcagggcctg tccacagcaa caaaagatac gtatgacgcc 1560
ctccatatgc aggcacttcc accacggtga taa 1593
```

SEQ ID NO: 615  moltype = AA  length = 529
FEATURE       Location/Qualifiers
REGION        1..529
              note = CAR-T C2 CD28/OX40/CD3z sequence
source        1..529
              mol_type = protein
              organism = synthetic construct
SEQUENCE: 615
MALPVTALLL PLALLLHAAR PEVQLVESGG GLVKPGGSLR LSCAASGFTF SGYAMSWVRQ 60
APGKGLEWVS TISSGGTYIY YPDSVKGRFT ISRDNAKNSL YLQMNSLRAE DTAVYYCARL 120
GGDNYYEYFD VWGKGTTVTV SSGGGGSGGG GSGGGGSDIV LTQSPASLAV SPGQRATITC 180
RASKSVSTSG YSYMHWYQQK PGQPPKLLIY LASNLESGVP ARFSGSGSGT DFTLTINPVE 240

```
ANDTANYYCQ  HSRELPFTFG  GGTKVEIKRT  TTTPAPRPPT  PAPTIASQPL  SLRPEACRPA  300
AGGAVHTRGL  DFACDIYIWA  PLAGTCGVLL  LSLVITLYCR  SKRSRLLHSD  YMNMTPRRPG  360
PTRKHYQPYA  PPRDFAAYRS  RRDQRLPPDA  HKPPGGGSFR  TPIQEEQADA  HSTLAKIRVK  420
FSRSADAPAY  KQGQNQLYNE  LNLGRREEYD  VLDKRRGRDP  EMGGKPRRKN  PQEGLYNELQ  480
KDKMAEAYSE  IGMKGERRRG  KGHDGLYQGL  STATKDTYDA  LHMQALPPR              529

SEQ ID NO: 616          moltype = DNA   length = 1452
FEATURE                 Location/Qualifiers
misc_feature            1..1452
                        note = CAR-T E6 OX40/CD3z sequence
source                  1..1452
                        mol_type = other DNA
                        organism = synthetic construct
SEQUENCE: 616
atggccctgc ccgtgaccgc tttgctgctc ccctggcgc tgctgctgca cgccgccagg   60
ccagaggtcc agctggttga gagtggcggt gggctggtta agcctggcgg ctccctgcgg  120
ctgagctgcg ccgcgagtgg atttactttc agccgatatg gatgagttg ggtgcggcaa  180
gctcccggga agaggctgga atgggtctca acaatctccg gggggggcac ttacatctat  240
taccccgact cagtcaaggg gagatttacc atttcacgag acaacgctaa gaataccctg  300
tatttgcaga tgaattctct gagagcagag gacacagctg tttactattg tacccgcgac  360
aactatggca ggaactacga ctacggtatg gactattggg gacaagggac attggttaca  420
gtgagcagtg gcggcggggg cagcggagga ggaggcagcg gtgggggcag cagataa    480
gtgctcacgc agtcacccgc gactctcagt ctctcacctg ggaacgagc taccctgacg  540
tgctctgcta cctcctcagt gtcatatatt cactggtatc agcaacgcc cgggcagtcc  600
cctagattgc tcatttatag tacctctaat ctggcctcag gtatccctgc acgatttct  660
ggatctggtt caggttctga ttacacccct actatctcta gcctgagcc tgaagacttt  720
gccgtttatt actgccagca gaggtctagc tccccattca cctttgggag tgggaccaag  780
gttgaaatta aaacgacaac cccggcccc agaccaccaa cgccagcccc caccatcgcc  840
agccaacccc tgtctctgag accagaagcc tgtaggcctg ccgccggtgg agctgtgcac  900
acaagaggac tggattttgc ctgtgatatc tacatttgg ccccgctcgc aggcacatgt  960
ggagtgctcc tcctctccct ggtgattacc ctgtactgcc ggaggaccca gaggctgccc 1020
cccgatgccc acaagccccc tgggggaggc agtttccgga ccccatcca agaggagcag 1080
gccgacgccc actccaccct ggccaagatc cgcgttaagt tctcccgatc agccgacgcg 1140
cctgcttaca agcagggcca gaaccaactg tacaacgagc tgaatcgg  tagacgggga 1200
gagtacgacg tgttggacaa acggagaggc cgcgacccca gaatgggcgg caagcctcgc 1260
aggaaaaacc cccaggaggg actgtacaat gagttgcaga agataagat  ggcagaagct 1320
tatagcgaga tcggaatgaa ggggggaagg agacgaggga aaggcacgga cggcctttat 1380
cagggcctgt ccacagcaac aaaagatacg tatgacgccc tccatatgca ggcacttcca 1440
ccacggtgat aa                                                      1452

SEQ ID NO: 617          moltype = AA   length = 482
FEATURE                 Location/Qualifiers
REGION                  1..482
                        note = CAR-T E6 OX40/CD3z sequence
source                  1..482
                        mol_type = protein
                        organism = synthetic construct
SEQUENCE: 617
MALPVTALLL  PLALLLHAAR  PEVQLVESGG  GLVKPGGSLR  LSCAASGFTF  SRYGMSWVRQ   60
APGKRLEWVS  TISGGGTYIY  YPDSVKGRFT  ISRDNAKNTL  YLQMNSLRAE  DTAVYYCTRD  120
NYGRNYDYGM  DYWGQGTLVT  VSSGGGGSGG  GGSGGGGSEI  VLTQSPATLS  LSPGERATLT  180
CSATSSVSYI  HWYQQRPGQS  PRLLIYSTSN  LASGIPARFS  GSGSGSDYTL  TISSLEPEDF  240
AVYYCQQRSS  SPFTFGSGTK  VEIKTTTPAP  RPPTPAPTIA  SQPLSLRPEA  CRPAAGGAVH  300
TRGLDFACDI  YIWAPLAGTC  GVLLLSLVIT  LYCRRDQRLP  PDAHKPPGGG  SFRTPIQEEQ  360
ADAHSTLAKI  RVKFSRSADA  PAYKQGQNQL  YNELNLGRRE  EYDVLDKRRG  RDPEMGGKPR  420
RKNPQEGLYN  ELQKDKMAEA  YSEIGMKGER  RRGKGHDGLY  QGLSTATKDT  YDALHMQALP  480
PR                                                                    482

SEQ ID NO: 618          moltype = DNA   length = 1575
FEATURE                 Location/Qualifiers
misc_feature            1..1575
                        note = CAR-T E6 CD28/OX40/CD3z sequence
source                  1..1575
                        mol_type = other DNA
                        organism = synthetic construct
SEQUENCE: 618
atggccctgc ccgtgaccgc tttgctgctc ccctggcgc tgctgctgca cgccgccagg   60
ccagaggtcc agctggttga gagtggcggt gggctggtta agcctggcgg ctccctgcgg  120
ctgagctgcg ccgcgagtgg atttactttc agccgatatg gatgagttg ggtgcggcaa  180
gctcccggga agaggctgga atgggtctca acaatctccg gggggggcac ttacatctat  240
taccccgact cagtcaaggg gagatttacc atttcacgag acaacgctaa gaataccctg  300
tatttgcaga tgaattctct gagagcagag gacacagctg tttactattg tacccgcgac  360
aactatggca ggaactacga ctacggtatg gactattggg gacaagggac attggttaca  420
gtgagcagtg gcggcggggg cagcggagga ggaggcagcg gtgggggcag cagataa    480
gtgctcacgc agtcacccgc gactctcagt ctctcacctg ggaacgagc taccctgacg  540
tgctctgcta cctcctcagt gtcatatatt cactggtatc agcaacgcc cgggcagtcc  600
cctagattgc tcatttatag tacctctaat ctggcctcag gtatccctgc acgatttct  660
ggatctggtt caggttctga ttacacccct actatctcta gcctgagcc tgaagacttt  720
gccgtttatt actgccagca gaggtctagc tccccattca cctttgggag tgggaccaag  780
```

-continued

```
gttgaaatta aaacgacaac cccggccccc agaccaccaa cgccagcccc caccatcgcc    840
agccaacccc tgtctctgag accagaagcc tgtaggcctg ccgccggtgg agctgtgcac    900
acaagaggac tggatttcgc ctgtgatatc tacatttggg ccccgctcgc aggcacatgt    960
ggagtgctcc tcctctccct ggtgattacc ctgtactgca gaagcaagcg gtctcggctc   1020
ctgcattctg attacatgaa catgacccca agaagccacc aggaaacatt ac           1080
cagccctacg ctccgccacg cgacttcgct gcctaccggt cccggaggga ccagaggctg   1140
cccccgatg cccacaagcc ccctggggga ggcagtttcc ggaccccat ccaagaggag    1200
caggccgacg cccactccac cctggccaag atccgcgtta agttctcccg atcagccgac   1260
gcgcctgctt acaagcaggg ccagaaccaa ctgtacaacg agctgaatct cggtagacgg   1320
gaagagtacg acgtgttgga caacgggaga ggccgcgacc cagaaatggg cggcaagcct   1380
cgcaggaaaa accccaggag gggactgtac aatgagttgc agaaagataa gatggcagaa   1440
gcttatagcg agatcggaat gaaggggaa aggagacgag ggaaaggaca cgacggcctt    1500
tatcagggcc tgtccacagc aacaaaagat acgtatgacg ccctccatat gcaggcactt   1560
ccaccacggt gataa                                                    1575

SEQ ID NO: 619           moltype = AA  length = 523
FEATURE                  Location/Qualifiers
REGION                   1..523
                         note = CAR-T E6 CD28/OX40/CD3z sequence
source                   1..523
                         mol_type = protein
                         organism = synthetic construct
SEQUENCE: 619
MALPVTALLL PLALLLHAAR PEVQLVESGG GLVKPGGSLR LSCAASGFTF SRYGMSWVRQ    60
APGKRLEWVS TISGGGTYIY YPDSVKGRFT ISRDNAKNTL YLQMNSLRAE DTAVYYCTRD   120
NYGRNYDYGM DYWGQGTLVT VSSGGGGSGG GGSGGGGSEI VLTQSPATLS LSPGERATLT   180
CSATSSVSYI HWYQQRPGQS PRLLIYSTSN LASGIPARFS GSGSGSDYTL TISSLEPEDF   240
AVYYCQQRSS SPFTFGSGTK VEIKTTTPAP RPPTPAPTIA SQPLSLRPEA CRPAAGGAVH   300
TRGLDFACDI YIWAPLAGTC GVLLLSLVIT LYCRSKRSRL LHSDYMNMTP RRPGPTRKHY   360
QPYAPPRDFA AYRSRRDQRL PPDAHKPPGG GSFRTPIQEE QADAHSTLAK IRVKFSRSAD   420
APAYKQGQNQ LYNELNLGRR EEYDVLDKRR GRDPEMGGKP RRKNPQEGLY NELQKDKMAE   480
AYSEIGMKGE RRRGKGHDGL YQGLSTATKD TYDALHMQAL PPR                     523

SEQ ID NO: 620           moltype = AA  length = 43
FEATURE                  Location/Qualifiers
REGION                   1..43
                         note = MUC1 FRAGMENT
source                   1..43
                         mol_type = protein
                         organism = synthetic construct
SEQUENCE: 620
SNIKFRPGSV VVQLTLAFRE GTINVHDVET QFNQYKTEAA SRY                      43

SEQ ID NO: 621           moltype = AA  length = 35
FEATURE                  Location/Qualifiers
REGION                   1..35
                         note = MUC1 FRAGMENT
source                   1..35
                         mol_type = protein
                         organism = synthetic construct
SEQUENCE: 621
SVVVQLTLAF REGTINVHDV ETQFNQYKTE AASRY                               35

SEQ ID NO: 622           moltype = AA  length = 24
FEATURE                  Location/Qualifiers
REGION                   1..24
                         note = Cytoplasmic MUC1 truncated segment
source                   1..24
                         mol_type = protein
                         organism = synthetic construct
SEQUENCE: 622
VQLTLAFREG TINVHDVETQ FNQY                                           24

SEQ ID NO: 623           moltype = AA  length = 24
FEATURE                  Location/Qualifiers
REGION                   1..24
                         note = Cytoplasmic MUC1 truncated segment
source                   1..24
                         mol_type = protein
                         organism = synthetic construct
SEQUENCE: 623
SNIKFRPGSV VVQLTLAFRE GTIN                                           24

SEQ ID NO: 624           moltype = DNA  length = 28
FEATURE                  Location/Qualifiers
misc_feature             1..28
                         note = Primer
source                   1..28
                         mol_type = other DNA
```

```
                        organism = synthetic construct
SEQUENCE: 624
attctaagct tgggccacca tggaactg                                           28

SEQ ID NO: 625          moltype = DNA   length = 41
FEATURE                 Location/Qualifiers
misc_feature            1..41
                        note = Primer
source                  1..41
                        mol_type = other DNA
                        organism = synthetic construct
SEQUENCE: 625
tctagagttt aaacttacta tttacccgga gacagggaga g                            41

SEQ ID NO: 626          moltype = DNA   length = 41
FEATURE                 Location/Qualifiers
misc_feature            1..41
                        note = Primer
source                  1..41
                        mol_type = other DNA
                        organism = synthetic construct
SEQUENCE: 626
agtatggccc agccggccga ggtgcagctg gtggagtctg g                            41

SEQ ID NO: 627          moltype = DNA   length = 26
FEATURE                 Location/Qualifiers
misc_feature            1..26
                        note = Primer
source                  1..26
                        mol_type = other DNA
                        organism = synthetic construct
SEQUENCE: 627
tagaaggcac agtcgaggct gatcag                                             26

SEQ ID NO: 628          moltype = DNA   length = 27
FEATURE                 Location/Qualifiers
misc_feature            1..27
                        note = Primer
source                  1..27
                        mol_type = other DNA
                        organism = synthetic construct
SEQUENCE: 628
attctaagct tgggccacca tggaagc                                            27

SEQ ID NO: 629          moltype = DNA   length = 40
FEATURE                 Location/Qualifiers
misc_feature            1..40
                        note = Primer
source                  1..40
                        mol_type = other DNA
                        organism = synthetic construct
SEQUENCE: 629
tctagagttt aaacttacta acactctccc ctgttgaagc                              40

SEQ ID NO: 630          moltype = DNA   length = 43
FEATURE                 Location/Qualifiers
misc_feature            1..43
                        note = Primer
source                  1..43
                        mol_type = other DNA
                        organism = synthetic construct
SEQUENCE: 630
agtatggccc agccggccga aattgtgttg acacagtctc cag                          43

SEQ ID NO: 631          moltype = DNA   length = 26
FEATURE                 Location/Qualifiers
misc_feature            1..26
                        note = Primer
source                  1..26
                        mol_type = other DNA
                        organism = synthetic construct
SEQUENCE: 631
tagaaggcac agtcgaggct gatcag                                             26

SEQ ID NO: 632          moltype = DNA   length = 33
FEATURE                 Location/Qualifiers
misc_feature            1..33
                        note = Primer
source                  1..33
```

```
                         mol_type = other DNA
                         organism = synthetic construct
SEQUENCE: 632
actgtcatat ggaggtgcag ctggtggagt ctg                             33

SEQ ID NO: 633           moltype = DNA   length = 37
FEATURE                  Location/Qualifiers
misc_feature             1..37
                         note = Primer
source                   1..37
                         mol_type = other DNA
                         organism = synthetic construct
SEQUENCE: 633
actgtctcga gtttaatttc cactttggtg ccgctgc                         37

SEQ ID NO: 634           moltype = DNA   length = 33
FEATURE                  Location/Qualifiers
misc_feature             1..33
                         note = Primer
source                   1..33
                         mol_type = other DNA
                         organism = synthetic construct
SEQUENCE: 634
actgtcatat ggaggtgcag ctggtggagt ctg                             33

SEQ ID NO: 635           moltype = DNA   length = 37
FEATURE                  Location/Qualifiers
misc_feature             1..37
                         note = Primer
source                   1..37
                         mol_type = other DNA
                         organism = synthetic construct
SEQUENCE: 635
actgtaccgg tttttaatttc cactttggtg ccgctgc                        37

SEQ ID NO: 636           moltype = DNA   length = 29
FEATURE                  Location/Qualifiers
misc_feature             1..29
                         note = Primer
source                   1..29
                         mol_type = other DNA
                         organism = synthetic construct
SEQUENCE: 636
cttcttcctc aggagcaagc tcaccgtgg                                  29

SEQ ID NO: 637           moltype = DNA   length = 18
FEATURE                  Location/Qualifiers
misc_feature             1..18
                         note = Primer
source                   1..18
                         mol_type = other DNA
                         organism = synthetic construct
SEQUENCE: 637
gagccgtcgg agtccagc                                              18

SEQ ID NO: 638           moltype = DNA   length = 18
FEATURE                  Location/Qualifiers
misc_feature             1..18
                         note = Primer
source                   1..18
                         mol_type = other DNA
                         organism = synthetic construct
SEQUENCE: 638
gcacctgaac tcctgggg                                              18

SEQ ID NO: 639           moltype = DNA   length = 22
FEATURE                  Location/Qualifiers
misc_feature             1..22
                         note = Primer
source                   1..22
                         mol_type = other DNA
                         organism = synthetic construct
SEQUENCE: 639
tttaatttcc actttggtgc cg                                         22

SEQ ID NO: 640           moltype = DNA   length = 32
FEATURE                  Location/Qualifiers
misc_feature             1..32
                         note = Primer
```

```
source                  1..32
                        mol_type = other DNA
                        organism = synthetic construct
SEQUENCE: 640
cgcggctagc ttaagcttgg taccgagggc ca                              32

SEQ ID NO: 641          moltype = DNA  length = 36
FEATURE                 Location/Qualifiers
misc_feature            1..36
                        note = Primer
source                  1..36
                        mol_type = other DNA
                        organism = synthetic construct
SEQUENCE: 641
cgcggcggcc gcctgatcag cgggtttaaa cttatc                          36

SEQ ID NO: 642          moltype = AA  length = 35
FEATURE                 Location/Qualifiers
REGION                  1..35
                        note = PSMGFR N-10
source                  1..35
                        mol_type = protein
                        organism = synthetic construct
SEQUENCE: 642
QFNQYKTEAA SRYNLTISDV SVSDVPFPFS AQSGA                           35

SEQ ID NO: 643          moltype = AA  length = 35
FEATURE                 Location/Qualifiers
REGION                  1..35
                        note = PSMGFR C-10
source                  1..35
                        mol_type = protein
                        organism = synthetic construct
SEQUENCE: 643
GTINVHDVET QFNQYKTEAA SRYNLTISDV SVSDV                           35
```

UNITED STATES PATENT AND TRADEMARK OFFICE
CERTIFICATE OF CORRECTION

PATENT NO. : 12,006,371 B2
APPLICATION NO. : 17/817525
DATED : June 11, 2024
INVENTOR(S) : Cynthia Bamdad and Benoit Smagghe It is certified that error appears in the above-identified patent and that said Letters Patent is hereby corrected as shown below:

In the Specification

SEQ ID NO: 390 in the first block of Column 173 should read:
DIQMTQSPSSLSASVGDRVTITCSASSSVSYMNWYQQTPGKAPKRWIYDTSKLASGVPSRFS
GSGSGTDYTFTISSLQPEDIATYYCQQWSSNPFTFGQGTKLQIIRGGGGSGGGGSGGGGSQV
QLVQSGGGVVQPGRSLRLSCKASGYTFTRYTMHWVRQAPGKGLEWIGYINPSRGYTNYNQK
VKDRFTISTDKSKSTAFLQMDSLRPEDTAVYYCARYYDDHYCLDYWGQGTTLTVSS (SEQ ID NO: 390)

Signed and Sealed this
Sixteenth Day of July, 2024

Katherine Kelly Vidal
*Director of the United States Patent and Trademark Office*